United States Patent
Cui et al.

(10) Patent No.: US 6,599,902 B2
(45) Date of Patent: Jul. 29, 2003

(54) 5-ARALKYSUFONYL-3-(PYRROL-2-YLMETHYLIDENE)-2-INDOLINONE DERIVATIVES AS KINASE INHIBITORS

(75) Inventors: Jingrong Cui, Foster City, CA (US); John Ramphal, Union City, CA (US); Congxin Liang, Sunnyvale, CA (US); Connie Li Sun, Foster City, CA (US); Chung Chen Wei, Foster City, CA (US); Peng Cho Tang, Morago, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 10/157,007

(22) Filed: May 30, 2002

(65) Prior Publication Data

US 2003/0125370 A1 Jul. 3, 2003

Related U.S. Application Data

(60) Provisional application No. 60/294,544, filed on May 30, 2001, and provisional application No. 60/328,408, filed on Oct. 10, 2001.

(51) Int. Cl.[7] .................... A61K 31/5377; A61P 35/00; C07D 403/06; C07D 413/04
(52) U.S. Cl. .................. 514/235.5; 514/414; 544/58.2; 544/58.4; 544/121; 544/130; 544/144; 544/373; 546/201; 546/227.4; 548/253; 548/255; 548/312.1; 548/468
(58) Field of Search .................. 544/130, 144, 544/373; 546/201; 548/468; 514/235.5

(56) References Cited

U.S. PATENT DOCUMENTS

| | | |
|---|---|---|
| 2,968,557 A | 1/1961 | Burgardt et al. |
| 4,002,749 A | 1/1977 | Rovnyak |
| 4,053,613 A | 10/1977 | Rovnyak et al. |
| 4,642,309 A | 2/1987 | Michel et al. |
| 4,826,847 A | 5/1989 | Michel et al. |
| 5,051,417 A | 9/1991 | Nadler et al. |
| 5,124,347 A | 6/1992 | Connor et al. |
| 5,196,446 A | 3/1993 | Levitzki et al. |
| 5,302,606 A | 4/1994 | Spada et al. |
| 5,322,950 A | 6/1994 | Sircar et al. |
| 5,374,652 A | 12/1994 | Buzzetti et al. |
| 5,382,593 A | 1/1995 | Le Baut et al. |
| 5,389,661 A | 2/1995 | Sircar et al. |
| 5,397,787 A | 3/1995 | Buzzetti et al. |
| 5,409,949 A | 4/1995 | Buzzetti et al. |
| 5,792,783 A * | 8/1998 | Tang et al. .................. 548/468 |
| 5,834,504 A | 11/1998 | Tang et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| 6,133,305 A | 10/2000 | Tang et al. |
| 6,395,374 B1 | 5/2002 | McAndrew |
| 6,395,734 B1 | 5/2002 | Tang et al. |

FOREIGN PATENT DOCUMENTS

| | | |
|---|---|---|
| AU | 286870 | 5/1967 |
| CA | 2012634 A1 | 9/1991 |
| DE | 2 159 360 | 6/1973 |
| DE | 2 159 361 | 6/1973 |
| DE | 2 159 362 | 6/1973 |
| DE | 2 159 363 | 6/1973 |
| DE | 2 321 656 A | 11/1973 |
| DE | 3 426 419 A | 1/1986 |
| EP | 0 252 713 B1 | 1/1988 |
| EP | 0 351 213 A2 | 1/1990 |
| EP | 0 525 472 A2 | 2/1993 |
| EP | 0 632 102 A1 | 1/1995 |
| EP | 0 662 473 A1 | 7/1995 |
| EP | 0 769 947 B1 | 5/1997 |
| EP | 0 788 890 A1 | 8/1997 |
| EP | 0 934 931 A2 | 8/1999 |
| EP | 1 082 305 A1 | 3/2001 |
| FR | 1398224 | 5/1964 |
| FR | 1599772 | 8/1970 |
| FR | 2689397 A1 | 10/1993 |
| GB | 809691 | 3/1959 |
| GB | 835473 | 5/1960 |
| JP | 62-29570 A | 2/1987 |
| JP | 62-39564 A | 2/1987 |
| JP | 63-141955 A | 6/1988 |
| JP | 5-58894 A | 3/1993 |
| WO | WO 91/13055 A2 | 9/1991 |
| WO | WO 92/07830 A2 | 5/1992 |
| WO | WO 92/20642 A1 | 11/1992 |
| WO | WO 93/01182 A1 | 1/1993 |
| WO | WO 94/14808 A1 | 7/1994 |
| WO | WO 95/01349 A1 | 1/1995 |

(List continued on next page.)

OTHER PUBLICATIONS

Andreani et al., "Potential Antitumor Agents. 25[1]. Synthesis and Cytotoxic Activity of 3–(2–Chloro–3–Indolymethylene)1, 3–Dihydroindol–2–Ones," *Anticancer Research* 16:3585–3588 (1996) © Elsevier, Paris.

Andreani et al., "Synthesis and cardiotonic activity of 2–indolinones," *Eur. J. Med. Chem.* 25:187–190 (1990).

Andreani et al., "Synthesis and cardiotonic activity of 2–indolinones bearing pyridyl groups," *Eur. J. Med. Chem.* 28:653–657 (1993) © Elsevier, Paris.

(List continued on next page.)

*Primary Examiner*—Robert W. Ramsuer
(74) *Attorney, Agent, or Firm*—Beth A. Burrous; Foley & Lardner

(57) ABSTRACT

The present invention relates to certain 5-aralkylsulfonyl-3-(pyrrol-2-yl-methylidene)-2-indolinone derivatives that inhibit kinases, in particular met kinase. Pharmaceutical compositions comprising these compounds, methods of treating diseases mediated by kinases utilizing pharmaceutical compositions comprising these compounds, and methods of preparing them are also disclosed.

23 Claims, No Drawings

FOREIGN PATENT DOCUMENTS

| | | |
|---|---|---|
| WO | WO 95/17181 A1 | 6/1995 |
| WO | WO 96/00226 A1 | 1/1996 |
| WO | WO 96/22976 A1 | 8/1996 |
| WO | WO 96/32380 A1 | 10/1996 |
| WO | WO 96/40116 A1 | 12/1996 |
| WO | WO 97/25986 A1 | 7/1997 |
| WO | WO 98/07695 A1 | 2/1998 |
| WO | WO 98/24432 A2 | 6/1998 |
| WO | WO 98/38984 A2 | 9/1998 |
| WO | WO 98/50356 A1 | 11/1998 |
| WO | WO 99/10325 A1 | 3/1999 |
| WO | WO 99/52869 A1 | 10/1999 |
| WO | WO 99/61422 A1 | 12/1999 |
| WO | WO 99/65869 A1 | 12/1999 |
| WO | WO 00/08202 A2 | 2/2000 |
| WO | WO 00/35906 A2 | 6/2000 |
| WO | WO 00/35909 A1 | 6/2000 |
| WO | WO 00/38519 A1 | 7/2000 |
| WO | WO 00/56709 A1 | 9/2000 |
| WO | WO 01/60814 A2 | 8/2001 |
| WO | WO 01/90068 A2 | 11/2001 |

OTHER PUBLICATIONS

Andreani et al., "Synthesis and cardiotonic activity of pyridylmethylene–2–indolinones," *Eur. J. Med. Chem.* 27:167–170 (1992) © Elsevier, Paris.

Andreani et al., "Synthesis and potential coanthracyclinic activity of substituted 3–(5–imidazo[2,1–b] thiazolylmethylene)–2–indolinones," *Eur. J. Med. Chem.* 32:919–924 (1997)© Elsevier, Paris.

Andreani et al., "Synthesis of lactams with potential cardiotonic activity," *Eur. J. Med. Chem.* 28:825–829 (1993).

Andreani et al., "In Vivo Cardiotonic Activity of Pyridylmethylene–2–indolinones," *Arzneimittel–Forschung Drug Research* 48:727–729 (1998) ©.

Bahner and Brotherton, "9–(4–Aminobenzylidene)fluorenes," *J. Med. Chem.* 12:722–723 (1969).

Bahner et al., "Benzylideneindenes with Oxygen Attached to the Indene Ring," *J. Med. Chem.* 12:721–722 (1969).

Bamfield et al., "Diels–Alder Reactions of Oxindolylideneacetone," *J. Chem. Soc. (C)* 1028–1030 (1966) ©.

Borsche et al., "Über vielkernige kondensierte Systeme mit heterocyclischen Ringen. XIII.," *Liebigs Ann. Chem.* 550:160–174 (1941).

Buzzetti et al., "Cinnamamide Analogs as Inhibitors of Protein Tyrosine Kinases," *II Farmaco* 48:615–636 (1993).

Chatten et al., "Substituted Oxindoles. Part VI. Polarographic Reduction of Substituted *trans*–3–Benzylideneindol–2(3H)–ones," *J. Chem. Soc. Perkin II*: 469–473 (1973).

Coda et al., "(Z)–and (E)–Arylidene–1,3–dihydroindol–2–ones: Configuration, Conformation and Infrared Carbonyl Stretching Frequencies," *J. Chem. Soc. Perkin Trans. II*: 615–619 (1984).

Coda et al., "3–(4–methylbenzilidene)–1,3–dihydroindol–2–one," *Journal of the Chemical Society, Perkin Transactions 2* 4:615–620 (1984) Database Crossfire, Beilstein Reference No. 6–21.

Decodts et al., "Suicide inhibitors of proteases. Lack of activity of halomethyl derivatives of some aromatic lactams," *Eur. J. Med. Chem* 18: 107–111 (1983).

Desimoni et al., "Catalysis with Inorganic Cations. V[1] Intramolecular Hetero Diels–Alder *versus* Ene Reactions: Effect of Magnesium perchlorate on Chemoselectivity,"*Tetrahedron* 52(36) 12009–12018 (1196) © Pergamon.

Elliott and Rivers, "Reduction of Some Oxindolylidene Derivatives to 3–Substituted Oxindoles by Sodium Borohydride," *J. Med. Chem.* 29:2438–2440 (1964).

Elliott et al., "1–methyl–2–(3–oxindolidenmethyl)–pyridinium," *Journal of Organic Chemistry* 29:2438–2440 (1964) Database Crossfire, Beilstein Reference No. 5–24.

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991) copyright Am. Clem. Soc.

Hirao et al., "Rhodium–Catalyzed Carbonylation of 2–Alkynylaniline: Syntheses of 1,3–Dihydroindol–2–ones," *Tetrahedron Letters* 36(35) 1995 ©Pergamon.

Hodges et al., "Chemical and biological properties of some oxindolidyl–3–methines," *Canadian J. Chemistry* 46:2189–2194 (1968).

Howard, Harry R., "Lactam Derivatives," U.S. Provisional Patent Application Number 60/015134.

Howard et al., "Synthesis and aldose reductase inhibitory activity of substituted 2(1H)–benzimidazolone–and oxindole–1–acetic acids," *Eur. J. Med. Chem.* 27:779–789 (1992) © Elsevier, Paris.

Katritzky et al., "Color and Constitution. Part 8[1]. Some Novel Dyestuffs Containing Indoxyl Residues," *J. Heterocyclic Chem.* 25:1287–1292 (1988).

Kobayashi et al., "Anti–tumor Activity of Indole Derivatives," *Yakugaku Zasshi* 97:1033–1039 (1977).

Kovac and Stetinova, "Furan derivatives. LXXX. Synthesis and properties of substituted furfurylidenoxindoles," *Chem. rvesu* 30:484–492 (1976).

Levitzki and Gazit, "Tyrosine Kinase Inhibition: An Approach to Drug Development," *Science* 267:1782–1788 (1995).

Mariani et al., "Inhibition of angiogenesis by FCE 26806, a potent tyrosine kinase inhibitor," *Experimental Therapeutics –Proceedings of the American Association for Cancer Research* 35:381 at abstract No. 2268 (Mar. 1994).

Mohammadi et al., "Structures of the Tyrosine Kinase Domain of Fibroblast Growth Factor Receptor in Complex with Inhibitors," *Science* 276:955–960 (1997) © American Association for the Advancement of Science.

Neber and Röcker, "On the action of benzaldehydes on the free o–aminophenylacetic acid (II)," *Chem. Ber.* 56:1710–1716 (1923) (German and English Translation).

Nodiff et al., "Antimalarial Phenanthrene Amino Alcohols. 3. Halogen–containing 9–phenanthrenemethanols," *Chemical Abstracts*, vol. 83, abstract No. 188214 (1975).

O'Sullivan and Rothery, "The Preparation and Possible Clinical Significance of 4'–Dialkylaminoisoindogenides," *Clinica Chimica Acta* 62:181–182 (1975) ©Elsevier Scientific Publishing Company.

Pavlenko et al., "Introduction of aminomethyl groups into heterocyclic CH–acid molecules," *Dopov. Akad. Nauk Ukr Rsrs, Ser. B: Geol., Khim. Biol. Nauki* 7:64–66 (1980).

Plowman et al., "Receptor Tyrosine Kinases as Targets for Drug Intervention," *DN&P* 7:334–339 (1994).

Quallich et al., Á General Oxindole Synthesis, *J. Synthetic Organic Chemistry*: 51–51 (1993).

Schuchter et al., "Successful Treatment of Murine Melanoma with Bryostatin 1," *Cancer Research* 51:682–687 (1991).

Shiraishi et al., "Specific inhibitors of Tyrosine–Specific Protein Kinase, Synthetic 4–Hydroxycinnamamide Derivatives," *Biochemical and Biophysical Research Communications* 147:322–328 (1987)© Academic Press.

Shiraishi et al., "Specific Inhibitors of Tyrosine–specific Protein Kinases: Properties of 4–Hydroxycinnamamide Derivatives *in Vitro*," *Cancer Research* 49:2374–2378 (1989).

Singh et al., "Indolinone Derivatives as Potential Antimicrobial Agents," *Zentralbl. Mikrobiol.* 144:105–109 (1989) copyright VEB Gustav Fischer Veriag Jena.

Spada, et al., "Small molecule inhibitors of tyrosine kinase activity," *Expert Opinion on Therapeutic Patents* 5:805–817 (1995) ©Ashley Publications.

Sun et al., "Design, Synthesis, and Evaluations of Substituted 3–[(3–or 4–Carboxyethylpyrrol–2–yl) methylidenyl] indolin–2–ones as Inhibitors of VEGF, FGF, and PDGF Receptor Tyrosine Kinases," *Journal of Medicinal Chemistry* 42: 5120–5130 (1999) ©American Chemical Society.

Sun et al, "Synthesis and Biological Evaluations of 3–Substituted Indolin–2–ones: A Novel Class of Tyrosine Kinase Inhibitors That Exhibit Selectivity toward Particular Receptor Tyrosine Kinases," *J. Med. Chem.* 41:2588–2603 (1998) ©The American Chemical Society.

Tacconi and Marinone, "Preparazione e caratteristiche di alcuni 3–ossindolidenderivati," *Ricerca Scientifica* 38:1239–1244 (1968).

Tacconi et al., "(Z)–and (E)–3–Alkylidene–1, 3–dihydroindol–2–ones: Influence of Configuration on the Transmission of the Inductive Effect to the Carbonyl Group," *J.C.S. Perkin II* 150–154 (1976).

Thompson et al., "Facile Dimerisation of 3–Benzylideneindoline–2–thiones," *J. Chem. Soc. Perkin Trans. (l)* 1835–1837 (1993).

Traxler, "Protein tyrosine kinase inhibitors in cancer treatment," *Expert Opinion on Therapeutic Patents* 7(6):571–588 (1997) © Ashley Publications Ltd.

Wahl et al., "3–benzilidene–5–methyl–1, 3–dihydroindol–2–one," *Ann. Chim.* 350 (1926), Database Crossfire, Beilstein Reference No. 2–21–00–00290.

Wahl, Beilstein Reg. No. 191439, *Bull. Soc. Chim. Fr.*, p. 1038 (1909).

Wahl, Beilstein Reg. No. 231732, *Bull. Soc. Chim. Fr.*, pp. 1035–1038 (1909).

Walker et al., "Synthesis of New 3–(Pyridylmethylene)–, 3–(Pyridylmethyl)–, 3–(Piperidylmethyl)–, and 3–(β–Alkylaminoethyl)–2–indolinones. The Reduction of Isoindogenides, Nitro Compounds, and Pyridines in a Series of 2–Indolinones," *J. Med. Chem.* 8:626–637 (1965).

Wright et al., "Cyclic Hydroxamic Acids Derived from Indole," *J. Am. Chem. Soc.* 78:221–224 (1956).

Wright et al., "Inhibition of Angiogenesis in Vitro and In Ovo With an Inhibitor of Cellular Protein Kinases, MDL 27032," *J. Cellular Physiology* 152:448–457 (1992).

Zhang et al., "Microtubule Effects of Welwistatin, a Cyanobacterial Indolinone that Circumvents Multiple Drug Resistance," *Molecular Pharmacology* 49:228–234 (1996) copyright The American Society for Pharmacology and Experimental Pharmaceutics.

\* cited by examiner

5-ARALKYSUFONYL-3-(PYRROL-2-YLMETHYLIDENE)-2-INDOLINONE DERIVATIVES AS KINASE INHIBITORS

RELATED APPLICATIONS

This application claims benefit of U.S. Provisional Application No. 60/294,544, filed on May 30, 2001, entitled "5-ARALKYLSUFONYL-3-(PYRROL-2-YLMETHYLIDENE)-2-INDOLINONE DERIVATIVES AS KINASE INHIBITORS", and of U.S. Provisional Application No. 60/328,408, filed on Oct. 10, 2001, entitled "5-ARALKYLSUFONYL-3-(PYRROL-2-YLMETHYLIDENE)-2-INDOLINONE DERIVATIVES AS KINASE INHIBITORS" the disclosures both of which are incorporated herein in their entirety by reference.

INTRODUCTION

The present invention relates generally to organic chemistry, biochemistry, pharmacology and medicine. More particularly, it relates to novel 5-aralkylsulfonyl-3-(pyrrol-2-ylmethylidene)-2-indolinone derivatives that inhibit kinases, in particular met kinase, pharmaceutical compositions comprising these compounds, methods of treating diseases mediated by kinases utilizing pharmaceutical compositions comprising these compounds, and methods of preparing them are disclosed.

BACKGROUND OF THE INVENTION

The following is offered as background information only to aid in understanding the invention, and is not admitted to be prior art to the present invention.

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non life threatening diseases such as psoriasis to extremely virulent diseases such as glioblastoma (brain cancer) (see U.S. Pat. No. 5,792,783 which is incorporated herein by reference in its entirety).

In view of the apparent link between PK-related cellular activities and wide variety of human disorders, it is no surprise that a great deal of effort is being expended in an attempt to identify ways to modulate PK activity. Some of this effort has involved biomimetic approaches using large molecules patterned on those involved in the actual cellular processes (e.g., mutant ligands (U.S. application. Ser. No. 4,966,849); soluble receptors and antibodies (App. No. WO 94/10202, Kendall and Thomas, *Proc. Nat'l Acad. Sci.*, 90:10705–09 (1994), Kim, et al., *Nature*, 362:841–844 (1993)); RNA ligands (Jelinek, et al., *Biochemistry*, 33:10450–56); Takano, et al., *Mol. Bio. Cell* 4:358A (1993); Kinsella, et al., *Exp. Cell Res.* 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinyleneazaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No.0 566 266 A1), selenaindoles and selenides (PCT WO 94/03427), tricyclic polyhydroxylic compounds (PCT WO 92/21660), benzylphosphonic acid compounds (PCT WO 91/15495) and indolinone compounds (U.S. Pat. No. 5,792,783) have all been described as PTK inhibitors useful in the treatment of cancer. However these compounds have limited utility because of toxicity or poor bioavailability. Accordingly, there is a need for compounds that overcome these limitations. The compounds of the present invention fulfil this need.

SUMMARY OF THE INVENTION

In one aspect, the present invention relates a compound of Formula (I):

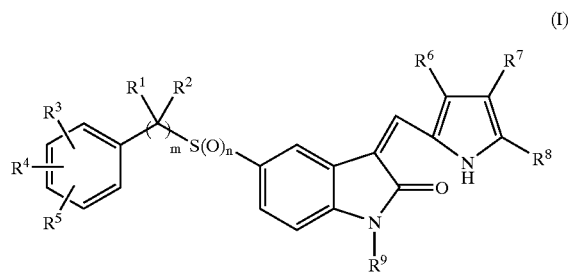

and pharmaceutically acceptable salts thereof, wherein:

n is 0, 1, or 2;

m is 1, 2, or 3;

$R^1$ and $R^2$ are each independently hydrogen or alkyl;

$R^3$, $R^4$, and $R^5$ each are independently hydrogen, halo, alkyl, cycloalkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —$CONR^{10}R^{11}$, —(alkylene)—$CONR^{10}R^{11}$, or —$NR^{10}R^{11}$, (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or $R^{10}$ and $R^{11}$ together with the nitrogen atom to which they are attached combine to form saturated or unsaturated heterocycloamino);

$R^6$ is hydrogen, alkyl, cycloalkyl, hydroxyalkyl, aminoalkyl, alkylaminoalkyl, dialkylaminoalkyl, carboxyalkyl, heterocyclylalkyl, aryl, heteroaryl, carboxy, alkoxycarbonyl, heterocyclylcarbonyl, aminoalkylcarbonyl, alkylaminoalkylcarbonyl, dialkylaminoalkylcarbonyl, —$CONR^{10}R^{11}$, or —(alkylene)—$CONR^{10}R^{11}$ (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy, or $R^{10}$ and $R^{11}$ together with the nitrogen atom to which they are attached combine to form saturated or unsaturated heterocycloamino);

$R^7$ and $R^8$ are independently hydrogen, alkyl, cycloalkyl, heterocyclylalkyl, —$COR^{12}$, —(alkylene)—$COR^{12}$ (where $R^{12}$ is alkoxy, hydroxy, or heterocyle, alkylamino, dialkylamino), —$SO_2R^{14}$, —$CONR^{13}R^{14}$, or —(alkylene)—$CONR^{13}R^{14}$ (where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s), or when $R^{13}$ and $R^{14}$ are attached to a nitrogen atom $R^{13}$ and $R^{14}$ together with the nitrogen atom to which they are attached form saturated or unsaturated heterocycloamino);

$R^6$ and $R^7$ or $R^7$ and $R^8$ can combine to form a saturated or unsaturated 5 to 8 membered ring, $R^9$ is:
(a) hydrogen or alkyl;
(b) —$PO(OR^{15})_2$ where each $R^{15}$ is independently hydrogen or alkyl;
(c) —$COR^{16}$ where $R^{16}$ is hydrogen or alkyl; or
(d) —$CHR^{17}NR^{18}R^{19}$ where $R^{17}$ is hydrogen or alkyl, and $R^{18}$ and $R^{19}$ are independently hydrogen or alkyl, or $R^{18}$ and $R^{19}$ together with the nitrogen atom to which they are attached form heterocycloamino.

In a second aspect, this invention is directed to a pharmaceutical composition comprising one or more compound(s) of Formula (I) or a pharmaceutically acceptable salt thereof and a pharmaceutically acceptable excipient.

In a third aspect, this invention is directed to a method of treating diseases mediated by abnormal protein kinase activity, in particular, receptor tyrosine kinases (RTKs), non-receptor protein tyrosine kinases (CTKs) and serine/threonine protein kinases (STKs), in an organism, in particular humans, which method comprises administering to said organism a pharmaceutical composition comprising a compound of Formula (I) and a pharmaceutically acceptable excipient. Specifically, the diseases mediated by EGFR, Met, HER2, HER3, HER4, IR, IGF-1R, IRR, PDGFRα, PDGFRβ, CSFIR, C-Kit, C-fms, Flk4, KDR/Flk-1, Flt-1, FGFR1, FGFR2, FGFR3, $FGFR^4$, Src, Frk, Btk, Csk, Abl, ZAP70, Fes/Fps, Fak, Jak, Ack, Yes, Fyn, Lyn, Lck, Blk, Hck, Fgr, Yrk, CDK2 and Raf. In particular, diseases mediated by Met.

Such diseases include by way of example and not limitation, cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease. Preferably, the disease is cancer such as acute myeloid leukemia, and colorectal cancer.

The above method can also be carried out in combination with one or more chemotherapeutic agents. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR® (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN® (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product based chemotherapeutic agents that the above method can be carried out in combination with include, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:
3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-pip eridine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-py ran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1] octane-3-carboxylic acid hydroxyamide; and (R) 3-[4-(4-fluoro-phenoxy)-benzenesulfonylamino]-tetrahydrofuran-3-carboxylic acid hydroxyamide; and pharmaceutically acceptable salts and solvates of these compounds.

Other anti-angiogenesis agents, including other COX-II inhibitors and other MMP inhibitors, can also be used in the present invention.

A compound of Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN.™ (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention. VEGF inhibitors, for example SU-5416 and SU-6668 (Sugen Inc. of South San Francisco, Calif., USA), can also be combined with a compound of Formula (I). VEGF inhibitors are described in, for example in WO 01/60814 A3 (published Aug. 23, 2001), WO 99/24440 (published May 20, 1999), PCT International Application PCT/IB99/00797 (filed May 3, 1999), in WO 95/21613 (published Aug. 17,1995), WO 99/61422 (published Dec. 2,1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun.26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sept. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with a compound of Formula (I), in accordance with the present invention.

A compound of Formula (I) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and antiproliferative agents such as other farnesyl protein transferase inhibitors, for example the farnesyl protein transferase inhibitors described in the references cited in the "Background" section, of U.S. Pat. No., 6,258,824 B1.

The above method can be also be carried out in combination with radiation therapy, wherein the amount of a compound of Formula (I) in combination with the radiation therapy effective in treating the above diseases.

Techniques for administering radiation therapy are known in the art, and these techniques can be used in the combination therapy described herein. The administration of the compound of the invention in this combination therapy can be determined as described herein.

In a fourth aspect, this invention is directed to a method of modulating the catalytic activity (e.g., inhibiting the catalytic activity) of PKs, in particular receptor tyrosine kinases (RTKs), non-receptor protein tyrosine kinases (CTKs) and serine/threonine protein kinases (STKs), using a compound of this invention or a pharmaceutical composition comprising a compound of this invention and a pharmaceutically acceptable excipient. The method may be carried out in vitro or in vivo. In particular, the receptor protein kinase whose catalytic activity is modulated by a compound of this invention is selected from the group consisting of Met, EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R, in particular Met. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In a fifth aspect, this invention is directed to the use of a compound of Formula (I) in the preparation of a medicament, which is useful in the treatment of a disease mediated by abnormal Met kinase activity.

In a sixth aspect, this invention is directed to intermediates of Formula (II) useful for preparing the compounds of Formula (I).

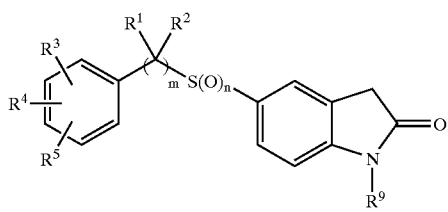

where m, n, and $R^1$–$R^5$ and $R^9$ are as defined in compounds of Formula (I).

In a seventh aspect, this invention is directed to a method of preparing a compound of Formula (I) which method comprises reacting a compound of Formula (II):

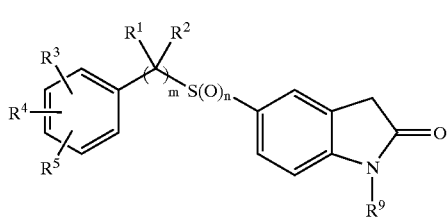

where m, n, and $R^1$–$R^5$ and $R^9$ are as defined in compounds of Formula (I), with a 2-pyrrolaldehyde of formula (III):

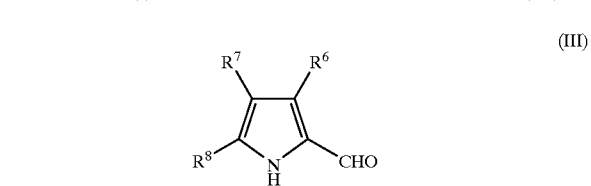

where $R^6$–$R^8$ are as defined in compounds of Formula (I), in the presence of a base;
(i) optionally modifying any of the $R^1$–$R^9$ groups; and
(ii) optionally preparing an acid addition salt; and
(iii) optionally preparing a free base.

Lastly, this invention is also directed to a method of identifying a chemical compound that modulates the catalytic activity of a protein kinase utilizing a compound of Formula (I) as a reference which method comprises by contacting cells expressing said protein kinase with said compound or a compound of Formula (I) and then monitoring said cells for an effect.

DETAILED DESCRIPTION OF THE INVENTION

Definitions

Unless otherwise stated the following terms used in the specification and claims have the meanings discussed below:

"Alkyl" refers to a saturated straight or branched hydrocarbon radical of one to six carbon atoms, preferably one to four carbon atoms e.g., methyl, ethyl, propyl, 2-propyl, n-butyl, iso-butyl, tert-butyl, pentyl, hexyl, and the like, preferably methyl, ethyl, propyl, or 2-propyl.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms e.g., cyclopropyl, cyclobutyl, cyclopentyl or cyclohexyl.

"Alkoxy" means a radical -OR where R is an alkyl as defined above e.g., methoxy, ethoxy, propoxy, butoxy and the like.

"Alkoxycarbonyl" means a radical —COOR where R is an alkyl as defined above e.g., methoxycarbonyl, ethoxycarbonyl, propoxycarbonyl, butoxycarbonyl, and the like.

"Alkylthio" means a radical —SR where R is an alkyl as defined above e.g., methylthio, ethylthio, propylthio, butylthio, and the like.

"Alkylamino" and "dialkylamino" means a radical —NHR and —NRR' respectively, where R and R' independently represent an alkyl group as defined herein. Representative examples include, but are not limited to methylamino, ethylamino, propylamino, dimethylamino, methylethylamino, di(1-methylethyl)amino, and the like.

"Alkylaminocarbonyl" and "dialkylaminocarbonyl" means a radical —ONHR and —CONRR' respectively, where R and R' independently represent an alkyl group as defined herein. Representative examples include, but are not limited to methylaminocarbonyl, ethylaminocarbonyl, propylaminocarbonyl, dimethylaminocarbonyl, methylethylaminocarbonyl, di(1-methylethyl)aminocarbonyl, and the like.

"Halo" means fluoro, chloro, bromo, or iodo, preferably fluoro and chloro.

"Haloalkyl" means alkyl substituted with one or more, preferably one, two or three, same or different halo atoms, e.g., —CH$_2$Cl, —CF$_3$, —CH$_2$CF$_3$, —CH$_2$CCl$_3$, and the like.

"Haloalkoxy" means a radical -OR where R is an haloalkyl as defined above e.g., trifluoromethoxy, trichloroethoxy, 2,2-dichloropropoxy, and the like.

"Hydroxyalkyl" means a saturated straight or branched monovalent hydrocarbon radical of one to six carbon atoms substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Alkoxyalkyl" means a saturated straight or branched monovalent hydrocarbon radical of one to six carbon atoms substituted with one or two alkoxy groups as defined above, e.g., methoxymethyl, 2-methoxyethyl, 2-methoxypropyl, 3-methoxypropyl, ethoxymethyl, 2-ethoxyethyl, and the like.

"Aminoalkyl" means a saturated straight or branched monovalent hydrocarbon radical of one to six carbon atoms substituted with one or two —NH$_2$ e.g., 2-aminoethyl, 3-aminopropyl, 2-aminopropyl, 2-, 3-, or 4-aminobutyl, and the like.

"Cycloalkylalkyl" means a saturated straight or branched monovalent hydrocarbon radical of one to six carbon atoms substituted with one or two cycloalkyl group as defined above e.g., cyclopropylmethyl, cyclopropylethyl, cyclobutylmethyl, cyclohexylethyl, and the like.

"Cycloalkylamino" means a —NRR' group where R is hydrogen or alkyl and R' is cycloalkyl e.g., cyclopropylamino, cyclobutylamino, cyclohexylamino, and the like.

"Cycloalkylaminoalkyl" means a —(alkylene)-NRR' group where R is hydrogen or alkyl and R' is cycloalkyl e.g., cyclopropylaminomethyl, cyclopropylaminoethyl, cyclobutylaminomethyl, cyclohexylaminoethyl, and the like.

"Cycloalkylalkylaminoalkyl" means a —(alkylene)-NRR' group where R is hydrogen or alkyl and R' is cycloalkylalkyl as defined above e.g., cyclopropylmethylaminomethyl, cyclopropylmethylaminoethyl, cyclobutylmethylaminomethyl, cyclohexylmethylaminoethyl, and the like.

"Aminoalkylcarbonyl" means a radical —COR where R is an aminoalkyl group as defined above e.g., 2-aminoethylcarbonyl, 3-aminopropylcarbonyl, 2-aminopropylcarbonyl, 2-, 3-, or 4-aminobutylcarbonyl, and the like.

"Alkylaminoalkyl" means a saturated straight or branched monovalent hydrocarbon radical of one to six carbon atoms substituted with one or two —NHR where R is alkyl, or acyl, e.g., 2-N-methylaminoethyl, 2-N-ethylaminoethyl, 2-N-acetylaminoethyl, and the like.

"Alkylaminoalkylcarbonyl" means a radical —COR where R is an alkylaminoalkyl group as defined above e.g., 2-N-methylaminoethylcarbonyl, 2-N-ethylaminoethylcarbonyl, 2-N-acetylaminoethylcarbonyl, and the like.

"Dialkylaminoalkyl" means a saturated straight or branched monovalent hydrocarbon radical of one to six carbon atoms substituted with one or two —NRR' where R and R' are independently selected from alkyl, e.g., 2-N,N-diethylaminoethyl, 2-N,N-diethylaminopropyl, and the like.

"Dialkylaminoalkylcarbonyl" means a radical —COR where R is an dialkylaminoalkyl group as defined above e.g., 2-N,N-diethylaminoethylcarbonyl, 2-N,N-diethylaminopropyl-carbonyl, and the like.

"Acyl" means a radical —C(O)R where R is hydrogen, alkyl, or haloalkyl as defined herein, e.g., formyl, acetyl, trifluoroacetyl, butanoyl, and the like.

"Carboxyalkyl" means a saturated straight or branched monovalent hydrocarbon radical of one to six carbon atoms substituted with one or two COOH group e.g., carboxymethyl, 2-carboxyethyl, 3-carboxypropyl, and the like.

"Cyanoalkyl" means a saturated straight or branched monovalent hydrocarbon radical of one to six carbon atoms substituted with one or two —CN group e.g., cyanomethyl, 2-cyanoethyl, 3-cyanopropyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. When substituted, the aryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino or dialkylamino.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more, more preferably one, two or three, even more preferably one or two substituents independently selected from the group consisting of alkyl, haloalkyl, halo, hydroxy, alkoxy, mercapto, alkylthio, cyano, acyl, nitro, haloalkyl, haloalkoxy, carboxy, alkoxycarbonyl, amino, alkylamino or dialkylamino.

"Heterocycle" means a saturated cyclic radical of 3 to 8 ring atoms in which one, two or three ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one or more, preferably one, two, or three substituents selected from alkyl (wherein the alkyl may be optionally substituted with one or two substituents independently selected from carboxy or ester group), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, aralkyl, heteroaralkyl, saturated or unsaturated heterocycloamino, saturated or unsaturated heterocycloaminoalkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optionally substituted heterocycle" means a saturated cyclic radical of 3 to 8 ring atoms in which one, two or three ring atoms are heteroatoms selected from N, O, or S(O)$_n$ (where n is an integer from 0 to 2), the remaining ring atoms being C, where one or two C atoms may optionally be replaced by a carbonyl group which is optionally substituted independently with one, two, or three substituents selected from alkyl (wherein the alkyl may be optionally substituted with one or two substituents independently selected from carboxy or ester group), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Saturated heterocycloamino" means a saturated cyclic radical of 3 to 8 ring atoms in which at least one of the ring atoms is nitrogen and optionally where one or two additionally ring atoms are heteroatoms selected from —NR$^a$— (where Ra is alkyl, substituted alkyl acyl, aryl, or heteroaryl), O, or S(O)$_n$ (where n is an integer from 0 to 2), the remaining ring atoms being C, where one or two C atoms may optionally be replaced by a carbonyl group. The heterocycloamino ring may be optionally substituted independently with one, two, or three substituents selected from alkyl, haloalkyl, cycloalkylamino, cycloalkylalkyl, cycloalkylaminoalkyl, cycloalkylalkylaminoalkyl, cyanoalkyl, carboxyalkyl, aminoalkyl, alkylaminoalkyl, dialkylaminoalkyl, hydroxyalkyl, alkoxyalkyl, halo, nitro, cyano, hydroxy, alkoxy, amino, alkylamino, dialkylamino, aryl, heteroaryl, aralkyl, heteroaralkyl, optionally substituted heterocycle, optionally substituted heterocyclylalkyl, and —COR (where R is alkyl). More specifically the term heterocycloamino includes, but is not limited to, piperidinlyl, piperazin-1-yl, pyrrolidin-1-yl, 2-(R) or (S)-pyrrolidin-1-ylmethylpyrrolidine, 2-(R) or (S)-cyclopropylaminomethylpyrrolidine, 3-(R) or (S)-pyrrolidin-1-ylpiperidine, 2-(R) or (S)-(3-hydroxypyrrolidin-1-ylmethyl)pyrrolidine, 2-(R) or (S)-(3-fluoropyrrolidin-1-ylmethyl)pyrrolidine, 2-oxo-pyrrolidin-1-yl, 2,5-dioxo-pyrrolidin-1-yl, 4-(4-cyclopropylamino)piperidine, morpholin-4-yl, thiomorpholin-4-yl, thiomorpholino-1-oxide, thiomorpholino-1,1-dioxide, 4-ethyloxycarbonylpiperazin-1-yl, 3-oxopiperazin-1-yl, 2-imidazolidon-1-yl, 2-pyrrolidinon-1-yl, 2-oxohomopiperazino, tetrahydropyrimidin-2-one, and the derivatives thereof. The heterocycloamino group is a subset of the heterocycle group defined above.

"Unsaturated heterocycloamino" means a non-aromatic cyclic radical of 4 to 8 ring atoms containing one or two double bonds within the ring provided that the ring is not aromatic, and in which at least one of the ring atoms is nitrogen and optionally where one or two additionally ring atoms are heteroatoms independently selected from —NR$^a$— (where R$^a$ is alkyl, substituted alkyl acyl, aryl, or heteroaryl), O, or S(O)n (where n is an integer from 0 to 2), the remaining ring atoms being C where one or two C atoms may optionally be replaced by a carbonyl group. The heterocycloamino ring may be optionally substituted independently with one, two, or three substituents selected from alkyl, haloalkyl, cyanoalkyl, carboxyalkyl, aminoalkyl, alkylaminoalkyl, dialkylaminoalkyl, hydroxyalkyl, alkoxyalkyl, halo, nitro, cyano, hydroxy, alkoxy, amino, alkylamino, dialkylamino, aryl, heteroaryl, aralkyl, heteroaralkyl, optionally substituted heterocycle, optionally substituted heterocyclylalkyl, and —COR (where R is alkyl).

"Hydroxy" refers to an —OH group.

"Aryloxy" refers to both an —OR where R is an aryl group, as defined herein. Representative examples include, but are not limited to, phenyloxy, F, Cl, or Br-phenyloxy, and the like, and derivatives thereof.

"Heteroaryloxy" refers to both an —OR where R is a heteroaryl group, as defined herein. Representative examples include, but are not limited to, pyridinyloxy, furanyloxy, thienyloxy, pyrimidinyloxy, pyrazinyloxy, and the like, and derivatives thereof.

"Acetylalkyl" means a alkyl group as defined above carrying a —C(O)CH$_3$ group, e.g., acetylmethyl, acetylethyl, acetylpropyl, and the like. "Cyano" refers to a —C≡N group.

"Nitro" refers to a —NO$_2$ group.

"Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$)CH$_2$phenyl, and the like and derivatives thereof.

"Phenylalkyl" means alkyl as defined above which is substituted with phenyl, e.g., —CH$_2$phenyl, —(CH$_2$)$_2$phenyl, —(CH$_2$)$_3$phenyl, CH$_3$CH(CH$_3$)CH$_2$phenyl, and the like and derivatives thereof. Phenylalkyl is a subset of the aralkyl group.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Optionally substituted heterocyclylalkyl" group means alkyl as defined above which is substituted with an optionally substituted heterocycle group, e.g., —CH$_2$pyrrolidin-1-yl, —(CH$_2$)$_2$piperidin-1-yl, and the like, and derivatives thereof.

"Saturated or unsaturated heterocycloaminoalkyl" group means alkyl as defined above which is substituted with a saturated or unsaturated heterocycloamino group, e.g., —CH$_2$pyrrolidin-1-yl, —(CH$_2$)$_2$piperidin-1-yl, —CH$_2$morpholin-1-yl, —(CH$_2$)$_2$morpholin-1-yl, and the like, and derivatives thereof.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone", "indolin-2-one" and "2-oxindole" are used interchangeably herein to refer to a molecule having the chemical structure:

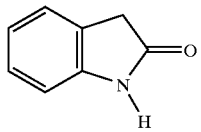

The term "pyrrole" refers to a molecule having the chemical structure:

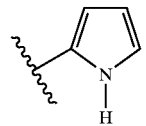

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the R$^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

It is contemplated that a compound of Formula (I) would be metabolized by enzymes in the body of the organism such as human being to generate a metabolite that can modulate the activity of the protein kinases. Such metabolites are within the scope of the present invention.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) may also act as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea. For example, a compound of Formula (I) where $R^9$ is —$CO_2R^{16}$ hydrolyze in vivo to generate a corresponding compound of Formula (I) where $R^9$ is hydrogen.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukaryotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

PREFERRED EMBODIMENTS

While the broadest definition is set forth in the Summary of the Invention, certain compounds of Formula (I) set forth below are preferred.

1. A preferred group of compounds is that wherein $R^1$ and $R^2$ are hydrogen; m is 1 and n is 2.
2. Another preferred group of compounds is that wherein $R^1$ and $R^2$ are hydrogen; m is 1 or 2, preferably 1; n is 2; and $R^3$ is hydrogen, halo, alkyl, haloalkyl, hydroxy, alkoxy, alkoxycarbonyl, haloalkoxy, cyano, carboxy, or nitro, preferably hydrogen, chloro, fluoro, bromo, iodo, methyl, trifluoromethyl, hydroxy, methoxy, methoxycarbonyl trifluoromethoxy, cyano, carboxy, or nitro. More preferably $R^3$ is hydrogen, chloro, fluoro or methyl and is located at the 2-position of the phenyl ring, the carbon atom attached to the methylenesulfonyl group being position 1 of the phenyl ring.
3. Another preferred group of compounds is that wherein $R^1$ and $R^2$ are hydrogen; m is 1 or 2, preferably 1; n is 2; and $R^4$ is hydrogen, halo, alkyl, haloalkyl, hydroxy, alkoxy, alkoxycarbonyl, haloalkoxy, cyano, carboxy, or nitro, preferably hydrogen, chloro, fluoro, methyl, trifluoromethyl, cyano, hydroxy, or methoxy, more preferably hydrogen.
4. Another preferred group of compounds is that wherein $R^1$ and $R^2$ are hydrogen; m is 1 or 2, preferably 1; n is 2; and $R^5$ is hydrogen, halo, alkyl, haloalkyl, hydroxy, alkoxy, haloalkoxy, cyano, or nitro, preferably hydrogen, methyl, chloro, fluoro, iodo, trifluoromethyl, hydroxy, methoxy, cyano or nitro. Even more preferably hydrogen, chloro or fluoro, and is located at the 6-position of the phenyl ring, the carbon atom attached to the methylenesulfonyl group being position 1 of the phenyl ring.
5. Another preferred group of compounds is that wherein $R^1$ and $R^2$ are hydrogen; m is 1 or 2, preferably 1; n is 2; $R^3$ is hydrogen or halo, preferably hydrogen, chloro, or fluoro, and is located at the 2-position of the phenyl ring, the carbon atom attached to the methylenesulfonyl group being position 1 of the phenyl ring; $R^4$ is hydrogen, cyano, trifluoromethyl, methoxy, cyano, fluoro, chloro, bromo, or nitro, most preferably hydrogen; and $R^5$ is hydrogen, halo, alkyl, preferably hydrogen, methyl, chloro, fluoro, iodo, trifluoromethyl, hydroxy, methoxy, cyano or nitro. Even more preferably $R^5$ is hydrogen, chloro or fluoro, and is located at the 6-position of the phenyl ring, the carbon atom attached to the methylenesulfonyl group being position 1 of the phenyl ring.
6. Another preferred group of compounds is that wherein $R^1$ and $R^2$ are hydrogen; m is 1 or 2, preferably 1; n is 2; and the phenyl ring carrying the $R^3$–$R^5$ groups is phenyl, 2-cyanophenyl, 3-cyanophenyl, 3-trifluoromethylphenyl, 3-methoxyphenyl, 3-trifluoromethoxy phenyl, 4-t-butylphenyl, 2-chlorophenyl, 3-chlorophenyl, 3-bromophenyl, 2-fluorophenyl, 3-fluoroplorophenyl, 4-fluorophenyl, 4-bromophenyl, 3-trifluoromethylphenyl, 2-iodophenyl, 3-iodophenyl, 2-chloro-6-fluorophenyl, 2,3-difluorophenyl, 2,3-dichlorophenyl, 2,4-trifluorophenyl, 2,4-difluorophenyl, 2,5-dichlorophenyl, 2,5-difluorophenyl, 3,5-difluorophenyl, 3,5-dichlorophenyl, 3,5-dimethoxyphenyl, 2,6 dimethoxyphenyl, 2,6-difluorophenyl, 3,4-difluorophenyl, 2,3,6-trifluorophenyl, 2-nitrophenyl, 2,6-dichlorophenyl, 2-fluoro-6-nitrophenyl, 2,6-diiodophenyl, or 2,6-dimethylphenyl, 2-fluoro-6-chlorophenyl, 2,6-dibromophenyl, 2-(2-morpholin-4-yl-ethoxy)-phenyl, preferably 2,6-dichlorophenyl, 2,6-difluorophenyl, 2-chlorophenyl or 2-fluorophenyl.
7. Another preferred group of compounds is that wherein $R^1$ and $R^2$ are hydrogen; m is 1 or 2, preferably 1; n is 2; $R^6$ and $R^8$ are independently hydrogen or alkyl, preferably hydrogen or methyl, most preferably methyl; and $R^7$ is:
   (a) —$COR^{12}$ where $R^{12}$ is alkoxy, hydroxy, or heterocyle, preferably $R^{12}$ is hydroxy; or
   (b) —(alkylene)—$COR^{12}$ (where $R^{12}$ is alkoxy, hydroxy, or heterocyle, alkylamino, dialkylamino), preferably hydroxy, more preferably 2-carboxyethyl or 3-carboxy propyl; or
   (c) —$CONR^{13}R^{14}$ where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group (s); preferably $R^{13}$ is hydrogen or methyl and $R^{14}$ is hydroxyalkyl, alkylaminoalkyl, dialkylaminoalkyl, heterocyclylalkyl, or heteroaralkyl wherein the alkyl chain in said groups is optionally substituted with a hydroxy group. Even more preferably, $R^{13}$ is hydrogen and $R^{14}$ is 2-diethylaminoethyl, 2-ethylaminoethyl, 3-diethylaminopropyl, 2-isopropylaminoethyl, 2-cyclopropylethyl, 3-ethylaminopropyl, 2-[1,2,3]-triazin-1-ylethyl, 3-morpholin-4-yl-2-hydroxypropyl, 3-[1,2,3]-triazin-1-yl-2-hydroxypropyl, 2-(3-oxopiperazin-1-yl)ethyl, 3-pyrrolidin-1-ylpropyl, 2-pyrrolidin-1-ylethyl, 2-hydroxyethyl, particularly preferably 2-diethylaminoethyl, or
   (d) —$CONR^{13}R^{14}$ where $R^{13}$ and $R^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. One of the ring carbons may be optionally replaced by carbonyl or oxygen and wherein the ring is substituted with one or two substituents independently selected group the group consisting of alkyl, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, $R^{13}$ and $R^{14}$ together with the nitrogen atom to which they are attached form 4-methylpiperazin-1-yl, 3,5-dimethylpiperazin-1-yl, piperidin-1-yl, morpholin-4-yl, 4-(pyrrolidin-1-yl)- piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypiperidin-1-yl, 3-diethylaminopyrrolidin-1-yl (wherein the stereochemistry at the C-3 carbon atom of the pyrrolidin-1-yl is RS, R or S), 4-(pyrrolidin-1-yl)-piperidin-1-yl, 3-hydroxypyrrolidin-1-yl (stereochemistry at the C-3 carbon atom of the pyrrolidin-1-yl is RS, R or S), 3-aminopyrrolidin-1-yl (stereochemistry at the C-3 carbon atom of the pyrrolidin-1-yl is RS, R, or S), 2-(hydroxymethyl)pyrrolidin-1-yl (stereochemistry at the C-2 carbon atom of the pyrrolidin-1-yl is RS, R or S), 2-methoxymethylpyrrolidin-1-yl (stereochemistry at the C-2 carbon atom of the pyrrolidin-1-yl is RS, R or S), 2-(3-hydroxypyrrolidin-1-ylmethyl)pyrrolidin-1-yl (the stereochemistry at the C-2 and C-3 carbons at the pyrrolidine ring is RS, R or S, preferably the stereochemistry at C-2 and C-3 carbons is R), 3-(pyrrolidin-1-ylmethyl)-piperidin-1-yl (the stereochemistry at the C-3 carbon of the piperidine ring is RS, R or S, preferably S), 2-(3-fluoropyrrolidin-1-ylmethyl)pyrrolidin-1-yl (the stereochemistry at the C-2 and C-3 carbons at the pyrrolidine ring is RS, R or S, preferably the stereochemistry at C-2 is R or S and C-3 carbon is R), 2-(4-fluoropiperidin-1-ylmethyl)pyrrolidin-1-yl (the stereochemistry at the C-4 and C-2 carbons at the piperidine and pyrrolidine ring respectively is RS, R or S, preferably the stereochemistry at C-2 carbon is R), or 2-(4-hydroxypiperidin-1-ylmethyl)pyrrolidin-1-yl (stereochemistry at the C-2 carbon atom of the pyrrolidin-1-yl is RS, R or S). Particularly, $R^{13}$ and $R^{14}$ together with the nitrogen atom to which they are attached form 2-(pyrrolidin-1-ylmethyl)pyrrolidin-1-yl (wherein the stereochemistry at the C-2 carbon atom of the pyrrolidin-1-yl is RS, R or S), preferably (R); or (e) —(alkylene)—CONR$^{13}$R$^{14}$ (where R$^{13}$ is hydrogen or alkyl, and R$^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s); preferably R$^{13}$ is hydrogen or methyl and R$^{14}$ is hydroxyalkyl, alkylaminoalkyl, dialkylaminoalkyl, heterocyclylalkyl, or heteroaralkyl wherein the alkyl chain in said groups is optionally substituted with a hydroxy group. Even more preferably, R$^{13}$ is hydrogen and R$^{14}$ is 2-diethylaminoethyl, 2-ethylaminoethyl, 3-diethylaminoethyl, 3-ethylaminoethyl, 2-triazin-1-ylethyl, 3-morpholin-4-yl-2-hydroxypropyl, 3-triazin-1-yl-2-hydroxypropyl, 2-(3-oxopiperazin-1-yl)ethyl, 3-pyrrolidin-1-ylpropyl, 2-hydroxyethyl, particularly preferably 2-diethylaminoethyl; or (f) —(alkylene)—CONR$^{13}$R$^{14}$ where R$^{13}$ and R$^{14}$ together with the nitrogen atom to which they are attached form saturated or unsaturated heterocycloamino; preferably saturated 5 or 6 membered heterocycloamino containing one or two nitrogen atoms in the ring, the remaining ring atoms being carbon. Additionally, one ring carbon may be optionally replaced by carbonyl or oxygen and the ring is substituted with one or two substituents independently selected group the group consisting of alkyl, halo, preferably fluoro, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, R$^{13}$ and R$^{14}$ together with the carbon atoms to which they are attached form 4-methylpiperazin-1-yl, 3,5-dimethylpiperazin-1-yl, piperidin-1-yl, morpholin-4-yl, 4-(pyrrolidin-1-yl)-piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypiperidin-1-yl, 3-diethylaminopyrrolidin-1-yl (wherein the stereochemistry at the C-3 carbon atom of the pyrrolidin-1-yl is RS, R or S), 3-dimethylaminopyrrolidin-1-yl, 4-(pyrrolidin-1-yl)-piperidin-1-yl (stereochemistry at the C-4 carbon atom of the pyrrolidin-1-yl is RS, R or S), 3-hydroxypyrrolidin-1-yl (stereochemistry at the C-3 carbon atom of the pyrrolidin-1-yl is RS, R or S), 2-(hydroxymethyl)-pyrrolidin-1-yl (stereochemistry at the C-2 carbon atom of the pyrrolidin-1-yl is RS, R or S), 2-methoxymethylpyrrolidin-1-yl (stereochemistry at the C-2 carbon atom of the pyrrolidin-1-yl is RS, R or S), 2-(3-hydroxypyrrolidin-1-ylmethyl)pyrrolidin-1-yl (the stereochemistry at the C-2 and C-3 carbons at the pyrrolidine ring is RS, R or S, preferably the stereochemistry at C-2 and C-3 carbons is R), 3-(pyrrolidin-1-ylmethyl)piperidin-1-yl (the stereochemistry at the C-3 carbon of the piperidine ring is RS, R or S, preferably S), 2-(3-fluoropyrrolidin-1-ylmethyl)pyrrolidin-1-yl (the stereochemistry at the C-2 and C-3 carbons at the pyrrolidine ring is RS, R or S, preferably the stereochemistry at C-2 carbon is R), or 2-(4-hydroxypiperidin-1-ylmethyl)pyrrolidin-1-yl (stereochemistry at the C-2 carbon atom of the pyrrolidin-1-yl is RS, R or S). Particularly R$^{13}$ and R$^{14}$ together with the nitrogen atom to which they are attached form 2-(pyrrolidin-1-ylmethyl)-pyrrolidin-1-yl (wherein the stereochemistry at the C-2 carbon atom of the pyrrolidin-1-yl is RS, R or S), preferably (S); or (g) —CONR$^{13}$R$^{14}$ where R$^{13}$ and R$^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. The saturated heterocycloamino ring is substituted with cycloalkylaminoalkyl, cycloalkylalkyl, cycloalkylalkylamino, cycloalkylamino, or cycloalkylalkylaminoalkyl, preferably cyclopropylmethyl, cyclopropylaminomethyl, cyclopropylmethylamino, or cyclopropylmethylaminomethyl. More preferably, R$^{13}$ and R$^{14}$ together with the carbon atoms to which they are attached form 2R-cyclopropylaminomethylpyrrolidin-1-yl, 2R-cyclopropylmethylaminomethylpyrrolidin-1-yl, 4-cyclopropylmethyl-piperazin-1-yl, or 4-cyclopropylaminopiperidin-1-yl; or (h) —CONR$^{13}$R$^{14}$ where R$^{13}$ and R$^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. The saturated heterocycloamino ring is substituted with optionally substituted heterocycle. More preferably, $R^{13}$ and $R^{14}$ together with the nitrogen atoms to which they are attached form 4-(pyrrolidin-1-yl)piperidin-1-yl, 4-(morpholin-4-yl)piperidin-1-yl, 3-(morpholin-4-yl)pyrrolidin-1-yl, 2-(morpholin-4-yl)pyrrolidin-1-yl, and 3-(morpholin-4-yl)azetidin-1-yl; or (i) heterocyclylalkyl containing 5 or 6 ring atoms wherein at least one ring atom is nitrogen atom and optionally containing an oxygen atom in the ring. The heterocyclyl ring is optionally substituted with cycloalkylalkyl or saturated heterocycloamino of 5 or 6 ring atoms. Preferably $R^7$ is morpholin-4-ylmethyl, 4-(pyrrolidin-1-yl)piperidin-1-yl, or 4-cyclopropylmethylpiperazin-1-yl.

8. Another preferred group of compounds is that wherein $R^1$ and $R^2$ are hydrogen; m is 1 or 2, preferably 1; n is 2; $R^7$ and $R^8$ are independently hydrogen or alkyl, preferably hydrogen or methyl, most preferably $R^8$ is methyl and the $R^7$ group hydrogen; and $R^6$ is:

(a) —$CONR^{10}R^{11}$ where $R^{10}$ is hydrogen or alkyl, and R'1 is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s); preferably $R^{10}$ is hydrogen or methyl and $R^{11}$ is hydroxyalkyl, alkylaminoalkyl, dialkylaminoalkyl, heterocyclylalkyl, or heteroaralkyl wherein the alkyl chain in said groups is optionally substituted with a hydroxy group. Even more preferably, $R^{10}$ is hydrogen and $R^{11}$ is 2-diethylaminoethyl, 2-ethylaminoethyl, 3-diethylaminopropyl, 3-ethylaminopropyl, 2-[1,2,3]-triazin-1-ylethyl, 3-morpholin-4-yl-2-hydroxypropyl, 3-[1,2,3]-triazin-1-yl-2-hydroxypropyl, 2-(3-oxopiperazin-1-yl)ethyl, 3-pyrrolidin-1-ylpropyl, 2-pyrrolidin-1-ylethyl, 2-hydroxyethyl, particularly preferably 2-diethylaminoethyl; or (b) —$CONR^{10}R^{11}$ where $R^{10}$ and $R^{11}$ together with the nitrogen atom to which they are attached form saturated or unsaturated heterocycloamino; preferably saturated 5 or 6 membered heterocycloamino containing one or two nitrogen atoms, the remaining ring atoms being carbon. One of the ring carbons may be optionally replaced by carbonyl or oxygen and the ring may be optionally substituted with one or two substituents independently selected group the group consisting of alkyl, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, $R^{10}$ and $R^{11}$ together with the nitrogen atom to which they are attached form 4-methylpiperazin-1-yl, 3,5-dimethylpiperazin-1-yl, piperidin-1-yl, morpholin-4-yl, 4-(pyrrolidin-1-yl)-piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypiperidin-1-yl, 4-aminopiperidin-1-yl, 3-diethylaminopyrrolidin-1-yl (wherein the stereochemistry at the C-3 carbon atom of the pyrrolidin-1-yl is RS, R or S), 4-(pyrrolidin-1-yl)-piperidin-1-yl (stereochemistry at the C-4 carbon atom of the pyrrolidin-1-yl is RS, R or S), 3-hydroxypyrrolidin-1-yl (stereochemistry at the C-3 carbon atom of the pyrrolidin-1-yl is RS, R or S), 3-aminopyrrolidin-1-yl (stereochemistry at the C-3 carbon atom is RS, R, S), 2-(hydroxymethyl)pyrrolidin-1-yl (stereochemistry at the C-2 carbon atom of the pyrrolidin-1-yl is RS, R or S), 2-methoxymethylpyrrolidi-1-yl (stereochemistry at the C-2 carbon atom of the pyrrolidin-1-yl is RS, R or S), or 2-(4-hydroxypiperidin-1-ylmethyl)pyrrolidin-1-yl (stereochemistry at the C-2 carbon atom of the pyrrolidin-1-yl is RS, R or S). Particularly $R^{10}$ and $R^{11}$ together with the nitrogen atom to which they are attached form 2-(pyrrolidin-1-ylmethyl)pyrrolidin-1-yl (wherein the stereochemistry at the C-2 carbon atom of the pyrrolidin-1-yl is RS, R or S), preferably (R).

Within the preferred groups 1–8 above, a more preferred group of compounds is that wherein $R^9$ is hydrogen, pyrrolidin-1-ylmethyl, or —$P(O)(OH)_2$; preferably hydrogen.

9. Another preferred group of compounds is represented by Formula (Ia):

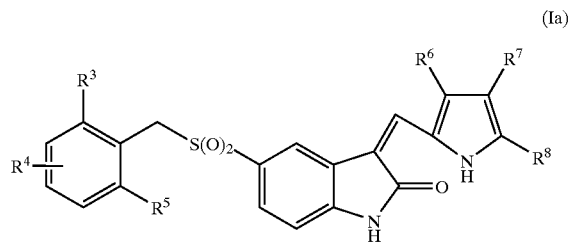

(Ia)

and pharmaceutically acceptable salts thereof, wherein:
each $R^3$, $R^4$, and $R^5$ are independently hydrogen, halo, alkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —$CONR^{10}R^{11}$, or —$NR^{10}R^{11}$, (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or $R^{10}$ and $R^{11}$ together with the nitrogen atom to which they are attached combine to form saturated or unsaturated heterocycloamino);

$R^6$ and $R^8$ are independently hydrogen or alkyl;
$R^7$ is heterocyclylalkyl, $COR^{12}$, —(alkylene)—$COR^{12}$ (where $R^{12}$ is alkoxy, hydroxy, or heterocyle, alkylamino, dialkylamino), —$CONR^{13}R^{14}$ or —(alkylene)—$CONR^{13}R^{14}$ (where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s); or $R^{13}$ and $R^{14}$ together with the nitrogen atom to which they are attached form saturated or unsaturated heterocycloamino).

In formula (Ia), a more preferred group of compounds are wherein:
$R^3$ is hydrogen, halo, alkyl, haloalkyl, hydroxy, alkoxy, alkoxycarbonyl, haloalkoxy, cyano, carboxy, or nitro, preferably hydrogen, chloro, fluoro, bromo, iodo, methyl, trifluoromethyl, hydroxy, methoxy, methoxycarbonyl trifluoromethoxy, cyano, carboxy, or nitro.

More preferably $R^3$ is hydrogen, chloro, fluoro or methyl, even more preferably chloro or fluoro.

$R^4$ is hydrogen, halo, alkyl, haloalkyl, hydroxy, alkoxy, alkoxycarbonyl, haloalkoxy, cyano, carboxy, or nitro, preferably hydrogen, chloro, fluoro, methyl, trifluoromethyl, cyano, hydroxy, or methoxy, more preferably hydrogen.

$R^5$ is hydrogen, halo, alkyl, haloalkyl, hydroxy, alkoxy, haloalkoxy, cyano, or nitro, preferably hydrogen, methyl, chloro, fluoro, iodo, trifluoromethyl, hydroxy, methoxy, cyano or nitro. Even more preferably chloro or fluoro.

Preferably, the phenyl ring carrying the $R^3$–$R^5$ groups is phenyl, 2-cyanophenyl, 3-cyanophenyl, 3-trifluoromethylphenyl, 3-methoxyphenyl, 2-chlorophenyl, 3-chlorophenyl, 3-bromophenyl, 2-fluorophenyl, 3-fluorophenyl, 4-fluorophenyl, 3-trifluorophenyl, 2-iodophenyl, 3-iodophenyl, 2,3-difluorophenyl, 2,4-difluorophenyl, 2,5-difluorophenyl, 3,5-difluorophenyl, 2,6-difluorophenyl, 3,4-difluorophenyl, 2,3,6-trifluorophenyl, 2-nitrophenyl, 2,6-dichlorophenyl, 2-fluoro-6-nitrophenyl, 2-fluoro-6-chlorophenyl, 2,6-dibromophenyl, 2,6-diiodophenyl, or 2,6-dimethylphenyl, particularly preferably 2,6-dichlorophenyl, 2,6-difluorophenyl, 2-chlorophenyl, or 2-fluorophenyl.

$R^6$ and $R^8$ are independently hydrogen or alkyl, preferably hydrogen or methyl, most preferably methyl; and $R^7$ is:

(i) —$OR^{12}$ where $R^{12}$ is alkoxy, hydroxy, or heterocyle, preferably $R^{12}$ is hydroxy; or (ii) —(alkylene)—$COR^{12}$ (where $R^{12}$ is alkoxy, hydroxy, or heterocyle, alkylamino, dialkylamino), preferably hydroxy, more preferably 2-carboxyethyl or 3-carboxypropyl; or (iii) —$CONR^{13}R^{14}$ where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s); preferably $R^{13}$ is hydrogen or methyl and $R^{14}$ is hydroxyalkyl, alkylaminoalkyl, dialkylaminoalkyl, heterocyclylalkyl, or heteroaralkyl wherein the alkyl chain in said groups is optionally substituted with a hydroxy group. Even more preferably, $R^{13}$ is hydrogen and $R^{14}$ is 2-diethylaminoethyl, 2-ethylaminoethyl, 3-diethylaminopropyl, 3-ethylaminopropyl, 2-[1,2,3]-triazin-1-ylethyl, 3-morpholin-4-yl-2-hydroxypropyl, 3-[1,2,3]-triazin-1-yl-2-hydroxypropyl, 2-(3-oxopiperazin-1-yl)ethyl, 3-pyrrolidin-1-ylpropyl, 2-pyrrolidin-1-ylethyl, 2-hydroxyethyl, particularly preferably 2-diethylaminoethyl; or (iv) —$CONR^{13}R^{14}$ where $R^{13}$ and $R^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. One of the ring carbons may be optionally replaced by carbonyl or oxygen and wherein the ring may be optionally substituted with one or two substituents independently selected group the group consisting of alkyl, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, $R^{13}$ and $R^{14}$ together with the nitrogen atom to which they are attached form 4-methylpiperazin-1-yl, 3,5-dimethylpiperazin-1-yl, piperidin-1-yl, morpholin-4-yl, 4-(pyrrolidin-1-yl)-piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypiperidin-1-yl, 4-aminopiperidin-1-yl, 3-diethylaminopyrrolidin-1-yl (wherein the stereochemistry at the C-3 carbon atom of the pyrrolidin-1-yl is RS, R or S), 4-(pyrrolidin-1-yl)-piperidin-1-yl (stereochemistry at the C-4 carbon atom of the pyrrolidin-1-yl is RS, R or S), 3-hydroxypyrrolidin-1-yl (stereochemistry at the C-3 carbon atom of the pyrrolidin-1-yl is RS, R or S), 3-aminopyrrolidin-1-yl, 2-(hydroxymethyl)pyrrolidin-1-yl (stereochemistry at the C-2 carbon atom of the pyrrolidin-1-yl is RS, R or S), 2-methoxymethylpyrrolidi-1-yl (stereochemistry at the C-2 carbon atom of the pyrrolidin-1-yl is RS, R or S) 2-(3-hydroxypyrrolidin-1-ylmethyl)pyrrolidin-1-yl (the stereochemistry at the C-2 and C-3 carbons at the pyrrolidine ring is RS, R or S, preferably the stereochemistry at C-2 and C-3 carbons is R), 3-(pyrrolidin-1-ylmethyl)piperidin-1-yl (the stereochemistry at the C-3 carbon of the piperidine ring is RS, R or S, preferably S), 2-(3-fluoropyrrolidin-1-ylmethyl)pyrrolidin-1-yl (the stereochemistry at the C-2 and C-3 carbons at the pyrrolidine ring is RS, R or S, preferably the stereochemistry at C-2 is R or S and C-3 carbon is R), 2-(4-fluoropiperidin-1-ylmethyl)pyrrolidin-1-yl (the stereochemistry at the C-4 and C-2 carbons at the piperidine and pyrrolidine ring respectively is RS, R or S, preferably the stereochemistry at C-2 carbon is R), or 2-(4-hydroxypiperidin-1-ylmethyl)pyrrolidin-1-yl (stereochemistry at the C-2 carbon atom of the pyrrolidin-1-yl is RS, R or S). Particularly, $R^{13}$ and $R^{14}$ together with the nitrogen atom to which they are. attached form 2-(pyrrolidin-1-ylmethyl)pyrrolidin-1-yl (wherein the stereochemistry at the C-2 carbon atom of the pyrrolidin-1-yl is RS, R or S), preferably (R); or (v) —(alkylene)—$CONR^{13}R^{14}$ (where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s). Even more preferably, $R^{13}$ is hydrogen and $R^{14}$ is 2-diethylaminoethyl, 2-ethylaminoethyl, 3-diethylaminopropyl, 3-ethylaminopropyl, 2-[1,2,3]-triazin-1-ylethyl, 3-morpholin-4-yl-2-hydroxypropyl, 3-[1,2,3]-triazin-1-yl-2-hydroxypropyl, 2-(3-oxopiperazin-1-yl)ethyl, 3-pyrrolidin-1-ylpropyl, 2-hydroxyethyl, particularly preferably 2-diethylaminoethyl; or (vi) —(alkylene)—$CONR^{13}R^{14}$ where $R^{13}$ and $R^{14}$ together with the nitrogen atom to which they are attached form saturated or unsaturated heterocycloamino; preferably saturated 5 or 6 membered heterocycloamino containing one or two nitrogen atoms in the ring, the rest of the ring atoms being carbon. Additionally, one of the ring carbons may be optionally replaced by carbonyl or oxygen and the ring may be optionally substituted with one or two substituents independently selected group the group consisting of alkyl, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, $R^{13}$ and $R^{14}$ together with the nitrogen atom to which they are attached form 4-methylpiperazin-1-yl, 3,5-dimethylpiperazin-1-yl, piperidin-1-yl, morpholin-4-yl, 4-(pyrrolidin-1-yl)-piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypyrrolidin-1-yl, 3-diethylaminopyrrolidin-1-yl (wherein the stereochemistry at the C-3 carbon atom of the pyrrolidin-1-yl is RS, R or S), 4-(pyrrolidin-1-yl)-piperidin-1-yl (stereochemistry at the C-4 carbon atom of the pyrrolidin-1-yl is RS, R or S), 3-hydroxypyrrolidin-1-yl (stereochemistry at the C-3 carbon atom of the pyrrolidin-1-yl is RS, R or S), 2-(hydroxymethyl)pyrrolidin-1-yl (stereochemistry at the C-2 carbon atom of the pyrrolidin-1-yl is RS, R or S), 2-methoxymethylpyrrolidin-1-yl (stereochemistry at the C-2 carbon atom of the pyrrolidin-1-yl is RS, R or S), 2-(3-hydroxypyrrolidin-1-ylmethyl)pyrrolidin-1-yl (the stereochemistry at the C-2 and C-3 carbons at the pyrrolidine ring is RS, R or S, preferably the stereochemistry at C-2 and C-3 carbons is R), 3-(pyrrolidin-1-ylmethyl)piperidin-1-yl (the stereochemistry at the C-3 carbon of the piperidine ring is RS, R or S, preferably S), 2-(3-fluoropyrrolidin-1-ylmethyl)pyrrolidin-1-yl (the stereochemistry at the C-2 and C-3 carbons at the pyrrolidine ring is RS, R or S, preferably the stereochemistry at C-2 is R or S and C-3 carbon is R), 2-(4-fluoropiperidin-1-ylmethyl)pyrrolidin-1-yl (the stereochemistry at the C-4 and C-2 carbons at the piperidine and pyrrolidine ring respectively is RS, R or S, preferably the stereochemistry at C-2 carbon is R), or 2-(4-hydroxypiperidin-1-ylmethyl)pyrrolidin-1-yl (stereochemistry at the C-2 carbon atom of the pyrrolidin-1-yl is RS, R or S). Particularly $R^{13}$ and $R^{14}$ together with the carbon atoms to which they are attached form 2-(pyrrolidin-1-ylmethyl)-pyrrolidin-1-yl (wherein the stereochemistry at the C-2 carbon atom of the pyrrolidin-1-yl is RS, R or S), preferably (S); or (vii) —$CONR^{13}R^{14}$ where $R^{13}$ and $R^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. The saturated heterocycloamino ring is optionally substituted with cycloalkylaminoalkyl, cycloalkylalkyl, cycloalkylalkylamino, cycloalkylamino, or cycloalkylalkylaminoalkyl, preferably cyclopropylmethyl, cyclopropylmethylamino, cyclopropylamino, cyclopropylaminomethyl, or cyclopropylmethyl-aminomethyl. More preferably, $R^{13}$ and $R^{14}$ together with the carbon atoms to which they are attached form 2R-cyclopropylaminomethylpyrrolidin-1-yl, 2R-cyclopropylmethylaminomethylpyrrolidin-1-yl, 4-cyclopropylmethyl-piperazin-1-yl, or 4-cyclopropylaminopiperidin-1-yl; or (viii) —$CONR^{13}R^{14}$ where $R^{13}$ and $R^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. The saturated heterocycloamino ring is substituted with optionally substituted heterocycle. More preferably, $R^{13}$ and $R^{14}$ together with the nitrogen atoms to which they are attached form 4-(pyrrolidin-1-yl)piperidin-1-yl, 4-(morpholin-4-yl)piperidin-1-yl, 3-(morpholin-4-yl)pyrrolidin-1-yl, and 3-(morpholin-4-yl)azetidin-1-yl; or (ix) heterocyclylalkyl containing 5 or 6 ring atoms wherein at least one ring atom is nitrogen atom and optionally containing an oxygen atom in the ring. The heterocyclyl ring is optionally substituted with cycloalkylalkyl or saturated heterocycloamino of 5 or 6 ring atoms. Preferably $R^7$ is morpholin-4-ylmethyl, 4-(pyrrolidin-1-yl)piperidin-1-yl, or 4-cyclopropylmethylpiperazin-1-yl.

10. Another preferred group of compounds is represented by Formula (Ib):

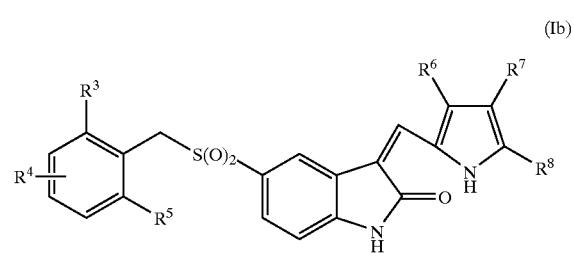

(Ib)

wherein:

$R^3$, $R^4$, and $R^5$ are each independently hydrogen, halo, alkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —$CONR^{10}R^{11}$, or —$NR^{10}R^{11}$, (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or $R^{10}$ and $R^{11}$ together with the nitrogen atom to which they are attached combine to form saturated or unsaturated heterocycloamino);

$R^6$ is hydroxyalkyl, aminoalkyl, alkylaminoalkyl, dialkylaminoalkyl, heterocyclylalkyl, aryl, heteroaryl, carboxy, alkoxycarbonyl, heterocyclylcarbonyl, aminoalkylcarbonyl, alkylaminoalkylcarbonyl, dialkylaminoalkylcarbonyl, —$CONR^{10}R^{11}$ (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or $R^{10}$ and $R^{11}$ together with the nitrogen atom to which they are attached combine to form saturated or unsaturated heterocycloamino);

$R^7$ and $R_8$ are independently hydrogen or alkyl; or a pharmaceutically acceptable salt thereof.

In formula (Ib), a more preferred group of compounds are wherein:

$R^3$ is hydrogen, halo, alkyl, haloalkyl, hydroxy, alkoxy, alkoxycarbonyl, haloalkoxy, cyano, carboxy, or nitro, preferably hydrogen, chloro, fluoro, bromo, iodo, methyl, trifluoromethyl, hydroxy, methoxy, methoxycarbonyl trifluoromethoxy, cyano, carboxy, or nitro. More preferably $R^3$ is hydrogen, chloro, fluoro or methyl.

$R^4$ is hydrogen, halo, alkyl, haloalkyl, hydroxy, alkoxy, alkoxycarbonyl, haloalkoxy, cyano, carboxy, or nitro, preferably hydrogen, chloro, fluoro, methyl, trifluoromethyl, cyano, hydroxy, or methoxy, more preferably hydrogen.

$R^5$ is hydrogen, halo, alkyl, haloalkyl, hydroxy, alkoxy, haloalkoxy, cyano, or nitro, preferably hydrogen, methyl, chloro, fluoro, iodo, trifluoromethyl, hydroxy, methoxy, cyano or nitro. Even more preferably hydrogen, chloro or fluoro.

11. Preferably, the phenyl ring carrying the $R^3$–$R^5$ groups is phenyl, 2-cyanophenyl, 3-cyanophenyl, 3-trifluoromethylphenyl, 3-methoxyphenyl, 3-trifluoromethoxy phenyl, 4-t-butylphenyl, 2-chlorophenyl, 3-chlorophenyl, 3-bromophenyl, 2-fluorophenyl, 3-fluoroplorophenyl, 4-fluorophenyl, 4-bromophenyl, 3-trifluoromethylphenyl, 2-iodophenyl, 3-iodophenyl, 2-chloro-6-fluorophenyl, 2,3-difluorophenyl, 2,3-dichlorophenyl, 2,4-trifluorophenyl, 2,4-difluorophenyl, 2,5-dichlorophenyl, 2,5-difluorophenyl, 3,5-difluorophenyl, 3,5-dichlorophenyl, 3,5-dimethoxyphenyl, 2,6 dimethoxyphenyl, 2,6-difluorophenyl, 3,4-difluorophenyl, 2,3,6-trifluorophenyl, 2-nitrophenyl, 2,6-dichlorophenyl, 2-fluoro-6-nitrophenyl, 2,6-diiodophenyl, or 2,6-dimethylphenyl, 2-fluoro-6-chlorophenyl, 2,6-dibromophenyl, 2-(2-morpholin-4-yl-ethoxy)-phenyl, preferably 2,6-dichlorophenyl, 2,6-difluorophenyl, 2-chlorophenyl or 2-fluorophenyl.

$R^7$ is hydrogen or alkyl, preferably hydrogen or methyl, more preferably hydrogen;

$R^8$ is hydrogen or alkyl, preferably hydrogen or methyl, more preferably methyl; and $R^6$ is:
(i) —CONR$^{10}$R$^{11}$ where R$^{10}$ is hydrogen or alkyl, and R$^{11}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s); preferably R$^{10}$ is hydrogen or methyl and R$^{11}$ is hydroxyalkyl, alkylaminoalkyl, dialkylaminoalkyl, heterocyclylalkyl, or heteroaralkyl wherein the alkyl chain in said groups is optionally substituted with a hydroxy group. Even more preferably, R$^{10}$ is hydrogen and R$^{11}$ is 2-diethylaminoethyl, 2-ethylaminoethyl, 3-diethylaminopropyl, 3-ethylaminopropyl, 2-t[1,2,3]-riazin-1-ylethyl, 3-morpholin-4-yl-2-hydroxypropyl, 3-[1,2,3]-triazin-1-yl-2-hydroxypropyl, 2-(3-oxopiperazin-1-yl)ethyl, 3-pyrrolidin-1-ylpropyl, 2-pyrrolidin-1-ylethyl, 2-hydroxyethyl, particularly preferably 2-diethylaminoethyl; or
(ii) —CONR$^{10}$R$^{11}$ where R$^{10}$ and R$^{11}$ together with the nitrogen atom to which they are attached form saturated or unsaturated heterocycloamino; preferably saturated 5 or 6 membered heterocycloamino containing one or two nitrogen atoms in the ring and wherein one ring carbon is optionally replaced by carbonyl or oxygen and wherein the ring is optionally substituted with one or two substituents independently selected group the group consisting of alkyl, hydroxy, dialkylamino, hydroxyalkyl, alkoxyalkyl, and optionally substituted heterocyclylalkyl wherein said heterocyclyl ring is 5 or 6 membered and contains one or two nitrogen atoms, the rest of the ring atoms being carbon. More preferably, R$^{10}$ and R$^{11}$ together with the nitrogen atom to which they are attached form 4-methylpiperazin-1-yl, 3,5-dimethylpiperazin-1-yl, piperidin-1-yl, morpholin-4-yl, 4-(pyrrolidin-1-yl)-piperidin-1-yl, 2-(pyrrolidin-1-ylmethyl)pyrrolidin-1-yl (wherein the stereochemistry at the C-2 carbon atom of the pyrrolidin-1-yl is RS, R or S), 4-hydroxypiperidin-1-yl, 3-diethylaminopyrrolidin-1-yl (wherein the stereochemistry at the C-4 carbon atom of the pyrrolidin-1-yl is RS, R or S), 4-(pyrrolidin-1-yl)-piperidin-1-yl (stereochemistry at the C-4 carbon atom of the pyrrolidin-1-yl is RS, R or S), 3-hydroxypyrrolidin-1-yl (stereochemistry at the C-3 carbon atom of the pyrrolidin-1-yl is RS, R or S), 2-(hydroxymethyl)pyrrolidin-1-yl (stereochemistry at the C-2 carbon atom of the pyrrolidin-1-yl is RS, R or S), 2-methoxymethylpyrrolidin-1-yl (stereochemistry at the C-2 carbon atom of the pyrrolidin-1-yl is RS, R or S), 2-(3-hydroxypyrrolidin-1-ylmethyl)pyrrolidin-1-yl (the stereochemistry at the C-2 and C-3 carbons at the pyrrolidine ring is RS, R or S, preferably the stereochemistry at C-2 and C-3 carbons is R), 3-(pyrrolidin-1-ylmethyl)piperidin-1-yl (the stereochemistry at the C-3 carbon of the piperidine ring is RS, R or S, preferably S), 2-(3-fluoropyrrolidin-1-ylmethyl)pyrrolidin-1-yl (the stereochemistry at the C-2 and C-3 carbons at the pyrrolidine ring is RS, R or S, preferably the stereochemistry at C-2 is R or S and C-3 carbon is R), 2-(4-fluoropiperidin-1-ylmethyl)pyrrolidin-1-yl (the stereochemistry at the C-4 and C-2 carbons at the piperidine and pyrrolidine ring respectively is RS, R or S, preferably the stereochemistry at C-2 carbon is R), or 2-(4-hydroxypiperidin-1-ylmethyl)pyrrolidin-1-yl (stereochemistry at the C-2 carbon atom of the pyrrolidin-1-yl is RS, R or S). Particularly R$^{13}$ and R$^{14}$ together with the nitrogen atom to which they are attached form 2-(pyrrolidin-1-ylmethyl) pyrrolidin-1-yl (wherein the stereochemistry at the C-2 carbon atom of the pyrrolidin-1-yl is RS, R or S), preferably (S)); or
(iii) —CONR$^{13}$R$^{14}$ where R$^{13}$ and R$^{14}$ together with the nitrogen atom to which they are attached form saturated or unsaturated heterocycloamino; preferably saturated 5 or 6 membered heterocycloamino containing one or two nitrogen atoms, the remaining ring atoms being carbon. The saturated heterocycloamino ring is optionally substituted with cycloalkylaminoalkyl, cycloalkylalkyl, cycloalkylamino, or cycloalkylalkylaminoalkyl, preferably cyclopropylmethyl, cyclopropylaminomethyl, or cyclopropylmethylaminomethyl. More preferably, R$^{13}$ and R$^{14}$ together with the carbon atoms to which they are attached form 2R-cyclopropylaminomethylpyrrolidin-1-yl, 2R-cyclopropylmethylaminomethylpyrrolidin-1-yl, 4-cyclopropylmethyl-piperazin-1-yl, or 4-cyclopropylaminopiperidin-1-yl; or
(iv) heterocyclylalkyl containing 5 or 6 ring atoms wherein at least one ring atom is nitrogen atom and optionally containing an oxygen atom in the ring. The heterocyclyl ring is optionally substituted with cycloalkylalkyl. Preferably $R^7$ is morpholin-4-ylmethyl or 4-cyclopropylmethylpiperazin-1-yl.

TABLE 1

Representative compounds of the Invention are as follows:

| Cpd # | $R^1$ | $R^2$ | $R^3, R^4, R^5(C_6H_2)$— | $R^6$ | $R^7$ | $R^8$ | $R^9$ |
|---|---|---|---|---|---|---|---|
| 1 | H | H | Phenyl | $CH_3$ | —$CONH(CH_2)_2N(C_2H_5)_2$ | $CH_3$ | H |
| 2 | H | H | 2-CN-phenyl | $CH_3$ | —$CONH(CH_2)_2N(C_2H_5)_2$ | $CH_3$ | H |
| 3 | H | H | 3-$CF_3$-phenyl | $CH_3$ | —$CONH(CH_2)_2N(C_2H_5)_2$ | $CH_3$ | H |
| 4 | H | H | 3-$OCH_3$-phenyl | $CH_3$ | —$CONH(CH_2)_2N(C_2H_5)_2$ | $CH_3$ | H |
| 5 | H | H | 2-CN-phenyl | $CH_3$ | —CO-(4-methylpiperazin-1-yl) | $CH_3$ | H |
| 6 | H | H | 3-$OCH_3$-phenyl | $CH_3$ | —CO-(4-methylpiperazin-1-yl) | $CH_3$ | H |
| 7 | H | H | 2-$NO_2$-phenyl | $CH_3$ | —CO-(4-methylpiperazin-1-yl) | $CH_3$ | H |
| 8 | H | H | 2-$NO_2$-phenyl | $CH_3$ | —$CONH(CH_2)_2N(C_2H_5)_2$ | $CH_3$ | H |
| 9 | H | H | Phenyl | $CH_3$ | —$CONH(CH_2)_2(1,2,3$-triazol-1-yl) | $CH_3$ | H |
| 10 | H | H | 2-$NO_2$-phenyl | $CH_3$ | —$CONH(CH_2)_2(1,2,3$-triazol-1-yl) | $CH_3$ | H |
| 11 | H | H | Phenyl | $CH_3$ | H | $CH_3$ | H |
| 12 | H | H | 4-$CO_2H$-phenyl | $CH_3$ | —CO-(4-methylpiperazin-1-yl) | $CH_3$ | H |
| 13 | H | H | 4-$CH_2CO_2H$-phenyl | $CH_3$ | —CO-(4-methylpiperazin-1-yl) | $CH_3$ | H |
| 14 | H | H | 2-$NO_2$-4-$CO_2H$-phenyl | $CH_3$ | —CO-(4-methylpiperazin-1-yl) | $CH_3$ | H |
| 15 | H | H | 4-$CO_2H$-phenyl | $CH_3$ | —$CONH(CH_2)_2N(C_2H_5)_2$ | $CH_3$ | H |
| 16 | H | H | 4-$CH_2CO_2H$-phenyl | $CH_3$ | —$CONH(CH_2)_2N(C_2H_5)_2$ | $CH_3$ | H |
| 17 | H | H | 2-$NO_2$-4-$CO_2H$-phenyl | $CH_3$ | —$CONH(CH_2)_2N(C_2H_5)_2$ | $CH_3$ | H |
| 18 | H | H | Phenyl | $CH_3$ | —CO-(4-methylpiperazin-1-yl) | $CH_3$ | $CH_3$ |
| 19 | H | H | 2-OH-3,5-diBr-phenyl | $CH_3$ | —$CONH(CH_2)_2N(C_2H_5)_2$ | $CH_3$ | H |
| 20 | H | H | 2-F-phenyl | $CH_3$ | —$CONH(CH_2)_2(1,2,3$-triazol-1-yl) | $CH_3$ | H |
| 21 | H | H | Phenyl | $CH_3$ | —$CONH(CH_2)_2N(C_2H_5)_2$ | $CH_3$ | H |
| 22 | H | H | 2-F-phenyl | $CH_3$ | —$CONH(CH_2)_2N(C_2H_5)_2$ | $CH_3$ | H |
| 23 | H | H | 2-Cl-phenyl | $CH_3$ | —$CONH(CH_2)_2N(C_2H_5)_2$ | $CH_3$ | H |
| 24 | H | H | 4-$CO_2CH_3$-phenyl | $CH_3$ | —$CONH(CH_2)_2N(C_2H_5)_2$ | $CH_3$ | H |
| 25 | H | H | 4-$OCF_3$-phenyl | $CH_3$ | —$CONH(CH_2)_2N(C_2H_5)_2$ | $CH_3$ | H |
| 26 | H | H | 2,4-di$CF_3$-phenyl | $CH_3$ | —CO-(4-methylpiperazin-1-yl) | $CH_3$ | H |
| 27 | H | H | 2,4-di$CF_3$-phenyl | $CH_3$ | —$CONH(CH_2)_2N(C_2H_5)_2$ | $CH_3$ | H |
| 28 | H | H | 4-Br | $CH_3$ | —CO-(4-methylpiperazin-1-yl) | $CH_3$ | H |
| 29 | H | H | 4-Br | $CH_3$ | —$CONH(CH_2)_2N(C_2H_5)_2$ | $CH_3$ | H |
| 30 | H | H | 2-I | $CH_3$ | —$CONH(CH_2)_2N(C_2H_5)_2$ | $CH_3$ | H |
| 31 | H | H | 2-I | $CH_3$ | —CO-(4-methylpiperazin-1-yl) | $CH_3$ | H |
| 32 | H | H | 4-CN-phenyl | $CH_3$ | —$CONH(CH_2)_2N(C_2H_5)_2$ | $CH_3$ | H |
| 33 | H | H | 4-CN-phenyl | $CH_3$ | —CO-(4-methylpiperazin-1-yl) | $CH_3$ | H |
| 34 | H | H | 3-$CO_2CH_3$-phenyl | $CH_3$ | —$CONH(CH_2)_2N(C_2H_5)_2$ | $CH_3$ | H |
| 35 | H | H | 3-$CO_2CH_3$-phenyl | $CH_3$ | —CO-(4-methylpiperazin-1-yl) | $CH_3$ | H |
| 36 | H | H | 3-$OCF_3$-phenyl | $CH_3$ | —CO-(4-methylpiperazin-1-yl) | $CH_3$ | H |
| 37 | H | H | 3-$OCF_3$-phenyl | $CH_3$ | —$CONH(CH_2)_2N(C_2H_5)_2$ | $CH_3$ | H |
| 38 | H | H | 3-CN-phenyl | $CH_3$ | —CO-(4-methylpiperazin-1-yl) | $CH_3$ | H |
| 39 | H | H | 3-CN-phenyl | $CH_3$ | —$CONH(CH_2)_2N(C_2H_5)_2$ | $CH_3$ | H |
| 40 | H | H | 3-I-phenyl | $CH_3$ | —CO-(4-methylpiperazin-1-yl) | $CH_3$ | H |
| 41 | H | H | 3-I-phenyl | $CH_3$ | —$CONH(CH_2)_2N(C_2H_5)_2$ | $CH_3$ | H |
| 42 | H | H | 3-Cl | $CH_3$ | —CO-(4-methylpiperazin-1-yl) | $CH_3$ | H |
| 43 | H | H | 2,4-diF-phenyl | $CH_3$ | —$CONH(CH_2)_2N(C_2H_5)_2$ | $CH_3$ | H |
| 44 | H | H | 4-$C(CH_3)_3$-phenyl | $CH_3$ | —CO-(4-methylpiperazin-1-yl) | $CH_3$ | H |
| 45 | H | H | 4-$C(CH_3)_3$-phenyl | $CH_3$ | —$CONH(CH_2)_2N(C_2H_5)_2$ | $CH_3$ | H |
| 46 | H | H | 2,6-diF-phenyl | $CH_3$ | —CO-(4-methylpiperazin-1-yl) | $CH_3$ | H |
| 47 | H | H | 2,6-diF-phenyl | $CH_3$ | —$CONH(CH_2)_2N(C_2H_5)_2$ | $CH_3$ | H |
| 48 | H | H | 3-Br-phenyl | $CH_3$ | —CO-(4-methylpiperazin-1-yl) | $CH_3$ | H |
| 49 | H | H | 3-Cl-phenyl | $CH_3$ | —$CONH(CH_2)_2N(C_2H_5)_2$ | $CH_3$ | H |
| 50 | H | H | 2,4-diF-phenyl | $CH_3$ | —CO-(4-methylpiperazin-1-yl) | $CH_3$ | H |
| 51 | H | H | 4-$NO_2$-phenyl | $CH_3$ | —CO-(4-methylpiperazin-1-yl) | $CH_3$ | H |
| 52 | H | H | 4-$NO_2$-phenyl | $CH_3$ | —$CONH(CH_2)_2N(C_2H_5)_2$ | $CH_3$ | H |
| 53 | H | H | 3-$NO_2$-phenyl | $CH_3$ | —CO-(4-methylpiperazin-1-yl) | $CH_3$ | H |
| 54 | H | H | 3-$NO_2$-phenyl | $CH_3$ | —$CONH(CH_2)_2N(C_2H_5)_2$ | $CH_3$ | H |
| 55 | H | H | 3-Br-phenyl | $CH_3$ | —$CONH(CH_2)_2N(C_2H_5)_2$ | $CH_3$ | H |
| 56 | H | H | 3,5-diF-phenyl | $CH_3$ | —CO-(4-methylpiperazin-1-yl) | $CH_3$ | H |
| 57 | H | H | 3,5-diF-phenyl | $CH_3$ | —$CONH(CH_2)_2N(C_2H_5)_2$ | $CH_3$ | H |
| 58 | H | H | 3,4-diF-phenyl | $CH_3$ | —CO-(4-methylpiperazin-1-yl) | $CH_3$ | H |
| 59 | H | H | 3,4-diF-phenyl | $CH_3$ | —$CONH(CH_2)_2N(C_2H_5)_2$ | $CH_3$ | H |
| 60 | H | H | 2,5-di$CF_3$-phenyl | $CH_3$ | —CO-(4-methylpiperazin-1-yl) | $CH_3$ | H |
| 61 | H | H | 2,5-di$CF_3$-phenyl | $CH_3$ | —$CONH(CH_2)_2N(C_2H_5)_2$ | $CH_3$ | H |
| 62 | H | H | 3,5-di$CF_3$-phenyl | $CH_3$ | —CO-(4-methylpiperazin-1-yl) | $CH_3$ | H |
| 63 | H | H | 3,5-di$CF_3$-phenyl | $CH_3$ | —$CONH(CH_2)_2N(C_2H_5)_2$ | $CH_3$ | H |
| 64 | H | H | 2-OH-5-$NO_2$-phenyl | $CH_3$ | —CO-(4-methylpiperazin-1-yl) | $CH_3$ | H |

TABLE 1-continued

Representative compounds of the Invention are as follows:

| Cpd # | $R^1$ | $R^2$ | $R^3, R^4, R^5(C_6H_2)-$ | $R^6$ | $R^7$ | $R^8$ | $R^9$ |
|---|---|---|---|---|---|---|---|
| 65 | H | H | 2-OH-5-$NO_2$-phenyl | $CH_3$ | —$CONH(CH_2)_2N(C_2H_5)_2$ | $CH_3$ | H |
| 66 | H | H | 2-$OCH_3$-5-$NO_2$-phenyl | $CH_3$ | —CO-(4-methylpiperazin-1-yl) | $CH_3$ | H |
| 67 | H | H | 2-$OCH_3$-5-$NO_2$-phenyl | $CH_3$ | —$CONH(CH_2)_2N(C_2H_5)_2$ | $CH_3$ | H |
| 68 | H | H | 2-F-phenyl | $CH_3$ | —CO-(4-methylpiperazin-1-yl) | $CH_3$ | H |
| 69 | H | H | 2-F-phenyl | $CH_3$ | —$CONH(CH_2)_2N(C_2H_5)_2$ | $CH_3$ | H |
| 70 | H | H | 3-F-phenyl | $CH_3$ | —CO-(4-methylpiperazin-1-yl) | $CH_3$ | H |
| 71 | H | H | 3-F-phenyl | $CH_3$ | —$CONH(CH_2)_2N(C_2H_5)_2$ | $CH_3$ | H |
| 72 | H | H | 4-F-phenyl | $CH_3$ | —CO-(4-methylpiperazin-1-yl) | $CH_3$ | H |
| 73 | H | H | 4-F-phenyl | $CH_3$ | —$CONH(CH_2)_2N(C_2H_5)_2$ | $CH_3$ | H |
| 74 | H | H | 4-$OCF_3$-phenyl | $CH_3$ | —CO-(4-methylpiperazin-1-yl) | $CH_3$ | H |
| 75 | H | H | 2-$CF_3$-phenyl | $CH_3$ | —CO-(4-methylpiperazin-1-yl) | $CH_3$ | H |
| 76 | H | H | 2-$CF_3$-phenyl | $CH_3$ | —$CONH(CH_2)_2N(C_2H_5)_2$ | $CH_3$ | H |
| 77 | H | H | 3-$CF_3$-phenyl | $CH_3$ | —CO-(4-methylpiperazin-1-yl) | $CH_3$ | H |
| 78 | H | H | 4-$CF_3$-phenyl | $CH_3$ | —$CONH(CH_2)_2N(C_2H_5)_2$ | $CH_3$ | H |
| 79 | H | H | 4-$CF_3$-phenyl | $CH_3$ | —CO-(4-methylpiperazin-1-yl) | $CH_3$ | H |
| 80 | H | H | 2,3,4,5,6-pentaF-phenyl | $CH_3$ | —CO-(4-methylpiperazin-1-yl) | $CH_3$ | H |
| 81 | H | H | 2,3,4,5,6-pentaF-phenyl | $CH_3$ | —$CONH(CH_2)_2N(C_2H_5)_2$ | $CH_3$ | H |
| 82 | H | H | 2,5-diF-phenyl | $CH_3$ | —CO-(4-methylpiperazin-1-yl) | $CH_3$ | H |
| 83 | H | H | 2,5-diF-phenyl | $CH_3$ | —$CONH(CH_2)_2N(C_2H_5)_2$ | $CH_3$ | H |
| 84 | H | H | 2,3,6-triF-phenyl | $CH_3$ | —CO-(4-methylpiperazin-1-yl) | $CH_3$ | H |
| 85 | H | H | 2,3,6-triF-phenyl | $CH_3$ | —$CONH(CH_2)_2N(C_2H_5)_2$ | $CH_3$ | H |
| 86 | H | H | 2,3-diF-phenyl | $CH_3$ | —CO-(4-methylpiperazin-1-yl) | $CH_3$ | H |
| 87 | H | H | 2,3-diF-phenyl | $CH_3$ | —$CONH(CH_2)_2N(C_2H_5)_2$ | $CH_3$ | H |
| 88 | H | H | 2,6-diCl-phenyl | $CH_3$ | —$CONH(CH_2)_2N(C_2H_5)_2$ | $CH_3$ | H |
| 89 | H | H | 4-phenyl-phenyl | $CH_3$ | —CO-(4-methylpiperazin-1-yl) | $CH_3$ | H |
| 90 | H | H | 4-phenyl-phenyl | $CH_3$ | —$CONH(CH_2)_2N(C_2H_5)_2$ | $CH_3$ | H |
| 91 | H | H | 2-F-6-$NO_2$-phenyl | $CH_3$ | —CO-(4-methylpiperazin-1-yl) | $CH_3$ | H |
| 92 | H | H | 2-F-6-$NO_2$-phenyl | $CH_3$ | —$CONH(CH_2)_2N(C_2H_5)_2$ | $CH_3$ | H |
| 93 | H | H | 2O-(2F-phenyl)-phenyl | $CH_3$ | —CO-(4-methylpiperazin-1-yl) | $CH_3$ | H |
| 94 | H | H | 2O-(2F-phenyl)-phenyl | $CH_3$ | —$CONH(CH_2)_2N(C_2H_5)_2$ | $CH_3$ | H |
| 96 | H | H | 2-Cl-phenyl | $CH_3$ | —CO-(4-methylpiperazin-1-yl) | $CH_3$ | H |
| 97 | H | H | 4-Cl-phenyl | $CH_3$ | —$CONH(CH_2)_2N(C_2H_5)_2$ | $CH_3$ | H |
| 98 | H | H | 4-Cl-phenyl | $CH_3$ | —CO-(4-methylpiperazin-1-yl) | $CH_3$ | H |
| 99 | H | H | Phenyl | $CH_3$ | $CO_2H$ | $CH_3$ | H |
| 100 | H | H | 4-$CO_2CH_3$-phenyl | $CH_3$ | —CO-(4-methylpiperazin-1-yl) | $CH_3$ | H |
| 101 | H | H | Phenyl | $CH_3$ | $CONHCH_2CH(OH)CH_2N(C_2H_5)_2$ | $CH_3$ | H |
| 102 | H | H | Phenyl | $CH_3$ | $CONH(CH_2)_2$(2H-tetrazol-5-yl) | $CH_3$ | H |
| 103 | H | H | Phenyl | $CONH(CH_2)_2$(pyrrolidin-1-yl) | H | $CH_3$ | H |
| 104 | H | H | Phenyl | $CONHCH_2)_2$(1,2,3-triazol-1-yl) | H | $CH_3$ | H |
| 105 | H | H | Phenyl | CO-(3R-dimethylamino-pyrrolidin-1-yl) | H | $CH_3$ | H |
| 106 | H | H | Phenyl | $CH_3$ | —$CONH(CH_2)_2N(C_2H_5)_2$ | H | H |
| 107 | H | H | Phenyl | $CH_3$ | $CONH(CH_2)_2$(pyrrolidin-1-yl) | $CH_3$ | H |
| 108 | H | H | Phenyl | $CH_3$ | $CONH(CH_2)_2N[CH(CH_3)_2]_2$ | $CH_3$ | H |
| 109 | H | H | 2-F-phenyl | $CH_3$ | $CON(CH_2)_2$(pyrrolidin-1-yl) | $CH_3$ | H |
| 110 | H | H | 2-F-phenyl | $CH_3$ | —$CONH(CH_2)_2N(C_2H_5)_2$ | $CH_3$ | H |
| 111 | H | H | 2-F-phenyl | $CONH(CH_2)_2$(pyrrolidin-1-yl) | H | $CH_3$ | H |
| 112 | H | H | 2-F-phenyl | $CH_3$ | $CONH(CH_2)_2N[CH(CH_3)_2]_2$ | $CH_3$ | H |
| 113 | H | H | 2-F-phenyl | $CONH(CH_2)_2$(1,2,3-triazol-1-yl) | H | $CH_3$ | H |
| 114 | H | H | 2-F-phenyl | $CH_3$ | CO-(3R,5S-dimethyl-piperazin-1-yl) | $CH_3$ | H |
| 115 | H | H | Phenyl | $CH_3$ | CO(3R,5S-dimethylpiperazin-1-yl) | $CH_3$ | H |
| 116 | H | H | 3-Cl-phenyl | $CH_3$ | —$CONH(CH_2)_2N(C_2H_5)_2$ | H | H |
| 117 | H | H | 3-Cl-phenyl | $CONH(CH_2)_2$(pyrrolidin-1-yl) | H | $CH_3$ | H |
| 118 | H | H | 3-Cl-phenyl | $CONH(CH_2)_2$(1,2,3-triazol-1-yl) | H | $CH_3$ | H |
| 119 | H | H | 3-Cl-phenyl | $CH_3$ | $CONH(CH_2)_2$(pyrrolidin-1-yl) | $CH_3$ | H |
| 120 | H | H | 3-Cl-phenyl | $CH_3$ | $CONH(CH_2)_2N[CH(CH_3)_2]_2$ | $CH_3$ | H |
| 121 | H | H | 3-Cl-phenyl | $CH_3$ | CO-(3R,5S-dimethylpiperazin-1-yl) | $CH_3$ | H |
| 122 | H | H | 3-Cl-phenyl | CO-(3R- | H | $CH_3$ | H |

TABLE 1-continued

Representative compounds of the Invention are as follows:

| Cpd # | R$^1$ | R$^2$ | R$^3$, R$^4$, R$^5$(C$_6$H$_2$)— | R$^6$ | R$^7$ | R$^8$ | R$^9$ |
|---|---|---|---|---|---|---|---|
| | | | | dimethylamino-pyrrolidin-1-yl) | | | |
| 125 | H | H | Phenyl | —(CH$_2$)$_2$CO$_2$H | H | CH$_2$CH$_3$ | H |
| 126 | H | H | Phenyl | CH$_3$ | —(CH$_2$)$_2$CO$_2$H | H | H |
| 127 | H | H | Phenyl | CH$_3$ | H | —CO-(4-methyl-piperazin-1-yl) | H |
| 128 | H | H | Phenyl | 4-F-phenyl | —CONH(CH$_2$)$_2$N(C$_2$H$_5$)$_2$ | CH$_3$ | H |
| 130 | H | H | Phenyl | 4-CO$_2$H-phenyl | H | CH$_3$ | H |
| 131 | H | H | Phenyl | —CH$_2$CO$_2$H | CH$_3$ | CO$_2$C$_2$H$_5$ | H |
| 132 | H | H | 2,6-di-Cl-phenyl | CH$_3$ | H | CH$_3$ | H |
| 134 | H | H | 2,6-di-Cl-phenyl | CH$_3$ | CO$_2$H | CH$_3$ | H |
| 135 | H | H | 2,6-di-Cl-phenyl | —CO(morpholin-4-yl) | H | CH$_3$ | H |
| 136 | H | H | 2,6-di-Cl-phenyl | —CO(4-methylpiperazin-1-yl) | H | CH$_3$ | H |
| 137 | H | H | 2,6-di-Cl-phenyl | —CON(CH$_3$)(1-methyl-piperidin-4-yl) | H | CH$_3$ | H |
| 138 | H | H | 2,6-di-Cl-phenyl | —CO-[4-(pyrrolidin-1-yl)-piperidin-1-yl] | H | CH$_3$ | H |
| 139 | H | H | 2,6-di-Cl-phenyl | CH$_3$ | —CO-[2S-(pyrrolidin-1-ylmethyl)-pyrrolidin-1-yl] | CH$_3$ | H |
| 140 | H | H | 2,6-di-Cl-phenyl | CH$_3$ | —CONHCH$_2$CH(OH)CH$_2$(morpholin-4-yl) | CH$_3$ | H |
| 141 | H | H | 2,6-di-Cl-phenyl | CH$_3$ | —CONHCH$_2$CH(OH)CH$_2$(1,2,3-triazol-1-yl) | CH$_3$ | H |
| 142 | H | H | 2,6-di-Cl-phenyl | CH$_3$ | —CONH(CH$_2$)$_2$-(3-oxo-piperazin-1-yl) | CH$_3$ | H |
| 143 | H | H | 2,6-di-Cl-phenyl | CH$_3$ | —CO-(4-hydroxypiperidin-1-yl) | CH$_3$ | H |
| 144 | H | H | 2,6-di-Cl-phenyl | COOH | H | CH$_3$ | H |
| 145 | H | H | 2,6-di-Cl-phenyl | CH$_3$ | CH$_2$COOH | CH$_3$ | H |
| 146 | H | H | 2,6-di-Cl-phenyl | —CONH(CH$_2$)$_2$-(3-oxo-piperazin-1-yl) | H | CH$_3$ | H |
| 147 | H | H | 2,6-di-Cl-phenyl | —CO-(4-hydroxypiperidin-1-yl) | H | CH$_3$ | H |
| 148 | H | H | 2,6-di-Cl-phenyl | —CO-(3-diethylamino-pyrrolidin-1-yl) | H | CH$_3$ | H |
| 149 | H | H | 2,6-di-Cl-phenyl | CH$_3$ | —CO-[4-(pyrrolidin-1-yl)-piperidin-1-yl] | CH$_3$ | H |
| 150 | H | H | 2,6-di-Cl-phenyl | CH$_3$ | —CO-(4-methylpiperazin-1-yl) | CH$_3$ | H |
| 151 | H | H | 2,6-di-Cl-phenyl | CH$_3$ | —CH$_2$(morpholin-4-yl) | CH$_3$ | H |
| 152 | H | H | 2,6-di-Cl-phenyl | CH$_3$ | —CO-[2R-(cyclopropylaminomethyl)-pyrrolin-1-yl] | CH$_3$ | H |
| 153 | H | H | 2,6-di-Cl-phenyl | CH$_3$ | —CO[2S-(3R-fluoro-pyrrolidin-1-ylmethyl)pyrrolidin-1-yl] | CH$_3$ | H |
| 154 | H | H | 2,6-di-Cl-phenyl | CH$_3$ | —CO-(4-cycloprpopylamino-piperidin-1-yl) | CH$_3$ | H |
| 155 | H | H | Phenyl | CH$_3$ | —(CH$_2$)$_2$COOH | CH$_3$ | H |
| 156 | H | H | Phenyl | CH$_3$ | —CH$_2$COOH | CH$_3$ | H |
| 157 | H | H | 2,6-di-Cl-phenyl | CH$_3$ | —CONH(CH$_2$)$_3$pyrrolidin-1-yl | CH$_3$ | H |
| 158 | H | H | 2,6-di-Cl-phenyl | CH$_3$ | —CONH(CH$_2$)$_3$pyrrolidin-1-yl | CH$_3$ | H |
| 159 | H | H | 2,6-di-Cl-phenyl | CH$_3$ | —CONH(CH$_2$)$_2$pyrrolidin-1-yl | CH$_3$ | H |
| 160 | H | H | 2,6-di-Cl-phenyl | CH$_3$ | —CONH(CH$_2$)$_2$OH | CH$_3$ | H |
| 161 | H | H | 2,6-di-Cl-phenyl | CONHCH$_2$CH(OH)CH$_2$ (1,2,3-triazol-1-yl) | H | CH$_3$ | H |
| 162 | H | H | 2,6-di-Cl-phenyl | CONHCH$_2$CH(OH)CH$_2$ (morpholin-4-yl) | H | CH$_3$ | H |
| 163 | H | H | 2,6-di-Cl-phenyl | CONH(CH$_2$)$_2$N(C$_2$H$_5$)$_2$ | H | CH$_3$ | H |
| 164 | H | H | 2,6-di-Cl-phenyl | CH$_3$ | —CON-methyl-(1-methyl-piperidin-4-yl) | CH$_3$ | H |
| 165 | H | H | 2,6-di-Cl-phenyl | CH$_3$ | —CO-(3-diethylamino-pyrrolidin-1-yl) | CH$_3$ | H |
| 166 | H | H | 2,6-di-Cl-phenyl | —CO(3R,5S-dimethyl-piperazin-1-yl) | H | CH$_3$ | H |
| 167 | H | H | 2,6-dimethyl-phenyl | CH$_3$ | COOH | CH$_3$ | H |
| 168 | H | H | 2,3-di-Cl-phenyl | CH$_3$ | COOH | CH$_3$ | H |
| 169 | H | H | 2,6-di-Cl-phenyl | CH$_3$ | —CONH(CH$_2$)$_2$-(3-oxo-piperazin-1-yl) | CH$_3$ | H |
| 170 | H | H | 2,6-di-Cl-phenyl | CH$_3$ | —CH$_2$CO-(4-hydroxypiperidin-1-yl) | CH$_3$ | H |
| 171 | H | H | 2,6-di-Cl-phenyl | CH$_3$ | —CH$_2$CO-morpholin-4-yl | CH$_3$ | H |
| 172 | H | H | 2,6-di-Cl-phenyl | CH$_3$ | —CO-(3R-hydroxypyrrolidin-1-yl) | CH$_3$ | H |
| 173 | H | H | 2,6-dimethyl-phenyl | CH$_3$ | —CO-morpholin-4-yl | CH$_3$ | H |

TABLE 1-continued

Representative compounds of the Invention are as follows:

| Cpd # | R¹ | R² | R³, R⁴, R⁵(C₆H₂)— | R⁶ | R⁷ | R⁸ | R⁹ |
|---|---|---|---|---|---|---|---|
| 174 | H | H | 2,6-di-Cl-phenyl | CH₃ | —CH₂CO-(3R, 5S-dimethylpiperazin-1-yl) | CH₃ | H |
| 175 | H | H | 2,6-di-Cl-phenyl | CH₃ | —CH₂CO-(4-methylpiperazin-1-yl) | CH₃ | H |
| 176 | H | H | 2,6-di-Cl-phenyl | CH₃ | —CH₂CO-(4-pyrrolidin-1-yl-piperidin-1-yl) | CH₃ | H |
| 177 | H | H | 2,6-di-Cl-phenyl | CH₃ | —CH₂CONH(CH₂)₂N(CH₂CH₃)₂ | CH₃ | H |
| 178 | H | H | 2,6-di-Cl-phenyl | CH₃ | —CH₂CON-methyl(1-methyl-piperidin-4-yl) | CH₃ | H |
| 179 | H | H | 2,6-di-Cl-phenyl | CH₃ | —CH₂CO-(3-diethylamino-pyrrolidin-1-yl) | CH₃ | H |
| 180 | H | H | 2,6-di-Cl-phenyl | CH₃ | —CH₂CONH(CH₂)₂-pyrrolidin-1-yl | CH₃ | H |
| 181 | H | H | 2,6-di-Cl-phenyl | CH₃ | —CH₂CO-(2S-morpholin-4-ylmethyl-pyrrolidin-1-yl) | CH₃ | H |
| 182 | H | H | 2,6-di-Cl-phenyl | CH₃ | —CH₂CO-[2S-(pyrrolidin-1-ylmethyl)-pyrrolidin-1-yl] | CH₃ | H |
| 183 | H | H | 2,6-di-Cl-phenyl | CH₃ | —CH₂CONHCH₂CH(OH)CH₂-morpholin-4-yl | CH₃ | H |
| 184 | H | H | 2,6-di-Cl-phenyl | CH₃ | —CH₂CONHCH₂CH(OH)CH₂-(1,2,3-triazol-1-yl) | CH₃ | H |
| 185 | H | H | 2,6-di-Cl-phenyl | CH₃ | —CO-(2R-methoxymethyl-pyrrolidin-1-yl) | CH₃ | H |
| 186 | H | H | 2,6-di-Cl-phenyl | CH₃ | —CO-(2S-methoxymethyl-pyrrolidin-1-yl) | CH₃ | H |
| 187 | H | H | 2,6-di-Cl-phenyl | CH₃ | —CO-(2R-hydroxymethyl-pyrrolidin-1-yl) | CH₃ | H |
| 188 | H | H | 2,6-di-Cl-phenyl | CH₃ | —CO-(2S-hydroxymethyl-pyrrolidin-1-yl) | CH₃ | H |
| 189 | H | H | 2,6-di-Cl-phenyl | CH₃ | —CO-[2S-(4-hydroxy-piperidin-1-yl)-pyrrolidin-1-yl] | CH₃ | H |
| 190 | H | H | 2,6-di-Cl-phenyl | CH₃ | —CH₂-(4-hydroxypiperidin-1-yl) | CH₃ | H |
| 191 | H | H | 2,6-di-Cl-phenyl | CH₃ | —CONH(CH₂)₂OCH₃ | CH₃ | H |
| 192 | H | H | 2,6-di-Cl-phenyl | CH₃ | —CONH(CH₂)₃OCH₃ | CH₃ | H |
| 193 | H | H | 2,6-di-Cl-phenyl | CH₃ | —CONH(CH₂)₂O(CH₂)₂OH | CH₃ | H |
| 194 | H | H | 2,6-di-Cl-phenyl | CH₃ | —CONHC(CH₃)(CH₂OH)₂ | CH₃ | H |
| 195 | H | H | 2,6-di-Cl-phenyl | CH₃ | —CONHC(CH₂OH)₃ | CH₃ | H |
| 196 | H | H | 2,6-dimethyl-phenyl | CH₃ | —CO-(3R,5S-dimethyl-piperazin-1-yl) | CH₃ | H |
| 197 | H | H | 2,6-dimethyl-phenyl | CH₃ | —CO-[2S-(pyrrolidin-1-ylmethyl)-pyrrolidin-1-yl) | CH₃ | H |
| 198 | H | H | 2,6-dimethyl-phenyl | CH₃ | —CO-(4-hydroxy-piperidin-1-yl) | CH₃ | H |
| 199 | H | H | 2,6-dimethyl-phenyl | CH₃ | —CO-[4-(pyrrolidin-1-yl)-pipoeridin-1-yl] | CH₃ | H |
| 200 | H | H | 2,6-dimethyl-phenyl | CH₃ | —CO-(4-methyl-piperazin-1-yl) | CH₃ | H |
| 201 | H | H | 2,6-di-Cl-phenyl | CH₃ | —CO-[2R-(pyrrolidin-1-ylmethyl)-pyrrolidin-1-yl] | CH₃ | H |
| 202 | H | H | 2,6-di-Cl-phenyl | CH₃ | —CONH(CH₂)₂-morpholin-4-yl | CH₃ | H |
| 203 | H | H | 2,6-di-Cl-phenyl | CH₃ | —CONH(CH₂)₃-morpholin-4-yl | CH₃ | H |
| 204 | H | H | 2,6-di-Cl-phenyl | CH₃ | —CO-[2S-(cyclopropylaminomethyl)-pyrrolidin-1-yl] | CH₃ | H |
| 205 | H | H | 2,6-di-Cl-phenyl | CH₃ | —CO-[4(morpholin-4-yl)-piperidin-1-yl] | CH₃ | H |
| 206 | H | H | 2,6-di-Cl-phenyl | CH₃ | —CH₂CO-[4(morpholin-4-yl)-piperidin-1-yl] | CH₃ | H |
| 207 | H | H | 2,6-di-Cl-phenyl | CH₃ | —CONH(CH₂)₂S(C₂H₅) | CH₃ | H |
| 208 | H | H | 2,6-di-Cl-phenyl | CH₃ | —CONHCH₂CF₃ | CH₃ | H |
| 209 | H | H | 2,6-di-Cl-phenyl | CH₃ | —(CH₂)₂COOH | CH₃ | H |
| 210 | H | H | 2,6-di-Cl-phenyl | CH₃ | —CO-[2S-(cyclopropylmethylamino-methyl)pyrrolidin-1-yl] | CH₃ | H |
| 211 | H | H | 2,6-di-Cl-phenyl | CH₃ | —CO-(3R,5S-dimethylpiperazin-1-yl) | CH₃ | H |
| 212 | H | H | 2,6-di-Cl-phenyl | CH₃ | —CO-[2S-(pyrrolidin-1-yl-methyl)-pyrrolidin-1-yl] | CH₃ | H |
| 213 | H | H | 2,6-di-Cl-phenyl | CH₃ | —CO-(4-hydroxy-piperidin-1-yl) | CH₃ | H |
| 214 | H | H | 2,6-di-Cl-phenyl | CH₃ | —CO-[4-(pyrrolidin-1-yl)-piperidin-1-yl] | CH₃ | H |
| 215 | H | H | 2,6-di-Cl-phenyl | CH₃ | —CO-(4-methylpiperazin-1-yl) | CH₃ | H |
| 216 | H | H | 2,6-di-Cl-phenyl | CH₃ | —CH₂-(3R-hydroxy-pyrrolidin-1-yl) | CH₃ | H |
| 217 | H | H | 2,6-di-Cl-phenyl | CH₃ | —CH₂-(3-hydroxy-piperidin-1-yl | CH₃ | H |
| 218 | H | H | Phenyl | CH₃ | —CO-[2S-(cyclopropylamino-methyl)pyrrolidin-1-yl | CH₃ | H |

TABLE 1-continued

Representative compounds of the Invention are as follows:

| Cpd # | R¹ | R² | R³, R⁴, R⁵(C₆H₂)— | R⁶ | R⁷ | R⁸ | R⁹ |
|---|---|---|---|---|---|---|---|
| 219 | H | H | 2,6-di-F-phenyl | $CH_3$ | —CO-[2S-(cyclopropylamino-methyl)pyrrolidin-1-yl | $CH_3$ | H |
| 220 | H | H | 3,5-di-Cl-phenyl | $CH_3$ | —CO-(4-hydroxy-pipeidin-1-yl) | $CH_3$ | H |
| 221 | H | H | 2,5-di-Cl-phenyl | $CH_3$ | —CO-(3R,5S-dimethyl-piperazin-1-yl) | $CH_3$ | H |
| 222 | H | H | 2,5-di-Cl-phenyl | $CH_3$ | COOH | $CH_3$ | H |
| 223 | H | H | 2,5-di-Cl-phenyl | $CH_3$ | —CO-[4-(pyrrolidin-1-yl)-piperidin-1-yl] | $CH_3$ | H |
| 224 | H | H | 2,6-di-Cl-phenyl | $CH_3$ | —CONH(CH₂)₂-pyridin-2-yl | $CH_3$ | H |
| 225 | H | H | Phenyl | $CH_3$ | —CO—CH₂-piperidin-1-yl | $CH_3$ | H |
| 226 | H | H | 2,6-di-Cl-phenyl | $CH_3$ | —CONH(CH₂)₂-pyridin-3-yl | $CH_3$ | H |
| 227 | H | H | 2,6-di-Cl-phenyl | $CH_3$ | —CONH(CH₂)₂-pyridin-4-yl | $CH_3$ | H |
| 228 | H | H | 2,6-di-Cl-phenyl | $CH_3$ | —CONHCH₂-(tetrahydrofuran-2-yl) | $CH_3$ | H |
| 229 | H | H | 2,6-di-Cl-phenyl | $CH_3$ | —CONHCH₂cyclopropyl | $CH_3$ | H |
| 230 | H | H | Phenyl | $CH_3$ | —CO-[2S-(pyrrolidin-1-yl-methyl)-pyrrolidin-1-yl] | $CH_3$ | H |
| 231 | H | H | Phenyl | $CH_3$ | —CH₂CO-(4-methyl-piperazin-1-yl) | $CH_3$ | H |
| 232 | H | H | Phenyl | $CH_3$ | —CH₂CO-(3R,5S-dimethyl-piperazin-1-yl) | $CH_3$ | H |
| 233 | H | H | Phenyl | $CH_3$ | —CH₂—CO-morpholin-4-yl | $CH_3$ | H |
| 234 | H | H | Phenyl | $CH_3$ | —CH₂CO-(4-hydroxy-piperidin-1-yl) | $CH_3$ | H |
| 235 | H | H | 2,6-di-Cl-phenyl | $CH_3$ | —CO-(tjiomorpholin-4-yl) | $CH_3$ | H |
| 236 | H | H | 2,6-di-Cl-phenyl | $CH_3$ | —CONH(CH₂)₂F | $CH_3$ | H |
| 237 | H | H | 2,6-di-Cl-phenyl | $CH_3$ | —CONH(CH₂)₃(imidazol-1-yl) | $CH_3$ | H |
| 238 | H | H | 2,6-di-Cl-phenyl | $CH_3$ | —CONHCH₃ | $CH_3$ | H |
| 239 | H | H | 2,6-di-Cl-phenyl | $CH_3$ | —CONH₂ | $CH_3$ | H |
| 240 | H | H | 2,6-di-Cl-phenyl | $CH_3$ | —CO-(dioxo-thiomorpholin-4-yl) | $CH_3$ | H |
| 241 | I. | H | 2,6-di-Cl-phenyl | $CH_3$ | —CONH(CH₂)₂(4-acetyl-piperazin-1-yl) | $CH_3$ | H |
| 242 | II. | H | 2,6-di-Cl-phenyl | $CH_3$ | —CH₂-(3R,5S-dimethyl-piperazin-1-yl) | $CH_3$ | H |
| 243 | H | H | Phenyl | $CH_3$ | —CH₂-(3R,5S-dimethyl-piperazin-1-yl) | $CH_3$ | H |
| 244 | H | H | 2,5-di-Cl-phenyl | $CH_3$ | —CO-(4-hydroxy-piperidin-1-yl) | $CH_3$ | H |
| 245 | H | H | 2,5-di-Cl-phenyl | $CH_3$ | —CO-[2S-(pyrrolidin-1-yl-methyl)-pyrrolidin-1-yl] | $CH_3$ | H |
| 246 | H | H | 2,5-di-Cl-phenyl | $CH_3$ | —CO-(4-methyl-piperazin-1-yl) | $CH_3$ | H |
| 247 | H | H | 3,5-di-Cl-phenyl | $CH_3$ | —CO-(3R,5S-dimethyl-piperazin-1-yl) | $CH_3$ | H |
| 248 | H | H | 3,5-di-Cl-phenyl | $CH_3$ | —CO-[4-pyrrolidin-1-yl)-piperidin-1-yl] | $CH_3$ | H |
| 249 | H | H | 3,5-di-Cl-phenyl | $CH_3$ | —CO-[2S-(pyrrolidin-1-yl-methyl)-pyrrolidiin-1-yl] | $CH_3$ | H |
| 250 | H | H | 3,5-di-Cl-phenyl | $CH_3$ | —CO-(4-methyl-piperizin-1-yl) | $CH_3$ | H |
| 251 | H | H | 2,6-di-Cl-phenyl | $CH_3$ | —CH₂-(4-cyclopropylmethyl-piperazin-1-yl) | $CH_3$ | H |
| 252 | H | H | 2,6-di-Cl-phenyl | $CH_3$ | —CH₂—CO-(2S-cyclopropylaminomethyl-pyrrolidin-1-yl) | $CH_3$ | H |
| 253 | H | H | 2,6-di-Cl-phenyl | $CH_3$ | —CH₂-(4-acetyl-piperazin-1-yl) | $CH_3$ | H |
| 254 | H | H | 2,6-di-Cl-phenyl | $CH_3$ | —CH₂-(4-aldehyde-piperazin-1-yl) | $CH_3$ | H |
| 255 | H | H | 2,6-di-Cl-phenyl | $CH_3$ | —CH₂-(methyl-cyclopropylamino) | $CH_3$ | H |
| 256 | H | H | 2,6-di-Cl-phenyl | $CH_3$ | —CH₂-(4-cyclopropyl-piperazin-1-yl) | $CH_3$ | H |
| 257 | H | H | 2,6-di-Cl-phenyl | $CH_3$ | —CH₂—CO-[(4R-hydroxy,2R-cyclopropylaminomethyl)-pyrrolidin-1-yl] | $CH_3$ | H |
| 258 | H | H | 2,6-di-Cl-phenyl | $CH_3$ | —CH₂—CO-[(3S-hydroxy,2R-cyclopropylaminomethyl)-pyrrolidin-1-yl] | $CH_3$ | H |
| 259 | H | H | 2,6-di-Cl-phenyl | $CH_3$ | —CONH(CH₂)₂-(3-acetylamino-pyrrolidin-1-yl) | $CH_3$ | H |
| 260 | H | H | 2,6-di-Cl-phenyl | $CH_3$ | —CH₂—CONH(CH₂)₂-piperazin-1-yl | $CH_3$ | H |
| 261 | H | H | 2,6-di-Cl-phenyl | $CH_3$ | —CH₂—CONH(CH₂)₂-(4-hydroxy-acetyl-piperazin-1-yl) | $CH_3$ | H |
| 262 | H | H | 2,6-di-Cl-phenyl | $CH_3$ | —CH₂—CO-[2S-(3R-hydroxy-pyrrolidin-1-ylmethyl)-pyrrolidin-1-yl] | $CH_3$ | H |
| 263 | H | H | 2,6-di-Cl-phenyl | $CH_3$ | —CH₂—CO-[3S-(pyrrolidin-1-ylmethyl)-piperidin-1-yl] | $CH_3$ | H |
| 264 | H | H | 2,6-di-Cl-phenyl | $CH_3$ | —CH₂CONH(CH₂)₂NHCH₂CF₃ | $CH_3$ | H |
| 265 | H | H | 2,6-di-Cl-phenyl | $CH_3$ | —CONH(CH₂)₂NHCH₂CF₃ | $CH_3$ | H |
| 266 | H | H | 2,6-di-Cl-phenyl | $CH_3$ | —CO—[2R- | $CH_3$ | H |

TABLE 1-continued

Representative compounds of the Invention are as follows:

| Cpd # | R¹ | R² | R³, R⁴, R⁵(C₆H₂)— | R⁶ | R⁷ | R⁸ | R⁹ |
|---|---|---|---|---|---|---|---|
| 267 | H | H | 2,6-di-Cl-phenyl | CH₃ | —CO-[4R-hydroxy-2S-(cyclopropylmethylamino-methyl)-pyrrolidin-1-yl]<br>—CO-[4R-hydroxy-2S-(cyclopropylamino-carbonyl)] | CH₃ | H |
| 268 | H | H | 2,6-di-Cl-phenyl | CH₃ | —CH₂—CO-[4R-hydroxy-2S-(cyclopropylamino-carbonyl)] | CH₃ | H |
| 269 | H | H | 2,6-di-Cl-phenyl | CH₃ | —CONHCH₂CH(OH)CH₂—pyrrolidin-1-yl | CH₃ | H |
| 270 | H | H | 2,6-di-Cl-phenyl | CH₃ | —CONHCH₂CH(OH)CH₂—cyclopropylamino | CH₃ | H |
| 271 | H | H | 2,6-di-Cl-phenyl | CH₃ | —CO-(4-cyclopropyl-piperazin-1-yl) | CH₃ | H |
| 272 | H | H | 2,6-di-Cl-phenyl | CH₃ | —CO-cyclopropylamino | CH₃ | H |
| 273 | H | H | 2,6-di-Cl-phenyl | CH₃ | —CH₂—CONH(CH₂)₂-(3-acetylamino-pyrrolidin-1-yl) | CH₃ | H |
| 274 | H | H | 2,6-di-Cl-phenyl | CH₃ | —CONH(CH₂)₂-(4-hydroxy-acetyl-piperazin-1-yl) | CH₃ | H |
| 275 | H | H | 2,6-di-Cl-phenyl | CH₃ | —CH₂CONHCH₂CH(OH)CH₂-pyrrolidin-1-yl | CH₃ | H |
| 276 | H | H | 2,6-di-Cl-phenyl | CH₃ | —CH₂CONHCH₂CH(OH)CH₂-cyclopropylamino | CH₃ | H |
| 277 | H | H | 2,6-di-Cl-phenyl | CH₃ | —CH₂CO-(4-cyclopropyl-piperazin-1-yl) | CH₃ | H |
| 278 | H | H | 2,6-di-Cl-phenyl | CH₃ | —CO-(4-cyclopropylmethyl-piperazin-1-yl) | CH₃ | H |
| 279 | H | H | 2,6-di-Cl-phenyl | CH₃ | —CH₂CO-(4-cyclopropylmethyl-piperazin-1-yl) | CH₃ | H |
| 280 | H | H | 2,6-di-Cl-phenyl | CH₃ | —CO-(3S-pyrrolidin-1-ylmethyl-piperidin-1-yl | CH₃ | H |
| 281 | H | H | 2,6-di-Cl-phenyl | CH₃ | —CO-{2S-[)cyclopropyl-methyl-amino)-methyl]-pyrrolidin-1-yl} | CH₃ | H |
| 282 | H | H | 2,6-di-Cl-phenyl | CH₃ | —CH₂—CO-(4R-hydroxy-2S-cyclopropylaminomethyl)-pyrrolidin-1-yl | CH₃ | H |
| 283 | H | H | 2,6-di-Cl-phenyl | CH₃ | —CO-(4R-hydroxy-2R-cyclopropylaminomethyl)-pyrrolidin-1-yl | CH₃ | H |
| 284 | H | H | 2,6-di-Cl-phenyl | CH₃ | —CO-(3S-hydroxy-2R-cyclopropylaminomethyl)-pyrrolidin-1-yl | CH₃ | H |
| 285 | H | H | 2,6-di-Cl-phenyl | CH₃ | —CO-[2S-(3R-hydroxy-pyrrolidin-1-ylmethyl)-pyrrolidin-1-yl)] | CH₃ | H |
| 286 | H | H | 2,6-di-Cl-phenyl | CH₃ | —CO-[2R-(3R-hydroxy-pyrrolidin-1-ylmethyl)-pyrrolidin-1-yl)] | CH₃ | H |
| 287 | H | H | 2,6-di-Cl-phenyl | CH₃ | —CH₂—CO-(3R-hydroxy-pyrrolidin-1-yl) | CH₃ | H |
| 288 | H | H | 2,6-di-Cl-phenyl | CH₃ | —CH₂—CO-[2R-(3R-hydroxy-pyrrolidin-1-ylmetyl)-pyrrolidin-1-yl] | CH₃ | H |
| 289 | H | H | 2,6-di-Cl-phenyl | CH₃ | —CO-[3R-(cyclopropylaminocarbonyl)-piperidin-1-yl] | CH₃ | H |
| 290 | H | H | 2,6-di-Cl-phenyl | CH₃ | —CH₂—CO-[3R-(cyclopropylaminocarbonyl)-piperidin-1-yl] | CH₃ | H |
| 291 | H | H | Phenyl | CH₃ | —CO-{2S-[(cyclopropyl-methyl-amino)-methyl]-pyrrolidin-1-yl} | CH₃ | H |
| 292 | H | H | 2,6-di-Cl-phenyl | CH₃ | —CH₂—CO-(3S-cyclopropylaminomethyl-piperidin-1-yl) | CH₃ | H |
| 293 | H | H | 2,6-di-Cl-phenyl | CH₃ | —CO-(3S-cyclopropylaminomethyl-piperidin-1-yl) | CH₃ | H |
| 294 | H | H | 2,6-di-Cl-phenyl | CH₃ | —CH₂—CO-[2S-(3R-fluoro-pyrrolidin-1-ylmethyl)-pyrrolidin-1-yl] | CH₃ | H |
| 295 | H | H | 2,6-di-Cl-phenyl | CH₃ | —CO-[2S-(4-fluoro-piperidin-1-ylmethyl)-pyrrolidin-1-yl] | CH₃ | H |
| 296 | H | H | 2,6-di-Cl-phenyl | CH₃ | —CH₂—CO-[2S-(4-fluoro-piperidin-1-ylmethyl)-pyrrolidin-1-yl] | CH₃ | H |
| 297 | H | H | 2,6-di-Cl-phenyl | CH₃ | —CO-[2R-(3R-fluoro-pyrrolidin-1-ylmethyl)-pyrrolidin-1-yl] | CH₃ | H |
| 298 | H | H | 2,6-di-Cl-phenyl | CH₃ | —CH₂—CO-[2R-(3R-fluoro-pyrrolidin-1-ylmethyl)-pyrrolidin-1-yl] | CH₃ | H |
| 299 | H | H | 2,6-di-Cl-phenyl | CH₃ | —CONH(CH₂)₂-(4-fluoro-piperidin-1-yl) | CH₃ | H |

TABLE 1-continued

Representative compounds of the Invention are as follows:

| Cpd # | $R^1$ | $R^2$ | $R^3, R^4, R^5(C_6H_2)$— | $R^6$ | $R^7$ | $R^8$ | $R^9$ |
|---|---|---|---|---|---|---|---|
| 300 | H | H | 2,6-di-Cl-phenyl | $CH_3$ | —$CH_2$—$CONH(CH_2)_2$-(4-fluoro-piperidin-1-yl) | $CH_3$ | H |
| 301 | H | H | 2,6-di-Cl-phenyl | $CH_3$ | —CO-(2S-cyclopropylaminomethyl-4R-hydroxy-pyrrolidin-1-yl) | $CH_3$ | H |
| 302 | H | H | 2,6-di-Cl-phenyl | $CH_3$ | —CO-[2R-(4-fluoro-piperidin-1-ylmethyl)-pyrrolidin-1-yl] | $CH_3$ | H |
| 303 | H | H | 2,6-di-Cl-phenyl | $CH_3$ | —$CH_2$—CO-[2R-(4-fluoro-piperidin-1-ylmethyl)-pyrrolidin-1-yl] | $CH_3$ | H |
| 304 | H | H | 2,6-di-Cl-phenyl | $CH_3$ | —CO-[2S-(3-fluoro-piperidin-1-ylmethyl-pyrrolidin-1-yl] | $CH_3$ | H |
| 305 | H | H | 2,6-di-Cl-phenyl | $CH_3$ | —$CH_2$—CO-[2S-(3-fluoro-piperidin-1-ylmethyl)-pyrrolidin-1-yl] | $CH_3$ | H |
| 306 | H | H | 2,6-di-Cl-phenyl | $CH_3$ | —$CH_2$—CO-[2S-(cyclopropyl-methyl-amino)methyl-pyrrolidin-1-yl] | $CH_3$ | H |
| 307 | H | H | 2,6-di-Cl-phenyl | $CH_3$ | —CO-[2R-(cyclopropyl-methyl-amino)methyl-pyrrolidin-1-yl] | $CH_3$ | H |
| 308 | H | H | 2,6-di-Cl-phenyl | $CH_3$ | -(1-methyl-piperidin-4-yl) | $CH_3$ | H |
| 309 | H | H | 2,6-di-Cl-phenyl | $CH_3$ | —$CH_2$-(4-fluoro-piperidin-1-yl) | $CH_3$ | H |
| 310 | H | H | 2,6-di-Cl-phenyl | $CH_3$ | —$CONH(CH_2)_2$-(3-fluoro-pyrrolidin-1-yl) | $CH_3$ | H |
| 311 | H | H | 2,6-di-Cl-phenyl | $CH_3$ | —$CH_2$—$CONH(CH_2)_2$-(3-fluoro-pyrrolidin-1-yl) | $CH_3$ | H |
| 312 | H | H | 2,6-di-Cl-phenyl | $CH_3$ | —$(CH_2)_2$—CO-[2R-(3R-pyrrolidin-1-ylmethyl)-pyrrolidin-1-yl] | $CH_3$ | H |
| 313 | H | H | 2,6-di-Cl-phenyl | $CH_3$ | —CO-[2R-(3R-pyrrolidin-1-ylmethyl)-pyrrolidin-1-yl] | $CH_3$ | H |
| 314 | H | H | 2,6-di-Cl-phenyl | $CH_3$ | —$CONH(CH_2)_2$-(3-fluoro-piperidin-1-yl) | $CH_3$ | H |
| 315 | H | H | 2,6-di-Cl-phenyl | $CH_3$ | —$CH_2$—$CONH(CH_2)_2$-(3-fluoro-piperidin-1-yl) | $CH_3$ | H |
| 316 | H | H | 2,6-di-F-phenyl | $CH_3$ | —CO-[2R-(pyrrolidin-1-ylmethyl)-pyrrolidin-1-yl] | $CH_3$ | H |
| 317 | H | H | 2,6-di-Cl-phenyl | $CH_3$ | —$(CH_2)_2$—CO-[2R-(pyrrolidin-1-ylmethyl)-pyrrolidin-1-yl] | $CH_3$ | H |
| 318 | H | H | 2,6-di-Cl-phenyl | $CH_3$ | —$CONH(CH_2)_2${4-[CO—$C(CH_3)_2(NH_2)$]-piperazin-1-yl} | $CH_3$ | H |
| 319 | H | H | 2,6-di-Cl-phenyl | $CH_3$ | —$(CH_2)_2$—CO-[3S-(pyrrolidin-1-ylmethyl)-piperidin-1-yl] | $CH_3$ | H |
| 320 | H | H | 2,6-di-Cl-phenyl | $CH_3$ | —CO-[3S-(pyrrolidin-1-ylmethyl)-piperidin-1-yl] | $CH_3$ | H |
| 321 | H | H | 2,6-di-Cl-phenyl | $CH_3$ | —$(CH_2)_2$—CO-(morpholin-4-yl) | $CH_3$ | H |
| 322 | H | H | 2,6-di-Cl-phenyl | $CH_3$ | —$CH_2$—$CONH(CH_2)_2$-(4-acetyl-piperazin-1-yl) | $CH_3$ | H |
| 323 | H | H | 2,6-di-Cl-phenyl | $CH_3$ | —$CONH(CH_2)_2$-(4-hydroxy-pyrrolidin-1-yl) | $CH_3$ | H |
| 324 | H | H | 2,6-di-Cl-phenyl | $CH_3$ | —$CH_2$—$CONH(CH_2)_2$-(4-hydroxy-pyrrolidin-1-yl) | $CH_3$ | H |
| 325 | H | H | 2,6-di-Cl-phenyl | $CH_3$ | —$(CH_2)_2$—CO-(4-methyl-piperazin-1-yl) | $CH_3$ | H |
| 326 | H | H | 2,6-di-Cl-phenyl | $CH_3$ | —$(CH_2)_2$—CO-(3R,5S-dimethyl-piperazin-1-yl) | $CH_3$ | H |
| 327 | H | H | 2,6-di-Cl-phenyl | $CH_3$ | —$(CH_2)_2$—CO-[2S-(pyrrolidin-1-ylmethyl)-pyrrolidin-1-yl] | $CH_3$ | H |
| 328 | H | H | 2,6-di-Cl-phenyl | $CH_3$ | —CO—$NCH_2$-(1-methyl-piperidin-4-yl) | $CH_3$ | H |
| 329 | H | H | 2,6-di-Cl-phenyl | $CH_3$ | —$CH_2$—CO—$NCH_2$-(1-methyl-piperidin-4-yl) | $CH_3$ | H |
| 330 | H | H | 2,6-di-Cl-phenyl | $CH_3$ | —$(CH_2)_2$—CO-(2S-cyclopropylaminomethyl-pyrrolidin-1-yl) | $CH_3$ | H |
| 331 | H | H | 2,6-di-Cl-phenyl | $CH_3$ | —$(CH_2)_2$—CO-(4-hydroxy-piperidin-1-yl) | $CH_3$ | H |
| 332 | H | H | 2,6-di-Cl-phenyl | $CH_3$ | —$(CH_2)_2$—CO-(3R-hydroxy-pyrrolidin-1-yl) | $CH_3$ | H |
| 333 | H | H | 2,6-di-Cl-phenyl | $CH_3$ | —$(CH_2)_2$—CO-[2R-(3R-hydroxy-pyrrolidin-1-ylmethyl)-pyrrolidin-1-yl] | $CH_3$ | H |
| 334 | H | H | 2,6-di-F-phenyl | $CH_3$ | —CO-(3R-hydroxy-pyrrolidin-1-yl) | $CH_3$ | H |
| 335 | H | H | 2,6-di-F-phenyl | $CH_3$ | —CO-(4-cylopropylamino-piperidin-1-yl) | $CH_3$ | H |
| 336 | H | H | 2,6-di-Cl-phenyl | $CH_3$ | —$(CH_2)_2$—CO-(4-cyclopropylamino-piperidin-1-yl) | $CH_3$ | H |

TABLE 1-continued

Representative compounds of the Invention are as follows:

| Cpd # | R¹ | R² | R³, R⁴, R⁵(C₆H₂)— | R⁶ | R⁷ | R⁸ | R⁹ |
|---|---|---|---|---|---|---|---|
| 337 | H | H | 2,6-di-Cl-phenyl | CH₃ | —CONH(CH₂)₂-pyrrolidin-1-yl | CH₃ | H |
| 338 | H | H | 2,6-di-Cl-phenyl | —CO-[2S-pyrrolidin-1-ylmethyl)-pyrrolidin-1-yl] | H | CH₃ | H |
| 339 | H | H | 2,6-di-Cl-phenyl | CH₃ | —CO-[2S-(3S-fluoro-pyrrolidin-1-ylmethyl)-pyrrolidin-1-yl] | CH₃ | H |
| 340 | H | H | 3,5-di-Cl-phenyl | CH₃ | COOH | CH₃ | H |
| 341 | H | H | 2-morpholin-4-yl-ethoxy-phenyl | CH₃ | —CH₂-(cyclopropyl-methyl-amino) | CH₃ | H |
| 342 | H | H | 2-morpholin-4-yl-ethoxy-phenyl | CH₃ | —CO-(3R-hydroxy-pyrrolidin-1-yl) | CH₃ | H |
| 343 | H | H | 2-morpholin-4-yl-ethoxy-phenyl | CH₃ | —CO-(4-methyl-piperazin-1-yl) | CH₃ | H |
| 344 | H | H | 2-morpholin-4-yl-ethoxy-phenyl | CH₃ | —CO-[2R-(pyrrolidin-1-ylmethyl-pyrrolidin1-yl] | CH₃ | H |
| 345 | H | H | 3,5-dimethoxy-phenyl | CH₃ | —CO-(4-cyclopropylamino-piperidin-1-yl) | CH₃ | H |
| 346 | H | H | 3,5-dimethoxy-phenyl | CH₃ | —CO-[2R-(cyclopropylaminomethyl)-pyrrolidin-1-yl] | CH₃ | H |
| 347 | H | H | 3,5-dimethoxy-phenyl | CH₃ | —CO-[2R-(cyclopropylmethylaminomethyl)-pyrrolidin-1-yl] | CH₃ | H |
| 348 | H | H | 3,5-dimethoxy-phenyl | CH₃ | —CO-[2R-(pyrrolidin-1-ylmethyl-pyrrolidin1-yl] | CH₃ | H |
| 349 | H | H | Phenyl | CH₃ | —CO-[2R-(pyrrolidin-1-ylmethyl-pyrrolidin1-yl] | CH₃ | H |
| 350 | H | H | 2,6-di-Cl-phenyl | CH₃ | —CO—N-(cyclopropyl)-(1R-pyrrolidin-2-ylmethyl) | CH₃ | H |
| 351 | H | H | 2,6-di-Cl-phenyl | CH₃ | —CO—N-(cyclopropylmethyl)-(1R-pyrrolidin-2-ylmethyl) | CH₃ | H |
| 352 | H | H | 2,6-dimethoxy-phenyl | CH₃ | —CO-[2R-(pyrrolidin-1-ylmethyl-pyrrolidin1-yl] | CH₃ | H |
| 353 | H | H | 2,6-di-F-phenyl | CH₃ | —CO-[2R-(cyclopropylmethylaminomethyl)-pyrrolidin-1-yl] | CH₃ | H |
| 354 | H | H | 2,6-diF-phenyl | CH₃ | —CO-[2R-(cyclopropylaminomethyl)-pyrrolidin-1-yl] | CH₃ | H |
| 355 | H | H | 2-F-phenyl | CH₃ | —CO-[2R-(cyclopropylaminomethyl)-pyrrolidin-1-yl] | CH₃ | H |
| 356 | H | H | 2-F-phenyl | CH₃ | —CO-[2R-(cyclopropylmethylaminomethyl)-pyrrolidin-1-yl] | CH₃ | H |
| 357 | H | H | 2-F-phenyl | CH₃ | —CO-[2R-(pyrrolidin-1-ylmethyl-pyrrolidin1-yl] | CH₃ | H |
| 358 | H | H | 2-Cl-phenyl | CH₃ | —CO-[2R-(pyrrolidin-1-ylmethyl-pyrrolidin1-yl] | CH₃ | H |
| 359 | H | H | 2-Cl-phenyl | CH₃ | —CO-[2R-(cyclopropylaminomethyl)-pyrrolidin-1-yl] | CH₃ | H |
| 360 | H | H | 2-Cl-phenyl | CH₃ | —CO-[2R-(cyclopropylmethylaminomethyl)-pyrrolidin-1-yl] | CH₃ | H |
| 361 | H | H | 2-Cl-phenyl | CH₃ | —CO-(4-cylcopropylamino-piperidin-1-yl) | CH₃ | H |
| 362 | H | H | 2-F-phenyl | CH₃ | —CO-(4-cyclopropylamino-piperidin-1-yl) | CH₃ | H |
| 363 | H | H | 2,6-diCl-phenyl | CH₃ | —CO-[2R-(2S-hydroxymethyl-pyrrolidin-1-ylmethyl)-pyrrolidin-1-yl] | CH₃ | H |
| 364 | H | H | 2-F-phenyl | CH₃ | —CO-(4-amino-piperidin-1-yl) | CH₃ | H |
| 365 | H | H | 2,6-di-Cl-phenyl | CH₃ | —CO-(4-amino-piperidin-1-yl) | CH₃ | H |
| 366 | H | H | 2,6-di-F-phenyl | CH₃ | —CO-(4-amino-piperidin-1-yl) | CH₃ | H |
| 367 | H | H | 2-Cl-phenyl | CH₃ | —CO-(4-amino-piperidin-1-yl) | CH₃ | H |
| 368 | H | H | 2-F-phenyl | CH₃ | —CO-(3S-amino-piperidin-1-yl) | CH₃ | H |
| 369 | H | H | 2-Cl-phenyl | CH₃ | —CO-(3S-amino-piperidin-1-yl) | CH₃ | H |
| 370 | H | H | 2,6-diCl-phenyl | CH₃ | —CO-(3S-amino-piperidin-1-yl) | CH₃ | H |
| 371 | H | H | 2,6-di-F-phenyl | CH₃ | —CO-(3S-amino-piperidin-1-yl) | CH₃ | H |
| 372 | H | H | 2,6-di-F-phenyl | CH₃ | —CO-(3R-amino-piperidin-1-yl) | CH₃ | H |
| 373 | H | H | 2,6-di-Cl-phenyl | CH₃ | —CO-(3R-amino-piperidin-1-yl) | CH₃ | H |
| 374 | H | H | 2-Cl-phenyl | CH₃ | —CO-(3R-amino-piperidin-1-yl) | CH₃ | H |
| 375 | H | H | 2-F-phenyl | CH₃ | —CO-(3R-amino-piperidin-1-yl) | CH₃ | H |

Utility

The compounds of Formula (I), (Ia) and (Ib) inhibit inhibit PKs such as receptor tyrosine kinases (RTKs) and cellular tyrosine kinases (CTKs), and serine-threonine kinases (STKs). The compounds of the present invention are therefore useful in the treatment of diseases mediated by abnormal PK activity. The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, *Neuron* 9:303–391.

It has been shown that tyrosine phosphorylation sites on growth factor receptors function as high-affinity binding sites for SH2 (src homology) domains of signaling molecules. Fantl et al., 1992, *Cell* 69:413–423, Songyang et al., 1994, *Mol. Cell. Biol.* 14:2777–2785), Songyang et al., 1993, *Cell* 72:767–778, and Koch et al., 1991, *Science* 252:668–678. Several intracellular substrate proteins that associate with RTKs have been identified. They may be divided into two principal groups: (1) substrates that have a catalytic domain, and (2) substrates that lack such domain but which serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step, which determines the selectivity of signaling pathways, recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein thus have utility in in vitro assays for such proteins as well as exhibiting in vivo therapeutic effects through interaction with such proteins.

Additionally, the compounds of the present invention provide a therapeutic approach to the treatment of many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., 1990, *Oncogene*, 5:519–524; De Vries et al., 1992, *Science*, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, *Biochein. Biophys. Res. Comm.*, 161:851–858; Vaisman et al., 1990, *J. Biol. Chem.*, 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology*, 3(10)699–702; Houck, et al., 1992, *J. Biol. Chem.*, 267:26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biological Chem.*, 267(16):10931–34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10):699–702; Folkham, 1991, *J. Natl. Cancer Inst.*, 82:4–6; Weidner, et al., 1991, *New Engl. J. Med.*, 324:1–5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in *XI$^{th}$ Congress of Thrombosis and Haemostasis* (Verstraeta, et al., eds.), pp. 583–596, Leuven University Press, Leuven) and arthritis, as well as malignant tumor growth may result from uncontrolled angiogenesis. See e.g., Folkman, 1971, *N. Engl. J. Med.*, 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, the present invention provides compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other components along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell*, 72:835–846; Quinn et al., 1993, *Proc. Natl. Acad. Sci. USA*, 90:7533–7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, the present invention provides compounds that regulate, modulate and/or inhibit vasculogenesis and/or angiogenesis by affecting the enzymatic activity of the KDR/FLK-1 receptor and interfering with the signal transduced by KDR/FLK-1. Thus the present invention provides a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggests the administration of compounds which inhibit the KDR/Flk-1 mediated signal transduction pathway may also be used in the treatment of hemangioma, restenois and diabetic retinopathy.

Furthermore, this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signaling molecules that facilitate the appropriate cellular response, e.g., cell division and metabolic effects to the extracellular microenvironment. See, Schlessinger and Ullrich, 1992, *Neuron*, 9:1–20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, *Proc. Natl. Acad. Sci. USA*, 90:7696–7700), phosphatidylinositol-3'-kinase (Hu et al., 1992, *Mol. Cell. Biol.*, 12:981–990), phospholipase cγ (Kashishian & Cooper, 1993, *Mol. Cell. Biol.*, 4:49–51), ras-GTPase-activating protein, (Kashishian et al., 1992, *EMBO J.*, 11:1373–1382), PTP-ID/syp (Kazlauskas et al., 1993, *Proc. Natl. Acad. Sci. USA*, 10 90:6939–6943), Grb2 (Arvidsson et al., 1994, *Mol. Cell. Biol.*, 14:6715–6726), and the adapter molecules Shc and Nck (Nishimura et al., 1993, *Mol. Cell. Biol.*, 13:6889–6896), have been shown to bind to regions involving different autophosphorylation sites. See generally, Claesson-Welsh, 1994, *Prog. Growth Factor Res.*, 5:37–54. Thus, it is likely that signal transduction pathways activated by KDR/FLK-1 include the ras pathway (Rozakis et al., 1992, *Nature*, 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, Kidney International 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, Br. J. Cancer 63:227–233, Torp et al., 1992, APMIS 100:713–719) HER2/neu (Slamon et al., 1989, Science 244:707–712) and PDGF-R (Kumabe et al., 1992, Oncogene, 7:627–633) are over-expressed in many tumors and/or persistently activated by autocrine loops. In fact, in the most common and severe cancers these receptor over-expressions (Akbasak and Suner-Akbasak et al., 1992, J. Neurol. Sci., 111:119–133, Dickson et al., 1992, Cancer Treatment Res. 61:249–273, Korc et al., 1992, J. Clin. Invest. 90:1352–1360) and autocrine loops (Lee and Donoghue, 1992, J. Cell. Biol., 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation.

The Met receptor has been commonly shown to be expressed in a number of human cancers. Jaing, W et al. Crit Rev Oncol-Hematol 29:209–48, 1999. For example, c-met has been associated with, among other cancers, colorectal, thyroid, pancreatic, gastric and hepatocellular carcinomas and lymphomas, as well as other diseases. Additionally c-met has been linked to leukemia. Over-expression of the c-met gene has also been detected in patients with Hodgkins disease and Burkitts disease. Met and its ligand, HGF, have also been shown to be co-expressed at elevated levels in a variety of human cancers, particularly sarcomas. Numerous studies have correlated the expression of Met and/or HGF/SF with the state of metastatic disease progression of different types of cancer, including lung, colon, breast, prostate, liver, pancreas, brain, kidney, ovaries, stomach, skin and bone. Effective treatment of advanced metastatic cancer is an unmet medical need. Patients usually die of metastatic cancer, rather than of there primary tumors.

Although progress has been made in treating many types of cancer, the treatments tend to be less effective toward metastatic disease. Thus, one aspect of the present invention is directed towards compounds and therapeutic approaches for the treatment of many kinds of metastatic cancers.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, J. Clin. Invest. 84:1418–1423) and small lung tumor cells (Macauley et al., 1990, Cancer Res., 50:2511–2517). In addition, IGF-I, while integrally involved in the normal growth and differentiation of the nervous system, also appears to be an autocrine stimulator of human gliomas. Sandberg-Nordqvist et al., 1993, Cancer Res. 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, Eukaryotic Gene Expression, 1:301–326. Baserga and Coppola suggest that IGF-IR plays a central role in the mechanism of transformation and, as such, could be a preferred target for therapeutic interventions for a broad spectrum of human malignancies. Baserga, 1995, Cancer Res., 55:249–252, Baserga, 1994, Cell 79:927–930, Coppola et al., 1994, Mol. Cell. Biol., 14:4588–4595.

STKs have been implicated in many types of cancer including, notably, breast cancer (Cance, et al., Int. J. Cancer, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, restenosis, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, DN&P 7:334–339.

As noted previously, not only RTKs but CTKs including, but not limited to, src, abl, fps, yes, fyn, lyn, lck, blk, hck, fgr and yrk (reviewed by Bolen et al., 1992, FASEB J., 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v-src}$) in chicken. Moreover, its cellular homolog, the proto-oncogene $pp60^{c-src}$ transmits oncogenic signals of many receptors. Over-expression of EGFR or HER2/neu in tumors leads to the constitutive activation of $pp60^{c-src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents. Additional disorders which may be treated or prevented using the compounds of this invention are immunological disorders such as autoimmune disease, AIDS and cardiovascular disorders such as atherosclerosis.

Finally, both RTKs and CTKs are currently suspected as being involved in hyperimmune disorders.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or a pharmaceutically acceptable salt thereof or of a pharmaceutical composition containing a compound of Formula (I) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths. The two dose strengths are made from the same granules by filling into different size hard gelatin capsules, size 3 for the 50 mg capsule and size 0 for the 200 mg capsule. The composition of the formulation may be, for example, as indicated in Table 2.

TABLE 2

| Ingredient Name/Grade | Concentration in Granulation (% w/w) | Amount in 50 mg Capsule (mg) | Amount in 200 mg Capsule (mg) |
|---|---|---|---|
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |
| Magnesium stearate NF | 0.5 | 0.38 | 1.52 |
| Capsule, Swedish yellow NF | | Size 3 | Size 0 |

The capsules may be packaged into brown glass or plastic bottles to protect the active compound from light. The containers containing the active compound capsule formulation must be stored at controlled room temperature (15–30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

At present, the therapeutically effective amounts of compounds of Formula (I) may range from approximately 25 mg/m² to 1500 mg/m² per day. Even more preferably 50 mg/qm qd till 400 mg/qd.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A compound of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound of this invention can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with Endostatin®, Gleevec®, Camptosar®, Herceptin®, Imclone C225, mitoxantrone or paclitaxel for the treatment of solid tumor cancers or leukemias such as, without limitation, acute myelogenous (non-lymphocytic) leukemia. The compounds of this invention can also be used with a COX-2 inhibitor.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

A. General Procedures for the Syntheses of 5-Arylmethanesulfonyl-1,3-dihydro-indol-2-one

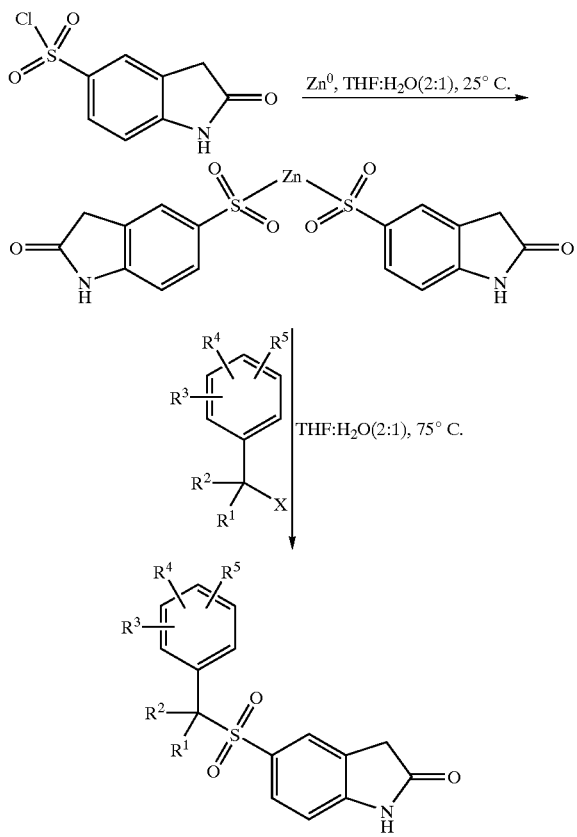

To a suspension of 5-chlorosulfonyloxindole (30 g, 129.9 mmol) in THF:water (2:1) (645 mL) (0.2 M) was added a presonicated (15 minutes) suspension of Zn dust (90% purity from Aldrich, 8.4 g, 129.9 mmol ) portionwise. The reaction mixture was stirred at 25° C. for 18 hours. TLC showed the complete disappearance of the starting material 5-chlorosulfonyl oxindole. The reaction mixture was concentrated to one quarter the reaction volume where the solid product was filtered, and washed repeatedly with water to remove zinc chloride. After high vacuum dry, 32.4 g (55%) of 5-zinc sulfinate-1,3-dihydro-indol-2-one was obtained as an off white solid.

$^1$H NMR (360 MHz, DMSO-$d_6$) δ 10.76 (br s, 1H, NH), 7.42 (s, 1H), 7.41 (d, J=8.1 Hz, 1H), 6.82 (d, J=8.0 Hz, 1H), 3.45 (s, 2H, $CH_2$).

To a suspension of 5-zinc sulfinate-1,3-dihydro-indol-2-one (1 molar equivalent) in THF:water (2:1) (0.2 M) was added the benzyl halides, preferably bromides, (2.2 molar equivalents). The reaction mixture was stirred at 70° C. (oil bath) for 24–48 hours. After the reaction was complete (TLC) the reaction mixture was cooled to room temperature, diluted with ethyl acetate, and separated from water layer. The ethyl acetate solution was further washed with water and separated after which time the solvents were evaporated, and the crude product was purified by one of two methods. If the product precipitated out it was filtered, washed with diethyl ether, and dried under high vacuum. If it did not precipitate, the product was purified on a silica gel column by eluting with MeOH—$CH_2Cl_2$.

Example 1

Synthesis of 5-(2-Trifluoromethyl-phenylmethanesulfonyl)-1,3-dihydro-indol-2-one

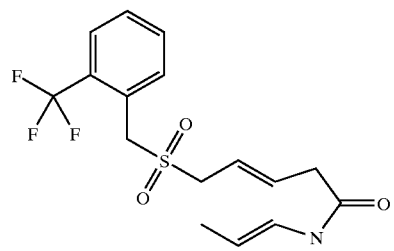

To a suspension of 5-zinc sulfinate-1,3-dihydro-indol-2-one (2 g, 4.4 mmol) in THF (14 mL) and water (7 mL) was added all at once 2-trifluoromethylbenzyl bromide (2.3 g, 9.7 mmol). The reaction mixture was stirred at 70° C. (oil bath) for 24 hours the reaction was complete TLC (70:30 $CH_2Cl_2$:MeOH, 60:40 EtOAc:hexane). The reaction mixture was cooled to room temperature, diluted with ethyl acetate, and separated from the water layer. The ethyl acetate solution was further washed with water and separated after which time the solvents were evaporated. The crude product was triturated with diethyl ether to provide 5-(2-trifluoromethylphenylmethanesulfonyl)-1,3-dihydro-indol-2-one (1.14 g, 73%) as an off white solid.

$^1$H-NMR (400 MHz, DMSO-$d_6$) δ 10.89 (br s, 1H, CONH), 7.75 (m, 1H, aromatic), 7.68 (m, 1H, aromatic), 7.58 (m, 1H, aromatic), 7.52 (m, 3H, aromatic), 6.98 (d, 1H, aromatic), 4.70 (s, 2H, $CH_2$), 3.58 (s, 2H, $CH_2$). MS m/z 354 [$M^+$–1].

Example 2

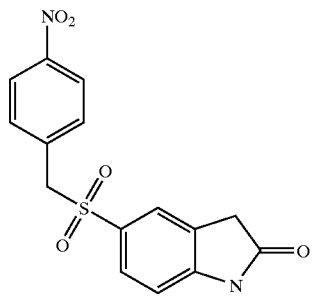

Synthesis of 5-(4-Nitrophenylmethanesulfonyl)-1,3-dihydro-indol-2-one

To a suspension of 5-zinc sulfinate-1,3-dihydro-indol-2-one (2 g, 4.4 mmol) in THF (14 mL) and water (7 mL) was added all at once 4-nitrobenzylbenzyl bromide (2.1 g, 9.7 mmol). The reaction mixture was stirred at 70° C. (oil bath) for 24 h. The reaction mixture was cooled to room temperature, diluted with ethyl acetate, and separated from the water layer. The ethyl acetate solution was further washed with water and separated after which time the solvents were evaporated. The crude product was triturated with diethyl ether to provide 5-(4-nitrophenylmethanesulfonyl)-1,3-dihydro-indol-2-one (1.14 g, 73%) as a yellow solid.

$^1$H-NMR (400 MHz, DMSO-d$_6$) δ 10.87 (br s, 1H, CONH), 8.18 (d, 2H, aromatic), 7.55 (m, 1H, aromatic), 7.49 (m, 1H, aromatic), 7.44 (d, 2H, aromatic), 6.93 (d, 2H, aromatic), 4.81 (s, 2H, CH$_2$), 3.56 (s, 2H, CH$_2$). MS m/z 331 [M$^+$−1].

Example 3

Synthesis of 3-(2-oxo-2,3-Dihydro-1H-indole-5-sulfonylmethyl)-benzonitrile

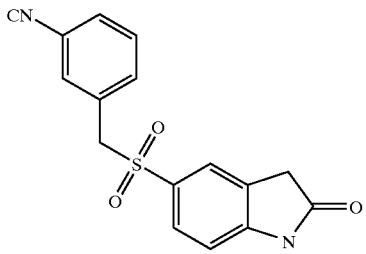

To a suspension of 5-zinc sulfinate-1,3-dihydro-indol-2-one (2 g, 4.4 mmol) in THF (14 mL) and water (7 mL) was added all at once 3-cyanobenzyl bromide (1.89 g, 9.7 mmol). The reaction mixture was stirred at 70° C. (oil bath) for 24 h. The reaction mixture was cooled to room temperature, diluted with ethyl acetate, and separated from the water layer. The ethyl acetate solution was further washed with water and separated after which time the solvents were evaporated. The crude product was triturated with diethyl ether to provide product 3-(2-oxo-2,3-dihydro-1H-indole-5-sulfonylmethyl)-benzonitrile (1.08 g, 79%) as a tan solid.

$^1$H-NMR (400 MHz, DMSO-d$_6$) δ 10.88 (br s, 1H, CONH), 7.82 (m, 1H, aromatic), 7.53 (multiplets, 5H, aromatic), 6.95 (d, 1H, aromatic), 4.70 (s, 2H, CH$_2$), 3.57 (s, 2H, CH$_2$). MS m/z 311 [M$^+$−1].

Example 4

Synthesis of 5-(2,4-Difluorophenylmethanesulfonyl)-1,3-dihydro-indol-2-one

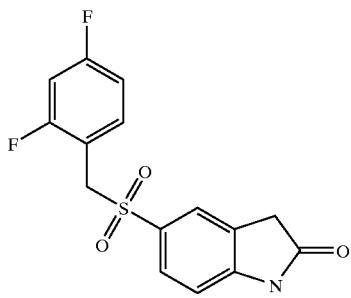

To a suspension of 5-zinc sulfinate-1,3-dihydro-indol-2-one (2 g, 4.4 mmol) in THF (14 mL) and water (7 mL) was added all at once 2,4-difluorobenzylbromide (2.01 g, 9.7 mmol). The reaction mixture was stirred at 70° C. (oil bath) for 24 h. The reaction mixture was cooled to room temperature, diluted with ethyl acetate, and separated from the water layer. The ethyl acetate solution was further washed with water and separated after which time the solvents were evaporated. The crude product was triturated with diethyl ether to provide product 5-(2,4-difluorophenylmethanesulfonyl)-1,3-dihydro-indol-2-one (1.02 g, 72%) as a tan solid.

$^1$H-NMR (400 MHz, DMSO-d$_6$) δ 10.88 (br s, 1H, CONH), 7.54 (s, 1H, aromatic), 7.45 (d, 1H, aromatic), 7.24 (multiplets, 2H, aromatic), 7.08 (m, 1H, aromatic), 6.95 (d, 1H, aromatic), 4.69 (s, 2H, CH$_2$), 3.54 (s, 2H, CH$_2$). MS m/z 322 [M$^+$−1].

Example 5

Synthesis of 5-Phenylmethanesulfonyl-1,3-dihydro-indol-2-one

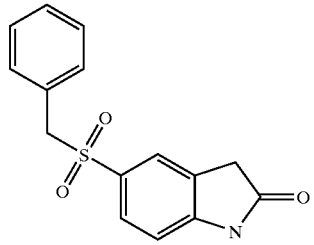

To a suspension of 5-zinc sulfinate-1,3-dihydro-indol-2-one (2 g, 4.4 mmol) in THF (14 mL) and water (7 mL) was added all at once benzyl bromide (1.6 g, 9.7 mmol). The reaction mixture was stirred at 70° C. (oil bath) for 24 hours. The reaction mixture was cooled to room temperature, diluted with ethyl acetate, and separated from the water layer. The ethyl acetate solution was further washed with water and separated after which time the solvents were evaporated. The crude product was triturated with diethyl ether to provide product 5-phenylmethanesulfonyl-1,3-dihydro-indol-2-one (1.07 g, 85%) as a cream solid.

$^1$H-NMR (400 MHz, DMSO-d$_6$) δ 10.84 (br s, 1H, CONH), 7.53 (multiplet, 1H, aromatic), 7.46 (dd, 1H, aromatic), 7.31 (m, 3H, aromatic), 7.16 (m, 2H, aromatic), 6.91 (d, 1H, aromatic), 4.58 (s, 2H, CH$_2$), 3.55 (s, 2H, CH$_2$). MS m/z 286 [M$^+$−1].

Example 6

Synthesis of 5-(2,6-Dimethyl-phenylmethanesulfonyl)-1,3-dihydro-indol-2-one

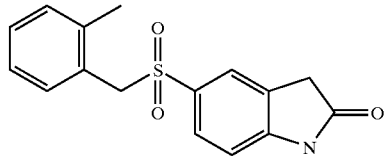

A mixture of 2,6-dimethylbenzylchloride (2 g, 13 mmol) and 5-zinc sulfinate-1,3-dihydro-indol-2-one (3 g, 6.5 mmol) in THF: H$_2$O (4:1) was stirred at room temperature for 30 mins, then at 75C for 36 hours. The reaction was diluted with ethyl acetate (500 mL), the organic layer was concentrated. The resulted waxy solid was triturated with ether to give a brown solid.

$^1$HNMR (400 MHz, DMSO d$_6$) δ 10.88 (s, 1H, NH), 7.6 (m, 2H), 7.12 (m, 1H), 7.0 (m, 3H), 4.58 (s, 2H, CH$_2$), 3.58 (s, 2H, CH$_2$), 2.24 (s, 6H, 2×CH$_3$). MS m/z 314.2 (M−1).

Example 7

5-(2,3-Dichloro-phenylmethanesulfonyl)-1,3-dihydro-indol-2-one

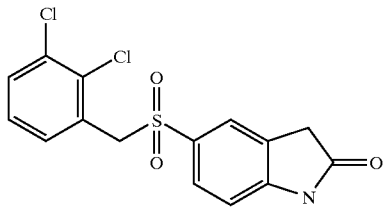

A mixture of 2,3-dichlorobenzylchloride (2 g, 10 mmol) and 5-zinc sulfinate-1,3-dihydro-indol-2-one (4.57 g, 10 mmol) in THF: H$_2$O (4:1) was stirred at room temperature for 2 hours, then at 75C for 36 hours. The reaction was diluted with ethyl acetate (500 mL), the organic layer was washed with water and then concentrated. The residue was triturated with ether to give 230 mg of 5-(2,3-dichlorophenylmethanesulfonyl)-1,3-dihydro-indol-2-one as a brown solid.

$^1$HNMR (400 MHz, DMSO d$_6$) δ 10.89 (s, 1H, NH), 7.63 (dd, J=1.6 & 8 Hz, 1H), 7.51 (br s, 1H), 7.47 (dd, 1H), 7.34 (t, J=8 Hz, 1H), 7.27 (dd, J=1.6 & 8 Hz, 1H), 6.93 (d, J=8 Hz, 1H), 4.76 (s, 2H, CH$_2$), 3.55 (s, 2H, CH$_2$). MS m/z 354 (M−1).

Example 8

5-(2,6-Dimethoxy-phenylmethanesulfonyl)-1,3-dihydro-indol-2-one

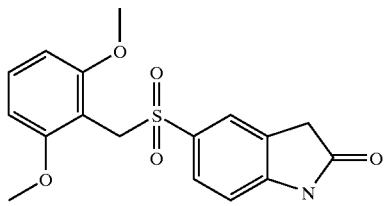

Similar procedure as above using 2,6-dimethoxybenzylchloride.

$^1$HNMR (400 MHz, CDCl$_3$) δ 9.17 (br s, 1H, NH), 7.57 (d, 1H), 7.50 (s, 1H), 7.22 (t, 1H), 6.91 (d, 1H), 6.43 (d, 2H), 4.59 (s, 2H), 3.56 (s, 6H, 2×OCH$_3$), 3.52 (s, 2H). MS m/z 346 [M−1].

Example 9

5-(3,5-Dimethoxy-phenylmethanesulfonyl)-1,3-dihydro-indol-2-one

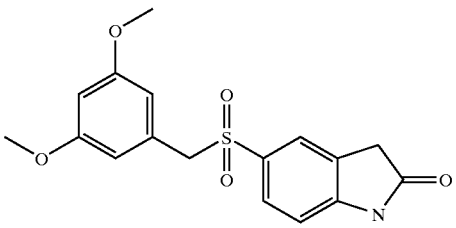

Similar procedure as above using 3,5-dimethoxybenzylchloride.

Example 10

5-[2-(2-Morpholin-4-yl-ethoxy)-phenylmethanesulfonyl]-1,3-dihydro-indol-2-one

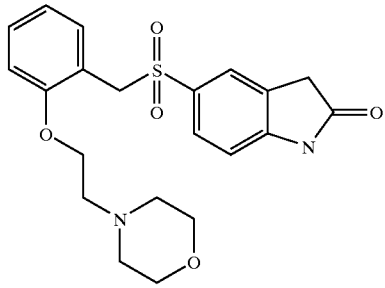

A mixture of 2-hydroxybenzyl alcohol (1.295 g, 10.4 mmol) and 4-(2-chloroethyl)morpholine hydrochloride (1.94 g, 10.4 mmol) in 2N NaOH (10.5 mL) was stirred at rt for 14 hours. The precipitate was collected by vacuum filtration, washed with 1N NaOH, redissolved in DCM and washed with 1N NaOH. The aqueous layer was extracted with more DCM (2×). The combined DCM was dried and concentrated to give [2-(2-morpholin-4-yl-ethoxy)-phenyl]-methanol which was used without further purification.

Thionyl chloride (5 mL, 2M in DCM) was added to a solution of [2-(2-morpholin-4-yl-ethoxy)-phenyl]-methanol (1.97 g, 8.3 mmol) in DCM (15 mL) at 0° C. The mixture was allowed to warm up to rt and stirred for 3 hours. The reaction was concentrated to give 4-[2-(2-chloromethyl-phenoxy)-ethyl]-morpholine hydrochloride.

$^1$H NMR (400 MHz, DMSO-d$_6$) δ 7.43 (dd, 1H), 7.37 9m, 1H), 7.07 (d, 1H), 7.0 (m, 1H), 4.81 (s, 2H), 4.5 (t, 2H), 3.96 (m, 2H), 3.85 (m, 2H), 3.59 (m, 2H), 3.52 (d, 2H), 3.27 (m, 2H).

A mixture of 5-chlorosulfonyl-2-oxindole (583 mg, 2.52 mmol), Na$_2$SO$_3$ (636 mg, 5.04 mmol) and Na$_2$HPO$_4$ (357 mg, 2.51 mmol) in water (5 mL) was heated to 65° C. for 14 hours. To the mixture was added 4-[2-(2-chloromethyl-phenoxy)-ethyl]-morpholine hydrochloride (655 mg, 2.24 mmol) and heating was continued for 4 more hours. The reaction was cooled to rt, poured into sat. NaHCO$_3$ and extracted with DCM (2×). The combined DCM was dried, concentrated and purified on a silica gel column to give 268 mg (26%) of 5-[2-(2-0orpholin-4-yl-ethoxy)-phenylmethanesulfonyl]-1,3-dihydro-indol-2-one as an off-white solid.

$^1$H NMR (400 MHz, CDCl$_3$) δ 8.11 (s, 1H, NH), 7.53 (dd, 1H), 7.41 (d, 1H), 7.28 (m, 1H), 7.21 (dd, 1H), 6.93 (t, 1H), 6.87 (d, 1H), 4.44 (s, 2H), 3.82 (t, 2H), 3.71 (m, 4H), 3.51 (s, 2H), 2.58 (t, 2H), 2.51 (m, 4H). MS m/z 415 [M−1].

Following the general procedure of 5-arylmethanesulfonyl-1,3-dihydroindol-2-one and using 5-zinc sulfinate-1,3-dihydro-indol-2-one and an appropriate benzyl halide the following compounds were prepared.

1. 5-(3-Methoxy-phenylmethanesulfonyl)-1,3-dihydro-indol-2-one

Cream solid, (1.07 g, 77%).

$^1$H-NMR (400 MHz, DMSO-d$_6$) δ 10.85 (br s, 1H, CONH), 7.75 (m, 1H, aromatic), 7.64 (m, 1H, aromatic), 7.23 (m, 1H, aromatic), 6.90 (m, 2H, aromatic), 6.70 (m, 2H, aromatic), 4.70 (s, 2H, CH$_2$), 3.56 (s, 2H, CH$_2$), 3.63 (s, 3H, OCH$_3$). MS m/z 316 [M$^+$−1].

2. 5-(3-Nitro-phenylmethanesulfonyl)-1,3-dihydro-indol-2-one

Tan solid, (1.03 g, 71%).

$^1$H-NMR (400 MHz, DMSO-d$_6$) δ 10.91 (br s, 1H, CONH), 8.42 (d, 1H, aromatic), 8.19 (d, 1H, aromatic), 7.49 (m, 2H, aromatic), 7.42 (dd, 1H, aromatic), 6.93 (d, 1H, aromatic), 5.10 (s, 2H, CH$_2$), 3.56 (s, 2H, CH$_2$). MS m/z 331 [M$^+$–1].

3. 5-(2-Nitro-phenylmethanesulfonyl)-1,3-dihydro-indol-2-one

Tan solid, (1.08 g, 74%).

$^1$H-NMR (400 MHz, DMSO-d$_6$) δ 10.90 (br s, 1H, CONH), 8.02 (dd, 1H, aromatic), 7.65 (m, 2H, aromatic), 7.45 (m, 2H, aromatic), 7.37 (dd, 1H, aromatic), 6.94 (d, 1H, aromatic), 5.05 (s, 2H, CH$_2$), 3.55 (s, 2H, CH$_2$). MS m/z 331 [M$^+$–1].

4. 5-(3-Trifluoromethoxy-phenylmethanesulfonyl)-1,3-dihydro-indol-2-one

Tan solid, (1.31 g, 81%).

$^1$H-NMR (400 MHz, DMSO-d$_6$) δ 10.86 (br s, 1H, CONH), 7.45 (m, 3H, aromatic), 7.32 (m, 1H, aromatic), 7.24 (d, 1H, aromatic), 7.09 (s, 1H, aromatic), 6.92 (d, 1H, aromatic), 4.69 (s, 2H, CH$_2$), 3.54 (s, 2H, CH$_2$). MS m/z 370 [M$^+$–1].

5. 5-(3-Bromo-phenylmethanesulfonyl)-1,3-dihydro-indol-2-one

Off white solid, (1.34 g, 83%).

$^1$H-NMR (400 MHz, DMSO-d$_6$) δ 10.88 (br s, 1H, CONH), 7.53 (m, 3H, aromatic), 7.35 (s, 1H, aromatic), 7.28 (t, 1H, aromatic), 7.16 (d, 1H, aromatic), 6.95 (d, 1H, aromatic), 4.59 (s, 2H, CH$_2$), 3.57 (s, 2H, CH$_2$). MS m/z 363 [M$^+$–3].

6. 5-(2,6-Difluorophenylmethanesulfonyl)-1,3-dihydro-indol-2-one

Off white solid, (1.12 g, 79%).

$^1$H-NMR (400 MHz, DMSO-d$_6$) δ 11.16 (br s, 1H, CONH), 7.50 (m, 3H, aromatic), 7.12 (t, 2H, aromatic), 6.95 (d, 1H, aromatic), 4.60 (s, 2H, CH$_2$), 3.55 (s, 2H, CH$_2$). MS m/z 322 [M$^+$–1].

7. 5-(3,5-Difluoro-phenylmethanesulfonyl)-1,3-dihydro-indol-2-one

Tan solid, (1.22 g, 86%).

$^1$H-NMR (400 MHz, DMSO-d$_6$) δ 10.89 (br s, 1H, CONH), 7.59 (s, 1H, aromatic), 7.49 (d, 1H, aromatic), 7.24 (m, 1H, aromatic), 6.95 (d, 1H, aromatic), 6.91 (m, 2H, aromatic), 4.68 (s, 2H, CH$_2$), 3.58 (s, 2H, CH$_2$). MS m/z 322 [M$^+$–1].

8. 5-(3,4-Difluoro-phenylmethanesulfonyl)-1,3-dihydro-indol-2-one

Red-pink solid, (1.21 g, 85%).

$^1$H-NMR (400 MHz, DMSO-d$_6$) δ 10.88 (br s, 1H, CONH), 7.56 (s, 1H, aromatic), 7.47 (d, 1H, aromatic), 7.37 (m, 1H, aromatic), 7.26 (m, 1H, aromatic), 6.95 (m, 2H, aromatic), 4.62 (s, 2H, CH$_2$), 3.58 (s, 2H, CH$_2$). MS m/z 322 [M$^+$–1].

9. 5-(2,4-Bis-trifluoromethyl-phenylmethanesulfonyl)-1,3-dihydro-indol-2-one

Tan solid, (1.51 g, 81%).

$^1$H-NMR (400 MHz, DMSO-d$_6$) δ 10.93 (br s, 1H, CONH), 8.00 (m, 2H, aromatic), 7.70 (s, 1H, aromatic), 7.54 (m, 2H, aromatic), 6.98 (d, 1H, aromatic), 4.85 (s, 2H, CH$_2$), 3.56 (s, 2H, CH$_2$). MS m/z 422 [M$^+$–1].

10. 5-(3,5-Bis-trifluoromethyl-phenylmethanesulfonyl)-1,3-dihydro-indol-2-one

Red-pink solid, (1.47 g, 79%).

$^1$H-NMR (400 MHz, DMSO-d$_6$) δ 10.92 (br s, 1H, CONH), 8.11 (m, 2H, aromatic), 7.76 (m, 2H, aromatic), 7.49 (m, 2H, aromatic), 6.95 (d, 1H, aromatic), 4.90 (s, 2H, CH$_2$), 3.54 (s, 2H, CH$_2$). MS m/z 422 [M$^+$–1].

11. 5-(2-Hydroxy-5-nitro-phenylmethanesulfonyl)-1,3-dihydro-indol-2-one

Orange-tan solid, (1.11 g, 72%).

$^1$H-NMR (400 MHz, DMSO-d$_6$) δ 10.86 (br s, 1H, CONH), 8.08 (dd, 1H, aromatic), 8.03 (s, 1H, aromatic), 7.46 (m, 2H, aromatic), 6.95 (m, 2H, aromatic), 4.57 (s, 2H, CH$_2$), 3.54 (s, 2H, CH$_2$). MS m/z 347 [M$^+$–1].

12. 5-(2-Methoxy-5-nitro-phenylmethanesulfonyl)-1,3-dihydro-indol-2-one

Tan solid, (1.13 g, 71%).

$^1$H-NMR (400 MHz, DMSO-d$_6$) δ 10.85 (br s, 1H, CONH), 8.23 (m, 1H, aromatic), 8.11 (s, 1H, aromatic), 7.45 (s, 1H, aromatic), 7.38 (m, 1H, aromatic), 7.10 (d, 1H, aromatic), 6.88 (m, 1H, aromatic), 4.63 (s, 2H, CH$_2$), 3.54 (s, 2H, CH$_2$). m/z 361 [M$^+$–1].

13. 5-(2-Fluoro-phenylmethanesulfonyl)-1,3-dihydro-indol-2-one

Off white solid, (1.19 g, 89%).

$^1$H-NMR (400 MHz, DMSO-d$_6$) δ 10.87 (br s, 1H, CONH), 7.51 (multiplets, 2H, aromatic), 7.48 (m, 1H, aromatic), 7.37 (m, 1H, aromatic), 7.25 (m, 2H, aromatic), 6.93 (d, 1H, aromatic), 5.05 (s, 2H, CH$_2$), 3.55 (s, 2H, CH$_2$), MS m/z 304 [M$^+$–1].

14. 5-(3-Fluoro-phenylmethanesulfonyl)-1,3-dihydro-indol-2-one

Tan solid, (1.01 g, 76%).

$^1$H-NMR (400 MHz, DMSO-d$_6$) δ 10.87 (br s, 1H, CONH), 7.56 (m, 1H, aromatic), 7.50 (m, 1H, aromatic), 7.35 (m, 1H, aromatic), 7.18 (m, 1H, aromatic), 7.00 (m, 3H, aromatic), 4.63 (s, 2H, CH$_2$), 3.56 (s, 2H, CH$_2$), MS m/z 304 [M$^+$–1].

15. 5-(4-Fluoro-phenylmethanesulfonyl)-1,3-dihydro-indol-2-one

Off white solid, (1.17 g, 88%).

$^1$H-NMR (400 MHz, DMSO-d$_6$) δ 10.85 (br s, 1H, CONH), 7.53 (m, 1H, aromatic), 7.47 (m, 1H, aromatic), 7.18 (m, 4H, aromatic), 6.92 (m, 1H, aromatic), 4.58 (s, 2H, CH$_2$), 3.56 (s, 2H, CH$_2$). MS m/z 304 [M$^+$–1].

16. 5-(4-Trifluoromethoxy-phenylmethanesulfonyl)-1,3-dihydro-indol-2-one

Off white solid, (1.29 g, 79%).

$^1$H-NMR (400 MHz, DMSO-d$_6$) δ 10.86 (br s, 1H, CONH), 7.52 (m, 2H, aromatic), 7.33 (m, 4H, aromatic), 6.93 (d, 1H, aromatic), 4.67 (s, 2H, CH$_2$), 3.55 (s, 2H, CH$_2$). MS m/z 370 [M$^+$–1].

17. 5-(3-Trifluoromethyl-phenylmethanesulfonyl)-1,3-dihydro-indol-2-one

Off white solid, (1.21 g, 78%).

$^1$H-NMR (400 MHz, DMSO-d$_6$) δ 10.88 (br s, 1H, CONH), 7.70 (d, 1H, aromatic), 7.57 (t, 1H, aromatic), 7.47 (m, 3H, aromatic), 7.42 (s, 1H, aromatic), 6.94 (d, 1H, aromatic), 4.74 (s, 2H, CH$_2$), 3.54 (s, 2H, CH$_2$), ), MS m/z 354 [M$^+$–1].

18. 5-(4-Trifluoromethyl-phenylmethanesulfonyl)-1,3-dihydro-indol-2-one

Off white solid, (1.14 g, 73%).

$^1$H-NMR (400 MHz, DMSO-d$_6$) δ 10.87 (br s, 1H, CONH), 7.69 (d, 2H, aromatic), 7.55 (s, 1H, aromatic), 7.49 (d, 1H, aromatic), 7.40 (d, 2H, aromatic), 6.93 (d, 1H, aromatic), 4.74 (s, 2H, CH$_2$), 3.56 (s, 2H, CH$_2$). MS m/z 354 [M$^+$–1].

19. 4-(2-Oxo-2,3-dihydro-1H-indole-5-sulfonylmethyl)-benzoic Acid

Cream solid, (1.04 g, 72%).

$^1$H-NMR (400 MHz, DMSO-d$_6$) δ 13.00 (br s, 1H, COOH), 10.86 (br s, 1H, CONH), 7.86 (d, 2H, aromatic), 7.57 (s, 1H, aromatic), 7.47 (d, 1H, aromatic), 7.27 (d, 2H, aromatic), 6.93 (d, 1H, aromatic), 4.69 (s, 2H, $CH_2$), 3.56 (s, 2H, $CH_2$), MS m/z 330 [$M^+$–1].

20. [4-(2-Oxo-2,3-dihydro-1H-indole-5-sulfonylmethyl)-phenyl]-acetic Acid

Cream solid, (1.18 g, 78%).

$^1$H-NMR (400 MHz, DMSO-$d_6$) δ 12.34 (br s, 1H, COOH), 10.84 (br s, 1H, CONH), 7.53 (m, 1H, aromatic), 7.47 (m, 1H, aromatic), 7.18 (d, 2H, aromatic), 7.09 (d, 2H, aromatic), 6.93 (d, 1H, aromatic), 4.54 (s, 2H, $CH_2$), 3.54 (s, 2H, $CH_2$), 3.33 (s, 2H, $CH_2$). MS m/z 344 [$M^+$–1].

21. 3-Nitro-4-(2-oxo-2,3-dihydro-1H-indole-5-sulfonylmethyl)-benzoic Acid

Cream solid, (1.17 g, 71%).

$^1$H-NMR (400 MHz, DMSO-$d_6$) δ 13.75 (br s, 1H, COOH), 10.91 (br s, 1H, CONH), 8.42 (m, 1H, aromatic), 8.19 (dd, 1H, aromatic), 7.49 (m, 3H, aromatic), 6.95 (d, 1H, aromatic), 5.15 (s, 2H, $CH_2$), 3.56 (s, 2H, $CH_2$). MS m/z 375 [$M^+$–1].

22. 5-Pentafluorophenylmethanesulfonyl-1,3-dihydro-indol-2-one

Pinkish-tan solid, (1.36 g, 82%).

$^1$H-NMR (400 MHz, DMSO-$d_6$) δ 10.91 (br s, 1H, CONH), 7.63 (s, 1H, aromatic), 7.59 (d, 1H, aromatic), 6.97 (d, 1H, aromatic), 4.74 (s, 2H, $CH_2$), 3.59 (s, 2H, $CH_2$). MS m/z 376 [$M^+$–1].

23. 5-(2,5-Difluoro-phenylmethanesulfonyl)-1,3-dihydro-indol-2-one

Pinkish-tan solid, (1.02 g, 72%).

$^1$H-NMR (400 MHz, DMSO-$d_6$) δ 10.88 (br s, 1H, CONH), 7.56 (s, 1H, aromatic), 7.51 (d, 1H, aromatic), 7.25 (m, 2H, aromatic), 7.10 (m, 1H, aromatic), 6.95 (d, 1H, aromatic), 4.61 (s, 2H, $CH_2$), 3.57 (s, 2H, $CH_2$). MS m/z 322 [$M^+$–1].

24. 5-(2,3,6-Trifluoro-phenylmethanesulfonyl)-1,3-dihydro-indol-2-one

Tan solid, (1.23 g, 82%).

$^1$H-NMR (400 MHz, DMSO-$d_6$) δ 10.90 (br s, 1H, CONH), 7.58 (m, 3H, aromatic), 7.16 (m, 1H, aromatic), 6.97 (d, 1H, aromatic), 4.67 (s, 2H, $CH_2$), 3.58 (s, 2H, $CH_2$). MS m/z 340 [$M^+$–1].

25. 5-(2,3-Difluoro-phenylmethanesulfonyl)-1,3-dihydro-indol-2-one

Tan solid, (1.25 g, 88%).

$^1$H-NMR (400 MHz, DMSO-$d_6$) δ 10.89 (br s, 1H, CONH), 7.57 (s, 1H, aromatic), 7.51 (d, 1H, aromatic), 7.44 (m, 1H, aromatic), 7.19 (m, 1H, aromatic), 7.03 (t, 1H, aromatic), 6.95 (d, 1H, aromatic), 4.68 (s, 2H, $CH_2$), 3.57 (s, 2H, $CH_2$). MS m/z 322 [$M^+$–1].

26. 5-(2,6-Dichloro-phenylmethanesulfonyl)-1,3-dihydro-indol-2-one

Cream solid, (1.31 g, 84%).

$^1$H-NMR (400 MHz, DMSO-$d_6$) δ 10.90 (br s, 1H, CONH), 7.57 (d, 2H, aromatic), 7.52 (d, 2H, aromatic), 7.42 (m, 1H, aromatic), 6.96 (d, 1H, aromatic), 4.83 (s, 2H, $CH_2$), 3.59 (s, 2H, $CH_2$). MS m/z 354 [$M^+$–1].

27. 5-(Biphenyl-2-ylmethanesulfonyl)-1,3-dihydro-indol-2-one

Pinkish-tan solid, (1.12 g, 71%).

$^1$H-NMR (400 MHz, DMSO-$d_6$) δ 10.86 (br s, 1H, CONH), 7.40 (m, 6H, aromatic), 7.17 (m, 3H, aromatic), 7.10 (m, 2H, aromatic), 6.83 (d, 1H, aromatic), 4.53 (s, 2H, $CH_2$), 3.46 (s, 2H, $CH_2$). MS m/z 362 [$M^+$–1].

28. 5-(2-Fluoro-6-nitro-phenylmethanesulfonyl)-1,3-dihydro-indol-2-one

Cream solid, (1.29 g, 84%).

$^1$H-NMR (400 MHz, DMSO-$d_6$) δ 10.92 (br s, 1H, CONH), 7.96 (d, 1H, aromatic), 7.70 (m, 2H, aromatic), 7.51 (d, 1H, aromatic), 7.47 (s, 1H, aromatic), 6.96 (d, 1H, aromatic), 5.01 (s, 2H, $CH_2$), 3.57 (s, 2H, $CH_2$). MS m/z 349 [$M^+$–1].

28. 5-[3-(4-Fluoro-phenoxy)-phenylmethanesulfonyl]-1,3-dihydro-indol-2-one

Tan solid, (1.45 g, 83%).

$^1$H-NMR (400 MHz, DMSO-$d_6$) δ 10.89 (br s, 1H, CONH), 7.53 (s, 1H, aromatic), 7.44 (m, 1H, aromatic), 7.32 (t, 1H, aromatic), 7.19 (m, 2H, aromatic), 6.94 (m, 5H, aromatic), 6.65 (m, 1H, aromatic), 4.58 (s, 2H, $CH_2$), 3.54 (s, 2H, $CH_2$). MS m/z 396 [$M^+$–1].

30. 5-(3,5-Dibromo-2-hydroxy-phenylmethanesulfonyl)-1,3-dihydro-indol-2-one

Orangish-tan solid, (1.64 g, 81%).

$^1$H-NMR (400 MHz, DMSO-$d_6$) δ 10.89 (br s, 1H, CONH), 9.69 (s, 1H, OH), 7.71 (s, 1H, aromatic), 7.51 (m, 2H, aromatic), 7.16 (s, 1H, aromatic), 6.96 (d, 1H, aromatic), 4.62 (s, 2H, $CH_2$), 3.32 (s, 2H, $CH_2$). MS m/z 458, 460, 461 [$M^+$–1].

31. 5-(2,3,5-Trifluoro-phenylmethanesulfonyl)-1,3-dihydro-indol-2-one

Pinkish-tan solid, (1.30 g, 87%).

$^1$H-NMR (400 MHz, DMSO-$d_6$) δ 10.91 (br s, 1H, CONH), 7.51 (m, 3H, aromatic), 6.97 (m, 2H, aromatic), 4.71 (s, 2H, $CH_2$), 3.58 (s, 2H, $CH_2$). MS m/z 340 [$M^+$–1].

32. 4-Methyl-5-phenylmethanesulfonyl-1,3-dihydro-indol-2-one

Tan solid, (913 mg, 69%).

$^1$H-NMR (400 MHz, DMSO-$d_6$) δ 10.78 (br s, 1H, CONH), 7.47 (d, 1H, aromatic), 7.28 (m, 3H, aromatic), 7.12 (m, 2H, aromatic), 6.75 (d, 1H, aromatic), 4.53 (s, 2H, $CH_2$), 3.53 (s, 2H, $CH_2$), 2.38 (s, 3H, $CH_3$). MS m/z 300 [$M^+$–1].

33. 5-(2-Fluoro-phenylmethanesulfonyl)-4-methyl-1,3-dihydro-indol-2-one

Off-white solid, (940 mg, 67%).

$^1$H-NMR (400 MHz, DMSO-$d_6$) δ 10.81 (br s, 1H, CONH), 7.50 (d, 1H, aromatic), 7.38 (m, 1H, aromatic), 7.25 (m, 1H, aromatic), 7.16 (m, 2H, aromatic), 6.75 (d, 1H, aromatic), 4.59 (s, 2H, $CH_2$), 3.55 (s, 2H, $CH_2$), 2.43 (s, 3H, $CH_2$). MS m/z 318 [$M^+$–1].

33. 2-(2-Oxo-2,3-dihydro-1H-indole-5-sulfonylmethyl)-benzonitrile

Creamish-tan solid, (1.08 g, 79%).

$^1$H-NMR (400 MHz, DMSO-$d_6$) δ 10.90 (br s, 1H, CONH), 7.84 (dd, 1H, aromatic), 7.69 (td, 1H, aromatic), 7.56 (td, 1H, aromatic), 7.49 (m, 2H, aromatic), 7.39 (d, 1H, aromatic), 6.96 (d, 1H, aromatic), 4.74 (s, 2H, $CH_2$), 3.56 (s, 2H, $CH_2$). MS m/z 311 [$M^+$–1].

34. 5-(3-Chloro-phenylmethanesulfonyl)-1,3-dihydro-indol-2-one

Tan solid (1.02 g, 72%).

$^1$H-NMR (400 MHz, DMSO-$d_6$) δ 10.88 (br s, 1H, CONH), 8.06 (m, 1H, aromatic), 7.54 (s, 1H, aromatic), 7.30 (m, 1H, aromatic), 7.39 (m, 1H, aromatic), 7.24 (s, 1H, aromatic), 7.11 (d, 1H, aromatic), 6.95 (d, 1H, aromatic), 4.63 (s, 2H, $CH_2$), 3.57 (s, 2H, $CH_2$). MS m/z 318 [$M^+$–3].

36. 4-(2-Oxo-2,3-dihydro-1H-indole-5-sulfonylmethyl)-benzoic Acid Methyl Ester

Tan solid (1.18 g, 78%).

$^1$H-NMR (400 MHz, DMSO-$d_6$) δ 10.86 (br s, 1H, CONH), 7.88 (d, 1H, aromatic), 7.56 (s, 1H, aromatic), 7.46 (d, 2H, aromatic), 7.30 (d, 2H, aromatic), 6.91 (d, 1H, aromatic), 4.70 (s, 2H, $CH_2$), 3.83 (s, 3H, $CH_3$), 3.57 (s, 2H, $CH_2$). MS m/z 344 [$M^+$–1].

37. 3-(2-Oxo-2,3-dihydro-1H-indole-5-sulfonylmethyl)-benzoic Acid Methyl Ester

Tan solid (1.12 g, 74%).

$^1$H-NMR (400 MHz, DMSO-d$_6$) δ 10.86 (br s, 1H, CONH), 7.91 (m, 1H, aromatic), 7.77 (s, 1H, aromatic), 7.54 (s, 1H, aromatic), 7.45 (m, 3H, aromatic), 6.93 (d, 1H, aromatic), 4.70 (s, 2H, CH$_2$), 3.84 (s, 3H, CH$_3$), 3.57 (s, 2H, CH$_2$). MS m/z 344 [M$^+$−1].

38. 5-(2,4-Bis-trifluoromethyl-phenylmethanesulfonyl)-1,3-dihydro-indol-2-one

Tan solid (1.56 g, 84%).

$^1$H-NMR (400 MHz, DMSO-d$_6$) δ 10.92 (br s, 1H, CONH), 8.13 (d, 1H, aromatic), 8.06 (s, 1H, aromatic), 7.76 (d, 1H, aromatic), 7.57 (m, 2H, aromatic), 7.00 (d, 1H, aromatic), 4.83 (s, 2H, CH$_2$), 3.58 (s, 2H, CH$_2$). MS m/z 422 [M$^+$−1].

39. 5-(2-Chloro-phenylmethanesulfonyl)-1,3-dihydro-indol-2-one

Tan solid (1.12 g, 79%).

$^1$H-NMR (400 MHz, DMSO-d$_6$) δ 10.87 (br s, 1H, CONH), 7.40 (m, 5H, aromatic), 7.09 (m, 1H, aromatic), 6.94 (m, 1H, aromatic), 4.68 (s, 2H, CH$_2$), 3.58 (s, 2H, CH$_2$). MS m/z 320 [M$^+$−1].

40. 5-(1-Phenyl-ethanesulfonyl)-1,3-dihydro-indol-2-one $^1$H-NMR (400 MHz, DMSO-d$_6$) δ 10.84 (br s, 1H, CONH), 7.40 (m, 2H, aromatic), 7.30 (m, 3H, aromatic), 7.22 (m, 2H, aromatic), 6.89 (d, 1H, aromatic), 4.60 (q, 1H, CH), 3.55 (d, 2H, CH$_2$), 1.53 (d, 3H, CH$_3$). MS m/z 300 [M$^+$−1].

B. Syntheses of Pyrrole Aldehydes

Example 1

Synthesis of 5-Formyl-2,4-dimethyl-1H-pyrrole-3-carboxylic Acid (Pyrrole Aldehyde-1)

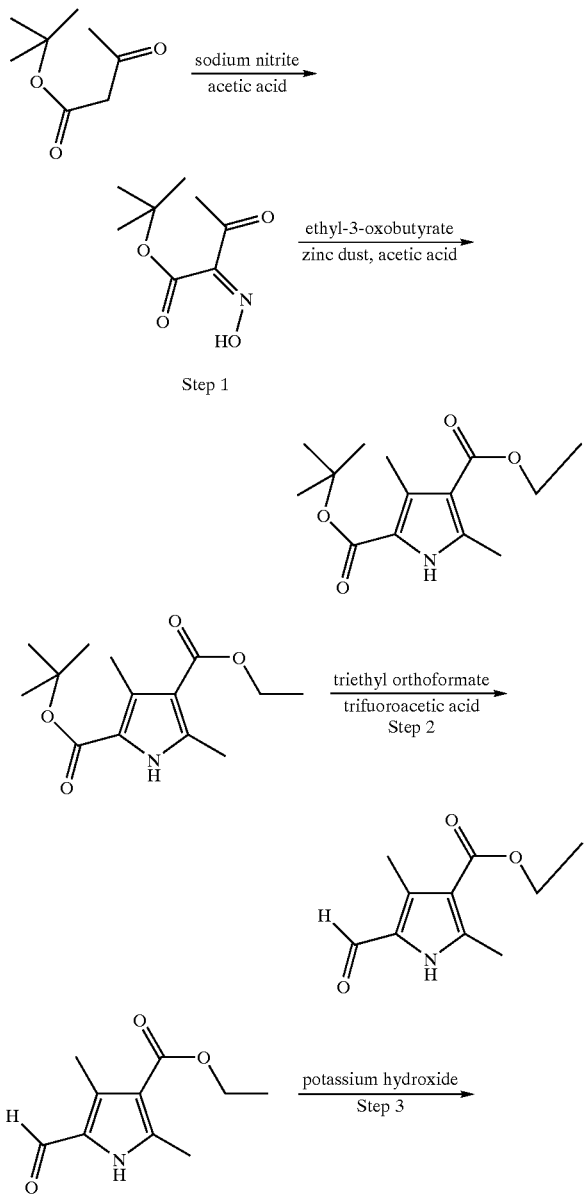

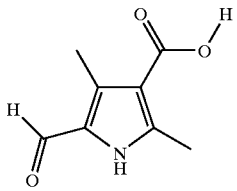

tert-Butyl-3-oxobutyrate (158 g, 1 mol) was dissolved in 200 mL of acetic acid in a 500 mL 3-neck round bottom flask equipped with a thermometer, addition funnel and mechanical stirring. The mixture was cooled in an ice bath to about 10° C. Sodium nitrite (69 g, 1 mol) was added over 75 minutes keeping the temperature under 15° C. The cold bath was removed and the mixture stirred for 30 minutes and then allowed to stand for 3.5 hours to give t-butyl-2-hydroximino-3-oxobutyrate.

Ethyl-3-oxobutyrate (130 g, 1 mol) was dissolved in 400 mL of acetic acid in a 2 L 3-neck round bottom flask equipped with a thermometer, an addition funnel, mechanical stirring and placed in an oil bath. Zinc dust (50 g, 0.76 mol) was added and the mixture heated to 60° C. with stirring. The crude t-butyl-2-hydroximino-3-oxobutyrate solution prepared above was cautiously added keeping the temperature at about 65° C. by slowing the addition and cooling the flask. More zinc dust (4×50 g, 3.06 mol) was added in portions during the addition with the last portion added after all the t-butyl ester had been added. The temperature of the mixture reached a maximum of 80° C. At the end of the additions the temperature was 64° C. The temperature was increased by heating to 70–75° C. for one hour and then poured into 5 L of water. The gray floating precipitate was collected by vacuum filtration and washed with 2 L of water to give 354 g of wet crude product. The crude product was dissolved in 1 L of hot methanol and hot filtered to remove zinc. The filtrate was cooled to give a precipitate that was collected by vacuum filtration to give 118 g of product. The filtrate was put in the refrigerator overnight to give a total of 173.2 g of 3,5-dimethyl-1H-pyrrole-2,4-dicarboxylic acid 2-tert-butyl ester 4-ethyl ester. 3,5-Dimethyl-1H-pyrrole-2,4-dicarboxylic acid 2-tert-butyl ester 4-ethyl ester (80.1 g, 0.3 mol) and 400 mL of trifluoroacetic acid were stirred for 5 minutes in a 2 L 3-neck round bottom flask equipped with mechanical stirring and warmed to 40° C. in an oil bath. The mixture was then cooled to −5° C. and triethyl orthoformate (67.0 g, 0.45 mol) was added all at once. The temperature increased to 15° C. The mixture was stirred for about 1 minute, removed from the cold bath and then stirred for 1 hour. The trifluoroacetic acid was removed by rotary evaporation and the residue put in the refrigerator where it solidified. The solid was dissolved by warming and poured into 500 g of ice. The mixture was extracted with 800 mL of dichloromethane to give a red solution and a brown precipitate, both of which were saved. The precipitate was isolated and washed with 150 mL of saturated sodium bicarbonate solution. The dichloromethane phase was washed with 150 mL of sodium bicarbonate and both bicarbonate solutions discarded. The dichloromethane solution was washed with 3 times with 100 mL of water each time. The dichloromethane solution was evaporated to dryness and the dark residue recrystallized twice from hot ethyl acetate after decolorizing with Darco to give golden yellow needles. The brown precipitate was recrystallized from 350 mL of hot ethyl acetate after decolorizing with Darco to give a yellow-red solid. All the recrystallized solids were combined and recrystallized from 500 mL of hot ethanol to give 37.4 g (63.9%) of 5-formyl-2,4-dimethyl-1H-pyrrole-3-carboxylic acid ethyl ester as yellow needles (mp 165.6–166.3° C., lit. 163–164° C.). The evaporated residues from the ethyl acetate and ethanol mother liquors were recrystallized from 500 mL of ethanol to give 10.1 g (17.1%) of a second crop of dirty yellow needles.

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH3. The solid was collected by filtration, washed with water and dried in a vacuum oven overnight to give 1.6 g (93%) of 5-formyl-2,4-dimethyl-1H-pyrrole-3-carboxylic acid.

$^1$H NMR (300 MHz, DMSO-$d_6$) δ 12.09 (s, br, 2H, NH & COOH), 9.59 (s, 1H, CHO), 2.44 (s, 3H, CH$_3$), 2.40 (s, 3H, CH$_3$). MS m/z 167 (M$^+$).

Example 2

Synthesis of 5-Aminocarbonyl-2,4-dimethyl-1H-pyrrole-3-carboxylic Acid General Amidation Procedure

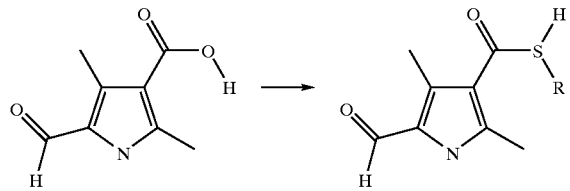

5-Formyl-2,4-dimethyl-1H-pyrrole-3-carboxylic acid is dissolved in DMF (0.3M) with stirring. To the solution is added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution is stirred for 12 h, and then DMF solvent was removed. The residue was purified on a silica gel column eluting with 1–5% methanol in dichloromethane to provide the product.

(a) Synthesis of 3,5-Dimethyl-4-(4-methyl-piperazine-1-carbonyl)-1H-pyrrole-2-carbaldehyde (Pyrrole Aldehyde-2)

5-Formyl-2,4-dimethyl-1H-pyrrole-3-carboxylic acid (5 g, 29.9 mmol) reacted with N-methylpiperazine (4.0 mL) to give 5.3 g (72%) of 3,5-imethyl-4-(4-methyl-piperazine-1-carbonyl)-1H-pyrrole-2-carbaldehyde.

$^1$H NMR (360 MHz, DMSO-$d_6$) δ 11.82 (s, 1H, NH), 9.50 (s, 1H, CHO), 3.14 (br m, 4H, 2×CH$_2$), 2.29 (br m, 4H, 2×CH$_2$), 2.19 (s, 3H, CH$_3$), 2.17 (s, 3H, 3H, CH$_3$). MS m/z 249 [M]$^+$.

(b) 5-Formyl-2,4-dimethyl-1H-pyrrole-3-carboxylic Acid (2-Diethylamino-ethyl)-amide (Pyrrole Aldehyde 3)

5-Formyl-2,4-dimethyl-1H-pyrrole-3-carboxylic acid (5 g, 2.99 mmol) reacted with N,N-diethylethylenediamine (4.62 mL) to give 6.19 g (78%) of 5-formyl-2,4-dimethyl-1H-pyrrole-3-carboxylic acid (2-diethylamino-ethyl)-amide.

$^1$H NMR (360 MHz, DMSO-d$_6$) δ 11.7 (br s, 1H, NH), 9.52 (s, 1H, CHO), 7.27 (m, 1H, CONH), 3.2 (m, 2H, NCH$_2$), 2.5 (m, 6H, 3×NCH$_2$), 2.35 (s, 3H, CH$_3$), 2.30 (s, 3H, CH$_3$), 0.95 (t, J=6.7 Hz, 6H, 2×NCH$_2$CH$_3$). MS m/z 266 (M$^+$+1).

(c) 5-Formyl-2,4-dimethyl-1H-pyrrole-3-carboxylic Acid (2-pyrrolidin-1-yl-ethyl)-amide (Pyrrole Aldehyde-4)

5-Formyl-2,4-dimethyl-1H-pyrrole-3-carboxylic acid (5 g, 29.9 mmol) reacted with 1-(2-aminoethyl)pyrrolidine (4.1 g, 35.9 mmol) to give 5.7 g (73%) of 5-formyl-2,4-dimethyl-1H-pyrrole-3-carboxylic acid (2-pyrrolidin-1-yl-ethyl)-amide.

$^1$H NMR (360 MHz, DMSO-d$_6$) δ 11.79 (br s, 1H, NH), 9.53 (s, 1H, CHO), 7.41 (m, 1H, CONH), 3.28–3.34 (m, 2H, NCH$_2$), 2.53–2.60 (m, 6H, NCH$_2$ and 2×NCH$_2$CH$_2$) 2.35 (s, 3H, CH$_3$), 2.3 (s, 3H, CH$_3$), 1.68 (m, 4H, 2×CH$_2$). MS m/z 264.1 (M$^+$).

(d) Synthesis of 5-Formyl-2,4-dimethyl-1H-pyrrole-3-carboxylic Acid (2-[1,2,3]Triazol-1-yl-ethyl)-amide (Pyrrole Aldehyde-5)

5-Formyl-2,4-dimethyl-1H-pyrrole-3-carboxylic acid (2 g, 11.96 mmol) reacted with 2-[1,2,3]triazol-1-yl-ethylamine (2.66 g, 14.36 mmol) to give 3.05 g (98%) of 5-formyl-2,4-dimethyl-1H-pyrrole-3-carboxylic acid (2-[1,2,3]triazol-1-yl-ethyl)-amide.

$^1$H NMR (360 MHz, DMSO-d$_6$) δ 11.83 (br s, 1H, NH), 9.52 (s, 1H, CHO), 8.12 (d, 1H, J=1.3 Hz, triazole hydrogen), 7.72 (d, 1H, J=1.27 Hz, triazole hydrogen), 7.63 (t, 1H, J=5.6 Hz, CONH), 4.55 (m, 2H, NCH$_2$), 3.66 (m, 2H, CH$_2$), 2.26 (s, 3H, CH$_3$), 2.21 (s, 3H, CH$_3$). MS m/z 262 (M$^+$+1).

(e) Synthesis of 3,5-Dimethyl-4-[(3R,5S)-3,5-dimethyl-piperazine-1-carbonyl]-1H-pyrrole-2-carbaldehyde (Pyrrole Aldehyde-6)

5-Formyl-2,4-dimethyl-1H-pyrrole-3-carboxylic acid (2 g, 11.96 mmol) reacted with cis-2,6-dimethylpiperazine (2.66 g, 14.36 mmol) to give 2.27 g (72%) of 3,5-dimethyl-4-[(3R,5S)-3,5-dimethyl-piperazine-1-carbonyl]-1H-pyrrole-2-carbaldehyde.

$^1$H NMR (360 MHz, DMSO-d$_6$) δ 11.84 (br s, 1H, NH), 9.51 (s, 1H, CHO), 4.30 (br s, 1H, NH), 2.50 (m, 4H, 2×CH$_2$), 2.28 (m, 8H, 2×CH$_3$ and 2×CH), 0.96 (m, 6H 2×CH$_3$). MS m/z 264 (M$^+$+1).

(f) 5-Formyl-2,4-dimethyl-1H-pyrrole-3-carboxylic Acid (3-Diethylamino-propyl)-amide (Pyrrole Aldehyde-7).

5-Formyl-2,4-dimethyl-1H-pyrrole-3-carboxylic acid (3.0 g, 17.9 mmol) reacted with diethylamino propylamine (2.57 g, 19.7 mmol) to give 3.19 g (64%) of 5-formyl-2,4-dimethyl-1H-pyrrole-3-carboxylic acid (3-diethylamino-propyl)-amide.

$^1$H NMR (360 MHz, DMSO-d$_6$) δ 11.78 (br s, 1H, NH), 9.52 (s, 1H, CHO), 7.5 (m, 1H, CONH), 3.21 (q, J=6.4 Hz, 2H, NCH$_2$CH$_3$), 2.5 (m, 6H, NCH$_2$CH$_3$ and 2×NCH$_2$), 2.35 (s, 3H, CH$_3$), 2.29 (s, 3H, CH$_3$), 1.63 (m, 2H, CH$_2$), 0.96 (t, J=6.8 Hz, 6H, NCH$_2$CH$_3$). MS m/z 280 (M$^+$+1).

(g) Synthesis of 5-Formyl-2,4-dimethyl-1H-pyrrole-3-carboxylic Acid (2-Diisopropylamino-ethyl)-amide (Pyrrole Aldehyde-8)

5-Formyl-2,4-dimethyl-1H-pyrrole-3-carboxylic acid (3.0 g, 17.9 mmol) reacted with diisopropylamino ethylamine (3.56 mL, 19.7 mmol) to give 4.93 g (94%) of 5-formyl-2,4-dimethyl-1H-pyrrole-3-carboxylic acid (3-diisopropylamino-ethyl)-amide.

$^1$H NMR (360 MHz, DMSO-d$_6$) δ 11.78 (br s, 1H, NH), 9.54 (s, 1H, CHO), 7.29 (m, 1H, CONH), 3.15 (m, 2H, CH$_2$), 2.51 (m, 4H, CH$_2$ and 2×CH), 2.38 (s, 3H, CH$_3$), 2.32 (s, 3H, CH$_3$), 0.97 (d, 12H, 4×CH$_3$). MS m/z 294 (M$^+$+1).

(h) Synthesis of 3,5-Dimethyl-4-[3-[(3R,5S)-3,5-dimethyl-piperazin-1-yl)]-3-oxo-propyl]-1H-pyrrole-2-carbaldehyde (Pyrrole Aldehyde-24)

3-(5-Formyl-2,4-dimethyl-1H-pyrrol-3-yl)-propionic acid (1.37 g, 6.50 mmol) reacted with cis-2,6-dimethylpiperazine (822 mg, 7.15 mmol) to give 1.42 g (75%) of 3,5-dimethyl-4-[3-[(3R,5S)-3,5-dimethyl-piperazin-1-yl)]-3-oxo-propyl]-1H-pyrrole-2-carbaldehyde.

$^1$HNMR (400 MHz, DMSO-d$_6$) δ 11.39 (br s, 1H, NH), 9.42 (s, 1H, CHO), 4.25 (m, 1H, CH$_2$), 3.54 (m, 1H, CH$_2$), 2.54 (m, 2H, CH$_2$), 2.45 (m, 2H, 2×CH), 2.36 (m, 4H, 2×CH$_2$), 2.20 (s, 3H, CH$_3$), 2.14 (s, 3H, CH$_3$), 1.94 (t, 1H, J=11.5 Hz, NH), 0.93 (d, 3H, J=5.9 Hz, CH$_3$), 0.88 (d, 3H, J=5.6 Hz, CH$_3$). MS m/z 292 [M$^+$+1].

Example 3

Synthesis of 5-Formyl-4-methyl-1H-pyrrole-3-carboxylic Acid (Pyrrole Aldehyde-9)

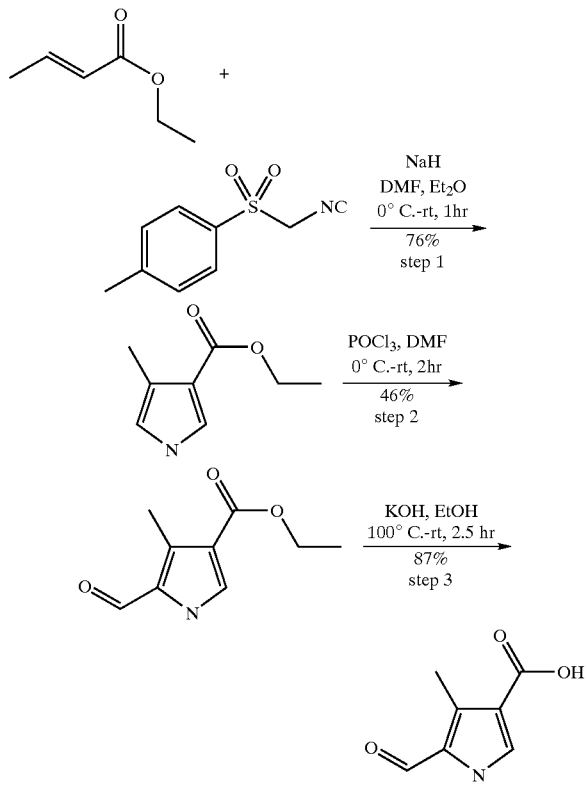

To a suspension of sodium hydride (4 g of 60% dispersion, 2eq, washed with diethyl ether) in diethyl ether (200 mL), cooled in an ice bath with stirring was added slowly a solution of ethyl crotonate (6.2 mL, 50 mmol) and p-tosylmethyl isocyanide (9.7 g, 50 mmol) in 80 mL of DMSO and 160 mL diethyl ether. Upon complete addition of the solution, the reaction mixture was stirred at room temperature for 1 hr. The reaction was quenched with 400 mL water and extracted into diethyl ether (2×100 mL), dried (MgSO$_4$) and concentrated to afford 6 g (78%) of 4-methyl-1H-pyrrole-3-carboxylic acid ethyl ester as a brown oil which solidified upon standing.

¹H NMR (300 MHz, DMSO-d₆) δ 11.1 (br s, 1H, NH), 9.78 (t, J=2.7 Hz, 1H), 6.56 (s, 1H), 4.12 (q, J=7.2 Hz, 2H, OCH₂CH₃), 2.15 (s, 3H, CH₃), 1.22 (t, J=7.2 Hz, 3H, OCH₂CH₃). MS m/z 153 [M⁺].
(Lit. ref.: Cheng et al., J. Heterocyclic Chem., 1976, 13, 1145–1147).

POCl₃ (4 mL, 1.1 eq) added to 9 mL (3 eq) of DMF cooled in an ice bath. After 15 mins, a solution of the 4-methyl-1H-pyrrole-3-carboxylic acid ethyl ester (6 g, 39.2 mmol) in DMF (2M, 20 mL) was added to the reaction and stirring continued at rt. After 2 hr, the reaction mixture was diluted with water (100 mL) and basified to pH=11 with 1N NaOH. The aqueous layer was extracted into DCM (2×250 mL), washing the combined organic layers with water (2×400 mL), dried (MgSO₄), filtered through a plug of silica and concentrated to afford a pinkish solid. Trituration with hexanes afforded 3.3 g (46%) of 5-formyl-4-methyl-1H-pyrrole-3-carboxylic acid ethyl ester as a tan solid ¹H NMR (300 MHz, DMSO-d₆) δ 12.4 (br s, 1H, NH), 9.69 (s, 1H, CHO), 7.59 (s, 1H), 4.16 (q, J=6.8 Hz, 2H, OCH₂CH₃), 2.48 (s, 3H, CH₃), 1.24 (t, J=6.8 Hz, 3H, OCH₂CH₃). MS m/z 181 [M⁺].
(Lit. ref.: Bonnett, Raymond; Hamzetash, Dariush; Valles, Maria Asuncion; J. Chem. Soc. Perkin Trans 1; 1987; 1387–1388).

KOH (5 g, 2 eq) was added to a suspension of 5-formyl-4-methyl-1H-pyrrole-3-carboxylic acid ethyl ester (8.13 g, 44.8 mmol) in water (100 mL) and EtOH (50 mL) with stirring. The mixture was heated to reflux for 2.5 hr, cooled to rt, concentrated to about ⅔ volume, diluted with water (300 mL) and acidified to pH=3 using 1N HCl. The white solid was collected by filtration and dried to afford 6 g (87%) of 5-formyl-4-methyl-1H-pyrrole-3-carboxylic acid as a tan solid.

¹H NMR (300 MHz, DMSO-d₆) δ 12.28 (br s, 1H, CO₂H), 12.13 (br s, 1H, NH), 9.68 (s, 1H, CHO), 7.55 (d, J=3.6 Hz, 1H), 3.32 (s, 3H, CH₃). MS m/z 153 [M⁺].

Example 4

Synthesis of 5-Aminocarbonyl-4-methyl-1H-pyrrole-3-carboxylic Acid General Amidation Procedure

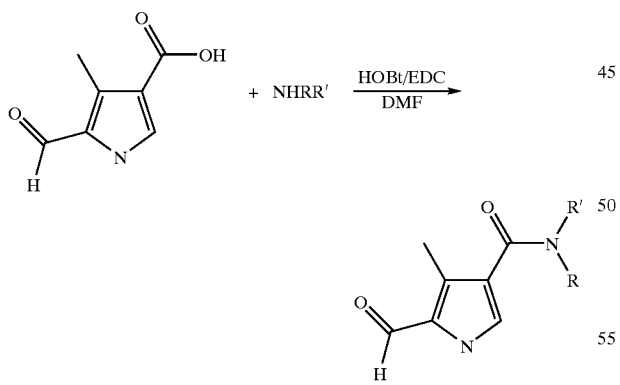

To the solution of 5-formyl-4-methyl-1H-pyrrole-3-carboxylic acid in DMF (0.3M) was added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution was stirred for 12 h, and then DMF solvent was removed. The residue was purified on a silica gel column eluting with 1–5% methanol in dichloromethane to provide the product.

Utilizing the procedure described in Example 4 above, following 5-aminocarbonyl-4-methyl-1H-pyrrole-3-carboxylic acid starting materials were prepared.

(a) Synthesis of 3-Methyl-4-(4-methyl-piperazine-1-carbonyl)-1H-pyrrole-2-carbaldehyde (Pyrrole Aldehyde-10)

5-Formyl-4-methyl-1H-pyrrole-3-carboxylic acid (500 mg, 3.27 mmol) reacted with 1-methylpiperazine (0.43 mL, 3.92 mmol) to give 3-methyl-4-(4-methyl-piperazine-1-carbonyl)-1H-pyrrole-2-carbaldehyde.

¹HNMR (300 MHz, DMSO-d₆) δ 12.25 (br s, 1H, NH), 9.66 (s, 1H, CHO), 7.35 (s, 1H), 3.7 (m, 4H, 2×CH₂), 3.16 (m, 4H, 2×CH₂), 2.73 (s, 3H, CH₃), 2.32 (s, 3H, CH₃). MS m/z 236 [M⁺+1].

(b) 5-Formyl-4-methyl-1H-pyrrole-3-carboxylic Acid (2-Diethylamino-ethyl)-amide (Pyrrole Aldehyde-11)

(c) Synthesis of 4-[(3R,5S)-3,5-Dimethyl-piperazine-1-carbonyl]-3-methyl-1H-pyrrole-2-carbaldehyde (Pyrrole Aldehyde-12)

5-Formyl-4-methyl-1H-pyrrole-3-carboxylic acid (1.00 g, 6.54 mmol) reacted with cis-2,6-dimethylpiperazine (822 mg, 7.19 mmol) to give 1.43 g (88%) of 4-[(3R,5S)-3,5-dimethyl-piperazine-1-carbonyl]-3-methyl-1H-pyrrole-2-carbaldehyde.

¹HNMR (300 MHz, DMSO-d₆) δ 12.08 (br s, 1H, NH), 9.65 (s, 1H, CHO), 7.23 (s, 1H), 4.09 (br s, 2H, CH₂), 2.62 (m, 2H, CH₂), 2.40 (br s, 2H, 2×CH), 2.29 (s, 3H, CH₃), 0.93 (br d, 6H, J=4.6 Hz, 2×CH₃). MS m/z 248 [M⁻–1].

Example 5

Synthesis of 5-Formyl-4-methyl-1H-pyrrole-2-carboxylic Acid (Pyrrole Aldehyde 13)

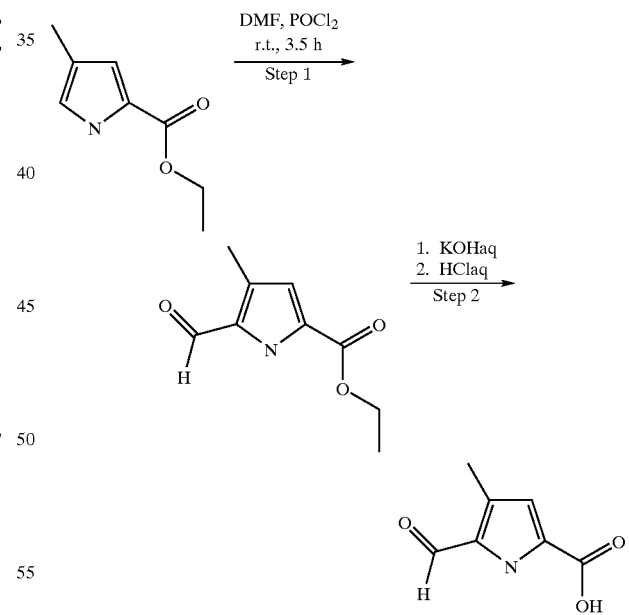

To the ice-cold solution of dimethylformamide (DMF) (3 mL, 39.2 mmol) was added phosphorus oxychloride (0.67 mL, 7.18 mmol) dropwise and the resultant mixture was stirred for 30 minutes. A solution of (1 g, 6.53 mmol) of 4-methyl-1H-pyrrole-2-carboxylic acid ethyl ester in 3 mL of DMF was added to the reaction. After 1 h, the reaction was warmed to room temperature for another 2.5 h. The reaction mixture was diluted with water (100 mL) and basified to pH=11 with 1N sodium hydroxide solution. The precipitate was removed by filtration, rinsing with water and dried to afford 0.8 g (68%) of 5-formyl-4-methyl-1H-pyrrole-2-carboxylic acid ethyl ester as a white solid.

$^1$H NMR (360 MHz, DMSO-$d_6$) δ 12.6 (br s, 1H, NH-1), 9.78 (s, 1H, CHO-5), 6.68 (s, 1H, H-3), 4.26 (q, J=7.0 Hz, 2H, OC$\underline{H}_2$CH$_3$), 2.28 (s, 3H, CH$_3$-4), 1.28 (t, J=7.0 Hz, 3H, OCH$_2$C$\underline{H}_3$). MS m/z 181 (M$^+$).

To a solution of 5-formyl-4-methyl-1H-pyrrole-2-carboxylic acid ethyl ester (0.8 g, 4.4 mmol) in 35 mL of water and 15 mL of ethanol was added potassium hydroxide (0.5 g, 8.9 mmol). The reaction mixture was heated to 100° C. for 1 h, cooled to room temperature, and evaporated ethanol. The water layer was acidified to pH=3 using 2N hydrogen chloride solution. The precipitate was filtered and washed with water to afford 0.67 g (68%) of 5-formyl-4-methyl-1H-pyrrole-2-carboxylic acid as a tan solid.

$^1$H NMR (360 MHz, DMSO-$d_6$) δ 12.92 (br s, 1H, CO$_2$H-5), 12.48 (br s, 1H, NH-1), 9.76 (s, 1H, CHO-5), 6.63 (s, 1H, H-3), 2.28 (s, 3H, CH$_3$-4). MS m/z 152 [M$^-$−1].

Utilizing 5-formyl-4-methyl-1H-pyrrole-2-carboxylic acid the following amides were prepared.

(a) 5-Formyl-4-methyl-1H-pyrrole-2-carboxylic Acid (2-Diethylamino-ethyl)-amide (Pyrrole Aldehyde-14)

To a solution of 5-formyl-4-methyl-1H-pyrrole-2-carboxylic acid (2.50 g, 16.32 mmol) in DMF (54 mL) was added 1-ethyl-3-(3-dimethylamino-propylcarbodiimide hydrochloride (EDC, 3.76 g, 19.59 mmol), 1-hydroxybenzotriazole (HOBt, 2.65 g, 19.59 mmol) followed by diethylaminoethyl amine (2.75 mL, 19.59 mmol). The reaction solution was stirred for 12 h, and then DMF solvent was removed. The residue was purified on a silica gel column eluting with 1–5% methanol in dichloromethane to provide 3.2 g (78%) of 5-formyl-4-methyl-1H-pyrrole-2-carboxylic acid (2-diethylamino-ethyl)-amide.

$^1$H NMR (360 MHz, DMSO-$d_6$) δ 12.22 (br s, 1H, N$\underline{H}$), 9.73 (s, 1H, C$\underline{H}$O), 8.29 (t, 1H, J=5.5 Hz, CON$\underline{H}$), 6.66 (s, 1H, H-3), 3.28 (m, 2H, C$\underline{H}_2$), 2.50 (m, 6H, 3×C$\underline{H}_2$), 2.30 (s, 3H, C$\underline{H}_3$), 0.94 (t, 6H, J=7.2 Hz, 2×C$\underline{H}_3$). MS m/z 252 [M$^+$+1].

Example 6

Synthesis of 3-Aminocarbonyl-5-methyl-1H-pyrrole-2-carbaldehyde B General Amidation Procedure

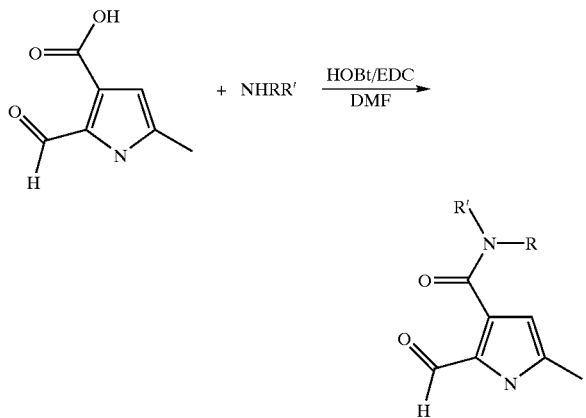

To the solution of 2-formyl-5-methyl-1H-pyrrole-3-carboxylic acid in DMF (0.3M) was added 1-ethyl-3-(3-dimethylamino-propylcarbodiimide hydrochloride (EDC, 1.2 equiv.), 1-hydroxybenzotriazole (HOBt, 1.2 eq) followed by the appropriate amine (1.2 eq). The reaction solution was stirred for 12 h, and then DMF solvent was removed. The residue was purified on a silica gel column eluting with 1–5% methanol in dichloromethane to provide the product.

Utilizing the reaction conditions described in Example 6 above, following compounds were prepared.

(a) 5-Methyl-3-(4-methyl-piperazine-1-carbonyl)-1H-pyrrole-2-carbaldehyde (Pyrrole Aldehyde-15)

(b) 2-Formyl-5-methyl-1H-pyrrole-3-carboxylic Acid (2-Diethylamino-ethyl)-amide (Pyrrole Aldehyde-16) as Follows.

2-Formyl-5-methyl-1H-pyrrole-3-carboxylic acid (3.0 g, 19.6 mmol) reacted with N,N-diethylethylenediamine (3.03 mL, 21.5 mmol) to give 4.65 g (94%) of 2-formyl-5-methyl-1H-pyrrole-3-carboxylic acid (2-diethylamino-ethyl)-amide.

$^1$HNMR (400 MHz, DMSO-$d_6$) δ 12.16 (br s, 1H, NH), 9.96 (s, 1H, CHO), 8.28 (m, 1H, CON$\underline{H}$), 6.40 (s, 1H, H-4), 3.27 (m, 2H, CH$_2$), 2.49 (m, 6H, 3×CH$_2$), 2.22 (s, 3H, CH$_3$), 0.95 (t, 6H, J=7.1 Hz, 2×C$\underline{H}_3$). MS m/z 252 [M$^+$+1].

(c) 2-Formyl-5-methyl-1H-pyrrole-3-carboxylic Acid (2-Pyrrolidin-1-yl-ethyl)-amide (Aldehyde-17) as Follows.

2-Formyl-5-methyl-1H-pyrrole-3-carboxylic acid (3.0 g, 19.6 mmol) reacted with 1-(2-aminoethyl)pyrrolidine (2.73 mL, 21.5 mmol) to give 3.71 g (76%) of 2-formyl-5-methyl-1H-pyrrole-3-carboxylic acid (2-pyrrolidin-1-yl-ethyl)-amide.

$^1$HNMR (400 MHz, DMSO-$d_6$) δ 12.16 (br s, 1H, NH), 9.96 (s, 1H, CHO), 8.32 (m, 1H, CON$\underline{H}$), 6.42 (s, 1H, H-4), 3.31 (m, 2H, CH$_2$), 2.54 (m, 6H, 3×CH$_2$), 2.23 (s, 3H, CH$_3$), 1.66 (m, 4H, 2×C$\underline{H}_2$). MS m/z 250 [M$^+$+1].

(d) 2-Formyl-5-methyl-1H-pyrrole-3-carboxylic Acid (2-[1,2,3]Triazol-1-yl-ethyl)-amide (Pyrrole Aldehyde-18) as Follows.

2-Formyl-5-methyl-1H-pyrrole-3-carboxylic acid (2.0 g, 13.06 mmol) reacted with 2-[1,2,3]triazol-1-yl-ethylamine (1.76 g, 15.67 mmol) to give 2.55 g (79%) of 2-formyl-5-methyl-1H-pyrrole-3-carboxylic acid (2-[1,2,3]triazol-1-yl-ethyl)-amide.

$^1$HNMR (400 MHz, DMSO-$d_6$) δ 12.17 (br s, 1H, N$\underline{H}$), 9.90 (s, 1H, C$\underline{H}$O), 8.32 (t, 1H, J=5.6 Hz, CON$\underline{H}$), 8.10 (d, 1H, J=0.85 Hz, triazole C$\underline{H}$), 7.70 (d, 1H, J=0.85 Hz, triazole C$\underline{H}$), 6.37 (s, 1H, H-4), 4.56 (m, 2H, CH$_2$), 3.65 (m, 2H, CH$_2$+CH$_3$), 2.22 (s, 3H, CH$_3$). MS m/z 248 [M$^+$+1].

(e) 3-[(3R)-3-Dimethylamino-pyrrolidin-1-ylcarbonyl]-5-methyl-1H-pyrrole-2-carbaldehyde (Pyrrole Aldehyde-19) as Follows.

2-Formyl-5-methyl-1H-pyrrole-3-carboxylic acid (536 mg, 3.50 mmol) reacted with (3R)-(+)-3-dimethylamino-pyrrolidine (480 mg, 4.20 mmol) to give 600 mg (69%) Of 3-[(3R)-3-dimethylamino-pyrrolidin-1-ylcarbonyl]-5-methyl-1H-pyrrole-2-carbaldehyde.

$^1$HNMR (400 MHz, DMSO-$d_6$) δ 12.23 (br s, 1H, N$\underline{H}$), 9.63 (s, 1H, C$\underline{H}$O), 6.28 (s, 1H, H-4), 3.89 (m, 2H, CH$_2$), 3.70 (m, 2H, CH$_2$), 2.76 (m, 7H, 2×C$\underline{H}_3$ and C$\underline{H}$), 2.29 (m, 1H, CH$_2$), 2.24 (s, 3H, CH$_3$), 2.15 (m, 1H, C$\underline{H}_2$). MS m/z 250 [M$^+$+1].

(f) 3-[(3S)-3-Dimethylamino-pyrrolidin-1-ylcarbonyl]-5-methyl-1H-pyrrole-2-carbaldehyde (Pyrrole Aldehyde-20) as Follows.

2-Formyl-5-methyl-1H-pyrrole-3-carboxylic acid (548 mg, 3.58 mmol) reacted with (3S)-(−)-3-dimethylamino-pyrrolidine (490 mg, 4.29 mmol) to give 460 mg (52%) of 3-[(3S)-3-dimethylamino-pyrrolidin-1-ylcarbonyl]-5-methyl-1H-pyrrole-2-carbaldehyde.

¹HNMR (400 MHz, DMSO-d₆) δ 12.22 (br s, 1H, NH), 9.63 (s, 1H, CHO), 6.28 (s, 1H, H-4), 3.90 (m, 2H, CH₂), 3.73 (m, 2H, CH₂), 2.73 (m, 7H, 2×CH₃ and CH), 2.28 (m, 1H, CH₂), 2.24 (s, 3H, CH₃), 2.21 (m, 1H, CH₂). MS m/z 250 [M⁺+1].

(g) 3-[(3R,5S)-3,5-Dimethyl-piperazine-1-carbonyl]-5-methyl-1H-pyrrole-2-carbaldehyde (Pyrrole Aldehyde-21) as Follows.

2-Formyl-5-methyl-1H-pyrrole-3-carboxylic acid (1.00 g, 6.53 mmol) reacted with cis-2,6-dimethylpiperazine (900 mg, 7.84 mmol) to give 1.2 g (74%) of 3-[(3R,5S)-3,5-dimethyl-piperazine-1-carbonyl]-5-methyl-1H-pyrrole-2-carbaldehyde.

¹HNMR (400 MHz, DMSO-d₆) δ 12.12 (br s, 1H, NH), 9.40 (s, 1H, CHO), 6.05 (s, 1H, H-4), 4.15 (m, 1H, CH₂), 3.65 (m, 1H, CH₂), 2.59 (m, 2H, CH₂), 2.30 (m, 2H, 2×CH), 2.24 (s, 3H, CH₃), 0.94 (m, 7H, 2×CH₃ and NH). MS m/z 250 [M⁺+1].

(h) 5-Formyl-2-methyl-4-[3-(4-methyl-piperazin-1-yl)-propyl]-1H-pyrrole-3-carboxylic Acid Ethyl Ester (Pyrrole Aldehyde-22).

(i) 3,5-Dimethyl-4-[3-(4-methyl-piperazin-1-yl)-3-oxo-propyl]-1H-pyrrole-2-carbaldehyde (Pyrrole Aldehyde-23) as Follows.

3-(5-Formyl-2,4-dimethyl-1H-pyrrol-3-yl)-propionic acid (1.37 g, 6.50 mmol) reacted with 1-methylpiperazine (719.6 mg, 7.15 mmol) to give 1.3 g (72%) of 3,5-dimethyl-4-[3-(4-methyl-piperazin-1-yl)-3-oxo-propyl]-1H-pyrrole-2-carbaldehyde.

¹HNMR (400 MHz, DMSO-d₆) δ 11.40 (br s, 1H, NH), 9.42 (s, 1H, CHO), 3.41 (m, 2H, CH₂), 3.31 (m, 2H, CH₂), 2.54 (m, 2H, CH₂), 2.37 (m, 2H, CH₂), 2.19 (s, 3H, CH₃), 2.18 (m, 2H, CH₂), 2.15 (s, 3H, CH₃), 2.12 (s, 3H, CH₃). MS m/z 278 [M⁺1].

Example 7

General Procedure for 3,5-Dimethyl-4-methylaminopyrrole Aldehydes

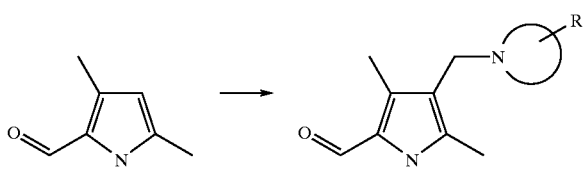

A mixture of 3,5-dimethyl-1H-pyrrole-2-carbaldehyde (2.5 g, 20 mmol) in THF (40 mL), water (20 mL), acetic acid (3 mL), formaldehyde (37% wt. % solution in water, 5 mL) and the appropriate amine (30 mL) was heated to reflux (oil bath 90–100° C.) for 6 hours and then stirred at rt for overnight. The reaction was concentrated to a volume of 30 mL, basified with 2N NaOH and extracted with ethyl acetate (2×150 mL) and DCM (4×100 mL). The combined organic layers were concentrated and the residue was purified on a silica gel column to give the desired product.

Utilizing the reaction conditions described in Example 7 above, the following compounds were prepared.

(a) 4-(4-Hydroxy-piperidin-1-ylmethyl)-3,5-dimethyl-1H-pyrrole-2-carbaldehyde

¹H NMR (400 MHz, DMSO-d₆) δ 11.50 (br s, 1H, NH), 9.43 (s, 1H, CHO), 4.50 (br s, 1H), 3.41 (v br s, 1H, OH), 3.15 (s, 2H), 2.60 (m, 2H), 2.22 (s, 3H, CH₃), 2.16 (s, 3H, CH₃), 1.94 (m, 2H), 1.66 (m, 2H), 1.27 (m, 2H).

(b) 4-(5-Formyl-2,4-dimethyl-1H-pyrrol-3-ylmethyl)-piperazine-1-carbaldehyde

¹H NMR (400 MHz, CDCl₃) δ 9.49 (s, 1H, CHO), 8.02 (s, 1H, CHO), 3.52 (m, 2H), 3.33 (t, 2H), 3.29 (s, 2H), 2.39 (m, 4H), 2.29 (s, 3H, CH₃), 2.28 (s, 3H, CH₃). MS m/z 250 [M⁺+1].

(c) 4-(4-Acetyl-piperazin-1-ylmethyl)-3,5-dimethyl-1H-pyrrole-2-carbaldehyde

¹H NMR (400 MHz, CDCl₃) δ 9.49 (s, 1H, CHO), 3.57 (m, 2H), 3.40 (m, 2H), 3.28 (s, 2H), 3.36 (m, 4H), 2.29 (s, 3H, CH₃), 2.27 (s, 3H, CH₃), 2.08 (s, 3H, COCH₃). MS m/z 264.2 [M⁺+1].

(d) 4-(3,5-Dimethyl-piperazin-1-ylmethyl)-3,5-dimethyl-1H-pyrrole-2-carbaldehyde MS m/z 250.2 [M⁺+1].

(e) 4-(4-Fluoro-piperidin-1-ylmethyl)-3,5-dimethyl-1H-pyrrole-2-carbaldehyde

MS m/z 239.2 [M⁺+1].

(f) 4-[(Cyclopropyl-methyl-amino)-methyl]-3,5-dimethyl-1H-pyrrole-2-carbaldehyde MS m/z 207 [M⁺+1].

(g) 4-((R)-3-Hydroxy-pyrrolidin-1-ylmethyl)-3,5-dimethyl-1H-pyrrole-2-carbaldehyde ¹H NMR (400 MHz, CDCl₃) δ 9.47 (s, 1H, CHO), 5.40 (s, 1H, OH), 4.12 (m, 1H), 3.42 (m, 2H), 2.83 (m, 1H), 2.61 (br t, 1H), 2.46 (m, 1H), 2.31 (m, 3H, CH₃), 2.26 (d, 3H, CH₃), 2.24 (m, 1H), 2.15 (m, 1H), 1.7 (m, 1H).

(h) 3,5-Dimethyl-4-morpholin-4-ylmethyl-1H-pyrrole-2-carbaldehyde

A mixture of 3,5-dimethyl-1H-pyrrole-2-carbaldehyde (1.85 g, 15 mmol), di-morpholine-methane (5 mL, 27 mL) in THF (40 mL), water (15 mL) and acetic acid (4 mL) was heated to reflux (oil bath 90–95° C.) for 6 hours. The reaction was concentrated to a volume of 20 mL, basified with Na₂CO₃ and extracted with ethyl acetate (3×75 mL). The combined extracts were dried, concentrated and the residue was purified on a silica gel column to give 2 g (36%) of the titled compound as a solid.

¹HNMR (400 MHz, DMSO-d₆) δ 11.51 (br s, 1H, NH), 9.44 (s, 1H, CHO), 3.51 (m, 4H), 3.19 (s, 2H), 2.28 (m, 4H), 2.23 (s, 3H, CH₃), 2.17 (s, 3H, CH₃).

C. General Procedure for the Synthesis of 3-Substituted 5-Arylmethanesulfonyl-1,3-dihydro-indol-2-one

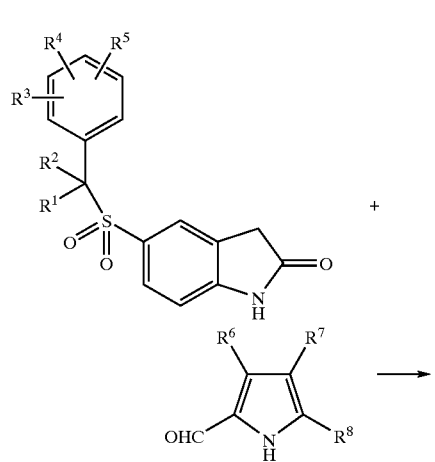

-continued

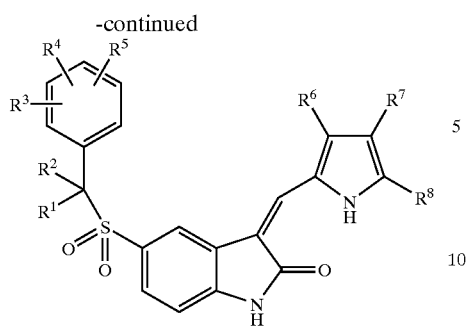

To a solution of 5-arylmethanesulfonyl-1,3-dihydro-indol-2-one (1 molar equivalent) and pyrrole aldehyde (1 molar equivalent) in ethanol (0.125 M) was added catalytic amount of piperidine. The reaction mixture was stirred at room temperature from 24–72 hours. Solid products ranging from yellow to orange to red had precipitated out, or a yellow to orange to red solution was observed. Precipitated products were filtered, washed by ethanol, and dried under high vacuum. In instances where no product had precipitated the product was purified on a silica gel column by eluting with MeOH—CH$_2$Cl$_2$.

Following the general synthetic procedure B the following compounds of formula (I) were prepared.

Example 1

Synthesis of 2,4-Dimethyl-5-[2-oxo-5-phenylmethanesulfonyl-1,2-dihydro-indol-(3Z)-ylidenemethyl]-1H-pyrrole-3-carboxylic Acid (2-Diethylamino-ethyl)-amide

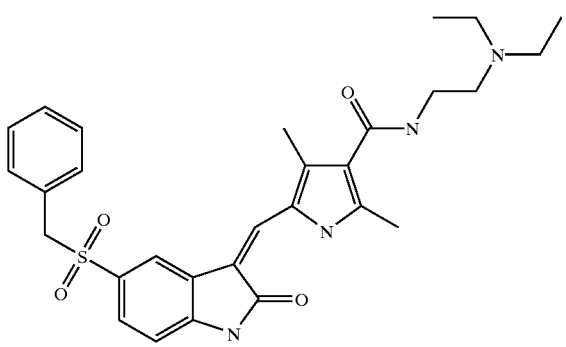

To a solution of 5-phenylmethanesulfonyl-1,3-dihydro-indol-2-one (100 mg, 0.34 mmol) and 5-formyl-2,4-dimethyl-1H-pyrrole-3-carboxylic acid (2-diethylamino-ethyl)-amide (92 mg, 0.34 mmol) in ethanol (4 mL) was added piperidine (0.1 mL). The reaction mixture was stirred at 25° C. for three days. An orange solid product was precipitated out, filtered, washed thrice with ethanol, and dried under high vacuum to provide to provide 99 mg (55%) of 2,4-dimethyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide as a yellow solid.

$^1$H-NMR (400 MHz, DMSO-d$_6$) δ 13.58 (br s, 1H, pyrrole NH), 11.30 (br s, 1H, CONH), 8.26 (m, 1H, aromatic), 7.83 (s, 1H, aromatic), 7.51 (m, 1H, aromatic), 7.39 (m, 1H, aromatic), 7.33 (m, 3H, aromatic), 7.29 (m, 2H, aromatic), 6.99 (m, 1H, aromatic), 4.62 (s, 2H, CH$_2$), 3.26 (m, 5H, CH$_2$+CH$_3$), 2.50 (m, 9H, 3×CH$_2$+CH$_3$), 0.98 (t, 6H, 2×CH$_3$). MS m/z 533 [M$^+$–1].

Example 2

Synthesis of [5-(2-Cyano-phenylmethanesulfonyl)-2-oxo-1,2-dihydro-indol-(3Z)-ylidenemethyl]-2,4-dimethyl-1H-pyrrole-3-carboxylic Acid (2-Diethylamino-ethyl)-amide

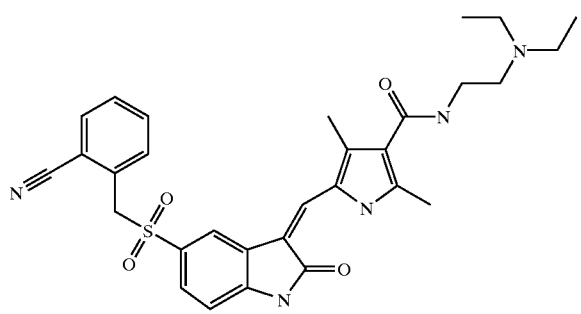

To a solution of 2-(2-Oxo-2,3-dihydro-1H-indole-5-sulfonylmethyl)-benzonitrile (100 mg, 0.32 mmol) and 5-formyl-2,4-dimethyl-1H-pyrrole-3-carboxylic acid (2-diethylamino-ethyl)-amide (85 mg, 0.32 mmol) in ethanol (4 mL) was added piperidine (0.1 mL). The reaction mixture was stirred at 25° C. for three days. The solvent was evaporated and the residue was purified on a silica gel column eluting with MeOH—CH$_2$Cl$_2$ 1:9 to provide 116 mg (65%) of [5-(2-Cyano-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide as a pale orange solid.

$^1$H-NMR (400 MHz, DMSO-d$_6$) δ 13.61 (br s, 1H, pyrrole NH), 11.43 (br s, 1H, CONH), 8.24 (s, 1H, aromatic), 7.83 (m, 1H, aromatic), 7.67 (m, 1H, aromatic), 7.54 (m, 2H, aromatic), 7.36 (m, 2H, aromatic), 7.02 (d, 1H, aromatic), 4.79 (s, 2H, CH$_2$), 3.31 (m, 5H, CH$_2$+CH$_3$), 2.50 (m, 9H, 3×CH$_2$+CH$_3$), 1.10 (t, 6H, 2H 558 [M$^+$–1].

Example 3

Synthesis of 2,4-Dimethyl-5-[2-oxo-5-(3-trifluoromethyl-phenylmethanesulfonyl)-1,2-dihydro-indol-(3Z)-ylidenemethyl]-1H-pyrrole-3-carboxylic Acid (2-Diethylamino-ethyl)-amide

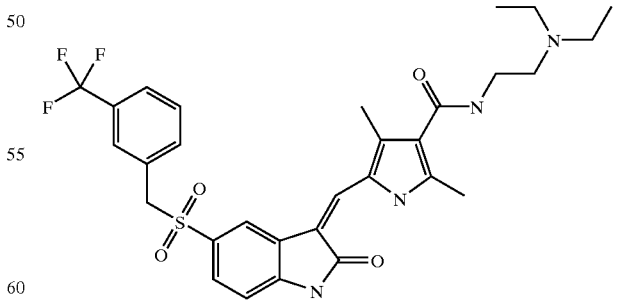

To a solution of 5-(3-Trifluoromethyl-phenylmethanesulfonyl)-1,3-dihydro-indol-2-one (100 mg, 0.28 mmol) and 5-formyl-2,4-dimethyl-1H-pyrrole-3-carboxylic acid (2-diethylamino-ethyl)-amide (75 mg, 0.28 mmol) in ethanol (4 mL) was added piperidine (0.1 mL).

The reaction mixture was stirred at 25° C. for three days. The solvent was evaporated and the residue was purified on a silica gel column eluting with MeOH—CH$_2$Cl$_2$ 1:9 to provide 105 mg (62%) of 2,4-dimethyl-5-[2-oxo-5-(3-trifluoromethyl-phenylmethanesulfonyl)-1,2-dihydro-indol-(3Z)-ylidenemethyl]-1H-pyrrole-3-carboxylic acid (2-diethylamino-ethyl)-amide as a pale orange solid.

$^1$H-NMR (400 MHz, DMSO-d$_6$) δ 13.60 (br s, 1H, pyrrole NH), 11.40 (br s, 1H, CONH), 8.58 (br s, 1H, NH), 8.21 (s, 1H, aromatic), 7.83 (s, 1H, aromatic), 7.67 (d, 1H, aromatic), 7.56 (t, 1H, aromatic), 7.49 (m, 2H, aromatic), 7.39 (dd, 1H, aromatic), 7.00 (d, 1H, aromatic), 4.79 (s, 2H, CH$_2$), 3.31 (m, 5H, CH$_2$+CH$_3$), 2.50 (m, 9H, 3×CH$_2$+CH$_3$), 1.12 (t, 6H, 2×CH$_3$). MS m/z 601 [M$^+$−1].

Example 4

Synthesis of 5-[5-(3-Methoxy-phenylmethanesulfonyl)-2-oxo-1,2-dihydro-indol-(3Z)-ylidenemethyl]-2,4-dimethyl-1H-pyrrole-3-carboxylic Acid (2-Diethylamino-ethyl)-amide

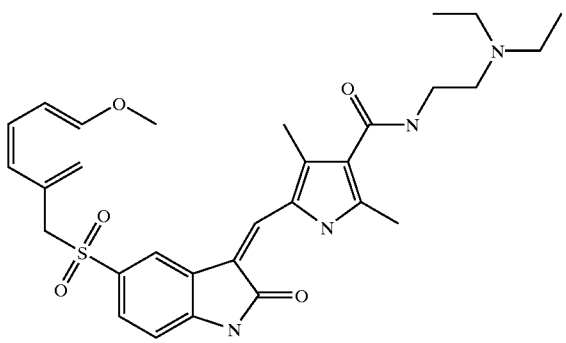

To a solution of 5-(3-methoxy-phenylmethanesulfonyl)-1,3-dihydro-indol-2-one (100 mg, 0.32 mmol) and 5-formyl-2,4-dimethyl-1H-pyrrole-3-carboxylic acid (2-diethylamino-ethyl)-amide (84 mg, 0.32 mmol) in ethanol (4 mL) was added piperidine (0.1 mL). The reaction mixture was stirred at 25° C. for three days. The solvent was evaporated and the residue was purified on a silica gel column eluting with MeOH—CH$_2$Cl$_2$ 1:9 to provide 125 mg (69%) of 5-[5-(3-methoxy-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide as a pale orange solid.

$^1$H-NMR (400 MHz, DMSO-d$_6$) δ 13.61 (br s, 1H, pyrrole NH), 11.39 (br s, 1H, CONH), 8.26 (m, 1H, aromatic), 7.84 (s, 1H, aromatic), 7.75 (v br s, 1H, NH), 7.42 (dd, 1H, aromatic), 7.21 (t, 1H, aromatic), 7.00 (d, 1H, aromatic), 6.88 (dd, 1H, aromatic), 6.73 (m, 2H, aromatic), 4.59 (s, 2H, CH$_2$), 3.64 (s, 3H, OCH$_3$), 3.26 (m, 5H, CH$_2$+CH$_3$), 2.50 (multiplets, 9H, 3×CH$_2$+CH$_3$), 1.12 (t, 6H, 2×CH$_3$). MS m/z 563 [M$^+$−1].

Example 5

Synthesis of 2-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile

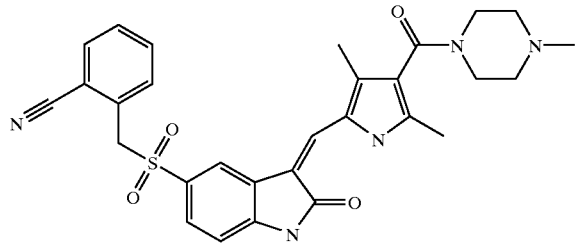

To a solution of 2-(2-oxo-2,3-dihydro-1H-indole-5-sulfonylmethyl)-benzonitrile (100 mg, 0.32 mmol) and 3,5-dimethyl-4-(4-methyl-piperazine-1-carbonyl)-1H-pyrrole-2-carbaldehyde (79 mg, 0.32 mmol) in ethanol (4 mL) was added piperidine (0.1 mL). The reaction mixture was stirred at 25° C. for three days. The solvent was evaporated and the residue was purified on a silica gel column eluting with MeOH—CH$_2$Cl$_2$ 10:90 to provide 123 mg (71%) of 2-{3-[1-[3,5-dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile as a pale orange solid.

$^1$H-NMR (400 MHz, DMSO-d$_6$) δ 13.53 (br s, 1H, pyrrole NH), 11.40 (br s, 1H, CONH), 8.24 (m, 1H, aromatic), 7.83 (m, 2H, aromatic), 7.66 (m, 1H, aromatic), 7.55 (m, 1H, aromatic), 7.35 (m, 2H, aromatic), 7.02 (d, 1H, aromatic), 4.79 (s, 2H, CH$_2$), 3.40 (m, 7H, 2×CH$_2$+CH$_3$), 2.30 (m, 7H, 2×CH$_2$+CH$_3$), 2.19 (s, 3H, CH$_3$). MS m/z 542 [M$^+$−1].

Example 6

Synthesis of 3-[1-[3,5-Dimethyl-4-(4-methyl-piperazine-1-carbonyl)-1H-pyrrol-2-yl]-meth-(Z)-ylidene]-5-(3-methoxy-phenylmethanesulfonyl)-1,3-dihydro-indol-2-one

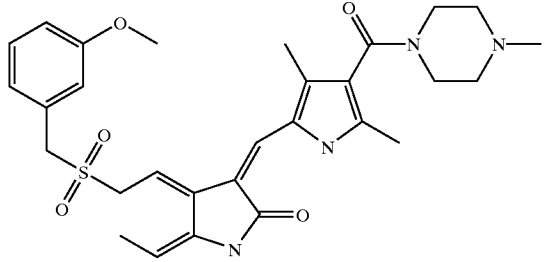

Pale orange solid, (110 mg, 63%).

$^1$H-NMR (400 MHz, DMSO-d$_6$) δ 13.54 (br s, 1H, pyrrole NH), 11.36 (br s, 1H, CONH), 8.25 (m, 1H, aromatic), 7.82 (s, 1H, aromatic), 7.42 (dd, 1H, aromatic), 7.21 (t, 1H, aromatic), 7.00 (d, 1H, aromatic), 6.88 (dd, 1H, aromatic), 6.73 (m, 2H, aromatic), 4.58 (s, 2H, CH$_2$), 3.63 (s, 3H, OCH$_3$), 3.40 (m, 7H, 2×CH$_2$+CH$_3$), 2.30 (m, 7H, 2×CH$_2$+CH$_3$), 2.20 (s, 3H, CH$_3$). MS m/z 547 [M$^+$−1].

Example 7

Synthesis of 3-[1-[3,5-Dimethyl-4-(4-methyl-piperazine-1-carbonyl)-1H-pyrrol-2-yl]-meth-(Z)-ylidene]-5-(2-nitro-phenylmethanesulfonyl)-1,3-dihydro-indol-2-one

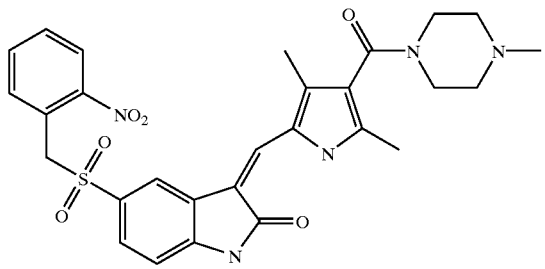

Pale greenish-tan solid, (135 mg, 45%).
$^1$H-NMR (400 MHz, DMSO-d$_6$) δ 13.43 (br s, 1H, pyrrole NH), 11.39 (br s, 1H, CONH), 8.16 (d, 1H, aromatic), 8.02 (dd, 1H, aromatic), 7.81 (s, 1H, aromatic), 7.66 (m, 2H, aromatic), 7.36 (dd, 1H, aromatic), 7.28 (dd, 1H, aromatic), 6.98 (d, 1H, aromatic), 5.10 (s, 2H, CH$_2$), 3.40 (m, 7H, 2×CH$_2$+CH$_3$), 2.30 (m, 7H, 2×CH$_2$+CH$_3$), 2.20 (s, 3H, CH$_3$). MS m/z 562 [M$^+$−1].

Example 8

Synthesis of 2,4-Dimethyl-5-[5-(2-nitro-phenylmethanesulfonyl)-2-oxo-1,2-dihydro-indol-(3Z)-ylidenemethyl]-1H-pyrrole-3-carboxylic Acid (2-Diethylamino-ethyl)-amide

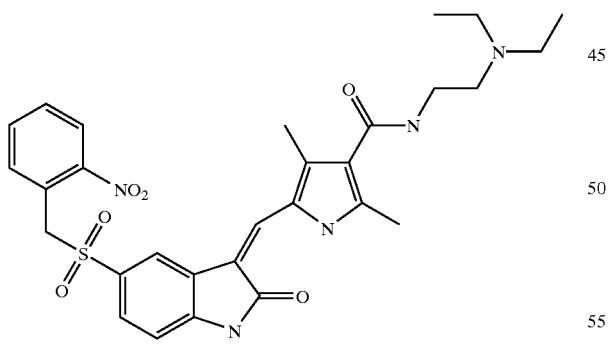

Pale greenish-yellow solid, (163 mg, 47%)
$^1$H-NMR (400 MHz, DMSO-d$_6$) δ 13.58 (br s, 1H, pyrrole NH), 11.38 (br s, 1H, CONH), 8.18 (m, 1H, aromatic), 8.02 (m, 1H, aromatic), 7.84 (s, 1H, aromatic), 7.65 (m, 2H, aromatic), 7.49 (m, 1H, aromatic), 7.36 (m, 1H, aromatic), 7.28 (m, 1H, aromatic), 6.98 (d, 1H, aromatic), 5.09 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 578 [M$^+$−1].

Example 9

Synthesis of 2,4-Dimethyl-5-[2-oxo-5-phenylmethanesulfonyl-1,2-dihydro-indol-(3Z)-ylidenemethyl]-1H-pyrrole-3-carboxylic Acid (2-[1,2,3]Triazol-1-yl-ethyl)-amide

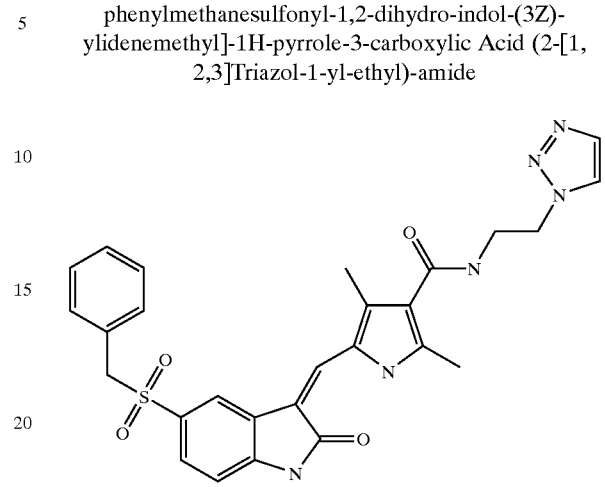

Yellow solid, (126 mg, 46%)
$^1$H-NMR (400 MHz, DMSO-d$_6$) δ 13.60 (br s, 1H, pyrrole NH), 11.30 (br s, 1H, CONH), 8.27 (m, 1H, aromatic), 8.17 (m, 1H, aromatic), 8.14 (s, 1H, aromatic), 7.79 (m, 1H, aromatic), 7.75 (t, 1H, CONH), 7.72 (s, 1H, aromatic), 7.37 (dd, 1H, aromatic), 7.28 (m, 2H, aromatic), 7.17 (m, 2H, aromatic), 6.97 (d, 1H, aromatic), 4.57 (m, 4H, 2×CH$_2$), 3.71 (m, 2H, CH$_2$), 3.30 (s, 3H, CH$_3$), 2.38 (s, 3H, CH$_3$). MS m/z 529 [M$^+$−1].

Example 10

Synthesis of 2,4-Dimethyl-5-[5-(2-nitro-phenylmethanesulfonyl)-2-oxo-1,2-dihydro-indol-(3Z)-ylidenemethyl]-1H-pyrrole-3-carboxylic Acid (2-[1,2,3]Triazol-1-yl-ethyl)-amide

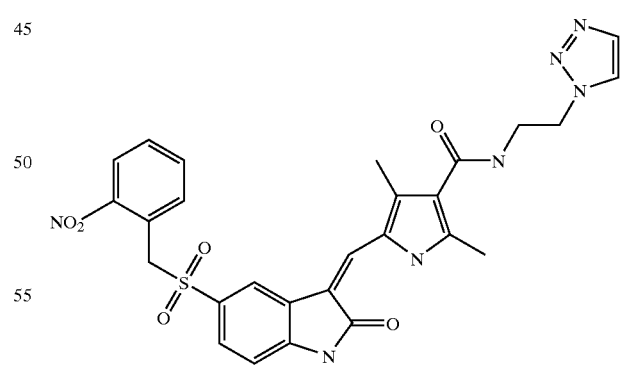

Pale yellow solid, (131 mg, 51%)
$^1$H-NMR (400 MHz, DMSO-d$_6$) δ 13.61 (br s, 1H, pyrrole NH), 10.80 (br s, 1H, CONH), 8.02 (m, 2H, aromatic), 7.65 (m, 3H, aromatic), 7.44 (m, 3H, aromatic), 7.35 (m, 2H, aromatic), 6.92 (d, 1H, aromatic), 5.05 (m, 4H, 2×CH$_2$), 3.70 (m, 2H, CH$_2$), 3.30 (s, 3H, CH$_3$), 2.35 (s, 3H, CH$_3$). MS m/z 574 [M$^+$−1].

Example 11

Synthesis of 3-[1-(3,5-Dimethyl-1H-pyrrol-2-yl)-meth-(Z)-ylidene]-5-phenylmethanesulfonyl-1,3-dihydro-indol-2-one

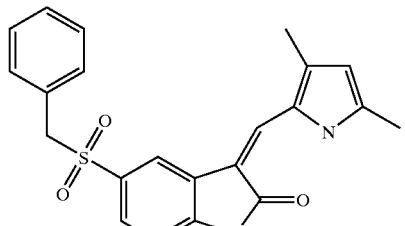

Bright red-orange solid, (60 mg, 48%)
$^1$H-NMR (400 MHz, DMSO-d$_6$) δ 13.30 (br s, 1H, pyrrole NH), 11.20 (br s, 1H, CONH), 8.30 (s, 1H, aromatic), 7.70 (s, 1H, CONH), 7.30 (m, 4H, aromatic), 7.25 (m, 2H, aromatic), 6.90 (m, 1H, aromatic), 6.10 (m, 1H, aromatic), 5.10 (s, 2H, CH$_2$), 3.30 (s, 3H, CH$_3$), 2.38 (s, 3H, CH$_3$). MS m/z 391[M$^+$–1].

Example 12

Synthesis of 4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid

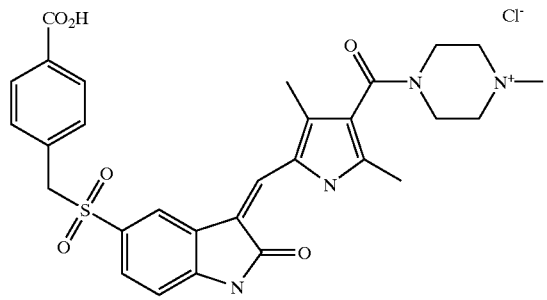

Brown solid, (93 mg, 52%)
$^1$H-NMR (400 MHz, DMSO-d$_6$) δ 13.59 (br s, 1H, pyrrole NH), 13.00 (v br s, 1H, COOH), 11.42 (br s, 1H, CONH), 8.25 (s, 1H, aromatic), 7.85 (m, 3H, aromatic), 7.39 (d, 1H, aromatic), 7.30 (m, 2H, aromatic), 7.00 (d, 1H, aromatic), 4.77 (s, 2H, CH$_2$), 3.30 (m, 7H, 2×CH$_2$+CH$_3$), 2.70 (m, 3H, CH$_3$), 2.33 (m, 5H, 2×CH$_2$+CH$_3$). MS m/z 563 [M$^+$].

Example 13

Synthesis of (4-{3-[1-[3,5-Dimethyl-4-(4-methyl-piperazine-1-carbonyl)-1H-pyrrol-2-yl]meth-(Z)-ylidene]-2-oxo-2,3-dihydro-1H-indole-5-sulfonylmethyl}-phenyl)-acetic acid

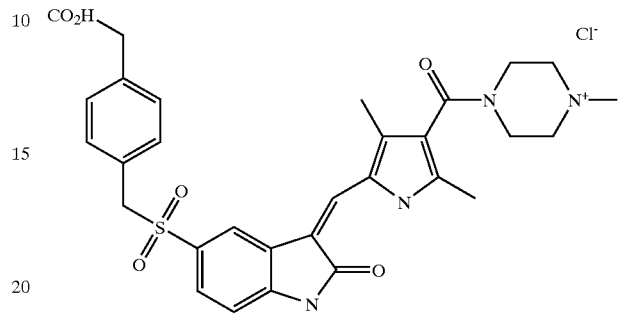

Brown solid, (88 mg, 45%)
$^1$H-NMR (400 MHz, DMSO-d$_6$) δ 13.59 (br s, 1H, pyrrole NH), 13.00 (v br s, 1H, COOH), 11.42 (br s, 1H, CONH), 8.33 (s, 1H, aromatic), 7.88 (s, 1H, aromatic), 7.43 (d, 1H, aromatic), 7.18 (multiplets, 4H, aromatic), 7.00 (d, 1H, aromatic), 4.60 (s, 2H, CH$_2$), 3.40 (m, 7H, 2×CH$_2$+CH$_3$), 2.00 (m, 2H, CH$_2$), 2.70 (m, 3H, CH$_3$), 2.33 (m, 5H, 2×CH$_2$+CH$_3$). MS m/z 577 [M$^+$].

Example 14

Synthesis of 4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-3-nitro-benzoic acid

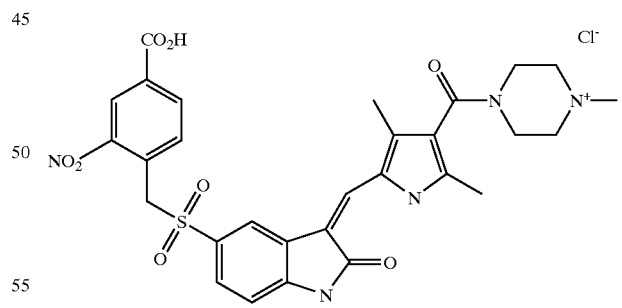

Brown solid, (85 mg, 49%)
$^1$H-NMR (400 MHz, DMSO-d$_6$) δ 13.70 (v br s, 1H, COOH), 13.60 (br s, 1H, pyrrole NH), 11.42 (br s, 1H, CONH), 8.42 (s, 1H, aromatic), 8.18 (m, 2H, aromatic), 7.82 (s, 1H, aromatic), 7.50 (d, 1H, aromatic), 7.30 (d, 1H, aromatic), 7.00 (d, 1H, aromatic), 5.20 (s, 2H, CH$_2$), 3.40 (m, 7H, 2×CH$_2$+CH$_3$), 2.80 (m, 3H, CH$_3$), 2.35 (m, 5H, 2×CH$_2$+CH$_3$). MS m/z 608 [M$^+$].

Example 15

Synthesis of 4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid

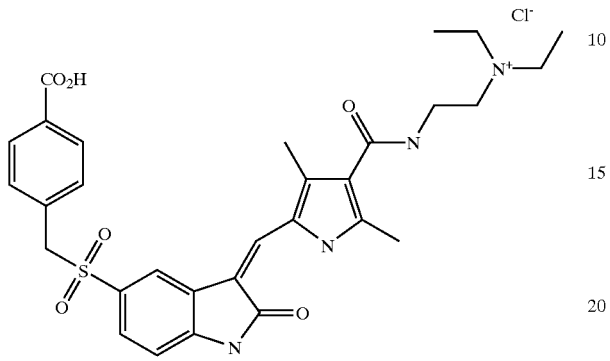

Pale orange solid, (99 mg, 51%)
$^1$H-NMR (400 MHz, DMSO-$d_6$) δ 13.70 (v br s, 1H, COOH), 13.59 (br s, 1H, pyrrole NH), 11.46 (br s, 1H, CONH), 8.41 (s, 1H, aromatic), 8.18 (m, 2H, aromatic), 7.83 (s, 1H, aromatic), 7.55 (m, 2H, aromatic), 7.30 (m, 1H, aromatic), 7.00 (m, 1H, aromatic), 5.20 (s, 2H, CH$_2$), 3.40 (m, 8H, 4×CH$_2$), 3.00 (m, 3H, CH$_3$), 2.80 (s, 3H, CH$_3$), 2.30 (m, 6H, 2×CH$_3$). MS m/z 579 [M$^+$].

Example 16

Synthesis of (4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-phenyl)-acetic acid

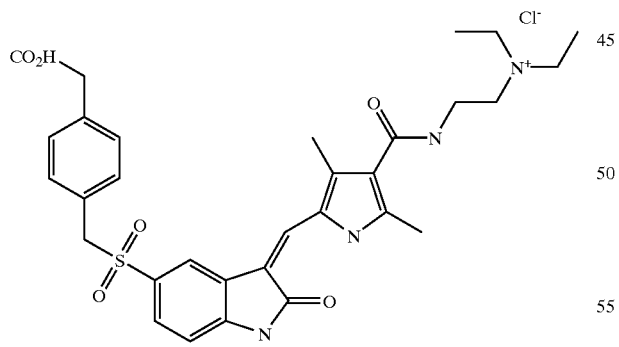

Brown solid, (89 mg, 45%)
$^1$H-NMR (400 MHz, DMSO-$d_6$) δ 13.70 (v br s, 1H, COOH), 13.59 (br s, 1H, pyrrole NH), 11.46 (br s, 1H, CONH), 8.35 (s, 1H, aromatic), 7.95 (t, 1H, CONH), 7.90 (s, 1H, aromatic), 7.44 (dd, 1H, aromatic), 7.18 (multiplets, 4H, aromatic), 7.00 (d, 1H, aromatic), 4.30 (s, 2H, CH$_2$), 3.58 (multiplets, 5H, CH$_3$+CH$_2$), 3.30 (m, 5H, CH$_2$+CH$_3$), 3.20 (m, 6H, 3×CH$_2$), 1.25 (m, 6H, 2×CH$_3$). MS m/z 593 [M$^+$].

Example 17

Synthesis of 4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-3-nitro-benzoic acid

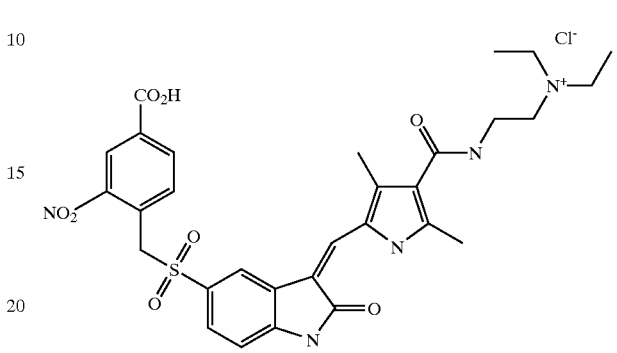

Pale orange-brown solid, (101 mg, 57%)
$^1$H-NMR (400 MHz, DMSO-$d_6$) δ 13.65 (br s, 1H, pyrrole NH), 11.46 (br s, 1H, CONH), 10.11 (v br s, 1H, COOH), 8.42 (d, 1H, aromatic), 8.18 (m, 2H, aromatic), 7.99 (t, 1H, CONH), 7.87 (s, 1H, aromatic), 7.49 (d, 1H, aromatic), 7.29 (dd, 1H, aromatic), 7.00 (d, 1H, aromatic), 5.20 (s, 2H, CH$_2$), 3.62 (m, 9H, CH$_3$+CH$_3$×CH$_2$), 3.20 (m, 5H, CH$_2$+CH$_3$), 1.25 (m, 6H, 2×CH$_3$). MS m/z 624 [M$^+$].

Example 18

Synthesis of 3-[1-[3,5-Dimethyl-4-(4-methyl-piperazine-1-carbonyl)-1H-pyrrol-2-yl]-meth-(Z)-ylidene]-1-methyl-5-phenylmethanesulfonyl-1,3-dihydro-indol-2-one

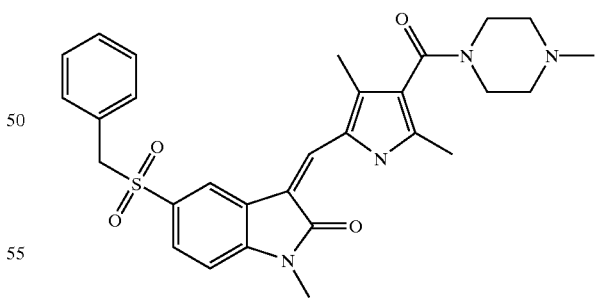

Pale yellow solid, (43 mg, 43%)
$^1$H-NMR (400 MHz, DMSO-$d_6$) δ 13.50 (br s, 1H, pyrrole NH), 8.28 (s, 1H, aromatic), 7.85 (m, 1H, aromatic), 7.48 (dd, 1H, aromatic), 7.31 (m, 3H, aromatic), 7.19 (m, 3H, aromatic) 4.64 (s, 2H, CH$_2$), 3.40 (m, 7H, 2×CH$_2$+CH$_3$), 2.30 (m, 7H, 2×CH$_2$+CH$_3$), 2.20 (s, 3H, CH$_3$), 1.09 (t, 3H, CH$_3$). MS m/z 531 [M$^+$−1].

Example 19

Synthesis of 5-[5-(3,5-Dibromo-2-hydroxy-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

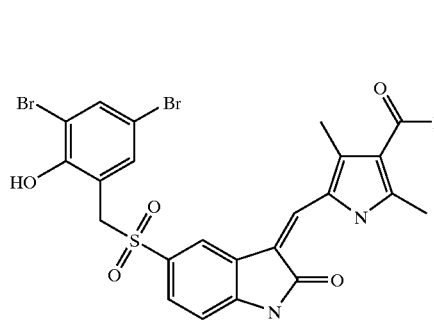

Red-brown solid, (60 mg, 37%)
MS m/z 707, 709 [M$^+$−1].

Example 20

Synthesis of 5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-[1,2,3]triazol-1-yl-ethyl)-amide

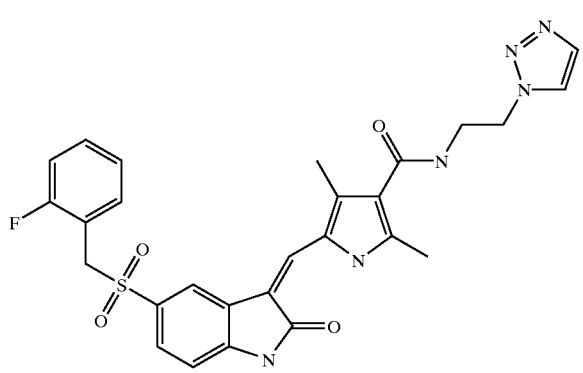

Orange solid, (131 mg, 52%)
$^1$H-NMR (400 MHz, DMSO-d$_6$) δ 13.57 (br s, 1H, pyrrole NH), 11.30 (br s, 1H, CONH), 8.28 (m, 1H, aromatic), 8.16 (m, 1H, aromatic), 7.83 (s, 1H, aromatic), 7.77 (t, 1H, CONH), 7.74 (s, 1H, aromatic), 7.38 (m, 2H, aromatic), 7.24 (m, 1H, aromatic), 7.16 (m, 2H, aromatic), 7.00 (d, 1H, aromatic), 4.57 (m, 4H, 2×CH$_2$), 3.71 (m, 2H, CH$_2$), 3.30 (s, 3H, CH$_3$), 2.38 (s, 3H, CH$_3$). MS m/z 547 [M$^+$−1].

Example 21

Synthesis of 2,4-Dimethyl-5-[4-methyl-2-oxo-5-phenylmethanesulfonyl-1,2-dihydro-indol-(3Z)-ylidenemethyl]-1H-pyrrole-3-carboxylic acid (2-Diethylamino-ethyl)-amide

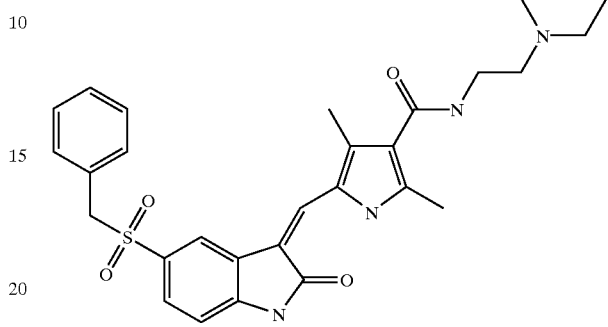

Orangish-red solid, (59 mg, 54%)
$^1$H-NMR (400 MHz, DMSO-d$_6$) δ 13.57 (br s, 1H, pyrrole NH), 11.20 (v br s, 1H, CONH), 7.77 (m, 1H, aromatic), 7.61 (d, 1H, aromatic), 7.50 (m, 1H, aromatic), 7.29 (m, 3H, aromatic), 7.18 (m, 2H, aromatic), 6.85 (t, 1H, aromatic), 4.65 (s, 2H, CH$_2$), 3.26 (m, 5H, CH$_2$+CH$_3$), 2.78 (s, 3H, CH$_3$), 2.50 (m, 9H, 3×CH$_2$+CH$_3$), 1.00 (t, 6H, 2×CH$_3$). MS m/z 549 [M$^+$+1].

Example 22

Synthesis of 5-[5-(2-Fluoro-phenylmethanesulfonyl)-4-methyl-2-oxo-1,2-dihydro-indol-(3Z)-ylidenemethyl]-2,4-dimethyl-1H-pyrrole-3-carboxylic acid (2-Diethylamino-ethyl)-amide

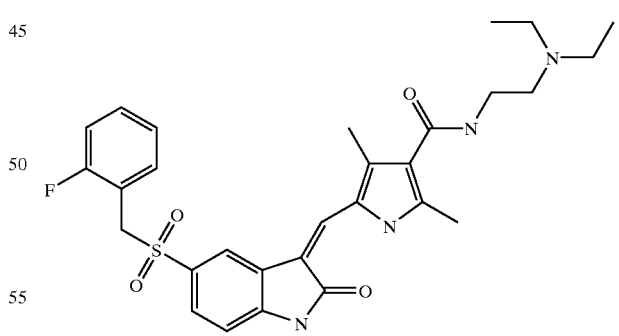

Orangish-red solid, (93 mg, 59%)
$^1$H-NMR (400 MHz, DMSO-d$_6$) δ 13.57 (br s, 1H, pyrrole NH), 1 1.20 (v br s, 1H, CONH), 7.78 (m, 1H, aromatic), 7.53 (d, 1H, aromatic), 7.50 (t, 1H, CONH), 7.39 (m, 1H, aromatic), 7.29 (m, 1H, aromatic), 7.18 (m, 2H, aromatic), 6.85 (m, 1H, aromatic), 4.65 (s, 2H, CH$_2$), 3.30 (m, 5H, CH$_2$+CH$_3$), 2.78 (s, 3H, CH$_3$), 2.50 (m, 9H, 3×CH$_2$+CH$_3$), 1.00 (t, 6H, 2×CH$_3$). MS m/z 567 [M$^+$+1].

Example 23

Synthesis of 5-[5-(2-Chlorophenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

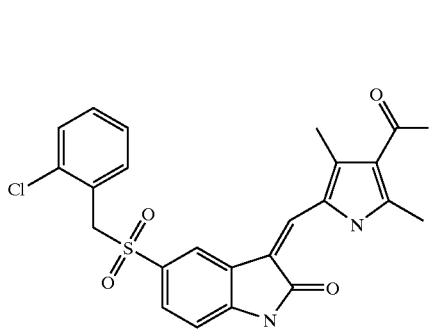

Orange solid, (76 mg, 58%)
MS m/z 569 [M⁺].

Example 24

Synthesis of 4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid Methyl Ester

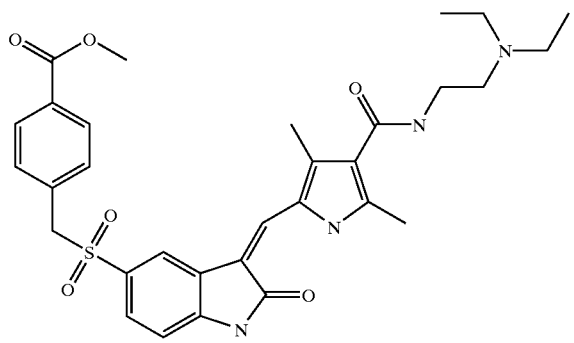

Yellowish-orange solid, (67 mg, 49%)
$^1$H-NMR (400 MHz, DMSO-d$_6$) δ 13.57 (br s, 1H, pyrrole NH), 11.37 (br s, 1H, CONH), 8.26 (m, 1H, aromatic), 7.88 (d, 2H, aromatic), 7.83 (s, 1H, aromatic), 7.48 (t, 1H, CONH), 7.34 (m, 3H, aromatic), 6.98 (d, 1H, aromatic), 4.73 (s, 2H, CH$_2$), 3.81 (s, 3H, CH$_3$), 3.30 (m, 5H, CH$_2$+CH$_3$), 2.50 (m, 9H, 3×CH$_2$+CH$_3$), 0.96 (t, 6H, 2×CH$_3$). MS m/z 593 [M⁺+1].

Example 25

Synthesis 5-[5-(4-Trifluoromethoxy-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

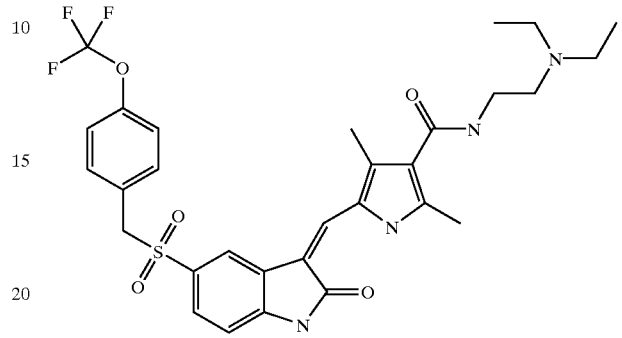

Orange solid, (57 mg, 41%)
$^1$H-NMR (400 MHz, DMSO-d$_6$) δ 13.57 (br s, 1H, pyrrole NH), 11.37 (br s, 1H, CONH), 8.25 (s, 1H, aromatic), 7.84 (s, 1H, aromatic), 7.48 (t, 1H, CONH), 7.41 (d, 1H, aromatic), 7.32 (m, 4H, aromatic), 7.01 (d, 1H, aromatic), 4.68 (s, 2H, CH$_2$), 3.29 (m, 5H, CH$_2$+CH$_3$), 2.50 (m, 9H, 3×CH$_2$+CH$_3$), 0.96 (t, 6H, 2×CH$_3$). MS m/z 617 [M⁺−1].

Example 26

Synthesis of 5-(2,4-bis-Trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

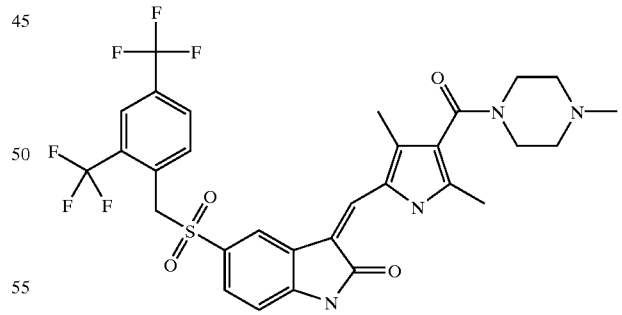

Yellow solid, (61 mg, 45%)
$^1$H-NMR (400 MHz, DMSO-d$_6$) δ 13.54 (br s, 1H, pyrrole NH), 11.41 (br s, 1H, CONH), 8.25 (m, 1H, aromatic), 8.15 (d, 1H, aromatic), 8.05 (s, 1H, aromatic), 7.84 (s, 1H, aromatic), 7.76 (d, 1H, aromatic), 7.46 (dd, 1H, aromatic), 7.06 (d, 1H, aromatic), 4.88 (s, 2H, CH$_2$), 3.32 (m, 7H, 2×CH$_2$+CH$_3$), 2.29 (m, 7H, 2×CH$_2$CH$_3$), 2.19 (s, 3H, CH$_3$). MS m/z 653 [M⁺−1].

Example 27

Synthesis of 5-[5-(2,4-bis-Trifluoromethyl-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

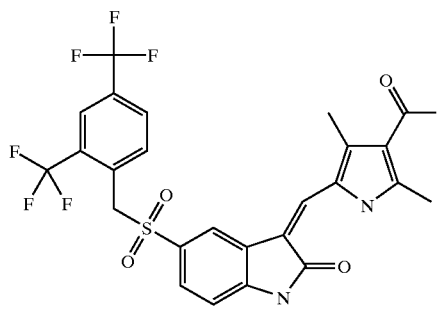

Orange solid, (56 mg, 49%)
$^1$H-NMR (400 MHz, DMSO-$d_6$) δ 13.59 (br s, 1H, pyrrole NH), 11.40 (v br s, 1H, CONH), 8.27 (s, 1H, aromatic), 8.15 (d, 1H, aromatic), 8.13 (s, 1H, aromatic), 7.86 (s, 1H, aromatic), 7.76 (d, 1H, aromatic), 7.47 (m, 2H, CONH+aromatic), 7.05 (d, 1H, aromatic), 4.88 (s, 2H, CH$_2$), 3.29 (m, 5H, CH$_2$+CH$_3$), 2.50 (m, 9H, 3×CH$_2$+CH$_3$), 0.96 (t, 6H, 2×CH$_3$). MS m/z 669 [M$^+$−1].

Example 28

Synthesis of 5-(4-Bromophenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

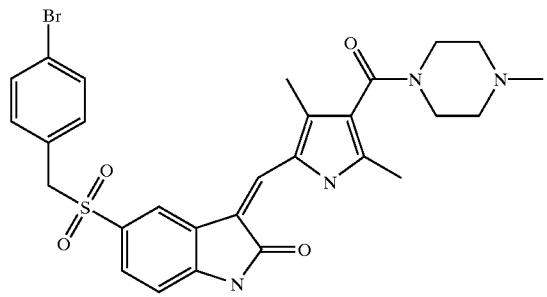

Yellowish-orange solid, (57 mg, 42%)
$^1$H-NMR (400 MHz, DMSO-$d_6$) δ 13.53 (br s, 1H, pyrrole NH), 11.00 (v br s, 1H, CONH), 8.21 (m, 1H, aromatic), 7.80 (s, 1H, aromatic), 7.51 (d, 2H, aromatic), 7.39 (dd, 1H, aromatic), 7.10 (d, 2H, aromatic), 7.01 (d, 1H, aromatic), 4.63 (s, 2H, CH$_2$), 3.28 (m, 7H, 2×CH$_2$+CH$_3$), 2.31 (m, 7H, 2×CH$_2$+CH$_3$), 2.20 (s, 3H, CH$_3$). MS m/z 595, 597 [M$^+$−1].

Example 29

Synthesis of 5-[5-(4-Bromophenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

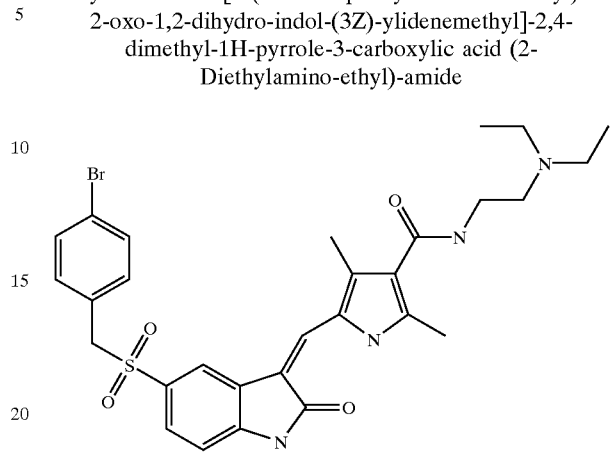

Orange solid, (49 mg, 51%)
$^1$H-NMR (400 MHz, DMSO-$d_6$) δ 13.58 (br s, 1H, pyrrole NH), 10.80 (v br s, 1H, CONH), 8.24 (m, 1H, aromatic), 7.83 (s, 1H, aromatic), 7.50 (m, 3H, CONH+aromatic), 7.38 (dd, 1H, aromatic), 7.13 (d, 2H, aromatic), 7.00 (d, 1H, aromatic), 4.63 (s, 2H, CH$_2$), 3.29 (m, 5H, CH$_2$+CH$_3$), 2.50 (m, 9H, 3×CH$_2$+CH$_3$), 0.96 (t, 6H, 2×CH$_3$). MS m/z 611, 613 [M$^+$−1].

Example 30

Synthesis of 5-[5-(2-Iodo-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

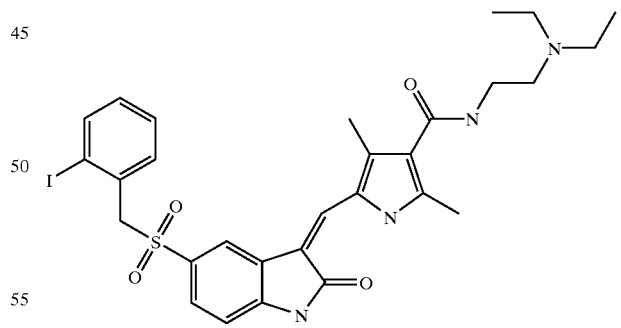

Orange solid, (67 mg, 59%)
$^1$H-NMR (400 MHz, DMSO-$d_6$) δ 13.57 (br s, 1H, pyrrole NH), 10.80 (v br s, 1H, CONH), 8.13 (m, 1H, aromatic), 7.81 (m, 1H, aromatic), 7.78 (m, 1H, aromatic), 7.48 (t, 1H, CONH), 7.5 (multiplets, 4H, aromatic), 7.08 (m, 1H, aromatic), 7.01 (d, 1H, aromatic), 4.63 (s, 2H, CH$_2$), 3.29 (m, 5H, CH$_2$+CH$_3$), 2.50 (multiplets, 9H, 3×CH$_2$+CH$_3$), 0.96 (t, 6H, 2×CH$_3$). MS m/z 659 [M$^+$−1].

Example 31

Synthesis of 3-[1-[3,5-Dimethyl-4-(4-methyl-piperazine-1-carbonyl)-1H-pyrrol-2-yl]-meth-(Z)-ylidene]-5-(2-iodo-phenylmethanesulfonyl)-1,3-dihydro-indol-2-one

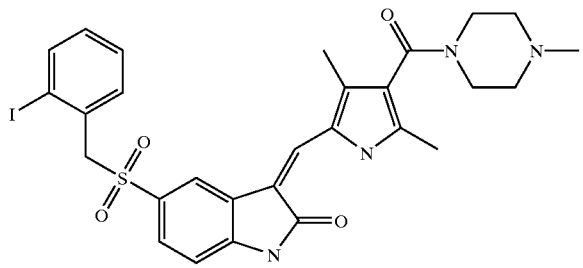

Yellow solid, (63 mg, 51%)
$^1$H-NMR (400 MHz, DMSO-$d_6$) δ 13.53 (br s, 1H, pyrrole NH), 11.10 (v br s, 1H, CONH), 8.11 (m, 1H, aromatic), 7.81 (d, 1H, aromatic), 7.75 (s, 1H, aromatic), 7.35 (multiplets, 3H, aromatic), 7.07 (m, 1H, aromatic), 6.99 (d, 1H, aromatic), 4.72 (s, 2H, CH$_2$), 3.31 (m, 7H, 2×CH$_2$+CH$_3$), 2.29 (m, 7H, 2×CH$_2$+CH$_3$), 2.19 (s, 3H, CH$_3$). MS m/z 645 [M$^+$+1].

Example 32

Synthesis of 5-[5-(4-Cyano-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

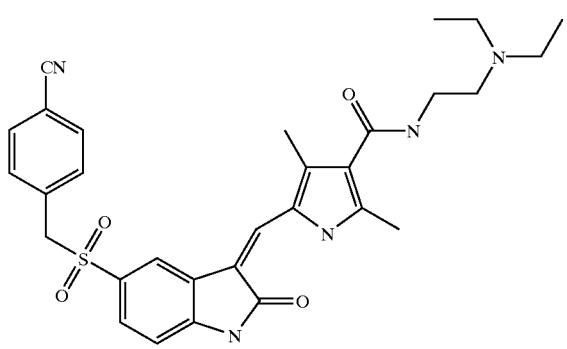

Orange solid, (47 mg, 51%)
$^1$H-NMR (400 MHz, DMSO-$d_6$) δ 13.57 (br s, 1H, pyrrole NH), 10.80 (v br s, 1H, CONH), 8.25 (m, 1H, aromatic), 7.82 (s, 1H, aromatic), 7.69 (d, 2H, aromatic), 7.48 (t, 1H, CONH), 7.40 (m, 3H, aromatic), 7.02 (d, 1H, aromatic), 7.01 (d, 1H, aromatic), 4.78 (s, 2H, CH$_2$), 3.29 (m, 5H, CH$_2$+CH$_3$), 2.50 (m, 9H, 3×CH$_2$CH$_3$), 0.98 (t, 6H, 2×CH$_3$). MS m/z 558 [M$^+$−1].

Example 33

Synthesis of 4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile

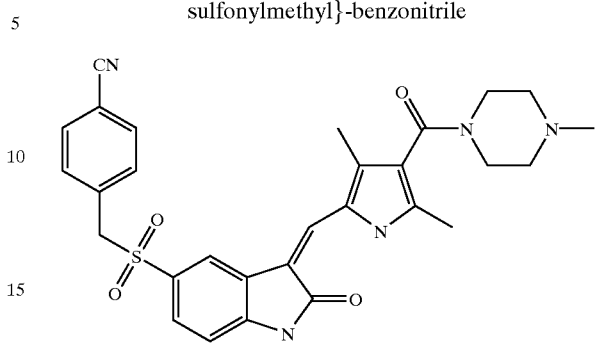

Orange solid, (57 mg, 55%)
MS m/z 543 [M$^+$].

Example 34

Synthesis of 3-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid

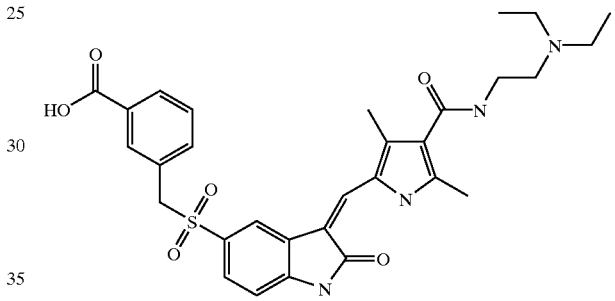

Orange solid, (61 mg, 69%)
$^1$H-NMR (400 MHz, DMSO-$d_6$) δ 13.58 (br s, 1H, pyrrole NH), 11.60 (v br s, 1H, CONH), 8.21 (m, 1H, aromatic), 7.90 (m, 1H, aromatic), 7.80 (m, 2H, aromatic), 7.47 (multiplets, 4H, CONH+aromatic), 7.00 (d, 1H, aromatic), 4.73 (s, 2H, CH$_2$), 3.80 (s, 3H, OCH$_3$), 3.28 (s, 5H, CH$_2$+CH$_3$), 2.50 (multiplets, 9H, 3×CH$_2$+CH$_3$), 0.98 (t, 6H, 2×CH$_3$). MS m/z 591 [M$^+$−1].

Example 35

Synthesis of 3-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid Methyl Ester

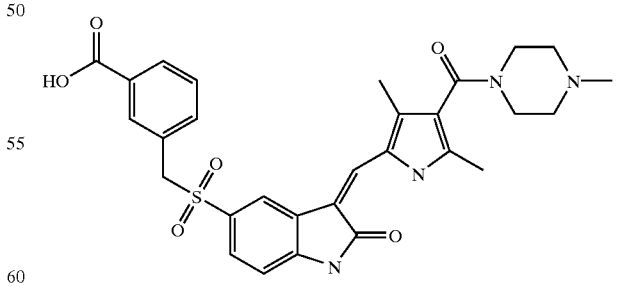

Yellow solid, (61 mg, 49%)
$^1$H-NMR (400 MHz, DMSO-$d_6$) δ 13.53 (br s, 1H, pyrrole NH), 11.20 (v br s, 1H, CONH), 8.19 (m, 1H, aromatic), 7.90 (m, 1H, aromatic), 7.78 (s, 2H, aromatic), 7.45 (multiplets, 3H, aromatic), 7.00 (d, 1H, aromatic), 4.72 (s, 2H, CH$_2$), 3.79 (s, 3H, OCH$_3$), 3.31 (m, 7H, 2×CH$_2$+CH$_3$), 2.29 (m, 7H, 2×CH$_2$+CH$_3$), 2.19 (s, 3H, CH$_3$). MS m/z 575 [M$^+$−1].

Example 36

Synthesis of 3-[1-[3,5-Dimethyl-4-(4-methyl-piperazine-1-carbonyl)-1H-pyrrol-2-yl]-meth-(Z)-ylidene]-5-(3-trifluoromethoxy-phenylmethanesulfonyl)-1,3-dihydro-indol-2-one

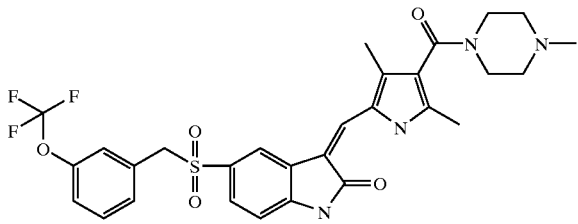

Yellow solid, (63 mg, 51%)
$^1$H-NMR (400 MHz, DMSO-$d_6$) δ 13.57 (br s, 1H, pyrrole NH), 11.37 (br s, 1H, CONH), 8.23 (s, 1H, aromatic), 7.83 (s, 1H, aromatic), 7.51 (m, 2H, aromatic), 7.40 (m, 1H, aromatic), 7.27 (m, 1H, aromatic), 7.15 (d, 1H, aromatic), 6.95 (d, 1H, aromatic), 4.66 (s, 2H, CH$_2$), 3.30 (m, 7H, 2×CH$_2$+CH$_3$), 2.50 (m, 10H, 2×CH$_2$+CH$_3$). MS m/z 601 [M$^+$–1].

Example 37

Synthesis of 2,4-Dimethyl-5-[2-oxo-5-(3-trifluoromethoxy-phenylmethanesulfonyl)-1,2-dihydro-indol-(3Z)-ylidenemethyl]-1H-pyrrole-3-carboxylic acid (2-Diethylamino-ethyl)-amide

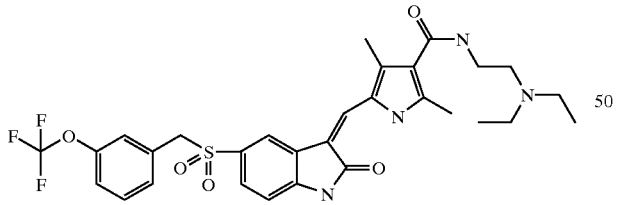

Yellow solid, (71 mg, 59%)
$^1$H-NMR (400 MHz, DMSO-$d_6$) δ 13.58 (br s, 1H, pyrrole NH), 11.37 (br s, 1H, CONH), 8.22 (s, 1H, aromatic), 7.82 (s, 1H, aromatic), 7.45 (m, 2H, CONH+aromatic), 7.38 (d, 1H, aromatic), 7.32 (d, 1H, aromatic), 7.24 (d, 1H, aromatic), 7.13 (s, 1H, aromatic), 6.98 (d, 1H, aromatic), 4.73 (s, 2H, CH$_2$), 3.30 (s, 5H, CH$_2$+CH$_3$), 2.50 (multiplets, 9H, 3×CH$_2$+CH$_3$), 0.98 (t, 6H, 2×CH$_3$). MS m/z 617 [M$^+$–1].

Example 38

Synthesis of 3-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile

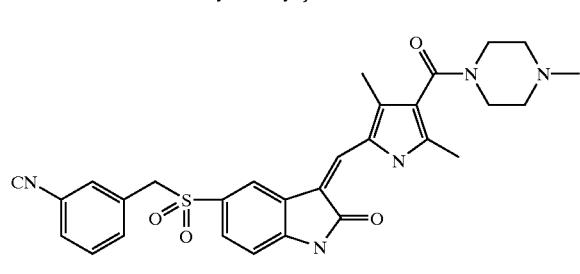

Orange solid, (68 mg, 47%)
$^1$H-NMR (400 MHz, DMSO-$d_6$) δ 13.53 (br s, 1H, pyrrole NH), 11.39 (br s, 1H, CONH), 8.22 (s, 1H, aromatic), 7.82 (m, 2H, aromatic), 7.50 (multiplets, 3H, aromatic), 7.38 (m, 1H, aromatic), 7.00 (d, 1H, aromatic), 4.74 (s, 2H, CH$_2$), 3.32 (m, 7H, 2×CH$_2$+CH$_3$), 2.31 (m, 7H, 2×CH$_2$+CH$_3$), 2.20 (s, 3H, CH$_3$). MS m/z 617 [M$^+$–1].

Example 39

Synthesis of 5-[5-(3-Cyano-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

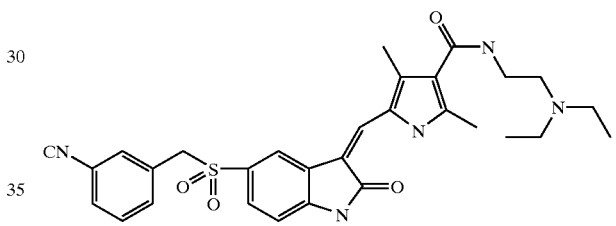

Yellow orange solid, (63 mg, 59%)
$^1$H-NMR (400 MHz, DMSO-$d_6$) δ 13.53 (br s, 1H, pyrrole NH), 11.39 (br s, 1H, CONH), 8.23 (m, 1H, aromatic), 7.82 (s, 1H, aromatic), 7.79 (d, 1H, aromatic), 7.61 (s, 1H, aromatic), 7.50 (m, 3H, aromatic+CONH), 7.37 (m, 1H, aromatic), 7.00 (d, 1H, aromatic), 4.73 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 558 [M$^+$–1].

Example 40

Synthesis of 3-[1-[3,5-Dimethyl-4-(4-methyl-piperazine-1-carbonyl)-1H-pyrrol-2-yl]-meth-(Z)-ylidene]-5-m-tolylmethanesulfonyl-1,3-dihydro-indol-2-one

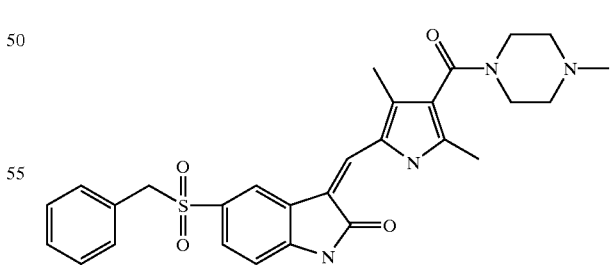

Orange solid, (81 mg, 64%)
$^1$H-NMR (400 MHz, DMSO-$d_6$) δ 13.54 (br s, 1H, pyrrole NH), 11.35 (br s, 1H, CONH), 8.18 (s, 1H, aromatic), 7.80 (s, 1H, aromatic), 7.67 (d, 1H, aromatic), 7.51 (s, 1H, aromatic), 7.41 (d, 1H, aromatic), 7.19 (d, 1H, aromatic), 7.11 (t, 1H, aromatic), 7.01 (d, 1H, aromatic), 4.61 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 643 [M$^+$–1].

Example 41

Synthesis of 2,4-Dimethyl-5-[2-oxo-5-m-tolylmethanesulfonyl-1,2-dihydro-indol-(3Z)-ylidenemethyl]-1H-pyrrole-3-carboxylic acid (2-Diethylamino-ethyl)-amide

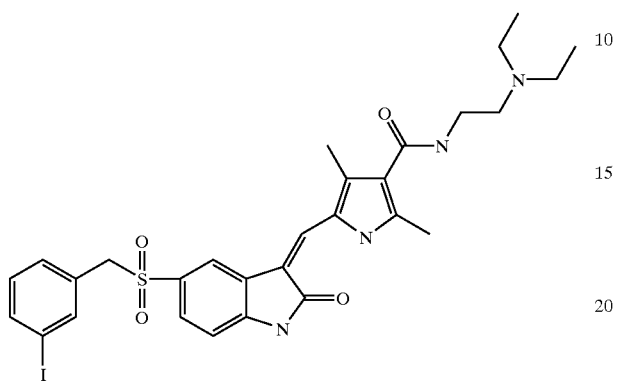

Yellow solid, (69 mg, 59%)
$^1$H-NMR (400 MHz, DMSO-d$_6$) δ 13.57 (br s, 1H, pyrrole NH), 11.34 (br s, 1H, CONH), 8.19 (s, 1H, aromatic), 7.82 (s, 1H, aromatic), 7.67 (d, 1H, aromatic), 7.51 (m, 2H, aromatic+CONH), 7.19 (d, 1H, aromatic), 7.12 (t, 1H, aromatic), 7.01 (d, 1H, aromatic), 4.61 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 659 [M$^+$−1].

Example 42

Synthesis of 5-(3-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

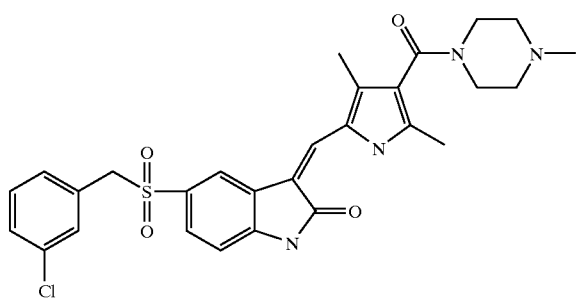

Yellow solid, (71 mg, 45%)
$^1$H-NMR (400 MHz, DMSO-d$_6$) δ 13.54 (br s, 1H, pyrrole NH), 11.39 (br s, 1H, CONH), 8.24 (s, 1H, aromatic), 7.83 (s, 1H, aromatic), 7.51 (m, 1H, aromatic), 7.33 (multiplets, 3H, aromatic), 7.11 (m, 1H, aromatic), 7.02 (d, 1H, aromatic), 6.95 (d, 1H, aromatic), 4.67 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 551 [M$^+$−1].

Example 43

Synthesis of 5-[5-(2,4-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide

Yellow solid, (61 mg, 55%)
$^1$H-NMR (400 MHz, DMSO-d$_6$) δ 13.59 (br s, 1H, pyrrole NH), 11.36 (br s, 1H, CONH), 8.27 (s, 1H, aromatic), 7.85 (m, 1H, aromatic), 7.50 (t, 1H, CONH), 7.37 (dd, 1H, aromatic), 7.26 (m, 2H, aromatic), 7.09 (m, 1H, aromatic), 7.01 (d, 1H, aromatic), 4.63 (s, 2H, CH$_2$), 3.28 (m, 5H, CH$_2$+CH$_3$), 2.50 (m, 9H, 3×CH$_2$+CH$_3$), 0.98 (t, 6H, 2×CH$_3$). MS m/z 569 [M$^+$−1].

Example 44

Synthesis of 5-(4-tert-Butyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

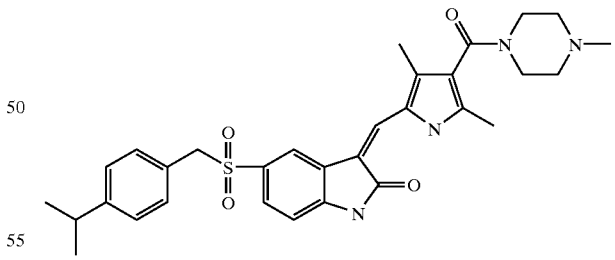

Yellow solid, (69 mg, 55%)
$^1$H-NMR (400 MHz, DMSO-d$_6$) δ 13.56 (br s, 1H, pyrrole NH), 11.36 (br s, 1H, CONH), 8.23 (s, 1H, aromatic), 7.81 (s, 1H, aromatic), 7.47 (dd 1H, aromatic), 7.32 (d, 2H, aromatic), 7.12 (d, 2H, aromatic), 7.01 (d, 1H, aromatic), 4.54 (s, 2H, CH$_2$), 3.32), 2.31 (m, 7H, 2×CH$_2$+CH$_3$), 2.19 (s, 3H, CH$_3$), 1.23 (s, 9H, t-Bu). MS m/z 573 [M$^+$−1].

Example 45

Synthesis of 5-[5-(4-tert-Butyl-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

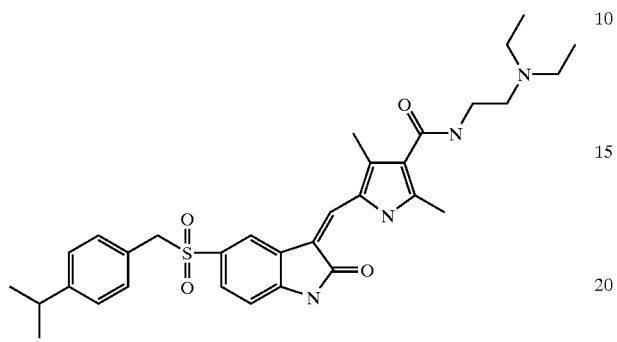

Yellow-orange solid, (62 mg, 51%)
$^1$H-NMR (400 MHz, DMSO-$d_6$) δ 13.60 (br s, 1H, pyrrole NH), 11.36 (br s, 1H, CONH), 8.26 (s, 1H, aromatic), 7.84 (s, 1H, aromatic), 7.47 (m, 2H, aromatic+CONH), 7.33 (d, 2H, aromatic), 7.13 (d, 2H, aromatic), 7.01 (d, 1H, aromatic), 4.55 (s, 2H, CH$_2$), 3.28 (m, 5H, CH$_2$+CH$_3$), 2.50 (multiplets, 9H, 3×CH$_2$+CH$_3$), 1.24 (s, 9H, t-Bu), 0.98 (t, 6H, 2×CH$_3$), MS m/z 589 [M$^+$−1].

Example 47

Synthesis of 5-[5-(2,6-Difluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

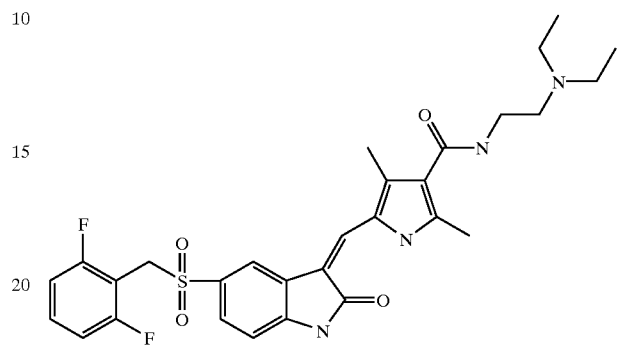

Orange solid, (77 mg, 59%).
$^1$H-NMR (400 MHz, DMSO-$d_6$) δ 13.60 (br s, 1H, pyrrole NH), 11.39 (br s, 1H, CONH), 8.33 (m, 1H, aromatic), 7.89 (s, 1H, aromatic), 7.46 (m, 3H, aromatic+CONH), 7.10 (m, 2H, aromatic), 7.01 (d, 1H, aromatic), 4.64 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$), MS m/z 569 [M$^+$−1].

Example 46

Synthesis of 5-(2,6-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

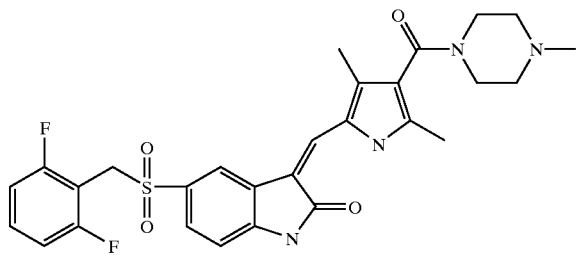

Orange solid, (67 mg, 53%)
$^1$H-NMR (400 MHz, DMSO-$d_6$) δ 13.56 (br s, 1H, pyrrole NH), 11.36 (br s, 1H, CONH), 8.32 (m, 1H, aromatic), 7.87 (s, 1H, aromatic), 7.46 (m, 2H, aromatic), 7.10 (m, 2H, aromatic), 7.01 (d, 1H, aromatic), 4.64 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 553 [M$^+$−1].

Example 48

Synthesis of 5-(3-Bromo-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

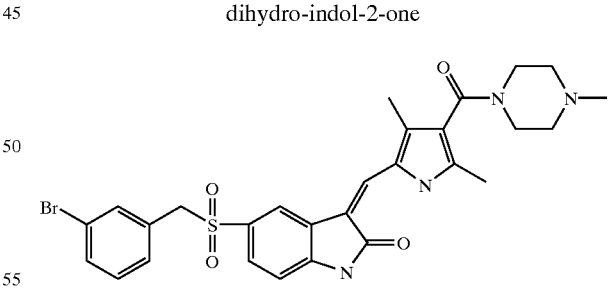

Orange solid, (73 mg, 59%)
$^1$H-NMR (400 MHz, DMSO-$d_6$) δ 13.53 (br s, 1H, pyrrole NH), 11.37 (br s, 1H, CONH), 8.22 (m, 1H, aromatic), 7.82 (s, 1H, aromatic), 7.52 (m, 1H, aromatic), 7.40 (m, 2H, aromatic), 7.27 (t, 1H, aromatic), 7.16 (d, 1H, aromatic), 7.01 (d, 1H, aromatic), 4.65 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 595, 597 [M$^+$−1].

Example 49

Synthesis of 5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

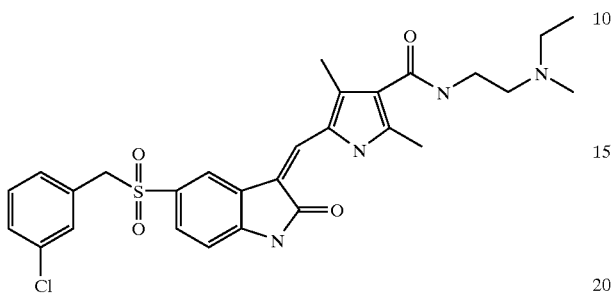

Orange-yellow solid, (72 mg, 69%)
$^1$-NMR (400 MHz, DMSO-$d_6$) δ 13.57 (br s, 1H, pyrrole NH), 11.34 (br s, 1H, CONH), 8.24 (s, 1H, aromatic), 7.83 (s, 1H, aromatic), 7.51 (m, 1H, CONH), 7.34 (m, 3H, aromatic), 7.26 (s, 1H, aromatic), 7.12 (d, 1H, aromatic), 7.01 (d, 1H, aromatic), 4.66 (s, 2H, CH$_2$), 3.31 (m, 5H, CH$_2$+CH$_3$), 2.50 (m, 9H, 3×CH$_2$+CH$_3$), 0.98 (t, 6H, 2×CH$_3$). MS m/z 567 [M$^+$−1].

Example 50

Synthesis of 5-(2,4-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

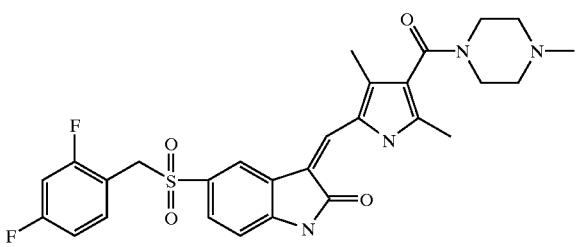

Orange-yellow solid, (75 mg, 68%)
$^{HL}$H-NMR (400 MHz, DMSO-$d_6$) δ 13.54 (br s, 1H, pyrrole NH), 11.38 (br s, 1H, CONH), 8.24 (s, 1H, aromatic), 7.84 (s, 1H, aromatic), 7.38 (m, 1H, aromatic), 7.24 (m, 2H, aromatic), 7.09 (m, 1H, aromatic), 7.00 (d, 1H, aromatic), 4.63 (s, 2H, CH$_2$), 3.30 (m, 7H, 2×CH$_2$+CH$_3$), 2.31 (m, 7H, 2×CH$_2$+CH$_3$), 2.19 (s, 3H). MS m/z 553 [M$^+$−1].

Example 51

Synthesis of 3-[1-[3,5-Dimethyl-4-(4-methyl-piperazine-1-carbonyl)-1H-pyrrol-2-yl]-meth-(Z)-ylidene]-5-(4-nitro-phenylmethanesulfonyl)-1,3-dihydro-indol-2-one

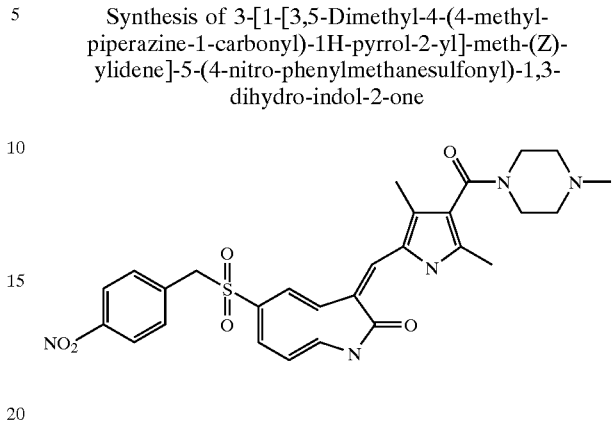

Orange solid, (62 mg, 61%)
$^{HL}$H-NMR (400 MHz, DMSO-$d_6$) δ 13.53 (br s, 1H, pyrrole NH), 10.80 (v br s, 1H, CONH), 8.24 (m, 1H, aromatic), 8.18 (d, 2H, aromatic), 7.81 (s, 1H, aromatic), 7.45 (d, 2H, aromatic), 7.39 (dd, 1H, aromatic), 7.01 (d, 1H, aromatic), 4.86 (s, 2H, CH$_2$), 3.33 (m, 7H, 2×CH$_2$+CH$_3$), 2.29 (m, 7H, 2×CH$_2$+CH$_3$), 2.20 (s, 3H, CH$_3$). MS m/z 562 [M$^+$−1].

Example 52

Synthesis of 2,4-Dimethyl-5-[5-(4-nitro-phenylmethanesulfonyl)-2-oxo-1,2-dihydro-indol-(3Z)-ylidenemethyl]-1H-pyrrole-3-carboxylic acid (2-Diethylamino-ethyl)-amide

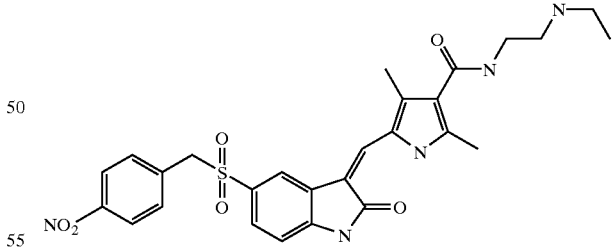

Yellow solid, (75 mg, 61%)
$^1$H-NMR (400 MHz, DMSO-$d_6$) δ 13.60 (br s, 1H, pyrrole NH), 11.41 (br s, 1H, CONH), 8.29 (s, 1H, aromatic), 8.19 (d, 2H, aromatic), 7.86 (s, 1H, aromatic), 7.57 (m, 1H, CONH), 7.46 (d, 2H, aromatic), 7.38 (m, 1H, aromatic), 7.01 (d, 1H, aromatic), 4.87 (s, 2H, CH$_2$), 3.31 (m, 5H, CH$_2$+CH$_3$), 2.53 (m, 9H, 3×CH$_2$+CH$_3$), 1.04 (m, 6H, 2×CH$_3$). MS m/z 578 [M$^+$−1].

Example 53

Synthesis of 3-[1-[3,5-Dimethyl-4-(4-methyl-piperazine-1-carbonyl)-1H-pyrrol-2-yl]-meth-(Z)-ylidene]-5-(3-nitro-phenylmethanesulfonyl)-1,3-dihydro-indol-2-one

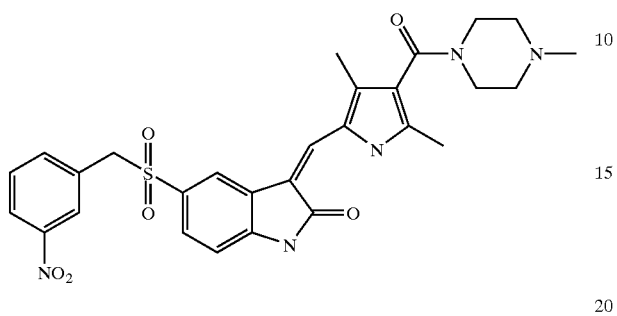

Orange solid, (71 mg, 68%)
$^1$H-NMR (400 MHz, DMSO-$d_6$) δ 13.53 (br s, 1H, pyrrole NH), 11.37 (br s, 1H, CONH), 8.22 (m, 2H, aromatic), 8.10 (d, 1H, aromatic), 7.82 (s, 1H, aromatic), 7.62 (m, 2H, aromatic), 7.40 (dd, 1H, aromatic), 6.95 (d, 1H, aromatic), 6.93 (d, 1H, aromatic), 4.73 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 562 [M$^+$−1].

Example 54

Synthesis of 2,4-Dimethyl-5-[5-(3-nitro-phenylmethanesulfonyl)-2-oxo-1,2-dihydro-indol-(3Z)-ylidenemethyl]-1H-pyrrole-3-carboxylic acid (2-Diethylamino-ethyl)-amide

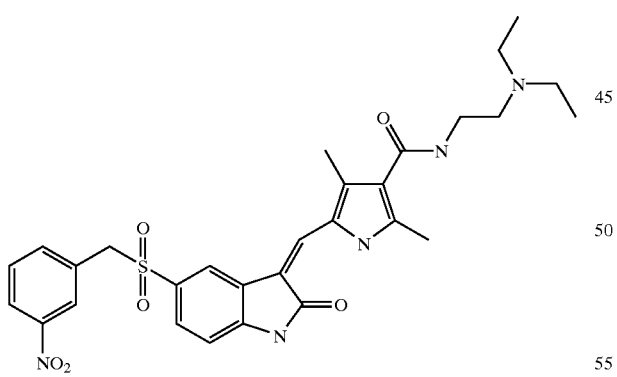

Orange solid, (73 mg, 64%)
$^1$H-NMR (400 MHz, DMSO-$d_6$) δ 13.53 (br s, 1H, pyrrole NH), 11.36 (br s, 1H, CONH), 8.24 (m, 1H, aromatic), 8.18 (m, 1H, aromatic), 8.06 (m, 1H, aromatic), 7.83 (s, 1H, aromatic), 7.61 (m, 2H, aromatic), 7.49 (t, 1H, CONH), 7.04 (dd, 1H, aromatic), 6.99 (d, 1H, aromatic), 4.73 (s, 2H, CH$_2$), 3.31 (m, 5H, CH$_2$+CH$_3$), 2.53 (multiplets, 9H, 3×CH$_2$+CH$_3$), 0.98 (t, 6H, 2×CH$_3$). MS m/z 578 [M$^+$−1].

Example 55

Synthesis of 5-[5-(3-Bromo-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

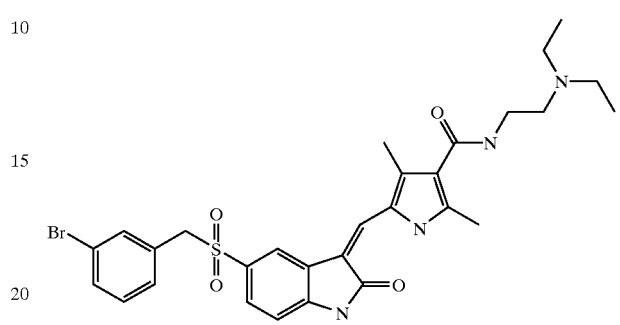

Orange-yellow solid, (69 mg, 62%)
$^1$H-NMR (400 MHz, DMSO-$d_6$) δ 13.59 (br s, 1H, pyrrole NH), 11.42 (br s, 1H, CONH), 8.24 (m, 1H, aromatic), 7.84 (s, 1H, aromatic), 7.63 (m, 1H, CONH), 7.53 (d, 1H, aromatic), 7.41 (m, 2H, aromatic), 7.27 (t, 1H, aromatic), 7.17 (d, 1H, aromatic), 7.02 (d, 1H, aromatic), 4.66 (s, 2H, CH$_2$), 3.33 (m, 5H, CH$_2$+CH$_3$), 2.50 (m, 9H, 3×CH$_2$+CH$_3$), 1.04 (m, 6H, 2×CH$_3$). MS m/z 612 [M$^+$−1].

Example 56

Synthesis of 5-(3,5-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

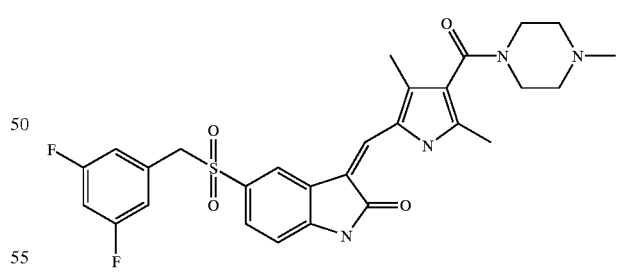

Yellow solid, (67 mg, 69%)
$^1$H-NMR (400 MHz, DMSO-$d_6$) δ 13.54 (br s, 1H, pyrrole NH), 10.80 (v br s, 1H, CONH), 8.26 (s, 1H, aromatic), 7.85 (s, 1H, aromatic), 7.42 (d, 1H, aromatic), 7.24 (m, 1H, aromatic), 7.02 (d, 1H, aromatic), 6.92 (d, 2H, aromatic), 4.70 (s, 2H, CH$_2$), 3.33 (m, 7H, 2×CH$_2$+CH$_3$), 2.31 (m, 7H, 2×CH$_2$+CH$_3$), 2.19 (s, 3H, CH$_3$). MS m/z 553 [M$^+$−1].

Example 57

Synthesis of 5-[5-(3,5-Difluoro-phenylmethanesulfonyl)-2-oxo-1,2-dihydro-indol-(3Z)-ylidenemethyl]-2,4-dimethyl-1H-pyrrole-3-carboxylic acid (2-Diethylaminoethyl)-amide

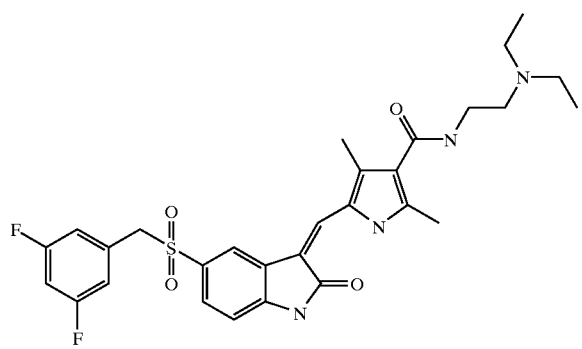

Yellow solid, (63 mg, 59%)
$^1$H-NMR (400 MHz, DMSO-d$_6$) δ 13.58 (br s, 1H, pyrrole NH), 11.40 (v br s, 1H, CONH), 8.27 (s, 1H, aromatic), 7.86 (s, 1H, aromatic), 7.50 (m, 1H, aromatic), 7.42 (m, 1H, aromatic), 7.24 (m, 1H, aromatic), 7.01 (d, 1H, aromatic), 6.90 (d, 2H, aromatic), 4.70 (s, 2H, CH$_2$), 3.33 (m, 5H, CH$_2$+CH$_3$), 2.50 (multiplets, 9H, 3×CH$_2$+CH$_3$), 0.98 (m, 6H, 2×CH$_3$). MS m/z 569 [M$^+$−1].

Example 58

Synthesis of 5-(3,4-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

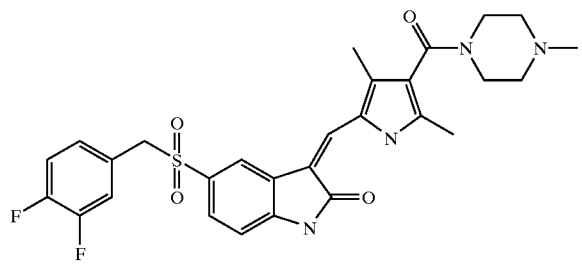

Orange solid, (54 mg, 57%)
$^1$H-NMR (400 MHz, DMSO-d$_6$) δ 13.54 (br s, 1H, pyrrole NH), 11.37 (v br s, 1H, CONH), 8.23 (s, 1H, aromatic), 7.83 (s, 1H, aromatic), 7.37 (m, 2H, aromatic), 7.25 (m, 1H, aromatic), 7.02 (m, 2H, aromatic), 4.66 (s, 2H, CH$_2$), 3.32 (m, 7H, 2×CH$_2$+CH$_3$), 2.32 (m, 7H, 2×CH$_2$+CH$_3$), 2.20 (s, 3H, CH$_3$). MS m/z 553 [M$^+$−1].

Example 59

Synthesis of 5-[5-(3,4-Difluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

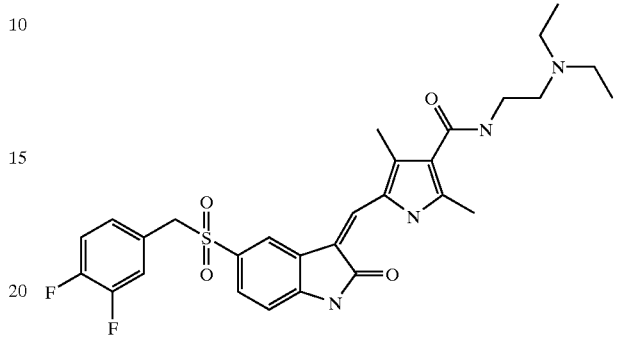

Orange solid, (59 mg, 52%)
$^1$H-NMR (400 MHz, DMSO-d$_6$) δ 13.58 (br s, 1H, pyrrole NH), 11.30 (v br s, 1H, CONH), 8.24 (m, 1H, aromatic), 7.85 (s, 1H, aromatic), 7.49 (t, 1H, CONH), 7.35 (m, 2H, aromatic), 7.25 (m, 1H, aromatic), 7.02 (m, 2H, aromatic), 4.66 (s, 2H, CH$_2$), 3.32 (m, 5H, CH$_2$+CH$_3$), 2.50 (multiplets, 9H, 3×CH$_2$+CH$_3$), 0.98 (m, 6H, 2×CH$_3$). MS m/z 571 [M$^+$+1].

Example 60

Synthesis of 5-(2,5-bis-Trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

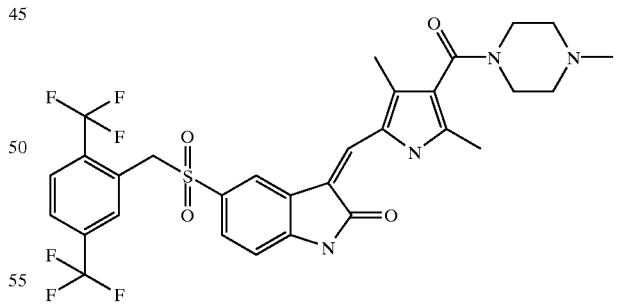

Orange solid, (59 mg, 67%)
$^1$H-NMR (400 MHz, DMSO-d$_6$) δ 13.55 (br s, 1H, pyrrole NH), 11.30 (br s, 1H, CONH), 8.23 (s, 1H, aromatic), 8.00 (m, 2H, aromatic), 7.83 (s, 1H, aromatic), 7.69 (s, 1H, aromatic), 7.42 (dd, 1H, aromatic), 7.04 (d, 1H, aromatic), 4.88 (s, 2H, CH$_2$), 3.31 (m, 7H, 2×CH$_2$+CH$_3$), 2.31 (m, 7H, 2×CH$_2$+CH$_3$), 2.20 (s, 3H, CH$_3$). MS m/z 653 [M$^-$−1].

Example 61

Synthesis of 5-[5-(2,5-bis-Trifluoromethyl-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

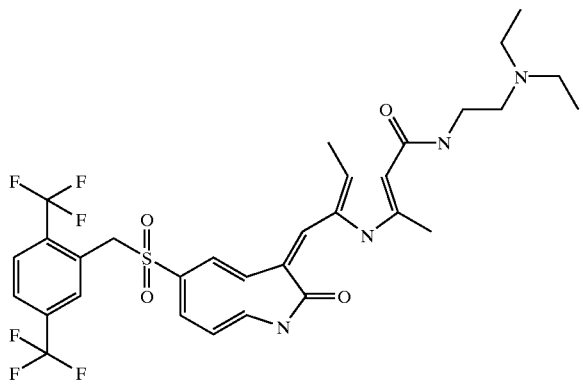

Orange-yellow solid, (64 mg, 67%)
$^1$H-NMR (400 MHz, DMSO-$d_6$) δ 13.59 (br s, 1H, pyrrole NH), 11.41 (br s, 1H, CONH), 8.24 (s, 1H, aromatic), 8.00 (m, 2H, aromatic), 7.83 (s, 1H, aromatic), 7.69 (s, 1H, aromatic), 7.50 (t, 1H, CONH), 7.42 (d, 1H, aromatic), 7.04 (d, 1H, aromatic), 4.88 (s, 2H, CH$_2$), 3.32 (m, 5H, CH$_2$+CH$_3$), 2.50 (multiplets, 9H, 3×CH$_2$+CH$_3$), 0.98 (m, 6H, 2×CH$_3$). MS m/z 669 [M$^+$−1].

Example 62

Synthesis of 5-(3,5-bis-Trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

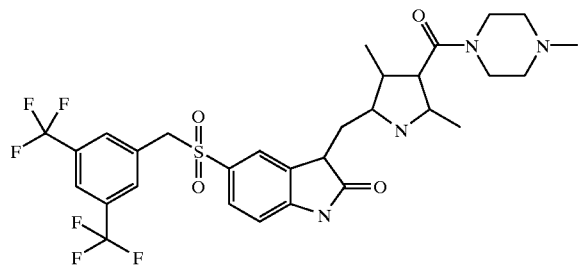

Orange-yellow solid, (67 mg, 61%)
$^1$H-NMR (400 MHz, DMSO-$d_6$) δ 13.55 (br s, 1H, pyrrole NH), 11.40 (br s, 1H, CONH), 8.15 (s, 1H, aromatic), 8.08 (s, 1H, aromatic), 7.80 (m, 2H, aromatic), 7.38 (dd, 1H, aromatic), 7.01 (d, 1H, aromatic), 4.91 (s, 2H, CH$_2$), 3.32 (m, 7H, 2×CH$_2$+CH$_3$), 2.30 (m, 7H, 2×CH$_2$+CH$_3$), 2.19 (s, 3H, CH$_3$). MS m/z 6.53 [M$^+$−1].

Example 63

Synthesis of 5-[5-(3,5-bis-Trifluoromethyl-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

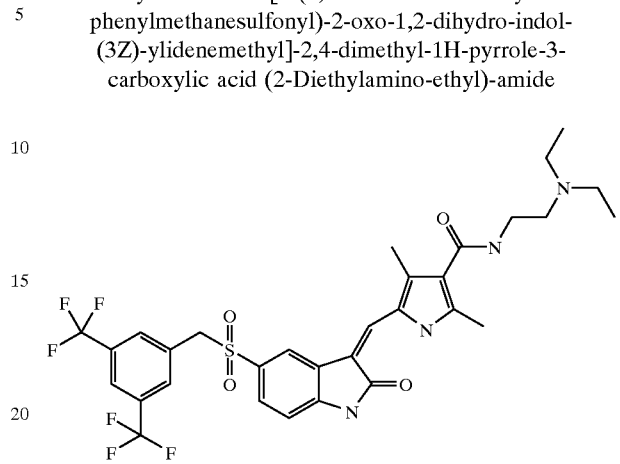

Orange-yellow solid, (74 mg, 63%)
$^1$H-NMR (400 MHz, DMSO-$d_6$) δ 13.55 (br s, 1H, pyrrole NH), 11.39 (br s, 1H, CONH), 8.15 (m, 1H, aromatic), 8.08 (s, 1H, aromatic), 7.80 (m, 3H, aromatic), 7.48 (t, 1H, CONH), 7.38 (dd, 1H, aromatic), 7.05 (d, 1H, aromatic), 4.91 (s, 2H, CH$_2$), 3.32 (m, 5H, CH$_2$+CH$_3$), 2.50 (multiplets, 9H, 3×CH$_2$+CH$_3$), 0.98 (m, 6H, 2×CH$_3$). MS m/z 669 [M$^+$−1].

Example 64

Synthesis of 3-[1-[3,5-Dimethyl-4-(4-methyl-piperazine-1-carbonyl)-1H-pyrrol-2-yl]-meth-(Z)-ylidene]-5-(2-hydroxy-5-nitro-phenylmethanesulfonyl)-1,3-dihydro-indol-2-one

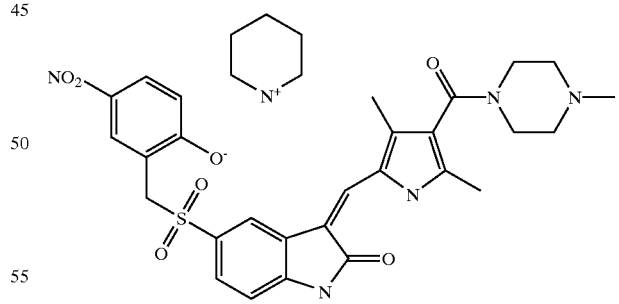

Orange-brown solid, (61 mg, 69%)
$^1$H-NMR (400 MHz, DMSO-$d_6$) δ 13.53 (br s, 1H, pyrrole NH), 11.34 (br s, 1H, CONH), 8.15 (s, 1H, aromatic), 8.04 (d, 1H, aromatic), 7.97 (dd, 1H, aromatic), 7.74 (s, 1H, aromatic), 7.36 (dd, 1H, aromatic), 6.96 (d, 1H, aromatic), 6.65 (d, 1H, aromatic), 4.58 (s, 2H, CH$_2$), 3.45 (m, 7H, 2×CH$_2$+CH$_3$), 2.28 (m, 7H, 2×CH$_2$+CH$_3$), 2.20 (s, 3H, CH$_3$). MS m/z 578 [M$^+$−1].

Example 65

Synthesis of 5-[5-(2-Hydroxy-5-nitro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

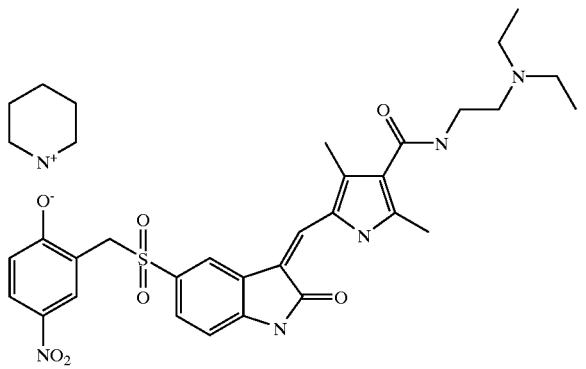

Orange-yellow solid, (54 mg, 57%)
$^1$-NMR (400 MHz, DMSO-$d_6$) δ 13.58 (br s, 1H, pyrrole NH), 11.37 (br s, 1H, CONH), 8.27 (s, 1H, aromatic), 7.84 (m, 1H, aromatic), 7.49 (t, 1H, CONH), 7.37 (multiplets, 2H, aromatic), 7.16 (m, 1H, aromatic), 7.02 (m, 3H, aromatic), 6.65 (d, 1H, aromatic), 4.67 (s, 2H, CH$_2$), 3.31 (m, 5H, CH$_2$+CH$_3$), 2.50 (multiplets, 9H, 3×CH$_2$+CH$_3$), 0.98 (m, 6H, 2×CH$_3$). MS m/z 594 [M$^+$−1].

Example 66

Synthesis of 3-[1-[3,5-Dimethyl-4-(4-methyl-piperazine-1-carbonyl)-1H-pyrrol-2-yl]-meth-(Z)-ylidene]-5-(2-methoxy-5-nitro-phenylmethanesulfonyl)-1,3-dihydro-indol-2-one

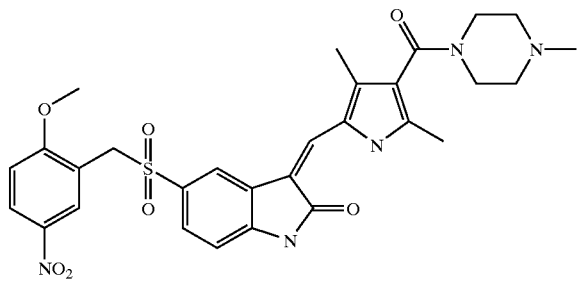

Orange-yellow solid, (61 mg, 57%)
$^1$H-NMR (400 MHz, DMSO-$d_6$) δ 13.53 (br s, 1H, pyrrole NH), 11.34 (br s, 1H, CONH), 8.20 (d, 1H, aromatic), 8.15 (d, 2H, aromatic), 7.79 (s, 1H, aromatic), 7.36 (d, 1H, aromatic), 7.03 (d, 1H, aromatic), 6.96 (d, 1H, aromatic), 4.65 (s, 2H, CH$_2$), 3.45 (s, 1H, OCH$_3$), 3.32 (m, 7H, 2×CH$_2$+CH$_3$), 2.28 (m, 7H, 2×CH$_2$+CH$_3$), 2.18 (s, 3H, CH$_3$). MS m/z 592 [M$^+$−1].

Example 67

Synthesis of 5-[5-(2-Methoxy-5-nitro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

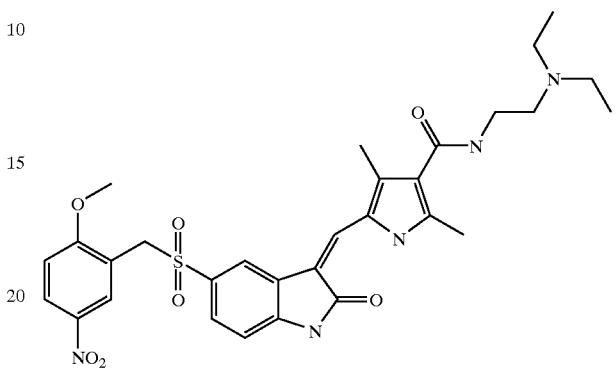

Orange-yellow solid, (62 mg, 61%)
$^1$H-NMR (400 MHz, DMSO-$d_6$) δ 13.58 (br s, 1H, pyrrole NH), 10.86 (br s, 1H, CONH), 8.24 (dd, 1H, aromatic), 8.15 (d, 2H, aromatic), 7.48 (m, 2H, aromatic), 7.39 (dd, 1H, aromatic), 7.09 (d, 1H, aromatic), 6.90 (d, 1H, aromatic), 4.63 (s, 2H, CH$_2$), 3.55 (s, 1H, OCH$_3$), 3.31 (m, 5H, CH$_2$+CH$_3$), 2.50 (multiplets, 9H, 3×CH$_2$+CH$_3$), 0.98 (m, 6H, 2×CH$_3$). MS m/z 608 [M$^+$−1].

Example 68

Synthesis of 3-[1-[3,5-Dimethyl-4-(4-methyl-piperazine-1-carbonyl)-1H-pyrrol-2-yl]-meth-(Z)-ylidene]-5-(2-fluoro-phenylmethanesulfonyl)-1,3-dihydro-indol-2-one

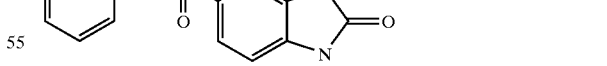

Orange-yellow solid, (63 mg, 60%)
$^1$H-NMR (400 MHz, DMSO-$d_6$) δ 13.54 (br s, 1H, pyrrole NH), 11.34 (br s, 1H, CONH), 8.26 (s, 1H, aromatic), 7.85 (s, 1H, aromatic), 7.38 (d, 2H, aromatic), 7.28 (m, 1H, aromatic), 7.17 (m, 2H, aromatic), 7.02 (d, 1H, aromatic), 4.64 (s, 2H, CH$_2$), 3.32 (m, 7H, 2×CH$_2$+CH$_3$), 2.31 (m, 7H, 2×CH$_2$+CH$_3$), 2.18 (s, 3H, CH$_3$). MS m/z 536 [M$^+$+1].

Example 69

Synthesis of 5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

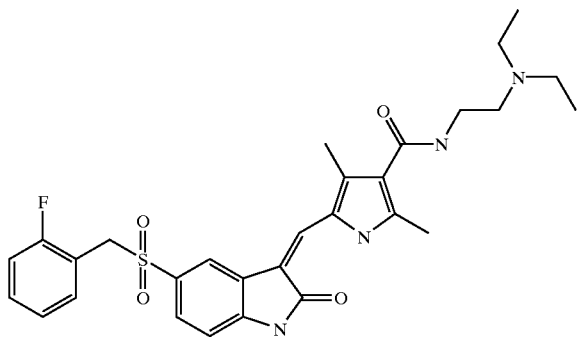

Orange solid, (73 mg, 63%)

$^1$-NMR (400 MHz, DMSO-d$_6$) δ 13.59 (br s, 1H, pyrrole NH), 11.37 (br s, 1H, CONH), 8.28 (s, 1H, aromatic), 7.85 (s, 1H, aromatic), 7.49 (t, 1H, CONH), 7.38 (m, 2H, aromatic), 7.26 (m, 1H, aromatic), 7.17 (m, 2H, aromatic), 7.02 (d, 1H, aromatic), 4.64 (s, 2H, CH$_2$), 3.29 (m, 5H, CH$_2$+CH$_3$), 2.50 (multiplets, 9H, 3×CH$_2$+CH$_3$), 0.98 (m, 6H, 2×CH$_3$). MS m/z 551 [M$^+$−1].

Example 70

Synthesis of 3-[1-[3,5-Dimethyl-4-(4-methyl-piperazine-1-carbonyl)-1H-pyrrol-2-yl]-meth-(Z)-ylidene]-5-(3-fluoro-phenylmethanesulfonyl)-1,3-dihydro-indol-2-one

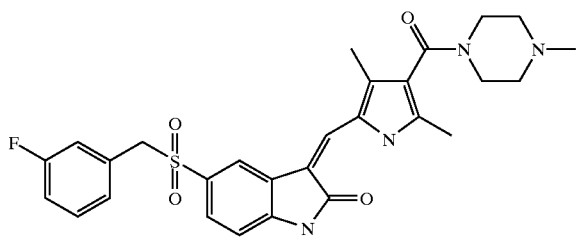

Orange-yellow solid, (53 mg, 59%)

$^1$H-NMR (400 MHz, DMSO-d$_6$) δ 13.54 (br s, 1H, pyrrole NH), 11.34 (br s, 1H, CONH), 8.26 (s, 1H, aromatic), 7.85 (s, 1H, aromatic), 7.38 (d, 1H, aromatic), 7.33 (m, 1H, aromatic), 7.16 (m, 1H, aromatic), 7.01 (m, 3H, aromatic), 4.64 (s, 2H, CH$_2$), 3.33 (m, 7H, 2×CH$_2$+CH$_3$), 2.31 (m, 7H, 2×CH$_2$+CH$_3$), 2.19 (s, 3H, CH$_3$). MS m/z 535 [M$^+$−1].

Example 71

Synthesis of 5-[5-(3-Fluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

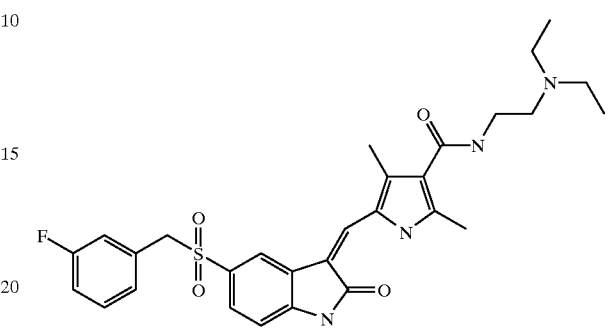

Orange solid, (71 mg, 62%)

$^1$H-NMR (400 MHz, DMSO-d$_6$) δ 13.56 (br s, 1H, pyrrole NH), 8.13 (s, 1H, aromatic), 7.96 (s, 1H, aromatic), 7.74 (m, 2H, aromatic), 7.50 (t, 1H, aromatic), 7.36 (d, 1H, aromatic), 6.89 (d, 1H, aromatic), 6.03 (d, 1H, aromatic), 4.44 (s, 2H, CH$_2$), 3.29 (m, 2H, CH$_2$), 2.96 (m, 3H, CH$_3$), 2.50 (multiplets, 9H, 3×CH$_2$+CH$_3$), 0.98 (m, 6H, 2×CH$_3$). MS m/z 551 [M$^+$−1].

Example 72

Synthesis of 3-[1-[3,5-Dimethyl-4-(4-methyl-piperazine-1-carbonyl)-1H-pyrrol-2-yl]-meth-(Z)-ylidene]-5-(4-fluoro-phenylmethanesulfonyl)-1,3-dihydro-indol-2-one

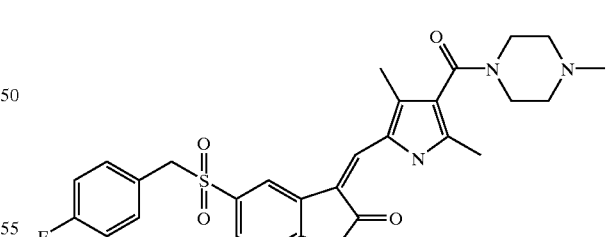

Yellow solid, (77 mg, 65%)

$^1$-NMR (400 MHz, DMSO-d$_6$) δ 13.54 (br s, 1H, pyrrole NH), 11.36 (br s, 1H, CONH), 8.26 (s, 1H, aromatic), 7.81 (m, 1H, aromatic), 7.38 (d, 1H, aromatic), 7.20 (m, 4H, aromatic), 7.01 (d, 1H, aromatic), 4.64 (s, 2H, CH$_2$), 3.33 (m, 7H, 2×CH$_2$+CH$_3$), 2.31 (m, 7H, 2×CH$_2$+CH$_3$), 2.19 (s, 3H, CH$_3$). MS m/z 535 [M$^+$−1].

Example 73

Synthesis of 5-[5-(4-Fluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

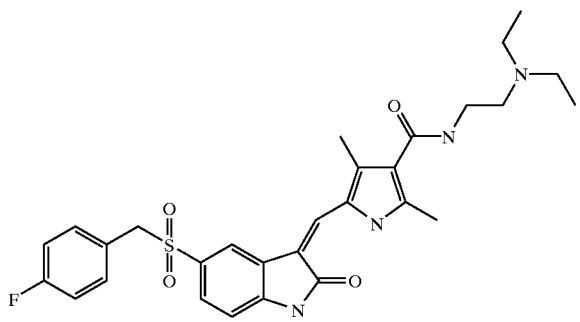

Orange solid, (77 mg, 65%)
$^1$H-NMR (400 MHz, DMSO-$d_6$) δ 13.58 (br s, 1H, pyrrole NH), 11.36 (br s, 1H, CONH), 8.26 (s, 1H, aromatic), 7.82 (m, 1H, aromatic), 7.49 (t, 1H, CONH), 7.36 (d, 1H, aromatic), 7.20 (multiplets, 4H, aromatic), 7.00 (d, 1H, aromatic), 4.64 (s, 2H, CH$_2$), 3.29 (m, 5H, CH$_2$+CH$_3$), 2.50 (multiplets, 9H, 3×CH$_2$+CH$_3$), 0.98 (m, 6H, 2×CH$_3$). MS m/z 551 [M$^+$–1].

Example 74

Synthesis of 3-[1-[3,5-Dimethyl-4-(4-methyl-piperazine-1-carbonyl)-1H-pyrrol-2-yl]-meth-(Z)-ylidene]-5-(4-trifluoromethoxy-phenylmethanesulfonyl)-1,3-dihydro-indol-2-one

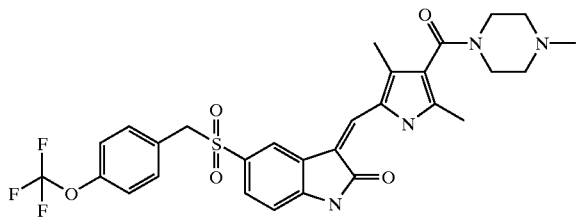

Orange solid, (63 mg, 66%)
$^1$H-NMR (400 MHz, DMSO-$d_6$) δ 13.54 (br s, 1H, pyrrole NH), 11.41 (br s, 1H, CONH), 8.20 (m, 1H, aromatic), 7.80 (m, 1H, aromatic), 7.42 (dd, 1H, aromatic), 7.31 (m, 4H, aromatic), 7.01 (d, 1H, aromatic), 4.68 (s, 2H, CH$_2$), 3.32 (m, 7H, 2×CH$_2$+CH$_3$), 2.29 (m, 7H, 2×CH$_2$+CH$_3$), 2.19 (s, 3H, CH$_3$). MS m/z 601 [M$^+$–1].

Example 75

Synthesis of 3-[1-[3,5-Dimethyl-4-(4-methyl-piperazine-1-carbonyl)-1H-pyrrol-2-yl]-meth-(Z)-ylidene]-5-(2-trifluoromethyl-phenylmethanesulfonyl)-1,3-dihydro-indol-2-one

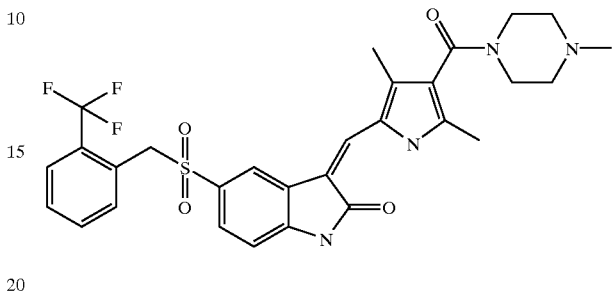

Yellow-orange solid, (71 mg, 68%)
$^1$H-NMR (400 MHz, DMSO-$d_6$) δ 13.55 (br s, 1H, pyrrole NH), 11.39 (br s, 1H, CONH), 8.24 (m, 1H, aromatic), 7.83 (s, 1H, aromatic), 7.70 (multiplets, 2H, aromatic), 7.60 (m, 1H, aromatic), 7.57 (d, 1H, aromatic), 7.41 (d, 1H, aromatic), 7.02 (d, 1H, aromatic), 4.75 (s, 2H, CH$_2$), 3.32 (m, 7H, 2×CH$_2$+CH$_3$), 2.31 (m, 7H, 2×CH$_2$+CH$_3$), 2.20 (s, 3H, CH$_3$). MS/z 585 [M$^+$–1].

Example 76

Synthesis of 2,4-Dimethyl-5-[2-oxo-5-(2-trifluoromethyl-phenylmethanesulfonyl)-1,2-dihydro-indol-(3Z)-ylidenemethyl]-1H-pyrrole-3-carboxylic acid (2-Diethylamino-ethyl)-amide

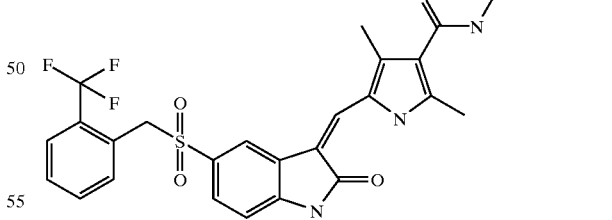

Yellow solid, (75 mg, 69%)
$^1$H-NMR (400 MHz, DMSO-$d_6$) δ 13.59 (br s, 1H, pyrrole NH), 11.37 (br s, 1H, CONH), 8.26 (s, 1H, aromatic), 7.84 (m, 1H, aromatic), 7.70 (multiplets, 2H, aromatic), 7.58 (t, 1H, CONH), 7.52 (m, 2H, aromatic), 7.40 (d, 1H, aromatic), 7.02 (d, 1H, aromatic), 4.75 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 601 [M$^+$–1].

Example 77

Synthesis of 3-[1-[3,5-Dimethyl-4-(4-methyl-piperazine-1-carbonyl)-1H-pyrrol-2-yl]-meth-(Z)-ylidene]-5-(3-trifluoromethyl-phenylmethanesulfonyl)-1,3-dihydro-indol-2-one

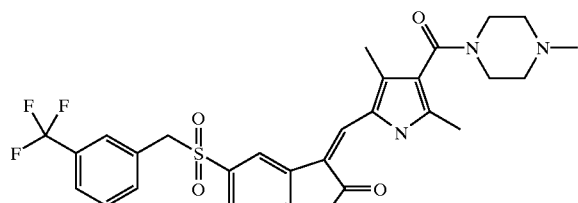

Orange solid, (74 mg, 66%)

$^1$H-NMR (400 MHz, DMSO-$d_6$) δ 13.53 (br s, 1H, pyrrole NH), 11.39 (br s, 1H, CONH), 8.20 (m, 1H, aromatic), 7.80 (m, 1H, aromatic), 7.68 (d, 1H, aromatic), 7.57 (t, 1H, aromatic), 7.49 (d, 1H, aromatic), 7.46 (s, 1H, aromatic), 7.39 (dd, 1H, aromatic), 7.01 (d, 1H, aromatic), 4.77 (s, 2H, CH$_2$), 3.32 (m, 7H, 2×CH$_2$+CH$_3$), 2.31 (m, 7H, 2×CH$_2$+CH$_3$), 2.20 (s, 3H, CH$_3$). MS m/z 585 [M$^+$−1].

Example 78

Synthesis of 2,4-Dimethyl-5-[2-oxo-5-(4-trifluoromethyl-phenylmethanesulfonyl)-1,2-dihydro-indol-(3Z)-ylidenemethyl]-1H-pyrrole-3-carboxylic acid (2-Diethylamino-ethyl)-amide

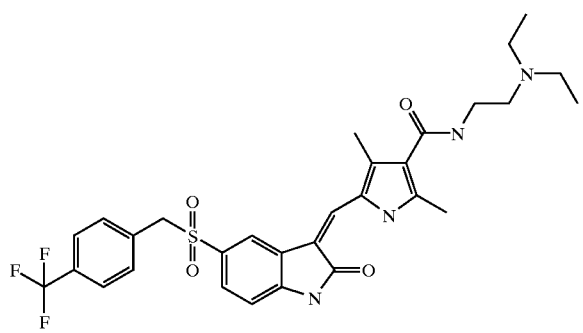

Yellow solid, (75 mg, 68%)

$^1$-NMR (400 MHz, DMSO-$d_6$) δ 13.59 (br s, 1H, pyrrole NH), 11.37 (br s, 1H, CONH), 8.26 (m, 1H, aromatic), 7.84 (m, 1H, aromatic), 7.70 (m, 2H, aromatic), 7.45 (t, 1H, CONH), 7.40 (m, 3H, aromatic), 7.01 (d, 1H, aromatic), 4.75 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 601 [M$^+$−1].

Example 79

Synthesis of 3-[1-[3,5-Dimethyl-4-(4-methyl-piperazine-1-carbonyl)-1H-pyrrol-2-yl]-meth-(Z)-ylidene]-5-(4-trifluoromethyl-phenylmethanesulfonyl)-1,3-dihydro-indol-2-one

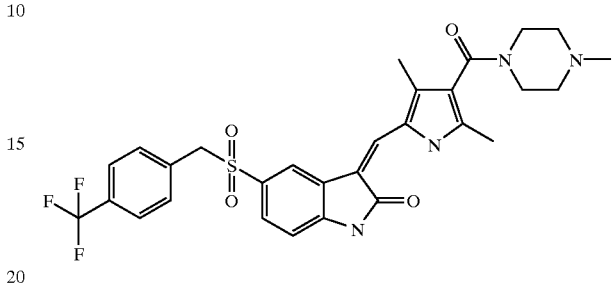

Yellow-orange solid, (77 mg, 62%)

$^1$H-NMR (400 MHz, DMSO-$d_6$) δ 13.53 (br s, 1H, pyrrole NH), 11.37 (br s, 1H, CONH), 8.26 (m, 1H, aromatic), 7.84 (m, 1H, aromatic), 7.70 (m, 2H, aromatic), 7.40 (m, 3H, aromatic), 7.01 (d, 1H, aromatic), 4.75 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 585 [M$^+$−1].

Example 80

Synthesis of 3-[1-[1-[3,5-Dimethyl-4-(4-methyl-piperazine-1-carbonyl)-1H-pyrrol-2-yl]-meth-(Z)-ylidene]-5-pentafluorophenylmethanesulfonyl-1,3-dihydro-indol-2-one

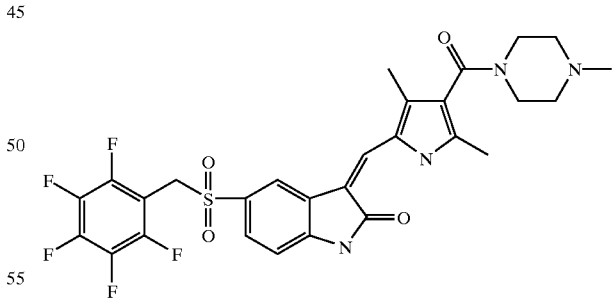

Orange solid, (69 mg, 58%)

$^1$H-NMR (400 MHz, DMSO-$d_6$) δ 13.55 (br s, 1H, pyrrole NH), 11.45 (br s, 1H, CONH), 8.29 (m, 1H, aromatic), 7.89 (m, 1H, aromatic), 7.51 (dd, 1H, aromatic), 7.06 (d, 1H, aromatic), 4.76 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 607 [M$^+$−1].

Example 81

Synthesis of 2,4-Dimethyl-5-[2-oxo-5-pentafluorophenylmethanesulfonyl-1,2-dihydro-indol-(3Z)-ylidenemethyl]-1H-pyrrole-3-carboxylic acid (2-Diethylamino-ethyl)-amide

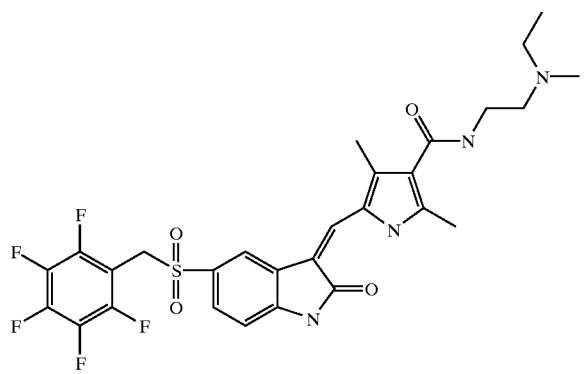

Yellow solid, (77 mg, 58%)
$^1$-NMR (400 MHz, DMSO-$d_6$) δ 13.55 (br s, 1H, pyrrole NH), 11.45 (br s, 1H, CONH), 8.29 (m, 1H, aromatic), 7.89 (m, 1H, aromatic), 7.52 (dd, 1H, aromatic), 7.48 (t, 1H, CONH), 7.06 (d, 1H, aromatic), 4.76 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 623 [M$^+$−1].

Example 82

Synthesis of 5-(2,5-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

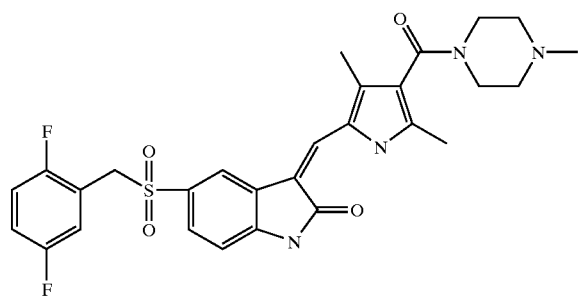

Yellow solid, (72 mg, 68%)
$^1$-NMR (400 MHz, DMSO-$d_6$) δ 13.55 (br s, 1H, pyrrole NH), 11.30 (v br s, 1H, CONH), 8.26 (m, 1H, aromatic), 7.85 (m, 1H, aromatic), 7.41 (dd, 1H, aromatic), 7.23 (m, 2H, aromatic), 7.12 (m, 1H, aromatic), 7.02 (d, 1H, aromatic), 4.65 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 553 [M$^+$−1].

Example 83

Synthesis of 5-[5-(2,4-Difluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

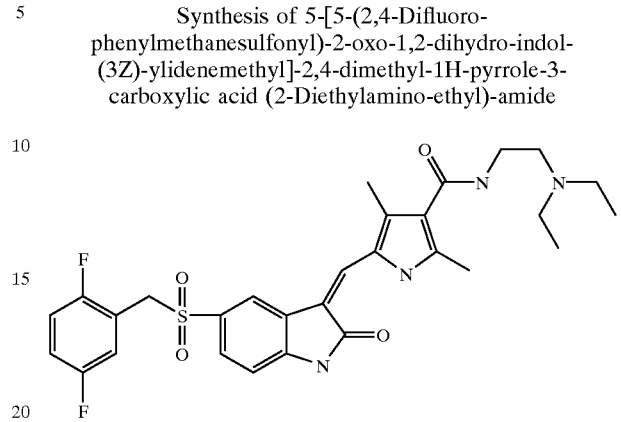

Yellow-orange solid, (73 mg, 68%)
$^1$H-NMR (400 MHz, DMSO-$d_6$) δ 13.55 (br s, 1H, pyrrole NH), 11.30 (v br s, 1H, CONH), 8.27 (m, 1H, aromatic), 7.86 (m, 1H, aromatic), 7.45 (t, 1H, CONH), 7.41 (dd, 1H, aromatic), 7.23 (m, 2H, aromatic), 7.12 (m, 1H, aromatic), 7.02 (d, 1H, aromatic), 4.65 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 571 [M$^+$+1].

Example 84

Synthesis of 3-[1-[3,5-Dimethyl-4-(4-methyl-piperazine-1-carbonyl)-1H-pyrrol-2-yl]-meth-(Z)-ylidene]-5-(2,3,6-trifluoro-phenylmethanesulfonyl)-1,3-dihydro-indol-2-one

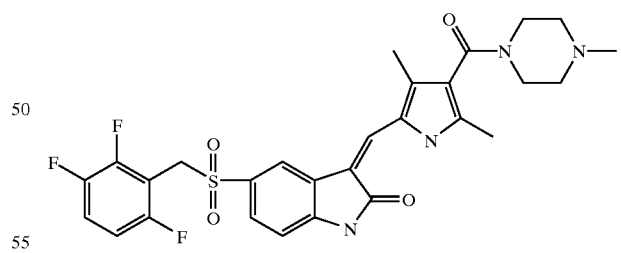

Yellow solid, (72 mg, 68%)
$^1$H-NMR (400 MHz, DMSO-$d_6$) δ 13.55 (br s, 1H, pyrrole NH), 11.30 (v br s, 1H, CONH), 8.32 (m, 1H, aromatic), 7.85 (s, 1H, aromatic), 7.74 (m, 1H, aromatic), 7.45 (dd, 1H, aromatic), 7.15 (m, 1H, aromatic), 7.05 (d, 1H, aromatic), 4.68 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 571 [M$^+$−1].

Example 85

Synthesis of 2,4-Dimethyl-5-[2-oxo-5-(2,3,6-trifluoro-phenylmethanesulfonyl)-1,2-dihydro-indol-(3Z)-ylidenemethyl]-1H-pyrrole-3-carboxylic acid (2-Diethylamino-ethyl)-amide

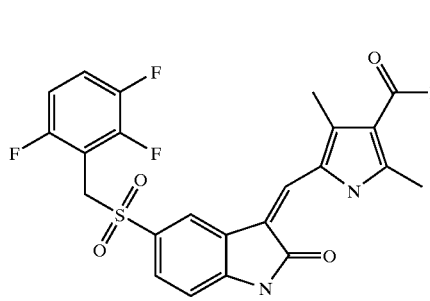

Yellow solid, (75 mg, 68%)
$^1$H-NMR (400 MHz, DMSO-$d_6$) δ 13.55 (br s, 1H, pyrrole NH), 11.30 (br s, 1H, CONH), 8.32 (m, 1H, aromatic), 7.85 (s, 1H, aromatic), 7.50 (multiplets, 3H, aromatic), 7.13 (m, 1H, aromatic), 7.03 (d, 1H, aromatic), 4.72 (s, 2H, CH$_2$), 3.30 (m, 2H, CH$_2$), 2.50 (m, 12H, 3×CH$_2$+2×CH$_3$), 0.98 (t, 6H, 2×CH$_3$). MS m/z 587 [M$^+$−1].

Example 86

Synthesis of 5-(2,3-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

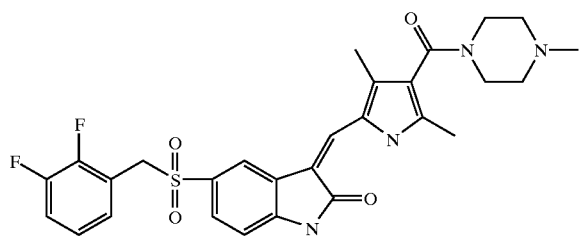

Yellow solid, (71 mg, 78%)
$^1$H-NMR (400 MHz, DMSO-$d_6$) δ 13.55 (br s, 1H, pyrrole NH), 11.30 (br s, 1H, CONH), 8.28 (m, 1H, aromatic), 7.85 (s, 1H, aromatic), 7.42 (m, 2H, aromatic), 7.18 (m, 1H, aromatic), 7.05 (m, 2H, aromatic), 4.73 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 553 [$^+$−1].

Example 87

Synthesis of 5-[5-(2,3-Difluoro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

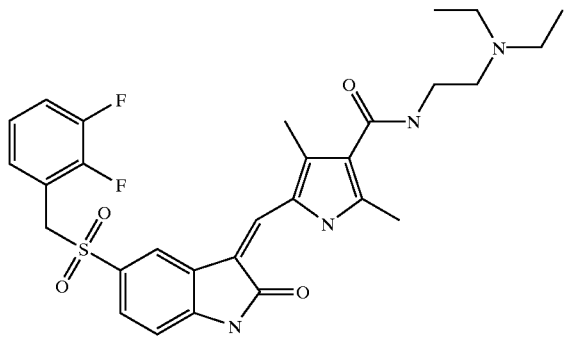

Yellow solid, (73 mg, 68%)
$^1$H-NMR (400 MHz, DMSO-$d_6$) δ 13.55 (br s, 1H, pyrrole NH), 11.30 (br s, 1H, CONH), 8.28 (m, 1H, aromatic), 7.87 (m, 1H, aromatic), 7.45 (m, 3H, aromatic+CONH), 7.18 (m, 1H, aromatic), 7.03 (m, 2H, aromatic), 4.72 (s, 2H, CH$_2$), 3.30 (m, 2H, CH$_2$), 2.50 (m, 12H, 3×CH$_2$+2×CH$_3$), 0.98 (t, 6H, 2×CH$_3$). MS m/z 569 M$^+$−1].

Example 88

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide

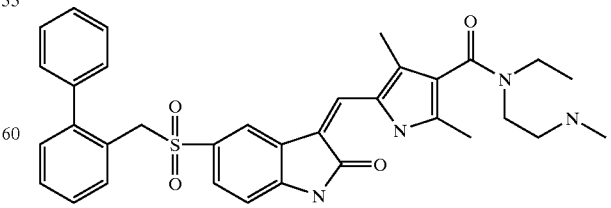

Yellow solid, (71 mg, 68%)
MS m/z 601 [M$^+$−1].

Example 89

Synthesis of 5-(Biphenyl-2-ylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one Yellow solid, (77 mg, 58%)
$^1$H-NMR (400 MHz, DMSO-$d_6$) δ 13.55 (br s, 1H, pyrrole NH), 11.35 (br s, 1H, CONH), 7.83 (m, 1H, aromatic), 7.65 (m, 1H, aromatic), 7.48 (m, 1H, aromatic), 7.40 (m, 2H, aromatic), 7.28 (m, 3H, aromatic), 7.16 (m, 2H, aromatic), 7.03 (m, 2H, aromatic), 6.91 (d, 1H, aromatic), 4.55 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 593 [M$^+$−1].

Example 90

Synthesis of 5-[5-(Biphenyl-2-ylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

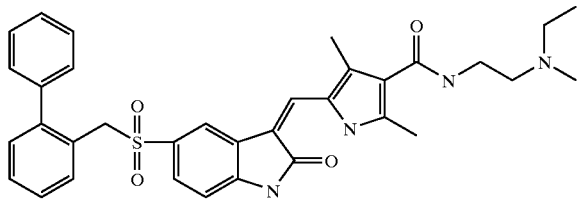

Yellow solid, (71 mg, 68%)
$^1$H-NMR (400 MHz, DMSO-d$_6$) δ 13.58 (br s, 1H, pyrrole NH), 11.35 (br s, 1H, CONH), 7.87 (m, 1H, aromatic), 7.67 (m, 1H, aromatic), 7.50 (m, 2H, aromatic), 7.40 (m, 2H, aromatic), 7.26 (m, 3H, aromatic), 7.16 (m, 2H, aromatic), 7.02 (m, 2H, aromatic), 6.90 (d, 1H, aromatic), 4.56 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 609 [M$^+$−1].

Example 91

Synthesis of 3-[1-[3,5-Dimethyl-4-(4-methyl-piperazine-1-carbonyl)-1H-pyrrol-2-yl]-meth-(Z)-ylidene]-5-(2-fluoro-6-nitro-phenylmethanesulfonyl)-1,3-dihydro-indol-2-one

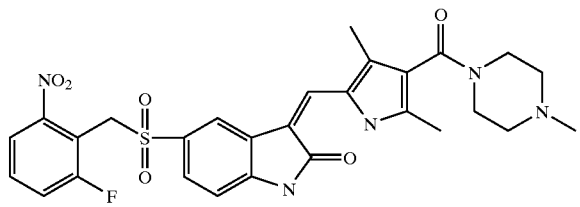

Yellow solid, (73 mg, 57%)
$^1$H-NMR (400 MHz, DMSO-d$_6$) δ 13.55 (br s, 1H, pyrrole NH), 11.30 (br s, 1H, CONH), 8.25 (m, 1H, aromatic), 7.95 (d, 1H, aromatic), 7.86 (m, 1H, aromatic), 7.67 (m, 2H, aromatic), 7.31 (dd, 1H, aromatic), 7.01 (d, 1H, aromatic), 5.05 (s, 2H, CH$_2$), 3.30 (m, 5H, CH$_2$+CH$_3$), 2.30 (m, 9H, 3×CH$_2$+CH$_3$), 2.19 (s, 3H, CH$_3$). MS m/z 580 [M$^+$−1].

Example 92

Synthesis of 5-[5-(2-Fluoro-6-nitro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

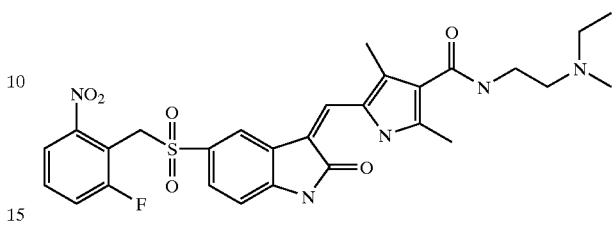

Orange solid, (73 mg, 57%)
$^1$H-NMR (400 MHz, DMSO-d$_6$) δ 13.61 (br s, 1H, pyrrole NH), 11.44 (br s, 1H, CONH), 8.28 (m, 1H, aromatic), 7.95 (d, 1H, aromatic), 7.89 (s, 1H, aromatic), 7.69 (m, 3H, aromatic+CONH), 7.31 (dd, 1H, aromatic), 7.01 (d, 1H, aromatic), 5.06 (s, 2H, CH$_2$), 3.30 (m, 5H, CH$_2$+CH$_3$), 2.50 (m, 9H, 3×CH$_2$+CH$_3$), 1.02 (m, 6H, 2×CH$_3$). MS m/z 596 [M$^+$−1].

Example 93

Synthesis of 3-[1-[3,5-Dimethyl-4-(4-methyl-piperazine-1-carbonyl)-1H-pyrrol-2-yl]-meth-(Z)-ylidene]-5-[2-(2-fluoro-phenoxy)-phenylmethanesulfonyl]-1,3-dihydro-indol-2-one

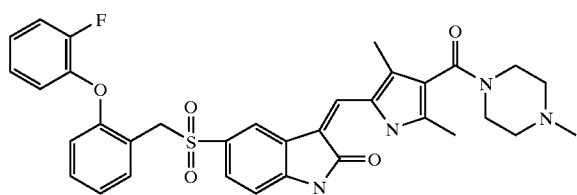

Yellow-orange solid, (73 mg, 51%)
$^1$H-NMR (400 MHz, DMSO-d$_6$) δ 13.54 (br s, 1H, pyrrole NH), 11.35 (br s, 1H, CONH), 8.17 (s, 1H, aromatic), 7.81 (s, 1H, aromatic), 7.30 (m, 3H, aromatic), 7.16 (m, 2H, aromatic), 6.95 (m, 4H, aromatic), 6.65 (s, 1H, aromatic), 4.62 (s, 2H, CH$_2$), 3.32 (m, 7H, 2×CH$_2$+CH$_3$), 2.31 (m, 7H, 2×CH$_2$+CH$_3$), 2.19 (s, 3H, CH$_3$). MS m/z 627 [M$^+$−1].

Example 94

Synthesis of 5-[5-[2-(2-Fluoro-phenoxy)-phenylmethanesulfonyl]-2-oxo-1,2-dihydro-indol-(3Z)-ylidenemethyl]-2,4-dimethyl-1H-pyrrole-3-carboxylic acid (2-diethylamino-ethyl)-amide

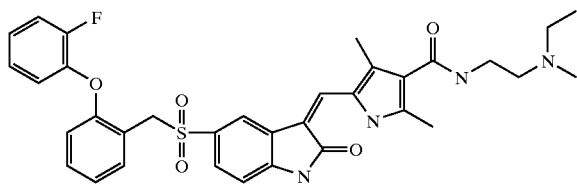

Yellow solid, (67 mg, 53%)
$^1$H-NMR (400 MHz, DMSO-d$_6$) δ 13.59 (br s, 1H, pyrrole NH), 11.35 (br s, 1H, CONH), 8.20 (m, 1H, aromatic), 7.78 (s, 1H, aromatic), 7.48 (t, 1H, CONH), 7.33 (m, 3H, aromatic), 7.16 (m, 2H, aromatic), 6.95 (m, 4H, aromatic), 6.65 (s, 1H, aromatic), 4.62 (s, 2H, CH$_2$), 3.30 (m, 2H, CH$_2$), 2.50 (m, 12H, 3×CH$_2$+2×CH$_3$), 0.98 (m, 6H, 2×CH$_3$). MS m/z 643 [M$^+$−1].

Example 96

Synthesis of 5-(2-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

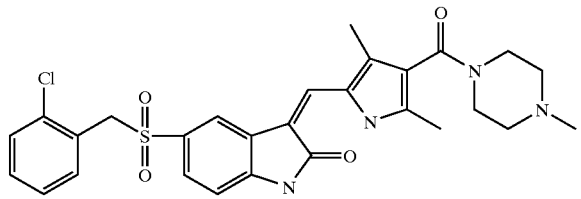

Yellow solid, (79 mg, 68%)
$^1$H-NMR (400 MHz, DMSO-d$_6$) δ 13.54 (br s, 1H, pyrrole NH), 11.37 (br s, 1H, CONH), 8.20 (m, 1H, aromatic), 7.81 (d, 1H, aromatic), 7.33 (multiplets, 5H, aromatic), 6.99 (d, 1H, aromatic), 4.74 (s, 2H, CH$_2$), 3.30 (m, 5H, CH$_2$+CH$_3$), 2.30 (m, 9H, 3×CH$_2$+CH$_3$), 2.19 (s, 3H, CH$_3$). MS m/z 551 [M$^+$−1].

Example 97

Synthesis of 5-[5-(4-Chloro-phenylmethanesulfonyl)-2-oxo-1,2-dihydro-indol-(3Z)-ylidenemethyl]-2,4-dimethyl-1H-pyrrole-3-carboxylic acid (2-Diethylamino-ethyl)-amide

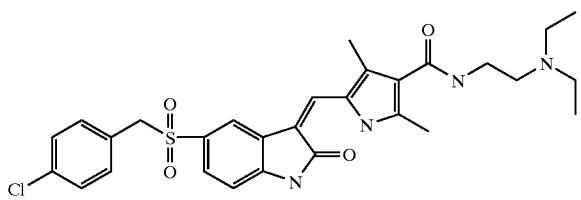

Yellow solid, (59 mg, 78%)
$^1$H-NMR (400 MHz, DMSO-d$_6$) δ 13.59 (br s, 1H, pyrrole NH), 10.80 (v br s, 1H, CONH), 8.25 (m, 1H, aromatic), 7.84 (m, 1H, aromatic), 7.48 (t, 1H, CONH), 7.39 (m, 3H, aromatic), 7.19 (d, 2H, aromatic), 7.01 (d, 1H, aromatic), 4.65 (s, 2H, CH$_2$), 3.30 (m, 5H, CH$_2$+CH$_3$), 2.50 (m, 9H, 3×CH$_2$+CH$_3$), 0.98 (t, 6H, 2×CH$_3$). MS m/z 569 [M$^+$+1].

Example 98

Synthesis of 5-(4-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

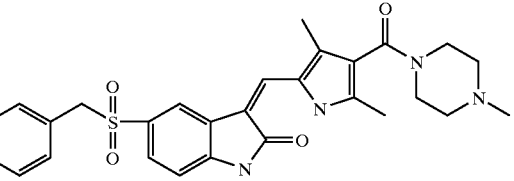

Yellow solid, (59 mg, 63%)
$^1$H-NMR (400 MHz, DMSO-d$_6$) δ 13.54 (br s, 1H, pyrrole NH), 8.21 (m, 1H, aromatic), 7.81 (s, 1H, aromatic), 7.38 (m, 3H, aromatic), 7.19 (m, 2H, aromatic), 7.19 (d, 1H, aromatic), 7.01 (d, 1H, aromatic), 4.65 (s, 2H, CH$_2$), 3.30 (m, 2H, CH$_2$), 2.30 (m, 12H, 3×CH$_2$+2×CH$_3$), 2.19 (s, 3H, CH$_3$). MS m/z 553 [M$^+$+1].

Example 99

Synthesis of 2,4-Dimethyl-5-[2-oxo-5-phenylmethanesulfonyl-1,2-dihydro-indol-(3Z)-ylidenemethyl]-1H-pyrrole-3-carboxylic acid

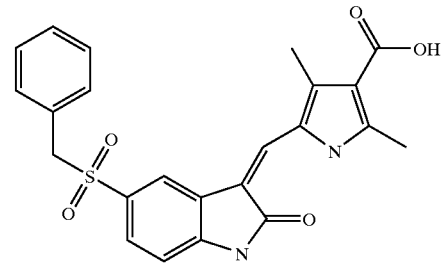

Orange solid, (57 mg, 61%)
MS m/z 437 [M$^+$+1].

Example 100

Synthesis of 4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid methyl ester

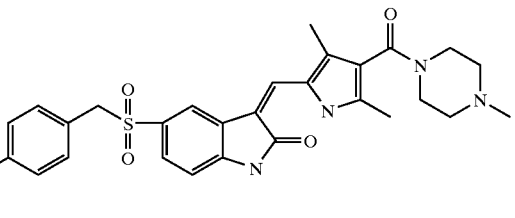

Yellow-orange solid, (69 mg, 61%)
$^1$H-NMR (400 MHz, DMSO-d$_6$) δ 13.53 (br s, 1H, pyrrole NH), 11.36 (br s, 1H, CONH), 8.21 (m, 1H, aromatic), 7.88 (d, 2H, aromatic), 7.79 (s, 1H, aromatic), 7.38 (dd 1H, aromatic), 7.31 (d, 2H, aromatic), 6.98 (d, 1H, aromatic), 4.72 (s, 2H, CH$_2$), 3.30 (m, 5H, CH$_2$+CH$_3$), 2.30 (m, 9H, 3×CH$_2$+CH$_3$), 2.19 (s, 3H, CH$_3$). MS m/z 575 [M$^+$−1].

Example 101

Synthesis of 2,4-Dimethyl-5-[2-oxo-5-phenylmethanesulfonyl-1,2-dihydro-indol-(3Z)-ylidenemethyl]-1H-pyrrole-3-carboxylic acid (3-Diethylamino-2-hydroxy-propyl)-amide

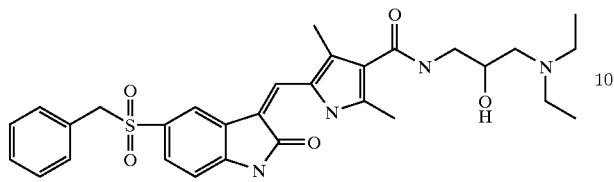

Yellow solid, (79 mg, 68%)
¹H-NMR (400 MHz, DMSO-d₆) δ 13.61 (br s, 1H, pyrrole NH), 11.45 (br s, 1H, CONH), 8.26 (m, 1H, aromatic), 7.84 (m, 2H, aromatic), 7.39 (dd, 1H, aromatic), 7.30 (m, 3H, aromatic), 7.19 (d, 2H, aromatic), 7.01 (d, 1H, aromatic), 4.65 (s, 2H, CH₂), 4.06 (m, 1H, CH), 3.37 (m, 5H, CH₂+CH₃), 3.05 (m, 2H, CH₂), 2.50 (m, 9H, 2×CH₂+CH₃), 1.18 (t, 6H, 2×CH₃). MS m/z 563 [M⁺−1].

Example 102

Synthesis of 2,4-Dimethyl-5-[2-oxo-5-phenylmethanesulfonyl-1,2-dihydro-indol-(3Z)-ylidenemethyl]-1H-pyrrole-3-carboxylic acid [2-(2H-Tetrazol-5-yl)-ethyl]-amide

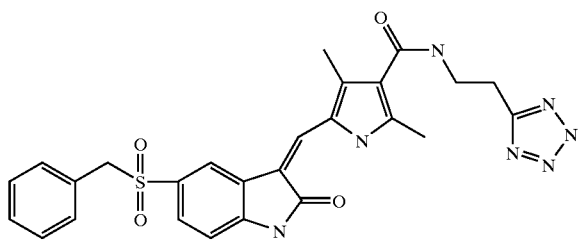

Yellow-orange solid, (69 mg, 61%)
MS m/z 530 [M⁺−1].

Example 103

Synthesis of 5-Methyl-2-[2-oxo-5-phenylmethanesulfonyl-1,2-dihydro-indol-(3Z)-ylidenemethyl]-1H-pyrrole-3-carboxylic acid (3-Pyrrolidin-1-yl-propyl)-amide

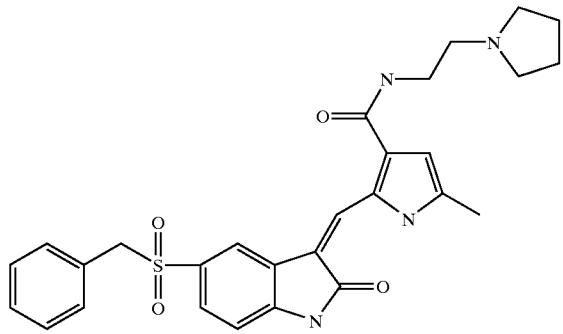

Yellow-orange solid, (62 mg, 51%)
¹H-NMR (400 MHz, DMSO-d₆) δ 13.61 (br s, 1H, pyrrole NH), 11.46 (br s, 1H, CONH), 8.68 (s, 1H, aromatic), 8.21 (t, 1H, CONH), 7.75 (m, 1H, aromatic), 7.43 (m, 3H, aromatic), 7.19 (m, 2H, aromatic), 7.02 (d, 1H, aromatic), 6.67 (m, 1H, aromatic), 4.66 (s, 2H, CH₂), 3.39 (m, 2H, CH₂), 2.58 (t, 2H, CH₂), 2.50 (m, 4H, 2×CH₂), 2.38 (s, 3H, CH₃), 1.70 (m, 4H, 2×CH₂). MS m/z 516 [M⁺−2].

Example 104

Synthesis of 5-Methyl-2-[2-oxo-5-phenylmethanesulfonyl-1,2-dihydro-indol-(3Z)-ylidenemethyl]-1H-pyrrole-3-carboxylic acid (3-[1,2,3]triazol-1-yl-propyl)-amide

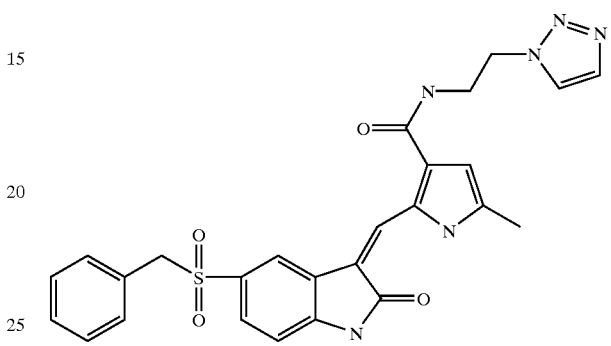

Yellow-orange solid, (62 mg, 51%)
¹H-NMR (400 MHz, DMSO-d₆) δ 13.60 (br s, 1H, pyrrole NH), 8.59 (s, 1H, aromatic), 8.42 (t, 1H, CONH), 8.14 (s, 1H, aromatic), 7.77 (m, 1H, aromatic), 7.73 (s, 1H, aromatic), 7.44 (dd, 1H, aromatic), 7.30 (m, 3H, aromatic), 7.20 (m, 2H, aromatic), 7.03 (d, 1H, aromatic), 6.59 (m, 1H, aromatic), 4.67 (s, 2H, CH₂), 4.59 (t, 2H, CH₂), 3.71 (t, 2H, CH₂), 2.38 (s, 3H, CH₃). MS m/z 517 [M⁺+1].

Example 105

Synthesis of 3-[1-((R)-(3-Dimethylamino-pyrrolidin-1-carbonyl)-5-methyl-1H-pyrrol-2-yl]-meth-(Z)-ylidene]-5-phenylmethanesulfonyl-1,3-dihydro-indol-2-one

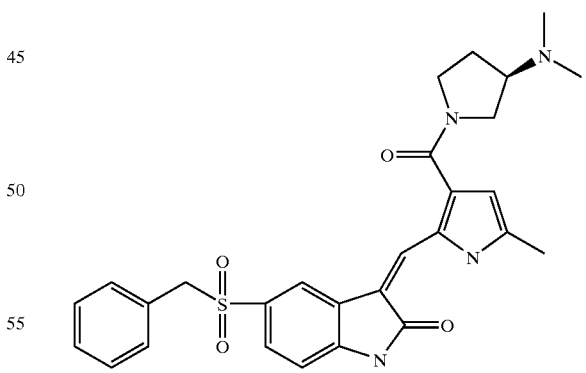

Yellow-orange solid, (72 mg, 54%)
¹H-NMR (400 MHz, DMSO-d₆) δ 13.64 (br s, 1H, pyrrole NH), 11.40 (br s, 1H, CONH), 8.03 (m, 1H, aromatic), 7.73 (m, 1H, aromatic), 7.42 (d, 1H, aromatic), 7.39 (m, 3H, aromatic), 7.19 (m, 2H, aromatic), 7.02 (d, 1H, aromatic), 6.53 (d, 1H, aromatic), 4.65 (s, 2H, CH₂), 3.50 (multiplets, 4H, 2×CH₂), 2.70 (m, 1H, CH), 2.40 (s, 3H, CH₃), 2.20 (s, 3H, CH₃), 2.14 (s, 3H, CH₃), 2.07 (m, 1H, CH), 1.75 (m, 1H, CH). MS m/z 517 [M⁺−1].

Example 106

Synthesis of 4-Methyl-5-[2-oxo-5-phenylmethanesulfonyl-1,2-dihydro-indol-(3Z)-ylidenemethyl]-1H-pyrrole-3-carboxylic acid (2-Diethylamino-ethyl)-amide

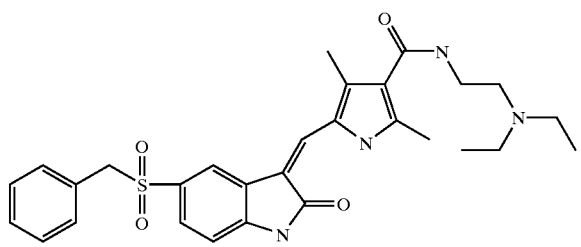

Yellow-orange solid, (65 mg, 54%)
$^1$H-NMR (400 MHz, DMSO-$d_6$) δ 13.53 (br s, 1H, pyrrole NH), 10.80 (v br s, 1H, CONH), 8.29 (m, 1H, aromatic), 7.89 (s, 1H, aromatic), 7.81 (m, 2H, aromatic), 7.41 (dd, 1H, aromatic), 7.31 (m, 3H, aromatic), 7.19 (m, 2H, aromatic), 6.99 (d, 1H, aromatic), 4.63 (s, 2H, CH$_2$), 3.26 (m, 2H, CH$_2$), 2.50 (multiplets, 9H, 3×CH$_2$+CH$_3$), 0.98 (t, 6H, 2×CH$_3$). MS m/z 519 [M$^+$−1].

Example 107

Synthesis of 2,4-Dimethyl-5-[2-oxo-5-phenylmethanesulfonyl-1,2-dihydro-indol-(3Z)-ylidenemethyl]-1H-pyrrole-3-carboxylic acid (2-Pyrrolidin-1-yl-ethyl)-amide

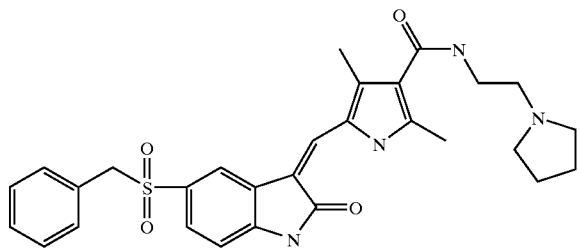

Yellow solid, (69 mg, 58%)
$^1$H-NMR (400 MHz, DMSO-$d_6$) δ 13.57 (br s, 1H, pyrrole NH), 8.68 (s, 1H, aromatic), 8.25 (m, 1H, aromatic), 7.82 (s, 1H, aromatic), 7.58 (t, 1H, CONH), 7.39 (dd, 1H, aromatic), 7.30 (m, 3H, aromatic), 7.19 (m, 2H, aromatic), 6.98 (d, 1H, aromatic), 4.61 (s, 2H, CH$_2$), 3.39 (m, 2H, CH$_2$), 2.50 (mulitplets, 10H, 2×CH$_2$+2×CH$_3$), 1.68 (m, 4H, 2×CH$_2$). MS m/z 533 [M$^+$+1].

Example 108

Synthesis of 2,4-Dimethyl-5-[2-oxo-5-phenylmethanesulfonyl-1,2-dihydro-indol-(3Z)-ylidenemethyl]-1H-pyrrole-3-carboxylic acid (2-Diisopropylamino-ethyl)-amide

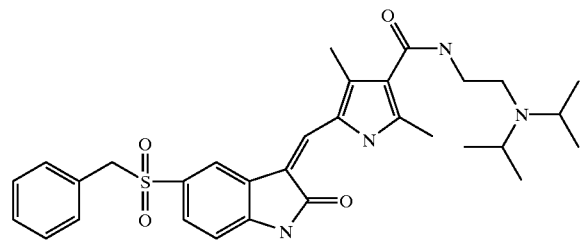

Yellow solid, (67 mg, 55%)
$^1$H-NMR (400 MHz, DMSO-$d_6$) δ 13.59 (br s, 1H, pyrrole NH), 10.90 (v br s, 1H, CONH), 8.26 (s, 1H, aromatic), 7.83 (s, 1H, aromatic), 7.32 (multiplets, 6H, aromatic), 6.99 (d, 2H, aromatic), 4.61 (s, 2H, CH$_2$), 3.30 (multiplets, 2H, CH$_2$), 3.00 (m, 2H, 2×CH), 2.50 (mulitplets, 8H, CH$_2$+2×CH$_3$), 1.04 (d, 12H, 4×CH$_3$). MS m/z 561 [M$^+$−1].

Example 109

Synthesis of 5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-Pyrrolidin-1-yl-ethyl)-amide

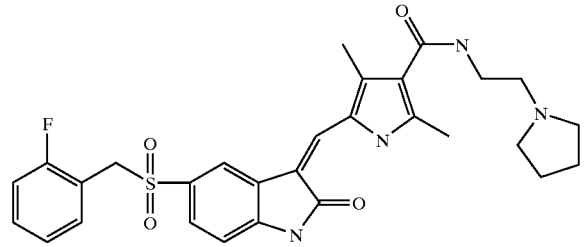

Yellow solid, (62 mg, 57%)
$^1$H-NMR (400 MHz, DMSO-$d_6$) δ 13.58 (br s, 1H, pyrrole NH), 10.90 (v br s, 1H, CONH), 8.27 (m, 1H, aromatic), 7.84 (s, 1H, aromatic), 7.59 (t, 1H, CONH), 7.37 (m, 2H, aromatic), 7.27 (m, 1H, aromatic), 7.17 (m, 2H, aromatic), 7.00 (d, 1H, aromatic), 4.64 (s, 2H, CH$_2$), 3.32 (m, 2H, CH$_2$), 2.50 (mulitplets, 10H, 2×CH$_2$+2×CH$_3$), 1.68 (m, 4H, 2×CH$_2$). MS m/z 549 [M$^+$−1].

Example 110

Synthesis of 5-[5-(2-Fluoro-phenylmethanesulfonyl)-2-oxo-1,2-dihydro-indol-(3Z)-ylidenemethyl]-4-methyl-1H-pyrrole-3-carboxylic acid (2-Diethylamino-ethyl)-amide

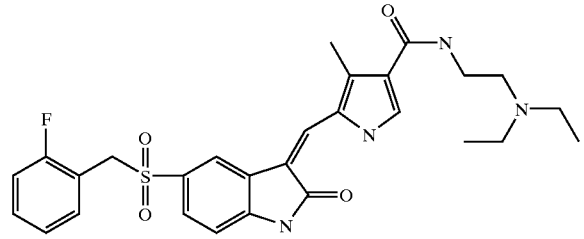

Yellow solid, (66 mg, 54%)
$^1$H-NMR (400 MHz, DMSO-$d_6$) δ 13.54 (br s, 1H, pyrrole NH), 10.90 (v br s, 1H, CONH), 8.30 (m, 1H, aromatic), 7.91 (s, 1H, aromatic), 7.80 (m, 2H, aromatic), 7.39 (multiplets, 2H, CONH+aromatic), 7.25 (m, 1H, aromatic), 7.16 (m, 2H, aromatic), 6.99 (d, 1H, aromatic), 4.65 (s, 2H, CH$_2$), 3.26 (m, 2H, CH$_2$), 2.50 (multiplets, 9H, 3×CH$_2$+CH$_3$), 0.98 (t, 6H, 2×CH$_3$). MS m/z 537 [M$^+$−1].

Example 111

Synthesis of 2-[5-(2-Fluoro-phenylmethanesulfonyl)-2-oxo-1,2-dihydro-indol-(3Z)-ylidenemethyl]-5-methyl-1H-pyrrole-3-carboxylic acid (3-Pyrrolidin-1-yl-propyl)-amide

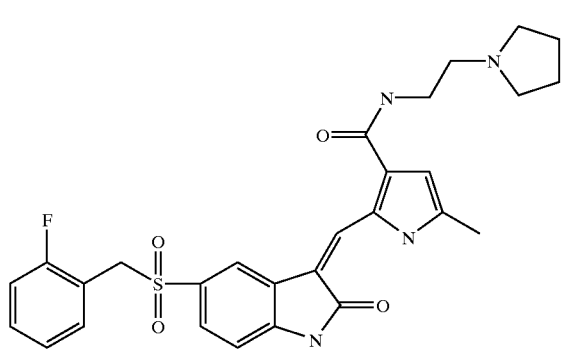

Yellow solid, (72 mg, 59%)
MS m/z 537 [M$^+$+1].

Example 112

Synthesis of 5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-Diisopropylamino-ethyl)-amide

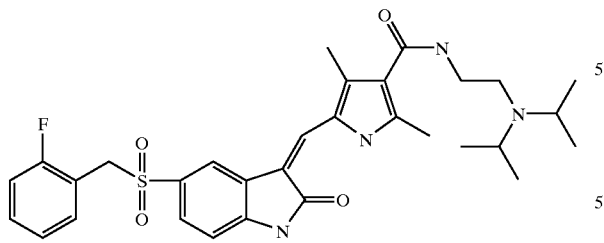

Yellow solid, (82 mg, 79%)
$^1$H-NMR (400 MHz, DMSO-$d_6$) δ 13.59 (br s, 1H, pyrrole NH), 11.30 (v br s, 1H, CONH), 8.27 (m, 1H, aromatic), 7.85 (s, 1H, aromatic), 7.49 (t, 1H, CONH), 7.39 (m, 2H, aromatic), 7.28 (m, 1H, aromatic), 7.17 (m, 2H, aromatic), 6.99 (d, 1H, aromatic), 4.62 (s, 2H, CH$_2$), 3.18 (m, 2H, CH$_2$), 3.00 (m, 2H, 2×CH), 2.50 (mulitplets, 8H, CH$_2$+2×CH$_3$), 0.99 (d, 12H, 4×CH$_3$). MS m/z 579 [M$^+$−1].

Example 113

2-[5-(2-Fluoro-phenylmethanesulfonyl)-2-oxo-1,2-dihydro-indol-(3Z)-ylidenemethyl]-5-methyl-1H-pyrrole-3-carboxylic acid (3-[1,2,3]Triazol-1-yl-propyl)-amide

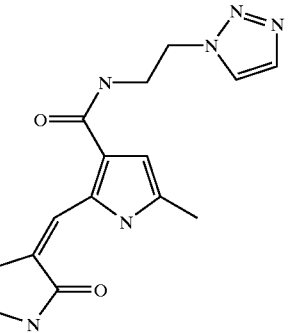

Yellow-orange solid, (72 mg, 59%)
MS m/z 533 [M$^+$−1].

Example 114

Synthesis of 3-[1-[4-((3R,5S)-3,5-Dimethyl-piperazine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

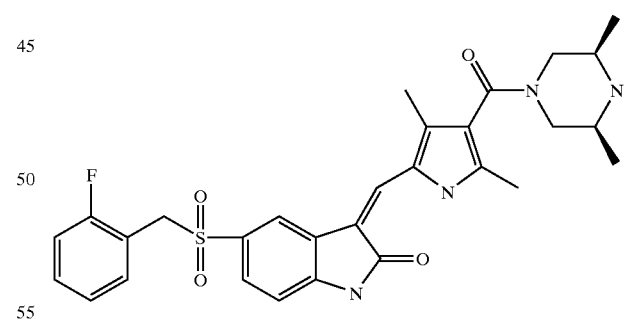

Yellow solid, (62 mg, 72%)
$^1$H-NMR (400 MHz, DMSO-$d_6$) δ 13.50 (br s, 1H, pyrrole NH), 10.80 (v br s, 1H, CONH), 8.26 (m, 1H, aromatic), 7.82 (m, 1H, aromatic), 7.38 (m, 2H, aromatic), 7.26 (m, 1H, aromatic), 7.17 (m, 2H, aromatic), 6.99 (d, 1H, aromatic), 4.62 (s, 2H, CH$_2$), 3.18 (m, 4H, 2×CH$_2$), 2.50 (mulitplets, 8H, 2×CH+2×CH$_3$), 0.98 (m, 6H, 2×CH$_3$). MS m/z 551 [M$^+$+1].

Example 115

Synthesis of 3-[1-[4-((3R,5S)-3,5-Dimethyl-piperazine-1-carbonyl)-3,5-dimethyl-1H-pyrrol-2-yl]-meth-(Z)-ylidene]-5-phenylmethanesulfonyl-1,3-dihydro-indol-2-one

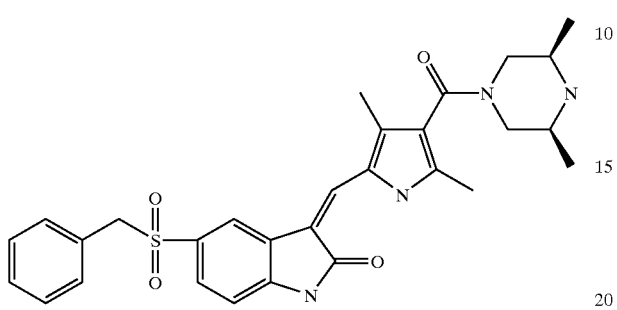

Yellow-orange solid, (72 mg, 69%)
$^1$H-NMR (400 MHz, DMSO-d$_6$) δ 13.50 (br s, 1H, pyrrole NH), 11.30 (br s, 1H, CONH), 8.24 (m, 1H, aromatic), 7.81 (s, 1H, aromatic), 7.40 (m, 1H, aromatic), 7.30 (m, 3H, aromatic), 7.18 (m, 2H, aromatic), 6.98 (d, 1H, aromatic), 4.61 (s, 2H, CH$_2$), 3.31 (m, 4H, 2×CH$_2$), 2.50 (mulitplets, 8H, 2×CH+2×CH$_3$), 0.97 (m, 6H, 2×CH$_3$). MS m/z 531 [M$^+$–1].

Example 116

Synthesis of 5-[5-(3-Chloro-phenylmethanesulfonyl)-2-oxo-1,2-dihydro-indol-(3Z)-ylidenemethyl]-4-methyl-1H-pyrrole-3-carboxylic acid (2-Diethylamino-ethyl)-amide

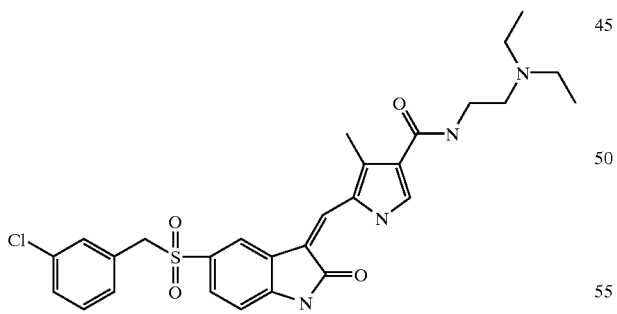

Yellow-orange solid, (62 mg, 71%)
$^1$H-NMR (400 MHz, DMSO-d$_6$) δ 13.53 (br s, 1H, pyrrole NH), 11.20 (v br s, 1H, CONH), 8.28 (m, 1H, aromatic), 7.90 (s, 1H, aromatic), 7.80 (m, 2H, aromatic), 7.38 (multiplets, 3H, CONH+aromatic), 7.27 (m, 1H, aromatic), 7.12 (d, 1H, aromatic), 7.00 (d, 1H, aromatic), 4.65 (s, 2H, CH$_2$), 3.26 (m, 2H, CH$_2$), 2.50 (multiplets, 9H, 3×CH$_2$+CH$_3$), 0.98 (t, 6H, 2×CH$_3$). MS m/z 553 [M$^+$–1].

Example 117

Synthesis of 2-[5-(3-Chloro-phenylmethanesulfonyl)-2-oxo-1,2-dihydro-indol-(3Z)-ylidenemethyl]-5-methyl-1H-pyrrole-3-carboxylic acid (3-Pyrrolidin-1-yl-propyl)-amide

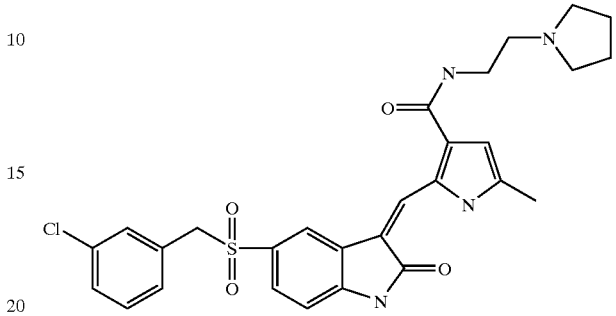

Yellow-orange solid, (67 mg, 73%)
$^1$H-NMR (400 MHz, DMSO-d$_6$) δ 13.61 (br s, 1H, pyrrole NH), 11.30 (br s, 1H, CONH), 8.71 (s, 1H, aromatic), 8.22 (t, 1H, aromatic), 7.77 (m, 1H, aromatic), 7.44 (dd, 1H, aromatic), 7.38 (multiplets, 2H, CONH+aromatic), 7.27 (s, 1H, aromatic), 7.17 (d, 1H, aromatic), 7.04 (d, 1H, aromatic), 6.67 (m, 1H, aromatic), 4.72 (s, 2H, CH$_2$), 3.39 (m, 4H, 2×CH$_2$), 2.50 (multiplets, 4H, 2×CH$_2$), 2.39 (s, 3H, CH$_3$), 1.69 (m, 4H, 2×CH$_2$). MS m/z 551 [M$^+$–1].

Example 118

Synthesis of 2-[5-(3-Chloro-phenylmethanesulfonyl)-2-oxo-1,2-dihydro-indol-(3Z)-ylidenemethyl]-5-methyl-1H-pyrrole-3-carboxylic acid (3-[1,2,3]Triazol-1-yl-propyl)-amide

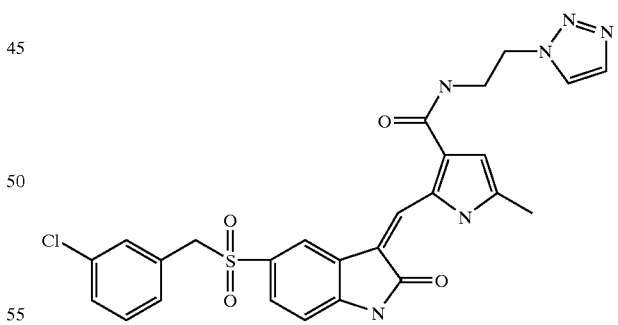

Yellow-orange solid, (65 mg, 77%)
$^1$H-NMR (400 MHz, DMSO-d$_6$) δ 13.60 (br s, 1H, pyrrole NH), 11.54 (s, 1H, CONH), 8.62 (s, 1H, aromatic), 8.42 (t, 1H, CONH), 8.14 (s, 1H, aromatic), 7.79 (s, 1H, aromatic), 7.73 (s, 1H, aromatic), 7.46 (m, 1H, aromatic), 7.36 (m, 2H, aromatic), 7.27 (s, 1H, aromatic), 7.17 (d, 1H, aromatic), 7.03 (d, 1H, aromatic), 6.59 (m, 1H, aromatic), 4.72 (s, 2H, CH$_2$), 4.60 (t, 2H, CH$_2$), 3.72 (t, 2H, CH$_2$), 2.38 (s, 3H, CH$_3$). MS m/z 553 [M$^+$+3].

Example 119

Synthesis of 5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-Pyrrolidin-1-yl-ethyl)-amide

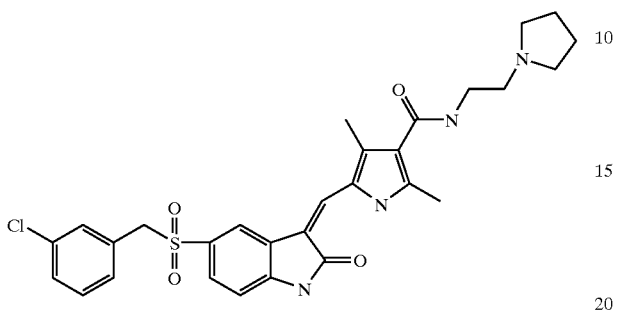

Yellow-orange solid, (77 mg, 74%)
$^1$H-NMR (400 MHz, DMSO-$d_6$) δ 13.57 (br s, 1H, pyrrole NH), 11.00 (v br s, 1H, CONH), 8.23 (m, 1H, aromatic), 7.83 (s, 1H, aromatic), 7.59 (t, 1H, CONH), 7.38 (multiplets, 3H, aromatic), 7.27 (s, 1H, aromatic), 7.13 (d, 1H, aromatic), 7.02 (d, 1H, aromatic), 4.67 (s, 2H, CH$_2$), 3.39 (m, 4H, 2×CH$_2$), 2.50 (multiplets, 4H, 2×CH$_2$+CH$_3$), 2.45 (s, 3H, CH$_3$), 1.69 (m, 4H, 2×CH$_2$). MS m/z 565 [M$^+$−1].

Example 120

Synthesis of 5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-Diisopropylamino-ethyl)-amide

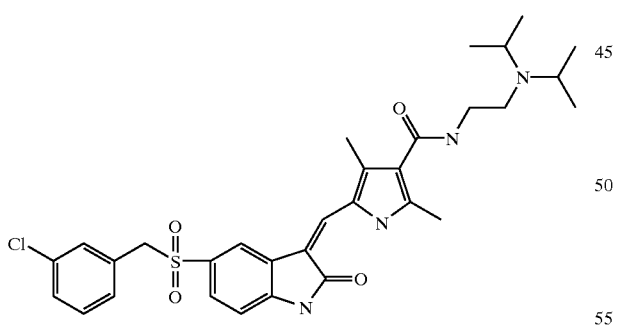

Yellow-orange solid, (67 mg, 59%)
$^1$H-NMR (400 MHz, DMSO-$d_6$) δ 13.58 (br s, 1H, pyrrole NH), 11.20 (v br s, 1H, CONH), 8.24 (m, 1H, aromatic), 7.83 (s, 1H, aromatic), 7.47 (t, 1H, CONH), 7.35 multiplets, 3H, aromatic), 7.27 (s, 1H, aromatic), 7.13 (d, 1H, aromatic), 7.01 (d, 1H, aromatic), 4.66 (s, 2H, CH$_2$), 3.21 (m, 2H, CH$_2$), 3.00 (m, 2H, 2×CH), 2.50 (mulitplets, 8H, CH$_2$+2×CH$_3$), 0.99 (d, 12H, 4×CH$_3$). MS m/z 597 [M$^+$+1].

Example 121

Synthesis of 5-(3-Chloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one

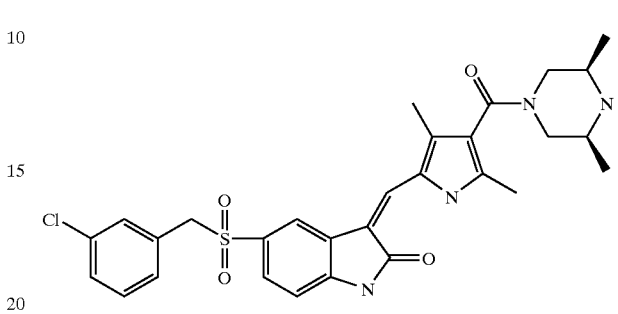

Yellow solid, (77 mg, 53%)
$^1$H-NMR (400 MHz, DMSO-$d_6$) δ 13.58 (br s, 1H, pyrrole NH), 7.30 (m, 8H, aromatic), 4.64 (s, 2H, CH$_2$), 3.31 (m, 4H, 2×CH$_2$), 2.00–3.00 (m, 8H, 2×CH+2×CH$_3$), 0.97 (m, 6H, 2×CH$_3$). MS m/z 565 [M$^+$−1].

Example 122

Synthesis of 5-(3-Chloro-phenylmethanesulfonyl)-3-[1-[3-((R)-3-dimethylamino-pyrrolidin-1-ylcarbonyl)-5-methyl-1H-pyrrol-2-yl]-meth-(Z)-ylidene]-1,3-dihydro-indol-2-one

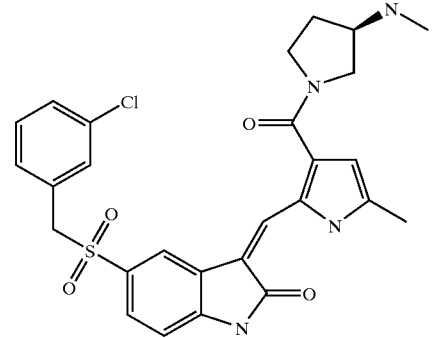

Yellow solid, (75 mg, 59%)
$^1$H-NMR (400 MHz, DMSO-$d_6$) δ 13.64 (br s, 1H, pyrrole NH), 8.06 (m, 1H, aromatic), 7.74 (s, 1H, aromatic), 7.37 (multiplets, 3H, aromatic), 7.25 (s, 1H, aromatic), 7.15 (m, 2H, aromatic), 7.04 (d, 1H, aromatic), 6.51 (d, 1H, aromatic), 4.70 (s, 2H, CH$_2$), 3.50 (multiplets, 5H, CH+2×CH$_2$), 2.41 (s, 3H, CH$_3$), 2.20 (s, 3H, CH$_3$), 2.13 (s, 3H, CH$_3$), 1.44 (m, 2H, CH$_2$). MS m/z 551 [M$^+$−1].

Example 125

Synthesis of 3-{5-Ethyl-2-[2-oxo-5-phenylmethanesulfonyl-1,2-dihydro-indol-(3Z)-ylidenemethyl]-1H-pyrrol-3-yl}-propionic acid

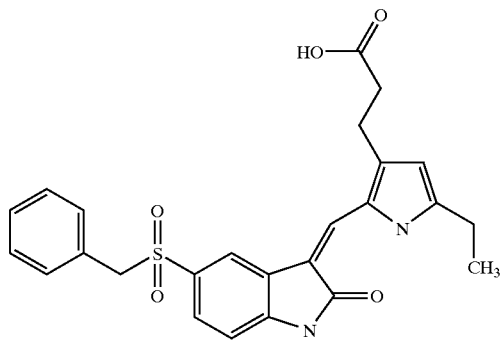

Example 126

Synthesis of 3-{4-Methyl-5-[2-oxo-5-phenylmethanesulfonyl-1,2-dihydro-indol-(3Z)-ylidenemethyl]-1H-pyrrol-3-yl}-propionic acid

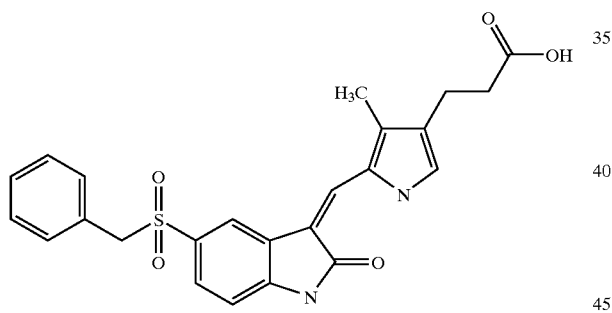

Example 127

Synthesis of 3-[1-[3-Methyl-5-(4-methyl-piperazine-1-carbonyl)-1H-pyrrol-2-yl]-meth-(Z)-ylidene]-5-phenylmethanesulfonyl-1,3-dihydro-indol-2-one

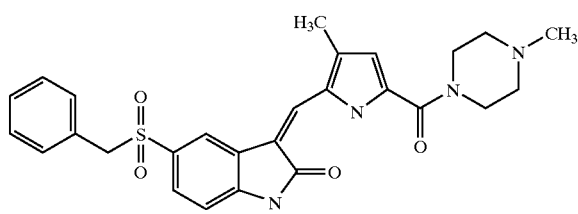

Example 128

Synthesis of 4-(4-Fluoro-phenyl)-2-methyl-5-[2-oxo-5-phenylmethanesulfonyl-1,2-dihydro-indol-(3Z)-ylidenemethyl]-1H-pyrrole-3-carboxylic acid (2-Diethylamino-ethyl)-amide

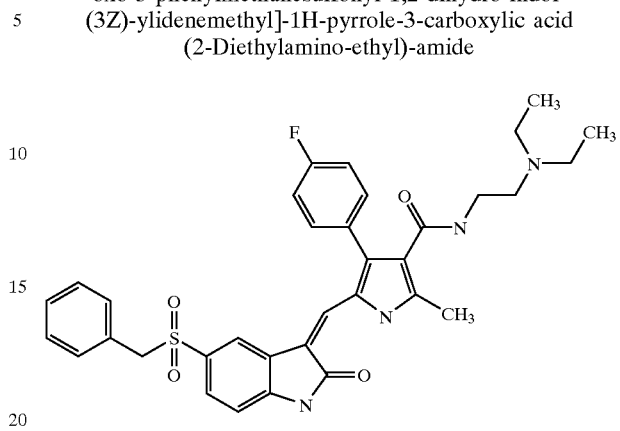

Example 130

Synthesis of 4-{5-Methyl-2-[2-oxo-5-phenylmethanesulfonyl-1,2-dihydro-indol-(3Z)-ylidenemethyl]-1H-pyrrol-3-yl}-benzoic acid

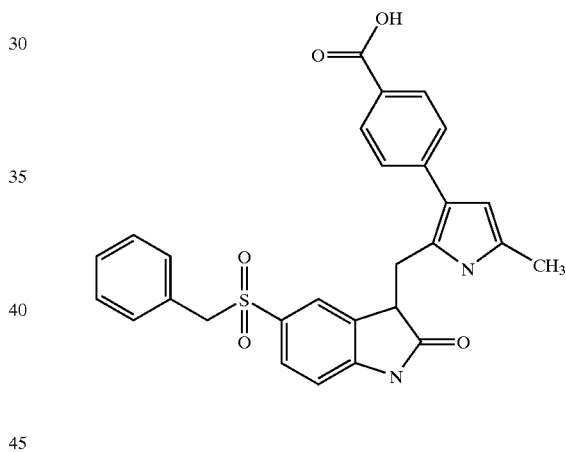

Example 131

Synthesis of 4-(2-Carboxy-ethyl)-3-methyl-5-[2-oxo-5-phenylmethanesulfonyl-1,2-dihydro-indol-(3Z)-ylidenemethyl]-1H-pyrrole-2-carboxylic acid ethyl ester

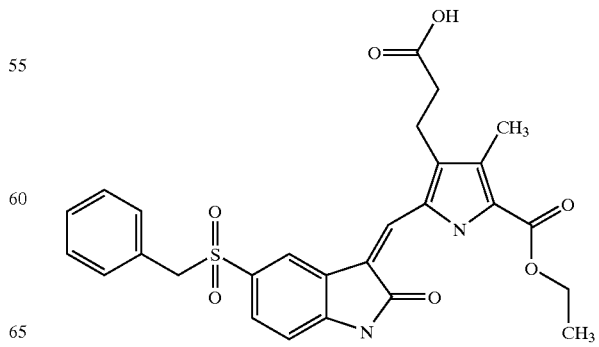

Example 132

Synthesis of 5-(2,6-Dichloro-phenylmethanesulfonyl)-3-[1-(3,5-dimethyl-1H-pyrrol-2-yl)-meth-(Z)-ylidene]-1,3-dihydro-indol-2-one

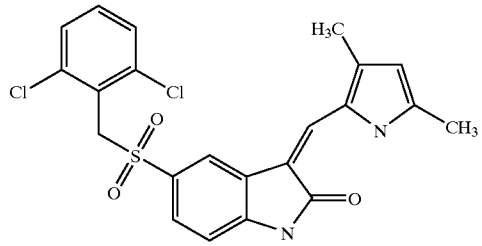

Yellow solid, (86 mg, 67%).
$^1$H NMR (400 MHz, DMSO-$d_6$) δ 13.38 (s, NH, 1H), 11.29 (s, NH, 1H), 8.17 (d, 1H), 7.76 (s, 1H), 7.47 (d, 1H), 7.46 (s, 1H), 7.37 (m, 2H), 7.00 (d, 1H), 6.07 (d, 1H), 4.84 (s, 2H), 2.33 (s, 6H). MS m/z 461 [M$^+$+1].

Example 134

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid

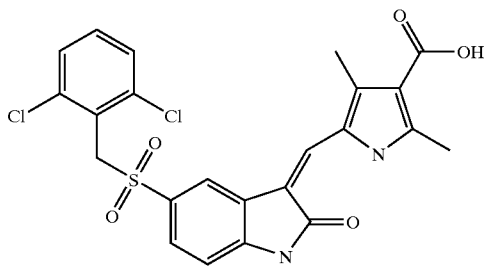

Orange solid, (106 mg, 75%)
$^1$H-NMR (400 MHz, DMSO-$d_6$) δ 13.74 (br s, 1H, pyrrole NH), 12.10 (v br s, 1H, COOH), 11.42 (br s, 1H, CONH), 8.32 (d, 1H), 7.92 (s, 1H), 7.47 (d, 1H), 7.46 (s, 1H), 7.37 (m, 2H), 7.04 (d, 1H), 4.86 (s, 2H, CH$_2$), 2.54 (s, 3H, CH$_3$), 2.48 (s, 3H), CH$_3$). MS m/z 503 [M$^-$1].

D. General Procedure for the Synthesis of 5-Arylmethanesulfonyl-1,3-dihydro-indol-2-one

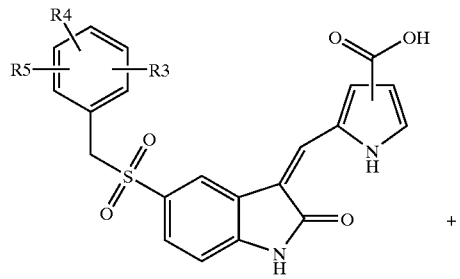

+

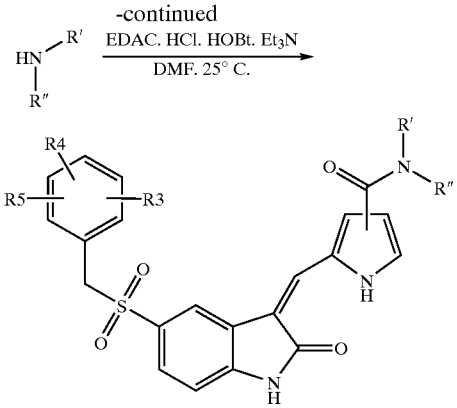

To a solution of 5-arylmethanesulfonyl-1,3-dihydro-indol-(3Z)-ylidene-methyl]-2,4-dimethyl-1H-pyrrole-3-carboxylic acid (1 molar equivalent), amine (2.5 molar equivalent), HOBt(1.2 molar equivalent), and EDAC.HCl (1.2 molar equivalent) in DMF (0.25 M) was added triethylamine(2.5 molar eqivalent). The reaction solution was stirred at room temperature from 24–96 hours as adjudged by TLC. A rust colored solution was observed. The product was purified on a silica gel column by eluting with MeOH—CH$_2$Cl$_2$.

Utilizing the General Synthetic procedure D and appropriate starting materials, following compounds of Fomula (I) were prepared.

Example 135

Synthesis of 5-(2,6-dichloro-phenylmethanesulfonyl)-3-[1-[5-methyl-3-(morpholine-4-carbonyl)-1H-pyrrol-2-yl]-meth-(Z)-ylidene]-1,3-dihydro-indol-2-one

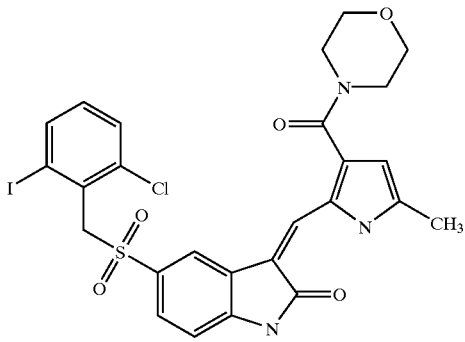

Yellow-orange solid, (83 mg, 53%).
$^1$H NMR (400 MHz, DMSO-$d_6$) δ 13.51 (s, NH, 1H), 11.53 (s, NH, 1H), 7.77 (d, 1H), 7.70 (s, 1H), 7.48 (m, 3H), 7.37 (m, 1H), 7.06 (d, 1H), 6.32 (d, 1H), 4.88 (s, 2H), 3.60 (m, 8H), 2.38 (s, 3H). MS m/z 560 [M$^+$+1].

Example 136

Synthesis of 5-(2,6-dichloro-phenylmethanesulfonyl)-3-[1-[5-methyl-3-(4-methyl-piperazine-1-carbonyl)-1H-pyrrol-2-yl]-meth-(Z)-ylidene]-1,3-dihydro-indol-2-one

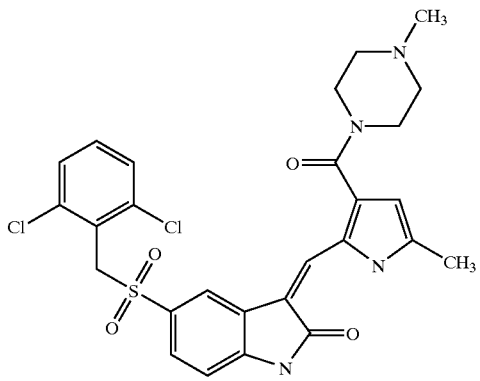

Yellow solid, (86 mg, 67%).
$^1$H NMR (400 MHz, DMSO-$d_6$) δ 13.44 (s, NH, 1H), 11.52 (s, NH, 1H), 7.75 (d, 1H), 7.63 (s, 1H), 7.47 (m, 3H), 7.37 (m, 1H), 7.06 (d, 1H), 6.29 (d, 1H), 4.88 (s, 2H), 3.58 (m, 4H), 2.38 (s, 3H), 2.34 (m, 4H), 2.20 (s, 3H). MS m/z 573 [M$^+$+1].

Example 137

Synthesis of 2-[5-(2,6-dichloro-phenylmethanesulfonyl)-2-oxo-1,2-dihydro-indol-(3Z)-ylidenemethyl]-5-methyl-1H-pyrrole-3-carboxylic acid Methyl-(1-methyl-piperidin-4-yl)-amide

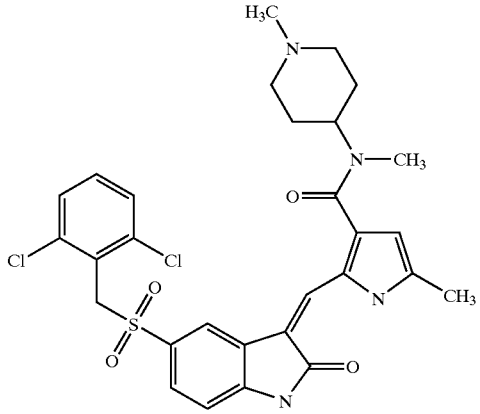

Yellow-orange solid, (95 mg, 57%).
$^1$H NMR (400 MHz, DMSO-$d_6$) δ 13.44 (br s, NH, 1H), 11.52 (s, NH, 1H), 7.58 (m, 1H), 7.47 (m, 4H), 7.37 (m, 1H), 7.06 (d, 1H), 6.29 (s, 1H), 4.87 (s, 2H), 4.00 (m, 1H), 2.87 (m, 5H), 2.48 (s, 3H), 2.39 (s, 3H), 2.14 (m, 3H), 1.81 (m, 2H), 1.59 (m, 1H). MS m/z 599 [M$^-$−1].

Example 138

Synthesis of 5-(2,6-dichloro-phenylmethanesulfonyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one

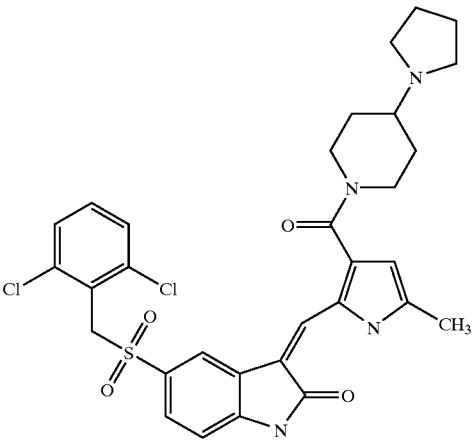

Yellow-orange solid, (91 mg, 52%).
$^1$H NMR (400 MHz, DMSO-$d_6$) δ 13.42 (s, NH, 1H), 11.53 (s, NH, 1H), 7.71 (s, 1H), 7.62 (s, 1H), 7.47 (m, 3H), 7.39 (m, 1H), 7.06 (d, 1H), 6.29 (d, 1H), 4.87 (s, 2H), 4.36 (m, 1H), 3.85 (m, 1H), 3.04 (m, 2H), 2.61 (m, 4H), 2.42 (m, 1H), 2.40 (s, 3H), 1.89 (m, 2H), 1.66 (m, 4H), 1.42 (m, 2H). MS m/z 627 [M$^+$+1].

Example 139

Synthesis of 5-(2,6-dichloro-phenylmethanesulfonyl)-3-[1-[3,5-dimethyl-4-((S)-2-pyrrolidin-1-ylmethyl-pyrrolidin-1-ylcarbonyl)-1H-pyrrol-2-yl]-meth-(Z)-ylidene]-1,3-dihydro-indol-2-one

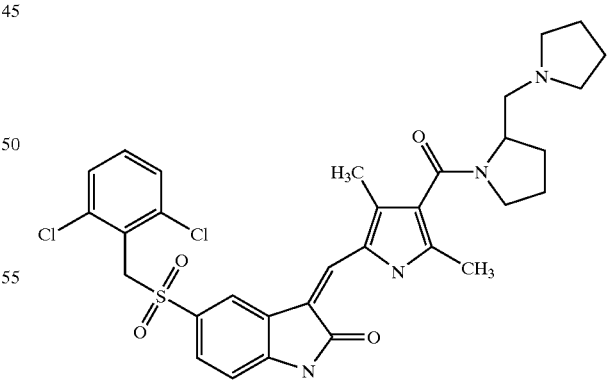

Yellow-orange solid, (92 mg, 51%).
$^1$H NMR (400 MHz, DMSO-$d_6$) δ 13.58 (s, NH, 1H), 11.40 (s, NH, 1H), 8.26 (s, 1H), 7.84 (s, 1H), 7.48 (m, 2H), 7.40 (m, 2H), 7.03 (d, 1H), 4.85 (s, 2H), 3.70 (m, 1H), 3.49 (m, 1H), 3.24 (m, 4H), 2.31 (s, 6H), 2.05 (m, 2H), 1.84 (m, 6H), 1.69 (m, 2H), 1.50 (m, 1H). MS m/z 639 [M$^-$−1].

Example 140

Synthesis of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (2-Hydroxy-3-morpholin-4-yl-propyl)-amide

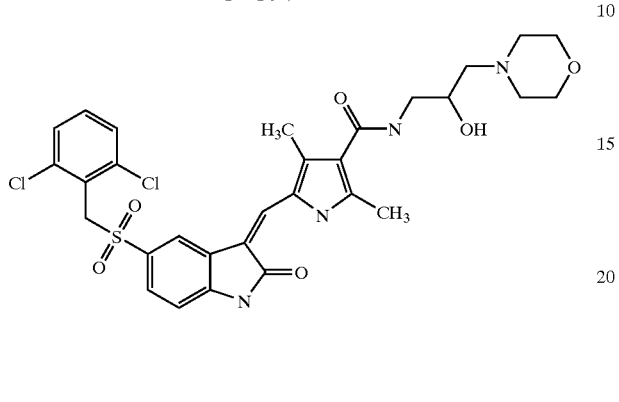

Yellow-orange solid, (89 mg, 49%).
$^1$H NMR (400 MHz, DMSO-d$_6$) δ 13.59 (s, NH, 1H), 11.40 (s, NH, 1H), 8.27 (d, 1H), 7.86 (s, 1H), 7.58 (m, 1H), 7.48 (m, 2H), 7.40 (m, 2H), 7.02 (d, 1H), 4.85 (s, 2H), 4.75 (m, 1H), 3.79 (m, 1H), 3.56 (m, 4H), 3.36 (m, 1H), 3.16 (m, 1H), 2.44 (s, 6H), 2.41 (m, 6H). MS m/z 645 [M$^-$−1].

Example 141

Synthesis of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (2-Hydroxy-3-[1,2,3]triazol-1-yl-propyl)-amide

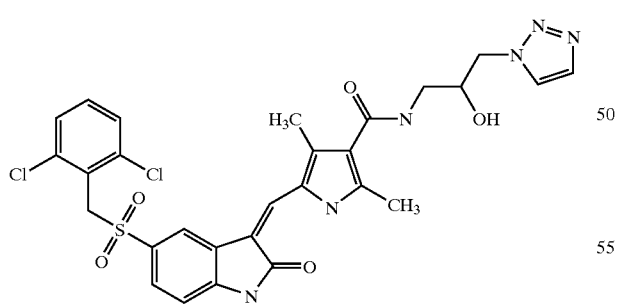

Yellow-orange solid, (93 mg, 53%).
$^1$H NMR (400 MHz, DMSO-d$_6$) δ 13.60 (s, NH, 1H), 11.41 (s, NH, 1H), 8.28 (d, 1H), 8.08 (d, 1H), 7.87 (s, 1H), 7.75 (m, 1H), 7.71 (d, 1H), 7.48 (m, 2H), 7.40 (m, 2H), 7.02 (d, 1H), 5.39 (d, 1H), 4.86 (s, 2H), 4.51 (dd, 1H), 4.29 (m, 1H), 4.01 (m, 1H), 3.27 (m, 2H), MS m/z 627 [M$^-$−1].

Example 142

Synthesis of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [2-(3-oxo-Piperazin-1-yl)-ethyl]-amide

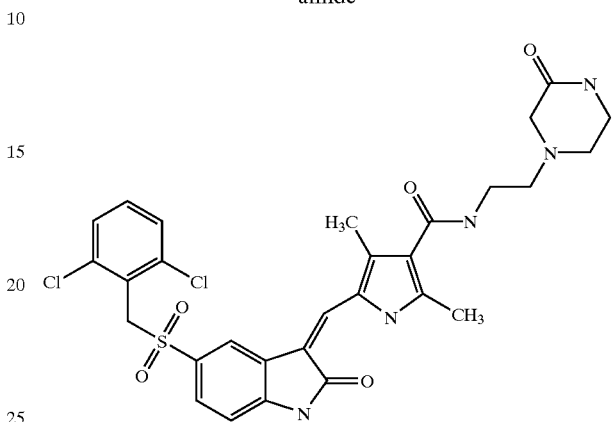

Orange solid, (89 mg, 51%).
$^1$H NMR (400 MHz, DMSO-d$_6$) δ 13.59 (s, NH, 1H), 11.40 (s, NH, 1H), 8.28 (d, 1H), 7.86 (s, 1H), 7.73 (m, 1H), 7.60 (m, 1H), 7.48 (m, 2H), 7.40 (m, 2H), 7.02 (d, 1H), 4.85 (s, 2H), 3.35 (m, 2H), 3.14 (m, 2H), 2.98 (s, 2H), 2.61 (m, 2H), 2.52 (m, 2H), 2.43 (s, 6H). MS m/z 628 [M$^-$−1].

Example 143

Synthesis of 5-(2,6-dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

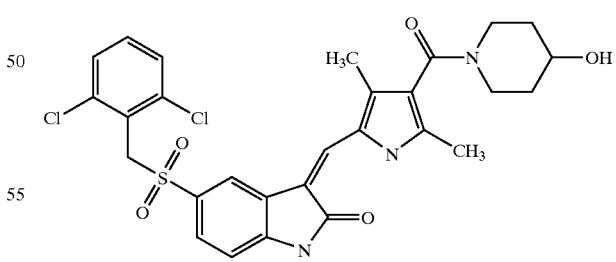

Yellow solid, (93 mg, 57%).
$^1$H NMR (400 MHz, DMSO-d$_6$) δ 13.51 (s, NH, 1H), 11.49 (s, NH, 1H), 8.26 (d, 1H), 7.84 (s, 1H), 7.48 (m, 2H), 7.40 (m, 2H), 7.02 (d, 1H), 4.85 (s, 2H), 4.77 (d, 1H), 1.29 (m, 1H), 3.69 (m, 1H), 3.51 (m, 1H), 3.13 (m, 2H), 2.28 (s, 6H), 1.69 (m, 2H), 1.29 (m, 2H). MS m/z 588 [M$^+$+1].

Example 144

Synthesis of 2-[5-(2,6-dichloro-phenylmethanesulfonyl)-2-oxo-1,2-dihydro-indol-(3Z)-ylidenemethyl]-5-methyl-1H-pyrrole-3-carboxylic acid

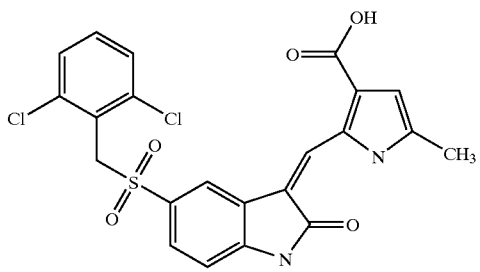

Yellow-orange solid, (72 mg, 53%).

$^1$H NMR (400 MHz, DMSO-d$_6$) δ 13.64 (s, NH, 1H), 12.68 (br s, 1H), 11.61 (s, NH, 1H), 8.38 (s, 1H), 7.64 (d, 1H), 7.54 (dd, 1H), 7.47 (m, 2H), 7.36 (m, 1H), 7.09 (d, 1H), 6.57 (d, 1H), 4.88 (s, 2H), 2.37 (s, 3H). MS m/z 489 [M$^-$−1].

Example 145

Synthesis of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid

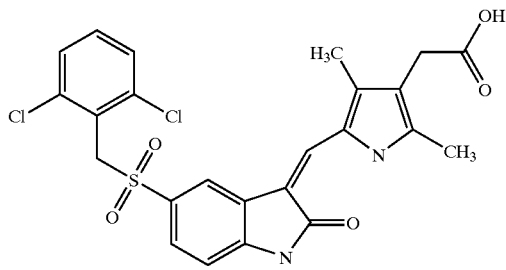

Brown-yellow solid, (75 mg, 52%).

$^1$H NMR (400 MHz, DMSO-d$_6$) δ 13.47 (s, NH, 1H), 12.09 (s, 1H), 11.29 (s, NH, 1H), 8.18 (d, 1H), 7.78 (s, 1H), 7.47 (m, 2H), 7.38 (m, 2H), 7.00 (d, 1H), 4.85 (s, 2H), 3.38 (s, 2H), 2.30 (s, 3H), 2.27 (s, 3H). MS m/z 519 [M$^+$+1].

Example 146

Synthesis of 2-[5-(2,6-dichloro-phenylmethanesulfonyl)-2-oxo-1,2-dihydro-indol-(3Z)-ylidenemethyl]-5-methyl-1H-pyrrole-3-carboxylic acid [2-(3-oxo-piperazin-1-yl)-ethyl]-amide

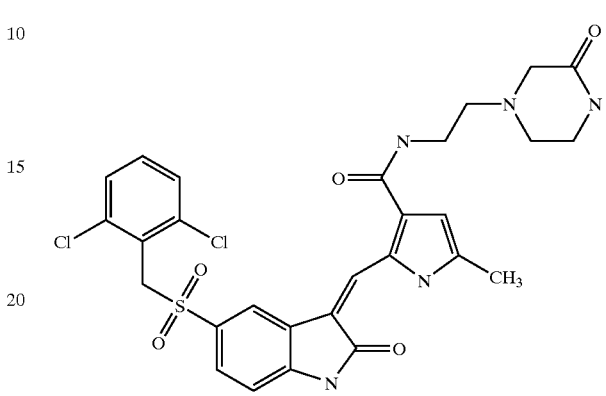

Yellow-orange solid, (87 mg, 51%).

$^1$H NMR (400 MHz, DMSO-d$_6$) δ 13.56 (s, NH, 1H), 11.55 (s, NH, 1H), 8.66 (s, 1H), 8.30 (m, 1H), 7.71 (m, 2H), 7.49 (m, 3H), 7.37 (m, 1H), 7.07 (d, 1H), 6.65 (d, 1H), 4.89 (s, 2H), 3.38 (m, 2H), 3.13 (m, 2H), 2.99 (s, 2H), 2.61 (m, 2H), 2.53 (m, 2H), 30 2.37 (s, 3H). MS m/z 614 [M$^-$−1].

Example 147

Synthesis of 5-(2,6-dichloro-phenylmethanesulfonyl)-3-[1-[3-(4-hydroxy-piperidine-1-carbonyl)-5-methyl-1H-pyrrol-2-yl]-meth-(Z)-ylidene]-1,3-dihydro-indol-2-one

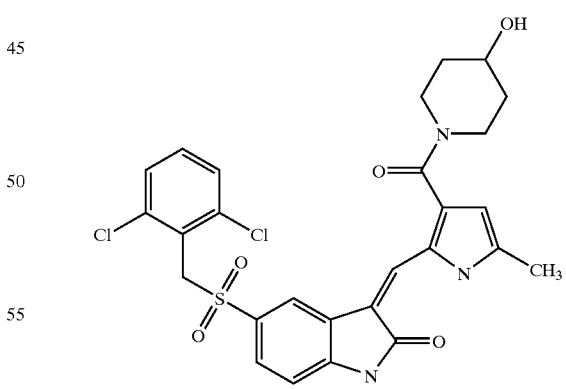

Yellow-orange solid, (85 mg, 53%).

$^1$H NMR (400 MHz, DMSO-d$_6$) δ 13.46 (s, NH, 1H), 11.51 (s, NH, 1H), 7.70 (s, 1H), 7.62 (s, 1H), 7.47 (m, 3H), 7.37 (m, 1H), 7.05 (d, 1H), 6.28 (d, 1H), 4.87 (s, 2H), 4.80 (d, 1H), 4.02 (m, 1H), 3.74 (m, 2H), 3.24 (m, 2H), 2.38 (s, 3H), 1.75 (m, 2H), 1.36 (m, 2H). MS m/z 572 [M$^-$−1].

Example 148

Synthesis of 5-(2,6-dichloro-phenylmethanesulfonyl)-3-[1-[3-(3-diethylamino-pyrrolidin-1-ylcarbonyl)-5-methyl-1H-pyrrol-2-yl]-meth-(Z)-ylidene]-1,3-dihydro-indol-2-one

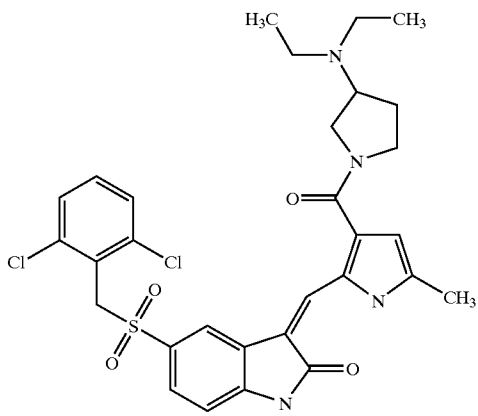

Yellow solid, (92 mg, 54%).

$^1$H NMR (400 MHz, DMSO-d$_6$) δ 13.59 (s, NH, 1H), 11.53 (s, NH, 1H), 8.03 (s, 1H), 7.70 (d, 1H), 7.47 (m, 3H), 7.38 (m, 1H), 7.06 (d, 1H), 6.52 (d, 1H), 4.88 (s, 2H), 3.69 (m, 2H), 3.52 (m, 1H), 3.22 (m, 2H), 2.58 (m, 4H), 2.39 (s, 3H), 2.07 (m, 1H), 1.74 (m, 1H), 0.93 (m, 6H). MS m/z 615 [M$^+$+1].

Example 149

Synthesis of 5-(2,6-dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

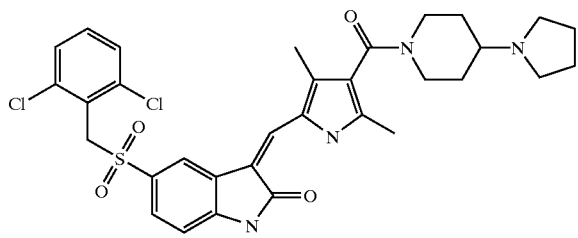

Yellow-orange solid, (91 mg, 51%).
MS m/z 641 [M$^+$+1].

Example 150

Synthesis of 5-(2,6-dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

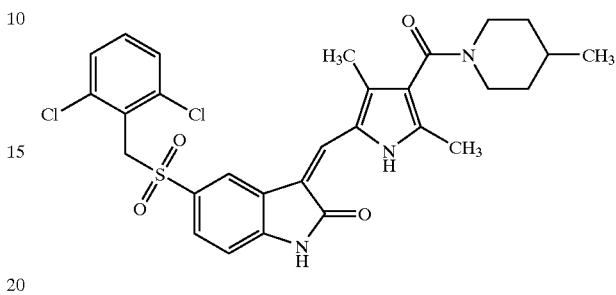

Yellow-orange solid, (84 mg, 51%).

$^1$H NMR (400 MHz, DMSO-d$_6$) δ 13.55 (s, NH, 1H), 11.79 (s, NH, 1H), 8.27 (s, 1H), 7.85 (s, 1H), 7.48 (m, 2H), 7.42 (m, 2H), 7.04 (d, J=8.2 Hz, 1H), 4.87 (s, 2H), 3.45 (m, 4H), 2.32 (m, 10H), 2.19 (s, 3H). MS m/z 585 [M$^-$−1].

Example 151

Synthesis of 5-(2,6-dichloro-phenylmethanesulfonyl)-3-[1-(3,5-dimethyl-4-morpholin-4-ylmethyl-1H-pyrrol-2-yl)-meth-(Z)-ylidene]-1,3-dihydro-indol-2-one

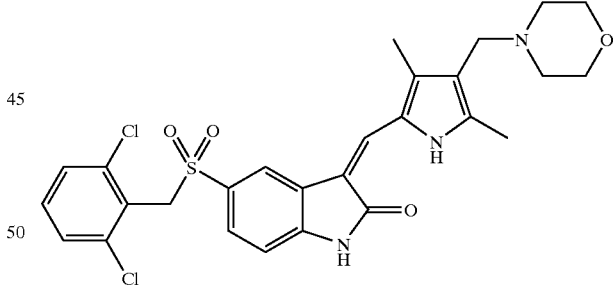

5-(2,6-Dichlorophenylmethanesulfonyl)-1,3-dihydro-indol-2-one was condensed with 3,5-dimethyl-4-morpholin-4-ylmethyl-1H-pyrrole-2-carbaldehyde to give 2.0 g of the titled compound as an orange solid.

$^1$H-NMR (400 MHz, DMSO-d$_6$) δ 13.47 (br s, 1H), 11.28 (s, 1H), 8.19 (s, 1H), 7.78 (s. 1H), 7.47 (m, 2H), 7.38 (m, 2H), 7.01 (d, 1H), 4.85 (s, 2H, CH$_2$), 3.28 (m, 2H, CH$_2$), 2.48 (s, 6H, 2×CH$_3$), 2.33 (m, 8H). MS m/z 558/560 [M$^+$+1].

Example 152

Synthesis of 3-[1-[4-((R)-2-cyclopropylaminomethyl-pyrrolidin-1-carbonyl)-3,5-dimethyl-1H-pyrrol-2-yl]-meth-(Z)-ylidene]-5-(2,6-dichlorophenylmethanesulfonyl)-1,3-dihydro-indol-2-one

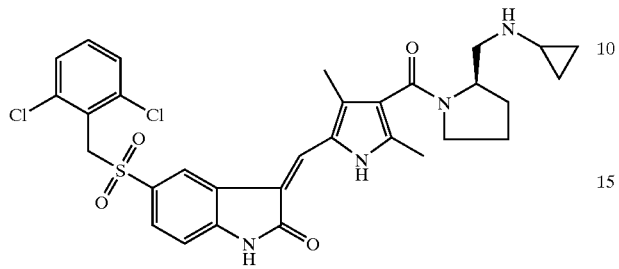

Step 1

To a mixture of (+)-carbobenzyloxy-D-proline (1.5 g, 6 mmol), EDAC (2.3 g, 2 eq.), HOBt (0.8 g, 2 eq.) in DMF (20 mL) was added triethylamine (1.5 mL) and cyclopropylamine (0.8 mL, 2 eq.). After stirring at RT for 18 h, the reaction was basified with sodium bicarbonate, poured to brine, and followed by extraction with dichloromethane. After concentration of the combined extracts, the residue was purified on a silica gel column eluting with 100% EtOAc to give 1.6 g (92%) of (R)-2-cyclopropylcarbamoyl-pyrrolidine-1-carboxylic acid benzyl ester.

Step 2

(R)-2-Cyclopropylcarbamoyl-pyrrolidine-1-carboxylic acid benzyl ester (2.6 g) was hydrogenated using 5% Pd/C (260 mg) in methanol (25 mL). The filtrate was concentrated to give 1.1 g (79%) of (R)-pyrrolidine-2-carboxylic acid cyclopropylamide.

Step 3

(R)-Pyrrolidine-2-carboxylic acid cyclopropylamide (0.5 g, 3.2 mmol) in THF (4 mL) was added to borane-tetrahydrofuran complex (6 mL, 1 M, 6 mmol) at 0° C. The reaction mixture was refluxed for overnight after which more $BH_3$ was added and heating was continued for another 2 h. The reaction mixture was acidified with 3M HCl soution and refluxed for 0.5 h. The reaction mixture was concentrated and the residue was basified with 2M NaOH solution. It crude reaction mixture was then extracted with 5% methanol in dichloromethane to give 0.4 g (89%) of cyclopropyl-(R)-1-pyrrolidin-2-ylmethyl-amine.

Step 4

5-(2,6-Dichlorophenylmethanesulfonyl)-1,3-dihydro-indol-2-one was condensed with 5-formyl-2,4-dimethyl-1H-pyrrole-3-carboxylic acid using the general condensation method to give 5-[5-(2,6-dichlorophenylmethanesulfonyl)-2-oxo-1,2-dihydro-indol-(3Z)-ylidenemethyl]-2,4-dimethyl-1H-pyrrole-3-carboxylic acid.

Step 5

To a mixture of 5-[5-(2,6-dichlorophenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), EDAC (76 mg, 2 eq.), HOBt (27 mg, 1 eq.) in DMF (4 mL) was added triethyamine (0.08 mL, 0.57 mmol) and cyclopropyl-(R)-1-pyrrolidin-2-ylmethyl-amine (0.05 mL). After stirring at rt for 18 h, the reaction was basified with sodium bicarbonate, followed by extraction with 5% of methanol in dichloromethane. After concentration, the residue was purified on a silica gel column eluting with 5% of methanol in dichloromethane to give 80 mg (64%) of the titled compound.

$^1$H-NMR (400 MHz, $CDCl_3$) δ 13.3 (br s, 1H), 9.4 (vbr s, 1H), 7.8 (s, 1H), 7.52 (d, 1H), 7.3 (m, 3H), 7.2 (m, 1H), 6.96 (d, 1H), 4.88 (s, 2H, $CH_2$), 3.3 (m, 2H, $CH_2$), 3.12 (m, 1H), 2.82 (m, 1H), 2.42 (3H, $CH_3$), 2.3 (s, 3H, $CH_3$), 1.7–2.0 (m, 6H), 0.44 (m, 2H), 0.32 (m, 2H). MS m/z 627/629 ($M^+$+1).

Example 153

Synthesis of 5-(2,6-dichlorophenylmethanesulfonyl)-3-[1-{4-[(S)-2-((R)-3-fluoro-pyrrolidin-1-ylmethyl)pyrrolidin-1-carbonyl]-3,5-dimethyl-1H-pyrrol-2-yl}-meth-(Z)-ylidene]-1,3-dihydro-indol-2-one

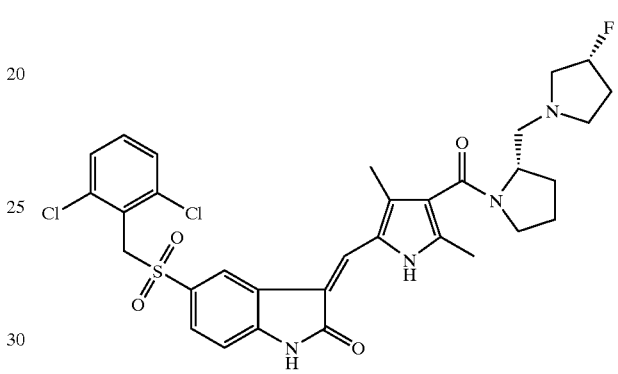

Step 1

To a mixture of N-(tert-butoxycarbonyl)-L-proline (2 g, 9.3 mmol), EDAC (3.5 g, 18 mmol), HOBt (1.35 g, 10 mmol) in DMF (20 mL) was added triethylamine (2 mL, 14 mmol) and (R)-(+)-3-pyrrolidinol (1.5 mL, 18 mmol). After stirring at room temperature for 48 h, the reaction was quenched with water and sodium bicarbonate solution. It was then extracted with 5% of methanol in dichloromethane. The residue was purified on a silica gel column eluting with 10% of methanol in dichloromethane to give 2.2 g (83%) of (S)-2-((R)-3-hydroxy-pyrrolidin-1-ylcarbonyl)-pyrrolidine-1-carboxylic acid tert-butyl ester.

Step 2

To a mixture of S)-2-((R)-3-hydroxy-pyrrolidin-1-ylcarbonyl)-pyrrolidine-1-carboxylic acid tert-butyl ester (0.8 g, 2.8 mmol) in dichloromethane (5 mL) at −78° C., was added slowly DAST (0.4 mL, 3 mmol). After stirring at room temperature for 3 h, the reaction mixture was diluted with methanol and concentrated. The residue was dissolved in EtOAc and washed with sodium bicarbonate solution (3×), sodium chloride (1×). After concentrating, the residue was purified to give 700 mg (87%) of (S)-2-((R)-3-fluoro-pyrrolidin-1-ylcarbonyl)-pyrrolidine-1-carboxylic acid tert-butyl ester.

Step 3

Trifluoroacetic acid (5 mL) was added to a solution of (S)-2-((R)-3-fluoro-pyrrolidin-1-ylcarbonyl)-pyrrolidine-1-carboxylic acid tert-butyl ester (700 mg, 2.4 mmol) in dichloromethane (5 mL). After stirring at room temperature for 2 h, the reaction mixture was concentrated. The residue was dissolved in methanol-water (1:1), neutralized to pH>10 with OH⁻ formed resin. After concentration, 400 mg (89%) of ((R)-3-fluoro-pyrrolidin-1-yl)-(S)-pyrrolidin-2-yl-methanone was obtained.

Step 4

To a mixture of LAH (250 mg, 6.6 mmol) in THF (5 mL) at 0° C. was added ((R)-3-fluoro-pyrrolidin-1-yl)-(S)-pyrrolidin-2-yl-methanone (400 mg, 2.1 mmol) in THF (5 mL). After refluxing for 20 h, the reaction mixture was cooled to 0° C. and quenched with saturated sodium sulfate solution. It was then extracted with 5% of methanol in dichloromethane. After concentration, 250 mg (69%) of (R)-3-fluoro-1-(S)-1-pyrrolidin-2-ylmethylpyrrolidine was obtained.

Step 5

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), EDAC (190 mg), HOBt (65 mg) in DMF (4 mL) was added triethyamine (0.16 mL) and (R)-3-fluoro-1-(S)-1-pyrrolidin-2-ylmethyl-pyrrolidine (135 mg, 0.78 mmol). After stirring at room temperature for 18 h, the reaction mixture was basified with sodium bicarbonate, followed by extraction with 5% of methanol in dichloromethane. After concentration, the residue was purified on a silica gel column eluting with 10% of methanol in dichloromethane to give 150 mg (46%) of the titled compound.

$^1$H-NMR (400 MHz, CDCl$_3$) δ 13.22 (br s, 1H), 8.18 (br s, 1H), 7.8 (s, 1H), 7.58 (d, 1H), 7.3 (m, 4H), 6.98 (d, 1H), 4.85 (s, 2H, CH$_2$), 3.22 (m, 1H), 3.0 (m, 1H), 2.9 (m, 1H), 2.54 (m, 2H), 2.42 (s, 3H, CH$_3$), 2.32 (s, 3H, CH$_3$), 1.8–2.1 (m, 7H), 1.6 (s, 4H). MS m/z 659/661 (M$^+$+1).

Example 154

Synthesis of 3-[1-[4-(4-Cyclopropylamino-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

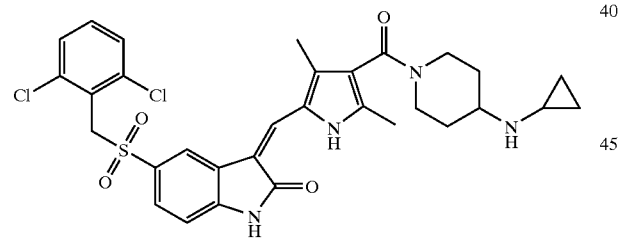

5-(2,6-Dichloro-phenylmethanesulfonyl)-1,3-dihydro-indol-2-one was condensed with 5-formyl-2,4-dimethyl-1H-pyrrole-3-carboxylic acid using the general condensation method to give 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid. This was then coupled with cyclopropyl-piperidin-4-yl-amine TFA salt (prepared as in lit. procedure by H. C. Hansen et al. *Bioorg. Med. Chem. Lett.* 10, 2000, 2435–2439.) using the general amidation procedure to give an orange solid.

$^1$H-NMR (400 MHz, DMSO-d$_6$) δ 13.54 (br s, 1H), 11.40 (br s, 1H), 8.29 (s, 1H), 7.87 (s, 1H), 7.38–7.51 (m, 4H), 7.04 (d, 1H), 4.88 (s, 2H, CH$_2$), 4.26 (m, 1H), 3.57 (m, 1H), 3.04 (m, 2H), 2.76 (m, 1H), 2.31 (s, 6H, 2×CH$_3$), 2.08 (m, 1H), 1.86 (m, 2H), 1.19 (m, 2H), 0.38 (m, 2H), 0.21 (m, 2H). MS m/z 627/629[M$^+$+1].

Example 155

Synthesis of 3-{2,4-Dimethyl-5-[2-oxo-5-phenylmethanesulfonyl-1,2-dihydro-indol-(3Z)-ylidenemethyl]-1H-pyrrol-3-yl}-propionic acid

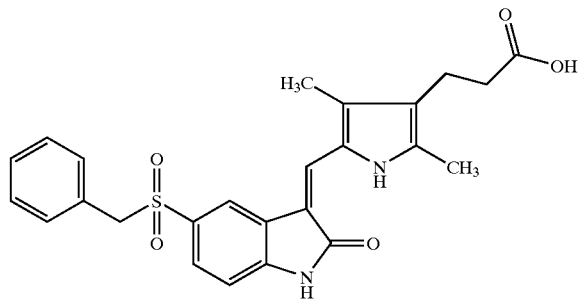

5-Phenylmethanesulfonyl-1,3-dihydro-indol-2-one was condensed with 3-(5-formyl-2,4-dimethyl-1H-pyrrol-3-yl)-propionic acid to give the titled compound.

Example 156

Synthesis of {2,4-Dimethyl-5-[2-oxo-5-phenylmethanesulfonyl-1,2-dihydro-indol-(3Z)-ylidenemethyl]-1H-pyrrol-3-yl}-acetic acid

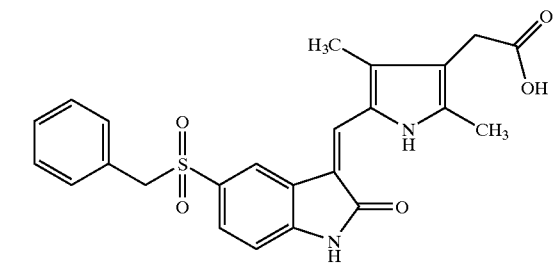

5-Phenylmethanesulfonyl-1,3-dihydro-indol-2-one was condensed with (5-formyl-2,4-dimethyl-1H-pyrrol-3-yl)-acetic acid to give the titled compound.

Example 157

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-Pyrrolidin-1-yl-propyl)-amide

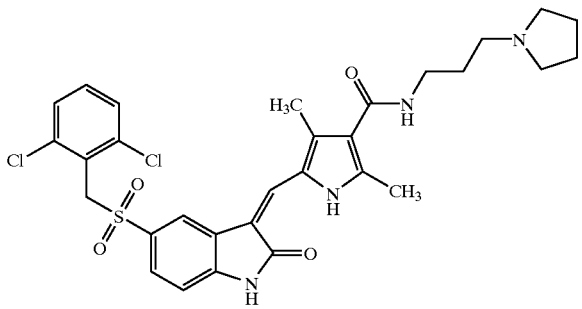

5-[5-(2,6-Dichloro-phenylmethanesulfonyl)-2-oxo-1,2-dihydro-indol-(3Z)-ylidenemethyl]-2,4-dimethyl-1H- pyrrole-3-carboxylic acid was coupled with 3-pyrrolidin-1-yl-propylamine to give the titled compound.

Example 158

Synthesis of 2-[5-(2,6-Dichloro-phenylmethanesulfonyl)-2-oxo-1,2-dihydro-indol-(3Z)-ylidenemethyl]-5-methyl-1H-pyrrole-3-carboxylic acid (3-Pyrrolidin-1-yl-propyl)-amide

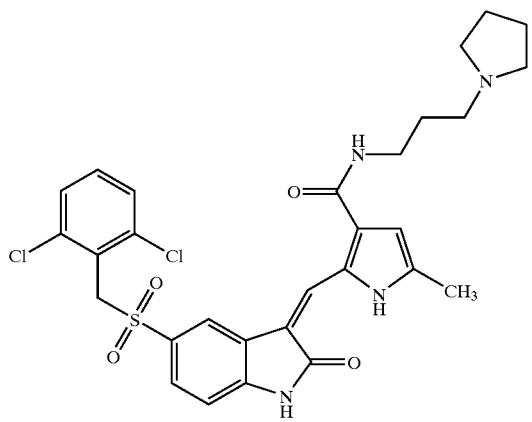

2-[5-(2,6-Dichloro-phenylmethanesulfonyl)-2-oxo-1,2-dihydro-indol-(3Z)-ylidenemethyl]-5-methyl-1H-pyrrole-3-carboxylic acid was coupled with 3-pyrrolidin-1-yl-propylamine to give the titled compound.

Example 159

Synthesis of 2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-Pyrrolidin-1-yl-ethyl)-amide

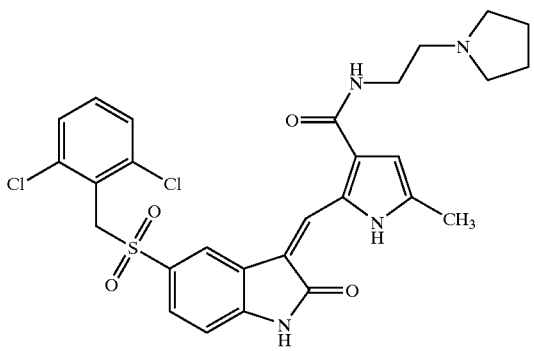

2-[5-(2,6-Dichloro-phenylmethanesulfonyl)-2-oxo-1,2-dihydro-indol-(3Z)-ylidenemethyl]-5-methyl-1H-pyrrole-3-carboxylic acid was coupled with 2-pyrrolidin-1-yl-ethylamine to give the titled compound.

Example 160

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-ethyl)-amide

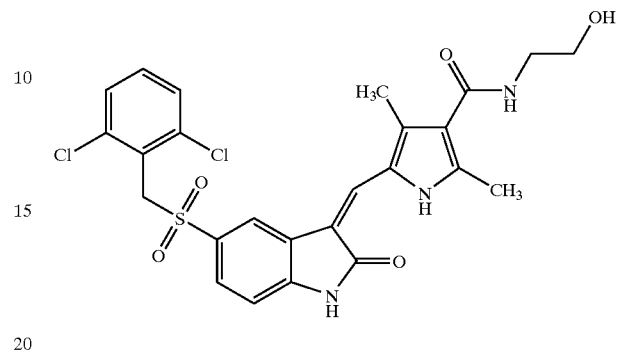

A mixture of 5-(2,6-Dichloro-phenylmethanesulfonyl)-1,3-dihydro-indol-2-one (150 mg, 0.42 mmol), 5-formyl-2,4-dimethyl-1H-pyrrole-3-carboxylic acid (2-hydroxy-ethyl)-amide (88 mg, 1 eq. 0 and piperidine (18 mg, 0.5 eq.) in ethanol (2 mL) was stirred at rt for 5 days. The reaction was concentrated and triturated with ethanol to give the titled compound as a pale yellow solid.
$^1$HNMR (400 MHz, DMSO-d$_6$) δ 13.6 (s, 1H, NH), 11.4 (s, 1H, NH), 8.27 (d, 1H), 7.86 (s, 1H), 7.6 (t, 1H, CONH), 7.49 (d, 1H), 7.47 (s, 1H), 7.42 (m, 2H), 7.02 (d, J=8 Hz, 1H), 4.86 (s, 2H), 4.71 (t, J=6 Hz, 1H, OH), 3.49 (q, J=6 Hz, 2H), 3.28 (m, 2H), 2.44 (s, 6H, 2×CH$_3$). MS m/z 546 [M−1].

Example 161

Synthesis of 2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-Hydroxy-3-[1,2,3]triazol-1-yl-propyl)-amide

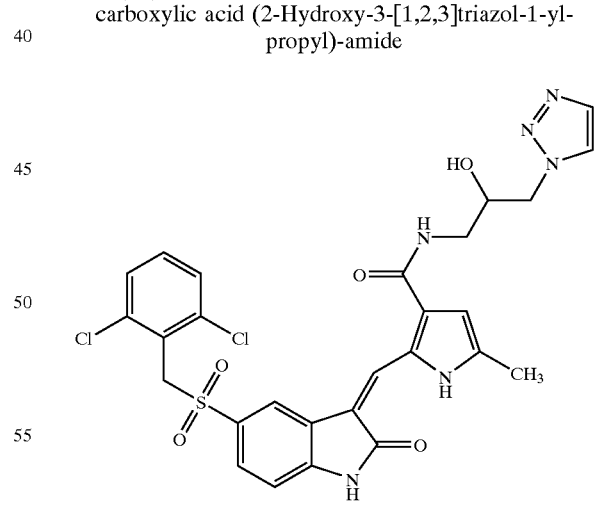

To a mixture of 2-[5-(2,6-dichloro-phenylmethanesulfonyl)-2-oxo-1,2-dihydro-indol-(3Z)-ylidenemethyl]-5-methyl-1H-pyrrole-3-carboxylic acid (100 mg, 0.2 mmol), HOBt (33 mg, 1.2 eq.), EDAC.HCl (47 mg, 1.2 eq.) and 1-amino-3-[1,2,3]triazol-1-yl-propan-2-ol (30 mg, 1.1 eq.) in DMF (2 mL) was added TEA (0.071 mL, 2.5 eq.). After stirring at rt for 2 weeks, the reaction was concentrated, diluted with DCM and several drops of methanol. After standing at rt for one hour, the resulted precipitate was collected by vacuum filtration, washed and dried to give the titled compound as a yellow solid.

¹HNMR (400 MHz, DMSO-d₆) δ 13.56 (s, 1H, NH), 11.56 (s, 1H, NH), 8.67 (s, 1H), 8.38 (t, 1H, CONH), 8.09 (d, 1H), 7.71 (d, 1H), 7.68 (d, 1H), 7.51 (dd, 1H), 7.48 (s, 1H) 7.46 (s, 1H), 7.35 (m, 1H), 7.08 (d, J=8 Hz, 1H), 6.73 (d, 1H), 5.4 (br, d 1H, OH), 4.89 (s, 2H), 4.52 (dd, 1H), 4.3 (dd, 1H), 4.04 (br s, 1H), 3.32 (m, 2H), 2.39 (s, 3H, CH₃). MS m/z 613 [M−1].

Example 162

Synthesis of 2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-Hydroxy-3-morpholin-4-yl-propyl)-amide

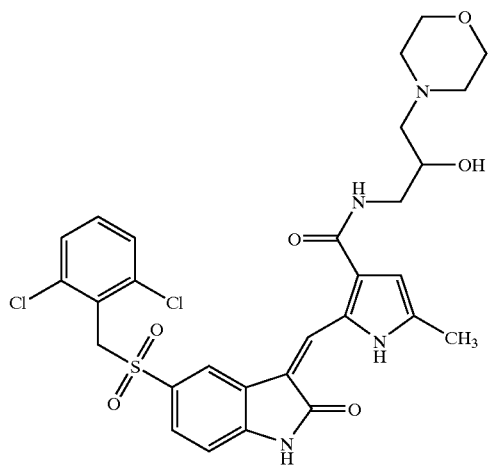

To a mixture of 2-[5-(2,6-dichloro-phenylmethanesulfonyl)-2-oxo-1,2-dihydro-indol-(3Z)-ylidenemethyl]-5-methyl-1H-pyrrole-3-carboxylic acid (100 mg, 0.2 mmol), HOBt (33 mg, 1.2 eq.), EDAC.HCl (47 mg, 1.2 eq.) and 1-amino-3-morpholin-4-yl-propan-2-ol (34 mg, 1.1 eq.) in DMF (2 mL) was added TEA (0.071 mL, 2.5 eq.). After stirring at rt for 2 weeks, the reaction was concentrated, diluted with DCM. Solid sodium bicarbonate was added to the mixture followed by stirring for 15 mins. The orange suspension was then loaded on to a silica gel to give the titled compound as an orange solid.

¹HNMR (400 MHz, DMSO-d₆) δ 13.52 (s, 1H, NH), 11.56 (s, 1H, NH), 8.65 (s, 1H), 8.23 (m, 1H, CONH), 7.69 (s, 1H), 7.48 (m, 2H), 7.36 (m, 2H), 7.08 (d, J=8 Hz, 1H), 6.69 (s, 1H), 4.89 (s, 2H), 3.85 (m, 1H, OH), 3.59 (m, 4H), 3.35 (m, 1H), 3.2 (m, 2H), 2.55 (m, 4H), 2.4 (m, 2H), 2.38 (s, 3H, CH₃). MS m/z 631 [M−1].

Example 163

Synthesis of 2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-Diethylamino-ethyl)-amide

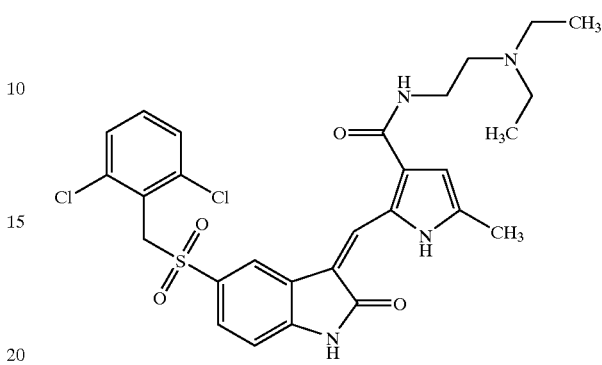

2-[5-(2,6-Dichloro-phenylmethanesulfonyl)-2-oxo-1,2-dihydro-indol-(3Z)-ylidenemethyl]-5-methyl-1H-pyrrole-3-carboxylic acid was coupled with N,N-diethylethylenediamine to give the titled compound.

Example 164

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid Methyl-(1-methyl-piperidin-4-yl)-amide

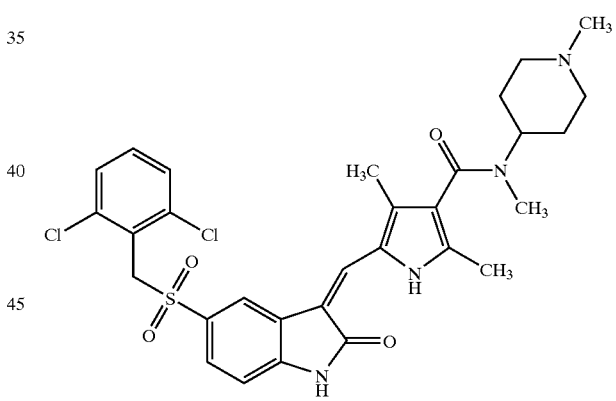

To a mixture of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), HOBt (33 mg, 1.2 eq.), EDAC.HCl (45 mg, 1.2 eq.) and methyl-(1-methyl-piperidin-4-yl)-amine (284 mg, 1.1 eq.) in DMF (2 mL) was added TEA (0.069 mL, 2.5 eq.). After stirring at rt for 2 days, the reaction was concentrated, diluted with DCM and added solid sodium bicarbonate. After stirring at rt for 15 mins, the suspension was loaded onto a silica gel column to give the titled compound as an orange solid.

¹HNMR (400 MHz, DMSO-d₆) δ 13.53 (s, 1H, NH), 11.41 (s, 1H, NH), 8.27 (d, 1H), 7.86 (s, 1H), 7.49 (d, 1H), 7.47 (s, 1H), 7.4 (m, 2H), 7.02 (d, J=8 Hz, 1H), 4.85 (s, 2H), 3.53 (m, 4H), 3.05 (m, 1H), 2.77 (m, 3H), 2.35 (m, 3H), 2.27 (s, 3H, CH₃), 2.26 (s, 3H, CH₃), 1.85 (m, 3H), 1.65 (m, 1H). MS m/z 613 [M−1].

Example 165

Synthesis of 5-(2,6-Dichloro-phenylmethanesulfonyl)-3-[1-[4-(3-diethylamino-pyrrolidine-1-carbonyl)-3,5-dimethyl-1H-pyrrol-2-yl]-meth-(Z)-ylidene]-1,3-dihydro-indol-2-one

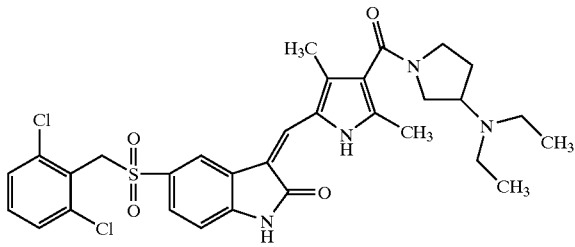

5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (95 mg, 0.19 mmol) was coupled with diethyl-pyrrolidin-3-yl-amine (50.6 mg, 0.25 mmol) using HOBt (1.2 eq.), EDAC.HCl (1.2 eq.) and TEA (3 eq.) at rt for 3 days to give the titled compound.

$^1$HNMR (400 MHz, DMSO-$d_6$) δ 13.55 (br s, 1H, NH), 11.40 (s, 1H, NH), 8.27 (s, 1H), 7.86 (s, 1H), 7.50 (d, 1H), 7.48 (s, 1H), 7.41 (m, 2H), 7.04 (d, J=8 Hz, 1H), 4.87 (s, 2H), 3.65 (m, 1H), 3.2–3.4 (m, 4H), 2.58 (m, 4H), 2.32 (s, 6H, 2×CH$_3$), 2.05 (m, 1H), 1.7 (m, 1H), 0.96 (m, 3H). MS m/z 629 [M+1].

Example 166

Synthesis of 5-(2,6-Dichloro-phenylmethanesulfonyl)-3-[1-[3-((3R,5S)-3,5-dimethyl-piperazine-1-carbonyl)-5-methyl-1H-pyrrol-2-yl]-meth-(Z)-ylidene]-1,3-dihydro-indol-2-one

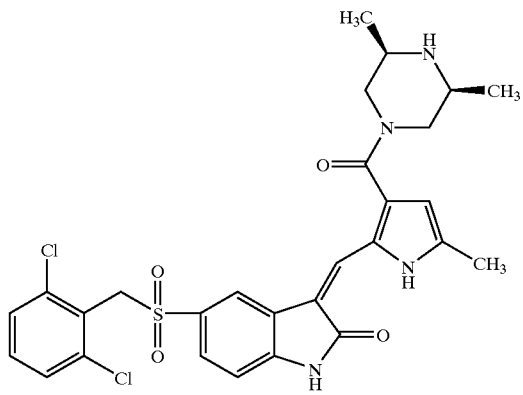

A mixture of 2-[5-(2,6-dichloro-phenylmethanesulfonyl)-2-oxo-1,2-dihydro-indol-(3Z)-ylidenemethyl]-5-methyl-1H-pyrrole-3-carboxylic acid (120 mg, 0.24 mmol), (2R, 6S)-2,6-dimethyl-piperazine (32 mg, 1.2 eq.), HOBt (1.2 eq.), EDAC.HCl (1.2 eq.) and TEA (3 eq.) in DMF (10 mL) was stirred at rt for overnight. The reaction was concentrated and purified on s silica gel column to give the titled compound.

$^1$HNMR (400 MHz, DMSO-$d_6$) δ 13.5 (br s, 1H, NH), 11.5 (br s, 1H, NH), 7.69 (d, 1H), 7.62 (s, 1H), 7.5 (d, 1H), 7.48 (s, 1H), 7.46 (s, 1H), 7.38 (m, 1H), 7.06 (d, J=8 Hz, 1H), 6.28 (s, 1H), 4.88 (s, 2H), 4.4 (m, 1H), 3.72 (m, 1H), 2.7 (m, 4H), 2.39 (s, 3H, CH$_3$), 1.05 (br s, 3H, CH$_3$), 0.9 (br s, 3H, CH$_3$). MS m/z 585 [M−1].

Example 167

Synthesis of 5-[5-(2,6-Dimethyl-phenylmethanesulfonyl)-2-oxo-1,2-dihydro-indol-(3Z)-ylidenemethyl]-2,4-dimethyl-1H-pyrrole-3-carboxylic acid

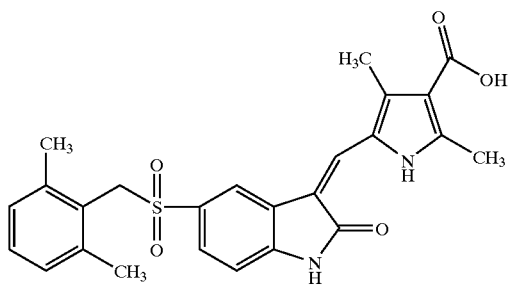

5-[(2,6-Dimethylbenzyl)sulfonyl]-1,3-dihydro-indol-2-one (315 mg, 1 mmol) was condensed with 5-formyl-2,4-dimethyl-1H-pyrrole-3-carboxylic acid (170 mg, 1 mmol) to give the titled compound as an orange-brown solid.

$^1$HNMR (400 MHz, DMSO-$d_6$) δ 13.78 (br s, 1H, NH), 11.45 (s, 1H), 8.31 (s, 1H), 7.91 (s, 1H), 7.53 (dd, 114), 7.02–7.14 (m, 4H), 4.63 (s, 2H), 2.54 (s, 6H, 2×CH$_3$), 2.26 (s, 6H, 2×CH$_3$).

Example 168

Synthesis of 5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid

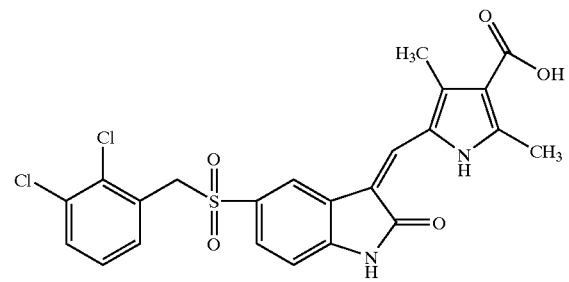

5-[(2,3-Dichlorobenzyl)sulfonyl]-1,3-dihydro-indol-2-one (315 mg, 1 mmol) was condensed with 5-formyl-2,4-dimethyl-1H-pyrrole-3-carboxylic acid (170 mg, 1 mmol) to give the titled compound as a solid.

$^1$HNMR (400 MHz, DMSO d$_6$) δ 13.73 (s, 1H, NH), 11.44 (s, 1H), 8.25 (s, 1H), 7.88 (s, 1H), 7.62 (d, 1H), 7.35 (m, 3H), 7.0 (d, 1H), 4.81 (s, 2H, CH$_2$), 2.54 (s, 6H), 2×CH$_3$). MS m/z 503.2 (M−1).

Example 169

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-oxo-piperazin-1-yl)-ethyl]-acetamide

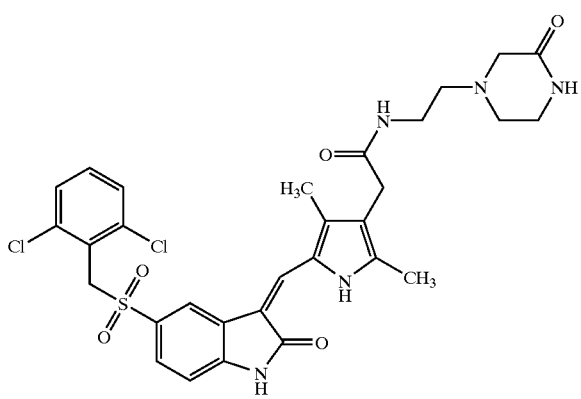

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (100 mg, 0.19 mmol), HOBt (3 mg, 0.1 eq.), EDAC.HCl (44 mg, 1.2 eq.) and 4-(2-amino-ethyl)-piperazin-2-one (30 mg, 1.1 eq.) in DMF (2 mL) at rt was added TEA (0.067 mL, 2.5 eq.). After stirring at rt for 7 days, the reaction was concentrated, diluted with DCM and then mixed with solid sodium bicarbonate. After stirring at rt for 15 mins, the suspension was loaded onto a silica gel column to give the titled compound as a pale orange solid.

$^1$HNMR (400 MHz, DMSO-$d_6$) δ 13.5 (br s, 1H, NH), 11.27 (s, 1H, NH), 8.17 (d, 1H), 7.77 (m, 1H, CONH), 7.76 (s, 1H), 7.71 (m, 1H, CONH), 7.51 (d, 1H), 7.49 (d, 1H), 7.38 (m, 2H), 7.0 (d, J=8 Hz, 1H), 4.84 (s, 2H), 3.25 (s, 2H), 3.3 (m, 2H), 3.2 (m, 2H), 2.92 (s, 2H), 2.53 (m, 2H), 2.4 (m, 2H), 2.3 (s, 3H, CH$_3$), 2.27 (s, 3H, CH$_3$), MS m/z 642 [M-1].

Example 170

Synthesis of 5-(2,6-Dichloro-phenylmethanesulfonyl)-3-[1-{4-[2-(4-hydroxy-piperidin-1-yl)-2-oxo-ethyl]-3,5-dimethyl-1H-pyrrol-2-yl}-meth-(Z)-ylidene]-1,3-dihydro-indol-2-one

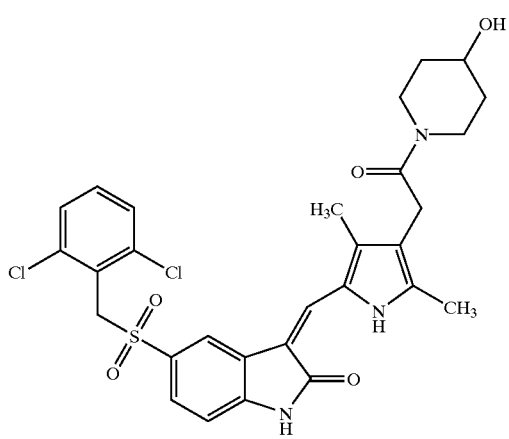

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (100 mg, 0.19 mmol), HOBt (3 mg, 0.1 eq.), EDAC.HCl (44 mg, 1.2 eq.) and piperazin-1-ol (21 mg, 1.1 eq.) in DMF (2 mL) at rt was added TEA (0.067 mL, 2.5 eq.). After stirring at rt for 7 days, the reaction was concentrated, diluted with DCM (10 mL) and methanol (0.5 mL) and then mixed with solid sodium bicarbonate. After stirring at rt for 15 mins, the suspension was loaded onto a silica gel column to give the titled compound as an orange solid.

$^1$HNMR (400 MHz, DMSO-$d_6$) δ 13.5 (br s, 1H, NH), 11.27 (s, 1H, NH), 8.17 (d, 1H), 7.76 (s, 1H), 7.49 (d, 1H), 7.46 (s, 1H), 7.37 (m, 2H), 7.0 (d, J=8 Hz, 1H), 4.85 (s, 2H), 4.72 (m, 1H, OH), 3.93 (m, 1H), 3.75 (m, 2H), 3.65 (m, 2H), 3.49 (d, 1H), 3.18 (m, 1H), 2.96 (m, 1H), 2.26 (s, 3H, CH$_3$), 2.23 (s, 3H, CH$_3$), 1.67 (m, 2H), 1.21 (m, 2H). MS m/z 600 [M-1].

Example 171

Synthesis of 5-(2,6-Dichloro-phenylmethanesulfonyl)-3-[1-[3,5-dimethyl-4-(2-morpholin-4-yl-2-oxo-ethyl)-1H-pyrrol-2-yl]-meth-(Z)-ylidene]-1,3-dihydro-indol-2-one

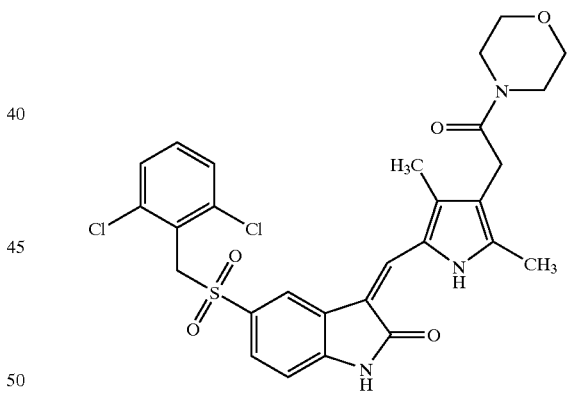

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (100 mg, 0.19 mmol), HOBt (3 mg, 0.1 eq.), EDAC.HCl (44 mg, 1.2 eq.) and morpholine (18 mg, 1.1 eq.) in DMF (2 mL) at rt was added TEA (0.067 mL, 2.5 eq.). After stirring at rt for 7 days, the reaction was concentrated, diluted with DCM (10 mL) and methanol (0.5 mL) and then mixed with solid sodium bicarbonate. After stirring at rt for 15 mins, the suspension was loaded onto a silica gel column to give the titled compound as a reddish-orange solid.

¹HNMR (400 MHz, DMSO-d₆) δ 13.5 (br s, 1H, NH), 11.27 (s, 1H, NH), 8.17 (d, 1H), 7.76 (s, 1H), 7.48 (d, 1H), 7.47 (s, 1H), 7.37 (m, 2H), 7.0 (d, J=8 Hz, 1H), 4.85 (s, 2H), 3.51 (s, 2H), 3.44 (m, 2H), 3.31 (m, 2H), 2.26 (s, 3H, CH₃), 2.23 (s, 3H, CH₃). MS m/z 586 [M−1].

Example 172

Synthesis of 5-(2,6-Dichloro-phenylmethanesulfonyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one

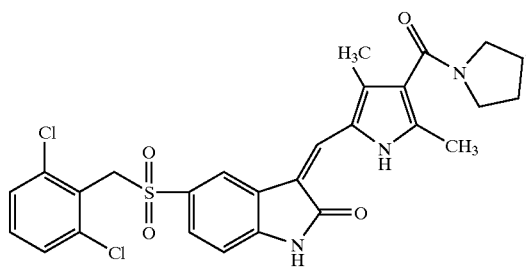

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), (R)-pyrrolidin-3-ol (34 mg, 0.2 mmol), HOBt (20 mg), EDAC.HCl (40 mg) and TEA (40 mg, 3 eq.) in DMF was stirred at 40° C. for 3 days. The reaction was concentrated and purified on a silica gel column to give the titled compound. MS m/z 572 [M−1].

Example 173

Synthesis of 3-[1-[3,5-Dimethyl-4-(morpholine-4-carbonyl)-1H-pyrrol-2-yl]-meth-(Z)-ylidene]-5-(2,6-dimethyl-phenylmethanesulfonyl)-1,3-dihydro-indol-2-one

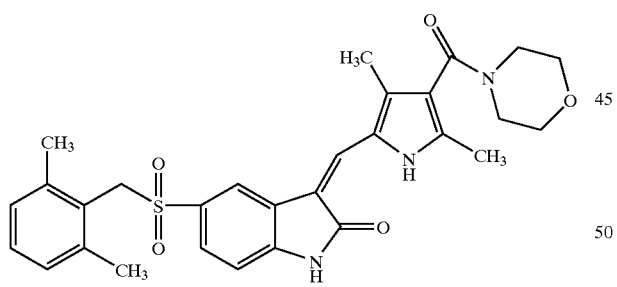

A mixture of 5-[5-(2,6-dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.26 mmol), morpholine (30 mg, 0.34 mmol), HOBt (42 mg, 1.2 eq.), EDAC.HCl (60 mg, 1.2 eq.) and TEA (80 mg, 3 eq.) in 0.2 M concentration of acetonitrile:DMF (3:1) was stirred at for overnight. The reaction was and purified on a silica gel column to give the titled compound.

¹HNMR (400 MHz, DMSO-d₆) δ 13.56 (br s, 1H, NH), 11.4 (br s, 1H, NH), 8.25 (d, 1H), 7.84 (s, 1H), 7.5 (dd, 1H), 7.11 (m, 1H), 7.03 (m, 3H), 4.63 (s, 2H), 3.55 (m, 4H), 2.31 (s, 6H, 2×CH₃), 2.25 (s, 6H, 2×CH₃), 1.5 (m, 2H), 1.2 (m, 2H).

Example 174

Synthesis of 5-(2,6-Dichloro-phenylmethanesulfonyl)-3-[1-{4-[2-((3R,5S)-3,5-dimethyl-piperazin-1-yl)-2-oxo-ethyl]-3,5-dimethyl-1H-pyrrol-2-yl}-meth-(Z)-ylidene]-1,3-dihydro-indol-2-one

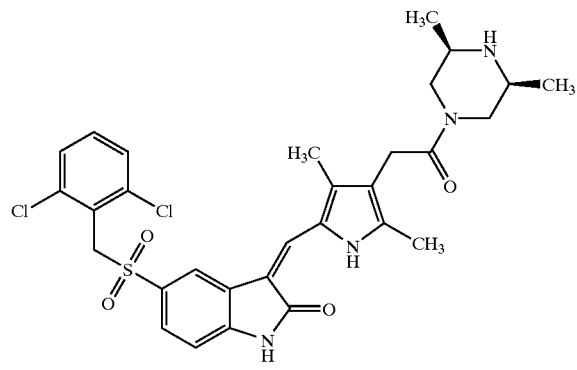

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with (3R, 5S)-3,5-dimethylpiperazine to give the titled compound.

¹HNMR (400 MHz, DMSO-d₆) δ 13.48 (br s, 1H, NH), 11.28 (s, 1H, NH), 8.18 (d, 1H), 7.77 (s, 1H), 7.49 (s, 1H), 7.47 (s, 1H), 7.38 (m, 2H), 7.02 (d, J=8 Hz, 1H), 4.85 (s, 2H), 4.3 (m, 1H), 3.9 (m, 1H), 2.65 (m, 4H), 2.45 (m, 2H), 2.26 (s, 3H, CH₃), 2.23 (s, 3H, CH₃), 1.0 (d, 6H, 2×CH₃). MS m/z 613 [M−1].

Example 175

Synthesis of 5-(2,6-Dichloro-phenylmethanesulfonyl)-3-[1-{3,5-dimethyl-4-[2-(4-methyl-piperazin-1-yl)-2-oxo-ethyl]-1H-pyrrol-2-yl}-meth-(Z)-ylidene]-1,3-dihydro-indol-2-one

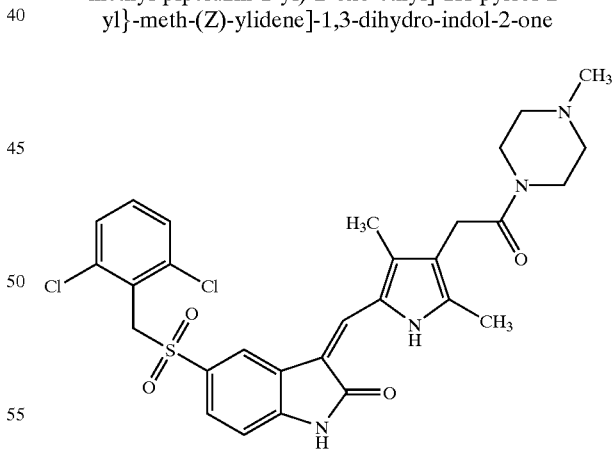

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with 4-methylpiperazine to give the titled compound.

¹HNMR(400MHz,DMSO-d₆) 13.7(brs, 1H, NH), 11.6(s, 1H, NH), 8.18(s, 1H), 7.70 (s, 1H), 7.5 (s, 1H), 7.48 (s, 1H), 7.39 (m, 2H), 7.0 (d, J=8 Hz, 1H), 4.87 (s, 2H), 3.45 (m, 4H), 2.43 (m, 2H), 2.3–2.4 (m, 4H), 2.26 (s, 3H, CH₃), 2.23 (s, 3H, CH₃), 2.23 (s, 3H, CH₃). MS m/z 599 [M−1].

Example 176

Synthesis of 5-(2,6-Dichloro-phenylmethanesulfonyl)-3-[1-(4-{2-[4-(ethyl-propyl-amino)-piperidin-1-yl]-2-oxo-ethyl}-3,5-dimethyl-1H-pyrrol-2-yl)-meth-(Z)-ylidene]-1,3-dihydro-indol-2-one

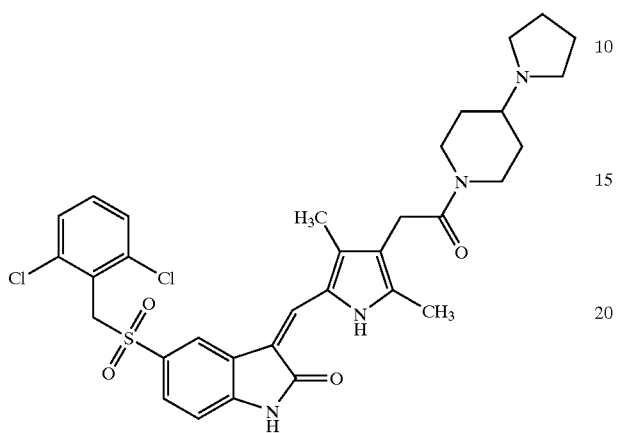

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with to give the titled compound.

$^{1}$HNMR (400 MHz, DMSO-d$_{6}$) δ 13.5 (br s, 1H, NH), 11.3 (s, 1H, NH), 8.18 (s, 1H), 7.76 (s, 1H), 7.49 (s, 1H), 7.47 (s, 1H), 7.38 (m, 2H), 7.01 (d, J=8 Hz, 1H), 4.85 (s, 2H), 4.35 (m, 1H), 4.07 (m, 1H), 3.5 (m, 2H), 2.97 (m, 6H), 2.6 (m, 1H), 2.26 (s, 3H, CH$_{3}$), 2.23 (s, 3H, CH$_{3}$), 1.97 (m, 2H), 1.8 (m, 4H), 1.4 (m, 2H). MS m/z 653 [M−1].

Example 177

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-diethylamino-ethyl)-acetamide

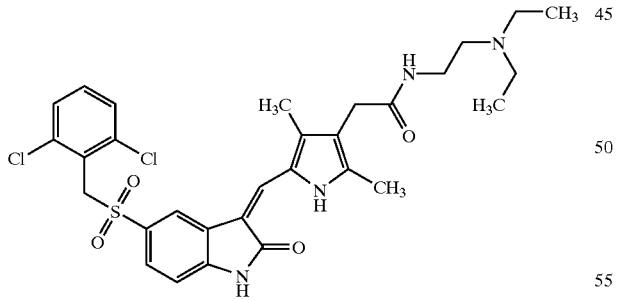

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with N,N-diethylethylenediamine to give the titled compound.

$^{1}$HNMR (400 MHz, DMSO-d$_{6}$) δ 13.5 (br s, 1H, NH), 11.3 (s, 1H, NH), 8.18 (s, 1H), 7.79 (s, 1H), 7.49 (s, 1H), 7.47 (s, 1H), 7.38 (m, 2H), 7.01 (d, J=8 Hz, 1H), 4.85 (s, 2H), 3.29 (m, 2H), 2.9 (m, 6H), 2.45 (m, 2H), 2.32 (s, 3H, CH$_{3}$), 2.28 (s, 3H, CH$_{3}$), 1.09 (m, 6H). MS m/z 615 [M−1].

Example 178

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-methyl-N-(1-methyl-piperidin-4-yl)-acetamide

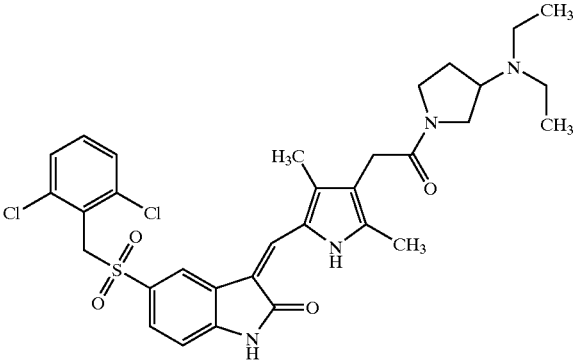

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with methyl-(1-methyl-piperidin-4-yl)-amine to give the titled compound.

$^{1}$HNMR (400 MHz, DMSO-d$_{6}$) δ 13.47 (br s, 1H, NH), 11.28 (s, 1H, NH), 8.17 (s, 1H), 7.76 (s, 1H), 7.49 (d, 1H), 7.47 (s, 1H), 7.38 (m, 2H), 7.0 (d, J=8 Hz, 1H), 4.85 (s, 2H), 2.95 (m, 4H), 2.43 (m, 1H), 2.3 (s, 2H), 2.2–2.26 (4s, 12H, 4×CH$_{3}$), 1.5 (m, 4H). MS m/z 627 [M−1].

Example 179

Synthesis of 5-(2,6-Dichloro-phenylmethanesulfonyl)-3-1-{[4-[2-(3-diethylamino-pyrrolidin-1-yl)-2-oxo-ethyl]-3,5-dimethyl-1H-pyrrol-2-yl}-meth-(Z)-ylidene]-1,3-dihydro-indol-2-one {2,4-Dimethyl-5-[2-oxo-5-phenylmethanesulfonyl-1,2-dihydro-indol-(3Z)-ylidenemethyl]-1H-pyrrol-3-yl}-acetic acid was coupled with to give the titled compound.

$^{1}$HNMR (400 MHz, DMSO-d$_{6}$) δ 13.46 (br s, 1H, NH), 11.27 (s, 1H, NH), 8.17 (s, 1H), 7.76 (s, 1H), 7.49 (s, 1H), 7.47 (s, 1H), 7.38 (m, 2H), 7.0 (d, J=8 Hz, 1H), 4.85 (s, 2H), 3.2–3.4 (m, 4H), 2.62 (m, 4H), 2.42 (m, 1H), 2.3 (s, 2H), 2.27 (s, 3H, CH$_{3}$), 2.24 (s, 3H, CH$_{3}$), 2.1 (m, 2H), 0.96 (m, 6H). MS m/z 641 [M−1].

Example 180

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide

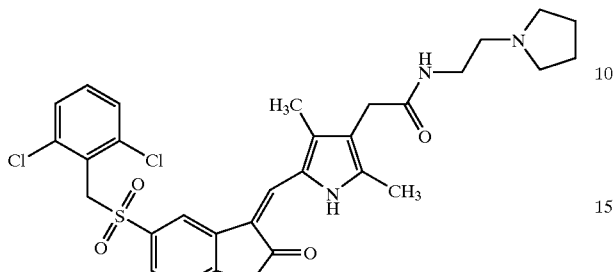

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with to give the titled compound.

$^1$HNMR (400 MHz, DMSO-d$_6$) δ 13.5 (br s, 1H, NH), 11.3 (s, 1H, NH), 8.18 (s, 1H), 8.05 (m, 1H, CONH), 7.77 (s, 1H), 7.49 (s, 1H), 7.47 (s, 1H), 7.38 (m, 2H), 7.01 (d, J=8 Hz, 1H), 4.87 (s, 2H), 3.3 (m, 2H), 3.06 (m, 4H), 3.0 (m, 2H), 2.43 (m, 2H), 2.32 (s, 3H, CH$_3$), 2.28 (s, 3H, CH$_3$), 1.84 (m, 4H). MS m/z 613 [M−1].

Example 181

Synthesis of 5-(2,6-Dichloro-phenylmethanesulfonyl)-3-[1-[3,5-dimethyl-4-((S)-2-morpholin-4-ylmethyl-pyrrolidine-1-carbonyl)-1H-pyrrol-2-yl]-meth-(Z)-ylidene]-1,3-dihydro-indol-2-one

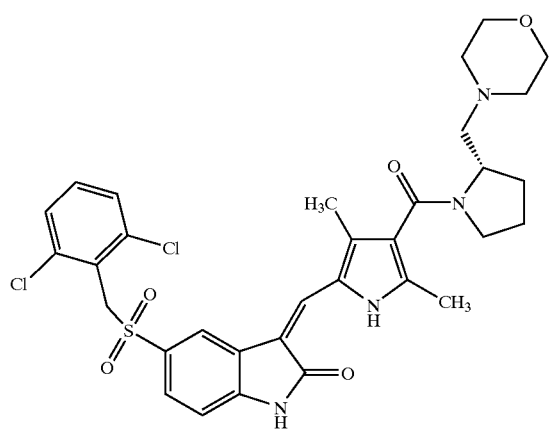

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), EDAC (80 mg, 0.41 mmol), HOBt (35 mg, 0.41 mmol) in DMF (5 mL) was added 4-(S)-1-pyrrolidin-2-ylmethyl-morpholine (70 mg, 0.41 mmol) and TEA (0.1 mL). The mixture was stirred at rt for 2 days. The reaction was concentrated and the residue was purified on a silica gel column to give 55 mg of the titled compound.

$^1$HNMR (400 MHz, DMSO-d$_6$) 13.32 (br s, 1H, NH), 8.72 (s, 1H), 7.83 (s, 1H), 7.51 (dd, 1H), 7.39 (s, 1H), 7.34 (d, 1H), 7.24 (t, 1H), 7.0 (d, 1H), 5.35 (s, 2H), 4.86 (s, 2H), 3.2–3.6 (m, 4H), 2.5–2.8 (m, 3H), 2.2–2.5 (m, 2H), 2.42 (s, 3H, CH$_3$), 2.28 (s, 3H, CH$_3$), 1.9–2.2 (m, 4H), 1.6–1.9 (m, 2H). MS m/z 655 [M−1].

Example 182

Synthesis of 5-(2,6-Dichloro-phenylmethanesulfonyl)-3-[1-[4-(2-{(S)-2-[(ethyl-propyl-amino)-methyl]-pyrrolidin-1-yl}-2-oxo-ethyl)-3,5-dimethyl-1H-pyrrol-2-yl]-meth-(Z)-ylidene]-1,3-dihydro-indol-2-one

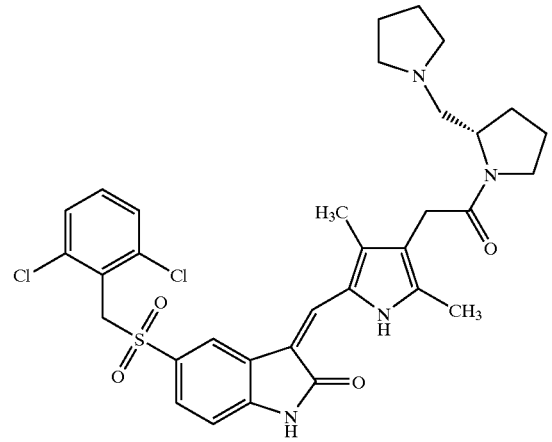

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with (S)-2-pyrrolidin-1-ylmethyl-pyrrolidine to give the titled compound.

$^1$HNMR (400 MHz, DMSO-d$_6$) δ 13.5 (br s, 1H, NH), 11.3 (s, 1H, NH), 8.18 (s, 1H), 7.77 (s, 1H), 7.49 (d, 1H), 7.47 (s, 1H), 7.38 (m, 2H), 7.01 (d, J=8 Hz, 1H), 4.85 (s, 2H), 4.2 (m, 2H), 3.6 (m, 2H), 3.49 (m, s, 2H), 3.3 (m, 2H), 3.12 (m, 2H), 2.43 (m, 1H), 2.28 (s, 3H, CH$_3$), 2.25 (s, 3H, CH$_3$), 1.9 (m, 4H), 1.87 (m, 4H). MS m/z 653 [M−1].

Example 183

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-morpholin-4-yl-propyl)-acetamide

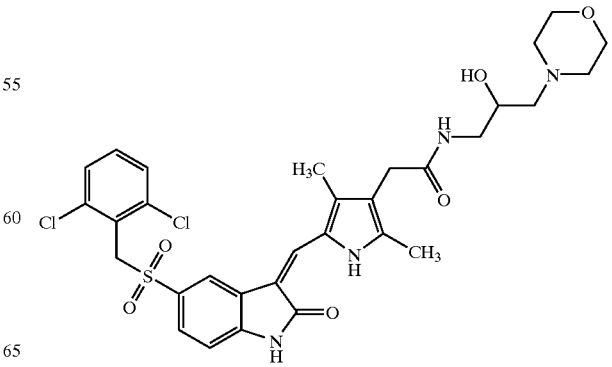

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with 1-amino-3-morpholin-4-yl-propan-2-ol to give the titled compound.

¹HNMR (400 MHz, DMSO-d₆) δ 13.5 (br s, 1H, NH), 11.3 (s, 1H, NH), 8.18 (s, 1H), 7.77 (s, 1H), 7.73 (m, 1H, CONH), 7.48 (s, 1H), 7.47 (s, 1H), 7.38 (m, 2H), 7.0 (d, J=8 Hz, 1H), 4.85 (s, 2H), 4.65 (m, 1H, OH), 3.65 (m, 1H), 3.52 (m, 4H), 3.3 (m, 4H), 3.35 (m, 4H), 2.31 (s, 3H, CH₃), 2.28 (s, 3H, CH₃), 2.2 (m, 2H). MS m/z 659 [M−1].

Example 184

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-[1,2,3]triazol-1-yl-propyl)-acetamide

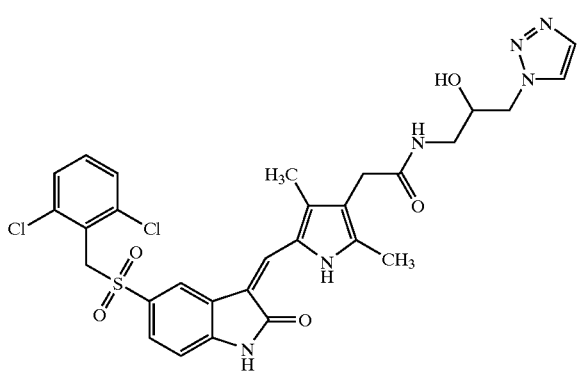

{2,4-Dimethyl-5-[2-oxo-5-phenylmethanesulfonyl-1,2-dihydro-indol-(3Z)-ylidenemethyl]-1H-pyrrol-3-yl}-acetic acid was coupled with 1-amino-3-[1,2,3]triazol-1-yl-propan-2-ol to give the titled compound.

¹HNMR (400 MHz, DMSO-d₆) δ 13.5 (br s, 1H, NH), 11.3 (s, 1H, NH), 8.17 (s, 1H), 8.03 (s, 1H), 7.96 (t, 1H, CONH), 7.70 (s, 1H), 7.69 (s, 1H), 7.48 (s, 1H), 7.46 (s, 1H), 7.39 (m, 2H), 7.0 (d, J=8 Hz, 1H), 5.33 (d, 1H, OH), 4.85 (s, 2H), 4.4 (m, 1H), 4.2 (m, 1H), 3.88 (m, 2H), 3.3 (m, 2H), 3.1 (m, 2H), 2.32 (s, 3H, CH₃), 2.29 (s, 3H, CH₃). MS m/z 641 [M−1].

Example 185

Synthesis of 5-(2,6-Dichloro-phenylmethanesulfonyl)-3-[1-[4-((R)-2-methoxymethyl-pyrrolidine-1-carbonyl)-3,5-dimethyl-1H-pyrrol-2-yl]-meth-(Z)-ylidene]-1,3-dihydro-indol-2-one

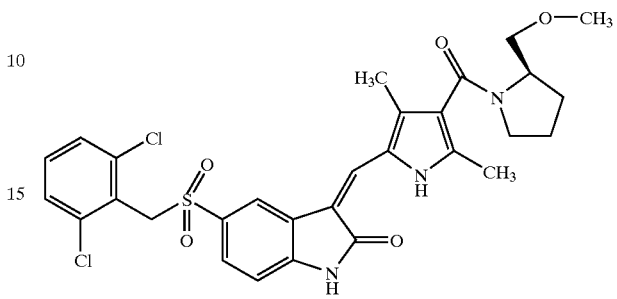

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) in DMF (5 mL) was added HOBt (32 mg, 1.2 eq.), EDAC.HCl (46 mg, 1.2 eq.) and TEA (50 mg, 2.5 eq.). After stirring at rt for 30 mins, to the mixture was added (S)-(+)-2-(methoxymethyl)pyrrolidine (46 mg, 2 eq.). After stirring at rt for overnight, the reaction was concentrated and the residue was purified on a silica gel column to give the titled compound.

¹HNMR (400 MHz, CDCl₃) δ 8.04 (s, 1H), 7.82 (s, 1H), 7.56 (d, 1H), 7.0–7.37 (m, 4H), 6.98 (d, 1H), 4.9 (s, 2H), 3.53 (m, 1H), 3.41 (m, 2H), 3.34 (s, 3H, OCH₃), 3.3 (m, 2H), 2.44 (s, 2H), 2.35 (s, 2H), 1.26 (s, 6H, 2×CH₃). MS m/z 600 [M−1].

Example 186.

Synthesis of 5-(2,6-Dichloro-phenylmethanesulfonyl)-3-[1-[4-((S)-2-methoxymethyl-pyrrolidine-1-carbonyl)-3,5-dimethyl-1H-pyrrol-2-yl]-meth-(Z)-ylidene]-1,3-dihydro-indol-2-one

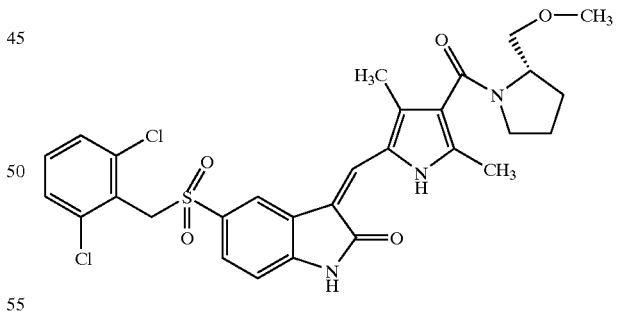

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) in DMF (5 mL) was added HOBt (32 mg, 1.2 eq.), EDAC.HCl (46 mg, 1.2 eq.) and TEA (50 mg, 2.5 eq.). After stirring at rt for 30 mins, to the mixture was added (R)-(-)-2-(methoxymethyl)pyrrolidine (46 mg, 2 eq.). After stirring at rt for overnight, the reaction was concentrated and the residue was purified on a silica gel column to give the titled compound.

MS m/z 600 [M−1].

Example 187

Synthesis of 5-(2,6-Dichloro-phenylmethanesulfonyl)-3-[1-[4-((R)-2-hydroxymethyl-pyrrolidine-1-carbonyl)-3,5-dimethyl-1H-pyrrol-2-yl]-meth-(Z)-ylidene]-1,3-dihydro-indol-2-one

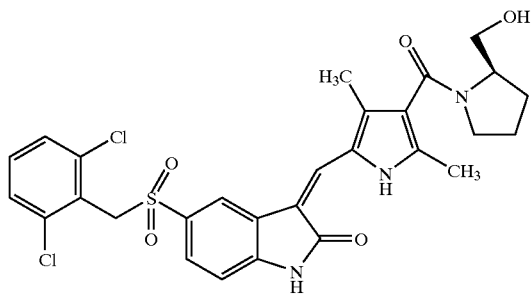

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) in DMF (5 mL) was added HOBt (32 mg, 1.2 eq.), EDAC.HCl (46 mg, 1.2 eq.) and TEA (50 mg, 2.5 eq.). After stirring at rt for 30 mins, to the mixture was added (S)-(+)-2-pyrrolidine methanol (2 eq.). After stirring at rt for overnight, the reaction was concentrated and the residue was purified on a silica gel column to give 52 mg of the titled compound.

$^1$HNMR (400 MHz, DMSO-$d_6$) 8.25 (s, 1H), 7.83 (s, 1H), 7.5 (m, 2H), 7.4 (m, 2H), 4.87 (s, 2H), 4.13 (m, 1H), 3.59 (m, 1H), 3.46 (m, 1H), 3.2 (m, 2H), 2.29 (s, 6H, 2×CH$_3$), 0.9 (m, 4H). MS m/z 586 [M−1].

Example 188

Synthesis of 5-(2,6-Dichloro-phenylmethanesulfonyl)-3-[1-[4-((S)-2-hydroxymethyl-pyrrolidine-1-carbonyl)-3,5-dimethyl-1H-pyrrol-2-yl]-meth-(Z)-ylidene]-1,3-dihydro-indol-2-one

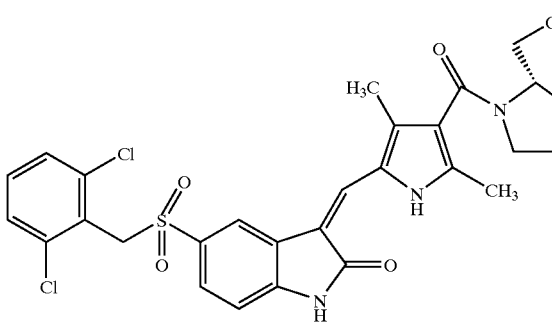

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) in DMF (5 mL) was added HOBt (32 mg, 1.2 eq.), EDAC.HCl (46 mg, 1.2 eq.) and TEA (50 mg, 2.5 eq.). After stirring at rt for 30 mins, to the mixture was added (R)-(−)-2-pyrrolidine methanol (2 eq.). After stirring at rt for overnight, the reaction was concentrated and the residue was purified on a silica gel column to give 54 mg of the titled compound as an orange solid.

MS m/z 586 [M−1].

Example 189

Synthesis of 5-(2,6-Dichloro-phenylmethanesulfonyl)-3-[1-{4-[(S)-2-(4-hydroxy-piperidin-1-ylmethyl)-pyrrolidine-1-carbonyl]-3,5-dimethyl-1H-pyrrol-2-yl}-meth-(Z)-ylidene]-1,3-dihydro-indol-2-one

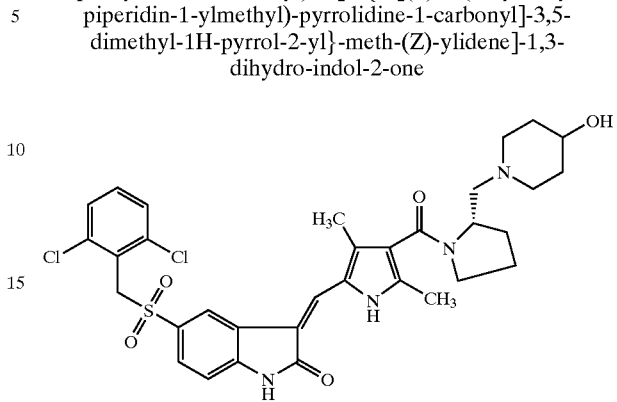

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (111 mg, 0.22 mmol), 1-(S)-1-pyrrolidin-2-ylmethyl-piperidin-4-ol (78 mg, 0.46 mmol), HOBt (46 mg, 0.34 mmol), EDAC (68 mg, 0.36 mmol) and TEA (0.068 mL, 0.44 mL) in DMF (2 mL) was stirred at rt for 48 hours. The reaction was concentrated, diluted with sat. sodium bicarbonate and extracted with DCM. The organic layer was washed with brine, dried and purified on a silica gel column to give 91 mg (62%) of the titled compound.

$^1$HNMR (400 MHz, DMSO-$d_6$) δ 13.53 (br s, 1H, NH), 11.41 (s, 1H, NH), 8.27 (d, 1H), 7.85 (s, 1H), 7.51 (s, 1H), 7.49 (s, 1H), 7.42 (m, 2H), 7.04 (d, J=8 Hz, 1H), 4.87 (s, 2H), 4.3–4.5 (m, 2H), 3.5 (m, 2H), 3,28 (m, 2H), 2.7–2.9 (m, 2H), 2.32 (s, 3H, CH$_3$), 2.31 (s, 3H, CH$_3$), 2.3 (m, 2H), 1.6–2.0 (m, 5H), 1.2–1.6 (m, 4H). MS m/z 669 [M−1].

Example 190

Synthesis of 5-(2,6-Dichloro-phenylmethanesulfonyl)-3-[1-[4-(4-hydroxy-piperidin-1-ylmethyl)-3,5-dimethyl-1H-pyrrol-2-yl]-meth-(Z)-ylidene]-1,3-dihydro-indol-2-one

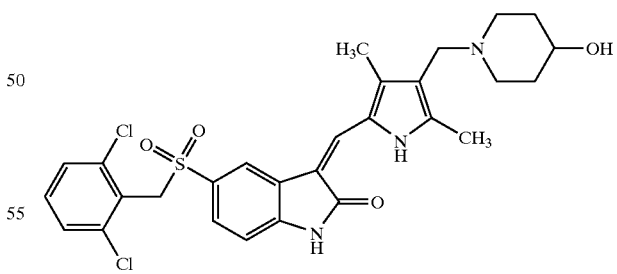

A mixture of 5-(2,6-dichloro-phenylmethanesulfonyl)-1,3-dihydro-indol-2-one (150 mg, 0.42 mmol), 4-(4-hydroxy-piperidin-1-ylmethyl)-3,5-dimethyl-1H-pyrrole-2-carbaldehyde (99 mg, 1 eq.) and piperidine (0.5 eq.) in ethanol (2 mL) was stirred at rt for days. The reaction was concentrated and the residue was purified on a silica gel column to give the titled compound as a pale greenish-brown solid.

¹HNMR (400 MHz, DMSO-d₆) δ 13.5 (s, 1H, NH), 11.32 (s, 1H, NH), 8.22 (br s, 1H), 7.8 (br s, 1H), 7.49 (s, 1H), 7.47 (s, 1H), 7.39 (m, 2H), 7.0 (d, J=8 Hz, 1H), 4.85 (s, 2H), 3.4 (m, 1H), 3.3 (m, 2H), 3.15 (m, 1H), 2.5 (m, 2H), 2.34 (s, 6H, 2×CH₃), 2.3–2.5 (m, 2H), 1.7 (m, 2H), 1.35 (m, 2H). MS m/z 572 [M−1].

Example 191

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Methoxy-ethyl)-amide

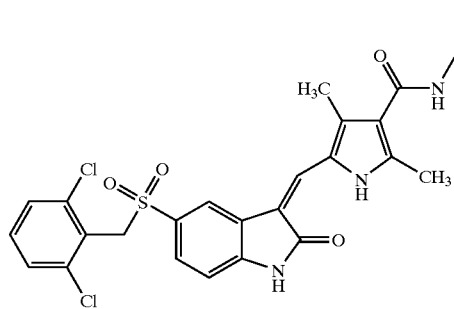

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-methoxy-ethylamine (35 mg, 1.1 eq.) in DMF (2 mL) was added TEA (0.066 mL, 2.5 eq.). After stirring at rt for 8 days, the reaction was concentrated, diluted with DCM, washed with sat. NaHCO₃ and water, concentrated and purified on a silica gel column to give the titled compound as a pale yellow solid.

¹HNMR (400 MHz, DMSO-d₆) δ 13.58 (br s, 1H, NH), 11.4 (s, 1H, NH), 8.27 (d, 1H), 7.86 (s, 1H), 7.69 (t, 1H, CONH), 7.49 (d, 1H), 7.47 (s, 1H), 7.4 (m, 2H), 7.0 (d, J=8 Hz, 1H), 4.86 (s, 2H), 3.43 (m, 2H), 3.38 (m, 2H), 3.27 (s, 3H, CH₃), 2.43 (s, 3H, CH₃), 2.42 (s, 3H, CH₃). MS m/z 562 [M+1].

Example 192

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-Methoxy-propyl)-amide

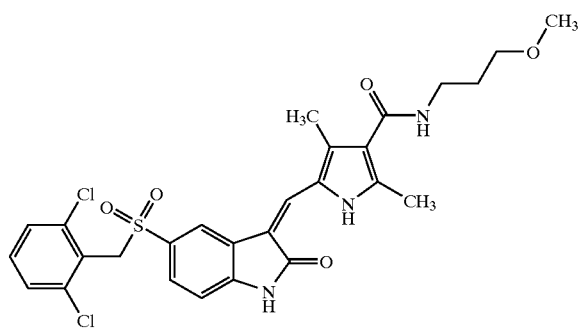

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 3-methoxy-propylamine (42 mg, 1.1 eq.) in DMF (2 mL) was added TEA (0.066 mL, 2.5 eq.). After stirring at rt for 10 days, the reaction was concentrated, diluted with DCM, washed with sat. NaHCO₃ and water, concentrated and purified on a silica gel column to give the titled compound as a pale orange waxy solid.

¹HNMR (400 MHz, DMSO-d₆) δ 13.59 (s, 1H, NH), 11.4 (s, 1H, NH), 8.27 (d, 1H), 7.86 (s, 1H), 7.67 (t, 1H, CONH), 7.49 (s, 1H), 7.47 (s, 1H), 7.4 (m, 2H), 7.02 (d, J=8 Hz, 1H), 4.86 (s, 2H), 3.38 (t, 2H), 3.25 (m, 2H), 3.23 (s, 3H, OCH₃), 2.43 (s, 6H, 2×CH₃), 1.73 (m, 2H). MS m/z 574 [M−1].

Example 193

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(2-Hydroxy-ethoxy)-ethyl]-amide

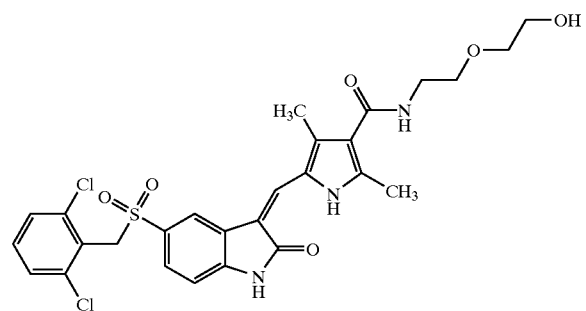

To a mixture of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-(2-amino-ethoxy)-ethanol (49 mg, 1.1 eq.) in DMF (2 mL) was added TEA (0.066 mL, 2.5 eq.). After stirring at rt for 7 days, the reaction was concentrated, diluted with DCM and then added solid sodium bicarbonate. After stirring at rt for 15 mins, the resulted suspension was loaded onto a silica gel column to give the titled compound as a yellow solid.

¹HNMR (400 MHz, DMSO-d₆) δ 13.58 (br s, 1H, NH), 11.4 (s, 1H, NH), 8.28 (d, 1H), 7.86 (s, 1H), 7.67 (t, 1H, CONH), 7.49 (d, 1H), 7.47 (s, 1H), 7.4 (m, 2H), 7.02 (d, J=8 Hz, 1H), 4.86 (s, 2H), 4.6 (t, 1H, OH), 3.51 (m, 4H), 3.45 (m, 2H), 3.37 (m, 2H), 2.43 (s, 6H, 2×CH₃). MS m/z 590 [M−1].

Example 194

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Hydroxy-1-hydroxymethyl-1-methyl-ethyl)-amide

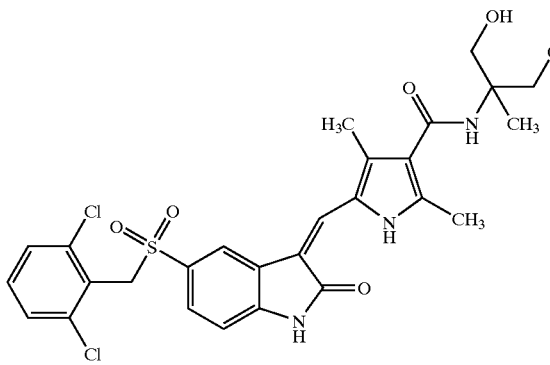

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-amino-2-methyl-propane-1,3-diol (49 mg, 1.1 eq.) in DMF (2 mL) was added TEA (0.066 mL, 2.5 eq.). After stirring at rt for 8 days, the reaction was concentrated, diluted with DCM and then added solid sodium bicarbonate. After stirring at rt for 15 mins, the resulted suspension was loaded onto a silica gel column to give the titled compound as a yellow solid.

$^1$HNMR (400 MHz, DMSO-d$_6$) δ 13.6 (br s, 1H, NH), 11.41 (s, 1H, NH), 8.27 (d, 1H), 7.86 (s, 1H), 7.49 (s, 1H), 7.47 (s, 1H), 7.4 (m, 2H), 7.02 (d, J=8 Hz, 1H), 6.89 (s, 1H, CONH), 4.92 (t, 2H, 2xOH), 4.86 (s, 2H), 3.57 (m, 2H), 3.51 (m, 2H), 2.44 (s, 6H, 2xCH$_3$), 1.24 (s, 3H, CH$_3$). MS m/z 590 [M−1].

Example 195

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Hydroxy-1,1-bis-hydroxymethyl-ethyl)-amide

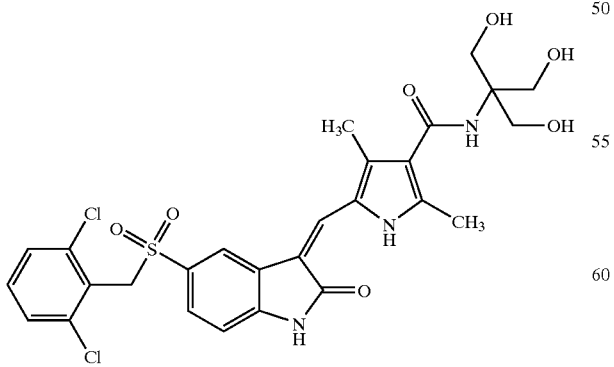

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-amino-2-hydroxymethyl-propane-1,3-diol (58 mg, 1.1 eq.) in DMF (2 mL) was added TEA (0.066 mL, 2.5 eq.). After stirring at rt for 9 days, the reaction was concentrated, diluted with DCM and then added solid sodium bicarbonate. After stirring at rt for 15 mins, the resulted suspension was loaded onto a silica gel column to give the titled compound as an orange solid.

$^1$HNMR (400 MHz, DMSO-d$_6$) δ 13.63 (br s, 1H, NH), 11.42 (s, 1H, NH), 8.28 (s, 1H), 7.88 (s, 1H), 7.49 (d, 1H), 7.47 (s, 1H), 7.42 (m, 2H), 7.03 (d, J=8 Hz, 1H), 6.8 (s, 1H), 4.9 (t, 3H, 3xOH), 4.86 (s, 2H), 3.63 (d, 6H) 2.47 (s, 3H, CH$_3$), 2.46 (s, 3H), CH$_3$). MS m/z 606 [M−1].

Example 196

Synthesis of 5-(2,6-Dimethyl-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one

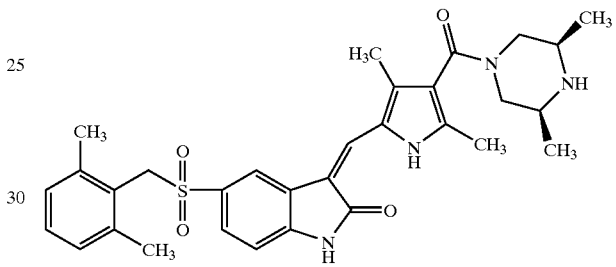

A mixture of 5-[5-(2,6-dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.26 mmol), (2R,6S)-2,6-dimethyl-piperazine (37 mg, 1.2 eq.), HOBt (50 mg, 1.2 eq.), EDAC.HCl (1.2 eq.) and TEA (3 eq.) in DMF (0.2 M) was stirred at rt for overnight. The reaction was concentrated, diluted with DCM, washed with water, filtered and concentrated to give the titled compound.

MS m/z 559 [M−1].

Example 197

Synthesis of 5-(2,6-Dimethyl-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one

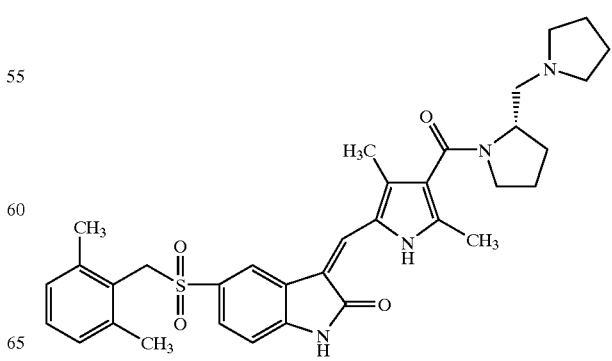

5-[5-(2,6-Dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.26 mmol) was coupled with (S)-2-pyrrolidin-1-ylmethyl-pyrrolidine (50 mg, 1.2 eq.), HOBt (42 mg, 1.2 eq.), EDAC.HCl (60 mg, 1.2 eq.) and TEA (3 eq.) in acetonitrile: DMF (3:1) to give the titled compound.

MS m/z 599 [M−1].

Example 198

Synthesis of 5-(2,6-Dimethyl-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

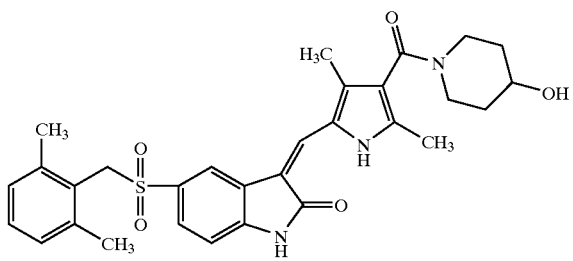

A mixture of 5-[5-(2,6-dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.26 mmol), piperidin-4-ol (1.2 eq.), HOBt (1.21 eq.), EDAC.HCl (1.2 eq.) and TEA (3 eq.) in DMF (0.2 M) was stirred at rt for overnight. The reaction was concentrated, diluted with DCM, washed with water, dried and concentrated. The residue was triturated with ethyl ether to give the titled compound.

$^1$HNMR (400 MHz, DMSO-d$_6$) δ 13.56 (br s, 1H, NH), 11.4 (s, 1H, NH), 8.25 (d, 1H), 7.84 (s, 1H), 7.5 (dd, 1H), 7.11 (m, 1H), 7.03 (m, 3H), 4.78 (d, 1H, OH), 4.63 (s, 2H), 3.7 (m, 1H), 3.12 (m, 4H), 2.29 (m, 6H, 2×CH$_3$), 2.25 (s, 6H, 2×CH$_3$), 1.3 (m, 4H). MS m/z 546 [M−1].

Example 199

Synthesis of 5-(2,6-Dimethyl-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

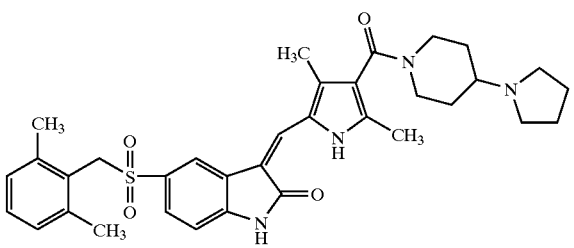

A mixture of 5-[5-(2,6-dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.2 mmol), 4-pyrrolidin-1-yl-piperidine (1.2 eq.), HOBt (1.2 eq.), EDAC.HCl (1.2 eq.) and TEA (3 eq.) in DMF (0.2 M) was stirred at rt for overnight. The reaction was concentrated, diluted with DCM, washed with water, dried and concentrated. The residue was triturated with ethyl ether to give the titled compound.

$^1$HNMR (400 MHz, DMSO-d$_6$) 13.56 (br s, 1H, NH), 11.4 (s, 1H, NH), 8.25 (d, 1H), 7.84 (s, 1H), 7.5 (dd, 1H), 7.11 (m, 1H), 7.03 (m, 3H), 4.63 (s, 2H), 3.2 (m, 2H), 3.0 (m, 4H), 2.65 (m, 3H), 2.3 (m, 6H, 2×CH$_3$), 2.25 (s, 6H, 2×CH$_3$), 1.9 (m, 2H), 1.7 (m, 4H), 1.3 (m, 2H). MS m/z 599 [M−1].

Example 200

Synthesis of 3-[1-[3,5-Dimethyl-4-(4-methyl-piperazine-1-carbonyl)-1H-pyrrol-2-yl]-meth-(Z)-ylidene]-5-(2,6-dimethyl-phenylmethanesulfonyl)-1,3-dihydro-indol-2-one

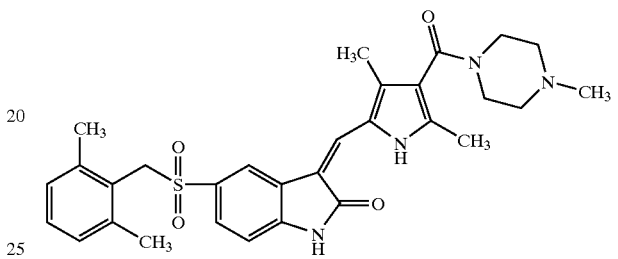

A mixture of 5-[5-(2,6-dimethyl-phenylmethanesulfonyl)-2-oxo-1,2-dihydro-indol-(3Z)-ylidenemethyl]-2,4-dimethyl-1H-pyrrole-3-carboxylic acid (120 mg, 0.26 mmol), 1-methyl-piperazine (1.2 eq.), HOBt (1.2 eq.), EDAC.HCl (1.2 eq.) and TEA (3 eq.) in DMF (0.2 M) was stirred at rt for overnight. The reaction was concentrated, diluted with DCM, washed with water, dried and concentrated. The residue was triturated with ethyl ether to give the titled compound.

$^1$HNMR (400 MHz, DMSO-d$_6$) δ 13.56 (br s, 1H, NH), 11.42 (s, 1H, NH), 8.25 (s, 1H), 7.84 (s, 1H), 7.5 (dd, 1H), 7.11 (m, 1H), 7.03 (m, 3H), 4.63 (s, 2H), 3.5 (m, 4H), 2.3 (m, 4H), 23 (s, 6H, 2×CH$_3$), 2.25 (s, 6H, 2×CH$_3$), 2.21 (s, 3H, CH$_3$). MS m/z 545 [M−1].

Example 201

Synthesis of 5-(2,6-Dichloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one

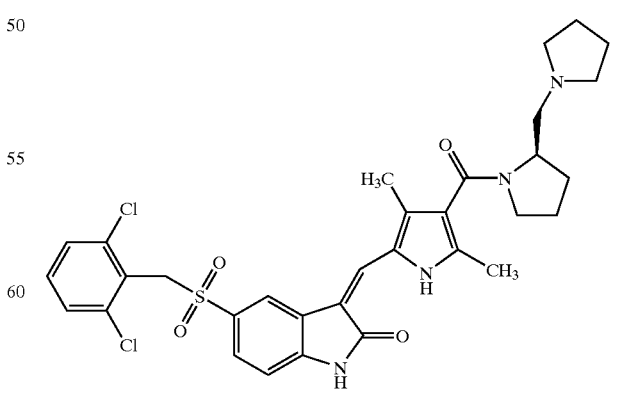

A mixture of (+)-carbobenzyloxy-D-proline (1.5 g, 6 mmol), EDAC (2.3 g, 12 mmol), HOBt (800 mg, 6 mmol), TEA (1.5 mL) and pyrrolidine (853 mg, 12 mmol) in DMF (20 mL) was stirred at rt for 18 hours. The reaction was diluted with water and sodium bicarbonate, extracted with DCM (3×). The combined DCM was concentrated and purified on a silica gel column to give (R)-2-(pyrrolidine-1-carbonyl)-pyrrolidine-1-carboxylic acid benzyl ester.

(R)-2-(pyrrolidine-1-carbonyl)-pyrrolidine-1-carboxylic acid benzyl ester was hydrogenated using Pd/C in methanol at rt for 20 hours to give pyrrolidin-1-yl-(R)-pyrrolidin-2-yl-methanone.

To a solution of pyrrolidin-1-yl-(R)-pyrrolidin-2-yl-methanone (1.2 g, 7.1 mmol) in THF (10 mL) at 0° C. was added $BH_3$ (10 mL, 10 mmol). The mixture was heated to reflux for 16 hours. The reaction was acidified with HCl and concentrated. The residue was basified to pH 10 with 2N NaOH and extracted with 5% methanol in DCM. The organic layer was concentrated and purified on a silica gel column to give 800 mg (73%) of (R)-2-pyrrolidin-1-ylmethyl-pyrrolidine.

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), EDAC (80 mg, 0.41 mmol), HOBt (35 mg, 0.41 mmol), TEA (0.1 mL) and (R)-2-pyrrolidin-1-ylmethyl-pyrrolidine (0.5 mL) in DMF (4 mL) was stirred at rt for overnight. The reaction was diluted with water and sodium bicarbonate, extracted with ethyl acetate. The organic layer was concentrated and purified on a silica gel column to give the titled compound.

$^1$HNMR (400 MHz, DMSO $d_6$) 13.65 (s, 1H), 11.42 (s, 1H), 8.28 (s, 1H), 7.88 (s, 1H), 7.36–7.52 (m, 4H), 7.04 (d, 1H), 4.84 (s, 2H, $CH_2$), 2.34 (s, 6H, 2×$CH_3$), 1.4–4.5 (m, aliphatic H). MS m/z 641 ($M^+$+1).

Example 202

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-morpholin-4-yl-ethyl)-amide

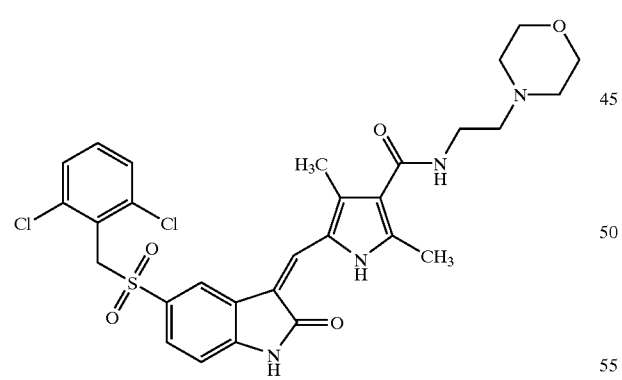

To a mixture of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-morpholin-4-yl-ethylamine (62 mg, 2.5 eq.) in DMF (2 mL) was added TEA (0.066 mL, 2.5 eq.). After stirring at rt for 6 days, the reaction was concentrated, diluted with DCM, washed with sat. $NaHCO_3$ and water, dried, concentrated and purified on a silica gel column to give the titled compound as a pale yellow waxy solid.

$^1$HNMR (400 MHz, DMSO-$d_6$) δ 13.6 (br s, 1H, NH), 11.41 (s, 1H, NH), 8.29 (d, 1H), 7.87 (s, 1H), 7.54 (m, 1H, CONH), 7.49 (d, 1H), 7.47 (s, 1H), 7.4 (m, 2H), 7.02 (d, J=8 Hz, 1H), 4.86 (s, 2H), 3.57 (m, 4H), 3.34 (m, 2H), 2.45 (s, 6H, 2×$CH_3$), 2.38–2.48 (m, 4H). MS m/z 615 [M–1].

Example 203

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-Morpholin-4-yl-propyl)-amide

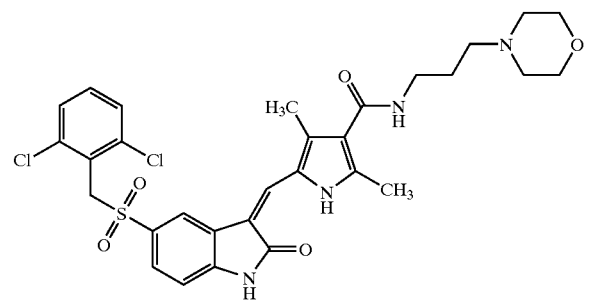

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), HOBt (31 mg, 1.2 eq.), EDAC.HCl (44 mg, 1.2 eq.) and 2-morpholin-4-yl-propylamine (69 mg, 2.5 eq.) in DMF (2 mL) was added TEA (0.066 mL, 2.5 eq.). After stirring at rt for 6 days, the reaction was concentrated, diluted with DCM, washed with sat. $NaHCO_3$ and water, dried, concentrated and purified on a silica gel column to give the titled compound as a pale yellow solid.

$^1$HNMR (400 MHz, DMSO-$d_6$) δ 13.59 (br s, 1H, NH), 11.4 (s, 1H, NH), 8.28 (d, 1H), 7.86 (s, 1H), 7.7 (br s, 1H, CONH), 7.49 (d, 1H), 7.47 (s, 1H), 7.4 (m, 2H), 7.02 (d, J=8 Hz, 1H), 4.86 (s, 2H), 3.56 (br s, 4H), 3.23 (m, 2H), 2.43 (s, 6H, 2×$CH_3$), 2.33 (m, 6H), 1.67 (m, 2H). MS m/z 629 [M–1].

Example 204

Synthesis of 3-[1-[4-((S)-2-Cyclopropylaminomethyl-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

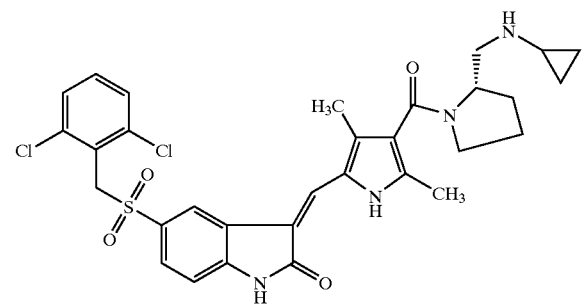

A mixture of carbobenzyloxy-L-proline (994 mg, 3.99 mmol), cyclopropylamine (0.41 mL, 5.9 mmol), HOBt (807 mg, 6 mmol), EDC (1.12 g, 5.9 mmol) and TEA (1.1 mL) in DMF (11 mL) was stirred at room temperature for 48 hours. The reaction was quenched with saturated sodium bicarbonate and extracted with dichloromethane. The organic layers were washed with brine, dried over sodium sulfate and concentrated. The residue was column chromatographed to give 985 mg (81%) of (S)-2-cyclopropylcarbamoyl-pyrrolidine-1-carboxylic acid benzyl ester.

(S)-2-cyclopropylcarbamoyl-pyrrolidine-1-carboxylic acid benzyl ester (907 mg, 3.14 mmol) was hydrogenated using Pd/C (5%, 61 mg) to give (S)-pyrrolidine-2-carboxylic acid cyclopropylamide.

To a solution of (S)-pyrrolidine-2-carboxylic acid cyclopropylamide (3.4 mmol) in THF (5 mL) at 0° C. was added $BH_3$ (6.3 mL, 1 M in THF) dropwise. It was then warmed to room temperature and heated to reflux for 20 hours. The cooled reaction was acidified with 3M HCl (2.5 mL) and stirred at 75° C. for 10 minutes. The reaction was concentrated and the residue was basified with 2M NaOH. It was then extracted with 10% of methanol in dichloromethane. The organic layer was dried and concentrated to give a yellow oil of cyclopropyl-(S)-1-pyrrolidine-2-ylmethyl-amine.

5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (167 mg, 0.33 mmol) was condensed with cyclopropyl-(S)-1-pyrrolidine-2-ylmethyl-amine (69 mg, 0.49 mmol) to give 152 mg (72%) of the titled compound.

$^1$HNMR (400 MHz, DMSO $d_6$) δ 13.52 (s, 1H, NH), 11.39 (s, 1H, NH), 8.26 (d, 1H), 7.85 (s, 1H), 7.37–7.50 (m, 4H), 7.03 (d, 1H), 4.87 (s, 2H, $CH_2$), 4.23 (m, 1H), 3.70 (m, 1H), 3.48 (m, 1H), 3.31 (m, 2H), 2.95 (m, 1H), 2.61 (m, 1H), 2.32 (s, 6H, 2×$CH_3$), 2.14 (m, 1H), 1.8–2.0 (m, 4H), 0.39 (m, 1H), 0.22 (m, 1H). MS m/z 627 ($M^+$+1).

Example 205

Synthesis of 5-(2,6-Dichloro-phenylmethanesulfonyl)-3-[1-[3,5-dimethyl-4-(4-morpholin-4-yl-piperidine-1-carbonyl)-1H-pyrrol-2-yl]-meth-(Z)-ylidene]-1,3-dihydro-indol-2-one

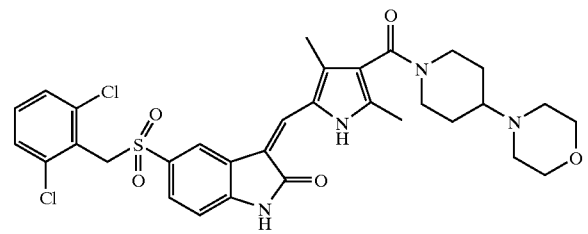

To a stirred mixture of 4-amino-1-benzylpiperidine (1.53 mL, 7.5 mmol), $K_2CO_3$ (2.28g, 16.5 mmol) and DMF (15 mL) heated at 50° C. was added dropwise over 60 min bis(2-bromoethyl) ether (0.96 mL, 7.65 mmol). After stirring for 6 hours at 80° C., the solvent was removed by blowing with a stream of nitrogen over 2 hours. The residue was purified on a silica gel column to give 1.7 g (87%) of 4-(1-benzyl-piperidin-4-yl)-morpholine as a waxy solid.

$^1$H NMR (400 MHz, DMSO-$d_6$) δ 7.31 (m, 4H), 7.26 (m, 1H), 3.72 (t, 4H), 3.49 (s, 2H), 2.94 (br d, 2H), 2.54 (t, 4H), 2.19 (tt, 1H), 1.96 (td, 2H), 1.78 (br d, 2H), 1.55 (m, 2H).

4-(1-benzyl-piperidin-4-yl)-morpholine (1.56 g, 6.0 mmol) was hydrogenated using Pd(OH)$_2$ (20% on carbon, 390 mg, 25 wt%), 1.7 M HCl (10.6 mL) in methanol (50 mL) at 50° C. for 10 hours. The resulted amine dihydrochloride off-white solid was subjected to free-basing using excess basic resin to give 932 mg (91%) of 4-piperidin-4-yl-morpholine as waxy crystalline solid.

$^1$H NMR (400 MHz, DMSO-$d_6$) δ 3.53 (br s, 4H), 3.30 (v br s, 1H), 2.92 (br d, 1H), 2.41 (s, 4H), 2.35 (m, 2H), 2.12 (br t, 1H), 1.65 (br d, 2H), 1.18 (br q, 2H). MS m/z 171 [$M^+$+1].

5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (1 eq.) and BOP (1.25 eq.) were suspended in DMF (5 mL) at rt and TEA (2.4 eq.) was added. After 15 mins, to the homogenous reaction mixture was added 4-piperidin-4-yl-morpholine (1.25 eq.) all at once. After stirring for 2 days, the reaction was added to a mixture of chloroform-isopropanol (5:1) and 5% aq. LiCl. The organic layer was separated, washed with 5% aq. LiCl (2×), 1 M aq. NaOH (3×), brine, dried and concentrated. The residue was purified to give the titled compound;

$^1$HNMR (400 MHz, DMSO $d_6$) δ 13.53 (br s, 1H, NH), 11.38 (s, 1H, NH), 8.2 (d, J=2 Hz, 1H), 7.84 (s, 1H), 7.47 (d, J=8 Hz, 1H), 7.41 (d, J=2 & 8 Hz, 1H), 7.37 (dd, 1H), 7.02 (d, J=8 Hz, 1H), 4.85 (s, 2H), 3.54 (br s, 4H), 3.32 (s, 6H), 2.43 (br s, 4H), 2.35 (m, 1H), 2.28 (m, 6H), 1.8 (br s, 2H), 1.23 (br s, 2H).

Example 206

Synthesis of 5-(2,6-Dichloro-phenylmethanesulfonyl)-3-[1-{3,5-dimethyl-4-[2-(4-morpholin-4-yl-piperidin-1-yl)-2-oxo-ethyl]-1H-pyrrol-2-yl}-meth-(Z)-ylidene]-1,3-dihydro-indol-2-one

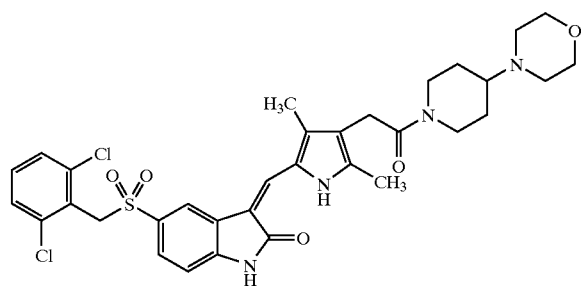

{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (1 eq.) and BOP (1.25 eq.) were suspended in DMF (5 mL) at rt and TEA (2.4 eq.) was added. After 15 mins, to the homogenous reaction mixture was added 4-piperidin-4-yl-morpholine (1.25 eq.) all at once. After stirring for 2 days, the reaction was added to a mixture of chloroform-isopropanol (5:1) and 5% aq. LiCl. The organic layer was separated, washed with 5% aq. LiCl (2×), 1 M aq. NaOH (3×), brine, dried and concentrated. The residue was purified to give the titled compound.

Example 207

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-ethylsulfanyl-ethyl)-amide

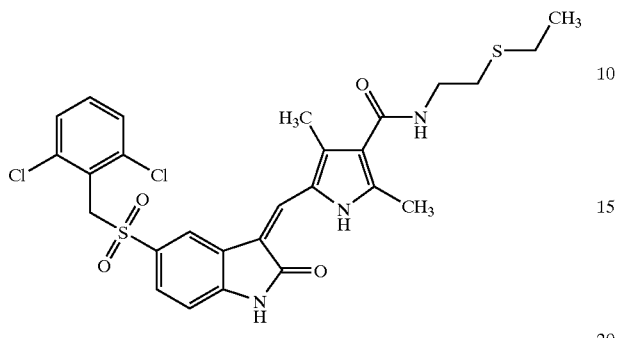

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), HOBt (32 mg, 1.2 eq.), EDAC.HCl (45 mg, 1.2 eq.), TEA (0.138 mL, 5 eq.) and 2-ethylsulfanyl-ethylamine hydrochloride salt (69 mg, 2.5 eq.) in DMF (2 mL) was stirred at rt for 7 days. The reaction was concentrated, diluted with DCM, washed with sat. NaHCO$_3$ and water, dried, concentrated and purified on a silica gel column to give the titled compound as a yellow waxy solid.

$^1$HNMR (400 MHz, DMSO-d$_6$) δ 13.59 (br s, 1H, NH), 11.4 (s, 1H, NH), 8.27 (s, 1H), 7.86 (s, 1H), 7.77 (t, 1H, CONH), 7.49 (s, 1H), 7.47 (s, 1H), 7.4 (m, 2), 7.02 (d, J=8 Hz, 1H), 4.86 (s, 2H), 3.38 (m, 2H), 2.66 (t, 2H), 2.55 (q, 2H), 2.44 (s, 6H, 2×CH$_3$), 1.17 (t, 3H). MS m/z 590 [M−1].

Example 208

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2,2,2-Trifluoro-ethyl)-amide

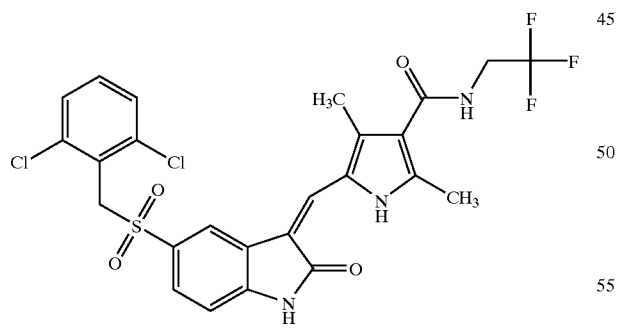

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), HOBt (32 mg, 1.2 eq.), EDAC.HCl (45 mg, 1.2 eq.), TEA (0.068 mL, 2.5 eq.) and 2,2,2-trifluoro-ethylamine (48 mg, 2.5 eq.) in DMF (2 mL) was stirred at rt for 7 days. The reaction was concentrated, diluted with DCM, washed with sat. NaHCO$_3$ and water, dried, concentrated and triturated with methanol to give the titled compound as a yellow solid.

$^1$HNMR (400 MHz, DMSO-d$_6$) 13.64 (br s, 1H, NH), 11.43 (s, 1H, NH), 8.32 (t, 1H, CONH), 8.29 (d, 1H), 7.88 (s, 1H), 7.49 (s, 1H), 7.47 (s, 1H), 7.4 (m, 2H), 7.03 (d, J=8 Hz, 1H), 4.86 (s, 2H), 4.04 (m, 2H), 2.44 (s, 3H, CH$_3$), 2.43 (s, 3H, CH$_3$). MS m/z 584 [M−1].

Example 209

Synthesis of 3-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-propionic acid

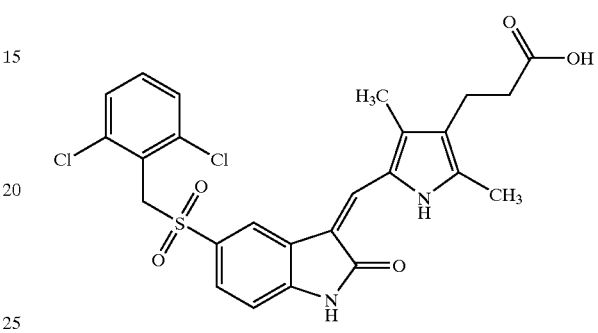

A mixture of 5-(2,6-dichloro-phenylmethanesulfonyl)-1,3-dihydro-indol-2-one(1 g, 2.82 mmol), 3-(5-formyl-2,4-dimethyl-1H-pyrrol-3-yl)-propionic acid (548 mg, 1 eq.) and piperidine (0.416 mL, 1.5 eq.) in ethanol (5 mL) was stirred at rt for 5 days. The reaction was concentrated, acidified with 2M HCl (pH 3), stirred for 15 mins, diluted with water and filtered. The solid was washed with water and triturated with ethanol to give the titled compound as a pale orange solid.

$^1$HNMR (400 MHz, DMSO-d$_6$) δ 13.43 (br s, 1H, NH), 12.08 (vbr s, 1H, COOH), 11.26 (s, 1H, NH), 8.18 (s, 1H), 7.75 (s, 1H), 7.48 (s, 1H), 7.47 (s, 1H), 7.39 (m, 2H), 7.0 (d, J=8 Hz, 1H), 4.85 (s, 2H), 2.64 (t, 2H), 2.35 (t, 2H), 2.31 (s, 3H, CH$_3$), 2.29 (s, 3H, CH$_3$). MS m/z 531 [M−1].

Example 210

Synthesis of 3-[1-(4-{(S)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one

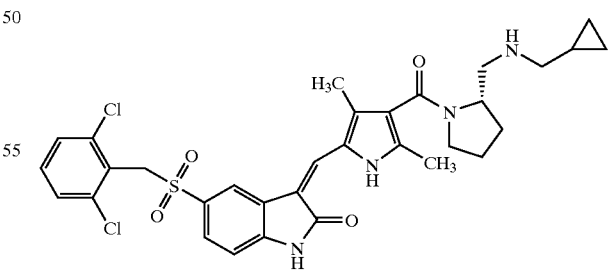

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), EDAC (76 mg), HOBt (27 mg) in DMF (4 mL) was added cyclopropylmethyl-(S)-1-pyrrolidin-2-ylmethyl-amine (0.05 mL) and TEA (0.08 mL). The mixture was stirred at rt for 2 days. The reaction was concentrated and the residue was purified on a silica gel column to give the titled compound.

$^1$HNMR (400 MHz, DMSO-$d_6$) δ 13.25 (br s, 1H, NH), 7.81 (s, 1H), 7.54 (dd, 1H), 7.18–7.32 (m, 4H), 6.97 (d, 1H), 4.88 (s, 2H), 4.45 (m, 1H, NH), 3.1 (m, 1H), 2.6–2.7 (m, 2H), 2.42 (s, 3H, CH$_3$), 2.32 (s, 3H, CH$_3$), 2.23 (m, 2H), 1.8–2.0 (m, 6H), 1.05 (m, 1H), 0.54 (m, 2H), 0.2 (m, 2H). MS m/z 639 [M−1].

Example 211

Synthesis of 5-(2,3-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one

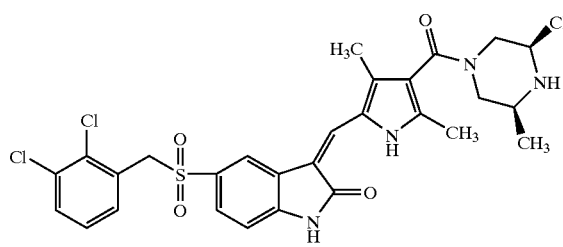

5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid (110 mg, 0.22 mmol) was coupled with (2S,6R)-2,6-dimethyl-piperazine (31 mg, 1.2 eq.) using HOBt (1.2 eq.), EDAC.HCl (1.2 eq.) and TEA (3 eq.) in DMSO. The reaction was concentrated and purified on a silica gel column to give the titled compound.

$^1$HNMR (400 MHz, DMSO-$d_6$) δ 13.56 (br s, 1H, NH), 11.4 (br s, 1H, NH), 8.17 (s, 1H), 7.82 (s, 1H), 7.60 (dd, 1H), 7.3–7.4 (m, 3H), 7.01 (d, J=8 Hz, 1H), 4.80 (s, 2H), 4.2 (m, 1H), 3.4 (m, 1H), 2.65 (m, 2H), 2.31 (m, 3H, CH$_3$), 2.3 (m, 2H), 2.29 (m, 3h, CH$_3$), 0.95 (m, 6H, 2×CH$_3$). MS m/z 601 [M+1].

Example 212

Synthesis of 5-(2,3-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one

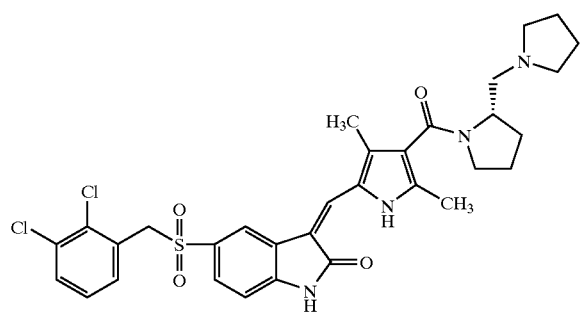

5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid (110 mg, 0.22 mmol) was coupled with (S)-2-pyrrolidin-1-ylmethyl-pyrrolidine (41 mg, 1.2 eq.) using HOBt (1.2 eq.), EDAC.HCl (1.2 eq.) and TEA (3 eq.) to give the titled compound. MS m/z 639 [M−1].

Example 213

Synthesis of 5-(2,3-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

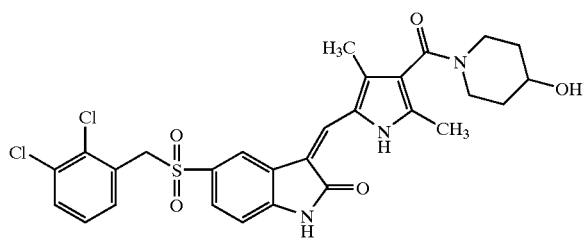

5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) was coupled with piperidin-4-ol (22 mg, 1.2 eq.) using HOBt (1.2 eq.), EDAC.HCl (1.2 eq.) and TEA (3 eq.) to give the titled compound.

$^1$HNMR (400 MHz, DMSO-$d_6$) δ 7.9 (s, 1H, NH), 7.72 (d, 1H), 7.47 (s, 1H), 7.43 (dd, 1H), 7.34 (dd, 1H), 7.26 (m, 1H), 7.21 (m, 1H), 6.92 (d, J=8 Hz, 1H), 4.66 (s, 2H), 4.15 (m, 1H), 3.8 (m, 2H), 3.6 (m, 1H), 2.26 (s, 3H, CH$_3$), 2.22 9s, 3H, CH$_3$), 1.3 (m, 4H). MS m/z 588 [M−1].

Example 214

Synthesis of 5-(2,3-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

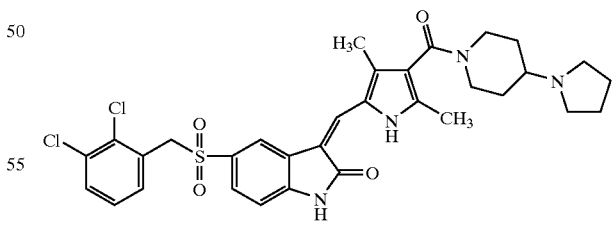

5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol) was coupled with 4-pyrrolidin-1-yl-piperidine (31 mg, 1.2 eq.) using HOBt (1.2 eq.), EDAC.HCl (1.2 eq.) and TEA (3 eq.) in DMF at rt for overnight to give the titled compound. MS m/z 639 [M−1].

Example 215

Synthesis of 5-(2,3-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

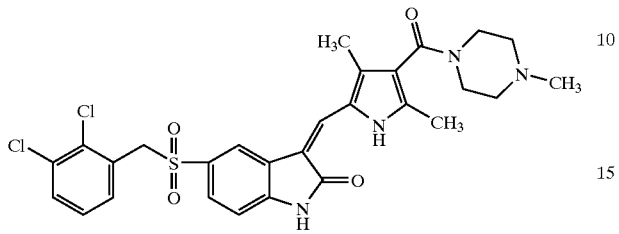

5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), was coupled with 1-methyl-piperazine (31 mg, 1.2 eq.) using HOBt (1.2 eq.), EDAC.HCl (1.2 eq.) and TEA (3 eq.) to give the titled compound.

$^1$HNMR (400 MHz, DMSO-$d_6$) 13.26 (br s, 1H, NH), 11.39 (br s, 1H, NH), 8.2 (d, 1H), 7.81 (s, 1H), 7.62 (dd, 1H), 7.36 (m, 2H), 7.26 (dd, 1H), 7.0 (d, J=8 Hz, 1H), 4.81 (s, 2H), 3.5 (m, 4H), 2.3 (s, 3H, $CH_3$), 2.29 (s, 3H, $CH_3$), 2.2–2.3 (m, 4H), 2.18 (s, 3H, $CH_3$). MS m/z 585 [M−1].

Example 216

Synthesis of 5-(2,6-Dichloro-phenylmethanesulfonyl)-3-[1-[4-((R)-3-hydroxy-pyrrolidin-1-ylmethyl)-3,5-dimethyl-1H-pyrrol-2-yl]-meth-(Z)-ylidene]-1,3-dihydro-indol-2-one

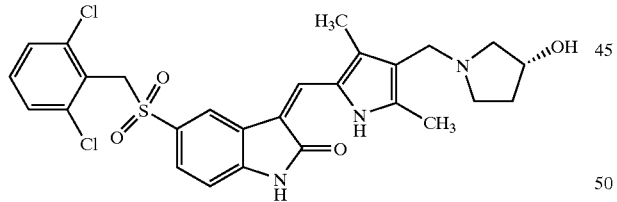

5-(2,6-Dichloro-phenylmethanesulfonyl)-1,3-dihydro-indol-2-one was condensed with 4-((R)-3-hydroxy-pyrrolidin-1-ylmethyl)-3,5-dimethyl-1H-pyrrole-2-carbaldehyde in ethanol and piperidine to give the titled compound as a yellow solid.

$^1$HNMR (400 MHz, DMSO-$d_6$) 13.42 (br s, 1H, NH), 11.28 (br s, 1H, NH), 8.19 (br s, 1H), 7.78 (br s, 1H), 7.49 (d, 1H), 7.47 (s, 1H), 7.37 (m, 2H), 7.0 (d, 1H), 4.85 (s, 2H), 4.62 (m, 1H), 4.15 (m, 1H), 3.37 (m, 1H), 3.29 (s, 2H), 2.65 (m, 1H), 2.43 (m, 1H), 2.34 (s, 3H, $CH_3$), 2.33 (s, 3H, $CH_3$), 2.25 (m, 1H), 1.97 (m, 1H), 1.50 (m, 1H). MS m/z 560 [M−1].

Example 217

Synthesis of 5-(2,6-Dichloro-phenylmethanesulfonyl)-3-[1-[4-(3-hydroxy-piperidin-1-ylmethyl)-3,5-dimethyl-1H-pyrrol-2-yl]-meth-(Z)-ylidene]-1,3-dihydro-indol-2-one

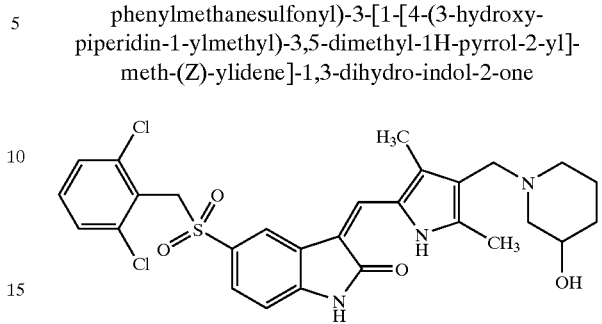

5-(2,6-Dichloro-phenylmethanesulfonyl)-1,3-dihydro-indol-2-one was condensed with 4-(3-hydroxy-piperidin-1-ylmethyl)-3,5-dimethyl-1H-pyrrole-2-carbaldehyde in ethanol and piperidine to give the titled compound as a yellow solid.

$^1$HNMR (400 MHz, DMSO-$d_6$) δ 13.5 (br s, 1H, NH), 11.28 (s, 1H, NH), 8.19 (s, 1H), 7.78 (s, 1H), 7.49 (s, 1H), 7.47 (s, 1H), 7.37 (m, 2H), 7.0 (d, 1H), 4.85 (s, 2H), 4.53 (m, 1H, OH), 3.36 (m, 1H), 3.29 (s, 2H), 2.76 (m, 1H), 2.62 (m, 1H), 2.32 (s, 3H, $CH_3$), 2.31 (s, 3H, $CH_3$), 1.79 (m, 2H), 1.61 (m, 2H), 1.36 (m, 1H), 1.03 (m, 1H). MS m/z 574 [M+1].

Example 218

Synthesis of 3-[1-[4-((S)-2-Cyclopropylaminomethyl-pyrrolidine-1-carbonyl)-3,5-dimethyl-1H-pyrrol-2-yl]-meth-(Z)-ylidene]-5-phenylmethanesulfonyl-1,3-dihydro-indol-2-one

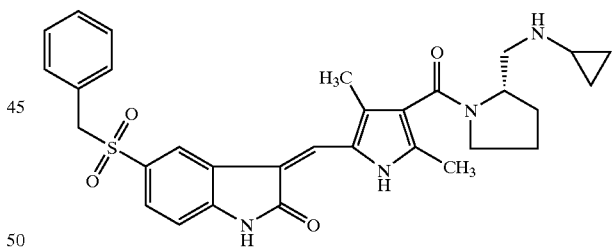

A mixture of 5-phenylmethanesulfonyl-1,3-dihydro-indol-2-one (27 mg), 4-((S)-2-cyclopropylaminomethyl-pyrrolidine-1-carbonyl)-3,5-dimethyl-1H-pyrrole-2-carbaldehyde (25 mg) and piperidine (1 drop) in ethanol (2mL) was stirred at rt for 4 hours, the precipitate was collected by vacuum filtration and purified on a silica gel column to give the titled compound.

$^1$HNMR (400 MHz, DMSO-$d_6$) δ 13.50 (s, 1H, NH), 11.36 (br s, 1H, NH), 8.23 (s, 1H), 7.81 (s, 1H), 7.38 (d, 1H), 7.31 (m, 3H), 7.18 (m, 2H), 6.98 (d, 1H), 4.61 (s, 2H), 4.24 (m, 1H), 3.71 (m, 1H), 3.23 (m, 2H), 2.97 (m, 1H), 2.62 (m, 1H), 2.32 (s, 6H, 2×$CH_3$), 2.16 (m, 1H), 1.9 (m, 4H), 0.4 (m, 2H), 0.24 (m, 2H). MS m/z 557 [M−1].

Example 219

Synthesis of 3-[1-[4-((S)-2-Cyclopropylaminomethyl-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

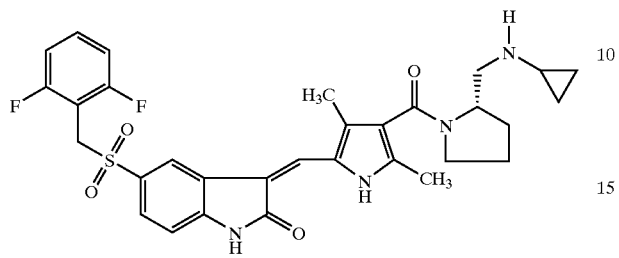

A mixture of 5-formyl-2,4-dimethyl-1H-pyrrole-3-carboxylic acid (270 mg, 1.61 mmol), cyclopropyl-(S)-1-pyrrolidin-2-ylmethyl-amine (220 mg, 1.57 mmol), HOBt (199 mg, 1.47 mmol), EDAC (344 mg, 1.8 mmol) and TEA (0.5 mL) in DMF (7 mL) was stirred at rt for 48 hours. The reaction was concentrated, diluted with sodium bicarbonate and extracted with DCM. The combined DCM was dried, concentrated and filtered through silica gel to give 4-((S)-2-cyclopropylaminomethyl-pyrrolidine-1-carbonyl)-3,5-dimethyl-1H-pyrrole-2-carbaldehyde.

A mixture of 5-(2,6-difluoro-phenylmethanesulfonyl)-1,3-dihydro-indol-2-one (280 mg, 0.87 mmol), 4-((S)-2-cyclopropylaminomethyl-pyrrolidine-1-carbonyl)-3,5-dimethyl-1H-pyrrole-2-carbaldehyde (250 mg, 0.86 mmol) and piperidine (2 drops) in ethanol (2 mL) was stirred at rt for 4 days. The reaction was concentrated and purified on a silica gel column to give the titled compound.

$^1$HNMR (400 MHz, DMSO-d$_6$) δ 13.51 (s, 1H, NH), 11.38 (br s, 1H, NH), 8.3 (s, 1H), 7.8 (s, 1H), 7.42 (m, 2H), 7.02 (m, 2H), 7.0 (d, 1H), 4.63 (s, 2H), 4.22 (m, 1H), 3.48 (m, 1H), 3.23 (m, 2H), 2.97 (m, 1H), 2.6 (m, 1H), 2.32 (s, 6H, 2×CH$_3$), 2.13 (m, 1H), 1.8 (m, 4H), 0.38 (m, 2H), 0.22 (m, 2H). MS m/z 593 [M−1].

Example 220

Synthesis of 5-(3,5-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

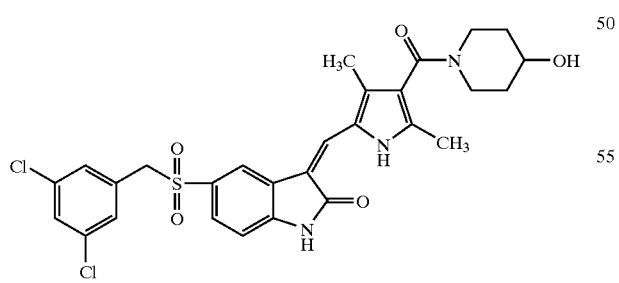

5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.24 mmol) was coupled with piperidin-4-ol (30 mg, 1.2 eq.) using HOBt (1.2 eq.), EDAC.HCl (1.2 eq.) and TEA (3 eq.) in DMF (25 mL) to give the titled compound.

$^1$HNMR (400 MHz, DMSO-d$_6$) 13.5 (br s, 1H, NH), 11.4 (s, 1H, NH), 8.21 (d, 1H), 7.82 (s, 1H), 7.58 (m, 1H), 7.4 (dd, 1H), 7.19 (m, 2H), 7.02 (d, 1H), 4.78 (d, 1H, OH), 4.68 (s, 2H), 4.0 (m, 1H), 3.7 (m, 1H), 3.5 (m, 1H), 3.12 (m, 2H), 2.29 (s, 6H, 2×CH$_3$), 1.72 (m, 2H), 1.28 (m, 2H). MS m/z 588 [M+1].

Example 221

Synthesis of 5-(2,5-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one

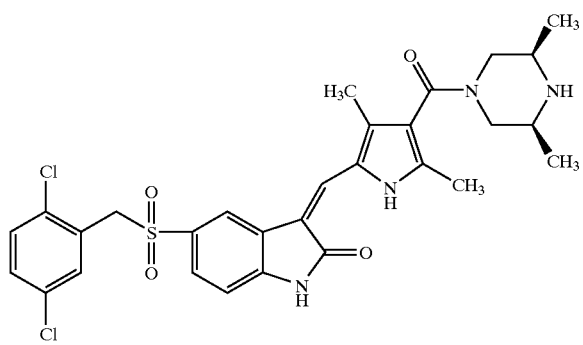

5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.2 mmol) was coupled with (2R,6S)-2,6-dimethyl-piperazine (50 mg, 0.2 mmol), HOBt (36 mg, 1.1 eq.), EDAC.HCl (40 mg, 1.1 eq.) and TEA (76 mg) in DMF (25 mL) at 75° C. for 2 hours to give the titled compound.

Example 222

Synthesis of 5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid

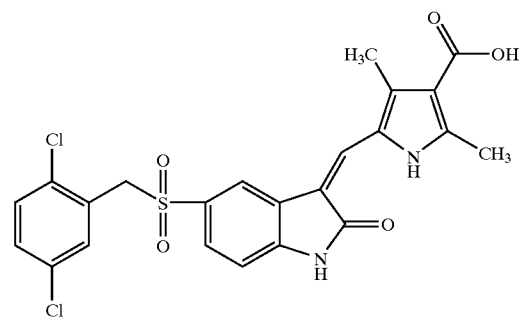

5-[(2,5-Dichlorobenzyl)sulfonyl]-1,3-dihydro-indol-2-one was condensed with 5-formyl-2,4-dimethyl-1H-pyrrole-3-carboxylic acid to give the titled compound as a yellow solid.

$^1$HNMR (400 MHz, DMSO d$_6$) δ 13.72 (br s, 1H, NH), 11.44 (s, 1H), 8.25 (d, 1H), 7.88 (s, 1H), 7.43 (d, 2H), 7.38 (d, 1H), 7.37 (dd, 1H), 7.0 (d, J=8 Hz, 1H), 4.74 (s, 2H), 2.54 (2s, 6H, 2×CH$_3$).

Example 223

Synthesis of 5-(2,5-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

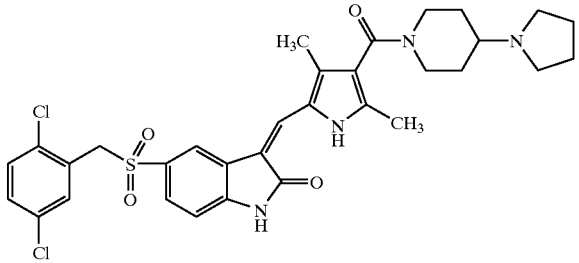

5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid was coupled with 4-pyrrolidin-1-yl-piperidine using HOBt, EDAC.HCl and TEA in DMF to give the titled compound.

Example 224

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Pyridin-2-yl-ethyl)-amide

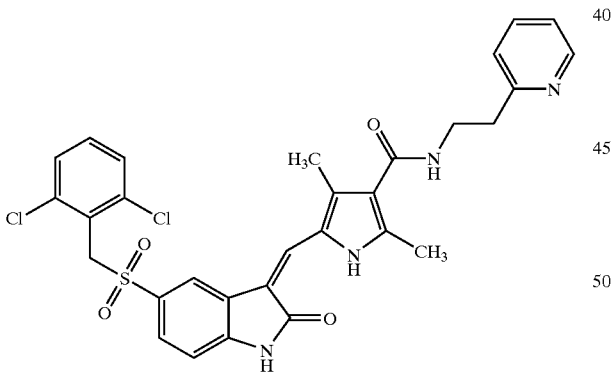

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 2-pyridin-2-yl-ethylamine (39 mg, 2 eq.). The mixture was stirred at rt for 3 days. The reaction was concentrated, diluted with DCM, washed with sat. NaHCO$_3$ and water, concentrated and triturated with methanol to give the titled compound as a yellow solid.

$^1$HNMR (400 MHz, DMSO-d$_6$) δ 13.43 (s, 1H, NH), 11.39 (s, 1H, NH), 8.5 (d, 1H), 8.27 (d, 1H), 7.84 (s, 1H), 7.7 (m, 2H), 7.49 (d, 1H), 7.47 (s, 1H), 7.4 (m, 2H), 7.22 (dd, 1H), 7.02 (d, J=8 Hz, 1H), 4.85 (s, 2H), 3.59 (q, 2H), 2.98 (t, 2H), 2.36 (s, 3H, CH$_3$), 2.34 (s, 3H, CH$_3$). MS m/z 607 [M−1].

Example 225

Synthesis of 3-[1-[3,5-Dimethyl-4-(2-piperidin-1-yl-acetyl)-1H-pyrrol-2-yl]-meth-(Z)-ylidene]-5-phenylmethanesulfonyl-1,3-dihydro-indol-2-one

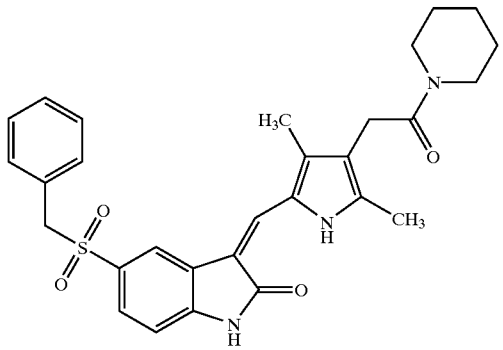

{2,4-Dimethyl-5-[2-oxo-5-phenylmethanesulfonyl-1,2-dihydro-indol-(3Z)-ylidenemethyl]-1H-pyrrol-3-yl}-acetic acid was condensed with piperidine to give the titled compound.

$^1$HNMR (400 MHz, DMSO-d$_6$) δ 13.45 (s, 1H, NH), 11.23 (s, 1H, NH), 8.14 (s, 1H), 7.72 (s, 1H), 7.3 (m, 4H), 7.17 (m, 2H), 6.94 (d, J=8 Hz, 1H), 4.59 (s, 2H), 3.48 (s, 2H), 3.45 (m, 4H), 2.26 (s, 3H, CH$_3$), 2.24 (s, 3H, CH$_3$), 1.55 (m, 2H), 1.41 (m, 4H). MS m/z 516 [M−1].

Example 226

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Pyridin-3-yl-ethyl)-amide

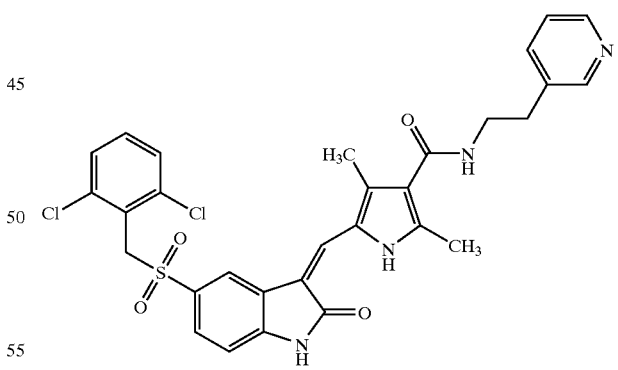

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 2-pyridin-3-yl-ethylamine (39 mg, 2 eq.). The mixture was stirred at rt for 18 hours. The reaction was concentrated, diluted with DCM, washed with sat. NaHCO$_3$ and water, concentrated and triturated with ethanol to give the titled compound as a yellow solid.

¹HNMR (400 MHz, DMSO-d₆) δ 13.55 (s, 1H, NH), 11.38 (s, 1H, NH), 8.46 (s, 1H), 8.41 (br d, 1H), 8.27 (d, 1H), 7.84 (s, 1H), 7.73 (t, 1H, CONH), 7.67 (dd, 1H), 7.49 (d, 1H), 7.46 (s, 1H), 7.39 (m, 2H), 7.31 (dd, 1H), 7.0 (d, J=8 Hz, 1H), 4.85 (s, 2H), 3.49 (q, 2H), 2.85 (t, 2H), 2.34 (s, 3H, CH₃), 2.32 (s, 3H, CH₃). MS m/z 609 [M+1].

Example 227

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Pyridin-4-yl-ethyl)-amide

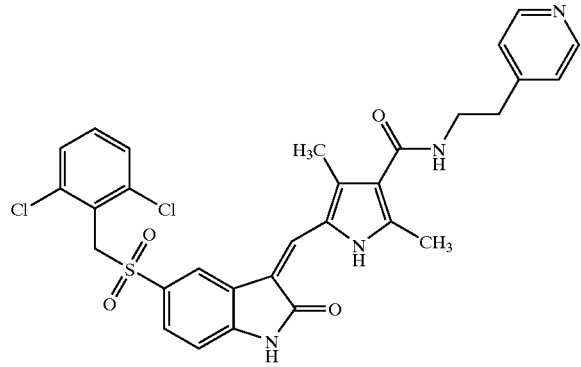

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 2-pyridin-4-yl-ethylamine (39 mg, 2 eq.). The mixture was stirred at rt for 18 hours. The reaction was concentrated, diluted with DCM, washed with sat. NaHCO₃ and water, concentrated and triturated with ethanol to give the titled compound as a yellow solid.

¹HNMR (400 MHz, DMSO-d₆) 13.56 (br s, 1H, NH), 11.4 (vbr s, 1H, NH), 8.46 (d, 2H), 8.28 (d, 1H), 7.84 (s, 1H), 7.74 (t, 1H, CONH), 7.49 (s, 1H), 7.47 (s, 1H), 7.4 (m, 2H), 7.28 (d, 2H), 7.02 (d, J=8 Hz, 1H), 4.85 (s, 2H), 3.51 (q, 2H), 2.86 (t, 2H), 2.34 (s, 3H, CH₃), 2.32 (s, 3H, CH₃). MS m/z 609 [M−1].

Example 228

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (Tetrahydro-furan-2-ylmethyl)-amide

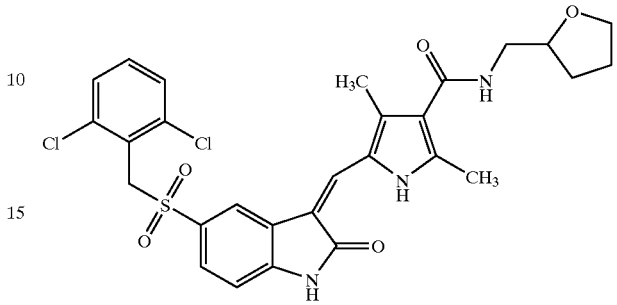

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added C-(tetrahydro-furan-2-yl)-methylamine (32 mg, 2 eq.). The mixture was stirred at rt for 18 hours. The reaction was concentrated, diluted with DCM, washed with sat.NaHCO₃ and water, concentrated and triturated with methanol to give the titled compound as a yellow solid.

¹HNMR (400 MHz, DMSO-d₆) δ 13.58 (s, 1H, NH), 11.4 (br s, 1H, NH), 8.26 (s, 1H), 7.85 (s, 1H), 7.72 (t, 1H, CONH), 7.49 (s, 1H), 7.47 (s, 1H), 7.4 (m, 2H), 7.02 (d, J=8 Hz, 1H), 4.85 (s, 2H), 3.94 (m, 1H), 3.76 (m, 1H), 3.63 (m, 1H), 3.26 (m, 2H), 2.43 (s, 3H, CH₃), 2.42 (s, 3H, CH₃), 1.9 (m, 1H), 1.82 (m, 2H), 1.6 (m, 1H). MS m/z 586 [M−1].

Example 229

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid Cyclopropylmethyl-amide

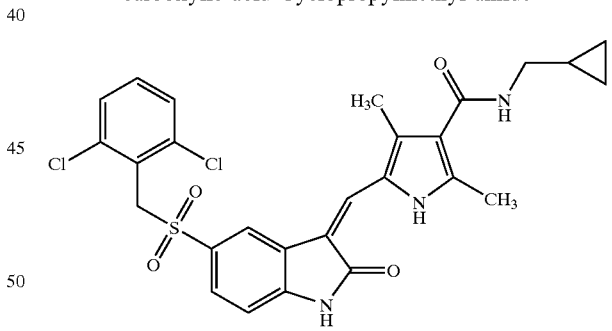

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added C-cyclopropyl-methylamine (23 mg, 2 eq.). The mixture was stirred at rt for 18 hours. The reaction was concentrated, diluted with DCM, washed with sat.NaHCO₃ and water, concentrated and triturated with methanol to give the titled compound as a yellow solid.

¹HNMR (400 MHz, DMSO-d₆) 13.6 (br s, 1H, NH), 11.41 (br s, 1H, NH), 8.28 (d, 1H), 7.87 (s, 1H), 7.78 (t, 1H, CONH), 7.50 (s, 1H), 7.48 (s, 1H), 7.41 (m, 2H), 7.04 (d, J=8 Hz, 1H), 4.87 (s, 2H), 3.12 (t, 2H), 2.45 (s, 6H, 2×CH₃), 1.02 (m, 1H), 0.42 (m, 2H), 0.22 (m, 2H). MS m/z 558 [M+1].

Example 230

Synthesis of 3-[1-{3,5-Dimethyl-4-[2-oxo-2-((S)-2-pyrrolidin-1-ylmethyl-pyrrolidin-1-yl)-ethyl]-1H-pyrrol-2-yl}-meth-(Z)-ylidene]-5-phenylmethanesulfonyl-1,3-dihydro-indol-2-one

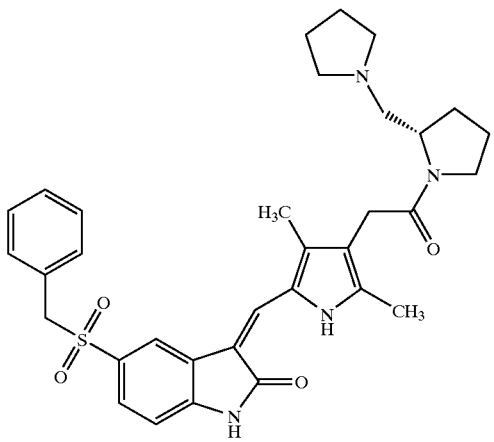

A mixture of 5-phenylmethanesulfonyl-1,3-dihydro-indol-2-one (100 mg, 0.35 mmol), 3,5-dimethyl-4-[2-oxo-2-((S)-2-pyrrolidin-1-ylmethyl-pyrrolidin-1-yl)-ethyl]-1H-pyrrole-2-carbaldehyde (110 mg, 1 eq.) and piperidine (0.5 eq.) in ethanol (2 mL) was stirred at rt for 48 hours. The reaction was concentrated, triturated with methanol, filtered and washed wit DCM to give the titled compound as a pale orange solid.

$^1$HNMR (400 MHz, DMSO-d$_6$) δ 13.44 (s, 1H, NH), 11.22 (s, 1H, NH), 8.14 (d, 1H), 7.72 (s, 1H), 7.32 (dd, 1H), 7.29 (m, 3H), 7.16 (m, 2H), 6.95 (d, J=8 Hz, 1H), 4.59 (s, 2H), 4.05–4.2 (m, 2H), 3.4–3.6 (m, 4H), 3.14 (d, 1H), 2.4–2.55 (m, 4H), 2.26 (s, 3H, CH$_3$), 2.24 (s, 3H, CH$_3$), 1.86 (m, 4H), 1.63 (m, 4H). MS m/z 585 [M−1].

Example 231

Synthesis of 3-[1-{3,5-Dimethyl-4-[2-(4-methyl-piperazin-1-yl)-2-oxo-ethyl]-1H-pyrrol-2-yl}-meth-(Z)-ylidene]-5-phenylmethanesulfonyl-1,3-dihydro-indol-2-one

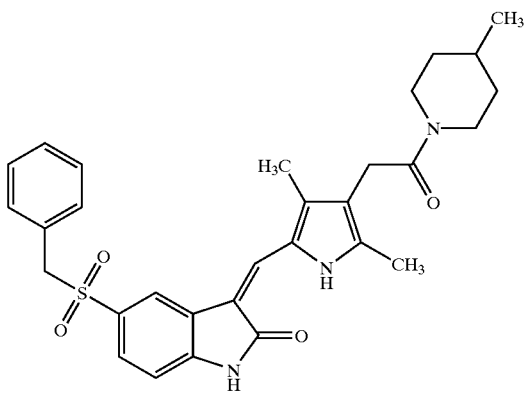

A mixture of 5-phenylmethanesulfonyl-1,3-dihydro-indol-2-one (100 mg, 0.35 mmol), 3,5-dimethyl-4-[2-(4-methyl-piperazin-1-yl)-2-oxo-ethyl]-1H-pyrrole-2-carbaldehyde (174 mg, 0.68 mmol) and piperidine (0.5 eq.) in ethanol (2 mL) was stirred at rt for 48 hours. The reaction was concentrated and triturated with acetone to give the titled compound as a pale orange solid.

$^1$HNMR (400 MHz, DMSO-d$_6$) δ 13.44 (s, 1H, NH), 11.23 (s, 1H, NH), 8.14 (d, 1H), 7.72 (s, 1H), 7.32 (dd, 1H), 7.28 (m, 3H), 7.16 (m, 2H), 6.95 (d, J=8 Hz, 1H), 4.59 (s, 2H), 3.5 (m, s, 4H), 3.44 (m, 2H), 2.25 (s, 3H, CH$_3$), 2.23 (s, 3H, CH$_3$), 2.2–2.3 (m, 4H), 2.16 (s, 3H, CH$_3$). MS m/z 531 [M−1].

Example 232

Synthesis of 3-[1-{4-[2-((3R,5S)-3,5-Dimethyl-piperazin-1-yl)-2-oxo-ethyl]-3,5-dimethyl-1H-pyrrol-2-yl}-meth-(Z)-ylidene]-5-phenylmethanesulfonyl-1,3-dihydro-indol-2-one

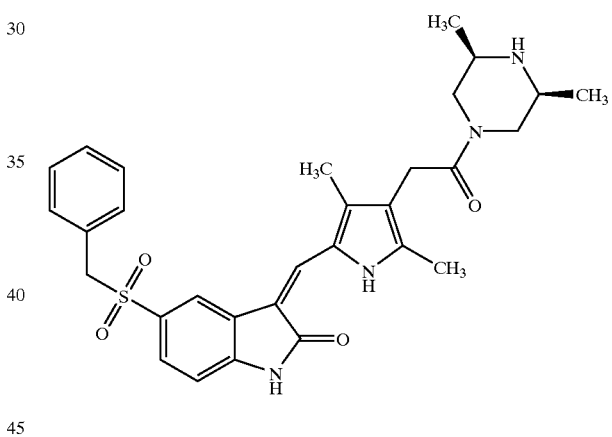

A mixture of 5-phenylmethanesulfonyl-1,3-dihydro-indol-2-one (100 mg, 0.35 mmol), 4-[2-((3R,5S)-3,5-dimethyl-piperazin-1-yl)-2-oxo-ethyl]-3,5-dimethyl-1H-pyrrole-2-carbaldehyde (184 mg, 0.68 mmol) and piperidine (0.5 eq.) in ethanol (2 mL) was stirred at rt for 48 hours. The reaction was concentrated and triturated with acetone to give the titled compound as a pale orange-red solid.

$^1$HNMR (400 MHz, DMSO-d$_6$) δ 13.44 (s, 1H, NH), 11.22 (br s, 1H, NH), 8.14 (d, 1H), 7.72 (s, 1H), 7.32 (dd, 1H), 7.29 (m, 3H), 7.16 (m, 2H), 6.95 (d, J=8 Hz, 1H), 4.59 (s, 2H), 4.22 (m, 1H), 3.8 (m, 1H), 2.5 (m, 4H), 2.45 (m, 1H), 2.26 (s, 3H, CH$_3$), 2.24 (s, 3H, CH$_3$), 2.02 (t, 1H, NH), 1.55 (m, 1H), 0.94 (s, 3H, CH$_3$), 0.92 (s, 3H, CH$_3$). MS m/z 545 [M−1].

Example 233

Synthesis of 3-[1-[3,5-Dimethyl-4-(2-morpholin-4-yl-2-oxo-ethyl)-1H-pyrrol-2-yl]-meth-(Z)-ylidene]-5-phenylmethanesulfonyl-1,3-dihydro-indol-2-one

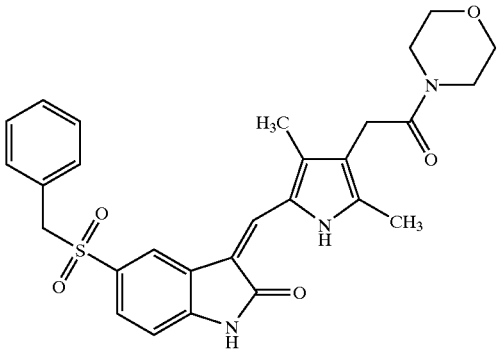

A mixture of 5-phenylmethanesulfonyl-1,3-dihydro-indol-2-one (100 mg, 0.35 mmol), 3,5-dimethyl-4-(2-morpholin-4-yl-2-oxo-ethyl)-1H-pyrrole-2-carbaldehyde (166 mg, 0.68 mmol) and piperidine (0.5 eq.) in ethanol (2 mL) was stirred at rt for 48 hours. The reaction was concentrated and triturated with methanol to give the titled compound as a pale orange solid.

$^1$HNMR (400 MHz, DMSO-$d_6$) δ 13.44 (s, 1H, NH), 11.24 (s, 1H, NH), 8.15 (d, 1H), 7.72 (s, 1H), 7.32 (dd, 1H), 7.29 (m, 3H), 7.16 (m, 2H), 6.95 (d, J=8 Hz, 1H), 4.59 (s, 2H), 3.54 (m, 6H), 3.51 (s, 2H), 3.44 (m, 2H), 2.26 (s, 3H, CH$_3$), 2.24 (s, 3H, CH$_3$). MS m/z 520 [M+1].

Example 234

Synthesis of 3-[1-{4-[2-(4-Hydroxy-piperidin-1-yl)-2-oxo-ethyl]-3,5-dimethyl-1H-pyrrol-2-yl}-meth-(Z)-ylidene]-5-phenylmethanesulfonyl-1,3-dihydro-indol-2-one

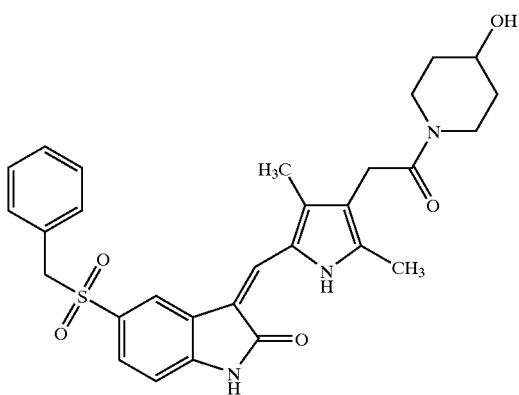

A mixture of 5-phenylmethanesulfonyl-1,3-dihydro-indol-2-one (100 mg, 0.35 mmol), 4-[2-(4-hydroxy-piperidin-1-yl)-2-oxo-ethyl]-3,5-dimethyl-1H-pyrrole-2-carbaldehyde (180 mg, 0.68 mmol) and piperidine (0.5 eq.) in ethanol (2 mL) was stirred at rt for 48 hours. The reaction was concentrated and triturated with methanol to give the titled compound as an orangish-red solid.

$^1$HNMR (400 MHz, DMSO-$d_6$) δ 13.45 (s, 1H, NH), 11.23 (s, 1H, NH), 8.14 (d, 1H), 7.72 (s, 1H), 7.32 (dd, 1H), 7.29 (m, 3H), 7.16 (m, 2H), 6.94 (d, J=8 Hz, 1H), 4.72 (d, 1H, OH), 4.59 (s, 2H), 3.92 (m, 1H), 3.76 (m, 1H), 3.66 (m, 1H), 3.5 (m, 2H), 3.18 (m, 1H), 2.97 (m, 1H), 2.26 (s, 3H, CH$_3$), 2.24 (s, 3H, CH$_3$), 1.67 (m, 2H), 1.22 (m, 2H). MS m/z 532 [M−1].

Example 235

Synthesis of 5-(2,6-Dichloro-phenylmethanesulfonyl)-3-[1-[3,5-dimethyl-4-(thiomorpholine-4-carbonyl)-1H-pyrrol-2-yl]-meth-(Z)-ylidene]-1,3-dihydro-indol-2-one

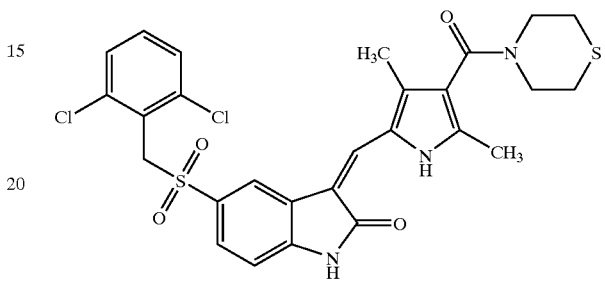

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added thiomorpholine (33 mg, 2 eq.). The mixture was stirred at rt for 2 hours. The reaction was concentrated, diluted with DCM, washed with sat. NaHCO$_3$ and water, concentrated and triturated with methanol to give the titled compound as an orange solid.

$^1$HNMR (400 MHz, DMSO-$d_6$) δ 13.55 (s, 1H, NH), 11.39 (s, 1H, NH), 8.28 (d, 1H), 7.86 (s, 1H), 7.49 (d, 1H), 7.47 (s, 1H), 7.4 (m, 2H), 7.02 (d, J=8 Hz, 1H), 4.85 (s, 2H), 3.7 (m, 4H), 2.57 (m, 4H), 2.3 (s, 3H, CH$_3$), 2.29 (s, 3H, CH$_3$). MS m/z 588 [M−1].

Example 236

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Fluoro-ethyl)-amide

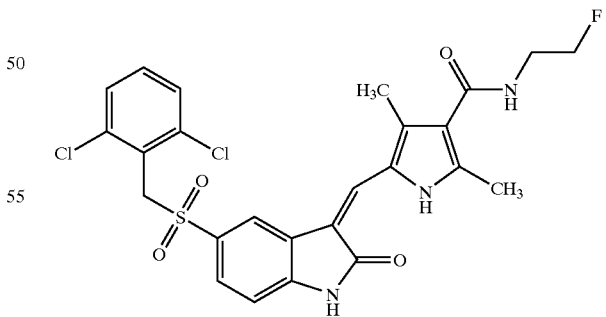

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 2-fluoro-ethylamine hydrochloride salt (32 mg, 2 eq.). The mixture was stirred at rt for 2 hours. The reaction was concentrated, diluted with DCM, washed with sat. NaHCO₃ and water, concentrated and triturated with methanol to give the titled compound as a yellow solid.

¹HNMR (400 MHz, DMSO-d₆) δ 13.6 (s, 1H, NH), 11.41 (s, 1H, NH), 8.28 (d, 1H), 7.89 (t, 1H, CONH), 7.86 (s, 1H), 7.49 (d, 1H), 7.47 (s, 1H), 7.4 (m, 2H), 7.02 (d, J=8 Hz, 1H), 4.86 (s, 2H), 4.57 (t, 1H), 4.45 (t, 1H), 3.54 (q, 1H), 3.48 (q, 1H), 2.43 (s, 6H, 2×CH₃). MS m/z 548 [M−1].

Example 237

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-Imidazol-1-yl-propyl)-amide

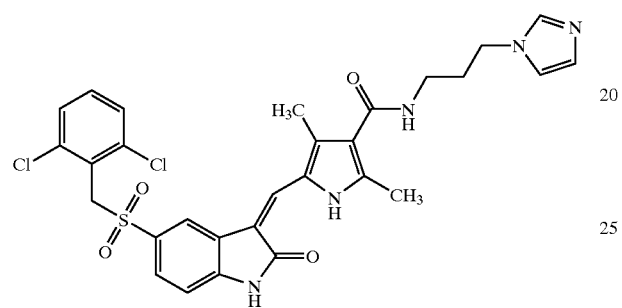

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 3-imidazol-1-yl-propylamine (40 mg, 2 eq.). The mixture was stirred at rt for 2 hours. The reaction was concentrated, diluted with DCM, washed with sat. NaHCO₃ and water, concentrated and triturated with methanol to give the titled compound as a yellow solid.

¹HNMR (400 MHz, DMSO-d₆) δ 13.6 (s, 1H, NH), 11.4 (s, 1H, NH), 8.28 (d, 1H), 7.87 (s, 1H), 7.76 (t, 1H, CONH), 7.66 (br s, 1H), 7.49 (d, 1H), 7.47 (s, 1H), 7.4 (m, 2H), 7.21 (br s, 1H), 7.02 (d, J=8 Hz, 1H), 4.86 (s, 2H), 4.02 (t, 2H), 3.18 (d, 2H), 2.43 (s, 6H, 2×CH₃), 1.93 (m, 2H). MS m/z 610 [M−1].

Example 238

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid methylamide

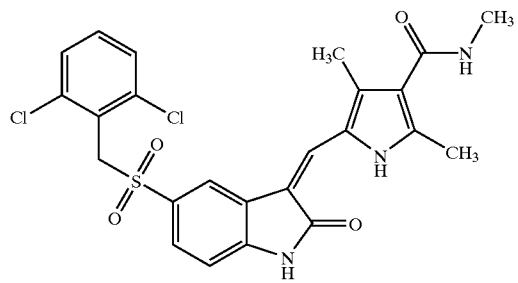

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added methylamine (2 eq.). The mixture was stirred at rt for 2 hours. The reaction was concentrated, diluted with DCM, washed with sat. NaHCO₃ and water, concentrated and triturated with methanol to give the titled compound as a yellow solid.

¹HNMR (400 MHz, DMSO-d₆) δ 13.58 (s, 1H, NH), 11.39 (s, 1H, NH), 8.28 (d, 1H), 7.86 (s, 1H), 7.57 (q, 1H, NH), 7.49 (d, 1H), 7.47 (s, 1H), 7.4 (m, 2H), 7.02 (d, J=8 Hz, 1H), 4.86 (s, 2H), 2.73 (d, 3H, NCH₃), 2.43 (s, 6H, 2×CH₃). MS m/z 516 [M−1].

Example 239

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid amide

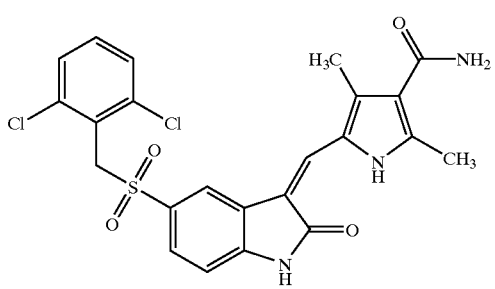

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added ammonia (2 eq.). The mixture was stirred at rt for 2 hours. The reaction was concentrated and triturated with methanol to give the titled compound as a yellow solid.

¹HNMR (400 MHz, DMSO-d₆) 13.59 (s, 1H, NH), 11.39 (s, 1H, NH), 8.28 (d, 1H), 7.87 (s, 1H), 7.49 (d, 1H), 7.47 (s, 1H), 7.4 (m, 2H), 7.17 (br s, 1H, NH), 7.1 (br s, 1H, NH), 7.02 (d, J=8 Hz, 1H), 4.86 (s, 2H), 2.46 (s, 6H, 2×CH₃). MS m/z 502 [M−1].

Example 240

Synthesis of 5-(2,6-Dichloro-phenylmethanesulfonyl)-3-[1-[4-(1,1-dioxo-1l6-thiomorpholine-4-carbonyl)-3,5-dimethyl-1H-pyrrol-2-yl]-meth-(Z)-ylidene]-1,3-dihydro-indol-2-one

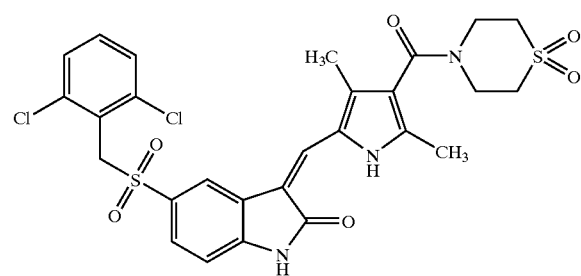

To a solution of 5-[5-(2,6-dichloro-phenylmethanesulfonyl)-2-oxo-1,2-dihydro-indol-(3Z)- ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added thiomorpholine 1,1-dioxide (44 mg, 2 eq.). The mixture was stirred at rt for 2 hours. The reaction was concentrated, diluted with DCM, washed with sat.NaHCO$_3$, water, concentrated and triturated with methanol to give the titled compound as a yellow solid.

$^1$HNMR(400MHz,DMSO-d$_6$) 13.58(s, 1H, NH), 11.41 (s, 1H, NH), 8.29 (d, 1H), 7.87 (s, 1H), 7.49 (d, 1H), 7.47 (s, 1H), 7.4 (m, 2H), 7.02 (d, J=8 Hz, 1H), 4.86 (s, 2H), 3.87 (br s, 4H), 3.16 (br m, 4H), 2.34 (s, 3H, CH$_3$), 2.32 (s, 3H, CH$_3$). MS m/z 620 [M–1].

Example 241

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-acetyl-piperazin-1-yl)-ethyl]-amide

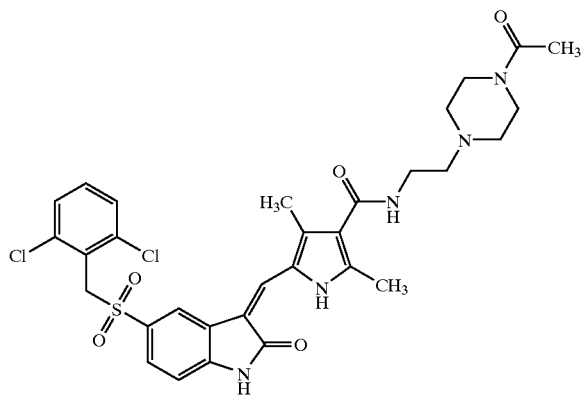

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (100 mg, 0.162 mmol) in DMA (2 mL) was added 1-[4-(2-amino-ethyl)-piperazin-1-yl]-ethanone (55 mg, 2 eq.). The mixture was stirred at rt for 2 hours. The reaction was concentrated, diluted with DCM, washed with sat.NaHCO$_3$, water, concentrated and triturated with methanol to give the titled compound as a yellow solid.

$^1$HNMR (400 MHz, DMSO-d$_6$) δ 13.59 (br s, 1H, NH), 11.39 (s, 1H, NH), 8.28 (d, 1H), 7.86 (s, 1H), 7.55 (t, 1H, CONH), 7.49 (s, 1H), 7.47 (s, 1H), 7.4 (m, 2H), 7.02 (d, J=8 Hz, 1H), 4.86 (s, 2H), 3.4 (m, 4H), 3.34 (m, 2H), 2.45 (s, 6H, 2×CH$_3$), 2.4–2.5 (m, 4H), 2.36 (m, 2H), 1.97 (s, 3H, COCH$_3$). MS m/z 656 [M–1].

Example 242

Synthesis of 5-(2,6-Dichloro-phenylmethanesulfonyl)-3-[1-[4-((3R,5S)-3,5-dimethyl-piperazin-1-ylmethyl)-3,5-dimethyl-1H-pyrrol-2-yl]-meth-(Z)-ylidene]-1,3-dihydro-indol-2-one

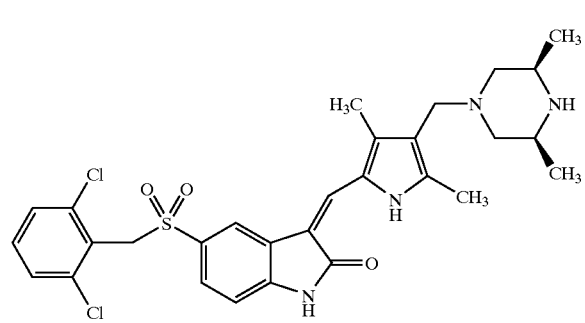

5-(2,6-Dichloro-phenylmethanesulfonyl)-1,3-dihydro-indol-2-one was condensed with 4-((3R,5S)-3,5-dimethyl-piperazin-1-ylmethyl)-3,5-dimethyl-1H-pyrrole-2-carbaldehyde in ethanol and piperidine to give the tiled compound.

$^1$HNMR (400 MHz, DMSO-d$_6$) δ 13.48 (br s, 1H, NH), 11.29 (br s, 1H, NH), 8.22 (br s, 1H), 7.80 (s, 1H), 7.49 (s, 1H), 7.47 (s, 1H), 7.37 (m, 2H), 7.0 (d, 1H), 4.85 (s, 2H), 3.29 (m, 4H), 2.83 (m, 2H), 2.33 (s, 3H, CH$_3$), 2.32 (s 3H, CH$_3$), 1.1 (m, 6H). MS m/z 587 [M–1].

Example 243

Synthesis of 3-[1-[4-((3R,5S)-3,5-Dimethyl-piperazin-1-ylmethyl)-3,5-dimethyl-1H-pyrrol-2-yl]-meth-(Z)-ylidene]-5-phenylmethanesulfonyl-1,3-dihydro-indol-2-one

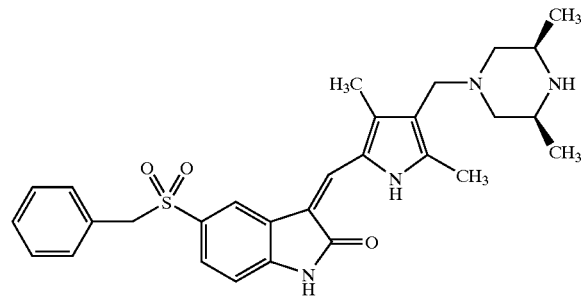

5-Phenylmethanesulfonyl-1,3-dihydro-indol-2-one was condensed with 4-((3R,5S)-3,5-dimethyl-piperazin-1-ylmethyl)-3,5-dimethyl-1H-pyrrole-2-carbaldehyde to give the titled compound.

Example 244

Synthesis of 5-(2,5-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one

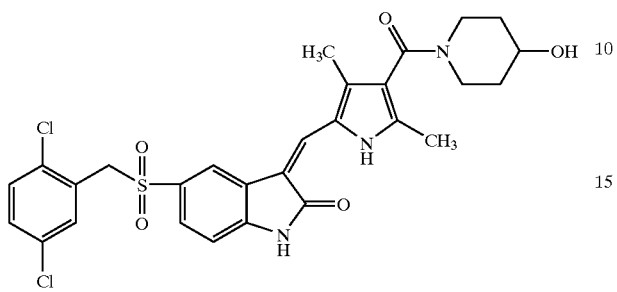

5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid 2,5-dioxo-pyrrolidin-1-yl ester (120 mg, 0.2 mmol) was condensed with piperidin-4-ol (21 mg, 0.2 mmol) to give 30 mg the titled compound.

$^1$HNMR (400 MHz, DMSO-d$_6$) δ 13.5 (br s, 1H, NH), 11.38 (s, 1H, NH), 8.19 (s, 1H), 7.8 (s, 1H), 7.43 (m, 2H), 7.38 (s, 1H), 7.36 (dd, 1H), 6.99 (d, 1H), 4.78 (d, 1H, OH), 4.73 (s, 2H), 4.0 (m, 1H), 3.71 (m, 1H), 3.5 (m, 1H), 3.13 (m, 2H), 2.29 (s, 6H, 2×CH$_3$), 1.72 (m, 2H), 1.29 (m, 2H).

Example 245

Synthesis of 5-(2,5-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one

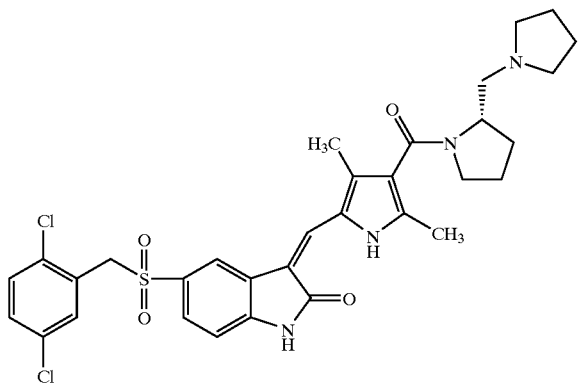

5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid 2,5-dioxo-pyrrolidin-1-yl ester (120 mg, 0.2 mmol) was coupled with (S)-2-pyrrolidin-1-ylmethyl-pyrrolidine (31 mg, 0.2 mmol) to give the titled compound.

Example 246

Synthesis of 5-(2,5-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

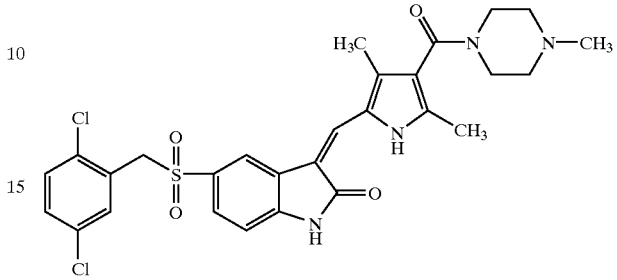

5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid 2,5-dioxo-pyrrolidin-1-yl ester was condensed with 1-methyl-piperazine to give the titled compound.

$^1$HNMR (400 MHz, DMSO-d$_6$) δ 13.56 (s, 1H, NH), 11.4 (s, 1H, NH), 8.2 (s, 1H), 7.81 (s, 1H), 7.43 (d, 2H), 7.38 (s, 1H), 7.36 (dd, 1H), 7.0 (d, 1H), 4.73 (s, 2H), 3.5 (m, 4H), 2.29 (s, 6H, 2×CH$_3$), 2.2–2.4 (m, 4H), 2.2 (s, 3H, NCH$_3$). MS m/z 587 [M−1].

Example 247

Synthesis of 5-(3,5-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one

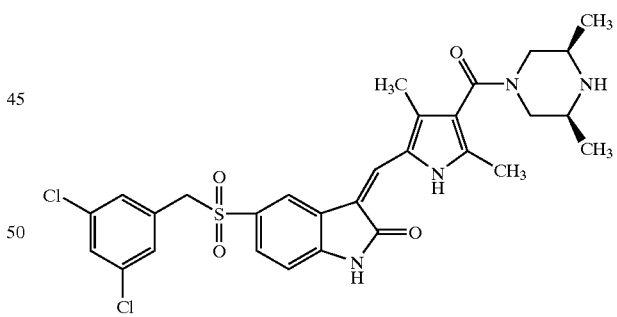

5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.24 mmol) was coupled with (2R,6S)-2,6-dimethyl-piperazine (34 mg, 1.2 eq.) using HOBt (1.2 eq.), EDAC.HCl (1.2 eq.) and TEA (1.2 eq.) to give the titled compound.

$^1$HNMR (400 MHz, DMSO-d$_6$) δ 13.55 (s, 1H, NH), 11.4 (br s, 1H, NH), 8.28 (d, 1H), 7.85 (s, 1H), 7.41 (dd, 1H), 7.24 (m, 2H), 7.11 (m, 1H), 7.02 (d, 1H), 4.66 (s, 2H), 3.5 (m, 4H), 2.32 (m, 2H), 2.31 (s, 9H, 3×CH$_3$), 2.19 (s, 3H, CH$_3$). MS m/z 599 [M−1].

Example 248

Synthesis of 5-(3,5-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one

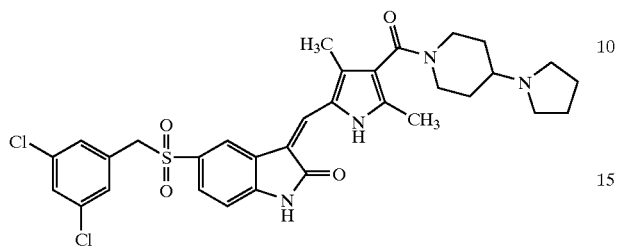

5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.24 mmol) was coupled with 4-pyrrolidin-1-yl-piperidine (45 mg, 1.2 eq.) using HOBt (1.2 eq.), EDAC.HCl (1.2 eq.) and TEA (3 eq.) in DMF (25 mL) to give the titled compound. MS m/z 639 [M−1].

Example 249

Synthesis of 5-(3,5-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one

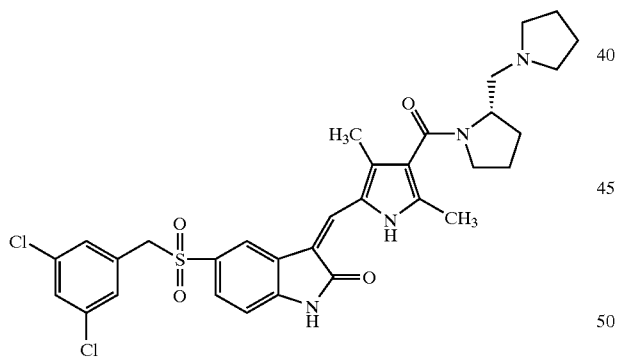

5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.24 mmol) was coupled with (S)-2-pyrrolidin-1-ylmethyl-pyrrolidine (40 mg, 1.2 eq.) using HOBt (1.2 eq.), EDAC.HCl (1.2 eq.) and TEA (3 eq.) at rt for 2 days to give the titled compound.

$^1$HNMR (400 MHz, DMSO-$d_6$) δ 13.5 (br s, 1H, NH), 11.39 (s, 1H, NH), 8.2 (d, 1H), 7.81 (s, 1H), 7.62 (dd, 1H), 7.36 (m, 2H), 7.26 (dd, 1H), 7.0 (d, 1H), 4.81 (s, 2H), 4.77 (d, 1H), 4.05 (br m, 1H), 3.7 (m, 2H), 3.5 (m, 1H), 3.3 (m, 4H), 2.9 (m, 1H), 2.29 (d, 6H, 2×CH$_3$), 1.7–1.9 (m, 3H), 1.2–16 (m, 3H).

Example 250

Synthesis of 5-(3,5-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one

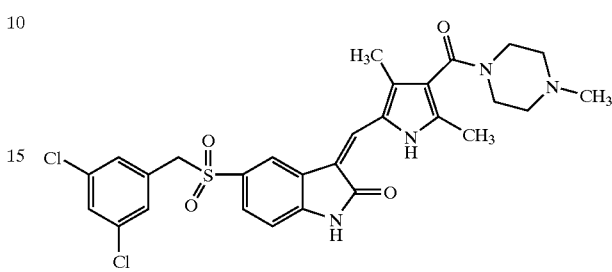

5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid (120 mg, 0.24 mmol) was coupled with 1-methyl-piperazine (30 mg, 1.2 eq.) using HOBt (1.2 eq.), EDAC.HCl (1.2 eq.) and TEA (3 eq.) to give the titled compound.

$^1$HNMR (400 MHz, DMSO-$d_6$) δ 13.48 (br s, 1H, NH), 11.4 (s, 1H, NH), 8.21 (d, 1H), 7.82 (s, 1H), 7.59 (t, 1H), 7.4 (dd, 1H), 7.19 (m, 2H), 7.02 (d, 1H), 4.68 (s, 2H), 3.2 (m, 4H), 2.47 (m, 4H), 2.29 (s, 6H, 2×CH$_3$), 2.17 (s, 3H, CH$_3$).

Example 251

Synthesis of 3-[1-[4-(4-Cyclopropylmethyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one

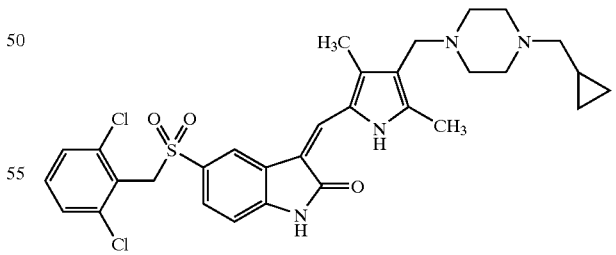

5-(2,6-Dichloro-phenylmethanesulfonyl)-1,3-dihydro-indol-2-one was condensed with 4-(4-cyclopropylmethyl-piperazin-1-ylmethyl)-3,5-dimethyl-1H-pyrrole-2-carbaldehyde in ethanol and piperidine to give the titled compound. MS m/z 613 [M−1].

Example 252

Synthesis of 3-[1-{4-[2-((S)-2-Cyclopropylaminomethyl-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

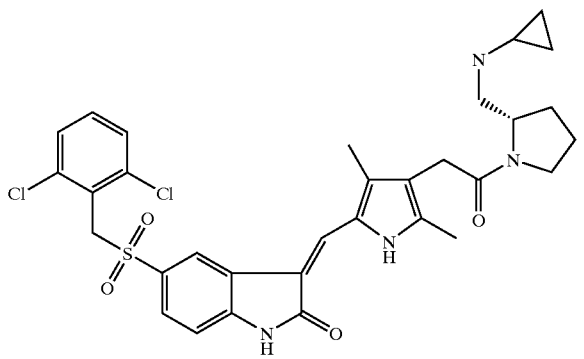

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (225 mg, 0.43 mmol), cyclopropyl-(S)-1-pyrrolidin-2-ylmethyl-amine (91 mg, 0.64 mmol), HOBt (91 mg, 0.67 mmol), EDAC (130 mg, 0.68 mmol) and TEA (0.15 mL, 1.1 mmol) in DMF was stirred at rt for 48 hours. The reaction was concentrated, diluted with sodium bicarbonate and extracted with DCM. The combined DCM was dried, concentrated and purified on a silica gel column to give 211 mg (76%) of the titled compound.

$^1$HNMR (400 MHz, DMSO-$d_6$) δ 13.48 (s, 1H, NH), 11.28 (br s, 1H, NH), 8.19 (s, 1H), 7.78 (s, 1H), 7.58 (d, 1H), 7.48 (s, 1H), 7.38 (m, 2H), 7.02 (d, 1H), 4.86 (s, 2H), 4.01 (m, 1H), 3.5 (m, 2H), 3.42 (d, 1H), 3.33 (s, 2H), 2.78 (m, 1H), 2.44 (m, 1H), 2.28 (s, 3H, CH$_3$), 2.25 (s, 3H, CH$_3$), 2.04 (m, 1H), 1.8 (m, 1H), 0.95 (t, 1H), 0.32 (m, 2H), 0.15 (m, 2H). MS m/z 639 [M−1].

Example 253

Synthesis of 3-[1-[4-(4-Acetyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one

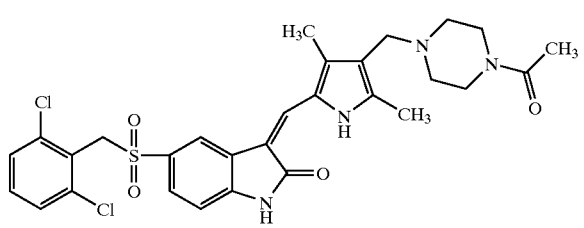

5-(2,6-Dichloro-phenylmethanesulfonyl)-1,3-dihydro-indol-2-one (357 mg, 1 mmol) was condensed with 4-(4-acetyl-piperazin-1-ylmethyl)-3,5-dimethyl-1H-pyrrole-2-carbaldehyde (263 mg, 1 mmol) in ethanol (3 mL) and piperidine (3 drops) at 95–100° C. for 2 hours to give the titled compound.

$^1$HNMR (400 MHz, DMSO-$d_6$) δ 13.45 (s, 1H, NH), 11.28 (s, 1H, NH), 8.2 (d, 1H), 7.79 (s, 1H), 7.49 (d, 1H), 7.46 (s, 1H), 7.37 (m, 2H), 7.0 (d, 1H), 4.85 (s, 2H), 3.37 (m, 4H), 3.31 (m, 4H), 2.33 (s, 3H, CH$_3$), 2.32 (s, 3H, CH$_3$), 2.25 (m, 2H), 1.96 (s, 3H, CH$_3$). MS m/z 599 [M−1].

Example 254

Synthesis of 4-{5-[5-(2,6-Dichloro-phenylmethanesulfonyl)-2-oxo-1,2-dihydro-indol-(3Z)-ylidenemethyl]-2,4-dimethyl-1H-pyrrol-3-ylmethyl}-piperazine-1-carbaldehyde

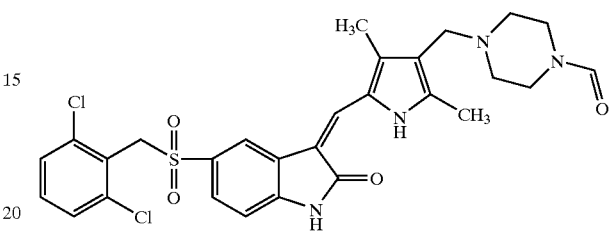

5-(2,6-Dichloro-phenylmethanesulfonyl)-1,3-dihydro-indol-2-one (178 mg) was condensed with 4-(5-formyl-2,4-dimethyl-1H-pyrrol-3-ylmethyl)-piperazine-1-carbaldehyde (125 mg) using piperidine (cat. amount) in ethanol at 80° C. for 4 hours to give the titled compound.

$^1$HNMR (400 MHz, DMSO-$d_6$) δ 13.48 (s, 1H, NH), 11.29 (s, 1H, NH), 8.21 (s, 1H), 7.97 (s, 1H), 7.49 (d, 1H), 7.47 (s, 1H), 7.38 (m, 2H), 7.0 (d, 1H), 4.85 (s, 2H), 3.3 (m, 8H), 2.33 (s, 3H, CH$_3$), 2.32 (s, 3H, CH$_3$), 2.2 (m, 2H). MS m/z 585 [M−1].

Example 255

Synthesis of Synthesis of 3-[1-{4-[(Cyclopropyl-methyl-amino)-methyl]-3,5-dimethyl-1H-pyrrol-2-yl}-meth-(Z)-ylidene]-5-(2,6-dichloro-phenylmethanesulfonyl)-1,3-dihydro-indol-2-one

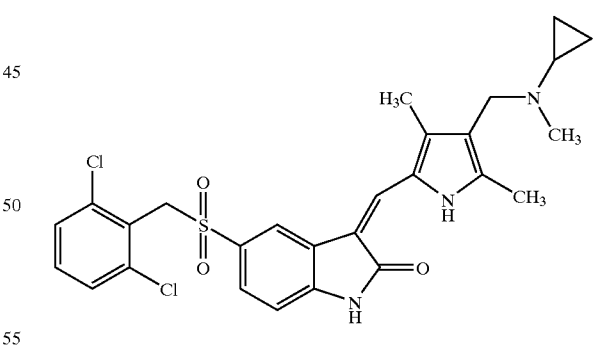

5-(2,6-Dichloro-phenylmethanesulfonyl)-1,3-dihydro-indol-2-one (178 mg) was condensed with 4-[(cyclopropyl-methyl-amino)-methyl]-3,5-dimethyl-1H-pyrroled-2-carbaldehyde (96 mg) to give the titled compound.

$^1$HNMR (400 MHz, DMSO-$d_6$) δ 13.5 (br s, 1H, NH), 11.3 (s, 1H, NH), 8.2 (s, 1H, NH), 7.78 (s, 1H), 7.5 (d, 1H), 7.48 (s, 1H), 7.4 (m, 2H), 7.01 (d, 1H), 4.86 (s, 2H), 3.45 (s, 2H), 2.33 (s, 3H, CH$_3$), 2.31 9s, 3H, CH$_3$), 2.14 (s, 3H, NCH$_3$), 1.68 (m, 1H), 0.45 (m, 2H), 0.3 (m, 2H). MS m/z 542 [M−1].

Example 256

Synthesis of 3-[1-[4-(4-Cyclopropyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one

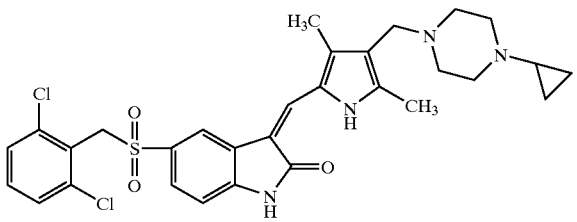

5-(2,6-Dichloro-phenylmethanesulfonyl)-1,3-dihydro-indol-2-one (178 mg) was condensed with 4-(4-cyclopropyl-piperazin-1-ylmethyl)-3,5-dimethyl-1H-pyrrole-2-carbaldehyde (125 mg) to give the titled compound.

$^1$HNMR (400 MHz, DMSO-$d_6$) δ 13.5 (br s, 1H, NH), 11.32 (s, 1H, NH), 8.26 (s, 1H), 7.8 (s, 1H), 7.52 (m, 2H), 7.45 (m, 2H), 7.08 (d, 1H), 4.9 (s, 2H), 3.35 (2H), 2.3–2.7 (m, 8H), 2.38 (s, 3H, $CH_3$), 2.36 (s, 3H, $CH_3$), 1.6 (m, 1H), 0.45 (m, 2H), 0.3 (m, 2H). MS m/z 597 [M–1].

Example 257

Synthesis of 3-[1-{4-[2-((2R,4R)-2-Cyclopropylaminomethyl-4-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

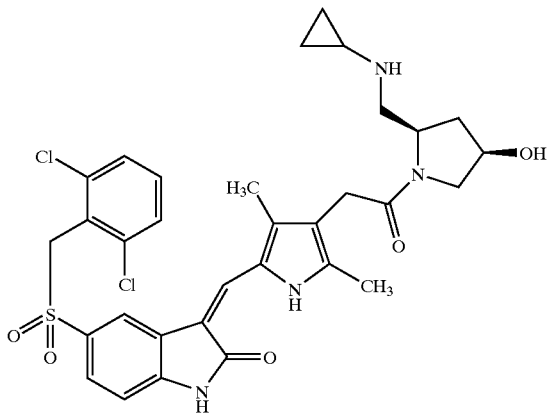

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (250 mg, 0.48 mmol), HOBt (78 mg, 1.2 eq.), EDC (110 mg, 1.2 eq.), TEA (0.17 mL, 2.5 eq.) and (3R,5R)-5-cyclopropylaminomethyl-pyrrolidin-3-ol (300 mg, 4 eq.) in DMF (10 mL) was stirred at rt for overnight. The reaction was concentrated, washed with water, sodium bicarbonate and brine, dried and concentrated. The residue was purified on a silica gel column to give 100 mg of the titled compound as a yellow solid.

$^1$HNMR (400 MHz, DMSO-$d_6$) δ 13.42 (s, 1H, NH), 11.02 (br s, 1H, NH), 8.07 (s, 1H), 7.68 (s, 1H), 7.46 (m, 3H), 7.38 (m, 1H), 7.03 (d, 1H), 4.88 (s, 2H), 4.23 (m, 1H), 4.1 (m, 1H), 3.52 (m, 1H), 3.42 (m, 3H), 3.08 (s, 2H), 3.02 (m, 1H), 2.72 (m, 1H), 2.31 (s, 3H, $CH_3$), 2.27 (s, 3H, $CH_3$), 2.13 (m, 2H), 1.73 (m, 1H), 0.38 (m, 2H), 0.24 (m, 2H). MS m/z 655 [M–1].

Example 258

Synthesis of 3-[1-{4-[2-((2R,3S)-2-Cyclopropylaminomethyl-3-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

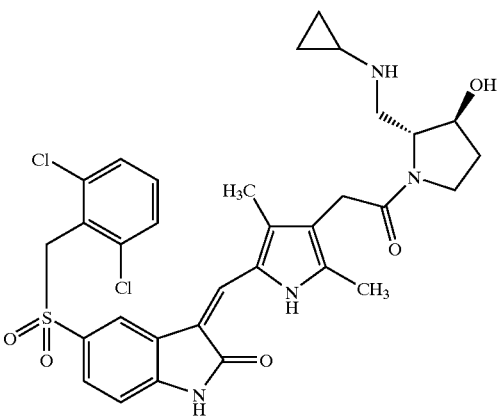

To a solution of trans-3-hydrocy-L-proline (10 g, 76 mmol) in THF (60 mL) at 0° C. was added slowly a solution of NaOH (6 g dissolved in 40 mL of water), followed by dropwise addition of di-tert-butyl-dicarbonate (33 g, 2 eq.) in THF (50 mL). The mixture was allowed to warm up to rt and stirred for overnight. The reaction was acidified to pH 4–5 and extracted with DCM to give 12 g of (2S,3S)-3-hydroxy-pyrrolidine-1,2-dicarboxylic acid 1-tert-butyl ester as a white solid.

$^1$HNMR (400 MHz, DMSO-$d_6$) δ 12.62 (s, 1H, COOH), 5.42 (s, 1H), 4.20 (m, 2H), 3.9 (d, 1H, OH), 3.25 (m, 2H), 1.85 (m, 1H), 1.72 (m, 1H), 1.37 (s, 3H), 12.32 (s, 6H). MS m/z 230 [M–1].

A mixture of (2S,3S)-3-hydroxy-pyrrolidine-1,2-dicarboxylic acid 1-tert-butyl ester (6 g), EDAC (6 g, 1.2 eq.), HOBt (4.2 g, 1.2 eq.), TEA (9 mL, 2.5 eq.) and cyclopropylamine (2.2 mL, 1.2 eq.) in DMF (30 mL) was stirred at rt for over the weekend. The insolubles were filtered off, the filtrate was concentrated, redissolved in ethyl acetate, washed with sodium bicarbonate and brine, dried and concentrated to give 5.6 g of (2S,3S)-2-cyclopropylcarbamoyl-3-hydroxy-pyrrolidine-1-carboxylic acid tert-butyl ester as a white solid.

A solution of (2S,3S)-2-cyclopropylcarbamoyl-3-hydroxy-pyrrolidine-1-carboxylic acid tert-butyl ester (5.6 g) in 30% of TFA in DCM (50 mL) was stirred at rt for 2 hours. The reaction was concentrated to give 3.5 g of (2S,3S)-3-hydroxy-pyrrolidine-2-carboxylic acid cyclopropylamide as a TFA salt.

$^1$HNMR (400 MHz, DMSO-$d_6$) δ 4.3 (m, 1H), 3.88 (m, 1H), 3.34 (m, 2H), 2.67 (m, 1H), 2.14 (m, 1H), 1.89 (m, 2H), 0.63 (m, 2H), 0.45 (m, 2H).

A mixture of (2S,3S)-3-hydroxy-pyrrolidine-2-carboxylic acid cyclopropylamide (3.5 g, 20 mmol) and LAH (2.3 g, 3 eq.) in THF (50 mL) was heated to reflux for 2 hours. The cooled reaction was diluted with water (2.3 mL), a few drops of 10% NaOH, then water (2.3 mL). After stirring for 30 mins, the insolubles were filtered off, the filtrate was concentrated to give 0.8 g of (2R,3S)-2-cyclopropylaminomethyl-pyrrolidin-3-ol as a pale yellow oil. MS m/z 157 [M$^+$+1].

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (250 mg, 0.48 mmol), HOBt (78 mg, 1.2 eq.), EDC (110 mg, 1.2 eq.), TEA (0.17 mL, 2.5 eq.) and (2R,3S)-2-cyclopropylaminomethyl-pyrrolidin-3-ol (300 mg, 4 eq.) in DMF (10 mL) was stirred at rt for overnight. The reaction was concentrated, washed with water, sodium bicarbonate and brine, dried and concentrated. The residue was purified on a silica gel column to give 100 mg of the titled compound as a yellow solid.

$^1$HNMR (400 MHz, DMSO-d$_6$) δ 13.42 (s, 1H, NH), 11.05 (br s, 1H, NH), 8.07 (s, 1H), 7.68 (s, 1H), 7.34–7.48 (m, 4H), 7.03 (d, 1H), 4.88 (s, 2H), 4.65 (m, 1H), 4.12 (m, 1H), 3.9 (m, 1H), 3.55 (m, 4H), 3.08 (s, 2H), 2.76 (m, 1H), 2.31 (s, 3H, CH$_3$), 2.27 (s, 3H, CH$_3$), 2.12 (m, 2H), 1.8 (m, 1H), 0.37 (m, 2H), 0.2 (m, 2H). MS m/z 655 [M−1].

Example 259

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-Acetylamino-pyrrolidin-1-yl)-ethyl]-amide

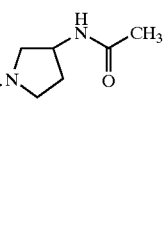

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (252 mg, 0.5 mmol) in DMF (10 mL) was added HOBt (101 mg, 1.5 eq.), EDAC.HCl (144 mg, 1.5 eq.) and TEA (152 mg, 3 eq.). After stirring at rf for 30 mins, to the mixture was added N-[1-(2-amino-ethyl)-pyrrolidin-3-yl]-acetamide (128 mg, 1.5 eq.). After stirring at 30° C. for 72 hours, the reaction was concentrated and the residue was purified on a silica gel column to give 213 mg (65%) of the titled compound as an orange solid.

Example 260

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-piperazin-1-yl-ethyl)-acetamide

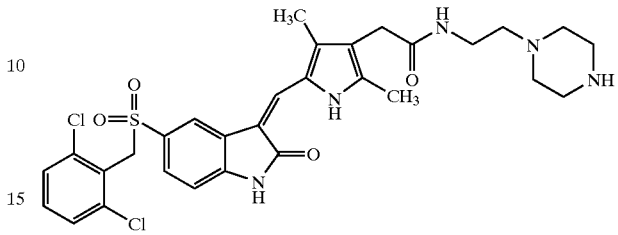

To a solution of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (519 mg, 1 mmol) in DMF (5 mL) was added HOBt (202 mg, 1.3 eq.), EDAC.HCl (288 mg, 1.5 eq) and TEA (302 mg, 3 eq.). After stirring at rt for 30 mins, to the mixture was added 4-(2-amino-ethyl)-piperazine-1-carboxylic acid tert-butyl ester (298 mg, 1.3 eq.). After stirring at 40° C. for 24 hours, the reaction was concentrated and the residue was purified on a silica gel column to give 4-[2-(2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetylamino)-ethyl]-piperazine-1-carboxylic acid tert-butyl ester as a yellow solid.

A solution of 4-[2-(2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetylamino)-ethyl]-piperazine-1-carboxylic acid tert-butyl ester (from the above reaction) and TFA (1 mL) in DCM (10 mL) was stirred at rt for overnight. The reaction was concentrated and purified to give 590 mg of the titled compound as a yellow solid.

$^1$HNMR (400 MHz, DMSO-d$_6$) δ 8.18 (s, 1H), 7.77 (s, 1H), 7.64 (m, 1H, NH), 7.46 (m, 2H), 7.37 (m, 2H), 7.0 (d, 1H), 4.85 (s, 2H), 3.24 (s, 2H), 3.12 (m, 4H), 2.63 (m, 2H), 2.2–2.3 (m, 12H). MS m/z 628 [M−1].

Example 261

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-{2-[4-(2-hydroxy-acetyl)-piperazin-1-yl]-ethyl}-acetamide

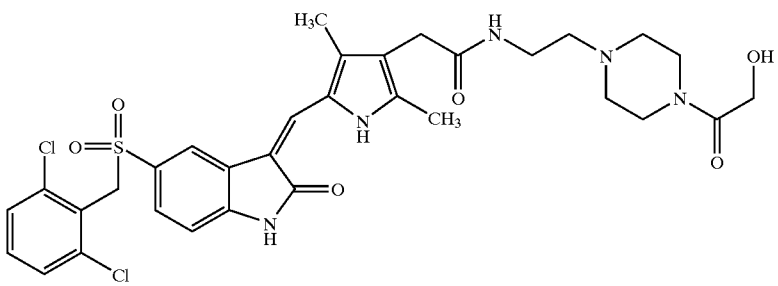

A mixture of 2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-N-(2-piperazin-1-yl-ethyl)-acetamide (300 mg, 0.475 mmol), acetoxyacetyl chloride (97 mg, 1.5 eq.) and TEA (0.5 mL) in DCM (10 mL) was stirred at rt for overnight. The precipitate was collected by vacuum filtration, washed with water and methanol to give 300 mg of acetic acid 2-{4-[2-(2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetylamino)-ethyl]-piperazin-1-yl}-2-oxo-ethyl ester as a red solid.

A mixture of acetic acid 2-{4-[2-(2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetylamino)-ethyl]-piperazin-1-yl}-2-oxo-ethyl ester (100 mg), 10% potassium carbonate in water and methanol (5 mL) was stirred at 40° C. for overnight. The reaction was concentrated, extracted with DCM. The combined DCM was dried, concentrated and purified on a silica gel column to give the titled compound as an orange-red solid. MS m/z 686 [M−1].

Example 262

Synthesis of 5-(2,6-Dichloro-phenylmethanesulfonyl)-3-[1-(4-{2-[(S)-2-((R)-3-hydroxy-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

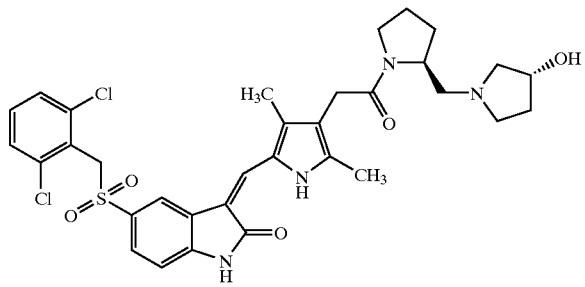

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (156 mg, 0.3 mmol), HOBt (80 mg) and EDAC (110 mg) in DMF (4 mL) was added TEA (3 drops). After stirring at rt for 2 hours, to the mixture was added (R)-1-(S)-1-pyrrolidin-2-ylmethyl-pyrrolidin-3-ol (300 mg). After stirring at rt for overnight, the reaction was concentrated and dissolved in ethyl acetate. It was then washed with water and sodium bicarbonate, dried and concentrated. The residue was purified on a silica gel column to give 210 mg of the titled compound. MS m/z 671 [M+ +1].

Example 263

Synthesis of 5-(2,6-Dichloro-phenylmethanesulfonyl)-3-[1-{3,5-dimethyl-4-[2-oxo-2-((S)-3-pyrrolidin-1-ylmethyl-piperidin-1-yl)-ethyl]-1H-pyrrol-2-yl}-meth-(Z)-ylidene]-1,3-dihydro-indol-2-one

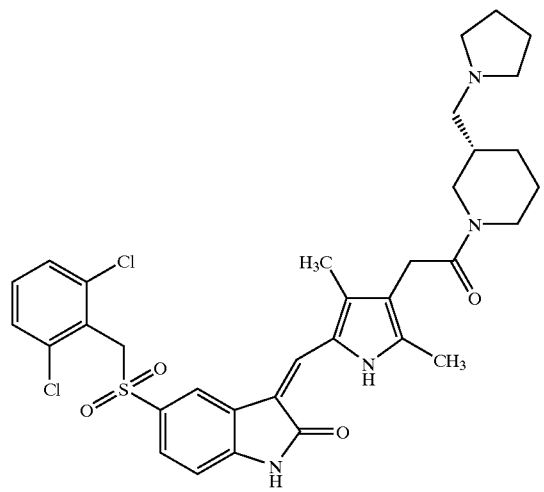

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (156 mg, 0.3 mmol), HOBt (80 mg) and EDAC (110 mg) in DMF (4 mL) was added TEA (3 drops). After stirring at rt for 2 hours, to the mixture was added (R)-3-pyrrolidin-1-ylmethyl-piperidine (250 mg). After stirring at rt for overnight, the reaction was concentrated and dissolved in ethyl acetate. It was then washed with water and sodium bicarbonate, dried and concentrated. The residue was purified on a silica gel column to give 172 mg of the titled compound. MS m/z 667 [M−1].

Example 264

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(2,2,2-trifluoro-ethylamino)-ethyl]-acetamide

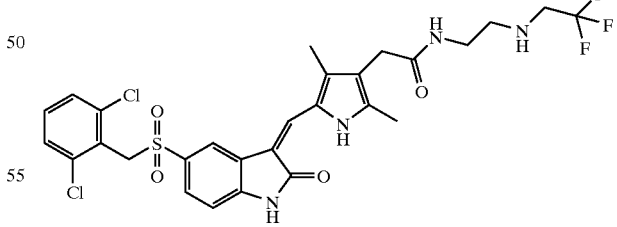

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (267 mg, 0.51 mmol), N-(2,2,2-trifluoro-ethyl)-ethane-1,2-diamine (123 mg, 0.86 mmol), HOBt (104 mg, 0.77 mmol), EDAC (154 mg, 0.81 mmol) and TEA (0.14 mL, 1 mmol) in DMF (3 mL) was stirred At rt for 48 hours. The reaction was concentrated, diluted with sat. sodium bicarbonate and extracted with DCM. The organic layer was washed with brine, dried and purified on a silica gel column to give 237 mg (72%) of the titled compound.

$^1$HNMR (400 MHz, DMSO-d$_6$) 13.48 (s, 1H, NH), 11.29 (s, 1H, NH), 8.2 (d, 1H), 7.79 (t, 1H, CONH), 7.78 (s, 1H), 7.5 (d, 1H), 7.48 (s, 1H), 7.39 (m, 2H), 7.02 (d, J=8 Hz, 1H), 4.87 (s, 2H), 3.31 (m, 1H, NH), 3.27 (s, 2H), 3.22 (m, 2H), 3.11 (m, 2H), 2.65 (m, 2H), 2.32 (s, 3H, CH$_3$), 2.29 (s, 3H, CH$_3$). MS m/z 641 [M−1].

Example 265

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(2,2,2-Trifluoro-ethylamino)-ethyl]-amide

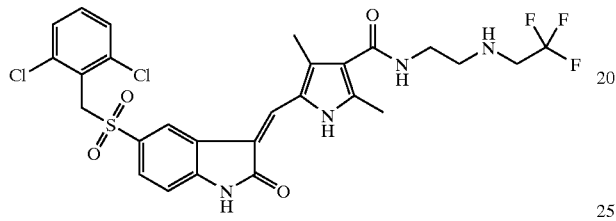

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (95 mg, 0.19 mmol), N-(2,2,2-trifluoro-ethyl)-methanediamine (59 mg, 0.41 mmol), HOBt (41 mg, 0.3 mmol), EDAC (59 mg, 0.3 mmol) and TEA (0.06 mL) in DMF (3 mL) was stirred at rt for 48 hours. The reaction was concentrated, diluted with sodium bicarbonate and extracted with DCM (2×). The combined DCM was washed with brine, dried and concentrated. The residue was purified on a silica gel column to give 82 mg (69%) of the titled compound.

$^1$HNMR (400 MHz, DMSO-d$_6$) δ 13.61 (s, 1H, NH), 11.42 (s, 1H, NH), 8.3 (d, 1H), 7.89 (s, 1H), 7.63 (t, 1H, CONH), 7.51 (d, 1H), 7.49 (s, 1H), 7.44 (dd, 1H), 7.39 (dd, 1H), 7.04 (d, 1h), 4.87 (s, 2H), 3.25–3.3 (m, 5H), 2.77 (m, 2H), 2.45 (s, 6H, 2×CH$_3$). MS m/z 629 [M$^+$+1].

Example 266

Synthesis of 3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one

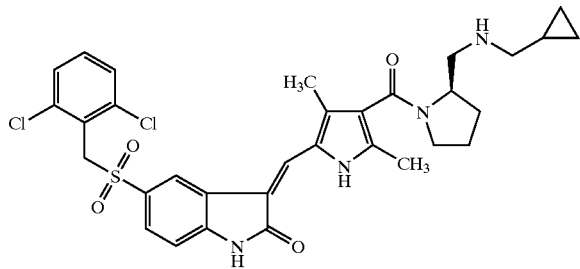

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), EDAC (150 mg, 0.78 mmol) and HOBt (54 mg, 0.4 mmol) in DMF (4 mL) was added cyclopropylmethyl-(R)-1-pyrrolidin-2-ylmethyl-amine (100 mg, 0.65 mmol) and TEA (0.12 mL). The mixture was stirred at rt for 20 hours. The reaction was diluted with water and NaHCO$_3$, extracted with 5% methanol in DCM. The combined extracts were concentrated and purified on a silica gel column to give the titled compound.

$^1$HNMR (400 MHz, DMSO-d$_6$) δ 13.55 (br s, 1H, NH), 11.45 (br s, 1H, NH), 8.28 (d, 1H), 7.86 (s, 1H), 7.37–7.5 (m, 4H), 7.04 (d, 1H), 4.83 (s, 2H), 4.33 (m, 1H), 2.66 (m, 2H), 2.34 (m & s, 6H), 1.65–2.15 (m, 7H), 0.96 (m, 1H), 0.31 (m, 2H), 0.25 (m, 2H). MS m/z 639 [M−1].

Example 267

Synthesis of (2S,4R)-1-{5-[5-(2,6-Dichloro-phenylmethanesulfonyl)-2-oxo-1,2-dihydro-indol-(3Z)-ylidenemethyl]-2,4-dimethyl-1H-pyrrole-3-carbonyl}-4-hydroxy-pyrrolidine-2-carboxylic acid Cyclopropylamide

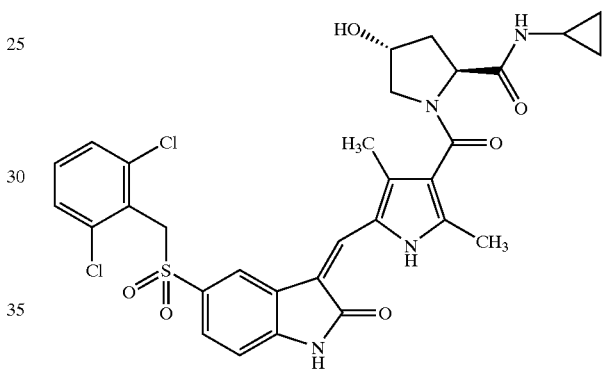

To a mixture of (2S,4R)-4-hydroxy-pyrrolidine-1,2-dicarboxylic acid 1-tert-butyl ester (6 g, 26 mmol), DCC (5.97 g, 29 mmol) and HOBt (0.8 g, 6 mmol) in DCM (26 mL) was added cyclopropylamine (2.1 mL, 31 mmol) and DIPEA (6.8 mL, 39 mmol). The mixture was stirred at rt for overnight. The insolubles were filtered off, the filtrate was concentrated, the residue was treated with 10% citric acid (60 mL) and extracted with DCM, washed with NaHCO$_3$ and concentrated to give 1.8 g of (2S,4R)-2-cyclopropylcarbamoyl-4-hydroxy-pyrrolidine-1-carboxylic acid tert-butyl ester as a light brown solid. More product was obtained by combining the citric acid solution and the NaHCO$_3$ wash, after concentrated, the residue was washed with lot of ethyl acetate. The combined ethyl acetate was concentrated and dried to give 4.2 g of the product. Total of 6 g (85%) of (2S,4R)-2-cyclopropylcarbamoyl-4-hydroxy-pyrrolidine-1-carboxylic acid tert-butyl ester was obtained.

$^1$HNMR (400 MHz, DMSO-d$_6$) δ 7.92 (d, 1H), 7.85 (d, 1H), 4.92 (d, 1H), 4.15 (br s, 1H), 3.97 (q, 1H), 3.2 (m, 1H), 2.55 (m, 1H), 1.9 (m, 1H), 1.71 (m, 1H), 1.32 (s, 3H, CH$_3$), 1.26 (6H, 2×CH$_3$), 0.53 (m, 2H), 0.31 (m, 2H).

A mixture of (2S,4R)-2-cyclopropylcarbamoyl-4-hydroxy-pyrrolidine-1-carboxylic acid tert-butyl ester (1.1 g) and TFA (20 mL) in DCM (30 mL) was stirred at rt for 2 hours. The reaction was concentrated to give (2S,4R)-4-hydroxy-pyrrolidine-2-carboxylic acid cyclopropylamide.

¹HNMR (400 MHz, DMSO-d₆) δ 9.53 (br s, 1H), 8.58 (br s, 1H, NH), 8.52 (d, 1H), 4.34 (d, 1H), 4.09 (m, 1H), 3.22 (m, 1H), 2.99 (m, 1H), 2.61 (m, 1H), 2.13 (m, 1H), 1.76 (m, 1H), 0.6 (m, 2H), 0.37 (m, 2H).

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (232 mg, 0.46 mmol), HOBt (68 mg, 0.51 mmol) and EDC (105 mg, 0.55 mmol) in DMF (8 mL) was added (2S,4R)-4-hydroxy-pyrrolidine-2-carboxylic acid cyclopropylamide (excess) and TEA (0.95 mL, 0.6 mmol). The mixture was stirred at rt for 3 days. The reaction was diluted with DCM (200 mL), washed with NH₄Cl, NaHCO₃, brine, dried and concentrated. The residue was purified on a silica gel column to give 92 mg of the titled compound. MS m/z 671 [M−1].

Example 268

Synthesis of (2S,4R)-1-(2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetyl)-4-hydroxy-pyrrolidine-2-carboxylic acid Cyclopropylamide

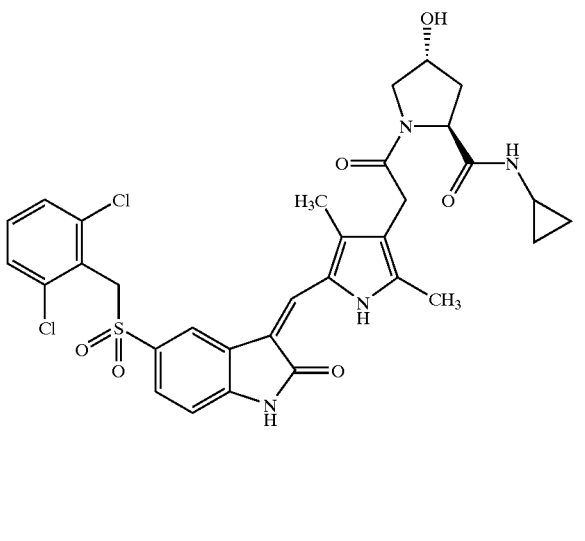

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (238 mg, 0.46 mmol), HOBt (68 mg, 0.51 mmol) and EDC (105 mg, 0.55 mmol) in DMF 98 mL) was added (2S,4R)-4-hydroxy-pyrrolidine-2-carboxylic acid cyclopropylamide (excess) and TEA (0. 95 mL, 0.6 mmol). The mixture was stirred at rt for 3 days. The reaction was diluted with DCM (200 mL), washed with NH₄Cl, NaHCO₃, brine, dried and concentrated. The residue was purified on a silica gel column to give 120 mg of the titled compound. MS m/z 655 [M−1].

Example 269

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-3-pyrrolidin-1-yl-propyl)-amide

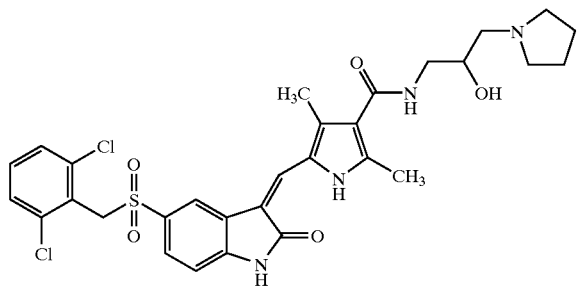

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with 1-amino-3-pyrrolidin-1-yl-propan-2-ol to give the titled compound as a yellow solid.

¹HNMR (400 MHz, DMSO-d₆) δ 13.6 (br s, 1H, NH), 11.41 (br s, 1H, NH), 8.28 (d, J=2 Hz, 1H), 7.87 (s, 1H), 7.61 (t, 1H, CONH), 7.49 (d, 1H), 7.47 (s, 1H), 7.42 (dd, J=2 & 8 Hz, 1H), 7.38 (dd, 1H), 7.03 (d, J=8 Hz, 1H), 4.86 (s, 1H), 3.74 (m, 1H), 3.28–3.4 (m, 2H), 3.16 (m, 1H), 2.55 (m, 4H), 2.45 (m, 6H), 2.4 (m, 2H), 1.67 (m, 4H). MS m/z 631 [M⁺+1].

Example 270

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-Cyclopropylamino-2-hydroxy-propyl)-amide

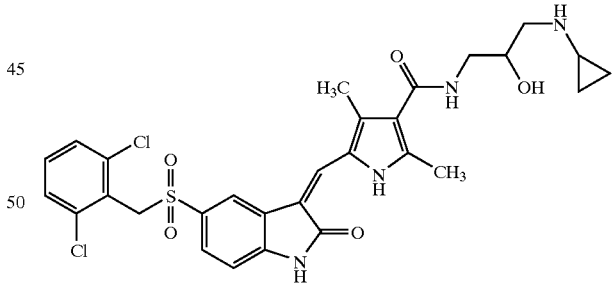

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with 1-amino-3-cyclopropylamino-propan-2-ol to give the titled compound as a yellow solid.

¹HNMR (400 MHz, DMSO-d₆) δ 13.61 (s, 1H, NH), 11.42 (br s, 1H, NH), 8.29 (d, J=2 Hz, 1H), 7.88 (s, 1H), 7.64 (m, 1H, CONH), 7.51 (d, 1H), 7.49 (s, 1H), 7.44 (dd, J=2 & 8 Hz, 1H), 7.39 (dd, 1H), 7.04 (d, J=8 Hz, 1H), 4.87 (s, 2H), 3.69 (m, 1H, OH), 3.2–3.4 (m, 3H), 2.66 (m, 1H), 2.56 (m, 1H), 2.46 (s, 6H, 2×CH₃), 2.1 (m, 1H), 1.9 (s, 1H), 0.35 (m, 2H), 0.22 (m, 2H). MS m/z 617 [M⁺+1].

Example 271

Synthesis of 3-[1-[4-(4-Cyclopropyl-piperazine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

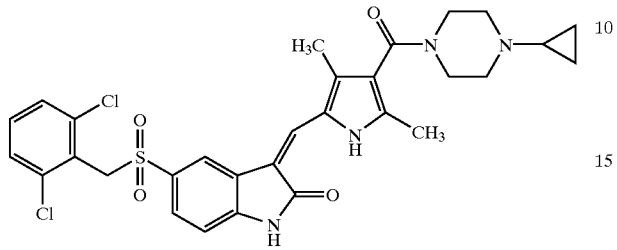

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with 1-cyclopropyl-piperazine to give the titled compound.

$^1$HNMR (400 MHz, DMSO-$d_6$) δ 13.57 (s, 1H, NH), 11.41 (s, 1H, NH), 8.28 (d, 1H), 7.87 (s, 1H), 7.51 (d, 1H), 7.49 (s, 1H), 7.44 (dd, 1H), 7.40 (dd, 1H), 7.04 (d, 1H), 4.87 (s, 1H), 3.2–3.6 (m, 8H), 2.32 (s, 3H, CH$_3$), 2.31 (s, 3H, CH$_3$), 1.65 (m, 1H), 0.43 (m, 2H), 0.33 (m, 2H). MS m/z 611 [M−1].

Example 272

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid Cyclopropylamide

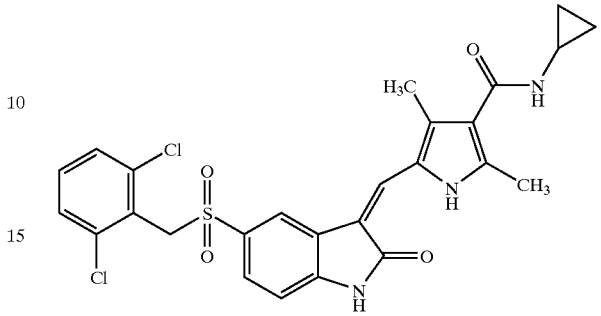

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with cyclopropylamine to give the titled compound.

$^1$HNMR (400 MHz, DMSO-$d_6$) δ 13.57 (br s, 1H, NH), 11.39 (s, 1H, NH), 8.27 (s, 1H), 7.85 (s, 1H), 7.78 (d, 1H), 7.49 (s, 1H), 7.47 (s, 1H), 7.42 (dd, 1H), 7.38 (m, 1H), 7.02 (d, 1H), 4.85 (s, 2H), 2.40 (s, 6H, 2×CH$_3$), 2.28 (s, 1H), 0.67 (m, 2H), 0.51 (m, 2H). MS m/z 542 [M−1].

Example 273

Synthesis of N-[2-(3-Acetylamino-pyrrolidin-1-yl)-ethyl]-2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetamide

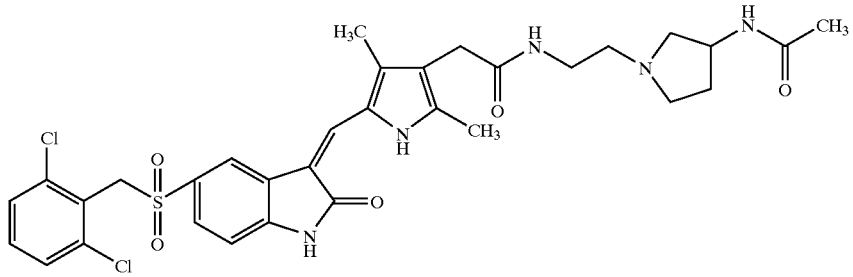

To a solution of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (260 mg, 0.5 mmol) in DMF (3 mL) was added HOBt (101 mg, 1.5 eq.), EDAC.HCl (144 mg, 3 eq.) and TEA (152 mg, 1.5 eq.). After stirring at rt for 30 mins, to the mixture was added N-[1-(2-amino-ethyl)-pyrrolidin-3-yl]-acetamide (128 mg, 1.5 eq.). After stirring at 40° C. for overnight, the cooled reaction was concentrated and the residue was purified on a silica gel column to give the title compound as a yellow solid.

$^1$HNMR (400 MHz, DMSO-$d_6$) δ 8.18 (s, 1H), 7.96 (m, 1H), 7.82 (m, 1H, NH), 7.78 (s, 1H), 7.48 (m, 2H), 7.38 (m, 2H), 7.0 (d, 1H), 4.85 (s, 2H), 4.1 (m, 1H), 3.27 (s, 2H), 3.16 (m, 2H), 2.8 (m, 1H), 2.68 (m, 1H), 2.54 (m, 2H), 2.42 (m, 2H), 2.32 (s, 3H), CH$_3$), 2.28 (s, 3H, CH$_3$), 2.04 (m, 2H), 1.77 (s, 3H, CH$_3$), 1.54 (m, 2H). MS m/z 670 [M−1].

Example 274

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid{2-[4-(2-hydroxy-acetyl)-piperazin-1-yl]-ethyl}-amide

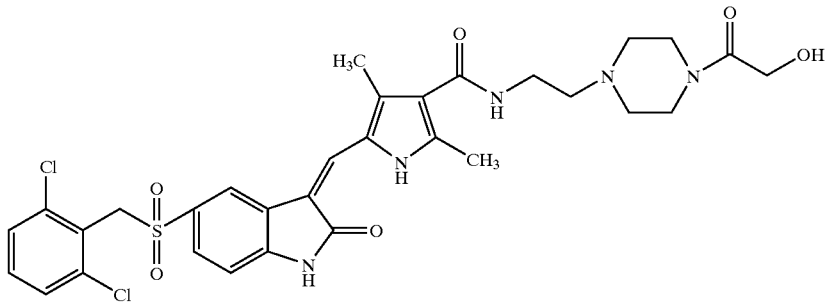

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (505 mg, 1 mmol) in DMF (10 mL) was added HOBt (202 mg, 1.3 eq.), EDAC.HCl (288 mg, 1.5 eq.) and TEA (302 mg, 3 eq.). After stirring at rt for 30 mins, to the mixture was added 4-(2-amino-ethyl)-piperazine-1-carboxylic acid tert-butyl ester (298 mg, 1.3 eq.). After stirring at 40° C. for overnight, the reaction was diluted with methanol (2 mL), the precipitate was collected by vacuum filtration, washed with methanol, water and dried to give 700 mg of 4-[2-({5-[5-(2,6-dichloro-phenylmethanesulfonyl)-2-oxo-1,2-dihydro-indol-(3Z)-ylidenemethyl]-2,4-dimethyl-1H-pyrrole-3-carbonyl}-amino)-ethyl]-piperazine-1-carboxylic acid tert-butyl ester as a yellow solid.

A mixture of 4-[2-({5-[5-(2,6-dichloro-phenylmethanesulfonyl)-2-oxo-1,2-dihydro-indol-(3Z)-ylidenemethyl]-2,4-dimethyl-1H-pyrrole-3-carbonyl}-amino)-ethyl]-piperazine-1-carboxylic acid tert-butyl ester (370 mg, 0.52 mmol) and TFA (3 mL) in DCM (20 mL) was stirred at rt for overnight. The reaction was concentrated and purified to give 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (2-piperazin-1-yl-ethyl)-amide.

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (2-piperazin-1-yl-ethyl)-amide (from the above reaction), acetoxyacetyl (141 mg) and TEA (2 mL) in DCM (10 mL) was stirred at rt for 4 hours. The precipitate was collected by vacuum filtration, washed and dried to give acetic acid 2-{4-[2-({5-[5-(2,6-dichlorophenylmethanesulfonyl)-2-oxo-1,2-dihydro-indol-(3Z)-ylidenemethyl]-2,4-dimethyl-1H-pyrrole-3-carbonyl}-amino)-ethyl]-piperazin-1-yl}-2-oxo-ethyl ester.

A mixture of acetic acid 2-{4-[2-({5-[5-(2,6-dichlorophenylmethanesulfonyl)-2-oxo-1,2-dihydro-indol-(3Z)-ylidenemethyl]-2,4-dimethyl-1H-pyrrole-3-carbonyl}-amino)-ethyl]-piperazin-1-yl}-2-oxo-ethyl ester (from the above reaction) and 10% potassium carbonate (2.67 g) in water (20 mL) and methanol (10 mL) was stirred at 40° C. for overnight. The precipitate was collected by vacuum filtration, washed with methanol, water and dried to give 305 mg (45% for 4 steps) of the titled compound as a yellow solid.

$^1$HNMR (400 MHz, DMSO-$d_6$) δ 13.58 (s, 1H, NH), 11.4 (s, 1H, NH), 8.3 (s, 1H), 7.88 (s, 1H), 7.55 (m, 1H, NH), 7.5 (m, 2H), 7.4 (m, 2H), 7.0 (d, 1H), 4.88 (s, 2H), 4.52 (m, 1H, OH), 4.05 (m, 2H), 3.43 (m, 2H), 3.3 (m, 4H), 2.44 (m, 12H). MS m/z 672 [M−1].

Example 275

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-pyrrolidin-1-yl-propyl)-acetamide

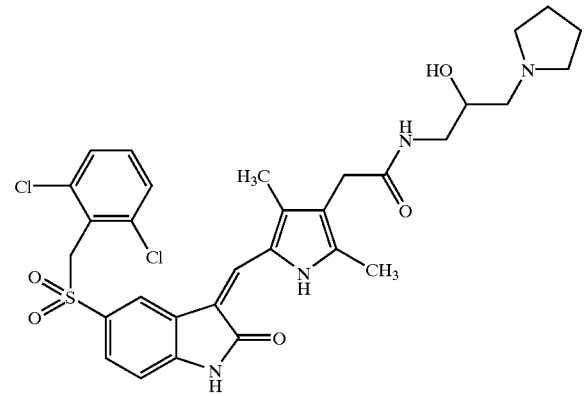

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (300 mg, 0.578 mmol), HOBt (78 mg, 1 eq.) and EDAC (222 mg, 2 eq.) in DMF (1.5 mL) was stirred at rt for 30 mins. To the mixture was added 1-amino-3-pyrrolidin-1-yl-propan-2-ol (170 mg, 2 eq.) in DMF (1.5 mL). After stirring at rt for overnight, the reaction was concentrated and purified on a silica gel column to give 169 mg (45%) of the titled compound.

$^1$HNMR (400 MHz, DMSO-$d_6$) δ 13.46 (s, 1H, NH), 11.3 (br s, 1H, NH), 8.16 (d, 1H), 7.75 (s & m, 2H), 7.48 (s, 1H), 7.46 (s, 1H), 7.37 (m, 2H), 7.01 (d, J=8 Hz, 1H), 4.85 (s, 2H), 4.7 (br s, 1H, OH), 3.5–3.6 (m, 2H), 3.35 (s, 2H), 3.2–3.4 (m, 2H), 2.95 (m, 1H), 2.4 (m, 4H), 2.31 (s, 3H, CH$_3$), 2.27 (s, 3H, CH$_3$), 1.61 (m, 4H). MS m/z 643 [M−1].

Example 276

Synthesis of N-(3-Cyclopropylamino-2-hydroxy-propyl)-2-{5-[5-(2,6-dichlorophenylmethanesulfonyl)-2-oxo-1,2-dihydro-indol-(3Z)-ylidenemethyl]-2,4-dimethyl-1H-pyrrol-3-yl}-acetamide

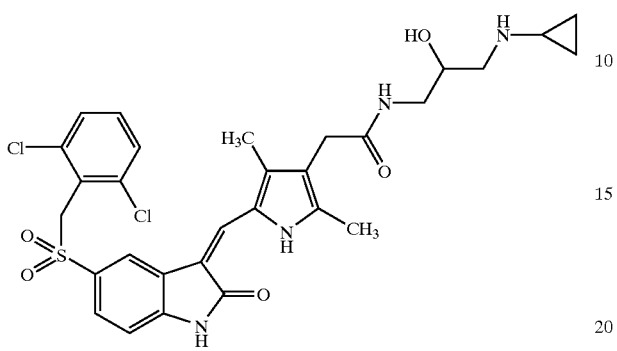

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (208 mg, 0.4 mmol), HOBt (54 mg, 1 eq.) and EDAC (153 mg, 2 eq.) in DMF (1.5 mL) was stirred at rt for 30 mins. To the mixture was added 1-amino-3-cyclopropylamino-propan-2-ol (104 mg, 2 eq.) in DMF (1.5 mL). After stirring at rt for overnight, the reaction was concentrated and purified on a silica gel column to give 115 mg (45%) of the titled compound.

$^1$HNMR (400 MHz, DMSO-$d_6$) δ 13.48 (s, 1H, NH), 11.25 (br s, 1H, NH), 8.19 (s, 1H), 7.78 (s, 1H), 7.76 (m, 1H, NH), 7.5 (d, 1H), 7.48 (s, 1H), 7.39 (m, 2H), 7.02 (d, J=8 Hz, 1H), 4.86 (s, 2H), 4.76 (d, 1H, OH), 3.56 (m, 1H, NH), 3.31 (m, 1H), 3.29 (s, 2H), 3.06 (m, 2H), 2.35–2.5 (m, 2H), 2.32 (s, 3H, CH$_3$), 2.29 (s, 3H, CH$_3$), 2.04 (m, 1H), 0.33 (m, 2H), 0.18 (m, 2H). MS m/z 629 [M−1].

Example 277

Synthesis of 3-[1-{4-[2-(4-Cyclopropyl-piperazin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

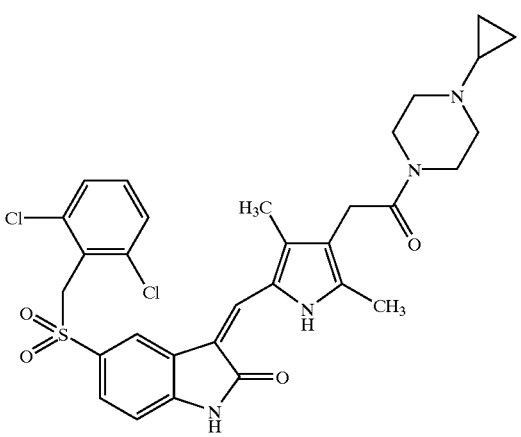

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (208 mg, 0.4 mmol), HOBt (54 mg, 1 eq.) and EDAC (153 mg, 2 eq.) in DMF (1.5 mL) was stirred at rt for 30 mins. To the mixture was added 1-cyclopropyl-piperazine (101 mg, 2 eq.) in DMF (1.5 mL). After stirring at rt for overnight, the precipitate was collected by vacuum filtration, washed with water, sodium bicarbonate and ether to give 108 mg (43%) of the titled compound.

$^1$HNMR (400 MHz, DMSO-$d_6$) δ 13.46 (s, 1H, NH), 11.26 (s, 1H, NH), 8.17 (d, 1H), 7.76 (s, 1H), 7.48 (d, 1H), 7.46 (s, 1H), 7.36 (m, 2H), 6.99 (d, J=8 Hz, 1H), 4.84 (s, 2H), 3.49 (s, 2H), 3.46 (m, 2H), 3.39 (m, 2H), 2.47 (m, 4H), 2.25 (s, 3H, CH$_3$), 2.22 (s, 3H, CH$_3$), 1.6 (m, 1H), 0.4 (m, 2H), 0.31 (m, 2H). MS m/z 625 [M−1].

Example 278

Synthesis of 3-[1-[4-(4-Cyclopropylmethyl-piperazine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

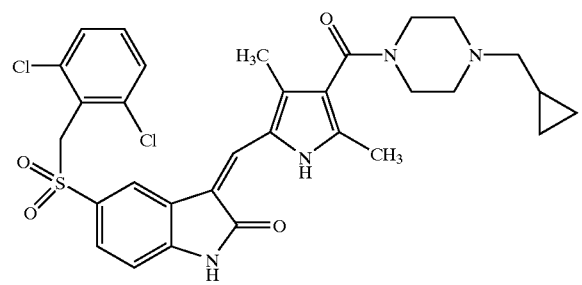

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), HOBt (54 mg, 1 eq.) and EDAC (154 mg, 2 eq.) in DMF (1.5 mL) was stirred at rt for 30 mins. To the mixture was added 1-cyclopropyl-piperazine (112 mg, 2 eq.) in DMF (1.5 mL). After stirring at rt for overnight, the precipitate was collected by vacuum filtration, washed with water, sodium bicarbonate and water and dried to give 227 mg (90%) of the titled compound.

$^1$HNMR (400 MHz, DMSO-$d_6$) δ 13.51 (s, 1H, NH), 11.36 (s, 1H, NH), 8.23 (d, 1H), 7.81 (s, 1H), 7.45 (d, 1H), 7.43 (s, 1H), 7.36 (m, 2H), 6.98 (d, J=8 Hz, 1H), 4.82 (s, 2H), 3.45 (m, 4H), 2.38 (m, 2H), 2.25 (s, 6H, 2×CH$_3$), 2.14 (d, 2H), 0.78 (m, 1H), 0.42 (m, 2H), 0.04 (m, 2H). MS m/z 625 [M−1].

Example 279

Synthesis of 3-[1-{4-[2-(4-Cyclopropylmethyl-piperazin-1-yl)-2-oxo-ethyl]-3,5-dimethyl-1H-pyrrol-2-yl}-meth-(Z)-ylidene]-5-(2,6-dichlorophenylmethanesulfonyl)-1,3-dihydro-indol-2-one

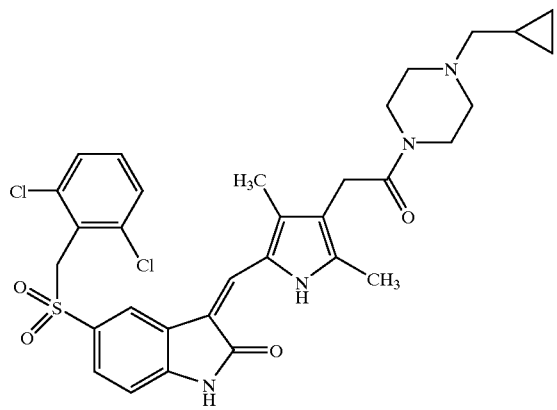

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (210 mg, 0.4 mmol), HOBt (54 mg, 1 eq.) and EDAC (77 mg, 1 eq.) in DMF (1.5 mL) was stirred at rt for 30 mins. To the mixture was added 1-cyclopropylmethyl-piperazine (112 mg, 2 eq.) in DMF (1.5 mL). After stirring at rt for overnight, the precipitate was collected by vacuum filtration, washed with water, sodium bicarbonate and water and then dried to give 240 mg (94%) of the titled compound.

$^1$HNMR (400 MHz, DMSO-$d_6$) δ 13.48 (s, 1H, NH), 11.28 (s, 1H, NH), 8.19 (s, 1H), 7.77 (s, 1H), 7.5 (d, 1H), 7.48 (s, 1H), 7.39 (m, 2H), 7.02 (d, J=8 Hz, 1H), 4.86 (s, 2H), 3.54 (m, 2H), 3.51 (s, 2H), 3.47 (m, 2H), 2.4 (m, 4H), 2.27 (s, 3H, $CH_3$), 2.24 (s, 3H, $CH_3$), 2.19 (m, 2H), 0.82 (m, 1H), 0.46 (m, 2H), 0.07 (m, 2H). MS m/z 639 [M−1].

Example 280

Synthesis of 5-(2,6-Dichloro-phenylmethanesulfonyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one

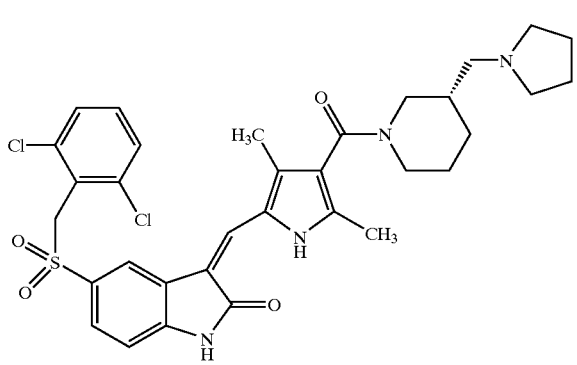

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (0.2 g, 0.4 mmol), HOBt (54 mg, 1 eq.), EDAC (77 mg, 1 eq.) in DMF (1.5 mL) was stirred at rt for 10 mins. To the mixture was added (R)-3-pyrrolidin-1-ylmethyl-piperidine (0.2 g, 3 eq.). After stirring at rt for over the weekend, the precipitate was collected by vacuum filtration, washed with water, sodium bicarbonate and water. The solid was then purified on a silica gel column to give 101 mg (46%) of the titled compound.

$^1$HNMR (400 MHz, DMSO $d_6$) δ 13.49 (s, 1H, NH), 11.38 (s, 1H, NH), 8.23 (s, 1H), 7.80 (s, 1H), 7.43 (m, 2H), 7.36 (m, 2H), 6.99 (d, 1H), 4.81 (s, 2H, $CH_2$), 2.9 (m, 1H), 2.22 (s, 6H, 2×$CH_3$), 0.8–2.5 (m, aliphatic H). MS m/z 653 (M−1).

Example 281

Synthesis of 3-[1-(4-{(S)-2-[(Cyclopropyl-methyl-amino)-methyl]-pyrrolidine-1-carbonyl}-3,5-dimethyl-1H-pyrrol-2-yl)-meth-(Z)-ylidene]-5-(2,6-dichlorophenylmethanesulfonyl)-1,3-dihydro-indol-2-one

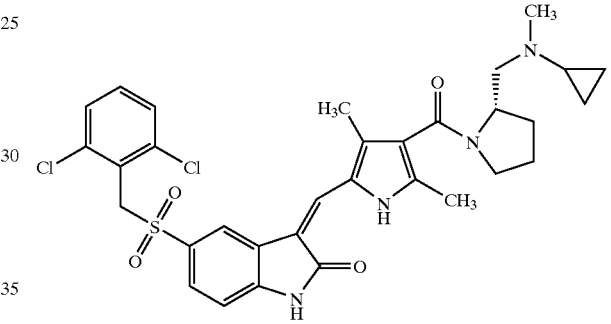

A mixture of (S)-pyrrolidine-1,2-dicarboxylic acid 1-tert-butyl ester (1 eq.), cyclopropyl-methyl-amine hydrochloride (1.2 eq.), HOBt (1.5 eq.), EDAC (1.5 eq.) and TEA (3 eq.) in DMF was stirred at rt for 48 hours. The reaction was concentrated, diluted with sodium bicarbonate and extracted with DCM. The combined DCM was washed with brine, dried, concentrated, purified on a silica gel column to give (S)-2-(cyclopropyl-methyl-carbamoyl)-pyrrolidine-1-carboxylic acid tert-butyl ester.

A solution of (S)-2-(cyclopropyl-methyl-carbamoyl)-pyrrolidine-1-carboxylic acid tert-butyl ester in 50% TFA in DCM was stirred at rt for 4 hours. The reaction was concentrated and purified to give (S)-pyrrolidine-2-carboxylic acid cyclopropylmethyl-amide.

To a solution of (S)-pyrrolidine-2-carboxylic acid cyclopropyl-methyl-amide in THF at 0° C. was added borane (2 eq., 1 M in THF) dropwise. The mixture was allowed to warm up to rt then heated to reflux for 24 hours. The cooled reaction was acidified with HCl and heated at 75° C. for 10 mins. The mixture was concentrated, basified with 2N NaOH and extracted with 10% methanol in DCM. The combined DCM was dried and concentrated to give cyclopropyl-methyl-(S)-1-pyrrolidin-2-ylmethyl-amine.

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (165 mg, 0.33 mmol), cyclopropyl-methyl-(S)-1-pyrrolidin-2-ylmethyl-amine (65 mg, 0.46 mmol), HOBt (687 mg, 0.5 mmol), EDAC (101 mg, 0.53 mmol) and TEA (0.1 mL) in DMF (4 mL) was stirred at rt for 48 hours. The reaction was concentrated, diluted with sodium bicarbonate, extracted with DCM. The combined DCM was dried, concentrated and purified on a silica gel column to give the titled compound.

¹HNMR (400 MHz, DMSO-d₆) δ 13.52 (br s, 1H, NH), 11.40 (s, 1H, NH), 8.27 (s, 1H), 7.85 (s, 1H), 7.5 (s, 1H), 7.48 (s, 1H), 7.41 (m, 2H), 7.04 (d, 1H), 4.87 (s, 2H), 4.35 (m, 1H), 3.72 (m, 1H), 3.48 (m, 2H), 3.23 (m, 2H), 2.8 (m, 1H), 2.4 (m, 2H), 2.32 (6H, 2×CH₃), 175–1.95 (m, 5H), 0.15–0.45 (m, 4H). MS m/z 639 [M−1].

Example 282

Synthesis of 3-[1-{4-[2-((2S,4R)-2-Cyclopropylaminomethyl-4-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

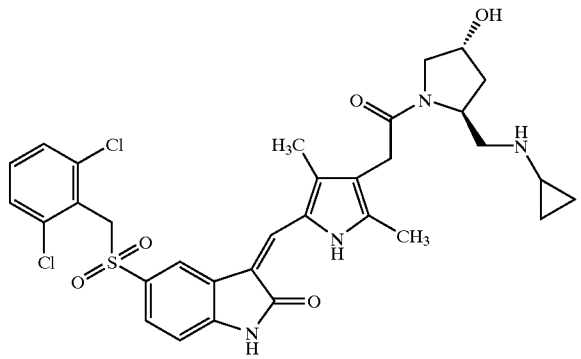

To a mixture of {5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetic acid (238 mg, 0.46 mmol), HOBt (69 mg, 1.2 eq.) and EDC (105 mg, 1.2 eq.) in DMF (8 mL) was added TEA (69 mg, 2.5 eq.) and (3R,5S)-5-cyclopropylaminomethyl-pyrrolidin-3-ol (312 mg, 4 eq.). After stirring at rt for 1 day, the reaction was diluted with DCM (200 mL), washed with ammonium chloride solution, sodium bicarbonate and brine, dried and concentrated. The residue was purified on a silica gel column to give 52 mg of the titled compound as a yellow solid.

¹HNMR (400 MHz, DMSO-d₆) δ 13.5 (s, 1H, NH), 11.3 (s, 1H, NH), 8.19 (d, 1H), 7.78 (s, 1H), 7.5 (s, 1H), 7.38 (m, 2H), 7.02 (d, J=8 Hz, 1H), 5.03 (d, 2H, OH), 4.86 (s, 2H), 4.29 (m, 1H), 4.1 (m, 1H), 2.56 (m, 1H), 3.43 (s, 2H), 2.9 (m, 1), 2.67 (m, 1H), 2.29 (s, 3H, CH₃), 2.26 (s, 3H, CH₃), 1.87 (m, 2H), 1.7 (m, 2H), 1.6 (m, 1H), 0.4 (m, 2H), 0.3 (m, 2H). MS m/z 657 [M+1].

Example 283

Synthesis of 3-[1-[4-((2R,4R)-2-Cyclopropylaminomethyl-4-hydroxy-pyrrolidine-1-carbonyl)-3,5-dimethyl-1H-pyrrol-2-yl]-meth-(Z)-ylidene]-5-(2,6-dichlorophenylmethanesulfonyl)-1,3-dihydro-indol-2-one

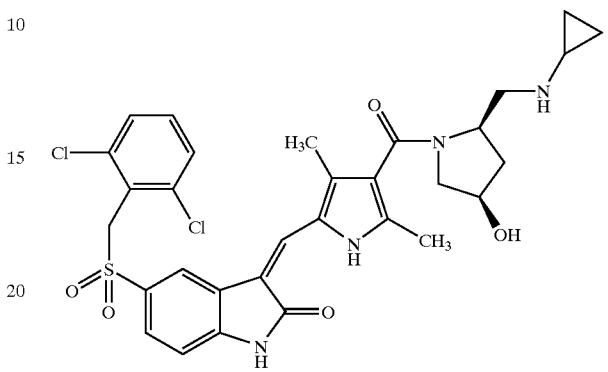

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), HOBt (81 mg, 1.2 eq.), EDC (115 mg, 1.2 eq.), TEA (0.17 mL, 2.5 eq.) and (3R,5R)-5-cyclopropylamninomethyl-pyrrolidin-3-ol (312 mg, 4 eq.) in DMF (10 mL) was stirred at rt for overnight. The reaction was concentrated, washed with water, sodium bicarbonate and brine, dried and concentrated. The residue was purified on a silica gel column to give 100 mg of the titled compound as a yellow solid.

¹HNMR (400 MHz, DMSO-d₆) δ 13.53 (br s, 1H, NH), 11.40 (s, 1H, NH), 8.27 (s, 1H), 7.85 (s, 1H), 7.51 (d, 1H), 7.42 (m, 3H), 7.04 (d, 1H), 4.87 (s, 2H), 4.25 (m, 1H), 4.1 (m, 1H), 3.75 (m, 1H), 3.31 (m, 1H), 3.10 (m, 1H), 2.94 (m, 2H), 2.45 (s, 6H, 2×CH₃), 2.18 (m, 3H), 1.74 (m, 1H), 0.41 (m, 2H), 0.25 (m, 2H). MS m/z 641 [M−1].

Example 284

Synthesis of 3-[1-[4-((2R,3S)-2-Cyclopropylaminomethyl-3-hydroxy-pyrrolidine-1-carbonyl)-3,5-dimethyl-1H-pyrrol-2-yl]-meth-(Z)-ylidene]-5-(2,6-dichlorophenylmethanesulfonyl)-1,3-dihydro-indol-2-one

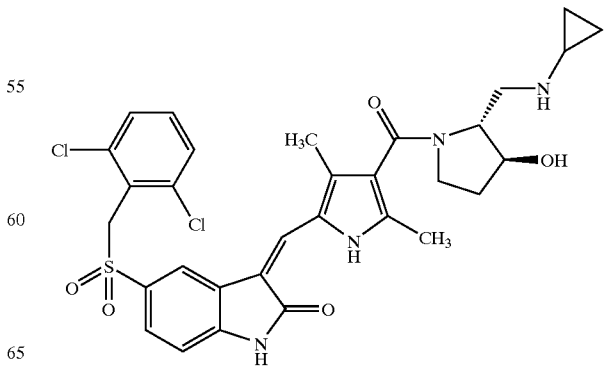

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), HOBt (81 mg, 1.2 eq.), EDC (115 mg, 1.2 eq.), TEA (0.17 mL, 2.5 eq.) and (2R,3S)-2-cyclopropylaminomethyl-pyrrolidin-3-ol (312 mg, 4 eq.) in DMF (10 mL) was stirred at rt for overnight. The reaction was concentrated, washed with water, sodium bicarbonate and brine, dried and concentrated. The residue was purified on a silica gel column to give 100 mg of the titled compound as a yellow solid.

$^1$HNMR (400 MHz, DMSO-d$_6$) δ 13.45 (br s, 1H, NH), 11.18 (br s, 1H, NH), 8.14 (s, 1H), 7.75 (s, 1H), 7.47 (m, 3H), 7.38 (m, 1H), 7.05 (d, 1H), 4.89 (s, 2H), 4.74 (m, 1H), 4.19 (m, 1H), 3.4 (m, 3H), 3.08 (m, 2H), 2.34 (s, 3H, CH$_3$), 2.32 (s, 3H, CH$_3$), 2.05 (m, 2H), 1.77 (m, 2H), 0.29 (m, 2H), 0.17 (m, 2H). MS m/z 641 [M−1].

Example 285

Synthesis of 5-(2,6-Dichloro-phenylmethanesulfonyl)-3-[1-{4-[(S)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

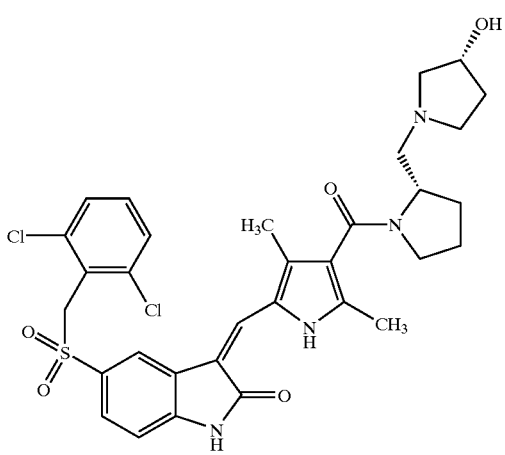

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), HOBt (54 mg, 1 eq.) and EDAC (77 mg, 1 eq.) in DMF (1.5 mL) was stirred at rt for 10 mins. To the mixture was then added (R)-1-(S)-1-pyrrolidin-2-ylmethyl-pyrrolidin-3-ol (200 mg, 3 eq.) in DMF (1.5 mL). After stirring at rt for over the weekend, the precipitate was collected by vacuum filtration, washed with water, sodium bicarbonate and water, and then dried. The solid was purified on a silica gel column to give 79 mg (30%) of the titled compound.

$^1$HNMR (400 MHz, DMSO-d$_6$) δ 13.46 (br s, 1H, NH), 11.45 (s, 1H, NH), 8.2 (s, 1H), 7.78 (s, 1H), 7.44 (d, 1H), 7.42 (s, 1H), 7.36 (m, 2H), 6.99 (d, J=8 Hz, 1H), 4.81 (s, 2H), 4.58 (m, 1H), 4.15 (m, 1H), 3.51 (m, 1H), 3.16 (m, 2H), 2.72 (m, 2H), 2.25 (s, 6H, 2×CH$_3$), 2.2–2.3 (m, 1H), 1.85 (m, 5H), 1.27 (m, 2H), 1.24 (m, 2H).

Example 286

Synthesis of 5-(2,6-Dichloro-phenylmethanesulfonyl)-3-[1-{4-[(R)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

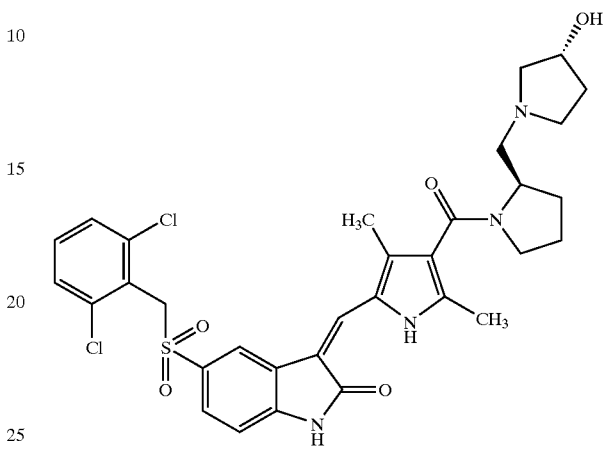

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (0.2 g, 0.4 mmol), HOBt (54 mg, 1 eq.), EDAC (77 mg, 1 eq.) in DMF (1.5 mL) was stirred at rt for 10 mins. To the mixture was added (R)-1-(R)-1-pyrrolidin-2-ylmethyl-pyrrolidin-3-ol (0.2 g, 3 eq.). After stirring at rt for over the weekend, the precipitate was collected by vacuum filtration, washed with water, sodium bicarbonate and water, and then dried. The solid was purified on a silica gel column to give 159 mg (61%) of the titled compound.

$^1$HNMR (400 MHz, DMSO d$_6$) δ 13.47 (s, 1H, NH), 11.38 (s, 1H), 8.20 (s, 1H), 7.79 (s, 1H), 7.44 (m, 2H), 7.36 (m, 2H), 6.99 (d, 1H), 4.81 (s, 2H, CH$_2$), 2.27 (s, 6H, 2×CH$_3$), 0.8–4.3 (m, aliphatic H). MS m/z 655.6 (M−1).

Example 287

5-(2,6-Dichloro-phenylmethanesulfonyl)-3-[1-{4-[2-((R)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one

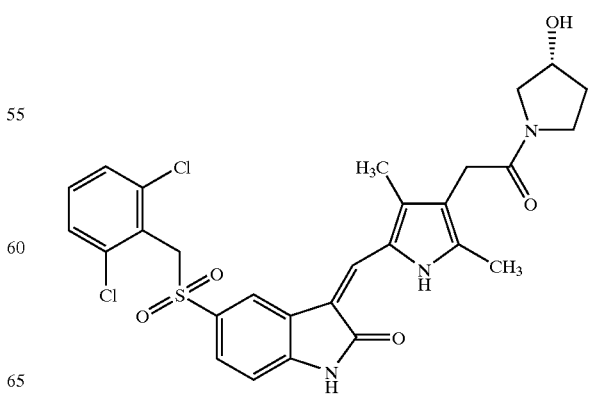

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 mg), HOBt (1 eq.), EDAC (2 eq.), TEA (3 eq.) and (R)-pyrrolidin-3-ol (3 eq.) in DMF (4 mL) was stirred at rt for overnight. The reaction was diluted with DCM, washed with water (2×) and 10% sodium carbonate (2×). The DCM was dried, concentrated and purified on a silica gel column to give 21 mg of the titled compound. MS m/z 588 [M$^+$+1].

Example 288

Synthesis of 5-(2,6-Dichloro-phenylmethanesulfonyl)-3-[1-(4-{2-[(R)-2-((R)-3-hydroxy-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

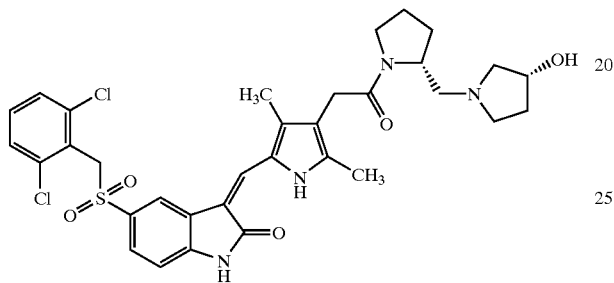

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 mg), HOBt (1 eq.), EDAC (2 eq.), TEA (3 eq.) and (R)-3-(R)-1-pyrrolidin-2-ylmethyl-cyclopentanol (3 eq.) in DMF (4 mL) was stirred at rt for overnight. The reaction was diluted with DCM, washed with water (2×) and 10% sodium carbonate (2×). The DCM was dried, concentrated and purified on a silica gel column to give 21 mg of the titled compound. MS m/z 671 [M$^+$+1].

Example 289

Synthesis of (R)-1-{5-[5-(2,6-Dichloro-phenylmethanesulfonyl)-2-oxo-1,2-dihydro-indol-(3Z)-ylidenemethyl]-2,4-dimethyl-1H-pyrrole-3-carbonyl}-piperidine-3-carboxylic acid cyclopropylamide

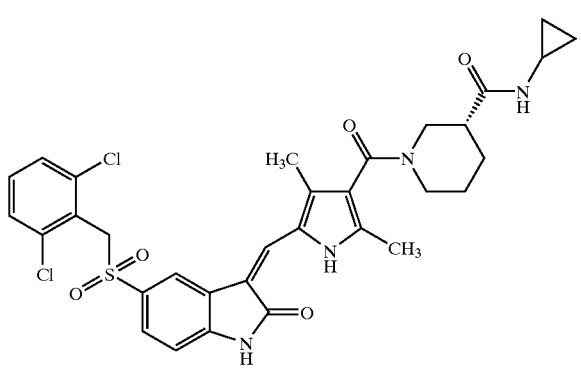

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), HOBt (65 mg), EDAC (191 mg), (R)-piperidine-3-carboxylic acid cyclopropylamide (250 mg) and TEA (7 drops) in DMF (3 mL) was stirred at rt for overnight. The reaction was diluted with DCM, washed with water, 10% sodium carbonate, dried and concentrated. The residue was purified on a silica gel column to give 200 mg of the titled compound.

$^1$HNMR (400 MHz, DMSO-d$_6$) δ 13.2 (br s, 1H, NH), 8.35 (s, 1H), 7.95 (m, 1H, CONH), 7.93 (s, 1H), 7.42 (m, 4H), 6.89 (d, 1H), 4.82 (s, 2H), 3.15 (m, 2H), 2.8 (m, 1H), 2.27 (s, 3H, CH$_3$), 3.25 (s, 3H, CH$_3$), 2.18 (m, 3H), 1.5–1.7 (m, 3H), 1.08 (m, 1H), 0.55 (m, 2H), 0.3 (m, 2H). MS m/z 655 [M$^+$+1].

Example 290

Synthesis of (R)-1-(2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetyl)-piperidine-3-carboxylic acid cyclopropylamide

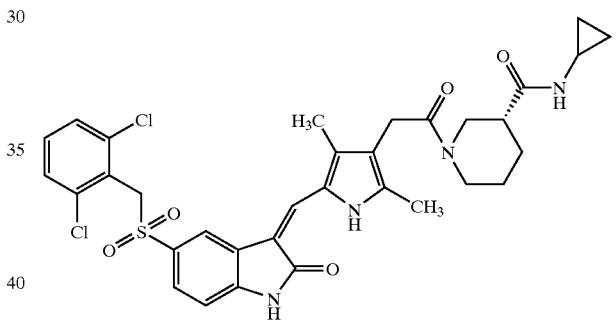

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (250 mg, 0.5 mmol), HOBt (65 mg), EDAC (191 mg), (R)-piperidine-3-carboxylic acid cyclopropylamide (250 mg) and TEA (7 drops) in DMF (3 mL) was stirred at rt for overnight. The reaction was diluted with DCM, washed with water, 10% sodium carbonate, dried and concentrated. The residue was purified on a silica gel column to give 107 mg of the titled compound.

$^1$HNMR (400 MHz, DMSO-d$_6$) δ 13.47 (s, 1H, NH), 11.26 (s, 1H, NH), 8.27 (s, 1H), 7.9 (m, 1H, CONH), 7.75 (s, 1H), 7.48 (s, 1H), 7.46 (s, 1H), 7.36 (m, 2H), 6.99 (d, J=8 Hz, 1H), 4.84 (s, 2H), 4.29 & 4.16 (2m, 1H), 6.87 (m, 1H), 3.51 (m, 2H), 3.04 (2t, 1H), 2.58 (m, 2H), 2.25 (s, 3H, CH$_3$), 2.22 (s, 3H, CH$_3$), 2.08 (m, 1H), 1.77 (m, 1H), 1.58 (m, 2H), 1.22 (m, 1H), 0.7 (m, 2H), 0.34 (m, 2H). MS m/z 669 [M$^+$+1].

Example 291

Synthesis of 3-[1-(4-{(S)-2-[(Cyclopropyl-methyl-amino)-methyl]-pyrrolidine-1-carbonyl}-3,5-dimethyl-1H-pyrrol-2-yl)-meth-(Z)-ylidene]-5-phenylmethanesulfonyl-1,3-dihydro-indol-2-one

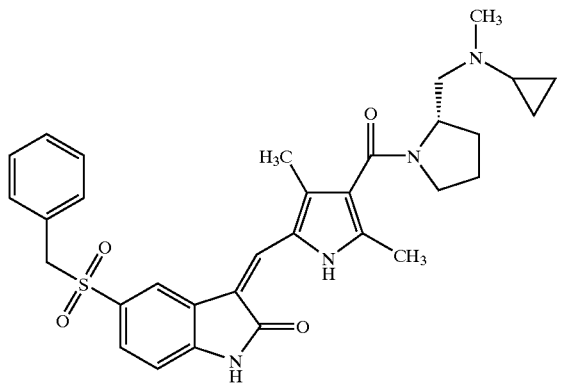

A mixture of 2,4-dimethyl-5-[2-oxo-5-phenylmethanesulfonyl-1,2-dihydro-indol-(3Z)-ylidenemethyl-1H-pyrrole-3-carboxylic acid (53 mg, 0.12 mmol), cyclopropyl-methyl-(S)-1-pyrrolidin-2-ylmethyl-amine (36 mg, 0.23 mmol), HOBt (29 mg), EDAC (45 mg) and TEA (0.05 mL) in DMF (2 mL) was stirred at rt for 48 hours. The reaction was concentrated, diluted with sat. sodium bicarbonate and extracted with DCM. The organic layer was washed with brine, dried and purified on a silica gel column to give 54 mg (79%) of the titled compound.

$^1$HNMR (400 MHz, DMSO-$d_6$) δ 13.5 (br s, 1H, NH), 11.36 (s, 1H, NH), 8.23 (s, 1H), 7.81 (s, 1H), 7.38 (d, 1H), 7.31 (m, 3H), 7.18 (m, 2H), 7.0 (d, J=8 Hz, 1H), 4.61 (s, 2H), 4.36 (m, 1H), 3.48 (m, 1H), 3.2 (m, 1H), 2.8 (m, 1H), 2.3–2.5 (m, 4H), 2.32 (s, 6H, 2×CH$_3$), 1.8–1.95 (m, 3H), 1.74 (m, 2H), 0.15–0.46 (m, 4H).

Example 292

Synthesis of 3-[1-{4-[2-((S)-3-Cyclopropylaminomethyl-piperidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one

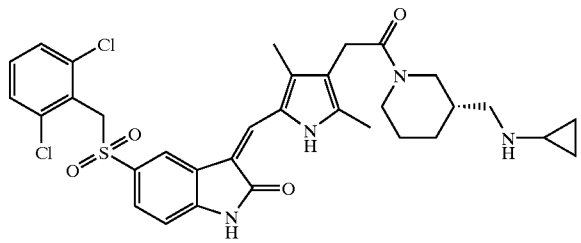

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 mg, 0.38 mmol), HOBt (52 mg), EDAC (130 mg), cyclopropyl-(R)-1-piperidin-3-ylmethyl-amine (103 mg) and TEA (7 drops) in DMF (2 mL) was stirred at rt for overnight. The reaction was concentrated and purified on a silica gel column to give 89 mg of the titled compound.

$^1$HNMR (400 MHz, DMSO-$d_6$) δ 13.48 (s, 1H, NH), 11.27 (br s, 1H, NH), 8.18 (s, 1H), 7.76 (s, 1H), 7.48 (s, 1H), 7.46 (s, 1H), 7.37 (m, 2H), 7.0 (d, J=8 Hz, 1H), 4.85 (s, 2H), 4.2 & 4.07 (2m, 1H), 3.78 (m, 1H), 3.49 (m, 2H), 3.05 (m, 1H), 2.75 (m, 1H), 2.40 (m, 3H), 2.26 (s, 3H, CH$_3$), 2.24 (s, 3H, CH$_3$), 1.96 (m, 1H), 1.72 (m, 1H), 1.75 (m, 1H), 1.46 (m, 1H), 1.25 (m, 1H), 1.14 (m, 1H), 0.31 (m, 2H), 0.16 (m, 2H). MS m/z 355 [M$^+$+1].

Example 293

Synthesis of 3-[1-[4-((S)-3-Cyclopropylaminomethyl-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

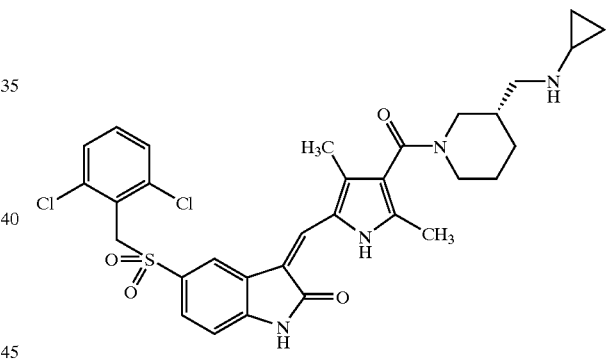

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), HOBt (54 mg, 1 eq.), EDAC (77 mg, 1 eq.), TEA (0.17 mL) and cyclopropyl-(R)-1-piperidin-3-ylmethyl-amine (110 mg, 0.48 mmol) in DMF (3 mL) was stirred at rt for overnight. The reaction was concentrated and purified on a silica gel column to give 45 mg of the titled compound.

$^1$HNMR (400 MHz, DMSO-$d_6$) δ 13.51 (br s, 1H, NH), 11.4 (br s, 1H, NH), 8.22 (s, 1H), 7.81 (s, 1H), 7.44 (d, 1H), 7.42 (s, 1H), 7.35 (m, 2H), 6.99 (d, J=8 Hz, 1H), 4.81 (s, 2H), 4.15 (m, 1H), 2.5–2.8 (m, 4H), 2.4 (m, 1H), 2.24 (s, 6H, 2×CH$_3$), 1.8 (m, 1H), 1.58 (m, 2H), 1.22 (m, 4H), 0.8 (m, 4H). MS m/z 641 [M−1].

Example 294

Synthesis of 5-(2,6-Dichloro-phenylmethanesulfonyl)-3-[1-(4-{2-[(S)-2-((R)-3-fluoro-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

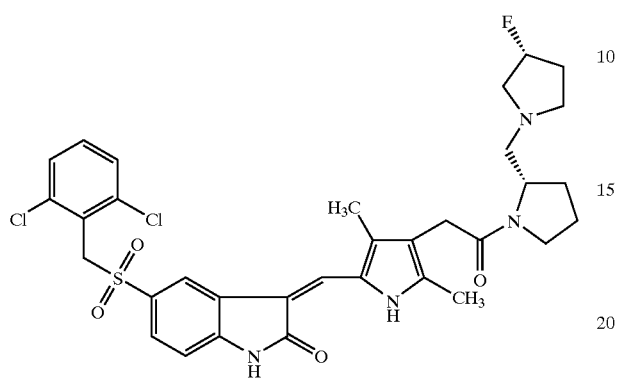

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 mg, 0.4 mmol), EDAC (150 mg) and HOBt (54 mg) in DMF (5 mL) was added (S)-3-fluoro-1-(S)-1-pyrrolidin-2-ylmethyl-pyrrolidine (100 mg, 0.58 mmol) and TEA (0.12 mL). The mixture was stirred at rt for 20 hours. The reaction was diluted with water and NaHCO$_3$, extracted with 5% methanol in DCM. The combined extracts were concentrated and the residue was purified on a silica gel column to give the titled compound. MS m/z 671 [M−1].

Example 295

Synthesis of 5-(2,6-Dichloro-phenylmethanesulfonyl)-3-[1-{4-[(S)-2-(4-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one

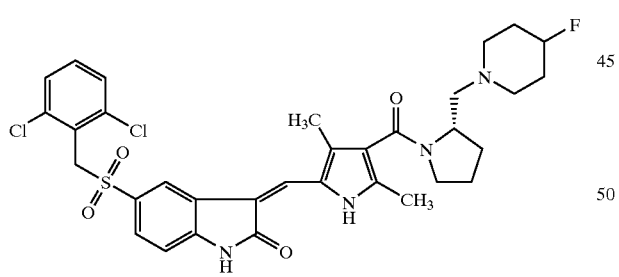

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), EDAC (150 mg, 0.78 mmol) and HOBt (54 mg, 0.4 mmol) was added 4-fluoro-1-(S)-1-pyrrolidin-2-ylmethyl-piperidine (100 mg, 0.53 mmol) and TEA (0.12 mL). The mixture was stirred at rt for 20 hours. The reaction was diluted with water and NaHCO$_3$, extracted with 5% methanol in DCM. The combined extracts were concentrated and the residue was purified on a silica gel column to give the titled compound.

$^1$HNMR (400 MHz, CDCl$_3$) δ 13.27 (br s, 1H, NH), 8.95 (s, 1H), 7.81 (s, 1H), 7.53 (dd, 1H), 7.31 (m, 2H), 7.19 (m, 1H), 6.96 (d, 1H), 4.88 (s, 2H), 4.5–4.75 (m, 2H), 3.7 (m, 1H), 3.3 (m, 2H), 2.77 (m, 2H), 2.42 (s, 3H, CH$_3$), 2.3 (m, 2H), 2.29 (s, 3H, CH$_3$), 1.7–2.1 (m, 9H). MS m/z 671 [M−1].

Example 296

Synthesis of 5-(2,6-Dichloro-phenylmethanesulfonyl)-3-[1-(4-{2-[(S)-2-(4-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

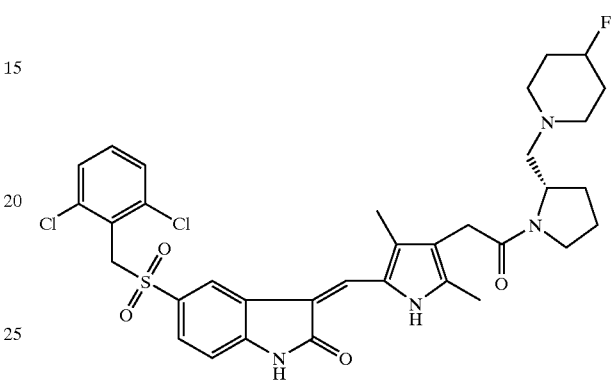

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 gm, 0.4 mmol), EDAC (150 mg, 0.78 mmol) and HOBt (54 mg, 0.4 mmol) was added (S)-3-fluoro-1-(S)-1-pyrrolidin-2-ylmethyl-pyrrolidine (100 mg, 0.53 mmol) and TEA (0.12 mL). The mixture was stirred at rt for 20 hours. The reaction was diluted with water and NaHCO$_3$, extracted with 5% methanol in DCM. The combined extracts were concentrated and the residue was purified on a silica gel column to give the titled compound. MS mm/z 685 [M−1].

Example 297

Synthesis of 5-(2,6-Dichloro-phenylmethanesulfonyl)-3-[1-{4-[(R)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

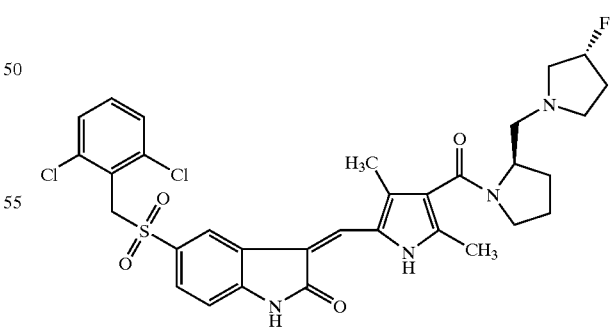

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), EDAC (150 mg, 0.78 mmol) and HOBt (54 mg, 0.4 mmol) was added (S)-3-fluoro-1-(R)-1-pyrrolidin-2-ylmethyl-pyrrolidine (100 mg, 0.58 mmol) and TEA (0.12 mL). The mixture was stirred at rt for 20 hours. The reaction was diluted with water and NaHCO$_3$, extracted with 5% methanol in DCM. The combined extracts were concentrated and the residue was purified on a silica gel column to give the titled compound.

$^1$HNMR (400 MHz, DMSO d$_6$) δ 13.28 (s, 1H, NH), 9.05 (s, 1H), 7.80 (d, 1H), 7.30 (m, 3H), 7.20 (m, 1H), 6.96 (d, 1H), 5.30 (s, 1H), 4.86 (s, 2H, CH$_2$), 4.47 (m, 1H), 3.7 (m, 1H), 2.7–3.1 (m, 3H), 2.6 (m, 2H), 2.43 (s, 3H, CH$_3$), 2.28 (s, 3H, CH$_3$), 1.65–2.2 (m, 9H). MS m/z 657 [M−1].

Example 298

Synthesis of 5-(2,6-Dichloro-phenylmethanesulfonyl)-3-[1-(4-{2-[(R)-2-((R)-3-fluoro-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

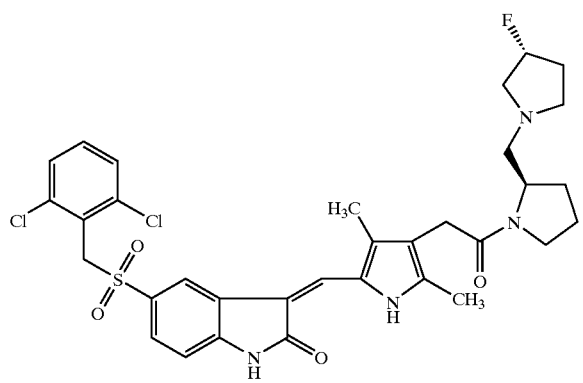

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl)}-acetic acid (200 mg, 0.39 mmol), EDAC (150 mg, 0.58 mmol), HOBt (59 mg, 0.4 mmol) in DMF (5 mL) was added (S)-3-fluoro-1-(R)-1-pyrrolidin-2-ylmethyl-pyrrolidine (100 mg, 0.58 mmol) and TEA (0.12 mL). The mixture was stirred at rt for 20 hours. The reaction was diluted with water and NaHCO$_3$, extracted with 5% methanol in DCM. The combined extracts were concentrated and the residue was purified on a silica gel column to give the titled compound. MS m/z 671 [M−1].

Example 299

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-Fluoro-piperidin-1-yl)-ethyl]-amide

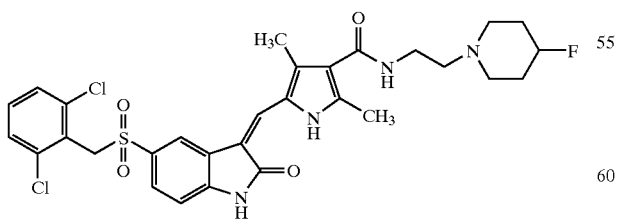

A mixture of 4-hydroxypyridine (4.04 g, 40 mmol), chloroacetonitrile (2.78 mL, 44 mmol) and potassium carbonate (22 g, 160 mmol) in acetonitrile (50 mL) was stirred at rt for overnight. The insolubles were filtered off, the filtrate was concentrated to give 5.6 g of (4-hydroxy-piperidin-1-yl)-acetonitrile.

DAST (4.36 mL, 33 mmol) was added to a solution of (4-hydroxy-piperidin-1-yl)-acetonitrile (4.25 g, 30 mmol) in DCM (80 mL) at −30° C., the mixture was then stirred at rt for overnight. The reaction was cooled to −30° C. and quenched with methanol (10 mL) for 30 mins. The organic layer was then washed with NaHCO$_3$ and dried. The residue was purified on a silica gel column to give 3 g (71%) of (4-fluoro-piperidin-1-yl)-acetonitrile.

A mixture of (4-fluoro-piperidin-1-yl)-acetonitrile (0.480 mg, 3.2 mmol) in THF 92 mL0 was added to LAH (148 mg, 1.2 eq.) in THF (15 mL). The mixture was heated at 50° C. for 18 hours. The cooled reaction was quenched with NaOH solution until white solid precipitated out. The solid was filtered off and the filtrate was concentrated to give 335 mg (71%) of 2-(4-fluoro-piperidin-1-yl)-ethylamine.

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (151 mg, 0.3 mmol), triethylamine (0.084 mL, 0.6 mmol) and BOP reagent (199 mg, 0.45 mmol) in DMF (0.5 mL) was added 2-(4-fluoro-piperidin-1-yl)-ethylamine (48 mg, 0.32 mmol) in DMF (0.5 mL). The mixture was stirred at rt for overnight. After the usual workup, the residue was purified on a silica gel column to give 90 mg (47%) of the titled compound.

MS m/z 631 [M−1].

Example 300

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(4-fluoro-piperidin-1-yl)-ethyl]-acetamide

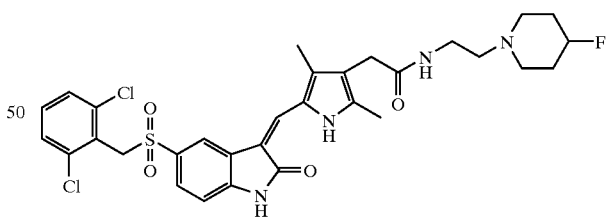

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (156 mg, 0.3 mmol), triethylamine (0.084 mL, 0.6 mmol) and BOP reagent (199 mg, 0.45 mmol) in DMF (0.5 mL) was added 2-(4-fluoro-piperidin-1-yl)-ethylamine (48 mg, 0.32 mmol) in DMF (0.5 mL). The mixture was stirred at rt for overnight. After the usual workup, the residue was purified on a silica gel column to give 110 mg (57%) of the titled compound. MS m/z 645 [M−1].

Example 301

Synthesis of 3-[1-[4-((2S,4R)-2-Cyclopropylaminomethyl-4-hydroxy-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

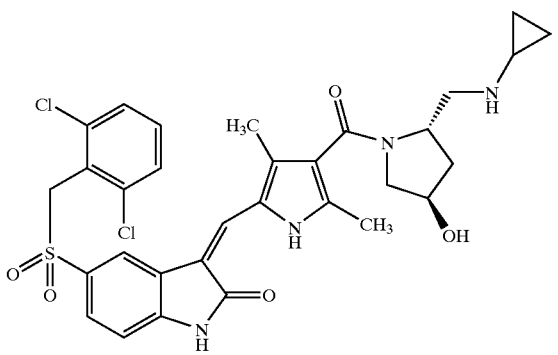

To a mixture of (2S,4R)-4-Hydroxy-pyrrolidine-1,2-dicarboxylic acid 1-tert-butyl ester (6 g, 26 mmol), HOBt (0.8 g, 6 mmol) and DCC (5.97 g, 29 mmol) in DCM (260 mL) was added cyclopropylamine (2.1 mL, 31 mmol) and DIPEA (6.8 mL, 39 mmol). The mixture was stirred at rt for overnight. The insolubles were filtered off, the filtrate was concentrated and extracted into ethyl acetate. The organic layer was concentrated and dried to give 6 g of (2S,4R)-2-cyclopropylcarbamoyl-4-hydroxy-pyrrolidine-1-carboxylic acid tert-butyl ester as a white solid.

$^1$HNMR (400 MHz, DMSO-d$_6$) δ 7.97 (d, 1H, CONH), 4.97 (d, J=7 Hz, 1H, OH), 4.2 (br s, 1H), 4.12 (q, 1H), 3.36 (m, 1H), 3.25 (m, 1H), 2.59 (m, 1H), 1.96 (m, 1H), 1.77 (m, 1H), 1.38 (s, 3H, CH$_3$), 1.32 (s, 6H, 2×CH$_3$), 0.59 (m, 2H), 0.37 (m, 2H).

A mixture of (2S,4R)-2-cyclopropylcarbamoyl-4-hydroxy-pyrrolidine-1-carboxylic acid tert-butyl ester (1.8 g, 6.6 mmol) and TFA (6 mL) in DCM (14 mL) was stirred at rt for 3 hours. The reaction was concentrated and dried to give 2 g of (2S,4R)4-hydroxy-pyrrolidine-2-carboxylic acid cyclopropylamide as a TFA salt.

MS m/z 171 [M$^+$+1].

A mixture of (2S,4R)-4-hydroxy-pyrrolidine-2-carboxylic acid cyclopropylamide TFA salt (from the above reaction) and LAH (910 mg, excess) in THF was heated to reflux for 4 hours. The reaction was cooled to 0° C., diluted with water (0.9 mL), 10% NaOH (0.9 mL) and then water (0.9 mL). The mixture was stirred for 30 mins, the insolubles were filtered off, the filtrate was concentrated and dried to give 900 mg of (3R, 5S)-5-cyclopropylaminomethyl-pyrrolidin-3-ol as a colorless oil.

MS m/z 157 [M$^+$+1].

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), HOBt (81 mg, 1.2 eq.), EDC (115 mg, 1.2 eq.), TEA (0.17 mL, 2.5 eq.) and (3R, 5S)-5-cyclopropylaminomethyl-pyrrolidin-3-ol (312 mg, 4 eq.) in DMF (10 mL) was stirred at rt for overnight, followed by heating at 45° C. for 5 hours. The reaction was concentrated, washed with water, sodium bicarbonate and brine, dried and concentrated. The residue was purified on a silica gel column to give the titled compound.

$^1$HNMR (400 MHz, DMSO-d$_6$) δ 13.35 (s, 1H, NH), 8.03 (s, 1H), 7.64 (s, 1H), 7.5 (d, 1H), 7.44 (m, 2H), 7.35 (d, 1H), 7.05 (d, 1H), 1.9 (s, 2H), 4.3 (m, 3H), 3.38 (m, 1H), 3.27 (m, 1H), 2.84 (m, 2H), 2.35 (s, 3H, CH$_3$), 2.32 (s, 3H, CH$_3$), 2.13 (m, 1H), 1.97 (m, 2H), 1.35 (m, 1H), 0.36 (m, 2H), 0.22 (m, 2H). MS m/z 643 [M−1].

Example 302

Synthesis of 5-(2,6-Dichloro-phenylmethanesulfonyl)-3-[1-{4-[(R)-2-(4-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one

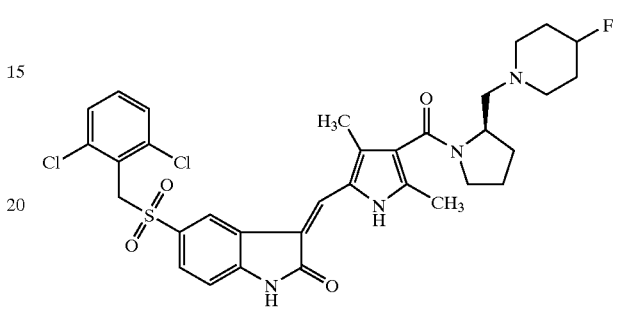

A mixture of (R)-pyrrolidine-1,2-dicarboxylic acid 1-tert-butyl ester (2 g, 9.3 mmol), EDAC (3.5 g, 16 mmol), HOBt (1.4 g, 18 mmol), TEA (2.5 mL) and piperidin-4-ol (1.8 g, 16 mmol) in DMF (20 mL) was stirred at rt for 20 hours. The reaction was diluted with water and sodium bicarbonate, extracted with 5% methanol in DCM. The DCM was concentrated and purified on a silica gel column to give 2.6 g of (R)-2-(4-hydroxy-piperidine-1-carbonyl)-pyrrolidine-1-carboxylic acid tert-butyl ester.

DAST (1.2 mL, 9 mmol) was added to a solution of (R)-2-(4-hydroxy-piperidine-1-carbonyl)-pyrrolidine-1-carboxylic acid tert-butyl ester (2.6 g, 8.7 mmol) in DCM at −78° C. The mixture was stirred at rt for 20 hours. The reaction was cooled to 0° C., quenched with sodium bicarbonate and extracted with DCM. The organic layer was concentrated and purified on a silica gel column to give 1.5 g of (R)-2-(4-fluoro-piperidine-1-carbonyl)-pyrrolidine-1-carboxylic acid tert-butyl ester.

A mixture of (R)-2-(4-fluoro-piperidine-1-carbonyl)-pyrrolidine-1-carboxylic acid tert-butyl ester (1.5 g, 5 mmol) and TFA (3 mL) in DCM (4 mL) was stirred at rt for one hour to give 1 g of (4-fluoro-piperidin-1-yl)-(R)-pyrrolidin-2-yl-methanone.

A mixture of (4-fluoro-piperidin-1-yl)-(R)-pyrrolidin-2-yl-methanone (1 g, 5 mmol) and LAH (1.1 g, 30 mmol) in THF (10 mL) was heated to reflux for 20 hours. The reaction was cooled to 0° C. and extracted wit 5% methanol in DCM. The organic layer was concentrated and purified on a silica gel column to give 700 mg of 4-fluoro-1-(R)-1-pyrrolidin-2-ylmethyl-piperidine.

TEA ((0.12 mL, 0.86 mmol) and 4-fluoro-1-(R)-1-pyrrolidin-2-ylmethyl-piperidine (100 mg, 0.54 mmol) were added to a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (200 mg, 0.4 mmol), HOBt (54 mg, 0.8 mmol) and EDAC (150 mg, 0.78 mmol) in DMF (5 mL). The mixture was stirred at rt for 20 hours. The reaction was diluted with water and sodium bicarbonate, extracted with 5% methanol in DCM. The organic layer was concentrated and purified on a silica gel column to give the titled compound.

$^1$HNMR (400 MHz, DMSO d$_6$) δ 13.50 (s, 1H, NH), 11.4 (s, 1H, NH), 8.26 (s, 1H), 7.85 (s, 1H), 7.36–7.5 (m, 4H), 7.03 (d, 1H), 4.86 (s, 2H, CH$_2$), 2.32 (s, 6H, 2×CH$_3$), 0.6–2.0 (m, 6H). MS m/z 673 (M$^+$+1).

Example 303

Synthesis of 5-(2,6-Dichloro-phenylmethanesulfonyl)-3-[1-(4-{2-[(R)-2-(4-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

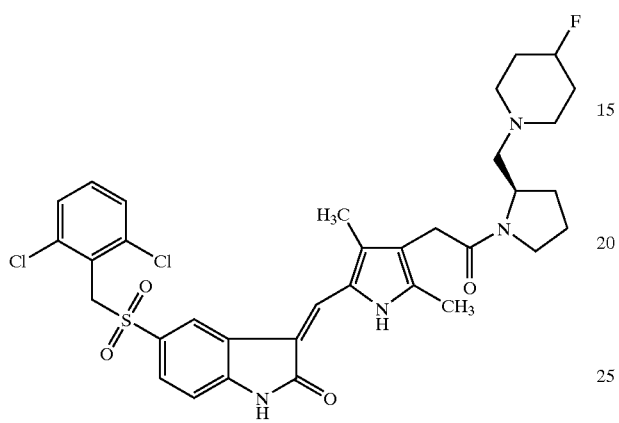

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (200 mg, 0.4 mmol), EDAC (150 mg, 0.78 mmol) and HOBt (54 mg, 0.4 mmol) in DMF (5 mL) was added 4-fluoro-1-(R)-1-pyrrolidin-2-ylmethyl-piperidine (100 mg, 0.54 mmol) and TEA (0.12 mL). The mixture was stirred at rt for 20 hours. The reaction was diluted with water and NaHCO$_3$, extracted with 5% methanol in DCM. The combined extracted were concentrated and the residue was purified on a silica gel column to give the titled compound. MS m/z 685 [M−1].

Example 304

Synthesis of 5-(2,6-Dichloro-phenylmethanesulfonyl)-3-[1-{4-[(S)-2-(3-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one

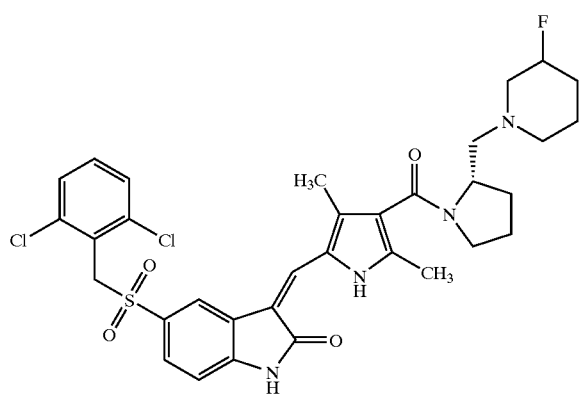

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (166 mg, 0.33 mmol), 3-fluoro-1-(S)-1-pyrrolidin-2-ylmethyl-piperidine (93 mg, 0.5 mmol), HOBt (66 mg, 0.49 mmol), EDAC (99 mg, 0.52 mmol) and TEA (0.1 mL, 0.72 mmol) in DMF (3 mL) was stirred at rt for 48 hours. The reaction was concentrated, diluted with sodium bicarbonate and extracted with DCM (2×). The combined DCM was washed with brine, dried and concentrated. The residue was purified on a silica gel column to give 162 mg (73%) of the titled compound.

$^1$HNMR (400 MHz, DMSO-d$_6$) δ 13.52 (br s, 1H, NH), 11.40 (s, 1H, NH), 8.27 (s, 1H), 7.85 (s, 1H), 7.51 (d, 1H), 7.48 (s, 1H), 7.42 (m, 2H), 7.04 (d, 1H), 4.87 (s, 2H), 4.3–4.7(m, 2H), 3.4–3.7 (m, 1H), 3.25 (m, 2H), 2.9 (m, 1H), 2.6 (m, 1H), 2.32 (s, 9H), 1.45–2.0 (m, 8H). MS m/z 673 [M$^+$+1].

Example 305

Synthesis of 5-(2,6-Dichloro-phenylmethanesulfonyl)-3-[1-(4-{2-[(S)-2-(3-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one

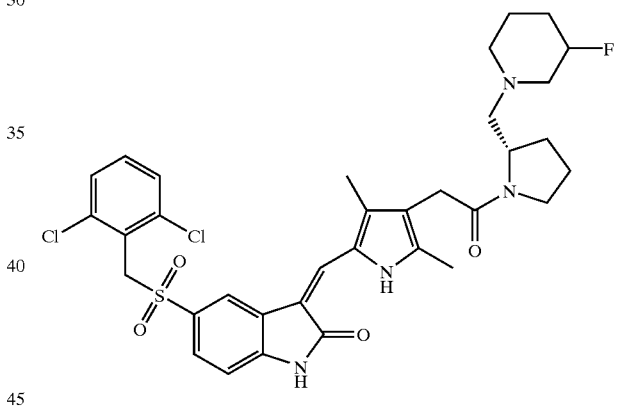

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (171 mg, 0.33 mmol), 3-fluoro-1-(S)-1-pyrrolidin-2-ylmethyl-piperidine (98 mg, 0.52 mmol), HOBt (67 mg, 0.49 mmol), EDAC (104 mg, 0.54 mmol) and TEA (0.1 mL, 0.72 mmol) in DMF (3 mL) was stirred at rt for 48 hours. The reaction was concentrated, diluted with sodium bicarbonate and extracted with DCM (2×). The combined DCM was washed with brine, dried and concentrated. The residue was purified on a silica gel column to give the titled compound.

$^1$HNMR (400 MHz, DMSO-d$_6$) δ 13.48 (s, 1H, NH), 11.28 (s, 1H, NH), 8.19 (d, 1H), 7.78 (s, 1H), 7.50 (d, 1H), 7.48 (s, 1H), 7.40 (m, 2H), 7.02 (d, 1H), 4.86 (s, 2H), 4.5–4.7 (m, 1H), 4.1 (m, 1H), 3.55 (m, 3H), 3.42 (m, 1H), 2.8 (m, 1H), 2.4 (m, 3H), 2.25–2.28 (m, 8H), 2.2 (m, 1H), 1.85 (m, 6H), 1.45 (m, 2H). MS m/z 687 [M$^+$+1].

Example 306

Synthesis of 3-[1-[4-(2-{(S)-2-[(Cyclopropyl-methyl-amino)-methyl]-pyrrolidin-1-yl}-2-oxo-ethyl)-3,5-dimethyl-1H-pyrrol-2-yl]-meth-(Z)-ylidene]-5-(2,6-dichloro-phenylmethanesulfonyl)-1,3-dihydro-indol-2-one

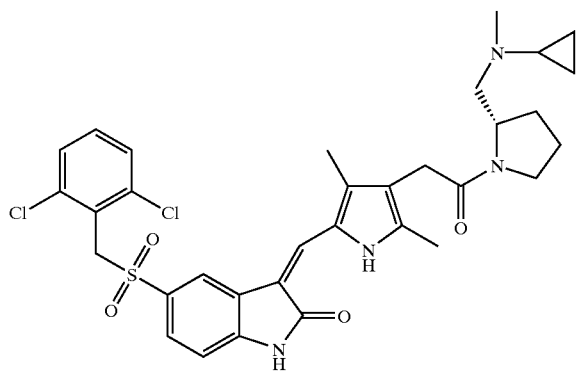

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (104 mg, 0.2 mmol), cyclopropyl-methyl-(S)-1-pyrrolidin-2-ylmethyl-amine (53 mg, 0.34 mmol), HOBt (43 mg, 0.32 mmol), EDAC (65 mg, 0.34 mmol) and TEA (0.06 mL) in DMF (3 mL) was stirred at rt for 48 hours. The reaction was concentrated, diluted with sodium bicarbonate and extracted with DCM. The combined DCM was dried, concentrated and purified on a silica gel column to give 89 mg (68%) of the titled compound.

$^1$HNMR (400 MHz, DMSO-$d_6$) δ 13.48 (s, 1H, NH), 11.28 (s, 1H, NH), 8.18 (d, 1H), 7.78 (s, 1H), 7.50 (d, 1H), 7.48 (s, 1H), 7.39 (m, 2H), 7.02 (d, 1H), 4.86 (s, 2H), 4.1 (m, 1H), 3.5 (m, 2H), 3.4 (d, 1H), 3.33 (s, 2H), 2.55 (m, 1H), 2.32 (m, 1H), 2.25–2.25 (m, 8H), 1.65–1.9 (m, 5H), 0.2–0.42 (m, 4H). MS m/z 653 [M−1].

mL) was stirred at rt for 48 hours. The reaction was concentrated, diluted with sodium bicarbonate and extracted with DCM. The combined DCM was washed with brine, dried, concentrated, purified on a silica gel column to give (R)-2-(cyclopropyl-methyl-carbamoyl)-pyrrolidine-1-carboxylic acid tert-butyl ester.

A solution of (R)-2-(cyclopropyl-methyl-carbamoyl)-pyrrolidine-1-carboxylic acid tert-butyl ester (958 mg, 3.57 mmol) in 50% TFA in DCM (5 mL) was stirred at rt for 4 hours. The reaction was concentrated and purified to give (R)-pyrrolidine-2-carboxylic acid cyclopropyl-methyl-amide.

To a solution of (R)-pyrrolidine-2-carboxylic acid cyclopropyl-methyl-amide (540 mg, 3.21 mmol) in THF (5 mL) at 0° C. was added borane (6.4 mL, 2 eq., 1 M in THF) dropwise. The mixture was allowed to warm up to rt then heated to reflux for 24 hours. The cooled reaction was acidified with HCl and heated at 75° C. for 10 mins. The mixture was concentrated, basified with 2N NaOH and extracted with 10% methanol in DCM. The combined DCM was dried and concentrated to give cyclopropyl-methyl-(R)-1-pyrrolidin-2-ylmethyl-amine.

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (146 mg, 0.29 mmol), cyclopropyl-methyl-(R)-1-pyrrolidin-2-ylmethyl-amine (71 mg, 0.46 mmol), HOBt (54 mg, 0.4 mmol), EDAC (74 mg, 0.39 mmol) and TEA (0.085 mL) in DMF (3 mL) was stirred at rt for 48 hours. The reaction was concentrated, diluted with sodium bicarbonate and extracted with DCM. The combined DCM was dried, concentrated and purified on a silica gel column to give 133 mg (71%) of the titled compound.

$^1$HNMR (400 MHz, DMSO-$d_6$) δ 13.52 (br s, 1H, NH), 11.4 (s, 1H, NH), 8.27 (s, 1H), 7.85 (s, 1H), 7.5 (d, 1H), 7.48 (s, 1H), 7.4 (m, 2H), 7.04 (d, 1H), 4.87 (s, 2H), 4.35 (m, 1H), 3.46 (m, 1H), 3.25 (m, 1H), 2.8 (m, 1H), 2.3–2.45 (m, 9H), 1.72–1.95 (m, 6H), 0.15–0.45 (m, 4H). MS m/z 639 [M−1].

Example 307

Synthesis of 3-[1-(4-{(R)-2-[(Cyclopropyl-methyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one

Example 308

Synthesis of 5-(2,6-Dichloro-phenylmethanesulfonyl)-3-[1-[3,5-dimethyl-4-(1-methyl-piperidin-4-yl)-1H-pyrrol-2-yl]-meth-(Z)-ylidene]-1,3-dihydro-indol-2-one

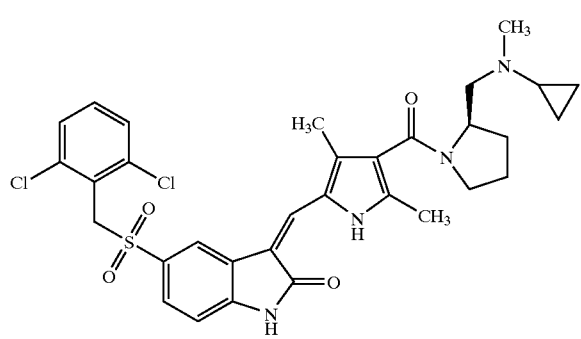

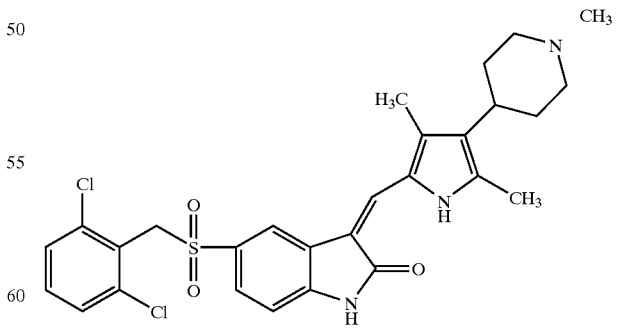

A mixture of (R)-pyrrolidine-1,2-dicarboxylic acid 1-tert-butyl ester (788 mg, 1 eq.), cyclopropyl-methyl-amine hydrochloride (478 mg, 1.2 eq.), HOBt (7.48 mg, 1.5 eq.), EDAC (1.05 g, 1.5 eq.) and TEA (1.5 mL, 3 eq.) in DMF (15

5-(2,6-Dichloro-phenylmethanesulfonyl)-1,3-dihydro-indol-2-one was condensed with 3,5-dimethyl-4-(1-methyl-piperidin-4-yl)-1H-pyrrole-2-carbaldehyde to give the titled compound.

Example 309

Synthesis of 5-(2,6-Dichloro-phenylmethanesulfonyl)-3-[1-[4-(4-fluoro-piperidin-1-ylmethyl)-3,5-dimethyl-1H-pyrrol-2-yl]-meth-(Z)-ylidene]-1,3-dihydro-indol-2-one

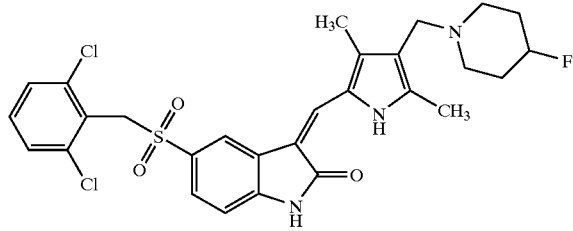

5-(2,6-Dichloro-phenylmethanesulfonyl)-1,3-dihydro-indol-2-one was condensed with 4-(4-fluoro-piperidin-1-ylmethyl)-3,5-dimethyl-1H-pyrrole-2-carbaldehyde in ethanol and piperidine to give the titled compound as an orange solid.

MS m/z 574 [M−1].

Example 310

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-Fluoro-pyrrolidin-1-yl)-ethyl]-amide

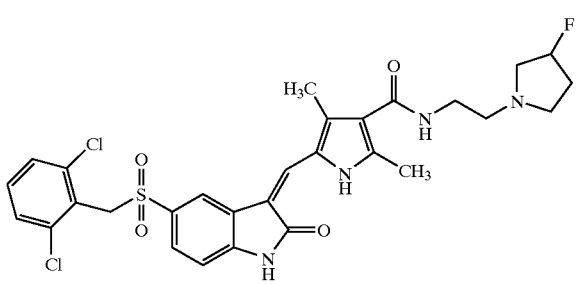

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.2 mmol), HOBt (40 mg, 1.5 eq.) and DCC (41 mg, 1 eq.) in DMF (2 mL) was added triethylamine (6 eq.), after stirring for 15 mins to the mixture was added 2-(3-fluoro-pyrrolidin-1-yl)-ethylamine, TFA salt 142 mg, 2 eq.) in DMF (1 mL). The mixture was stirred at 40° C. for overnight. The reaction was diluted with water (20 mL) and extracted with 20% IPA in DCM (2×100 mL). The organic layer was concentrated, the residue was purified on a silica gel column to give the titled compound.

MS m/z 619 (M$^+$+1).

Example 311

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-fluoro-pyrrolidin-1-yl)-ethyl]-acetamide

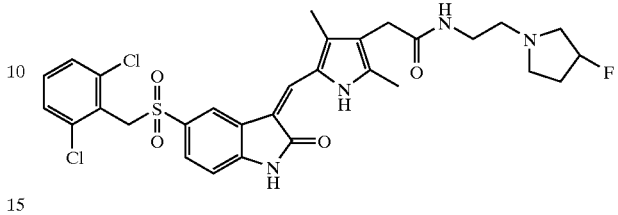

To a mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (100 mg, 0.19 mmol), HOBt (39 mg, 1.5 eq.) and DCC (40 mg, 1 eq.) in DMF (2 mL) was added triethylamine (2 eq.), after stirring for 15 mins to the mixture was added 2-(3-fluoro-pyrrolidin-1-yl)-ethylamine, ditrifluoroacetate salt (139 mg, 2 eq.) in DMF (1 mL). The mixture was stirred at 50° C. for overnight. The reaction was diluted with water (20 mL) and extracted with 20% IPA in DCM (2×100 mL). The organic layer was concentrated, the residue was purified on a silica gel column to give the titled compound. $^1$HNMR (400 MHz, DMSO-d$_6$) δ 13.45 (s, 1H, NH), 11.25 (s, 1H, NH), 8.17 (d, 1H), 7.78 (t, 1H, NH), 7.76 (s, 1H), 7.48 (d, 1H), 7.46 (s, 1H), 7.39 (s, 1H), 7.37 (d, 1H), 7.01 (d, 1H), 4.85 (s, 2H), 3.25 (s, 2H), 3.15 (m, 2H), 2.75 (m, 1H), 2.45 (m, 2H), 2.3 (s, 3H, CH$_3$), 2.27 (s, 3H, CH$_3$), 1.7 (m, 2H), 1.6 (m, 2H), 1.5 (m, 2H).

Example 312

Synthesis of 5-(2,6-Dichloro-phenylmethanesulfonyl)-3-[1-(4-{3-[(R)-2-((R)-3-fluoro-pyrrolidin-1-ylmethyl)-pyrrolidin-1-yl]-3-oxo-propyl}-3,5-dimethyl-1H-pyrrol-2-yl)-meth-(Z)-ylidene]-1,3-dihydro-indol-2-one

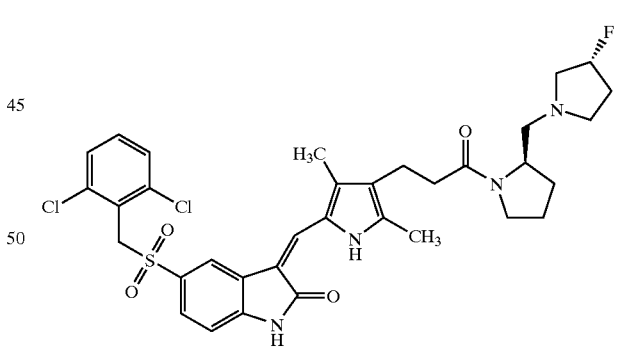

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (114 mg, 0.21 mmol), (S)-3-fluoro-1-(R)-1-pyrrolidin-2-ylmethyl-pyrrolidine (53 mg, 0.31 mmol), HOBt (43 mg, 0.33 mmol), EDAC (65 mg, 0.33 mmol), TEA (0.06 mL, 0.43 mmol) in DMF (3 mL) was stirred at rt for 48 hours. The reaction was concentrated, diluted with sodium bicarbonate and extracted with DCM (2×). The combined DCM was washed with brine, dried and concentrated. The residue was purified on a silica gel column to give 95 mg (66%) of the titled compound. MS m/z 687 [M$^+$+1].

Example 313

Synthesis of 5-(2,6-Difluoro-phenylmethanesulfonyl)-3-[1-{4-[(R)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

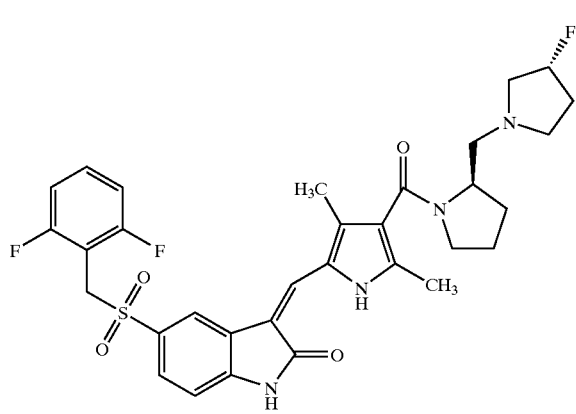

A mixture of 5-[5-(2,6-difluoro-phenylmethanesulfonyl)-2-oxo-1,2-dihydro-indol-(3Z)-ylidenemethyl]-2,4-dimethyl-1H-pyrrole-3-carboxylic acid (101 mg, 0.21 mmol), (S)-3-fluoro-1-(R)-1-pyrrolidin-2-ylmethyl-pyrrolidine (53 mg, 0.31 mmol), HOBt (44 mg, 0.33 mmol), EDAC (63 mg, 0.33 mmol), TEA (0.06 mL, 0.43 mmol) in DMF (3 mL) was stirred at rt for 48 hours. The reaction was concentrated, diluted with sodium bicarbonate and extracted with DCM (2×). The combined DCM was washed with brine, dried and concentrated. The residue was purified on a silica gel column to give 88 mg (67%) of the titled compound.

MS m/z 625 [M−1].

Example 314

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-Fluoro-piperidin-1-yl)-ethyl]-amide

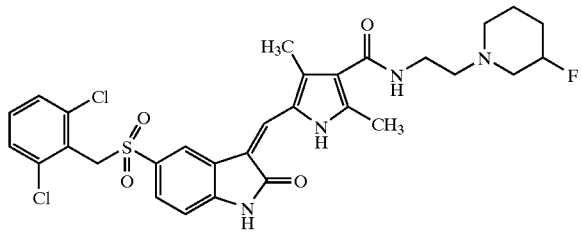

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with 2-(3-fluoro-piperidin-1-yl)-ethylamine to give the titled compound.

Example 315

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-fluoro-piperidin-1-yl)-ethyl]-acetamide

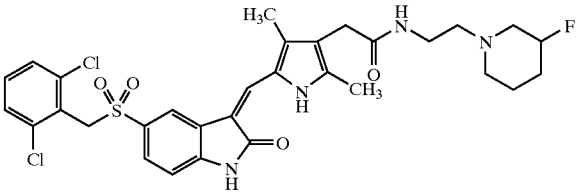

{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid was coupled with 2-(3-fluoro-piperidin-1-yl)-ethylamine to give the titled compound.

Example 316

Synthesis of 5-(2,6-Difluoro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one

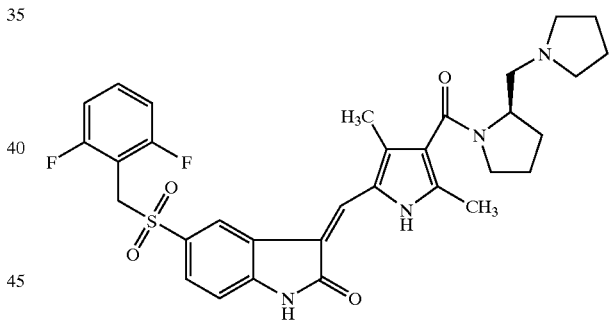

To a mixture of 5-[5-(2,6-difluoro-phenylmethanesulfonyl)-2-oxo-1,2-dihydro-indol-(3Z)-ylidenemethyl]-2,4-dimethyl-1H-pyrrole-3-carboxylic acid (138 mg, 0.33 mmol), EDAC (97 mg, 0.51 mmol) and HOBt (67 mg, 0.5 mmol) in DMF (4 mL) was added (R)-2-pyrrolidin-1-ylmethyl-pyrrolidine (106 mg, 0.68 mmol) and TEA (0.1 mL). The mixture was stirred at rt for 20 hours. The reaction was diluted with water and NaHCO$_3$, extracted with DCM. The combined DCM was concentrated and the residue was purified on a silica gel column to give the titled compound.

$^1$HNMR (400 MHz, DMSO-d$_6$) δ 13.52 (br s, 1H, NH), 11.39 (s, 1H, NH), 8.30 (s, 1H), 7.85 (s, 1H), 7.44 (m, 2H), 7.08 (t, 2H), 7.0 (d, 1H), 4.62 (s, 2H), 4.34 (m, 1H), 3.4–3.7 (m, 1H), 3.25 (m, 2H), 2.5–2.9 (m, 2H), 2.3 (s, 6H, 2×CH$_3$), 2.2 (m, 1H), 1.4–2.1 (m, 9H), 1.5 (m, 1H). MS m/z 607.6 [M−1].

Example 317

Synthesis of 5-(2,6-Dichloro-phenylmethanesulfonyl)-3-[1-{3,5-dimethyl-4-[3-oxo-3-((R)-2-pyrrolidin-1-ylmethyl-pyrrolidin-1-yl)-propyl]-1H-pyrrol-2-yl}-meth-(Z)-ylidene]-1,3-dihydro-indol-2-one

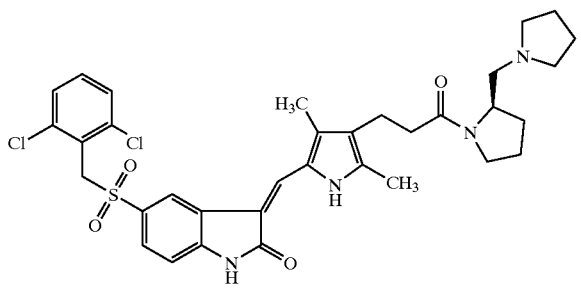

To a mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (178 mg, 0.33 mmol), EDAC (97 mg, 0.51 mmol) and HOBt (67 mg, 0.5 mmol) in DMF (4 mL) was added (R)-2-pyrrolidin-1-ylmethyl-pyrrolidine (106 mg, 0.68 mmol) and TEA (0.1 mL). The mixture was stirred at rt for 20 hours. The reaction was diluted with water and NaHCO$_3$, extracted with DCM. The combined DCM was concentrated and the residue was purified on a silica gel column to give the titled compound.

$^1$HNMR (400 MHz, DMSO-d$_6$) δ 13.43 (s, 1H, NH), 11.26 (s, 1H, NH), 8.19 (d, 1H), 7.76 (d, 1H), 7.47 (d, 2H), 7.38 (m, 2H), 6.99 (d, 1H), 4.85 (s, 2H), 4.05 & 3.8 (m, 1H), 2.65 (m, 2H), 2.4 (m, 4H), 2.31 (s, 3H, CH$_3$), 2.3 (m, 2H), 2.29 (s, 3H, CH$_3$), 1.84 (m, 2H), 1.74 (m, 2H), 1.64 (m, 2H), 1.59 (m, 2H). MS m/z 667 [M−1].

Example 318

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid {2-[4-(2-amino-2-methyl-propionyl)-piperazin-1-yl]-ethyl}-amide

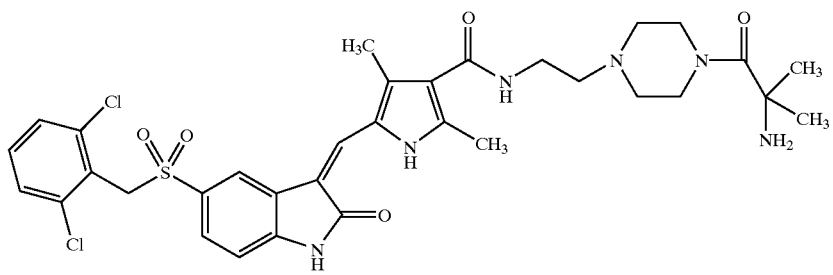

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (2-piperazin-1-yl-ethyl)-amide (150 mg, 0.24 mmol) and N-Boc D-alanine (19 mg, 1 eq.) in DCM (5 mL) cooled in an ice bath was added diethyl cyanophosphonate (48 mg, 1.2 eq.) in DCM (0.5 mL) followed by a dropwise addition of TEA (0.04 mL, 1 eq.) in DCM (0.5 mL). The mixture was then stirred at rt for overnight. The reaction was diluted with DCM, washed with 10% potassium carbonate, water, dried and concentrated to give (2-{4-[2-({5-[5-(2,6-dichloro-phenylmethanesulfonyl)-2-oxo-1,2-dihydro-indol-(3Z)-ylidenemethyl]-2,4-dimethyl-1H-pyrrole-3-carbonyl}-amino)-ethyl]-piperazin-1-yl}-1,1-dimethyl-2-oxo-ethyl)-carbamic acid tert-butyl ester as a red wax.

To a mixture of (2-{4-[2-({5-[5-(2,6-dichloro-phenylmethanesulfonyl)-2-oxo-1,2-dihydro-indol-(3Z)-ylidenemethyl]-2,4-dimethyl-1H-pyrrole-3-carbonyl}-amino)-ethyl]-piperazin-1-yl}-1,1-dimethyl-2-oxo-ethyl)-carbamic acid tert-butyl ester (from the above reaction) in DCM (3 mL) was added 6N HCl in ethyl acetate. The mixture was stirred at 40° C. for 3 hours. The reaction was concentrated, basified to pH 7–8 with 2N NaOH, extracted with DCM and concentrated. The residue was purified on a silica gel column to give 40 mg the titled compound as a red solid.

$^1$HNMR (400 MHz, DMSO-d$_6$) δ 13.6 (s, 1H, NH), 8.28 (d, 1H), 7.87 (s, 1H), 7.55 (t, 1H, CONH), 7.49 (s, 1H), 7.47 (s, 1H), 7.39 (m, 2H), 7.02 (d, J=8 Hz, 1H), 4.85 (s, 2H), 3.72 (m, 4H), 3.4 (m, 2H), 2.45 (s, 6H, 2×CH$_3$), 2.4 (m, 4H), 1.26 (s, 6H, 2×CH$_3$). MS m/z 699 [M−1].

Example 319

Synthesis of 5-(2,6-Dichloro-phenylmethanesulfonyl)-3-[1-{3,5-dimethyl-4-[3-oxo-3-((S)-3-pyrrolidin-1-ylmethyl-piperidin-1-yl)-propyl]-1H-pyrrol-2-yl}-meth-(Z)-ylidene]-1,3-dihydro-indol-2-one

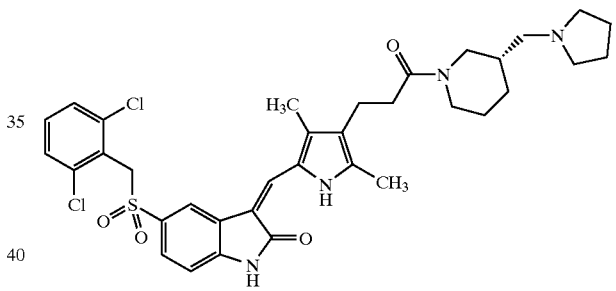

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (267 mg), HATU (1.2 eq.), (R)-3-pyrrolidin-1-ylmethyl-piperidine (2×) in DMF (2.5 mL) was stirred at rt for 2 hours. The reaction was concentrated, diluted with DCM, washed with water (2×), sodium carbonate (2×), dried and concentrated. The residue was purified on a silica gel column to give 145 mg of the titled compound as a yellow solid.

¹HNMR (400 MHz, DMSO-d₆) δ 13.44 (br s, 1H, NH), 11.26 (s, 1H, NH), 8.18 (s, 1H), 7.75 (s, 1H), 7.48 (s, 1H), 7.46 (d, 1H), 7.28 (m, 2H), 7.0 (d, J=8 Hz, 1H), 4.84 (s, 2H), 4.02 & 4.35 (2m, 1H), 3.65 (m, 1H), 3.29 (s, 2H), 2.75 (m, 2H), 2.62 (m, 3H), 2.3–2.45 (m, 6H), 2.31 (s, 3H, CH₃), 2.29 (s, 3H, CH₃), 1.5–1.7 (m, 6H), 1.1–1.25 (m, 2H). MS m/z 683 [M⁺+1].

Example 320

Synthesis of 5-(2,6-Difluoro-phenylmethanesulfonyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one

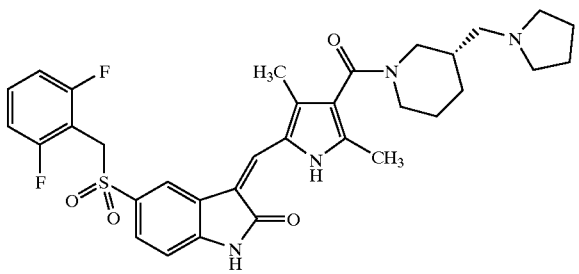

A mixture of 5-[5-(2,6-difluoro-phenylmethanesulfonyl)-2-oxo-1,2-dihydro-indol-(3Z)-ylidenemethyl]-2,4-dimethyl-1H-pyrrole-3-carboxylic acid (236 mg), HATU (1.2 eq.), (R)-3-pyrrolidin-1-ylmethyl-piperidine (2×) in DMF (2.5 mL) was stirred at rt for 2 hours. The reaction was concentrated, diluted with DCM, washed with water (2×), sodium carbonate (2×), dried and concentrated. The residue was purified on a silica gel column to give 120 mg of the titled compound as a yellow solid.

¹HNMR (400 MHz, DMSO-d₆) δ 13.53 (br s, 1H, NH), 11.38 (s, 1H, NH), 8.31 (s, 1H), 7.86 (s, 1H), 7.45 (m, 2H), 7.08 (m, 2H), 7.08 (t, 2H), 7.0 (d, J=8 Hz, 1H), 4.62 (s, 2H), 4.3 (m, 1H), 3.55 (m, 2H), 3.29 (s, 2H), 3.0 (m, 3H), 2.3 (br s, 9H), 1.2–1.8 (m, 8H). MS m/z 623 [M⁺+1].

Example 321

Synthesis of 5-(2,6-Dichloro-phenylmethanesulfonyl)-3-[1-[3,5-dimethyl-4-(3-morpholin-4-yl-3-oxo-propyl)-1H-pyrrol-2-yl]-meth-(Z)-ylidene]-1,3-dihydro-indol-2-one

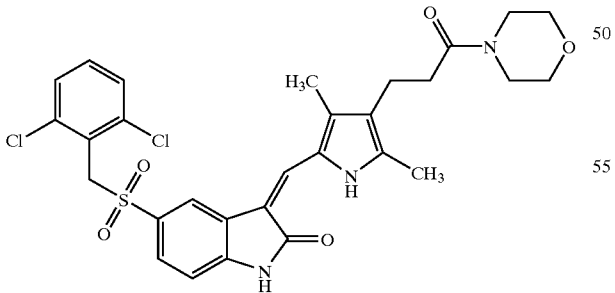

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (100 mg, 0.19 mmol), DIPEA (45 mg, 1.9 eq.) and morpholine (82 mg, 5 eq.) in DMF (2 mL) was stirred at rt for 30 mins. To the mixture was added HATU (85 mg, 1.2 eq.) was added and stirring was continued for another 3 hours. The reaction was concentrated, diluted with DCM, washed with sat.NaHCO₃ and water, concentrated and triturated with methanol to give the titled compound as a pale orange solid.

¹HNMR (400 MHz, DMSO-d₆) δ 13.5 (s, 1H, NH), 11.22 (br s, 1H, NH), 8.16 (d, 1H), 7.74 (s, 1H), 7.49 (d, 1H), 7.47 (s, 1H), 7.38 (m, 2H), 6.99 (d, J=8 Hz, 1H), 4.85 (s, 2H), 3.49 (m, 2H), 3.42 (m, 4H), 3.34 (m, 2H), 2.63 (t, 2H), 2.43 (m, 2H), 2.31 (s, 3H, CH₃), 2.29 (s, 3H, CH₃). MS m/z 602 [M+1].

Example 322

Synthesis of N-[2-(4-Acetyl-piperazin-1-yl)-ethyl]-2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetamide

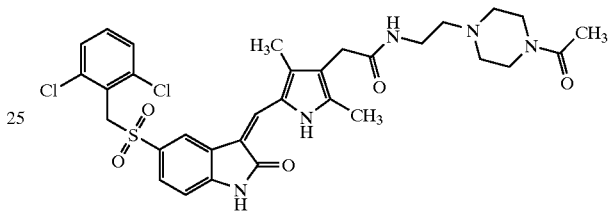

{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid was coupled with 1-[4-(2-amino-ethyl)-piperazin-1-yl]-ethanone to give the titled compound.

¹HNMR (400 MHz, DMSO-d₆) δ 13.47 (s, 1H, NH), 11.26 (s, 1H, NH), 8.18 (d, 1H), 7.77 (s, 1H), 7.67 (t, 1H, CONH), 7.48 (d, 1H), 7.46 (s, 1H), 7.39 (m, 2H), 7.0 (d, J=8 Hz, 1H), 4.85 (s, 2H), 3.35 (m, 4H), 3.14 (m, 4H), 2.33 (m, 4H), 2.31 (s, 3H, CH₃). 2.28 (s, 3H, CH₃), 2.25 (m, 2H), 1.92 (s, 3H, COCH₃). MS m/z 629 [M−1].

Example 323

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-Hydroxy-piperidin-1-yl)-ethyl]-amide

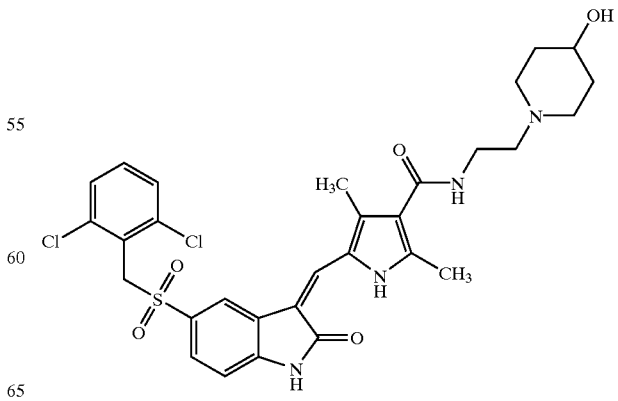

A mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (100 mg, 0.19 mmol), DIPEA (115 mg, 5 eq.) and 1-(2-amino-ethyl)-piperidin-4-ol TFA salt (88 mg, 1.2 eq.) in 2 mL) was stirred at rt for 45 mins. To the mixture was added HATU (83 mg, 1.1 eq.). After stirring for 18 hours, the reaction was concentrated and purified on a silica gel column to give the titled compound as a yellow solid.

$^1$HNMR (400 MHz, DMSO-d$_6$) δ 8.09 (br s, 1H), 7.69 (s, 1H), 7.48 (d, 1H), 7.46 (s, 1H), 7.41 (t, 1H, CONH), 7.35 (m, 2H), 6.92 (d, J=8 Hz, 1H), 4.82 (s, 2H), 4.75 (br s, 1H, OH), 3.42 (m, 1H), 3.30 (m, 2H), 2.72 (m, 2H), 2.43 (s, 3H, CH$_3$), 2.42 (s, 3H, CH$_3$), 2.4 (m, 2H), 2.04 (m, 2H), 1.69 (m, 2H), 1.37 (m, 2H). MS m/z 631 [M−1].

Example 324

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(4-hydroxy-piperidin-1-yl)-ethyl]-acetamide

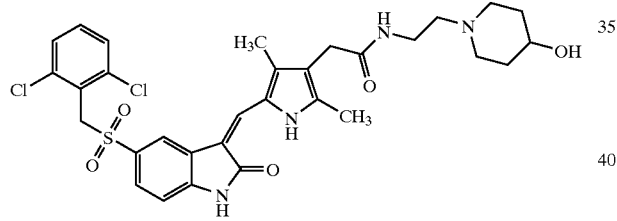

A mixture of {5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetic acid (100 mg, 0.19 mmol), DIPEA (115 mg, 5 eq.) and 1-(2-amino-ethyl)-piperidin-4-ol TFA salt (88 mg, 1.2 eq.) in 2 mL) was stirred at rt for 45 mins. To the mixture was added HATU (83 mg, 1.1 eq.). After stirring for 18 hours, the reaction was concentrated and purified on a silica gel column to give the titled compound as an orange solid.

$^1$HNMR (400 MHz, DMSO-d$_6$) δ 13.47 (s, 1H, NH), 11.29 (s, 1H, NH), 8.18 (d, 1H), 7.77 (s, 1H), 7.48 (s, 1H), 7.46 (s, 1H), 7.37 (m, 2H), 7.0 (d, J=8 Hz, 1H), 4.85 (s, 2H), 4.72 (br s, 1H, OH), 3.51 (m, 2H), 3.26 (m, s 4H), 3.1 (m, 1H), 2.9 (m, 2H), 2.6 (m, 2H), 2.31 (s, 3H, CH$_3$), 2.278 (s, 3H, CH$_3$), 1.71 (m, 2H), 1.45 (m, 2H). MS m/z 629 [M−1].

Example 325

Synthesis of 5-(2,6-Dichloro-phenylmethanesulfonyl)-3-[1-{3,5-dimethyl-4-[3-(4-methyl-piperazin-1-yl)-3-oxo-propyl]-1H-pyrrol-2-yl}-meth-(Z)-ylidene]-1,3-dihydro-indol-2-one

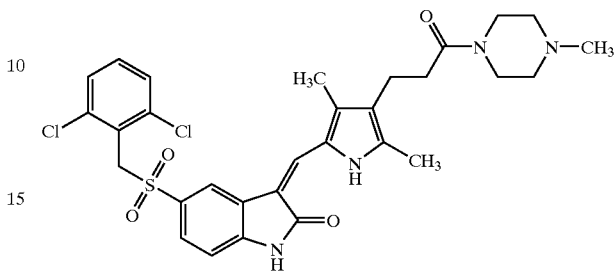

A mixture of 5-(2,6-Dichloro-phenylmethanesulfonyl)-1,3-dihydro-indol-2-one (122 mg, 0.34 mmol), 3,5-dimethyl-4-[3-(4-methyl-piperazin-1-yl)-3-oxo-propyl]-1H-pyrrole-2-carbaldehyde (1.4 eq.) and piperidine (0.5 eq.) in ethanol (2 mL) was stirred at rt for 72 hours. The reaction was concentrated and purified on a silica gel column to give the titled compound as a dark orange brown solid. $^1$HNMR (400 MHz, DMSO-d$_6$) δ 13.44 (s, 1H, NH), 11.25 (s, 1H, NH), 8.18 (d, 1H), 7.75 (s, 11H), 7.48 (s, 1H), 7.46 (s, 1H), 7.38 (m, 2H), 6.99 (d, J=8 Hz, 1H), 4.85 (s, 2H), 3.3–3.42 (m, 2H), 2.62 (m, 2H), 2.44 (m, 2H), 2.30 (s, 3H, CH$_3$), 2.28 (s, 3H, CH$_3$), 2.1–2.2 (m, 4H), 2.11 (s, 3H, CH$_3$). MS m/z 613 [M−1].

Example 326

Synthesis of 5-(2,6-Dichloro-phenylmethanesulfonyl)-3-[1-{4-[3-((3R, 5S)-3,5-dimethyl-piperazin-1-yl)-3-oxo-propyl]-3,5-dimethyl-1H-pyrrol-2-yl}-meth-(Z)-ylidene]-1,3-dihydro-indol-2-one

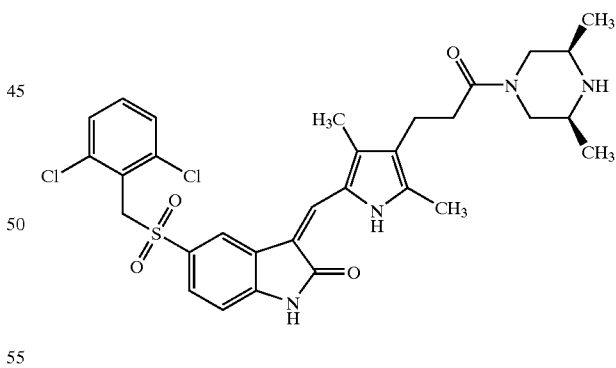

A mixture of 5-(2,6-dichloro-phenylmethanesulfonyl)-1,3-dihydro-indol-2-one (122 mg, 0.34 mmol), 4-[3-((3R, 5S)-3,5-dimethyl-piperazin-1-yl)-3-oxo-propyl]-3,5-dimethyl-1H-pyrrole-2-carbaldehyde (139 mg, 1.4 eq.) and piperidine (0.5 eq.) in ethanol (2 mL) was stirred at rt for 72 hours. The reaction was concentrated and purified on a silica gel column to give the titled compound as a dark brown orange solid.

$^1$HNMR (400 MHz, DMSO-d$_6$) δ 13.44 (s, 1H, NH), 11.25 (s, 1H, NH), 8.18 (d, 1H), 7.75 (s, 1H), 7.48 (s, 1H), 7.46 (s, 1H), 7.37 (m, 2H), 7.0 (d, J=8 Hz, 1H), 4.85 (s, 2H), 4.25 (m, 1H), 3.57 (m, 1H), 3.3–3.4 (m, 4H), 2.62 (m, 2H), 2.4 (m, 2H), 2.3 (s, 3H, CH$_3$), 2.29 (s, 3H, CH$_3$), 1.96 (t, 1H, NH), 0.9 (m, 6H, 2×CH$_3$). MS m/z 629 [M−1].

Example 327

Synthesis of 5-(2,6-Dichloro-phenylmethanesulfonyl)-3-[1-{3,5-dimethyl-4-[3-oxo-3-((S)-2-pyrrolidin-1-ylmethyl-pyrrolidin-1-yl)-propyl]-1H-pyrrol-2-yl}-meth-(Z)-ylidene]-1,3-dihydro-indol-2-one

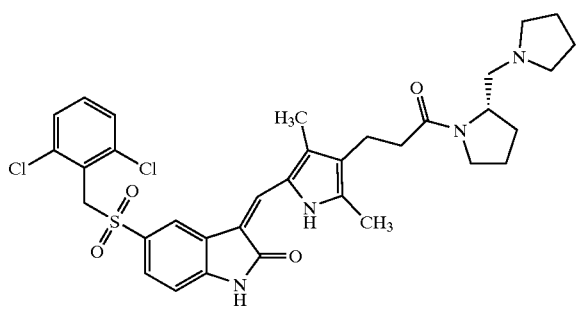

A mixture of 5-(2,6-dichloro-phenylmethanesulfonyl)-1,3-dihydro-indol-2-one (100 mg, 0.28 mmol), 3,5-dimethyl-4-[3-oxo-3-((S)-2-pyrrolidin-1-ylmethyl-pyrrolidin-1-yl)-propyl]-1H-pyrrole-2-carbaldehyde (1.7 eq.) and piperidine (1.5 eq.) in ethanol (2 mL) was stirred at rt for 96 hours. The reaction was concentrated and purified on a silica gel column to give the titled compound as a pale orange solid.

$^1$HNMR (400 MHz, DMSO-d$_6$) δ 13.44 (s, 1H, NH), 11.28 (s, 1H, NH), 8.18 (s, 1H), 7.76 (s, 1H), 7.48 (s, 1H), 7.46 (s, 1H), 7.37 (m, 2H), 7.0 (d, J=8 Hz, 1H), 4.84 (s, 2H), 4.18 (m, 1H), 3.2–3.4 (m, 4H), 2.97 (m, 2H), 2.64 (m, 2H), 2.38 (m, 2H), 2.32 (s, 3H, CH$_3$), 2.29 (s, 3H, CH$_3$), 2.1 (m, 2H), 1.6–1.8 (m, 4H), 1.08 (m, 4H). MS m/z 667 [M−1].

Example 328

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (1-Methyl-piperidin-4-ylmethyl)-amide

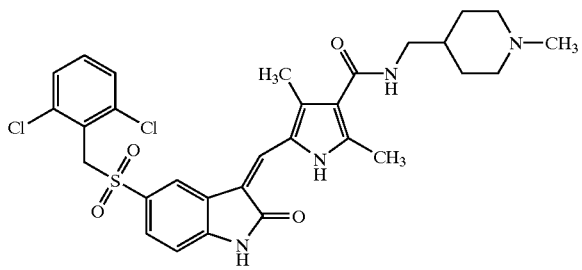

To a solution of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid [1,2,3]triazolo[4,5-b]pyridin-3-yl ester (300 mg, 0.48 mmol), DIPEA (136 mg, 2.2 eq.) and C-(1-methyl-piperidin-4-yl)-methylamine TFA salt (186 mg, 1.1 eq.) in DMF (5 mL) was stirred at rt for 72 hours. The reaction was concentrated, diluted with DCM, washed with sat.NaHCO$_3$ and water, concentrated and purified on a silica gel column to give the titled compound as an orange solid.

$^1$HNMR (400 MHz, DMSO-d$_6$) δ 13.6 (s, 1H, NH), 11.43 (s, 1H, NH), 8.27 (d, 1H), 7.86 (s, 1H), 7.49 (s, 1H), 7.47 (s, 1H), 7.4 (m, 2H), 7.01 (d, J=8 Hz, 1H), 4.88 (s, 2H), 3.3 (m, 2H), 2.69 (m, 2H), 2.43 (s, 6H, 2×CH$_3$), 1.8 (m, 3H, NCH$_3$), 1.7 (m, 1H), 1.38 (m, 2H), 1.21 (m, 2H). MS m/z 613 [M−1].

Example 329

Synthesis of 2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(1-methyl-piperidin-4-ylmethyl)-acetamide

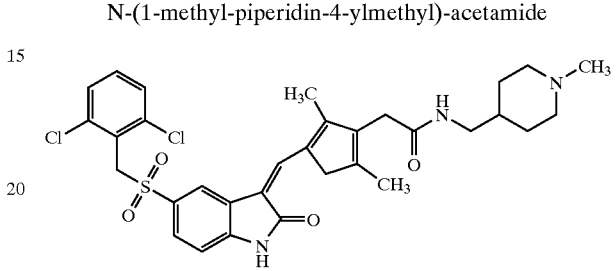

A mixture of 5-(2,6-Dichloro-phenylmethanesulfonyl)-1,3-dihydro-indol-2-one (400 mg, 1.12 mmol), 2-(5-formyl-2,4-dimethyl-1H-pyrrol-3-yl)-N-(1-methyl-piperidin-4-ylmethyl)-acetamide (295 mg, 1.2 q.) and piperidine (1.5 eq.) was stirred at rt for 96 hours. The reaction was concentrated and purified on a silica gel column to give the titled compound as a brown solid.

$^1$HNMR (400 MHz, DMSO-d$_6$) δ 13.46 (s, 1H, NH), 11.3 (s, 1H, NH), 8.17 (d, 1H), 7.89 (t, 1H, CONH), 7.76 (s, 1H), 7.48 (s, 1H), 7.46 (s, 1H), 7.38 (m, 2H), 7.0 (d, J=8 Hz, 1H), 4.87 (s, 2H), 3.4 (m, 2H), 2.91 (m, 4H), 2.31 (s, 2H), 2.27 (s, 6H, 2×CH$_3$), 1.6 (m, 3H, NCH$_3$), 1.4 (m, 1H), 1.1–1.25 (m, 4H). MS m/z 627 [M−1].

Example 330

Synthesis of 3-[1-{4-[3-((S)-2-Cyclopropylaminomethyl-pyrrolidin-1-yl)-3-oxo-propyl]-3,5-dimethyl-1H-pyrrol-2-yl}-meth-(Z)-ylidene]-5-(2,6-dichloro-phenylmethanesulfonyl)-1,3-dihydro-indol-2-one

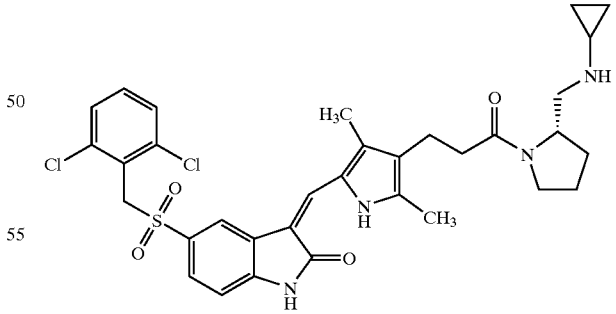

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (100 mg, 0.19 mmol) and DIPEA (45 mg, 1.9 eq.) in DMF (2 mL) was stirred at rt for 30 mins. To the mixture was added HATU (85 mg, 1.2 eq.). After stirring for another 3 hours, to the mixture was added cyclopropyl-(S)-1-pyrrolidin-2-ylmethyl-amine (29 mg, 1.1 eq.). After stirring for 72 hours, the reaction was concentrated and purified on a silica gel column to give the titled compound as an orange solid.

¹HNMR (400 MHz, DMSO-d$_6$) δ 13.46 (s, 1H, NH), 8.2 (d, 1H), 7.78 (s, 1H), 7.5 (s, 1H), 7.48 (s, 1H), 7.39 (m, 2H), 7.01 (d, J=8 Hz, 1H), 4.86 (s, 2H), 3.4 (m, 2H), 2.65 (m, 2H), 2.4 (m, 2H), 2.34 (s, 3H, CH$_3$), 2.31 (s, 3H, CH$_3$), 1.8 (m, 6H), 0.65 (m, 2H), 0.4 (m, 2H). MS m/z 653 [M−1].

Example 331

Synthesis of 5-(2,6-Dichloro-phenylmethanesulfonyl)-3-[1-{4-[3-(4-hydroxy-piperidin-1-yl)-3-oxo-propyl]-3,5-dimethyl-pyrrol-2-yl}-meth-(Z)-ylidene]-1,3-dihydro-indol-2-one

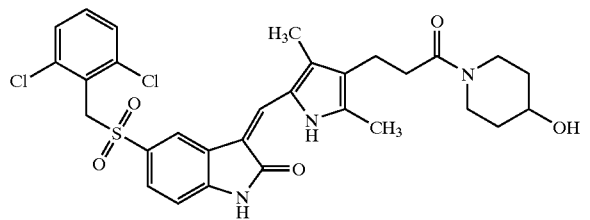

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (100 mg, 0.19 mmol) and DIPEA (45 mg, 1.9 eq.) in DMF (2 mL) was stirred at rt for 15 mins. To the mixture was added HATU (85 mg, 1.2 eq.). After stirring for another 30 mins, to the mixture was added piperidin-4-ol (38 mg, 2 eq.). After stirring for 48 hours, the reaction was concentrated and purified on a silica gel column to give the titled compound as an orange solid.

¹HNMR (400 MHz, DMSO-d$_6$) δ 13.44 (s, 1H, NH), 11.25 (s, 1H, NH), 8.17 (d, 1H), 7.75 (s, 1H), 7.48 (s, 1H), 7.46 (s, 1H), 7.38 (m, 2H), 7.0 (d, J =8 Hz, 1H), 4.85 (s, 2H), 4.69 (d, 1H, OH), 3.9 (m, 1H), 3.6 (m, 2H), 3.08 (m, 1H), 2.95 (m, 1H), 2.6 (m, 2H), 2.4 (m, 2H), 2.31 (s, 3H, CH$_3$), 2.28 (s, 3H, CH$_3$), 1.63 (m, 2H), 1.22 (m, 2H). MS m/z 614 [M−1].

Example 332

Synthesis of 5-[(E)-3-Chloro-2-(1-chloro-vinyl)-penta-2,4-diene-1-sulfonyl]-3-[-1-{4-[3-((R)-3-hydroxy-pyrrolidin-1-yl)-3-oxo-propyl]-3,5-dimethyl-1H-pyrrol-2-yl}-meth-(Z)-ylidene]-1,3-dihydro-indol-2-one

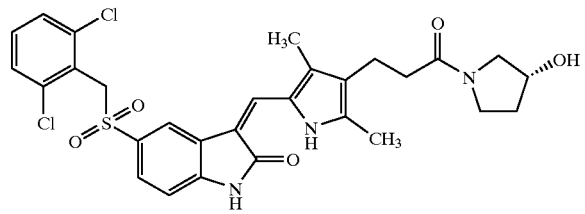

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (267 mg), (R)-pyrrolidin-3-ol (2 eq.), HATU (1.2 eq.) and TEA (0.2 mL) in DMF (2 mL) was stirred at rt for 2 hours. The reaction was concentrated, diluted with DCM, washed with water (2×), sodium carbonate (2×), dried and concentrated. The residue was purified on a silica gel column to give 16 mg of the titled compound as a yellow solid.

¹HNMR (400 MHz, DMSO-d$_6$) δ 13.38 (br s, 1H, NH), 11.2 (s, 1H, NH), 8.12 (d, 1H), 7.70 (s, 1H), 7.43 (d, 1H), 7.41 (s, 1H), 7.32 (m, 2H), 6.95 (d, J=8 Hz, 1H), 4.91 & 4.83 (2m, 1H), 4.8 (s, 2H), 4.16 (m, 2H), 3.35 (m, 2H), 3.2 (m, 2H), 2.57 (m, 2H), 2.3 (m, 2H), 2.27 (s, 3H, CH$_3$), 2.24 (s, 3H, CH$_3$). MS m/z 602 [M$^+$+1].

Example 333

Synthesis of 5-(2,6-Dichloro-phenylmethanesulfonyl)-3-[1-(4-{3-[(R)-2-((R)-3-hydroxy-pyrrolidin-1-ylmethyl)-pyrrolidin-1-yl]-3-oxo-propyl}-3 5-dimethyl-1H-pyrrol-2-yl)-meth-(Z)-ylidene]-1,3-dihydro-indol-2-one

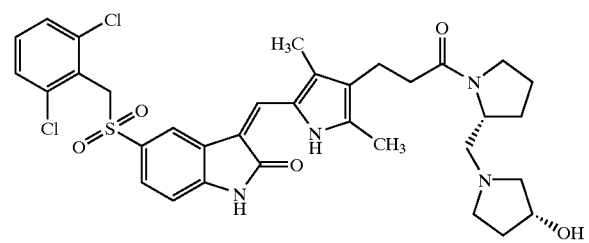

A mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (267 mg), (R)-1-(R)-1-pyrrolidin-2-ylmethyl-pyrrolidin-3-ol (2 eq.), HATU (1.2 eq.) and TEA (0.2 mL) in DMF (2 mL) was stirred at rt for 2 hours. The reaction was concentrated, diluted with DCM, washed with water (2×), sodium carbonate (2×), dried and concentrated. The residue was purified on a silica gel column to give 36 mg of the titled compound as a yellow solid. MS m/z 685 [M$^+$+1].

Example 334

Synthesis of 5-(2,6-Difluoro-phenylmethanesulfonyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one

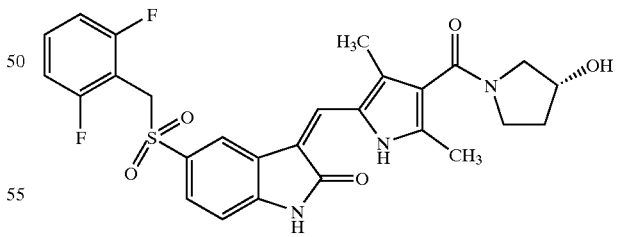

A mixture of 5-[5-(2,6-difluoro-phenylmethanesulfonyl)-2-oxo-1,2-dihydro-indol-(3Z)-ylidenemethyl]-2,4-dimethyl-1H-pyrrole-3-carboxylic acid (236 mg), (R)-pyrrolidin-3-ol (2 eq.), HATU (1.2 eq.) and TEA (0.2 mL) in DMF (3 mL) was stirred at rt for 2 hours. The reaction was concentrated, diluted with DCM, washed with water (2×), sodium carbonate (2×), dried and concentrated. The residue was purified on a silica gel column to give 16 mg of the titled compound as a yellow solid.

Example 335

Synthesis of 3-[1-[4-(4-Cyclopropylamino-piperidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

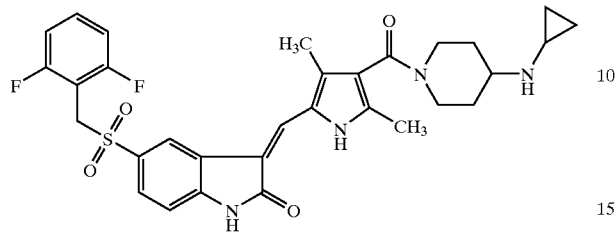

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (156 mg, 0.33 mmol), EDAC (135 mg, 0.7 mmol) and HOBt (45 mg, 0.33 mmol) in DMF (4 mL) was added cyclopropyl-piperidin-4-yl-amine (100 mg, 0.7 mmol) and TEA (0.14 mL). The mixture was stirred at rt for 2 days. The reaction was diluted with and NaHCO$_3$, extracted with DCM. The combined extracts were concentrated and the residue was purified on a silica gel column to give the titled compound.

$^1$HNMR (400 MHz, DMSO-d$_6$) δ 13.52 (br s, 1H, NH), 11.38 (s, 1H, NH), 8.30 (d, 1H), 7.95 (s, 1H), 7.44 (m, 2H), 6.88 (t, 2H), 7.0 (d, 1H), 4.62 (s, 2H), 4.32 (m, 1H), 3.3 (m, 2H), 3.0 (m, 2H), 2.77 (m, 1H), 2.3 (s, 6H, 2×CH$_3$), 2.07 (m, 1H), 1.85 (m, 2H), 1.2 (m, 2H), 0.37 (m, 2H), 0.2 (m, 2H). MS m/z 593 [M−1].

Example 336

Synthesis of 3-[1-{4-[3-(4-Cyclopropylamino-piperidin-1-yl)-3-oxo-propyl]-3,5-dimethyl-1H-pyrrol-2-yl}-meth-(Z)-ylidene]-5-(2,6-dichloro-phenylmethanesulfonyl)-1,3-dihydro-indol-2-one

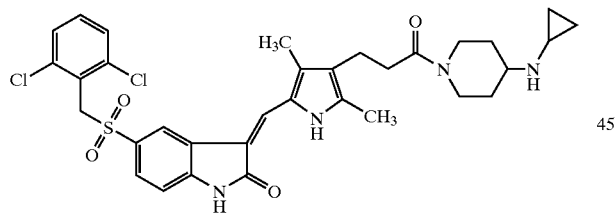

To a mixture of 3-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-propionic acid (178 mg, 0.33 mmol), EDAC (135 mg, 0.7 mmol) and HOBt (45 mg, 0.33 mmol) in DMF (4 mL) was added cyclopropyl-piperidin-4-yl-amine (100 mg, 0.7 mmol) and TEA (0.14 mL). The mixture was stirred at rt for 2 days. The reaction was diluted with and NaHCO$_3$, extracted with DCM. The combined extracts were concentrated and the residue was purified on a silica gel column to give the titled compound.

$^1$HNMR (400 MHz, DMSO-d$_6$) δ 13.29 (s, 1H, NH), 11.11 (s, 1H, NH), 8.03 (d, 1H), 7.61 (s, 1H), 7.34 (d, 2H), 7.25 (m, 2H), 6.85 (d, 1H), 4.85 (s, 2H), 4.19 (d, 3.7 (d, 1H), 3.28 (m, 1H), 2.95 (t, 1H), 2.63 (m, 4H), 2.44 (m, 2H), 2.32 (s, 3H, CH$_3$), 2.29 (s, 3H, CH$_3$), 2.02 (m, 1H), 1.75 (d, 2H), 1.01 (m, 2H), 0.33 (m, 2H), 0.15 (m, 2H). MS m/z 653 [M−1].

Example 337

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-Pyrrolidin-1-yl)-amide

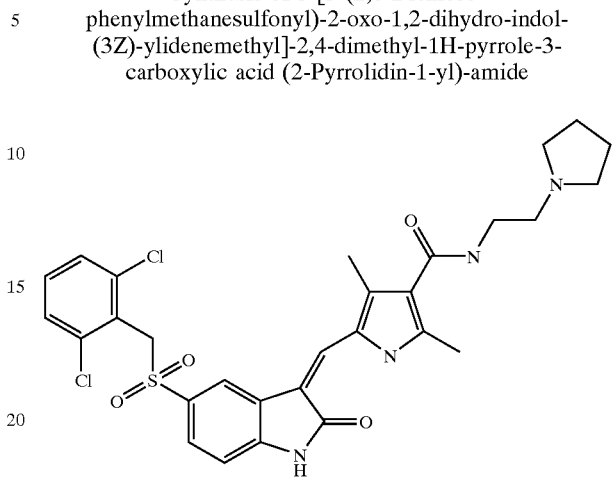

5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid was coupled with 2-pyrrolidin-1-yl-ethylamine to give the titled compound.

Example 338

Synthesis of 5-(2,6-Dichloro-phenylmethanesulfonyl)-3-[1-[5-methyl-3((S)-2-pyrrolidin-1-ylmethyl-pyrrolidine-1-carbonyl)-1H-pyrrol-2-yl]-meth-(Z)-ylidene]- H-pyrrol-2-yl]-meth-(Z)-ylidene[-1.3dihydro-indol-2-one 1,3-dihydro-indol-2-one

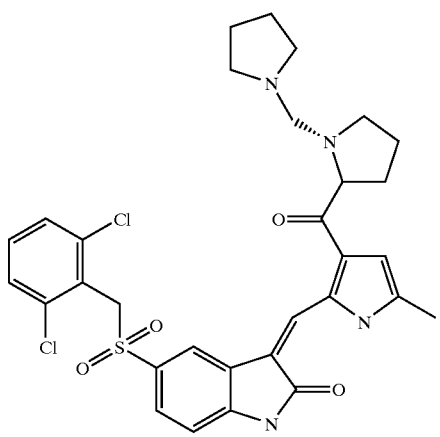

2-[5-(2,6-Dichloro-phenylmethanesulfonyl)-2-oxo-1,2-dihydro-indol-(3Z)-ylidenemethyl]-5-methyl-1H-pyrrole-3-carboxylic acid (150 mg, 0.3 mmol) was coupled with (S)-2-pyrrolidin-1-ylmethyl-pyrrolidine (47 mg, 1 eq.) using HOBt (1 eq.), EDAC.HCl (1 eq.) and TEA (3 eq.) in DMF (10 mL) stirring at rt over the weekend to give the titled compound. MS m/z 625 [M−1].

Example 339

Synthesis of 5-(2,6-Dichloro-phenylmethanesulfonyl)-3-[1-{4-[(S)-2-((S)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

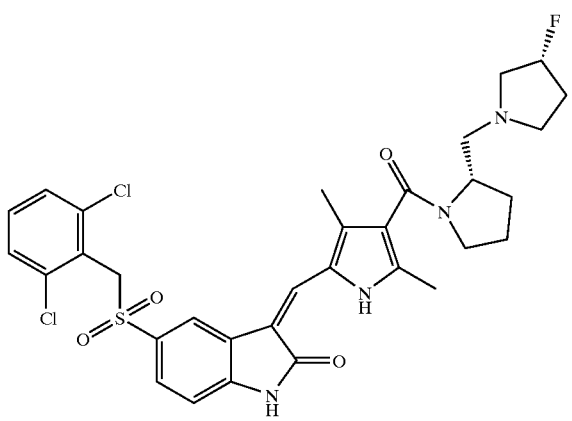

To a mixture of 5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid (250 mg, 0.5 mmol), EDAC (190 mg) and HOBt (65 mg) in DMF (4 mL) was added (S)-3-fluoro-1-(S)-1-pyrrolidin-2-ylmethyl-pyrrolidine (135 mg, 0.78 mmol) and TEA (0.16 mL). The mixture was stirred at rt for 20 hours. The reaction was diluted with water and NaHCO$_3$, extracted with 5% methanol in DCM. The combined extracts were concentrated and purified on a silica gel column to give the titled compound. MS m/z 661 [M$^+$+1].

Example 340

Synthesis of 5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid

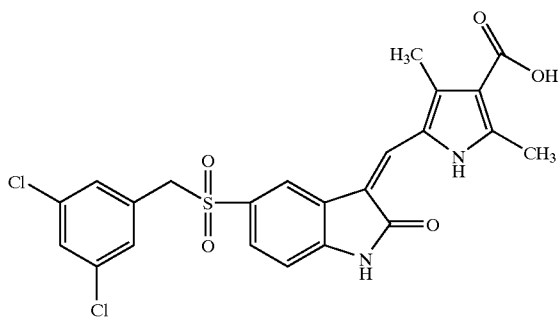

A mixture of 5-(3,5-dichloro-phenylmethanesulfonyl)-1,3-dihydro-indol-2-one (356 mg, 1 mmol), 5-formyl-2,4-dimethyl-1H-pyrrole-3-carboxylic acid (167 mg) and piperidine (cat. amount) in ethanol was stirred at rt for 2 days. The reaction was concentrated and triturated with HCl (2M solution) to give the titled compound.

$^1$HNMR (400 MHz, DMSO d$_6$) δ 7.95 (s, 1H), 7.64 (s, 1H), 7.34 (s, 1H), 7.33 (s, 2H), 6.96 (d, 1H), 4.65 (s, 2H), 2.53 (s, 3H, CH$_3$), 2.52 (s, 3H, CH$_3$).

Example 341

Synthesis of 3-[1-{4-[(Cyclopropyl-methyl-amino)-methyl]-3,5-dimethyl-1H-pyrrol-2-yl}-meth-(Z)-ylidene]-5-[2-(2-morpholin-4-yl-ethoxy)-phenylmethanesulfonyl]-1,3-dihydro-indol-2-one

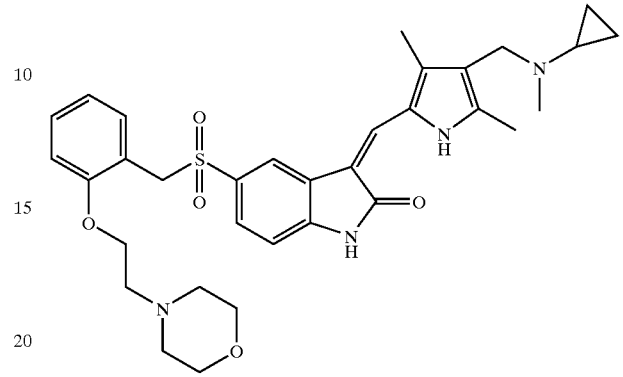

5-[2-(2-Morpholin-4-yl-ethoxy)-phenylmethanesulfonyl]-1,3-dihydro-indol-2-one (39 mg, 0.094 mmol) was condensed with 4-[(cyclopropyl-methyl-amino)-methyl]-3,5-dimethyl-1H-pyrrole-2-carbaldehyde (21 mg, 0.1 mmol) and piperidine (1 drop) in ethanol (1.5 mL) at rt for 48 hours. The solvent was removed and the residue was purified on a silica gel column to give 26 mg (46%) of the titled compound.

$^1$HNMR (400 MHz, DMSO d$_6$) δ 13.42 (s, 1H), 11.22 (s, 1H), 7.98 (d, 1H), 7.67 (s, 1H), 7.26 (m, 2H), 7.13 (dd, 1H), 6.95 (t, 1H), 6.88 (d, 1H), 6.84 (d, 1H), 4.52 (s, 2H), 3.58 (t, 2H), 3.46 (m, 6H), 2.33 (s, 3H, CH3), 2.31 (s, 3H, CH$_3$), 2.28 (m, 6H), 2.15 (s, 3H, CH$_3$), 1.68 (m, 1H), 0.44 (m, 2H), 0.3 (m, 2H). MS m/z 603 [M−1].

Example 342

Synthesis of 3-[1-[4-((R)-3-Hydroxy-pyrrolidine-1-carbonyl)-3,5-dimethyl-1H-pyrrol-2-yl]-meth-(Z)-ylidene]-5-[2-(2-morpholin-4-yl-ethoxy)-phenylmethanesulfonyl]-1,3-dihydro-indol-2-one

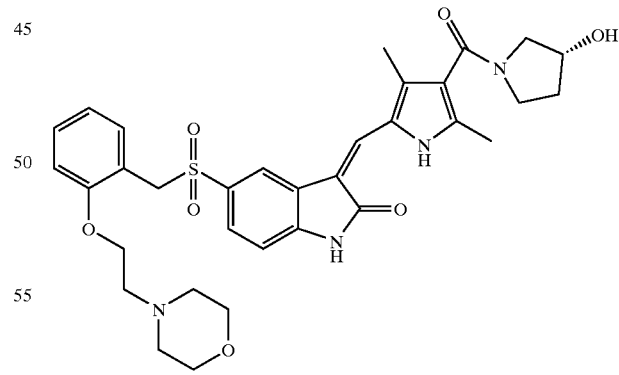

5-[2-(2-Morpholin-4-yl-ethoxy)-phenylmethanesulfonyl]-1,3-dihydro-indol-2-one (42 mg, 0.1 mmol) was condensed with 4-((R)-3-hydroxy-pyrrolidine-1-carbonyl)-3,5-dimethyl-1H-pyrrole-2-carbaldehyde (24 mg, 0.1 mmol) and piperidine (1 drop) in ethanol (1.5 mL) at rt for 48 hours. The solvent was removed and the residue was purified on a silica gel column to give 44 mg (69%) of the titled compound.

¹HNMR (400 MHz, DMSO d₆) δ 13.48 (s, 1H), 11.33 (s, 1H), 8.08 (s, 1H), 7.75 (s, 1H), 7.27 (m, 2H), 7.17 (dd, 1H), 6.91 (m, 3H), 4.94 & 5.0 (2m, 1H), 4.54 (s, 2H), 4.35 & 4.22 (2m, 1H), 3.59 (t, 2H), 3.47 (m, 4H), 3.3–3.5 (m, 4H), 2.31 (s, 6H, 2×CH₃), 2.29 (m, 6H), 1.8 & 1.95 (2m, 2H). MS m/z 633 [M−1].

Example 343

Synthesis of 3-[1-[3,5-Dimethyl-4-(4-methyl-piperazine-1-carbonyl)-1H-pyrrol-2-yl]-meth-(Z)-ylidene]-5-[2-(2-morpholin-4-yl-ethoxy)-phenylmethanesulfonyl]-1,3-dihydro-indol-2-one

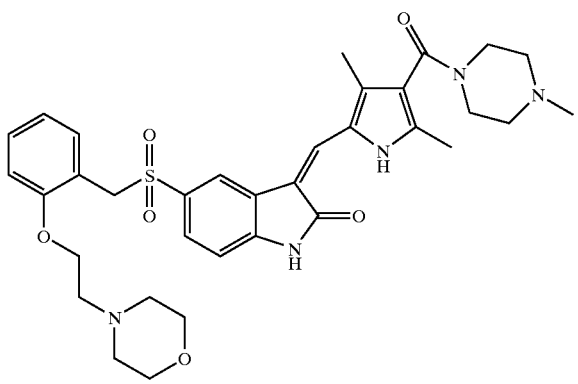

5-[2-(2-Morpholin-4-yl-ethoxy)-phenylmethanesulfonyl]-1,3-dihydro-indol-2-one (46 mg, 0.12 mmol) was condensed with 3,5-dimethyl-4-(4-methyl-piperazine-1-carbonyl)-1H-pyrrole-2-carbaldehyde (30 mg, 0.12 mmol) and piperidine (1 drop) in ethanol (1.5 mL) at rt for 48 hours. The solid was collected by vacuum filtration and purified on a silica gel column to give 39 mg (55%) of the titled compound.

¹HNMR (400 MHz, DMSO d₆) 13.52 (s, 1H), 11.34 (s, 1H), 8.1 (d, 1H), 7.77 (s, 1H), 7.28 (m, 2H), 7.17 (dd, 1H), 6.95 (t, 1H), 6.9 (d, 1H), 6.84 (d, 1H), 4.54 (s, 2H), 3.59 (t, 2H), 3.47 (m, 4H), 3.4–3.6 (m, 4H), 2.2–2.4 (m, 4H), 2.31 (s, 6H, 2×CH₃), 2.29 (m, 6H), 2.20 (s, 3H). MS m/z 646 [M−1].

Example 344

Synthesis of 3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-[2-(2-morpholin-4-yl-ethoxy)-phenylmethanesulfonyl]-1,3-dihydro-indol-2-one

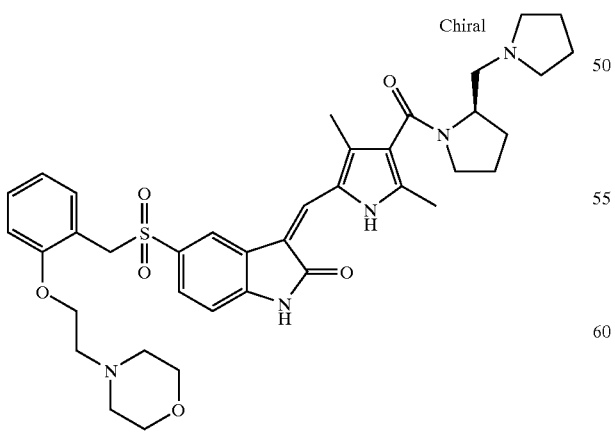

5-[2-(2-Morpholin-4-yl-ethoxy)-phenylmethanesulfonyl]-1,3-dihydro-indol-2-one (41 mg, 0.1 mmol) was condensed with 3,5-dimethyl-4-((R)-2-pyrrolidin-1-ylmethyl-pyrrolidine-1-carbonyl)-1H-pyrrole-2-carbaldehyde (35 mg, 0.1 mmol) and piperidine (1 drop) in ethanol (1.5 mL) at rt for 48 hours. The solid was collected by vacuum filtration and purified on a silica gel column to give 36 mg (35%) of the titled compound.

¹HNMR (400 MHz, DMSO d₆) δ 13.55 (s, 1H), 11.36 (s, 1H), 8.13 (s, 1H), 7.79 (s, 1H), 7.28 (m, 2H), 7.16 (d, 1H), 6.95 (t, 1H), 6.9 (d, 1H), 6.85 (d, 1H), 4.55 (s, 2H), 4.46 (m, 1H), 3.8 (m, 1H), 3.6 (m, 2H), 3.47 (m, 4H), 3.5–3.7 (m, 2H), 3.2 (m, 1H), 3.1 (m, 1H), 2.37 (s, 6H, 2×CH₃), 2.29 (m, 6H), 2.1–2.4 (m, 3H), 2.04 (m, 2H), 1.88 (m, 4H), 1.73 (m, 2H). MS m/z 700 [M−1].

Example 345

Synthesis of 3-[1-[4-(4-Cyclopropylamino-piperidine-1-carbonyl)-3,5-dimethyl-1H-pyrrol-2-yl]-meth-(Z)-ylidene]-5-(3,5-dimethoxy-phenylmethanesulfonyl)-1,3-dihydro-indol-2-one

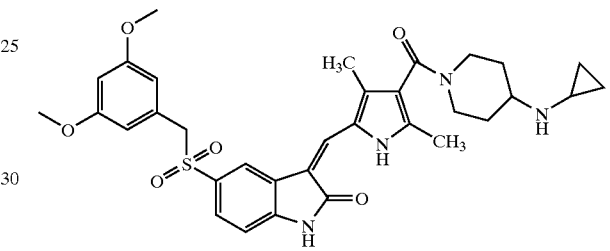

¹H NMR (400 MHz, DMSO-d₆) δ 13.56 (br s, 1H, NH), 11.40 (s, 1H, NH), 8.29 (d, 1H), 7.87 (s, 1H), 7.47 (dd, 1H), 7.05 (d, 1H), 6.47 (dd, 1H), 6.34 (d, 2H), 4.58 (s, 2H), 3.65 (s, 6H, 2×OCH₃), 3.06 (m, 3H), 2.8 (m, 1H), 2.34 (s, 6H, 2×CH₃), 2.1 (m, 1H), 1.89 (m, 3H), 1.21 (m, 2H), 0.39 (m, 2H), 0.24 (m, 2H). MS m/z 617 [M−1].

Example 346

Synthesis of 3-[1-[4-((R)-2-Cyclopropylaminomethyl-pyrrolidine-1-carbonyl)-3,5-dimethyl-1H-pyrrol-2-yl]-meth-(Z)-ylidene]-5-(3,5-dimethoxy-phenylmethanesulfonyl)-1,3-dihydro-indol-2-one

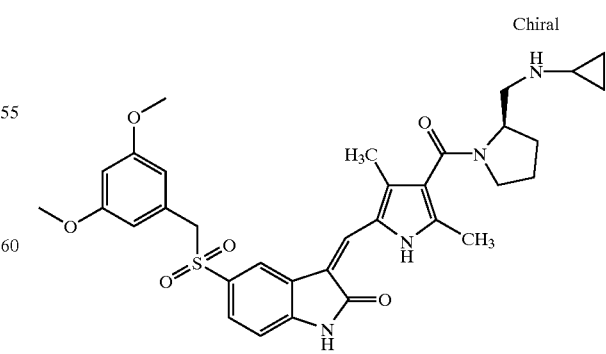

MS m/z 617 [M−1].

Example 347

Synthesis of 3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(3,5-dimethoxy-phenylmethanesulfonyl)-1,3-dihydro-indol-2-one

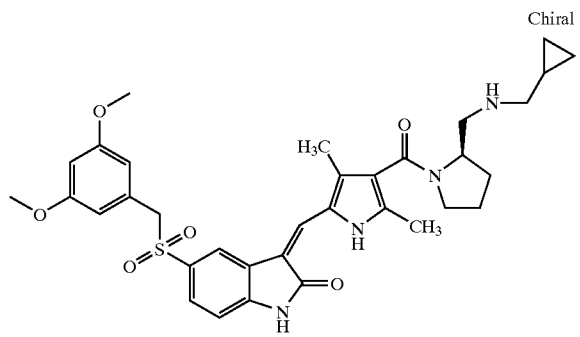

MS m/z 631 [M−1].

Example 348

Synthesis of 5-(3,5-Dimethoxy-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one

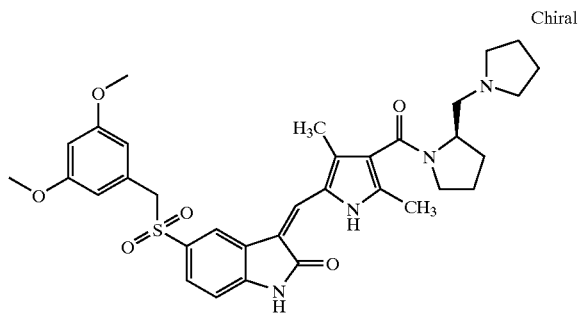

$^1$H NMR (400 MHz, DMSO-$d_6$) δ 13.49 (br s, 1H, NH), 11.35 (s, 1H, NH), 8.22 (s, 1H), 7.8 (s, 1H), 7.42 (d, 1H), 6.99 (d, 1H), 6.41 (s, 1H), 6.30 (s, 2H), 4.52 (s, 2H), 4.28 (m, 1H), 3.6 (s, 6H, 2×OCH$_3$), 3.47 (m, 1H), 3.36 (m, 1H), 3.21 (m, 1H), 2.64 (m, 1H), 2.3 (s, 6H, 2×CH$_3$), 2.17 (m, 2h), 1.8–2.0 (m, 5H), 1.66 (m, 3H), 1.48 (m, 2H). MS m/z 631 [M−1].

Example 349

Synthesis of 3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-phenylmethanesulfonyl-1,3-dihydro-indol-2-one

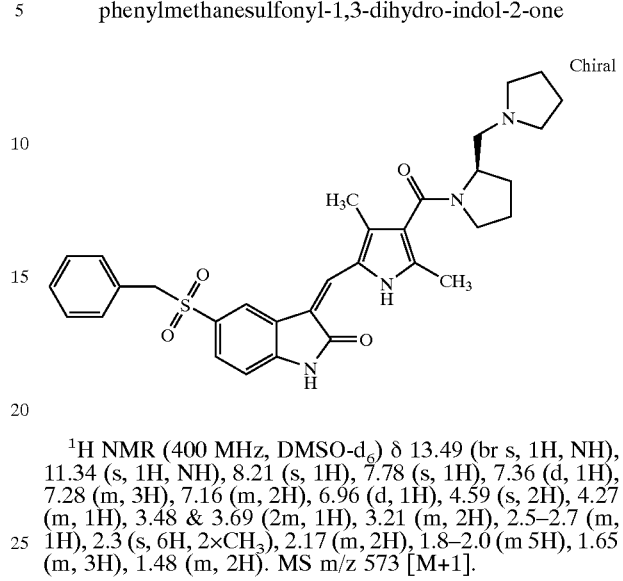

$^1$H NMR (400 MHz, DMSO-$d_6$) δ 13.49 (br s, 1H, NH), 11.34 (s, 1H, NH), 8.21 (s, 1H), 7.78 (s, 1H), 7.36 (d, 1H), 7.28 (m, 3H), 7.16 (m, 2H), 6.96 (d, 1H), 4.59 (s, 2H), 4.27 (m, 1H), 3.48 & 3.69 (2m, 1H), 3.21 (m, 2H), 2.5–2.7 (m, 1H), 2.3 (s, 6H, 2×CH$_3$), 2.17 (m, 2H), 1.8–2.0 (m 5H), 1.65 (m, 3H), 1.48 (m, 2H). MS m/z 573 [M+1].

Example 350

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid Cyclopropyl-(R)-1-pyrrolidin-2-ylmethyl-amide

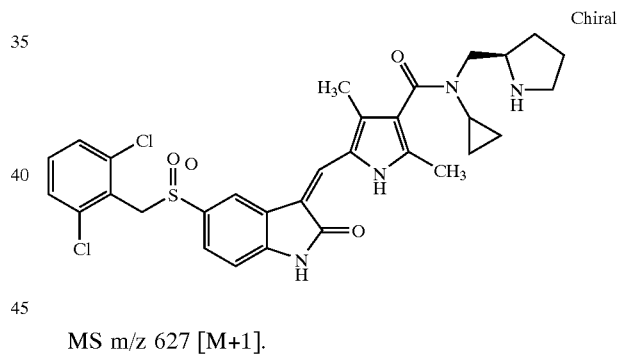

MS m/z 627 [M+1].

Example 351

Synthesis of 5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid Cyclopropylmethyl-(R)-1-pyrrolidin-2-ylmethyl-amide

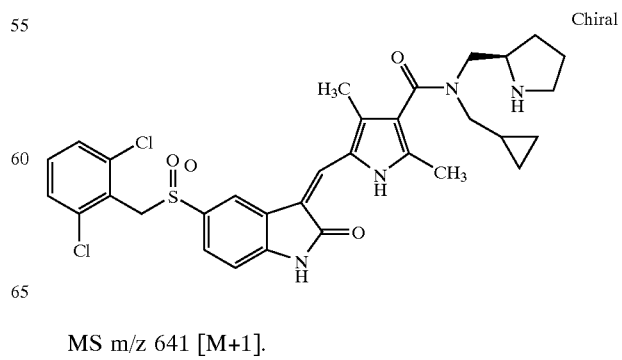

MS m/z 641 [M+1].

Example 352

Synthesis of 5-(2,6-Dimethoxy-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one

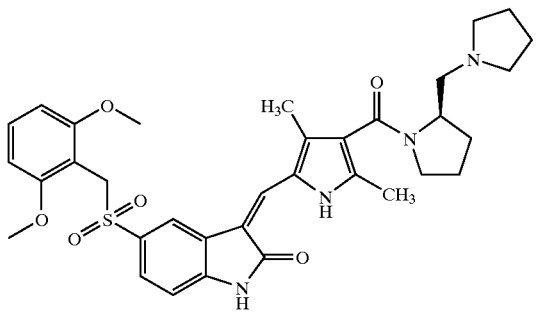

$^1$H NMR (400 MHz, DMSO-d$_6$) δ 13.56 (br s, 1H, NH), 11.33 (s, 1H, NH), 8.14 (s, 1H), 7.81 (s, 1H), 7.27 (dd, 1H), 7.21 (t, 1H), 6.94 (d, 1H), 6.53 (d, 2H), 4.48 (s, 2H), 4.46 (m, 1H), 3.78 (m, 1H), 3.65 (m, 1H), 3.43 (s, 6H, 2×OCH$_3$), 3.18 (m, 1H), 3.06 (m, 1H), 2.35 (s, 6H, 2×CH$_3$), 2.16 (m, 2H), 2.03 (m, 3H), 1.87 (m, 4H), 1.7 (m, 3H), MS m/z 631 [M−1].

Example 353

Synthesis of 3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-difluoro-phenylmethanesulfonyl)-1,3-dihydro-indol-2-one

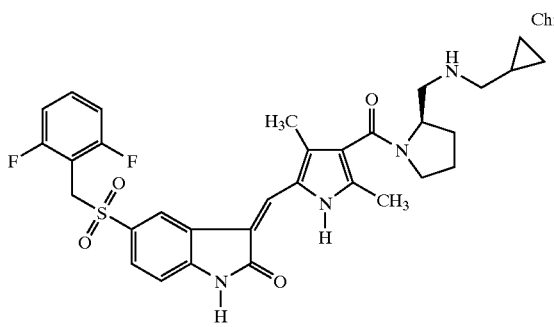

MS m/z 607 [M−1].

Example 354

Synthesis of 3-[1-[4-((R)-2-Cyclopropylaminomethyl-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

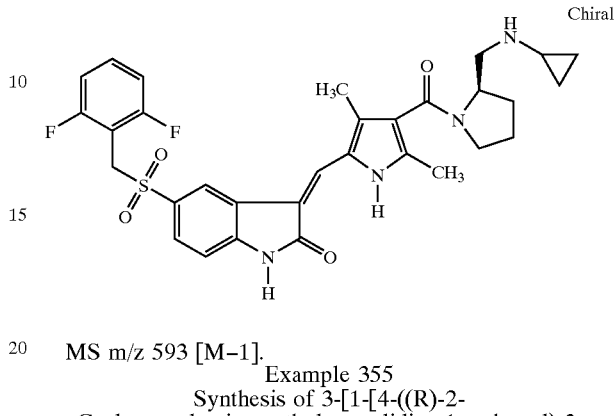

MS m/z 593 [M−1].

Example 355

Synthesis of 3-[1-[4-((R)-2-Cyclopropylaminomethyl-pyrrolidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

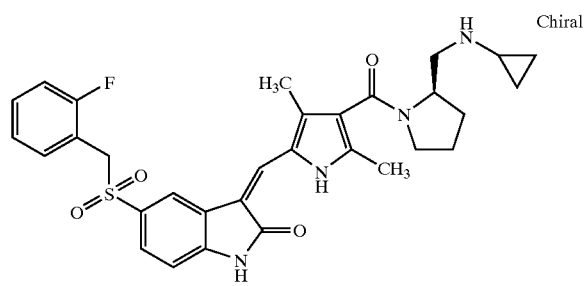

Yellow solid.
$^1$H NMR (400 MHz, DMSO-d$_6$) 13.48 (br s, 1H, NH), 11.35 (br s, 1H, NH), 8.23 (s, 1H), 7.80 (s, 1H), 7.36 (m, 2H), 7.23 (m, 1H), 7.15 (m, 2H), 6.97 (d, 1H), 4.62 (s, 2H), 4.2 (m, 1H), 3.46 (m, 1H), 3.22 (m, 2H), 2.94 (m, 1H), 2.58 (m, 1H), 2.3 (s, 6H, 2×CH$_3$), 2.11 (m, 1H), 1.88 (m, 4H), 0.35 (m, 2H), 0.19 (m, 2H). MS m/z 575 [M−1].

Example 356

Synthesis of 3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2-fluoro-phenylmethanesulfonyl)-1,3-dihydro-indol-2-one

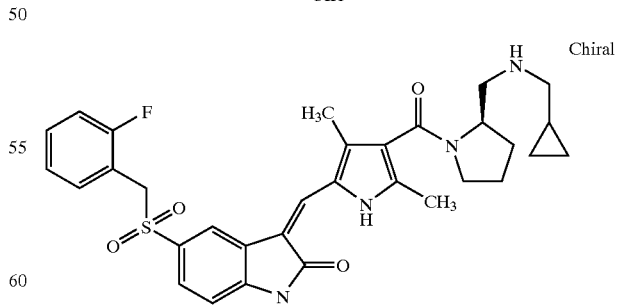

$^1$H NMR (400 MHz, DMSO-d$_6$) δ 13.51 (br s, 1H, NH), 8.25 (d, 1H), 7.82 (s, 1H), 7.37 (m, 2H), 7.25 (dt, 1H), 7.16 (m, 2H), 6.99 (d, 1H), 4.64 (s, 2H), 4.22 (m, 1H), 3.49 (m, 1H), 3.24 (m, 2H), 2.86 (m, 1H), 2.6 (m, 1H), 2.41 (m, 2H), 232 (s, 6H, 2×CH$_3$), 2.08 (m, 1H), 1.9 (m, 3H), 1.7 (m, 1H), 0.41 (m, 2H), 0.11 (m, 2H). MS m/z 589 [M−1].

Example 357

Synthesis of 3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-(2-fluoro-phenylmethanesulfonyl)-1,3-dihydro-indol-2-one

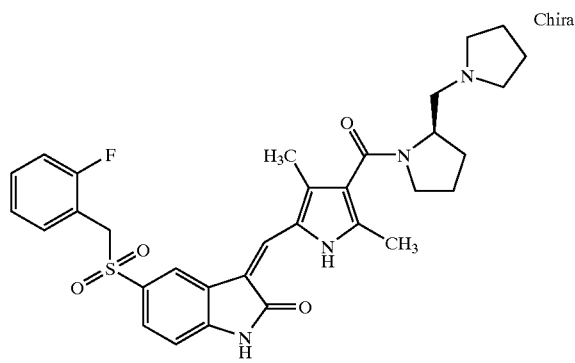

Yellow solid.
$^1$H NMR (400 MHz, DMSO-$d_6$) δ 13.48 (br s, 1H, NH), 11.36 (s, 1H, NH), 8.23 (s, 1H), 7.80 (s, 1H), 7.36 (m, 2H), 7.23 (dt, 1H), 7.15 (m, 2H), 6.97 (d, 1H), 4.62 (s, 2H), 4.28 (m, 1H), 3.46 (m, 1H), 3.22 (m, 2H), 2.53 (m, 2H), 2.3 (s, 6H, 2×CH$_3$), 2.2 (m, 1H), 1.88 (m, 5H), 1.67 (m, 3H), 1.49 (m, 2H). MS m/z 589 [M−1].

Example 358

Synthesis of 5-(2-Chloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one

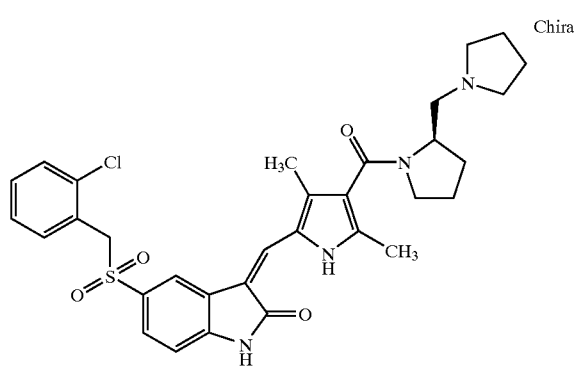

Yellow solid.
$^1$H NMR (400 MHz, DMSO-$d_6$) δ 13.48 (br s, 1H, NH), 11.36 (s, 1H, NH) 8.17 (s, 1H), 7.77 (s, 1H), 7.4 (m, 1H), 7.32 (m, 4H), 6.97 (d, 1H), 4.72 (s, 2H), 4.26 (m, 1H), 3.46 (m, 1H), 3.21 (m, 2H), 2.53 (m, 2H), 2.30 (s, 3H, CH$_3$), 2.29 (s, 3H, CH$_3$), 2.18 (m, 1H), 1.9 (m, 5H), 1.67 (m, 3H), 1.48 (m, 2H). MS m/z 605 [M−1].

Example 359

Synthesis of 5-(2-Chloro-phenylmethanesulfonyl)-3-[1-[4-((R)-2-cyclopropylaminomethyl-pyrrolidine-1-carbonyl)-3,5-dimethyl-1H-pyrrol-2-yl]-meth-(Z)-ylidene]-1,3-dihydro-indol-2-one

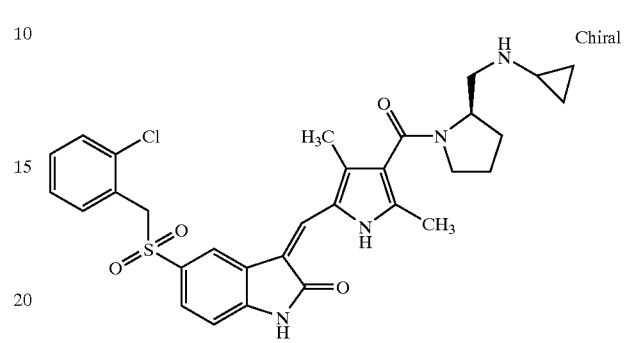

Yellow solid.
$^1$H NMR (400 MHz, DMSO-$d_6$) δ 13.46 (br s, 1H, NH), 11.34 (br s, 1H, NH), 8.17 (d, 1H), 7.77 (s, 1H), 7.38 (m, 1H), 7.32 (m, 4H), 6.97 (d, 1H), 4.72 (s, 2H), 4.2 (m, 1H), 3.45 (m, 1H), 3.2 (m, 2H), 2.94 (m, 1H), 2.57 (m, 1H), 2.3 (s, 6H, 2×CH$_3$), 1.87 (m, 1H), 1.87 (m, 3H), 1.68 (m, 1H), 0.35 (m, 2H), 0.2 (m, 2H). MS m/z 591 [M−1].

Example 360

Synthesis of 5-(2-Chloro-phenylmethanesulfonyl)-3-[1-(4-{(R)-2-[(cyclopropylmethyl-amino)-methyl]-pyrrolidine-1-carbonyl}-3,5-dimethyl-1H-pyrrol-2-yl)-meth-(Z)-ylidene]-1,3-dihydro-indol-2-one

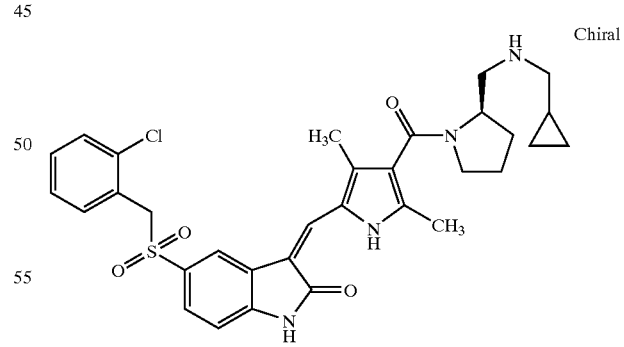

$^1$H NMR (400 MHz, DMSO-$d_6$) δ 13.51 (br s, 1H, NH), 8.19 (d, 1H) 7.8 (s, 1H), 7.4 (m, 1H), 7.34 (m, 4H), 6.99 (d, 1H), 4.74 (s, 2H), 4.25 (m, 1H), 3.48 (m 1H), 3.27 (m, 2H), 2.9 (m, 1H), 2.66 (m, 1H), 2.33 (s, 6H, 2×CH$_3$), 1.86 (m, 5H), 1.7 (m, 1H), 0.44 (m, 2H), 0.14 (m, 2H). MS m/z 605 [M−1].

Example 361

Synthesis of 5-(2-Chloro-phenylmethanesulfonyl)-3-[1-[4-(4-cyclopropylamino-piperidine-1-carbonyl)-3,5-dimethyl-1H-pyrrol-2-yl]-meth-(Z)-ylidene]-1,3-dihydro-indol-2-one

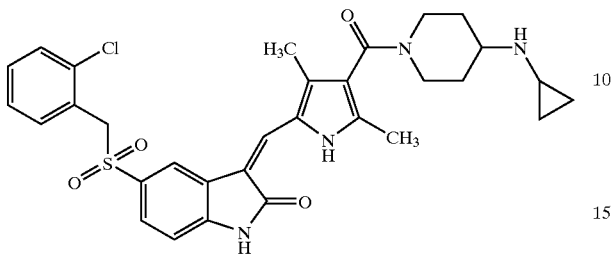

Yellow solid.

$^1$H NMR (400 MHz, DMSO-d$_6$) δ 13.49 (br s, 1H, NH), 11.37 (br s, 1H, NH) 8.19 (d, 1H), 7.8 (s, 1H), 7.39 (m, 1H), 7.33 (m, 4H), 6.98 (d, 1H), 4.73 (s, 2H), 4.27 (m, 1H), 3.57 (m, 1H), 3.01 (m, 2H), 2.74 (m, 1H), 2.29 (s, 6H, 2×CH$_3$), 2.29 (m, 1H), 2.06 (m, 1H), 1.85 (m, 2H), 1.17 (m, 2H), 0.35 (m, 2H), 0.19 (m, 2H). MS m/z 591 [M−1].

Example 362

Synthesis of 3-[1-[4-(4-Cyclopropylamino-piperidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

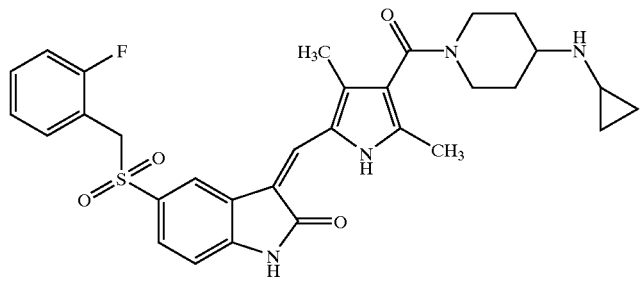

Yellow solid.

$^1$H NMR (400MHz, DMSO-d$_6$) δ 13.5 (br s, 1H, NH), 11.35 (br s, 1H, NH), 8.24 (d, 1H), 7.81 (s, 1H), 7.35 (m, 2H), 7.23 (dt, 1H), 7.15 (m, 2H), 6.97 (d, 1H), 4.62 (s, 2H), 4.25 (m, 1H), 3.55 (m, 1H), 3.01 (m, 2H), 2.72 (m, 1H), 2.28 (s, 6H, 2×CH$_3$), 2.23 (m, 1H), 2.05 (m, 1H), 1.83 (m, 2H), 1.16 (m, 2H), 0.34 (m, 2H), 0.17 (m, 2H). MS m/z 575 [M−1].

Example 363

Synthesis of 5-(2,6-Dichloro-phenylmethanesulfonyl)-3-[1-{4-[(R)-2-((S)-2-hydroxymethyl-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one

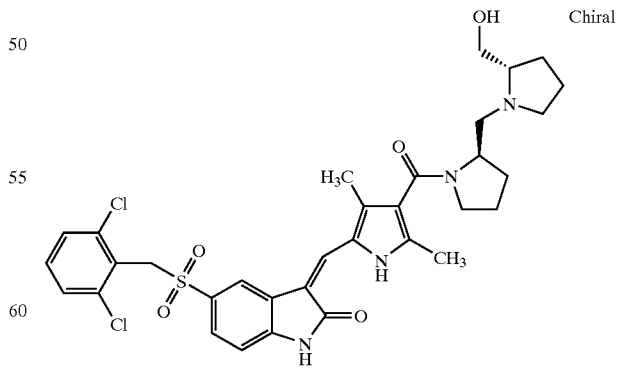

Orange solid.

$^1$H NMR (400 MHz, DMSO-d$_6$) δ 13.5 (br s, 1H, NH), 11.36 (s, 1H, NH), 8.22 (d, 1H), 7.81 (s, 1H), 7.47 (d, 2H), 7.4 (m, 2H), 7.01 (d, J=8 Hz, 1H), 4.85 (s, 2H), 4.2–4.4 (m, 2H), 3.0–3.8 (m, 6H), 2.0–2.6 (m, 2H), 2.29 (2s, 6H, 2×CH₃), 1.4–2.0 (m, 9H), MS m/z 669 [M−1].

Example 364

Synthesis of 3-[1-[4-(4-Amino-piperidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

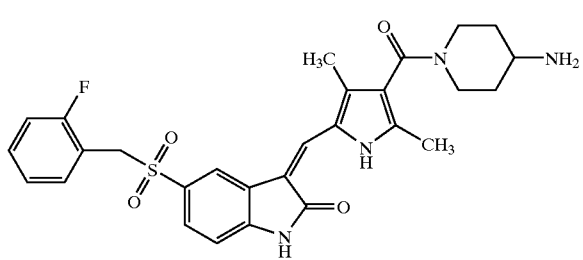

¹H NMR (400 MHz, DMSO-d₆) δ 13.5 (br s, 1H, NH), 8.24 (d, J=2 Hz, 1H), 7.81 (s, 1H), 7.36 (m, 2H), 7.23 (m, 1H), 7.15 (m, 2H), 6.98 (d, J=8 Hz, 1H), 4.62 (s, 2H), 4.27 (br s, 2H), 3.53 (br s, 2H), 2.96 (m, 2H), 2.71 (m, 1H), 2.3 (s, 3H, CH₃), 2.27 (s, 3H, CH₃), 1.72 (br s, 2H), 1.12 (br s, 2H). MS m/z 535 [M−1].

Example 365

Synthesis of 3-[1-[4-(4-Amino-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

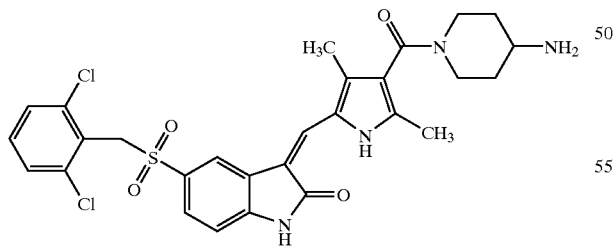

¹H NMR (400 MHz, DMSO-d₆) δ 13.53 (br s, 1H, NH), 8.26 (d, 1H), 7.84 (s, 1H), 7.47 (s, 2H), 7.42 (dd, 1H), 7.37 (m, 1H), 7.02 (d, J=8 Hz, 1H), 4.85 (s, 2H), 4.35 (br s, 2H), 3.6 (br s, 2H), 2.95 (m 3H), 2.31 (s, 3H, CH₃), 2.27 (s, 3H, CH₃), 1.77 (br s, 2H), 1.21 (br s, 2H). MS m/z 587 [M−1].

Example 366

3-[1-[4-(4-Amino-piperidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

¹H NMR (400 MHz, DMSO-d₆) δ 13.52 (br s, 1H, NH), 8.29 (d, J=2 Hz, 1H), 7.84 (s, 1H), 7.44 (m, 1H), 7.40 (dd, J=2 & 8 Hz, 1H), 7.08 (t, 2H), 7.0 (d, J=8 Hz, 1H), 4.62 (s, 2H), 4.25 (br s, 2H), 2.96 (m, 2H), 2.79 (m, 1H), 2.3 (s, 3H, CH₃), 2.27 (s, 3H, CH₃), 1.7 (br s, 2H), 1.11 (br s, 2H). MS m/z 553 [M−1].

Example 367

Synthesis of 3-[1-[4-(4-Amino-piperidine-1-carbonyl)-3,5-dimethyl-1H-pyrrol-2-yl]-meth-(Z)-ylidene]-5-(2-chloro-phenylmethanesulfonyl)-1,3-dihydro-indol-2-one MS m/z 551 [M−1].

Example 368

Syntheisis of 3-[1-[4-((S)-3-Amino-pyrrolidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

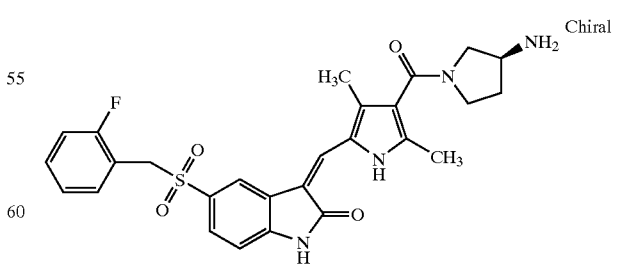

MS m/z 521 [M−1].

Example 369

Synthesis of 3-[1-[4-((S)-3-Amino-pyrrolidine-1-carbonyl)-3,5-dimethyl-1H-pyrrol-2-yl]-meth-(Z)-ylidene]-5-(2-chloro-phenylmethanesulfonyl)-1,3-dihydro-indol-2-one

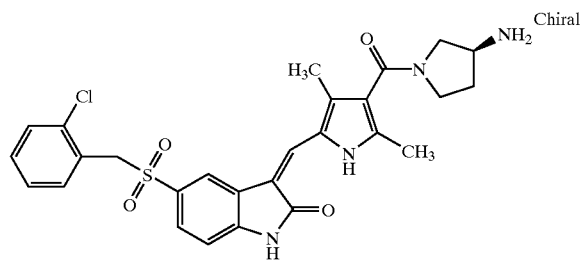

MS m/z 537 [M−1].

Example 370

Synthesis of 3-[1-[4-((S)-3-Amino-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

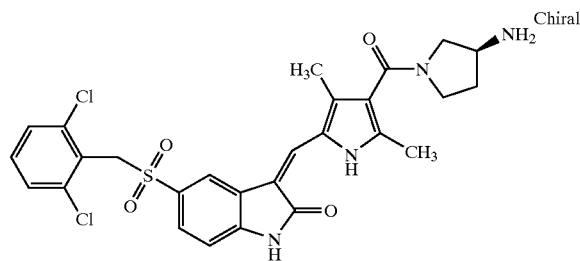

MS m/z 571 [M−1].

Example 371

Synthesis of 3-[1-[4-((S)-3-Amino-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

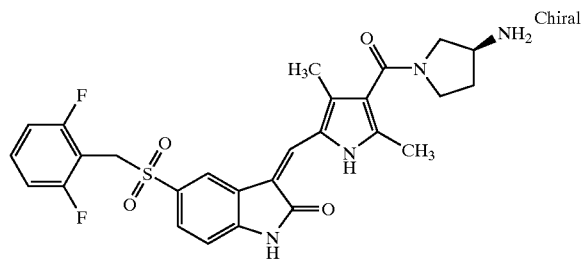

MS m/z 539 [M−1].

Example 372

Synthesis of 3-[1-[4-((R)-3-Amino-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one

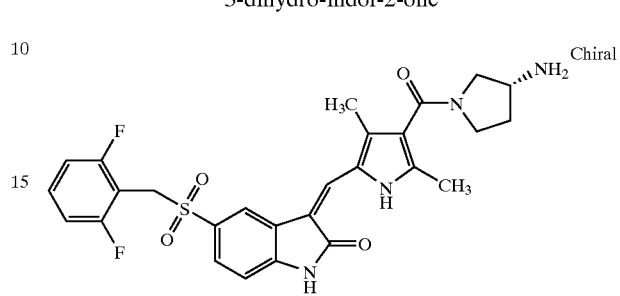

MS m/z 539[M−1].

Example 373

Synthesis of 3-[1-[4-((R)-3-Amino-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one

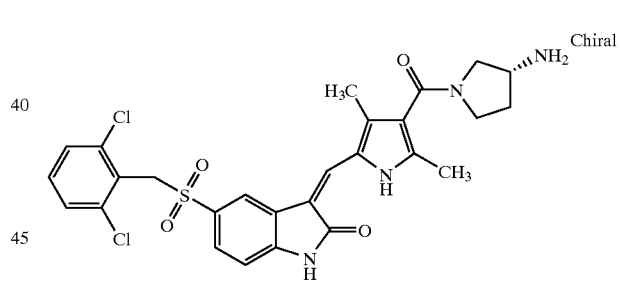

MS m/z 573 [M+1].

Example 374

Synthesis of 3-[1-[4-((R)-3-Amino-pyrrolidine-1-carbonyl)-3,5-dimethyl-1H-pyrrol-2-yl]-meth-(Z)-ylidene]-5-(2-chloro-phenylmethanesulfonyl)-1,3-dihydro-indol-2-one MS m/z 537 [M−1].

Example 375

Synthesis of 3-[1-[4-((R)-3-Amino-pyrrolidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one

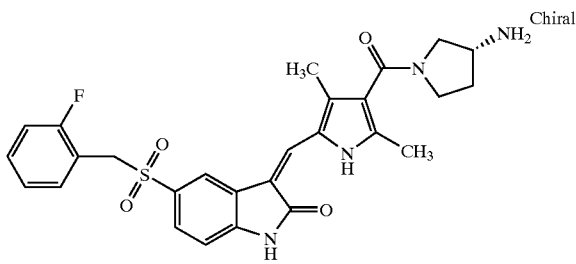

MS m/z 521 [M−1].

BIOLOGICAL EXAMPLES

A. Assay Procedures

The following assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art.

Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-FLK-1 BIOASSAY

This assay analyzes the tyrosine kinase activity of GST-Flk1 on poly(glu,tyr) peptides.

Materials and Reagents:
1. Corning 96-well ELISA plates (Corning Catalog No. 5805-96).
2. poly(glu,tyr) 4:1, lyophilizate (Sigma Catalog #P0275).
3. Preparation of poly(glu,tyr)(pEY) coated assay plates: Coat 2 ug/well of poly(glu,tyr)(pEY) in 100 ul PBS, hold at room temperature for 2 hours or at 4° C. overnight. Cover plates well to prevent evaporation.
4. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
5. PBST Buffer: to 1 L of PBS Buffer, add 1.0 ml Tween-20.
6. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
7. 1% BSA in PBS: To make a 1× working solution, add 10 g BSA to approx. 990 ml PBS buffer, stir to dissolve. Adjust total volume to 1 L with PBS buffer, filter to remove particulate matter.
8. 50 mM Hepes pH 7.5.
9. GST-Flklcd purified from sf9 recombinant baculovirus transformation (SUGEN, Inc.).
10. 4% DMSO in $dH_2O$.
11. 10 mM ATP in $dH_2O$.
12. 40 mM $MnCl_2$
13. Kinase Dilution Buffer (KDB): mix 10 ml Hepes (pH 7.5), 1 ml 5M NaCl, 40 μL 100 mM sodium orthovanadate and 0.4 ml of 5% BSA in $dH_2O$ with 88.56 ml $dH_2O$.
14. NUNC 96-well V bottom polypropylene plates, Applied Scientific Catalog # AS-72092
15. EDTA: mix 14.12 g ethylenediaminetetraacetic acid (EDTA) to approx. 70 ml $dH_2O$. Add 10 N NaOH until EDTA dissolves. Adjust pH to 8.0. Adjust total volume to 100 ml with $dH_2O$.
16. 1° Antibody Dilution Buffer: mix 10 ml of 5% BSA in PBS buffer with 89.5 ml TBST.
17. Anti-phosphotyrosine monoclonal antibody conjugated to horseradish peroxidase (PY99 HRP, Santa Cruz Biotech).
18. 2,2'-Azinobis(3-ethylbenzthiazoline-6-sulfonic acid (ABTS, Moss, Cat. No. ABST).
19. 10% SDS.

Procedure:
1. Coat Corning 96-well ELISA plates with 2 μg of polyEY peptide in sterile PBS as described in step 3 of Materials and Reagents.
2. Remove unbound liquid from wells by inverting plate. Wash once with TBST. Pat the plate on a paper towel to remove excess liquid.
3. Add 100 μl of 1% BSA in PBS to each well. Incubate, with shaking, for 1 hr. at room temperature.
4. Repeat step 2.
5. Soak wells with 50 mM HEPES (pH7.5) (150 μl/well).
6. Dilute test compound with $dH_2O$/4% DMSO to 4 times the desired final assay concentration in 96-well polypropylene plates.
7. Add 25 μl diluted test compound to ELISA plate. In control wells, place 25 μl of $dH_2O$/4% DMSO.

8. Add 25 µl of 40 mM MnCl₂ with 4× ATP (2 µM) to each well.
9. Add 25 µl 0.5M EDTA to negative control wells.
10. Dilute GST-Flk1 to 0.005 µg(5 ng)/well with KDB.
11. Add 50 µl of diluted enzyme to each well.
12. Incubate, with shaking, for 15 minutes at room temperature.
13. Stop reaction by adding 50 µl of 250 mM EDTA (pH 8.0).
14. Wash 3× with TBST and pat plate on paper towel to remove excess liquid.
15. Add 100 µl per well anti-phosphotyrosine HRP conjugate, 1:5,000 dilution in antibody dilution buffer. Incubate, with shaking, for 90 min. at room temperature.
16. Wash as in step 14.
17. Add 100 µl of room temperature ABTS solution to each well.
18. Incubate, with shaking, for 10 to 15 minutes. Remove any bubbles.
19. Stop reaction by adding 20 µl of 10% SDS to each well.
20. Read results on Dynatech MR7000 ELISA reader with test filter at 410 nM and reference filter at 630 nM.

PYK2 BIOASSAY

This assay is used to measure the in vitro kinase activity of HA epitope-tagged full length pyk2 (FL.pyk2-HA) in an ELISA assay.

Materials and reagents:
1. Corning 96-well Elisa plates.
2. 12CA5 monoclonal anti-HA antibody (SUGEN, Inc.)
3. PBS (Dulbecco's Phosphate-Buffered Saline (Gibco Catalog #450–1300EB)
4. TBST Buffer: for 1 L, mix 8.766 g NaCl, 6.057 g TRIS and 1 ml of 0.1% Triton X-100 in approx. 900 ml dH₂O. Adjust pH to 7.2, bring volume to 1 L.
5. Blocking Buffer: for 1 L, mix 100 g 10% BSA, 12.1 g 100 mM TRIS, 58.44 g 1 M NaCl and 10 mL of 1% TWEEN-20.
6. FL.pyk2-HA from sf9 cell lysates (SUGEN, Inc.).
7. 4% DMSO in MilliQue H₂O.
8. 10 mM ATP in dH₂O.
9. 1M MnCl₂.
10. 1M MgCl₂.
11. 1M Dithiothreitol (DTT).
12. 10× Kinase buffer phosphorylation: mix 5.0 ml 1 M Hepes (pH 7.5), 0.2 ml 1 M MnCl₂, 1.0 ml 1 M MgCl₂, 1.0 ml 10% Triton X-100 in 2.8 ml dH₂O. Just prior to use, add 0.1 ml 1 M DTT.
13. NUNC 96-well V bottom polypropylene plates.
14. 500 mM EDTA in dH₂O.
15. Antibody dilution buffer: for 100 mL, 1 mL 5% BSA/PBS and 1 mL 10% Tween-20 in 88 mL TBS.
16. HRP-conjugated anti-Ptyr PY99), Santa Cruz Biotech Cat. No. SC-7020.
17. ABTS, Moss, Cat. No. ABST-2000.
18. 10% SDS.

Procedure:
1. Coat Corning 96 well ELISA plates with 0.5 µg per well 12CA5 anti-HA antibody in 100 µl PBS. Store overnight at 4° C.
2. Remove unbound HA antibody from wells by inverting plate. Wash plate with dH₂O. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1 hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5 M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 BIOASSAY

This assay is used to measure the in vitro kinase activity of FGF1-R in an ELISA assay.

Materials and Reagents:
1. Costar 96-well Elisa plates (Corning Catalog #3369).
2. Poly(Glu-Tyr) (Sigma Catalog #PO275).
3. PBS (Gibco Catalog #450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer. Mix 500 µl 1 M Hepes (GIBCO), 20 µl 5% BSA/PBS, 10 µl 100 mM sodium orthovanadate and 50 µl 5M NaCl.
8. 10 mM ATP
9. ATP/MnCl₂ phosphorylation mix: mix 20 µL ATP, 400 µL 1 M MnCl₂ and 9.56 ml dH₂O.
10. NUNC 96-well V bottom polypropylene plates (Applied Scientific Catalog #AS-72092).
11. 0.5M EDTA.
12. 0.05% TBST Add 500 µL TWEEN to 1 liter TBS.
13. Rabbit polyclonal anti-phosphotyrosine serum (SUGEN, Inc.).
14. Goat anti-rabbit IgG peroxidase conjugate (Biosource, Catalog #ALI0404).
15. ABTS Solution.
16. ABTS/H₂O₂ solution.

Procedure:
1. Coat Costar 96 well ELISA plates with 1 µg per well Poly(Glu,Tyr) in 100 µl PBS. Store overnight at 4° C.
2. Wash coated plates once with PBS.

3. Add 150 µL of 5% BSA/PBS Blocking Buffer to each well. Incubate, with shaking, for 1hr.room temperature.
4. Wash plate 2× with PBS, then once with 50 mM Hepes. Pat plates on a paper towel to remove excess liquid and bubbles.
5. Add 25 µL of 0.4 mM test compound in 4% DMSO or 4% DMSO alone (controls) to plate.
6. Dilute purified GST-FGFRl in Kinase Dilution Buffer (5 ng kinase/50 ul KDB/well).
7. Add 50 µL of diluted kinase to each well.
8. Start kinase reaction by adding 25 µl/well of freshly prepared ATP/Mn++ (0.4 ml 1 M $MnCl_2$, 40 µL 10 mM ATP, 9.56 ml $dH_2O$), freshly prepared).
9. This is a fast kinase reaction and must be stopped with 25 µL of 0.5M EDTA in a manner similar to the addition of ATP.
10. Wash plate 4× with fresh TBST.
11. Make up Antibody Dilution Buffer: Per 50 ml: Mix 5 ml of 5% BSA, 250 µl of 5% milk and 50 µl of 100 mM sodium vanadate, bring to final volume with 0.05% TBST.
12. Add 100 µl per well of anti-phosphotyrosine (1:10000 dilution in ADB). Incubate, with shaking for 1hr. at room temperature.
13. Wash as in step 10.
14. Add 100 µl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 µl of $ABTS/H_2O_2$ solution to each well.
17. Incubate, with shaking, for 10 to 20 minutes. Remove any bubbles.
18. Read assay on Dynatech MR7000 elisa reader: test filter at 410 nM, reference filtrate 630 nM.

EGFR BIOASSAY

This assay is used to the in vitro kinase activity of FGF1-R in an ELISA assay.
Materials and Reagents:
1. Corning 96-well Elisa plates.
2. SUMO1monoclonal anti-EGFR antibody (SUGEN, Inc.).
3. PBS
4. TBST Buffer
5. Blocking Buffer: for 100 ml, mix 5.0 g Carnation Instant Non-fat Milk® with 100 ml of PBS.
6. A431 cell lysate (SUGEN, Inc.).
7. TBS Buffer:
8. TBS+10% DMSO: for 1 L, mix 1.514 g TRIS, 2.192 g NaCl and 25 ml DMSO; bring to 1 liter total volume with $dH_2O$.
9. ATP (Adenosine-5'-triphosphate, from Equine muscle, Sigma Cat. No. A-5394), 1.0 mM solution in $dH_2O$. This reagent should be made up immediately prior to use and kept on ice.
10. 1.0 mM $MnCl_2$.
11. $ATP/MnCl_2$ phosphorylation mix: to make 10 ml, mix 300 µl of 1 mM ATP, 500 µl $MnCl_2$ and 9.2 ml $dH_2O$. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. $ABTS/H_2O_2$.
19. 0.2 M HCl.

Procedure:
1. Coat Corning 96 well ELISA plates with 0.5 µg SUMO1 in 100 µl PBS per well, store overnight at 4° C.
2. Remove unbound SUMO1 from wells by inverting plate to remove liquid. Wash 1× with $dH_2O$. Pat the plate on a paper towel to remove excess liquid.
3. Add 150 µl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 µg lysate/100 µl PBS).
6. Add 100 µl of diluted lysate to each well. Shake at room temperature for 1 hr.
7. Wash plates as in 4, above.
8. Add 120 µl TBS to ELISA plate containing captured EGFR.
9. Dilute test compound 1:10 in TBS, place in well
10. Add 13.5 µl diluted test compound to ELISA plate. To control wells, add 13.5 µl TBS in 10% DMSO.
11. Incubate, with shaking, for 30 minutes at room temperature.
12. Add 15 µl phosphorylation mix to all wells except negative control well. Final well volume should be approximately 150 µl with 3 µM ATP/5 mM $MnCl_2$ final concentration in each well. Incubate with shaking for 5 minutes.
13. Stop reaction by adding 16.5 µl of EDTA solution while shaking. Shake for additional 1 min.
14. Wash 4× with deionized water, 2× with TBST.
15. Add 100 µl anti-phosphotyrosine (1:3000 dilution in TBST) per well. Incubate, with shaking, for 30–45 min. at room temperature.
16. Wash as in 4, above.
17. Add 100 µl Biosource Goat anti-rabbit IgG peroxidase conjugate (1:2000 dilution in TBST) to each well. Incubate with shaking for 30 min. at room temperature.
18. Wash as in 4, above.
19. Add 100 µl of $ABTS/H_2O_2$ solution to each well.
20. Incubate 5 to 10 minutes with shaking. Remove any bubbles.
21. If necessary, stop reaction by adding 100 µl 0.2 M HCl per well.
22. Read assay on Dynatech MR7000 ELISA reader: test filter at 410 nM, reference filter at 630 nM.

PDGFR BIOASSAY

This assay is used to the in vitro kinase activity of FGF1-R in an ELISA assay.
Materials and Reagents:
1. Corning 96-well Elisa plates
2. 28D4C10 monoclonal anti-PDGFR antibody (SUGEN, Inc.).

3. PBS.
4. TBST Buffer.
5. Blocking Buffer (same as for EGFR bioassay).
6. PDGFR-β expressing NIH 3T3cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 μl 1 M TRIS, 200 μl 5M NaCl, 100 μl 1 M $MnCl_2$ and 50 μl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. $ABTS/H_2O_2$.
19. 0.2 M HCl.

Procedure:
1. Coat Corning 96 well ELISA plates with 0.5 μg 28D4C10 in 100 μl PBS per well, store overnight at 4° C.
2. Remove unbound 28D4C10 from wells by inverting plate to remove liquid. Wash 1× with $dH_2O$. Pat the plate on a paper towel to remove excess liquid.
3. Add 150 μl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 μg lysate/100 μl HNTG).
6. Add 100 μl of diluted lysate to each well. Shake at room temperature for 60 min.
7. Wash plates as described in Step 4.
8. Add 80 μl working kinase buffer mix to ELISA plate containing captured PDGFR.
9. Dilute test compound 1:10 in TBS in 96-well polypropylene plates.
10. Add 10 μl diluted test compound to ELISA plate. To control wells, add 10 μl TBS+10% DMSO. Incubate with shaking for 30 minutes at room temperature.
11. Add 10 μl ATP directly to all wells except negative control well (final well volume should be approximately 100 μl with 20 μM ATP in each well.) Incubate 30 minutes with shaking.
12. Stop reaction by adding 10 μl of EDTA solution to each well.
13. Wash 4× with deionized water, twice with TBST.
14. Add 100 μl anti-phosphotyrosine (1:3000 dilution in TBST) per well. Incubate with shaking for 30–45 min. at room temperature.
15. Wash as in Step 4.
16. Add 100 μl Biosource Goat anti-rabbit IgG peroxidase conjugate (1:2000 dilution in TBST) to each well. Incubate with shaking for 30 min. at room temperature.
17. Wash as in Step 4.
18. Add 100 μl of $ABTS/H_2O_2$ solution to each well.
19. Incubate 10 to 30 minutes with shaking. Remove any bubbles.
20. If necessary stop reaction with the addition of 100 μl 0.2 M HCl per well.
21. Read assay on Dynatech MR7000 ELISA reader with test filter at 410 nM and reference filter at 630 nM.

CELLULAR HER-2 KINASE ASSAY

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081)
5. HEPES (GIBCO Catalog #15630-080).
6. Growth Media Mix 500 ml DMEM, 55 ml heat inactivated FBS, 10 ml HEPES and 5.5 ml L-Glutamine.
7. Starve Media Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog #25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 uL of 10 mM HCl. Add 100 uL 10 mM NaOH. Add 800 uL PBS and transfer to an Eppendorf tube, store at −20° C. until ready to use.
18. HNTG Lysis Buffer For Stock 5× HNTG, mix 23.83 g Hepes, 43.83 g NaCl, 500 ml glycerol and 100 ml Triton X-100 and enough $dH_2O$ to make 1 L of total solution. For 1× HNTG*, mix 2 ml HNTG, 100 μL 0.1M $Na_3VO_4$, 250 μL 0.2M $Na_4P_2O_7$ and 100 μL EDTA.
19. EDTA.
20. $Na_3VO_4$. To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat #ALI0404).
24. ABTS Solution.
25. 30% Hydrogen peroxide solution.

26. ABTS/$H_2O_2$.
27. 0.2 M HCl.

Procedure:
1. Coat Corning 96 well ELISA plates with SUMO1 at 1.0 ug per well in PBS, 100 ul final volume/well. Store overnight at 4° C.
2. On day of use, remove coating buffer and wash plate 3 times with $dH_2O$ and once with TBST buffer. All washes in this assay should be done in this manner, unless otherwise specified.
3. Add 100 ul of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 ul per well, in a 96 well microtiter plate. Incubate seeded cells overnight at 37° under 5% $CO_2$.
7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 $\mu l$ sample and media into 90 $\mu l$ of starve media. The final DMSO concentration should be 1% or lower. A standard serial dilution may also be used.
9. Incubate under 5% $CO_2$ at 37° C. for 2 hours.
10. Prepare EGF ligand by diluting stock EGF (16.5 uM) in warm DMEM to 150 nM.
11. Prepare fresh HNTG* sufficient for 100 ul per well; place on ice.
12. After 2 hour incubation with test compound, add prepared EGF ligand to cells, 50 ul per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 ul per well. Place on ice for 5 minutes. Meanwhile, remove blocking buffer from ELISA plate and wash.
15. Scrape cells from plate with a micropipettor and homogenize cell material by repeatedly aspirating and dispensing the HNTG* lysis buffer. Transfer lysate to a coated, blocked, washed ELISA plate. Or, use a Costar transfer cartridge to transfer lysate to the plate.
16. Incubate, with shaking, at room temperature for 1 hr.
17. Remove lysate, wash. Transfer freshly diluted anti-Ptyr antibody (1:3000 in TBST) to ELISA plate, 100 ul per well.
18. Incubate, with shaking, at room temperature, for 30 min.
19. Remove anti-Ptyr antibody, wash. Transfer freshly diluted BIOSOURCE antibody to ELISA plate(1:8000 in TBST, 100 ul per well).
20. Incubate, with shaking, at room temperature for 30 min.
21. Remove BIOSOURCE antibody, wash. Transfer freshly prepared ABTS/$H_2O_2$ solution to ELISA plate, 100 ul per well.
22. Incubate, with shaking, for 5–10 minutes. Remove any bubbles.
23. Stop reaction with the addition of 100 ul of 0.2M HCl per well.
24. Read assay on Dynatech MR7000 ELISA reader with test filter set at 410 nM and reference filter at 630 nM.

CDK2/CYCLIN A ASSAY

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog #1450-401).
2. Amersham Redivue [$\gamma^{33}P$] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in $dH_2O$ at a concentration of 5 mg/ml.
6. Peptide/ATP Mixture: for 10 ml, mix 9.979 ml $dH_2O$, 0.00125 ml "cold" ATP, 0.010 ml Debtide and 0.010 ml $\gamma^{33}P$ ATP. The ultimate concentration per well will be 0.5 $\mu M$ "cold" ATP, 0.1 $\mu g$ Debtide and 0.2 $\mu Ci$ $\gamma^{33}P$ ATP.
7. Kinase buffer: for 10 ml, mix 8.85 ml $dH_2O$, 0.625 ml TRIS(pH 7.4), 0.25 ml 1 M $MgCl_2$, 0.25 ml 10% NP40 and 0.025 ml 1 M DTT, added fresh just prior to use.
8. 10 mM ATP in $dH_2O$.
9. 1M Tris, pH adjusted to 7.4 with HCl.
10. 1M $MgCl_2$.
11. 1M DTT.
12. PBS (Gibco Catalog #14190-144).
13. 0.5M EDTA.
14. Stop solution: For 10 ml, mix 9.25 ml PBS, 0.005 ml 100 mM ATP, 0.1 ml 0.5 M EDTA, 0.1 ml 10% Triton X-100 and 1.25 ml of 20 mg/ml SPA beads.

Procedure:
1. Prepare solutions of test compounds at 5× the desired final concentration in 5% DMSO. Add 10 ul to each well. For negative controls, use 10 ul 5% DMSO alone in wells.
2. Dilute 5 $\mu l$ of cdk2/cyclin A solution with 2.1 ml 2× kinase buffer.
3. Add 20 ul enzyme to each well.
4. Add 10 $\mu L$ of 0.5 M EDTA to the negative control wells.
5. To start kinase reaction, add 20 $\mu L$ of peptide/ATP mixture to each well. Incubate for 1 hr. without shaking.
6. Add 200 $\mu l$ stop solution to each well.
7. Hold at least 10 min.
8. Spin plate at approx. 2300 rpm for 3–5 min.
9. Count plate using Trilux or similar reader.

MET TRANSPHOSPHORYLATION ASSAY

This assay is used to measure phosphotyrosine levels on a poly(glutamic acid:tyrosine (4:1)) substrate as a means for identifying agonists/antagonists of met transphosphorylation of the substrate.

Materials and Reagents:
1. Corning 96-well Elisa plates, Corning Catalog #25805-96.
2. Poly(glu, tyr) 4:1, Sigma, Cat. No; P 0275.
3. PBS, Gibco Catalog #450-1300EB
4. 50 mM HEPES
5. Blocking Buffer: Dissolve 25 g Bovine Serum Albumin, Sigma Cat. No A-7888, in 500 ml PBS, filter through a 4 μm filter.
6. Purified GST fusion protein containing the Met kinase domain. Sugen, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 ml, mix 10 mL 1 M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4× ATP Reaction Mixture: for 10 mL, mix 0.4 mL 1 M manganese chloride and 0.02 mL 0.1 M ATP in 9.56 mL $dH_2O$.
12. 4× Negative Controls Mixture: for 10 mL, mix 0.4 mL 1 M manganese chloride in 9.6 mL $dH_2O$.
13. NUNC 96-well V bottom polypropylene plates, Applied Scientific Catalog #S-72092
14. 500 mM EDTA.
15. Antibody Dilution Buffer: for 100 mL, mix 10 mL 5% BSA/PBS, 0.5 mL 5% Carnation Instant Milk® in PBS and 0.1 mL 0.1 M sodium orthovanadate in 88.4 mL TBST.
16. Rabbit polyclonal antophosphotyrosine antibody, Sugen, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2 μL $H_2O_2$ five minutes before use.
20. 0.2 M HCl Procedure:
1. Coat ELISA plates with 2 μg Poly(Glu-Tyr) in 100 μL PBS, store overnight at 4° C.
2. Block plate with 150 μL of 5% BSA/PBS for 60 min.
3. Wash plate twice with PBS, once with 50 mM Hepes buffer pH 7.4.
4. Add 50 μl of the diluted kinase to all wells. (Purified kinase is diluted with Kinase Dilution Buffer. Final concentration should be 10 ng/well.)
5. Add 25 μL of the test compound (in 4% DMSO) or DMSO alone (4% in $dH_2O$) for controls to plate.
6. Incubate the kinase/compound mixture for 15 minutes.
7. Add 25 μL of 40 mM $MnCl_2$ to the negative control wells.
8. Add 25 μL ATP/$MnCl_2$ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/$H_2O_2$ solution to each well.
16. If necessary, stop the development reaction with the addition of 100 μl of 0.2M HCl per well.
17. Read plate on Dynatech MR7000 elisa reader with the test filter at 410 nM and the reference filter at 630 nM.

The compounds of Formula (I) had activity of 10 μM–1nM in this assay.

IGF-1 Transphosphorylation Assay

This assay is used to measure the phosphotyrosine level in poly(glutamic acid:tyrosine)(4:1) for the identification of agonists/antagonists of gst-IGF-1transphosphorylation of a substrate.

Materials and Reagents:
1. Corning 96-well Elisa plates.
2. Poly (Glu-tyr) (4:1), Sigma Cat. No. P 0275.
3. PBS, Gibco Catalog #450-1300EB
4. 50 mM HEPES
5. TBB Blocking Buffer: for 1 L, mix 100 g BSA, 12.1 gTRIS (pH 7.5), 58.44 g sodium chloride and 10 mL 1% TWEEN-20.
6. Purified GST fusion protein containing the IGF-1 kinase domain (Sugen, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2× Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4× ATP Reaction Mixture: for 10 mL, mix 0.4 mL 1 M $MnCl_2$ and 0.008 mL 0.01 M ATP and 9.56 mL $dH_2O$.
12. 4× Negative Controls Mixture: mix 0.4 mL 1 M manganese chloride in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk® in PBS and 0.1 mL 0.1 M sodium orthovanadate in 88.4 mL TBST.
16. Rabbit Polyclonal antiphosphotyrosine antibody, Sugen, Inc.
17. Goat anti-rabbit HRP conjugated antibody, Biosource.
18. ABTS Solution.
20. ABTS/$H_2O_2$: mix 15 mL ABTS with 2 μL $H_2O_2$ 5 minutes before using.
21. 0.2 M HCl in $dH_2O$.

Procedure:
1. Coat ELISA plate with 2.0 μg /well Poly(Glu, Tyr) 4:1 (Sigma P0275) in 100 μl PBS. Store plate overnight at 4° C.

2. ash plate once with PBS.
3. Add 100 µl of TBB Blocking Buffer to each well. Incubate plate for 1hour with shaking at room temperature.
4. Wash plate once with PBS, then twice with 50 mM Hepes buffer pH 7.5.
5. Add 25 µL of test compound in 4% DMSO (obtained by diluting a stock solution of 10 mM test compound in 100% DMSO with $dH_2O$) to plate.
6. Add 10.0 ng of gst-IGF-1 kinase in 50 µl Kinase Dilution Buffer) to all wells.
7. Start kinase reaction by adding 25 µl 4× ATP Reaction Mixture to all test wells and positive control wells. Add 25 µl 4× Negative Controls Mixture to all negative control wells. Incubates for 10 minutes with shaking at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room temperature for 1 hour.
13. Wash plate as in step 9, follow with one wash with PBS to reduce bubbles and excess Tween-20.
14. Develop by adding 100 µl/well $ABTS/H_2O_2$ to each well
15. After about 5 minutes, read on ELISA reader with test filter at 410 nm and referenced filter at 630 nm.

BRDU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

Materials and Reagents:
1. The appropriate ligand.
2. The appropriate engineered cells.
3. BrdU Labeling Reagent: 10 mM, in PBS (pH 7.4) (Boehringer Mannheim, Germany).
4. FixDenat: fixation solution (ready to use)(Boehringer Mannheim, Germany).
5. Anti-BrdU-POD: mouse monoclonal antibody conjugated with peroxidase (Boehringer Mannheim, Germany).
6. TMB Substrate Solution: tetramethylbenzidine (TMB, Boehringer Mannheim, Germany).
7. PBS Washing Solution: 1× PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0% CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration=10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution (1:200 dilution in PBS, 1% BSA) is added (50 µl/well) and the plate is incubated for 90 minutes at room temperature on a plate shaker.
8. The antibody conjugate is thoroughly removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

EGF-Induced Her-2-driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

EGF-Induced Her-4-driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

PDGF-Induced BrdU Incorporation Assay

Materials and Reagents:
1. Human PDGF B/B (Boehringer Mannheim, Germany).
2. 3T3/EGFRc7.

FGF-Induced BrdU Incorporation Assay
Materials and Reagents:
1. Human FGF2/bFGF (Gibco BRL, USA).
2. 3T3c7/EGFr IGF1-Induced BrdU Incorporation Assay
Materials and Reagents:
1. Human, recombinant (G511, Promega Corp., USA)
2. 3T3/IGF1r.

Insulin-Induced BrdU Incorporation Assay
Materials and Reagents:
1. Insulin, crystalline, bovine, Zinc (13007, Gibco BRL, USA).
2. 3T3/H25.

HGF-Induced BrdU Incorporation Assay
Materials and Reagents:
1. Recombinant human HGF (Cat. No. 249-HG, R&D Systems, Inc. USA).
2. BxPC-3cells (ATCC CRL-1687).

Procedure:
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 $\mu$l serum-free medium (RPMI with 0.1% BSA) for 24 hours.
3. On day 3, 25 $\mu$l containing ligand (prepared at 1 $\mu$g/ml in RPMI with 0.1% BSA; final HGF conc. is 200 ng/ml) and test compounds are added to the cells. The negative control wells receive 25 $\mu$l serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 $\mu$M, and 1:3 dilutions are used (i.e. final test compound concentration range is 0.137–100 $\mu$M).
4. After 18 hours of ligand activation, 12.5 $\mu$l of diluted BrdU labeling reagent (1:100 in RPMI, 0.1% BSA) is added to each well and the cells are incubated with BrdU (final concentration is 10 $\mu$M) for 1hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
8. Same as General Procedure.
9. Same as General Procedure.
10. Same as General Procedure.

HUV-EC-C Assay

This assay is used to measure a compound's activity against PDGF-R, FGF-R, VEGF, aFGF or Flk-1/KDR, all of which are naturally expressed by HUV-EC cells.

DAY 0
1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×$10^5$ cells/ml.
3. Add cells to 96-well flat-bottom plates at 100 $\mu$l/well or 0.8–1.0×$10^4$ cells/well, incubate ~24 h at 37° C., 5% $CO_2$.

DAY 1
1. Make up two-fold test compound titrations in separate 96-well plates, generally 50 $\mu$M on down to 0 $\mu$M. Use the same assay medium as mentioned in day 0, step 2 above. Titrations are made by adding 90 $\mu$l/well of test compound at 200 $\mu$M (4× the final well concentration) to the top well of a particular plate column. Since the stock test compound is usually 20 mM in DMSO, the 200 $\mu$M drug concentration contains 2% DMSO.

A diluent made up to 2% DMSO in assay medium (F12K +0.5% fetal bovine serum) is used as diluent for the test compound titrations in order to dilute the test compound but keep the DMSO concentration constant. Add this diluent to the remaining wells in the column at 60 $\mu$l/well. Take 60 $\mu$l from the 120 $\mu$l of 200 $\mu$M test compound dilution in the top well of the column and mix with the 60 $\mu$l in the second well of the column. Take 60 $\mu$l from this well and mix with the 60 $\mu$l in the third well of the column, and so on until two-fold titrations are completed. When the next-to-the-last well is mixed, take 60 $\mu$l of the 120 $\mu$l in this well and discard it. Leave the last well with 60 $\mu$l of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.
2. Transfer 50 $\mu$l/well of the test compound dilutions to the 96-well assay plates containing the 0.8–1.0×$10^4$ cells/ 100 $\mu$l/well of the HUV-EC-C cells from day 0 and incubate ~2 h at 37° C., 5% $CO_2$.
3. In triplicate, add 50 $\mu$l/well of 80 $\mu$g/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 $\mu$l test compound dilution, 50 $\mu$l growth factor or media, and 100 $\mu$l cells, which calculates to 200 $\mu$l/well total. Thus the 4× concentrations of test compound and growth factors become 1× once everything has been added to the wells.

DAY 2

1. Add $^3$H-thymidine (Amersham, catalogue no. TRK-686) at 1 µCi/well (10 µl/well of 100 µCi/ml solution made up in RPMI media+10% heat-inactivated fetal bovine serum) and incubate ~24 h at 37° C., 5% $CO_2$. RPMI is obtained from Gibco BRL, catalogue no. 11875-051.

DAY 3

1. Freeze plates overnight at −20° C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastrointestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC #CCL 107), A375 cells (melanoma, ATCC #CRL 1619), A431 cells (epidermoid carcinoma, ATCC #CRL 1555), Calu 6 cells (lung, ATCC #HTB 56), PC3 cells (prostate, ATCC #CRL 1435), SKOV3TP5 cells and NIH 3T3fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated.

P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

C-Kit Assay

This assay is used to detect the level of c-kit tyrosine phosphorylation.

MO7E (human acute myeloid leukemia) cells are serum starved overnight in 0.1% serum. Cells are pre-treated with the compound (concurrent with serum starvation), prior to ligand stimulation. Cells are stimulated with 250 ng/ml rh-SCF for 15 minutes. Following stimulation, cells were lysed and immunoprecipitated with an anti-c-kit antibody. Phosphotyrosine and protein levels were determined by Western blotting.

MTT Proliferation Assay

MO7E cells are serum starved and pre-treated with compound as described for the phosphorylation experiments. Cells areplated @ 4×10$^5$ cells/well in a 96 well dish, in 100 µl RPMI+10% serum. rh-SCF (100 ng/mL) is added and the plate is incubated for 48 hours. After 48 hours, 10 µl of 5 mg/ml MTT [3-(4,5-dimethythiazol-2-yl)-2,5-diphenyl tetrazolium bromide) is added and allowed to incubate for 4 hours. acid isopropanol (100 µl of 0.04N HCl in isopropanol) is added and the optical density was measured at a wavelength of 550 nm.

Apoptosis Assay

MO7E cells are incubated+/−SCF and+/−compound in 10% FBS with rh-GM-CSF(10 ng/mL) and rh-IL-3 (10 ng/mL). Samples are assayed at 24 and 48 hours. To measure activated caspase-3, samples are washed with PBS and permeabilized with ice-cold 70% ethanol. The cells are then stained with PE-conjugated polyclonal rabbit anti-active caspase-3 and analyzed by FACS. To measure cleaved PARP, samples are lysed and analyzed by western blotting with an anti-PARP antibody.

Additional assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. Pat.

No. 6,130,238 to Peng et al. which is incorporated by reference, including any drawings, herein.

Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$. $IC_{50}$, the dose required to achieve 50% inhibition, can be measured using standard techniques such as those described herein. $LD_{50}$. the dosage which results in 50% toxicity, can also be measured by standard techniques as well (Mossman, 1983, *J. Immunol. Methods*, 65:55-63), by measuring the amount of LDH released (Korzeniewski and Callewaert, 1983, *J. Immunol. Methods*, 64:313, Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula (I):

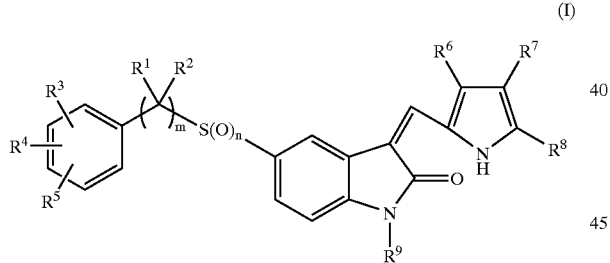

(I)

wherein:
n is 0,1, or 2;
m is 1,2, or 3;
$R^1$ and $R^2$ are independently hydrogen or alkyl;
$R^3$, $R^4$, and $R^5$ are independently hydrogen, halo, alkyl, cycloalkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —(alkylene)—$CONR^{10}R^{11}$, —$CONR^{10}R^{11}$, or —$NR^{10}R^{11}$, (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy, or $R^{10}$ and $R^{11}$ together with the nitrogen atom to which they are attached combine to form saturated or unsaturated heterocycloamino);

$R^6$ is hydrogen, alkyl, cycloalkyl, hydroxyalkyl, aminoalkyl, alkylaminoalkyl, dialkylaminoalkyl, carboxyalkyl, heterocyclylalkyl, aryl, heteroaryl, carboxy, alkoxycarbonyl, heterocyclylcarbonyl, aminoalkylcarbonyl, alkylaminoalkylcarbonyl, dialkylaminoalkylcarbonyl, —$CONR^{10}R^{11}$ or —(alkylene)—$CONR^{10}R^{11}$ (where $R^{10}$ is hydrogen or alkyl, and $R^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or $R^{10}$ and $R^{11}$ together with the nitrogen atom to which they are attached combine to form saturated or unsaturated heterocycloamino);

$R^7$ and $R^8$ are independently hydrogen, alkyl, cycloalkyl, heterocyclylalkyl, —$COR^{12}$, —(alkylene)—$COR^{12}$ (where $R^{12}$ is alkoxy, hydroxy, or heterocyle, alkylamino, dialkylamino), —$SO_2R^{14}$, —$CONR^{13}R^{14}$, or —(alkylene)—$CONR^{13}R^{14}$ (where $R^{13}$ is hydrogen or alkyl, and $R^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s), or when $R^{13}$ and $R^{14}$ are attached to a nitrogen atom $R^{13}$ and $R^{14}$ together with the nitrogen atom to which they are attached form saturated or unsaturated heterocycloamino);

$R^6$ and $R^7$ or $R^7$ and $R^8$ can combine to form a saturated or unsaturated 5 to 8 membered ring; and $R^9$ is:
(a) hydrogen or alkyl;
(b) —$PO(OR^{15})_2$ where each $R^{15}$ is independently hydrogen or alkyl;
(c) —$COR^{16}$ where $R^{16}$ is hydrogen or alkyl; or
(d) —$CHR^{17}NR^{18}R^{19}$ where $R^{17}$ is hydrogen or alkyl, and $R^{18}$ and $R^{19}$ are independently hydrogen or alkyl or $R^{18}$ and $R^{19}$ together with the nitrogen atom to which they are attached form heterocycloamino; or a pharmaceutically acceptable salt thereof.

2. A compound of Formula (Ia):

(Ia)

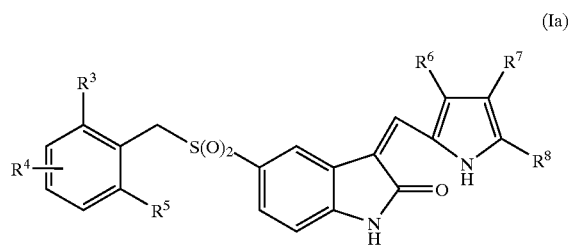

wherein:
$R^3$, $R^4$, and $R^5$ are independently hydrogen, halo, cycloalkyl, alkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —$CONR^{10}R^{11}$, —(alkylene)—

CONR$^{10}$R$^{11}$, or —NR$^{10}$R$^{11}$, (where R$^{10}$ is hydrogen or alkyl, and R$^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy, or R$^{10}$ and R$^{11}$ together with the nitrogen atom to which they are attached combine to form saturated or unsaturated heterocycloamino);

R$^6$ and R$^8$ are independently hydrogen or alkyl; and

R$^7$ is heterocyclylalkyl, —COR$^{12}$, —(alkylene)—COR$^{12}$ (where R$^{12}$ is alkoxy, hydroxy, or heterocyle, alkylamino, dialkylamino), —SO$_2$R$^{14}$, —CONR$^{13}$R$^{14}$ or —(alkylene)—CONR$^{13}$R$^{14}$ (where R$^{13}$ is hydrogen or alkyl, and R$^{14}$ is aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, or heterocyclylalkyl wherein the alkyl chain in aminoalkyl, heteroaralkyl, heteroaralkyl, or heterocyclylalkyl is optionally substituted with one or two hydroxy group(s), or when R$^{13}$ and R$^{14}$ are attached to a nitrogen atom R$^{13}$ and R$^{14}$ together with the nitrogen atom to which they are attached form saturated or unsaturated heterocycloamino); or a pharmaceutically acceptable salt thereof.

3. A compound of Formula (Ib):

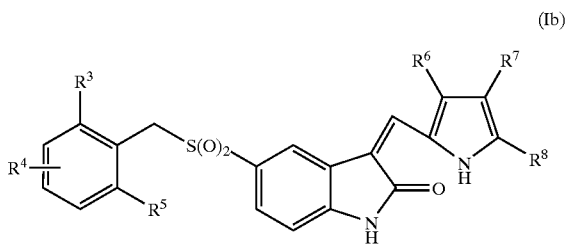

(Ib)

wherein:

R$^3$, R$^4$, and R$^5$ are independently hydrogen, halo, alkyl, cycloalkyl, haloalkyl, hydroxy, alkoxy, alkoxycarbonyl, haloalkoxy, cyano, carboxy, carboxyalkyl, nitro, aryl, aryloxy, heteroaryl, heteroaryloxy, —CONR$^{10}$R$^{11}$, —(alkylene)—CONR$^{10}$R$^{11}$, or —NR$^{10}$R$^{11}$, (where R$^{10}$ is hydrogen or alkyl, and R$^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy, or R$^{10}$ and R$^{11}$ together with the nitrogen atom to which they are attached combine to form saturated or unsaturated heterocycloamino);

R$^6$ is heterocyclylalkyl, alkyl, cycloalkyl, hydroxyalkyl, aminoalkyl, alkylaminoalkyl, dialkylaminoalkyl, heterocyclylalkyl, aryl, heteroaryl, carboxy, alkoxycarbonyl, heterocyclylcarbonyl, aminoalkylcarbonyl, alkylaminoalkylcarbonyl, dialkylaminoalkylcarbonyl, —(alkylene)—CONR$^{10}$R$^{11}$, —CONR$^{10}$R$^{11}$ (where R$^{10}$ is hydrogen or alkyl, and R$^{11}$ is aryl, heteroaryl, heterocycle, aminoalkyl, alkylaminoalkyl, dialkylaminoalkyl, hydroxyalkyl, acetylalkyl, cyanoalkyl, carboxyalkyl, alkoxycarbonylalkyl, heteroaralkyl, aralkyl, or heterocyclylalkyl wherein the alkyl chain in aminoalkyl, alkylaminoalkyl, dialkylaminoalkyl, aralkyl, heteroaralkyl, or heterocyclylalkyl is optionally substituted with one or two hydroxy or R$^{10}$ and R$^{11}$ together with the nitrogen atom to which they are attached combine to form saturated or unsaturated heterocycloamino); and R$^7$ and R$^8$ are independently hydrogen or alkyl; or a pharmaceutically acceptable salt thereof.

4. A pharmaceutical composition, comprising a compound or salt of claim 1 and a pharmaceutically acceptable carrier or excipient.

5. A method for the modulation of the catalytic activity of a protein kinase comprising contacting said protein kinase with a compound or salt of claim 1.

6. The method of claim 5 wherein said protein kinase is selected from the group consisting of a receptor tyrosine kinase, a non-receptor tyrosine kinase and a serine-threonine kinase.

7. The method of claim 5 wherein said protein kinase is Met kinase.

8. A method for treating or preventing a protein kinase related disorder in an organism in need of such treatment comprising administering a therapeutically effective amount of a pharmaceutical composition comprising a compound or salt of claim 1 and a pharmaceutically acceptable carrier or excipient to said patient.

9. The method of claim 8 wherein said protein kinase related disorder is selected from the group consisting of a receptor tyrosine kinase related disorder, a non-receptor tyrosine kinase related disorder and a serine-threonine kinase related disorder.

10. The method of claim 8 wherein said protein tyrosine kinase related disorder is mediated by Met kinase.

11. The method of claim 10 wherein said protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

12. The method of claim 10 wherein said protein kinase related disorder is selected from the group consisting of diabetes, an autoimmune disorder, a hyperproliferation disorder, restenosis, fibrosis, psoriasis, von Hippel-Lindau disease, osteoarthritis, rheumatoid arthritis, angiogenesis, an inflammatory disorder, an immunological disorder and a cardiovascular disorder.

13. A compound selected from the group consisting of:

2,4-Dimethyl-5-[2-oxo-5-phenylmethanesulfonyl-1,2-dihydro-indol-(3z)-ylidenemethyl]-1h-pyrrole-3-carboxylic acid (2-diethylamino-ethyl)-amide,
[5-(2-Cyano-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
2,4-Dimethyl-5-[2-oxo-5-(3-trifluoromethyl-phenylmethanesulfonyl)-1,2-dihydro-indol-(3Z)-ylidenemethyl]-1H-pyrrole-3-carboxylic acid (2-diethylamino-ethyl)-amide,
5-[5-(3-Methoxy-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
2-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile, 3-[1-[3,5-Dimethyl-4-(4-methyl-piperazine-1-carbonyl)-1H-pyrrol-2-yl]-meth-(Z)-ylidene]-5-(3-methoxy-phenylmethanesulfonyl)-1,3-dihydro-indol-2-one,
3-[1-[3,5-Dimethyl-4-(4-methyl-piperazine-1-carbonyl)-1H-pyrrol-2-yl]-meth-(Z)-ylidene]-5-(2-nitro-phenylmethanesulfonyl)-1,3-dihydro-indol-2-one,
2,4-Dimethyl-5-[5-(2-nitro-phenylmethanesulfonyl)-2-oxo-1,2-dihydro-indol-(3Z)-ylidenemethyl]-1H-pyrrole-3-carboxylic acid (2-diethylamino-ethyl)-amide,
2,4-Dimethyl-5-[2-oxo-5-phenylmethanesulfonyl-1,2-dihydro-indol-(3Z)-ylidenemethyl]-1H-pyrrole-3-carboxylic acid (2-[1,2,3]triazol-1-yl-ethyl)-amide,
2,4-Dimethyl-5-[5-(2-nitro-phenylmethanesulfonyl)-2-oxo-1,2-dihydro-indol-(3Z)-ylidenemethyl]-1H-pyrrole-3-carboxylic acid (2-[1,2,3]triazol-1-yl-ethyl)-amide,
3-[1-(3,5-Dimethyl-1H-pyrrol-2-yl)-meth-(Z)-ylidene]-5-phenylmethanesulfonyl-1,3-dihydro-indol-2-one,
4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid,
4-{5-[5-(4-Carboxymethyl-phenylmethanesulfonyl)-2-oxo-1,2-dihydro-indol-(3Z)-ylidenemethyl]-2,4-dimethyl-1H-pyrrole-3-carbonyl}-1-methyl-piperazin-1-ium,
4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-3-nitro-benzoic acid,
4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid,
(4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-phenyl)-acetic acid,
4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-3-nitro-benzoic acid,
3-[1-[3,5-Dimethyl-4-(4-methyl-piperazine-1-carbonyl)-1H-pyrrol-2-yl]-meth-(Z)-ylidene]-1-methyl-5-phenylmethanesulfonyl-1,3-dihydro-indol-2-one,
5-[5-(3,5-Dibromo-2-hydroxy-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-[1,2,3] triazol-1-yl-ethyl)-amide,
2,4-Dimethyl-5-[4-methyl-2-oxo-5-phenylmethanesulfonyl-1,2-dihydro-indol-(3Z)-ylidenemethyl]-1H-pyrrole-3-carboxylic acid (2-diethylamino-ethyl)-amide,
5-[5-(2-Fluoro-phenylmethanesulfonyl)-4-methyl-2-oxo-1,2-dihydro-indol-(3Z)-ylidenemethyl]-2,4-dimethyl-1H-pyrrole-3-carboxylic acid (2-diethylamino-ethyl)-amide,
3-[1-(5-Methyl-3H-imidazol-4-yl)-meth-(Z)-ylidene]-5-phenylmethanesulfonyl-1,3-dihydro-indol-2-one,
5-[5-(2-Chloro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
4-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid methyl ester,
5-[5-(4-trifluoromethoxy-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(2,4-Bis-trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,4-Bis-trifluoromethyl-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(4-Bromo-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(4-Bromo-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-[5-(2-Iodo-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2-iodo-phenylmethanesulfonyl)-1,3-dihydro-indol-2-one,
5-[5-(4-Cyano-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile,
3-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indole-5-sulfonylmethyl}-benzoic acid methyl ester,
3-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid methyl ester,
3-[1-[3,5-Dimethyl-4-(4-methyl-piperazine-1-carbonyl)-1H-pyrrol-2-yl]-meth-(Z)-ylidene]-5-(3-trifluoromethoxy-phenylmethanesulfonyl)-1,3-dihydro-indol-2-one,
2,4-Dimethyl-5-[2-oxo-5-(3-trifluoromethoxy-phenylmethanesulfonyl)-1,2-dihydro-indol-(3Z)-ylidenemethyl]-1H-pyrrole-3-carboxylic acid (2-diethylamino-ethyl)-amide,
3-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzonitrile,
5-[5-(3-Cyano-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-m-tolylmethanesulfonyl-1,3-dihydro-indol-2-one,
2,4-Dimethyl-5-[2-oxo-5-m-tolylmethanesulfonyl-1,2-dihydro-indol-(3Z)-ylidenemethyl]-1H-pyrrole-3-carboxylic acid (2-diethylamino-ethyl)-amide,
5-(3-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,4-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(4-tert-Butyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(4-tert-Butyl-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(2,6-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,6-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(3-Bromo-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(2,4-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
3-[1-[3,5-Dimethyl-4-(4-methyl-piperazine-1-carbonyl)-1H-pyrrol-2-yl]-meth-(Z)-ylidene]-5-(4-nitro-phenylmethanesulfonyl)-1,3-dihydro-indol-2-one,
2,4-Dimethyl-5-[5-(4-nitro-phenylmethanesulfonyl)-2-oxo-1,2-dihydro-indol-(3Z)-ylidenemethyl]-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(3-nitro-phenylmethanesulfonyl)-1,3-dihydro-indol-2-one,
2,4-Dimethyl-5-[5-(3-nitro-phenylmethanesulfonyl)-2-oxo-1,2-dihydro-indol-(3Z)-ylidenemethyl]-1H-pyrrole-3-carboxylic acid (2-diethylamino-ethyl)-amide,
5-[5-(3-Bromo-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(3,5-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(3,5-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide, -continued 5-(3,4-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(3,4-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(2,5-Bis-trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,5-Bis-trifluoromethyl-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(3,5-Bis-trifluoromethyl-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(3,5-Bis-trifluoromethyl-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2-hydroxy-5-nitro-phenylmethanesulfonyl)-1,3-dihydro-indol-2-one,
5-[5-(2-Hydroxy-5-nitro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2-methoxy-5-nitro-phenylmethanesulfonyl)-1,3-dihydro-indol-2-one,
5-[5-(2-Methoxy-5-nitro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2-fluoro-phenylmethanesulfonyl)-1,3-dihydro-indol-2-one,
5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(3-fluoro-phenylmethanesulfonyl)-1,3-dihydro-indol-2-one,
5-[5-(3-Fluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(4-fluoro-phenylmethanesulfonyl)-1,3-dihydro-indol-2-one,
5-[5-(4-Fluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(4-trifluoromethoxy-phenylmethanesulfonyl)-1,3-dihydro-indol-2-one,
3-[1-[3,5-Dimethyl-4-(4-methyl-piperazine-1-carbonyl)-1H-pyrrol-2-yl]-meth-(Z)-ylidene]-5-(2-trifluoromethyl-phenylmethanesulfonyl)-1,3-dihydro-indol-2-one,
2,4-Dimethyl-5-[2-oxo-5-(2-trifluoromethyl-phenylmethanesulfonyl)-1,2-dihydro-indol-(3Z)-ylidenemethyl]-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(3-trifluoromethyl-phenylmethanesulfonyl)-1,3-dihydro-indol-2-one,
2,4-Dimethyl-5-[2-oxo-5-(4-trifluoromethyl-phenylmethanesulfonyl)-1,2-dihydro-indol-(3Z)-ylidenemethyl]-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(4-trifluoromethyl-phenylmethanesulfonyl)-1,3-dihydro-indol-2-one,
5-(2,5-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,4-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2,3,6-trifluoro-phenylmethanesulfonyl)-1,3-dihydro-indol-2-one,
2,4-Dimethyl-5-[2-oxo-5-(2,3,6-trifluoro-phenylmethanesulfonyl)-1,2-dihydro-indol-(3Z)-ylidenemethyl]-1H-pyrrole-3-carboxylic acid (2-diethylamino-ethyl)-amide,
5-(2,3-Difluoro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(2,3-Difluoro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(Biphenyl-2-ylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(Biphenyl-2-ylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-(2-fluoro-6-nitro-phenylmethanesulfonyl)-1,3-dihydro-indol-2-one,
5-[5-(2-Fluoro-6-nitro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
3-[1-[3,5-Dimethyl-4-(4-methyl-piperazine-1-carbonyl)-1H-pyrrol-2-yl]-meth-(Z)-ylidene]-5-[2-(2-fluoro-phenoxy)-phenylmethanesulfonyl]-1,3-dihydro-indol-2-one,
5-[5-[2-(2-Fluoro-phenoxy)-phenylmethanesulfonyl]-2-oxo-1,2-dihydro-indol-(3Z)-ylidenemethyl]-2,4-dimethyl-1H-pyrrole-3-carboxylic acid (2-diethylamino-ethyl)-amide,
5-(2-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-[5-(4-Chloro-phenylmethanesulfonyl)-2-oxo-1,2-dihydro-indol-(3Z)-ylidenemethyl]-2,4-dimethyl-1H-pyrrole-3-carboxylic acid (2-diethylamino-ethyl)-amide,
5-(4-Chloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
2,4-Dimethyl-5-[2-oxo-5-phenylmethanesulfonyl-1,2-dihydro-indol-(3Z)-ylidenemethyl]-1H-pyrrole-3-carboxylic acid,
4-{3-[1-[3,5-Dimethyl-4-(4-methyl-piperazine-1-carbonyl)-1H-pyrrol-2-yl]-meth-(Z)-ylidene]-2-oxo-2,3-dihydro-1H-indole-5-sulfonylmethyl}-benzoic acid methyl ester,
2,4-Dimethyl-5-[2-oxo-5-phenylmethanesulfonyl-1,2-dihydro-indol-(3Z)-ylidenemethyl]-1H-pyrrole-3-carboxylic acid (3-diethylamino-2-hydroxy-propyl)-amide,
2,4-Dimethyl-5-[2-oxo-5-phenylmethanesulfonyl-1,2-dihydro-indol-(3Z)-ylidenemethyl]-1H-pyrrole-3-carboxylic acid [2-(2H-tetrazol-5-yl)-ethyl]-amide,
5-Methyl-2-[2-oxo-5-phenylmethanesulfonyl-1,2-dihydro-indol-(3Z)-ylidenemethyl]-1H-pyrrole-3-carboxylic acid (3-pyrrolidin-1-yl-propyl)-amide,
5-Methyl-2-[2-oxo-5-phenylmethanesulfonyl-1,2-dihydro-indol-(3Z)-ylidenemethyl]-1H-pyrrole-3-carboxylic acid (3-[1,2,3]triazol-1-yl-propyl)-amide,
3-[1-[3-(3-Dimethylamino-pyrrolidin-1-ylcarbonyl)-5-methyl-1H-pyrrol-2-yl]-meth-(Z)-ylidene]-5-phenylmethanesulfonyl-1,3-dihydro-indol-2-one,
4-Methyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide,
2,4-Dimethyl-5-[2-oxo-5-phenylmethanesulfonyl-1,2-dihydro-indol-(3Z)-ylidenemethyl]-1H-pyrrole-3-carboxylic acid (2-pyrrolidin-1-yl-ethyl)-amide,
2,4-Dimethyl-5-[2-oxo-5-phenylmethanesulfonyl-1,2-dihydro-indol-(3Z)-ylidenemethyl]-1H-pyrrole-3-carboxylic acid (2-diisopropylamino-ethyl)-amide,
5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide,
5-[5-(2-Fluoro-phenylmethanesulfonyl)-2-oxo-1,2-dihydro-indol-(3Z)-ylidenemethyl]-4-methyl-1H-pyrrole-3-carboxylic acid (2-diethylamino-ethyl)-amide,
2-[5-(2-Fluoro-phenylmethanesulfonyl)-2-oxo-1,2-dihydro-indol-(3Z)-ylidenemethyl]-5-methyl-1H-pyrrole-3-carboxylic acid (3-pyrrolidin-1-yl-propyl)-amide,
5-[5-(2-Fluoro-phenylmethanesulfonyl)-2-oxo-1,2-dihydro-indol-(3Z)-ylidenemethyl]-2,4-dimethyl-1H-pyrrole-3-carboxylic acid (2-diisopropylamino-ethyl)-amide,
2-[5-(2-Fluoro-phenylmethanesulfonyl)-2-oxo-1,2-dihydro-indol-(3Z)-ylidenemethyl]-5-methyl-1H-pyrrole-3-carboxylic acid (3-[1,2,3]triazol-1-yl-propyl)-amide,
3-[1-[4-((3R,5S)-3,5-Dimethyl-piperazine-1-carbonyl)-3,5-dimethyl-1H- pyrrol-2-yl]-meth-(Z)-ylidene]-5-(2-fluoro-phenylmethanesulfonyl)-1,3-dihydro-indol-2-one,
3-[1-[4-((3R,5S)-3,5-Dimethyl-piperazine-1-carbonyl)-3,5-dimethyl-1H-pyrrol-2-yl]-meth-(Z)-ylidene]-5-phenylmethanesulfonyl-1,3-dihydro-indol-2-one,
5-[5-(3-Chloro-phenylmethanesulfonyl)-2-oxo-1,2-dihydro-indol-(3Z)-ylidenemethyl]-4-methyl-1H-pyrrole-3-carboxylic acid (2-diethylamino-ethyl)-amide,
2-[5-(3-Chloro-phenylmethanesulfonyl)-2-oxo-1,2-dihydro-indol-(3Z)-ylidenemethyl]-5-methyl-1H-pyrrole-3-carboxylic acid (3-pyrrolidin-1-yl-propyl)-amide,
2-[5-(3-Chloro-phenylmethanesulfonyl)-2-oxo-1,2-dihydro-indol-(3Z)-ylidenemethyl]-5-methyl-1H-pyrrole-3-carboxylic acid (3-[1,2,3]triazol-1-yl-propyl)-amide,
5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-pyrrolidin-1-yl-ethyl)-amide,
5-[5-(3-Chloro-phenylmethanesulfonyl)-2-oxo-1,2-dihydro-indol-(3Z)-ylidenemethyl]-2,4-dimethyl-1H-pyrrole-3-carboxylic acid (2-diisopropylamino-ethyl)-amide,
5-(3-Chloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one,
5-(3-Chloro-phenylmethanesulfonyl)-3-[1-[3-((R)-3-dimethylamino-pyrrolidin-1-ylcarbonyl)-5-methyl-1H-pyrrol-2-yl]-meth-(Z)-ylidene]-1,3-dihydro-indol-2-one,
3-{5-Ethyl-2-[2-oxo-5-phenylmethanesulfonyl-1,2-dihydro-indol-(3Z)-ylidenemethyl]-1H-pyrrol-3-yl}-propionic acid,
3-{4-Methyl-5-[2-oxo-5-phenylmethanesulfonyl-1,2-dihydro-indol-(3Z)-ylidenemethyl]-1H-pyrrol-3-yl}-propionic acid,
3-[1-[3-Methyl-5-(4-methyl-piperazine-1-carbonyl)-1H-pyrrol-2-yl]-meth-(Z)-ylidene]-5-phenylmethanesulfonyl-1,3-dihydro-indol-2-one,
4-(4-Fluoro-phenyl)-2-methyl-5-[2-oxo-5-phenylmethanesulfonyl-1,2-dihydro-indol-(3Z)-ylidenemethyl]-1H-pyrrole-3-carboxylic acid (2-diethylamino-ethyl)-amide,
4-{5-Methyl-2-[2-oxo-5-phenylmethanesulfonyl-1,2-dihydro-indol-(3Z)-ylidenemethyl]-1H-pyrrol-3-yl}-benzoic acid,
3-[1-(4-Morpholin-4-yl-phenyl)-meth-(Z)-ylidene]-5-phenylmethanesulfonyl-1,3-dihydro-indol-2-one,
4-(2-Carboxy-ethyl)-3-methyl-5-[2-oxo-5-phenylmethanesulfonyl-1,2-dihydro-indol-(3Z)-ylidenemethyl]-1H-pyrrole-2-carboxylic acid ethyl ester,
5-(2,6-Dichloro-phenylmethanesulfonyl)-3-[1-(3,5-dimethyl-1H-pyrrol-2-yl)-meth-(Z)-ylidene]-1,3-dihydro-indol-2-one,
5-(2,6-Dichloro-phenylmethanesulfonyl)-3-[1-[5-methyl-3-(morpholine-4-carbonyl)-1H-pyrrol-2-yl]-meth-(Z)-ylidene]-1,3-dihydro-indol-2-one,
5-(2,6-Dichloro-phenylmethanesulfonyl)-3-[1-[5-methyl-3-(4-methyl-piperazine-1-carbonyl)-1H-pyrrol-2-yl]-meth-(Z)-ylidene]-1,3-dihydro-indol-2-one,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid methyl-(1-methyl-piperidin-4-yl)-amide,
5-(2,6-Dichloro-phenylmethanesulfonyl)-3-[1-[5-methyl-3-(4-pyrrolidin-1-yl-piperidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-[3,5-dimethyl-4-((S)-2-pyrrolidin-1-ylmethyl-pyrrolidin-1-ylcarbonyl)-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-3-morpholin-4-yl-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-3-[1,2,3]triazol-1-yl-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-oxo-piperazin-1-yl)-ethyl]-amide,
5-(2,6-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid,
{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetic acid,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid [2-(3-oxo-piperazin-1-yl)-ethyl]-amide, 5-(2,6-Dichloro-phenylmethanesulfonyl)-3-[1-[3-(4-hydroxy-piperidine-1-carbonyl)-5-methyl-1H-pyrrol-2-yl]-meth-(Z)-ylidene]-1,3-dihydro-indol-2-one,
5-(2,6-Dichloro-phenylmethanesulfonyl)-3-[1-[3-(3-diethylamino-pyrrolidin-1-ylcarbonyl)-5-methyl-1H-pyrrol-2-yl]-meth-(Z)-ylidene]-1,3-dihydro-indol-2-one,
5-(2,6-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-(2,6-Dichloro-phenylmethanesulfonyl)-3-[1-(3,5-dimethyl-4-morpholin-4-ylmethyl-1H-pyrrol-2-yl)-meth-(Z)-ylidene]-1,3-dihydro-indol-2-one,
3-[1-[4-((R)-2-Cyclopropylaminomethyl-pyrrolidin-1-carbonyl)-3,5-dimethyl-1H-pyrrol-2-yl]-meth-(Z)-ylidene]-5-(2,6-dichlorophenylmethanesulfonyl)-1,3-dihydro-indol-2-one,
5-(2,6-Dichloro-phenylmethanesulfonyl)-3-[1-{4-[(S)-2-((R)-3-fluoro-pyrrolidin 1-ylmethyl)pyrrolidin-1-carbonyl]-3,5-dimethyl-1H-pyrrol-2-yl}-meth-(Z)-ylidene]-1,3-dihydro-indol-2-one,
3-[1-[4-(4-Cyclopropylamino-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-{2,4-Dimethyl-5-[2-oxo-5-phenylmethanesulfonyl-1,2-dihydro-indol-(3Z)-ylidenemethyl]-1H-pyrrol-3-yl}-propionic acid,
{2,4-Dimethyl-5-[2-oxo-5-phenylmethanesulfonyl-1,2-dihydro-indol-(3Z)-ylidenemethyl]-1H-pyrrol-3-yl}-acetic acid,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-pyrrolidin-1-yl-propyl)-amide,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid (3-pyrrolidin-1-yl-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-fluoro-piperidin-1-yl)-ethyl]-amide,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-hydroxy-3-[1,2,3]triazol-1-yl-propyl)-amide,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-hydroxy-3-morpholin-4-yl-propyl)-amide,
2-[5-(2,6-Dichloro-phenylmethanesulfonyl)-2-oxo-1,2-dihydro-indol-(3Z)-ylidenemethyl]-5-methyl-1H-pyrrole-3-carboxylic acid (2-diethylamino-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid methyl-(1-methyl-piperidin-4-yl)-amide,
5-(2,6-Dichloro-phenylmethanesulfonyl)-3-[1-[4-(3-diethylamino-pyrrolidine-1-carbonyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-[3-((3R,5S)-3,5-dimethyl-piperazine-1-carbonyl)-5-methyl-1H-pyrrol-2-yl]-meth-(Z)-ylidene]-1,3-dihydro-indol-2-one,
5-[5-(2,6-Dimethyl-phenylmethanesulfonyl)-2-oxo-1,2-dihydro-indol-(3Z)-ylidenemethyl]-2,4-dimethyl-1H-pyrrole-3-carboxylic acid,
5-[5-(2,3-Dichloro-phenylmethanesulfonyl)-2-oxo-1,2-dihydro-indol-(3Z)-ylidenemethyl]-2,4-dimethyl-1H-pyrrole-3-carboxylic acid,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-oxo-piperazin-1-yl)-ethyl]-acetamide,
5-(2,6-Dichloro-phenylmethanesulfonyl)-3-[1-{4-[2-(4-hydroxy-piperidin-1-yl)-2-oxo-ethyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-[3,5-dimethyl-4-(2-morpholin-4-yl-2-oxo-ethyl)-1H-pyrrol-2-yl]-meth-(Z)-ylidene]-1,3-dihydro-indol-2-one,
5-(2,6-Dichloro-phenylmethanesulfonyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one,
3-[1-[3,5-Dimethyl-4-(morpholine-4-carbonyl)-1H-pyrrol-2-yl]-meth-(Z)-ylidene]-5-(2,6-dimethyl-phenylmethanesulfonyl)-1,3-dihydro-indol-2-one,
5-(2,6-Dichloro-phenylmethanesulfonyl)-3-[1-{4-[2-((3R,5S)-3,5-dimethyl-piperazin-1-yl)-2-oxo-ethyl]-3,5-dimethyl-1H-pyrrol-2-yl}-meth-(Z)-ylidene]-1,3-dihydro-indol-2-one;
5-(2,6-Dichloro-phenylmethanesulfonyl)-3-[1-{3,5-dimethyl-4-[2-(4-methyl-piperazin-1-yl)-2-oxo-ethyl]-1H-pyrrol-2-yl}-meth-(Z)-ylidene]-1,3-dihydro-indol-2-one, 5-(2,6-Dichloro-phenylmethanesulfonyl)-3-[1-(4-{2-[4-(ethyl-propyl-amino)-piperidin-1-yl]-2-oxo-ethyl}-3,5-dimethyl-1H-pyrrol-2-yl)-meth-(Z)-ylidene]-1,3-dihydro-indol-2-one,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-diethylamino-ethyl)-acetamide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-methyl-N-(1-methyl-piperidin-4-yl)-acetamide,
5-(2,6-Dichloro-phenylmethanesulfonyl)-3-[1-{4-[2-(3-diethylamino-pyrrolidin-1-yl)-2-oxo-ethyl]-3,5-dimethyl-1H-pyrrol-2-yl}-meth-(Z)-ylidene]-1,3-dihydro-indol-2-one,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-pyrrolidin-1-yl-ethyl)-acetamide,
5-(2,6-Dichloro-phenylmethanesulfonyl)-3-[1-[3,5-dimethyl-4-((S)-2-morpholin-4-ylmethyl-pyrrolidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-[4-(2-{(S)-2-[(ethyl-propyl-amino)-methyl]-pyrrolidin-1-yl}-2-oxo-ethyl)-3,5-dimethyl-1H-pyrrol-2-yl]-meth-(Z)-ylidene]-1,3-dihydro-indol-2-one,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-morpholin-4-yl-propyl)-acetamide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-[1,2,3]triazol-1-yl-propyl)-acetamide,
5-(2,6-Dichloro-phenylmethanesulfonyl)-3-[1-[4-((R)-2-methoxymethyl-pyrrolidine-1-carbonyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-[4-((S)-2-methoxymethyl-pyrrolidine-1-carbonyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-[4-((R)-2-hydroxymethyl-pyrrolidine-1-carbonyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-[4-((S)-2-hydroxymethyl-pyrrolidine-1-carbonyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-{4-[(S)-2-(4-hydroxy-piperidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-[4-(4-hydroxy-piperidin-1-ylmethyl)-3,5-dimethyl-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-methoxy-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-methoxy-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(2-hydroxy-ethoxy)-ethyl]-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-1-hydroxymethyl-1-methyl-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-1,1-bis-hydroxymethyl-ethyl)-amide,
5-(2,6-Dimethyl-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one,
5-(2,6-Dimethyl-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one,
5-(2,6-Dimethyl-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one,
5-(2,6-Dimethyl-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one,
3-[1-[3,5-Dimethyl-4-(4-methyl-piperazine-1-carbonyl)-1H-pyrrol-2-yl]-meth-(Z)-ylidene]-5-(2,6-dimethyl-phenylmethanesulfonyl)-1,3-dihydro-indol-2-one,
5-(2,6-Dichloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-morpholin-4-yl-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-morpholin-4-yl-propyl)-amide,
3-[1-[4-((S)-2-Cyclopropylaminomethyl-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-[3,5-dimethyl-4-(4-morpholin-4-yl-piperidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-{3,5-dimethyl-4-[2-(4-morpholin-4-yl-piperidin-1-yl)-2-oxo-ethyl]-1H-pyrrol-2-yl}-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-ethylsulfanyl-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2,2,2-trifluoro-ethyl)-amide,
3-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-propionic acid,
3-[1-(4-{(S)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one,
5-(2,3-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one,
5-(2,3-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one,
5-(2,3-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one,
5-(2,3-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one,
5-(2,3-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-(2,6-Dichloro-phenylmethanesulfonyl)-3-[1-[4-((R)-3-hydroxy-pyrrolidin-1-ylmethyl)-3,5-dimethyl-1H-pyrrol-2-yl]-meth-(Z)-ylidene]-1,3-dihydro-indol-2-one,
5-(2,6-Dichloro-phenylmethanesulfonyl)-3-[1-[4-(3-hydroxy-piperidin-1-ylmethyl)-3,5-dimethyl-1H-pyrrol-2-yl]-meth-(Z)-ylidene]-1,3-dihydro-indol-2-one,
3-[1-[4-((S)-2-Cyclopropylaminomethyl-pyrrolidine-1-carbonyl)-3,5-dimethyl-1H-pyrrol-2-yl]-meth-(Z)-ylidene]-5-phenylmethanesulfonyl-1,3-dihydro-indol-2-one,
3-[1-[4-((S)-2-Cyclopropylaminomethyl-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
5-(3,5-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one,
5-(2,5-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one,
5-[5-(2,5-Dichloro-phenylmethanesulfonyl)-2-oxo-1,2-dihydro-indol-(3Z)-ylidenemethyl]-2,4-dimethyl-1H-pyrrole-3-carboxylic acid,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-pyridin-2-yl-ethyl)-amide,
3-[1-[3,5-Dimethyl-4-(2-piperidin-1-yl-acetyl)-1H-pyrrol-2-yl]-meth-(Z)-ylidene]-5-phenylmethanesulfonyl-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-pyridin-3-yl-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (tetrahydro-furan-2-ylmethyl)-amide,
5-[5-2,6-Dichloro-phenylmethanesulfonyl)-2-oxo-1,2-dihydro-indol-(3Z)-ylidenemethyl]-2,4-dimethyl-1H-pyrrole-3-carboxylic acid cyclopropylmethyl-amide,
3-[1-{3,5-Dimethyl-4-[2-oxo-2-((S)-2-pyrrolidin-1-ylmethyl-pyrrolidin-1-yl)-ethyl]-1H-pyrrol-2-yl}-meth-(Z)-ylidene]-5-phenylmethanesulfonyl-1,3-dihydro-indol-2-one, 3-[1-{3,5-Dimethyl-4-[2-(4-methyl-piperazin-1-yl)-2-oxo-ethyl]-1H-pyrrol-2-yl}-meth-(Z)-ylidene]-5-phenylmethanesulfonyl-1,3-dihydro-indol-2-one,
3-[1-{4-[2-((3R,5S)-3,5-Dimethyl-piperazin-1-yl)-2-oxo-ethyl]-3,5-dimethyl-1H-pyrrol-2-yl}-meth-(Z)-ylidene]-5-phenylmethanesulfonyl-1,3-dihydro-indol-2-one,
3-[1-{3,5-Dimethyl-4-(2-morpholin-4-yl-2-oxo-ethyl)-1H-pyrrol-2-yl]-meth-(Z)-ylidene]-5-phenylmethanesulfonyl-1,3-dihydro-indol-2-one,
3-[1-{4-[2-(4-Hydroxy-piperidin-1-yl)-2-oxo-ethyl]-3,5-dimethyl-1H-pyrrol-2-yl}-meth-(Z)-ylidene]-5-phenylmethanesulfonyl-1,3-dihydro-indol-2-one,
5-(2,6-Dichloro-phenylmethanesulfonyl)-3-[1-[3,5-dimethyl-4-(thiomorpholine-4-carbonyl)-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-fluoro-ethyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (3-imidazol-1-yl-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid methylamide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid amide,
5-(2,6-Dichloro-phenylmethanesulfonyl)-3-[1-[4-(1,1-dioxo-1l6-thiomorpholine-4-carbonyl)-3,5-dimethyl-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-acetyl-piperazin-1-yl)-ethyl]-amide,
5-(2,6-Dichloro-phenylmethanesulfonyl)-3-[1-[4-((3R,5S)-3,5-dimethyl-piperazin-1-ylmethyl)-3,5-dimethyl-1H-pyrrol-2-yl]-meth-(Z)-ylidene]-1,3-dihydro-indol-2-one,
3-[1-[4-((3R,5S)-3,5-Dimethyl-piperazin-1-ylmethyl)-3,5-dimethyl-1H-pyrrol-2-yl]-meth-(Z)-ylidene]-5-phenylmethanesulfonyl-1,3-dihydro-indol-2-one,
5-(2,5-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one,
5-(2,5-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one,
5-(2,5-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
5-(3,5-Dichloro-phenylmethanesulfonyl)-3-[1-[4-((3R,5S)-3,5-dimethyl-piperazine-1-carbonyl)-3,5-dimethyl-1H-pyrrol-2-yl]-meth-(Z)-ylidene]-1,3-dihydro-indol-2-one,
5-(3,5-Dichloro-phenylmethanesulfonyl)-3-[1-[3,5-dimethyl-4-(4-pyrrolidin-1-yl-piperidine-1-carbonyl)-1H-pyrrol-2-yl]-meth-(Z)-ylidene]-1,3-dihydro-indol-2-one,
5-(3,5-Dichloro-phenylmethanesulfonyl)-3-[1-[3,5-dimethyl-4-((S)-2-pyrrolidin-1-ylmethyl-pyrrolidine-1-carbonyl)-1H-pyrrol-2-yl]-meth-(Z)-ylidene]-1,3-dihydro-indol-2-one,
5-(3,5-Dichloro-phenylmethanesulfonyl)-3-[1-[3,5-dimethyl-4-(4-methyl-piperazine-1-carbonyl)-1H-pyrrol-2-yl]-meth-(Z)-ylidene]-1,3-dihydro-indol-2-one,
3-[1-[4-(4-Cyclopropylmethyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-{4-[2-((S)-2-Cyclopropylaminomethyl-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-[4-(4-Acetyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one,
4-{5-[5-(2,6-Dichloro-phenylmethanesulfonyl)-2-oxo-1,2-dihydro-indol-(3Z)-ylidenemethyl]-2,4-dimethyl-1H-pyrrol-3-ylmethyl}-piperazine-1-carbaldehyde,
3-[1-{4-[(Cyclopropyl-methyl-amino)-methyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-[4-(4-Cyclopropyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-{4-[2-((2R,4R)-2-Cyclopropylaminomethyl-4-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-{4-[2-((2R,3S)-2-Cylopropylaminomethyl-3-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-acetylamino-pyrrolidin-1-yl)-ethyl]-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-piperazin-1-yl-ethyl)-acetamide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-{2-[4-(2-hydroxy-acetyl)-piperazin-1-yl]-ethyl}-acetamide,
5-(2,6-Dichloro-phenylmethanesulfonyl)-3-[1-(4-{2-[(S)-2-((R)-3-hydroxy-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
5-(2,6-Dichloro-phenylmethanesulfonyl)-3-[1-{3,5-dimethyl-4-[2-oxo-2-((S)-3-pyrrolidin-1-ylmethyl-piperidin-1-yl)-ethyl]-1H-pyrrol-2-yl}-meth-(Z)-ylidene]-1,3-dihydro-indol-2-one,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(2,2,2-trifluoro-ethylamino)-ethyl]-acetamide,
3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one,
(2S,4R)-1-{5-[5-(2,6-Dichloro-phenylmethanesulfonyl)-2-oxo-1,2-dihydro-indol-(3Z)-ylidenemethyl]-2,4-dimethyl-1H-pyrrole-3-carbonyl}-4-hydroxy-pyrrolidine-2-carboxylic acid cyclopropylamide,
(2S,4R)-1-(2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetyl)-4-hydroxy-pyrrolidine-2-carboxylic acid cyclopropylamide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-3-pyrrolidin-1-yl-propyl)-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carabaxylic acid (3-cyclopropylamino-2-hydroxy-propyl)-amide,
3-[1-[4-(4-Cyclopropyl-piperazine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid cyclopropylamide,
N-[2-(3-Acetylamino-pyrrolidin-1-yl)-ethyl]-2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetamide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid {2-[4-(2-hydroxy-acetyl)-piperazin-1-yl]-ethyl}-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(2-hydroxy-3-pyrrolidin-1-yl-propyl)-acetamide,
N-(3-Cyclopropylamino-2-hydroxy-propyl)-2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetamide,
3-[1-{4-[2-(4-Cyclopropyl-piperazin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-[4-(4-Cyclopropylmethyl-piperazine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-{4-[2-(4-Cyclopropylmethyl-piperazin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one,
3-[1-(4-{(S)-2-[(Cyclopropyl-methyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one,
3-[1-{4-[2-((2S,4R)-2-Cyclopropylaminomethyl-4-hydroxy-pyrrolidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-[4-((2R,4R)-2-Cyclopropylaminomethyl-4-hydroxy-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-[4-((2R,3S)-2-Cyclopropylaminomethyl-3-hydroxy-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-{4-[(S)-2-((R)-3-hydroxy-pyrrolidin-1-ylmethyl)-pyrrolidine-1-carbonyl]-3,5-dimethyl-1H- pyrrol-2-yl}-meth-(Z)-ylidene]-1,3-dihydro-indol-2-one,
5-(2,6-Dichloro-phenylmethanesulfonyl)-3-[1-{4-[(R)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-{4-[2-((R)-3-hydroxy-pyrrolidin-1-yl)-2-oxo-ethyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{2-[(R)-2-((R)-3-hydroxy-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
(R)-1-{5-[(2,6-Dichloro-phenylmethanesulfonyl)-2-oxo-1,2-dihydro-indol-(3Z)-ylidenemethyl]-2,4-dimethyl-1H-pyrrole-3-carbonyl}-piperidine-3-carboxylic acid cyclopropylamide,
(R)-1-(2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-acetyl)-piperidine-3-carboxylic acid cyclopropylamide,
3-[1-(4-{(S)-2-[(Cyclopropyl-methyl-amino)-methyl]-pyrrolidine-1-carbonyl}-3,5-dimethyl-1H-pyrrol-2-yl)-meth-(Z)-ylidene]-5-phenylmethanesulfonyl-1,3-dihydro-indol-2-one,
3-[1-{4-[2-((S)-3-Cyclopropylaminomethyl-piperidin-1-yl)-2-oxo-ethyl]-3,5-dimethyl-1H-pyrrol-2-yl}-meth-(Z)-ylidene]-5-(2,6-dichloro-phenylmethanesulfonyl)-1,3-dihydro-indol-2-one,
3-[1-[4-((S)-3-Cyclopropylaminomethyl-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-(4-{2-[(S)-2-((R)-3-fluoro-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
5-(2,6-Dichloro-phenylmethanesulfonyl)-3-[1-{4-[(S)-2-(4-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{2-[(S)-2-(4-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
5-(2,6-Dichloro-phenylmethanesulfonyl)-3-[1-{4-[(R)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{2-[(R)-2-((R)-3-fluoro-pyrrolidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-fluoro-piperidin-1-yl)-ethyl]-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(4-fluoro-piperidin-1-yl)-ethyl]-acetamide,
3-[1-[4-((2S,4R)-2-Cyclopropylaminomethyl-4-hydroxy-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-{4-[(R)-2-(4-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{2-[(R)-2-(4-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
5-(2,6-Dichloro-phenylmethanesulfonyl)-3-[1-{4-[(S)-2-(3-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{2-[(S)-2-(3-fluoro-piperidin-1-ylmethyl)-pyrrolidin-1-yl]-2-oxo-ethyl}-3,5-dimethyl-1H-pyrrol-2-yl)-meth-(Z)-ylidene]-1,3-dihydro-indol-2-one,
3-[1-[4-(2-{(S)-2-[(Cyclopropyl-methyl-amino)-methyl]-pyrrolidin-1-yl}-2-oxo-ethyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-[4-({(R)-2-[(Cyclopropyl-methyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-[3,5-dimethyl-4-(1-methyl-piperidin-4-yl)-1H-pyrrol-2-yl]-meth-(Z)-ylidene]-1,3-dihydro-indol-2-one,
5-(2,6-Dichloro-phenylmethanesulfonyl)-3-[1-[4-(4-fluoro-piperidin-1-ylmethyl)-3,5-dimethyl-1H-pyrrol-2-yl]-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-fluoro-pyrrolidin-1-yl)-ethyl]-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-fluoro-pyrrolidin-1-yl)-ethyl]-acetamide,
5-(2,6-Dichloro-phenylmethanesulfonyl)-3-[1-(4-{3-[(R)-2-((R)-3-fluoro-pyrrolidin-1-ylmethyl)-pyrrolidin-1-yl]-3-oxo-propyl}-3,5-dimethyl-1H-pyrrol-2-yl)-meth-(Z)-ylidene]-1,3-dihydro-indol-2-one,
5-(2,6-Difluoro-phenylmethanesulfonyl)-3-[1-{4-[(R)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(3-fluoro-piperidin-1-yl)-ethyl]-amide,
5-(2,6-Difluoro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(3-fluoro-piperidin-1-yl)-ethyl]-acetamide,
5-(2,6-Dichloro-phenylmethanesulfonyl)-3-[1-{3,5-dimethyl-4-[3-oxo-3-((R)-2-pyrrolidin-1-ylmethyl-pyrrolidin-1-yl)-propyl]-1H-pyrrol-2-yl}-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid {2-[4-(2-amino-2-methyl-propionyl)-piperazin-1-yl]-ethyl}-amide,
5-(2,6-Dichloro-phenylmethanesulfonyl)-3-[1-{3,5-dimethyl-4-[3-oxo-3-((S)-3-pyrrolidin-1-ylmethyl-piperidin-1-yl)-propyl]-1H-pyrrol-2-yl}-meth-(Z)-ylidene]-1,3-dihydro-indol-2-one,
5-(2,6-Difluoro-phenylmethanesulfonyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-[3,5-dimethyl-4-(3-morpholin-4-yl-3-oxo-propyl)-1H-pyrrol-2-yl]-meth-(Z)-ylidene]-1,3-dihydro-indol-2-one,
N-[2-(4-Acetyl-piperazin-1-yl)-ethyl]-2-{5-[5-(2,6-dichloro-phenylmethanesulfonyl)-2-oxo-1,2-dihydro-indol-(3Z)-ylidenemethyl]-2,4-dimethyl-1H-pyrrol-3-yl}-acetamide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid [2-(4-hydroxy-piperidin-1-yl)-ethyl]-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-[2-(4-hydroxy-piperidin-1-yl)-ethyl]-acetamide,
5-(2,6-Dichloro-phenylmethanesulfonyl)-3-[1-{3,5-dimethyl-4-[3-(4-methyl-piperazin-1-yl)-3-oxo-propyl]-1H-pyrrol-2-yl}-meth-(Z)-ylidene]-1,3-dihydro-indol-2-one,
5-(2,6-Dichloro-phenylmethanesulfonyl)-3-[1-{4-[3-((3R,5S)-3,5-dimethyl-piperazin-1-yl)-3-oxo-propyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-{3,5-dimethyl-4-[3-oxo-3-((S)-2-pyrrolidin-1-ylmethyl-pyrrolidin-1-yl)-propyl]-1H-pyrrol-2-yl}-meth-(Z)-ylidene]-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (1-methyl-piperidin-4-ylmethyl)-amide,
2-{5-[5-(2,6-Dichloro-phenylmethanesulfonyl)-2-oxo-1,2-dihydro-indol-(3Z)-ylidenemethyl]-2,4-dimethyl-1H-pyrrol-3-yl}-N-(1-methyl-piperidin-4-ylmethyl)-acetamide,
3-[1-{4-[3-((S)-2-Cyclopropylaminomethyl-pyrrolidin-1-yl)-3-oxo-propyl]-3,5-dimethyl-1H-pyrrol-2-yl}-meth-(Z)-ylidene]-5-(2,6-dichloro-phenylmethanesulfonyl)-1,3-dihydro-indol-2-one,
5-(2,6-Dichloro-phenylmethanesulfonyl)-3-[1-{4-[3-(4-hydroxy-piperidin-1-yl)-3-oxo-propyl]-3,5-dimethyl-pyrrol-2-yl}-meth-(Z)-ylidene]-1,3-dihydro-indol-2-one,
5-[(E)-3-Chloro-2-(1-chloro-vinyl)-penta-2,4-diene-1-sulfonyl]-3-[1-{4-[3-((R)-3-hydroxy-pyrrolidin-1-yl)-3-oxo-propyl]-3,5-dimethyl-1H-pyrrol-2-yl}-meth-(Z)-ylidene]-1,3-dihydro-indol-2-one,
5-(2,6-Dichloro-phenylmethanesulfonyl)-3-[1-(4-{3-[(R)-2-((R)-3-hydroxy-pyrrolidin-1-ylmethyl)-pyrrolidin-1-yl]-3-oxo-propyl}-3,5-dimethyl-1H-pyrrol-2-yl)-meth-(Z)-ylidene]-1,3-dihydro-indol-2-one,
5-(2,6-Difluoro-phenylmethanesulfonyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one,
3-[1-[4-(4-Cyclopropylamino-piperidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
3-[1-{4-[3-(4-Cyclopropylamino-piperidin-1-yl)-3-oxo-propyl]-3,5-dimethyl-1H-pyrrol-2-yl}-meth-(Z)-ylidene]-5-(2,6-dichloro-phenylmethanesulfonyl)-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-pyrrolidin-1-yl)-amide, 5-(2,6-Dichloro-phenylmethanesulfonyl)-3-[1-[5-methyl-3((S)-2-pyrrolidin-1-ylmethyl-pyrrolidine-1-carbonyl)-1H-pyrrol-2-yl]-meth-(Z)-ylidene]-1,3-dihydro-indol-2-one,
5-(2,6-Dichloro-phenylmethanesulfonyl)-3-[1-{4-[(S)-2-((S)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one,
5-[5-(3,5-Dichloro-phenylmethanesulfonyl)-2-oxo-1,2-dihydro-indol-(3Z)-ylidenemethyl]-2,4-dimethyl-1H-pyrrole-3-carboxylic acid,
3-[1-{4-[(Cyclopropyl-methyl-amino)-methyl]-3,5-dimethyl-1H-pyrrol-2-yl}-meth-(Z)-ylidene]-5-[2-(2-morpholin-4-yl-ethoxy)-phenylmethanesulfonyl]-1,3-dihydro-indol-2-one,
3-[1-[4-((R)-3-Hydroxy-pyrrolidine-1-carbonyl)-3,5-dimethyl-1H-pyrrol-2-yl]-meth-(Z)-ylidene]-5-[2-(2-morpholin-4-yl-ethoxy)-phenylmethanesulfonyl]-1,3-dihydro-indol-2-one,
3-[1-[3,5-Dimethyl-4-(4-methyl-piperazine-1-carbonyl)-1H-pyrrol-2-yl]-meth-(Z)-ylidene]-5-[2-(2-morpholin-4-yl-ethoxy)-phenylmethanesulfonyl]-1,3-dihydro-indol-2-one,
3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-[2-(2-morpholin-4-yl-ethoxy)-phenylmethanesulfonyl]-1,3-dihydro-indol-2-one,
3-[1-[4-(4-Cyclopropylamino-piperidine-1-carbonyl)-3,5-dimethyl-1H-pyrrol-2-yl]-meth-(Z)-ylidene]-5-(3,5-dimethoxy-phenylmethanesulfonyl)-1,3-dihydro-indol-2-one,
3-[1-[4-((R)-2-Cyclopropylaminomethyl-pyrrolidine-1-carbonyl)-3,5-dimethyl-1H-pyrrol-2-yl]-meth-(Z)-ylidene]-5-(3,5-dimethoxy-phenylmethanesulfonyl)-1,3-dihydro-indol-2-one,
3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(3,5-dimethoxy-phenylmethanesulfonyl)-1,3-dihydro-indol-2-one,
5-(3,5-Dimethoxy-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one,
3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-phenylmethanesulfonyl-1,3-dihydro-indol-2-one,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid cyclopropyl-(R)-1-pyrrolidin-2-ylmethyl-amide,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid cyclopropylmethyl-(R)-1-pyrrolidin-2-ylmethyl-amide,
5-(2,6-Dimethoxy-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one,
3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2,6-difluoro-phenylmethanesulfonyl)-1,3-dihydro-indol-2-one,
3-[1-[4-((R)-2-Cyclopropylaminomethyl-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
3-[1-(4-{(R)-2-[(Cyclopropylmethyl-amino)-methyl]-pyrrolidine-1-carbonyl}-3,5-dimethyl-1H-pyrrol-2-yl)-meth-(Z)-ylidene]-5-(2-fluoro-phenylmethanesulfonyl)-1,3-dihydro-indol-2-one,
3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-(2-fluoro-phenylmethanesulfonyl)-1,3-dihydro-indol-2-one,
5-(2-Chloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one,
5-(2-Chloro-phenylmethanesulfonyl)-3-[1-[4-((R)-2-cyclopropylaminomethyl-pyrrolidine-1-carbonyl)-3,5-dimethyl-1H-pyrrol-2-yl]-meth-(Z)-ylidene]-1,3-dihydro-indol-2-one,
5-(2-Chloro-phenylmethanesulfonyl)-3-[1-(4-{(R)-2-[(cyclopropylmethyl-amino)-methyl]-pyrrolidine-1-carbonyl}-3,5-dimethyl-1H-pyrrol-2-yl)-meth-(Z)-ylidene]-1,3-dihydro-indol-2-one,
5-(2-Chloro-phenylmethanesulfonyl)-3-[1-[4-(4-cyclopropylamino-piperidine-1-carbonyl)-3,5-dimethyl-1H-pyrrol-2-yl]-meth-(Z)-ylidene]-1,3-dihydro-indol-2-one,
3-[1-[4-(4-Cyclopropylamino-piperidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one,
5-(2,6-Dichloro-phenylmethanesulfonyl)-3-[1-{4-[(R)-2-((S)-2-hydroxymethyl-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one,
3-[1-[4-(4-Amino-piperidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one,
3-[1-[4-(4-Amino-piperidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-[4-(4-Amino-piperidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
3-[1-[4-(4-Amino-piperidine-1-carbonyl)-3,5-dimethyl-1H-pyrrol-2-yl]-meth-(Z)-ylidene]-5-(2-chloro-phenylmethanesulfonyl)-1,3-dihydro-indol-2-one,
3-[1-[4-((S)-3-Amino-pyrrolidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one,
3-[1-[4-((S)-3-Amino-pyrrolidine-1-carbonyl)-3,5-dimethyl-1H-pyrrol-2-yl]-meth-(Z)-ylidene]-5-(2-chloro-phenylmethanesulfonyl)-1,3-dihydro-indol-2-one,
3-[1-[4-((S)-3-Amino-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-[4-((S)-3-Amino-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
3-[1-[4-((R)-3-Amino-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one,
3-[1-[4-((R)-3-Amino-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one,
3-[1-[4-((R)-3-Amino-pyrrolidine-1-carbonyl)-3,5-dimethyl-1H-pyrrol-2-yl]-meth-(Z)-ylidene]-5-(2-chloro-phenylmethanesulfonyl)-1,3-dihydro-indol-2-one, and
3-[1-[4-((R)-3-Amino-pyrrolidine-1-carbonyl)-3,5-dimethyl-1H-pyrrol-2-yl]-meth-(Z)-ylidene]-5-(2-fluoro-phenylmethanesulfonyl)-1,3-dihydro-indol-2-one,
(4-{3-[1-[3,5-dimethyl-4-(4-methyl-piperazine-1-carbonyl)-1H-pyrrol-2-yl]meth-(Z)-ylidene]-2-oxo-2,3-dihydro-1H-indole-5-sulfonylmethyl}-phenyl)-acetic acid,
3-[1-[1-[3,5-dimethyl-4-(4-methyl-piperazine-1-carbonyl)-1H-pyrrol-2-yl]-meth-(Z)-ylidene]-5-pentafluorophenylmethanesulfonyl-1,3-dihydro-indol-2-one,
2,4-dimethyl-5-[2-oxo-5-pentafluorophenylmethanesulfonyl-1,2-dihydro-indol(3Z)-ylidenemethyl]-1H-pyrrole-3-carboxylic acid (2-diethylamino-ethyl)-amide,
5-[5-(2,6-dichloro-phenylmethanesulfonyl)-2-oxo-1,2-dihydro-indol-(3Z)-ylidenemethyl]-2,4-dimethyl-1H-pyrrole-3-carboxylic acid,
5-[5-(2,6-Dichloro-phenylmethanesulfonyl)-2-oxo-1,2-dihydro-indol-(3Z)-ylidenemethyl]-2,4-dimethyl-1H-pyrrole-3-carboxylic acid (2-hydroxy-ethyl)-amide, and
5-(2,6-Dichloro-phenylmethanesulfonyl)-3-[1-[4-((S)-2-methoxymethyl-pyrrolidine-1-carbonyl)-3,5-dimethyl-1H-pyrrol-2-yl]-meth-(Z)-ylidene]-1,3-dihydro-indol-2-one.

14. A pharmaceutical composition, comprising a compound or salt of claim 13 and a pharmaceutically acceptable carrier or excipient.

15. A method for the modulation of the catalytic activity of a protein kinase comprising contacting said protein kinase with a compound or salt of claim 13.

16. The method of claim 15 wherein said protein kinase is selected from the group consisting of a receptor tyrosine kinase, a non-receptor tyrosine kinase and a serine-threonine kinase.

17. The method of claim 16 wherein said protein kinase is Met kinase.

18. A method for treating or preventing a protein kinase related disorder in an organism in need of such treatment comprising administering a therapeutically effective amount of a pharmaceutical composition comprising a compound or salt of claim 13 and a pharmaceutically acceptable carrier or excipient to said patient.

19. The method of claim 18 wherein said protein kinase related disorder is slected from the group consisting of a receptor tyrosine kinase related disorder, a non-receptor tyrosine kinase related disorder and a serine-threonine kinase related disorder.

20. The method of claim 18 wherein said protein tyrosine kinase related disorder is mediated by Met kinase.

21. The method of claim 20 wherein said protein kinase related disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

22. The method of claim 20 wherein said protein kinase related disorder is selected from the group consisting of diabetes, an autoimmune disorder, a hyperproliferation disorder, restenosis, fibrosis, psoriasis, von Hippel-Lindau disease, osteoarthritis, rheumatoid arthritis, angiogenesis, an inflammatory disorder, an immunological disorder and a cardiovascular disorder.

23. A compound, optionally in the form of a pharmaceutically acceptable salt, selected from the group consisting of:

5-(2,6-Dichlorophenylmethanesulfonyl)-3-{1-[3,5-dimethyl-4-(4-morpholin-4-yl-methyl)-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(pyrrolidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(cyclopropylaminomethyl)pyrrolidin-1-carbonyl]-1H-pyrrol-2-yl]-meth-(Z)-ylidene}-1,3-dihydro-indol-2-one;

5-(2,6-Dichlorophenylmethanesulfonyl)-3-{1-[3,5-dimethyl-4-[4-(cyclopropylmethyl)piperazin-1-ylmethyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(cyclopropylmethylaminomethyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(3R-hydroxypyrrolidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[3S-(pyrrolidin-1-yl-methyl)piperidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2S-(3R-fluoropyrrolidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(3R-pyrrolidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[2R-(4-fluoropiperidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[4-(pyrrolidin-1-yl)-piperidin-1-ylcarbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[4-(cyclopropyl-amino)piperidin-1-ylcarbonyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[4-(cyclopropyl-amino)piperidin-1-ylmethyl]-1H-pyrrol-2-yl]-meth-(Z)-ylidene}-1,3-dihydro-indol-2-one;

5-(2,6-Dichloro-phenylmethanesulfonyl)-3-{1-[3,5-dimethyl-4-[4-(pyrrolidin-1-yl)-piperidin-1-ylmethyl]-1H-pyrrol-2-yl]-meth-(Z)-ylidene}-1,3-dihydro-indol-2-one;

5-(2,6-Difluoro-phenylmethanesulfonyl)-3-{1-[3,5-dimethyl-4-[2R-(pyrrolidin-1-yl-methyl)pyrrolidin-1-carbonyl]-1H-pyrrol-2-yl]-meth-(Z)-ylidene}-1,3-dihydro-indol-2-one;

5-(2,6-Dichloro-phenylmethanesulfonyl)-3-[1-[3,5-dimethyl4-((S)-2-pyrrolidin-1-ylmethyl-pyrrolidine-1-carbonyl)-1H-pyrrol-2-yl]-meth-(Z)-ylidene]-1,3-dihydro-indol-2-one;

5-(2,6-Dichloro-phenylmethanesulfonyl)-3-[1-[4-(4-hydroxy-piperidine-1-carbonyl)-3,5-dimethyl-1H-pyrrol-2-yl]-meth-(Z)-ylidene]-1,3-dihydro-indol-2-one;

5-(2,6-Dichloro-phenylmethanesulfonyl)-3-[1-[4-((R)-3-hydroxy-pyrrolidine-1-carbonyl)-3,5-dimethyl-1H-pyrrol-2-yl]-meth-(Z)-ylidene]-1,3-dihydro-indol-2-one;

5-(2,6-Dichloro-phenylmethanesulfonyl)-3-[1-[3,5-dimethyl4-morpholin-4-ylmethyl-1H-pyrrol-2-yl)-meth-(Z)-ylidene]-1,3-dihydro-indol-2-one;

5-(2,6-Dichloro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one;

3-[1-[4-((R)-2-Cyclopropylaminomethyl-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one;

5-(2,6-Dichloro-phenylmethanesulfonyl)-3-[1-{4-[(S)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one;

3-[1-(4-{(R)-2-[(Cyclopropyhnethyl-amino)-methyl]-pyrrolidine-1-carbonyl}-3,5-dimethyl-1H-pyrrol-2-yl)-meth-(Z)-ylidene]-5-(2,6-dichloro-phenylmethanesulfonyl)-1,3-dihydro-indol-2-one;

3-[1-[4-((2R, 4R)-2-Cyclopropylaminomethyl-4-hydroxy-pyrrolidine-1-carbonyl)-3,5-dimethyl-1H-pyrrol-2-yl]-meth-(Z)-ylidene]-5-(2,6-dichloro-phenylmethanesulfonyl)-1,3-dihydro-indol-2-one;

5-(2,6-Dichloro-phenylmethanesulfonyl)-3-[1-{4-[(S)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one 5-(2,6-Dichloro-phenyhnethanesulfonyl)-3-[1-{4-[(R)-2-((R)-3-hydroxy-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one;

5-(2,6-Dichloro-phenylmethanesulfonyl)-3-[1-[3,5-dimethyl-4-((S)-3-pyrrolidin-1-ylmethyl-piperidine-1-carbonyl)-1H-pyrrol-2-yl]-meth-(Z)-ylidene]-1,3-dihydro-indol-2-one;

5-(2,6-Dichloro-phenylmethanesulfonyl)-3-[1-{4-[(R)-2-((R)-3-fluoro-pyrrolidin-1-ylmethyl)-pyrrolidine-1-carbonyl]-3,5-dimethyl-1H-pyrrol-2-yl}-meth-(Z)-ylidene]-1,3-dihydro-indol-2-one;

5-(2,6-Dichloro-phenylmethanesulfonyl)-3-[1-[4-(4-fluoro-piperidin-1-ylmethyl)-3,5-dimethyl-1H-pyrrol-2-yl]-meth-(Z)-ylidene]-1,3-dihydro-indol-2-one;

5-[5-(2,6-Dichloro-phenylmethanesulfonyl)-2-oxo-1,2-dihydro-indol-(3Z)-ylidenemethyl]-2,4-dimethyl-1H- pyrrole-3-carboxylic acid [2-(3-fluoro-pyrrolidin-1-yl)-ethyl]-amide;

3-[1-[4-(4-Cyclopropylamino-piperidine-1-carbonyl)-3,5-dimethyl-1H-pyrrol-2-yl]-meth-(Z)-ylidene]-5-(2,6-dichloro-phenyhethanesulfonyl)-1,3-dihydro-indol-2-one;

5-(2,6-Difluoro-phenylmethanesulfonyl)-3-[1-[3,5-dimethyl-4-((R)-2-pyrrolidin-1-ylmethyl-pyrrolidine-1-carbonyl)-1H-pyrrol-2-yl]-meth-(Z)-ylidene]-1,3-dihydro-indol-2-one;

5-(2,6-Dichloro-phenylmethanesulfonyl)-3-[1-{3,5-dimethyl-4-[3-oxo-3-((S)-2-pyrrolidin-1-ylmethyl-pyrrolidin-1-yl)-propyl]-1H-pyrrol-2-yl }-meth-(Z)-ylidene]-1,3-dihydro-indol-2-one;

3-[1-[4-(4-Cyclopropylamino-piperidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one;

3-[1-[4-((R)-2-Cyclopropylaminomethyl-pyrrolidine-1-carbonyl)-3,5-dimethyl-1H-pyrrol-2-yl]-meth-(Z)-ylidene]-5-(2,6-difluoro-phenylmethanesulfonyl)-1,3-dihydro-indol-2-one;

3-[1-(4-{(R)-2-[(Cyclopropylmethyl-amino)-methyl]-pyrrolidine-1-carbonyl}-3,5-dimethyl-H-pyrrol-2-yl)-meth-(Z)-ylidene]-5-(2,6-difluoro-phenylmethanesulfonyl)-1,3-dihydro-indol-2-one;

3-[1-[3,5-Dimethyl-4-((R)-2-pyrrolidin-1-ylmethyl-pyrrolidine-1-carbonyl)-1H-pyrrol-2-yl]-meth-(Z)-ylidene]-5-phenylmethanesulfonyl-1,3-dihydro-indol-2-one;

3-[1-[4-(4-Cyclopropylmethyl-piperazin-1-ylmethyl)-3,5-dimethyl-1H-pyrrol-2-yl]-meth-(Z)-ylidene]-5-(2,6-dichloro-phenylmethanesulfonyl)-1,3-dihydro-indol-2-one;

5-(2,6-Dichloro-phenylmethanesulfonyl)-3-[1-{4-[(R)-2-(4-fluoro-piperidin-1-ylmethyl)-pyrrolidine-1-carbonyl]-3,5-dimethyl-1H-pyrrol-2-yl}-meth-(Z)-ylidene]-1,3-dihydro-indol-2-one; and 5-(2,6-dichloro-phenylmethanesulfonyl)-3-[1-{4-[(S)-2-((R)-3-fluoro-pyrrolidin-1-ylmethyl)pyrrolidin-1-carbonyl]-3,5-dimethyl-1H-pyrrol-2-yl}-meth-(Z)-ylidene]-1,3-dihydro-indol-2-one.

* * * * *